US012545672B2

(12) United States Patent
Gerusz et al.

(10) Patent No.: US 12,545,672 B2
(45) Date of Patent: Feb. 10, 2026

(54) ANTIBIOTIC COMPOUNDS, METHODS OF MANUFACTURING THE SAME, PHARMACEUTICAL COMPOSITIONS CONTAINING THE SAME AND USES THEREOF

(71) Applicant: Debiopharm International S.A., Lausanne (CH)

(72) Inventors: Vincent Gerusz, Neuvecelle (FR); Vasileios Tatsis, Oxford (GB); Mihiro Sunose, Nottingham (GB); Juan Bravo, Epalinges (CH); Terry Finn, Geneva (CH); Danig Pohin, Aigle (CH); Pierre-Michel Regenass, Charrat (CH)

(73) Assignee: Debiopharm International S.A., Lausanne (CH)

( * ) Notice: Subject to any disclaimer, the term of this patent is extended or adjusted under 35 U.S.C. 154(b) by 905 days.

(21) Appl. No.: 17/292,600

(22) PCT Filed: Nov. 11, 2019

(86) PCT No.: PCT/EP2019/080903
§ 371 (c)(1),
(2) Date: May 10, 2021

(87) PCT Pub. No.: WO2020/099341
PCT Pub. Date: May 22, 2020

(65) Prior Publication Data

US 2023/0035837 A1 Feb. 2, 2023

(30) Foreign Application Priority Data

Nov. 12, 2018 (EP) .................................... 18205619
Dec. 17, 2018 (EP) .................................... 18213016

(51) Int. Cl.
*A61P 31/04* (2006.01)
*C07D 471/04* (2006.01)
*C07D 491/20* (2006.01)
*C07F 9/6561* (2006.01)

(52) U.S. Cl.
CPC ............ *C07D 471/04* (2013.01); *A61P 31/04* (2018.01); *C07D 491/20* (2013.01); *C07F 9/6561* (2013.01)

(58) Field of Classification Search
CPC ..... C07D 471/04; C07D 491/20; A61P 31/04; C07F 9/6561
See application file for complete search history.

(56) References Cited

U.S. PATENT DOCUMENTS

2015/0210719 A1* 7/2015 Guillemont .......... C07D 513/14 544/131
2017/0174683 A1 6/2017 Guillemont et al.

FOREIGN PATENT DOCUMENTS

| | | | | |
|---|---|---|---|---|
| CL | 2022001660 | A1 | 3/2023 | |
| CN | 101415701 | A | 4/2009 | |
| JP | 2003-511448 | A | 3/2003 | |
| JP | 2005-519984 | A | 7/2005 | |
| JP | 2006-523207 | A | 10/2006 | |
| JP | 2008-505194 | A | 2/2008 | |
| JP | 2009-518399 | A | 5/2009 | |
| JP | 2010-501474 | A | 1/2010 | |
| JP | 2015-521617 | A | 7/2015 | |
| JP | 2015-528438 | A | 9/2015 | |
| WO | WO 2001/027103 | A1 | 4/2001 | |
| WO | WO 2003/088897 | A2 | 10/2003 | |
| WO | WO-2007053131 | A2 * | 5/2007 | .............. A61P 31/00 |
| WO | WO-2007067416 | A2 * | 6/2007 | .............. A61P 31/04 |
| WO | WO 2008/009122 | A1 | 1/2008 | |
| WO | WO 2008/098374 | A1 | 8/2008 | |
| WO | WO 2013/190384 | A1 | 12/2013 | |
| WO | WO 2015/013671 | A1 | 1/2015 | |
| WO | WO 2016/014974 | A2 | 1/2016 | |
| WO | WO 2021/123372 | A1 | 6/2021 | |

OTHER PUBLICATIONS

Patani GA, LaVoie EJ. Bioisosterism: A Rational Approach in Drug Design. Chem Rev. Dec. 19, 1996;96(8):3147-3176. (Year: 1996).*
International Search Report and Written Opinion for PCT/EP2019/080903 dated Mar. 17, 2020.
International Preliminary Report on Patentability for PCT/EP2019/080903 dated May 20, 2021.
Extended European Search Report for EP18205619.2 mailed Mar. 11, 2019.
Yao et al., Activation of Exogenous Fatty Acids to Acyl-Acyl Carrier Protein Cannot Bypass FabI Inhibition in Neisseria. J Biol Chem. Jan. 1, 2016;291(1):171-81. doi: 10.1074/jbc.M115.699462. Epub Nov. 13, 2015. PMID: 26567338; PMCID: PMC4697154.

* cited by examiner

*Primary Examiner* — James H Alstrum-Acevedo
*Assistant Examiner* — Pierre Paul Eleniste
(74) *Attorney, Agent, or Firm* — Wolf, Greenfield & Sacks, P.C.

(57) ABSTRACT

The present invention provides compounds of the general structure (I), which are suitable as antibiotic compounds for the treatment of *N. gonorrhoeae* infections and related infections.

(I)

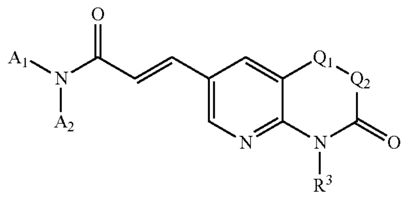

20 Claims, No Drawings

ANTIBIOTIC COMPOUNDS, METHODS OF MANUFACTURING THE SAME, PHARMACEUTICAL COMPOSITIONS CONTAINING THE SAME AND USES THEREOF

STATEMENT OF RIGHTS TO INVENTIONS MADE UNDER FEDERALLY SPONSORED RESEARCH

This invention was made with government support under the CarbX Agreement No. 4500003908 under the partnership for CarbX and the National Institute of Allergy and Infectious Diseases. The government has certain rights in the invention.

CROSS REFERENCE TO RELATED APPLICATIONS(S)

This Application is a National stage filing under 35 U.S.C. 371 of International Application No. PCT/EP2019/080903, filed Nov. 11, 2019, which claims priority to European Application No. 18205619.2, filed Nov. 12, 2018, and European Application No. 18213016.1, filed Dec. 17, 2018, each of which is herein incorporated by reference in their entirety.

FIELD OF THE INVENTION

The present invention provides novel compounds that are therapeutically active as antibiotic compounds. The present invention furthermore provides pharmaceutical compositions comprising the compounds of the invention. It also provides uses of these compounds and compositions for the treatment of bacterial infections caused by *N. gonorrhoeae*. Moreover, methods of making the compounds of the present invention are also provided.

BACKGROUND OF THE INVENTION

*Neisseria gonorrhoeae* is a species of Gram-negative diplococci bacteria responsible for the sexually transmitted infection gonorrhea, that typically causes an uncomplicated (non-disseminated) disease.

The most common site of *N. gonorrhoeae* infection is the urogenital tract. Men with this infection may experience dysuria with penile discharge, and women may have mild vaginal mucopurulent discharge, severe pelvic pain. Other *N. gonorrhoeae* infections include anorectal, conjunctival, pharyngeal, and ovatian/uterine. In women, gonococci may cause endocervical infections, or upper genital tract disease. Gonococcal infections of women are closely associated with infertility. If untreated, local *N. gonorrhoeae* infections can progress to bacteremia with attendant septic arthritis. When infection involves the eyes, especially in newborns, blindness can result if treatment is not prompt. Rarely, bacteremia results in dissemination (complicated gonorrhea) to the joints, skin, endocardium or meninges.

Gonorrhea treatment is complicated by the ability of *N. gonorrhoeae* to develop resistance to antimicrobials. In 2007, emergence of fluoroquinolone-resistant *N. gonorrhoeae* in the United States prompted health authorities to cease recommending fluoroquinolones for treatment of gonorrhea in the United States. Recent treatment failures with cefixime or other oral cephalosporins have been reported in Asia, Europe, South Africa and Canada. Ceftriaxone treatment failures for pharyngeal infections have been reported in Australia, Japan, and Europe. Consequently, global organizations such as WHO recommend that local resistance data should determine the choice of therapy.

Recently there have been sporadic reports of *N. gonorrhoeae* strains resistant to both cephalosporins and macrolides, thereby leaving no treatment options for these patients. The fear is that, due to the ability of *Neisseria* sp., to rapidly disseminate and integrate their genetic material (promiscuous transformation), these ultra-drug resistant genotypes can spread rapidly.

FabI inhibition is a relatively new concept for developing antibiotic compounds. FabI is an enzyme involved in bacterial fatty acid synthesis. Administration of compounds inhibiting this enzyme may selectively affect bacteria relying on this enzyme without affecting the host (patient). Antibiotic agents relying on this working principle are disclosed for instance in WO 03/088897 A2 and WO 2013/190384 A1, the content of which is incorporated in its entirety into the present application. These compounds are, however, primarily directed to the treatment of *S. aureus* infections. Further compounds with FabI inhibitory action, but focusing primarily on the treatment of infections other than *N. gonorrhoeae*, are disclosed in WO 2007/053131 A, WO 2007/067416 A, WO 01/27103 A, WO 2008/098374 A, Yao et al., J. Biol. Chem., 2016, 291, 171-181, WO 2008/009122 A, US 2015/210719 A and US 2017/174683 A.

Problems Underlying the Invention

In view of the above situation, there is a need for providing further drugs and pharmaceutical compositions that show antibiotic activity against *N. gonorrhoeae.*

It is particularly desired to obtain such further drugs and pharmaceutical compositions, which may be used as fall-back treatment of bacterial infections caused by *N. gonorrhoeae* if the standard treatment with ceftriaxone is not effective.

There is, furthermore, a need for further antibiotic drugs and medicaments for treating a variety of related bacterial infections.

It is further desired that such antibiotic drugs and pharmaceutical compositions exhibit an acceptable therapeutic index and no serious side effects.

SUMMARY OF THE INVENTION

The present invention solves the above problems by providing compounds and pharmaceutical compositions that are effective in the treatment of infections by *N. gonorrhoeae* and related bacteria.

The compounds of the present invention act as antibiotic agents by means of a working mechanism involving FabI inhibition. This mechanism differs from that of cephalosporins, which act by disruption of peptidoglycan layers of bacterial cell walls. Moreover, the compounds of the present invention have a chemical structure different from that of cephalosporins. It may therefore be expected that the compounds and pharmaceutical compositions of the present invention are effective also in strains that are resistant to ceftriaxone.

The compounds and pharmaceutical compositions of the present invention furthermore show a high therapeutic index and low side effects.

According to one embodiment, the compounds and pharmaceutical compositions of the present invention show chemical, physical and pharmacokinetic properties suitable for oral and/or intramuscular administration.

In one embodiment, the present invention also provides therapeutic uses of the compounds described herein and methods of treatment of bacterial infections involving the administration of the compounds of the present invention to patients in need thereof.

In other embodiments, the present invention further provides methods for preparing the compounds of the present invention.

Thus the present invention provides in particular the following:

1. Compound, which is selected from the group of compounds represented by general formula I

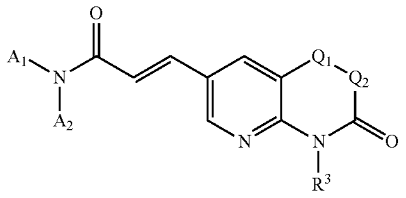

I wherein $A_1$ represents a moiety selected from the groups $A_{11}$ and $A_{12}$ having the following structures $A_{11}$

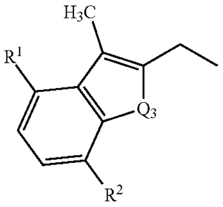

and $A_{12}$

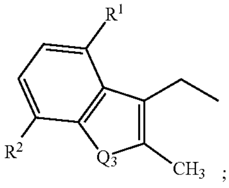

;

wherein the line connected to the exocyclic methylene group represents a single covalent bond formed with the nitrogen atom of formula I;

$A_2$ represents a methyl group;

or $A_1$ and $A_2$ together with the nitrogen atom to which they are bonded form the following moiety $A_3$:

$A_3$

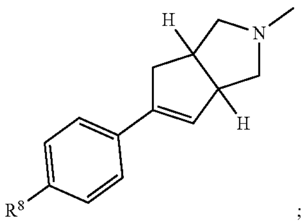

;

wherein the exocyclic line connected to the nitrogen atom of the bicycle represents the covalent bond between nitrogen and carbonyl group in the left-hand side of formula I;

$Q_1$ represents —CH═CR$^7$—, $CH_2$ or NH;

$Q_2$ represents CR$^4$R$^5$, or CR$^4$R$^5$—CR$^6$R$^7$, wherein the CR$^4$R$^5$ group binds to $Q_1$;

or $Q_1$-$Q_2$ represents —N═CR$^7$—CHR$^7$— or its tautomer —NH—CR$^7$═CR$^7$—

$Q_3$ represents O or S;

$R^1$ represents a group selected from H, —$NH_2$;

$R^2$ represents a group selected from H, —O—Ar$^1$, —O-Het$^1$, —NR$^9$R$^{10}$, —O-Alk$^1$, wherein Ar$^1$ represents a phenyl group that may optionally be substituted by one or more groups individually selected from —CN, —O—$C_{1-4}$-alkyl, —O—$(CH_2)_{1-4}$—NR$^9$R$^{10}$, or wherein the phenyl group may carry two substituent groups at adjacent ring atoms such that these adjacent substituent groups may be bonded together to form a 5-membered heterocycle having one or two heteroatoms individually selected from N and O, wherein Het$^1$ represents an aromatic heterocycle with 5 or 6 ring atoms including 1 or 2 heteroatoms individually selected from N, S and O, or a non-aromatic partially or fully saturated heterocycle with 6 ring atoms including 1 heteroatom selected from N and O, which Het$^1$ group may optionally be substituted by one or more groups individually selected from —$C_{1-4}$-alkyl, —O—$C_{1-4}$-alkyl, —CN, —$(CH_2)_{0-4}$—OH; wherein R$^9$ is selected from H and —$C_{1-4}$-alkyl; wherein R$^{10}$ is selected from H, —$C_{1-4}$-alkyl and —C(═O)—$CH_3$; wherein Alk$^1$ represents an alkyl group having 1 to 6 carbon atoms, which is linear, branched, cyclic or a combination thereof, which Alk$^1$ group may optionally be substituted by one or more groups selected from —OH, —O-alkyl $R^3$ represents a group selected from H, —$PO_3R^{3a}{}_2$, —$CH_2$—$OPO_3R^{3a}{}_2$ and —$CH_2$—O—C(═O)—R$^{3b}$.

$R^{3a}$ represents a hydrogen atom or a cation suitable for forming a pharmaceutically acceptable salt or —$CH_2$—O—C(═O)—R$^{3b}$ or —CHMe—O—C(═O)—R$^{3b}$ or —$CMe_2$-O—C(═O)—R$^{3b}$ or —$CH_2$—O—C(═O)—O—R$^{3b}$ or —CHMe—O—C(═O)—O—R$^{3b}$ or —$CMe_2$-O—C(═O)—O—R$^{3b}$.

$R^{3b}$ represents an alkyl group having 1 to 11 carbon atoms, which is linear, branched, cyclic or a combination thereof, which R$^{3b}$ group may optionally be substituted by one or more groups independently selected from —OH, and —O—$C_{1-6}$-alkyl;

$R^4$ represents a group selected from H, $C_{1-4}$-alkyl, CN and $C_{1-4}$-alkylene-F;

$R^5$ represents a group selected from H, $C_{1-4}$-alkyl, $C_{1-4}$-alkylene-OH, $C_{1-4}$-alkylene-OR$^3$, —OH, —$OPO_3R^{3a}{}_2$;

or $R^4$ and $R^5$ together form a cyclic group having 4 to 6 ring members formed by methylene groups and optionally an oxygen atom;

$R^6$ represents a group selected from H, —OH, $C_{1-4}$-alkyl, —$OPO_3R^{3a}{}_2$;

$R^7$ represents a group selected from H, $C_{1-4}$-alkyl, $C_{1-4}$-alkylene-OH, $C_{1-4}$-alkylene-OR$^3$, $C_{1-4}$-alkylene-F, —CN;

or $R^6$ and $R^7$ together form a cyclic group having 4 to 6 ring members formed by methylene groups and optionally an oxygen atom; the cyclic group may optionally carry a substituent selected from —OH, —O-alkyl;

$R^8$ represents a group selected from —O—Ar$^2$ and —O-Het$^2$;

wherein $Ar^2$ represents a phenyl group that may optionally be substituted by one or more groups individually selected from —CN, —O—$C_{1-4}$-alkyl or wherein the phenyl group may carry two substituent groups at adjacent ring atoms such that these adjacent substituent groups may be bonded together to form a 5-membered heterocycle having one or two heteroatoms individually selected from N, S and O, wherein said heterocycle may optionally carry one or two substituents selected from oxo, halogen, —O—$C_{1-4}$-alkyl, $C_{1-4}$-alkyl, and CN;

and wherein $Het^2$ represents an aromatic heterocycle with 5 or 6 ring atoms including 1 or 2 heteroatoms individually selected from N, S and O, which may optionally be substituted by one or more groups individually selected from —O—$C_{1-4}$-alkyl, —CN, F, $C_{1-4}$-alkyl.

2. Compound according to item 1, wherein $Q_2$ represents $CR^4R^5$—$CR^6R^7$, wherein the $CR^4R^5$ group binds to $Q_1$; or $Q_1$-$Q_2$ represents —N═$CR^7$—$CHR^7$— or its tautomer —NH—$CR^7$═$CR^7$—;

$R^4$ represents a group selected from $C_{1-4}$-alkyl, CN and $C_{1-4}$-alkylene-F; and $R^5$ represents a group selected from H, $C_{1-4}$-alkyl, $C_{1-4}$-alkylene-OH, $C_{1-4}$-alkylene-$OR^3$, —OH, —$OPO_3R^{3a}{}_2$;

and the remaining variable groups are as defined in claim 1.

3. Compound according to item 1, wherein $Q_2$ represents $CR^4R^5$—$CR^6R^7$, wherein the $CR^4R^5$ group binds to $Q_1$; or $Q_1$-$Q_2$ represents —N═$CR^7$—$CHR^7$— or its tautomer —NH—$CR^7$═$CR^7$—;

$R^4$ represents a group selected from H, $C_{1-4}$-alkyl, CN and $C_{1-4}$-alkylene-F; and $R^5$ represents a group selected from $C_{1-4}$-alkyl, $C_{1-4}$-alkylene-OH, $C_{1-4}$-alkylene-$OR^3$, —OH, —$OPO_3R^{3a}{}_2$;

and the remaining variable groups are as defined in claim 1.

4. Compound according to item 1, 2 or 3 wherein the compound is selected from the group of compounds represented by general formula II

II

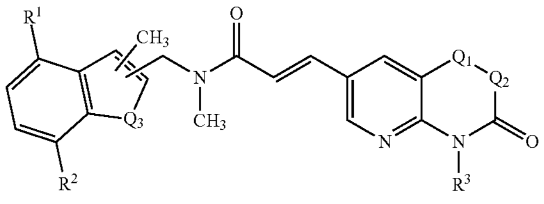

wherein $R^1$, $R^2$, $R^3$, $Q_1$, $Q_2$, $Q_3$ have the same meanings as specified in item 1 above;

and wherein the five-membered heterocycle comprising $Q_3$ is bonded to the methylene-amide moiety at the 2-position and to the methyl group at the 3-position or is bonded to the methylene-amide moiety at the 3-position and to the methyl group at the 2-position.

5. Compound according to item 4, wherein the compound is selected from the group of compounds represented by general formula III

III

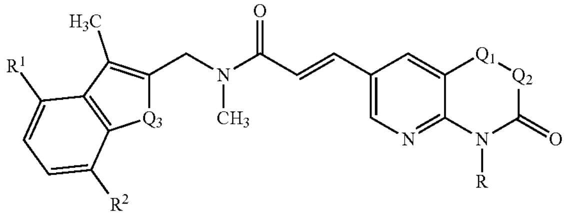

wherein $R^1$, $R^2$, $R^3$, $Q_1$, $Q_2$, $Q_3$ have the same meanings as specified in item 1, 2 or 3 above.

6. Compound according to item 5, wherein the compound is selected from the group of compounds represented by general formula IV

IV

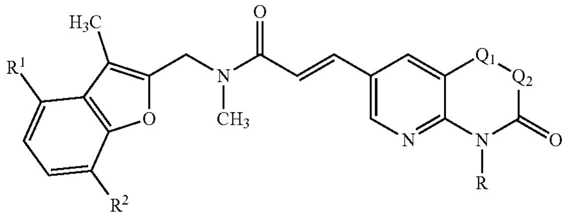

wherein $R^1$, $R^2$, $R^3$, $Q_1$, $Q_2$ have the same meanings as specified in item 1, 2 or 3 above.

7. Compound according to item 6, wherein the compound is selected from the group of compounds represented by general formula Va or general formula Vb Va

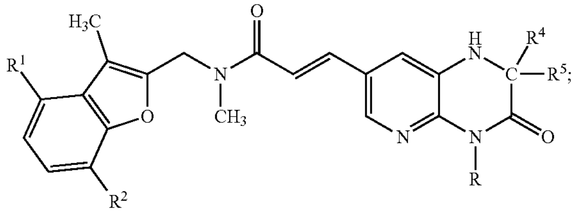

wherein $R^1$, $R^2$ and $R^3$ have the same meanings as specified in item 1 above; $R^4$ represents a group selected from H, $C_{1-4}$-alkyl and $C_{1-4}$-alkylene-F and $R^5$ represents a group selected from H, $C_{1-4}$-alkyl, $C_{1-4}$-alkylene-OH, $C_{1-4}$-alkylene-$OR^3$;

or

Vb

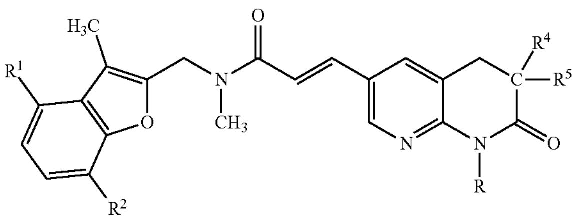

wherein $R^1$, $R^2$ and $R^3$ have the same meanings as specified in item 1 above; $R^4$ represents a group selected from H, $C_{1-4}$-alkyl and $C_{1-4}$-alkylene-F; and $R^5$ represents a group selected from H, $C_{1-4}$-alkyl, $C_{1-4}$-alkylene-OH, $C_{1-4}$-alkylene-$OR^3$, —OH; and —$OPO_3R^{3a}{}_2$.

8. Compound according to item 7, wherein $R^1$ represents H, $NH_2$;

$R^2$ represents H;

$R^3$ represents a group selected from H, —$PO_3R^{3a}{}_2$, —$CH_2$—$OPO_3R^{3a}{}_2$ and —$CH_2$—O—C(═O)—$R^{3b}$.

$R^{3a}$ represents a hydrogen atom or a cation suitable for forming a pharmaceutically acceptable salt or —$CH_2$—O—C(═O)—$R^{3b}$ or —CHMe—O—C(═O)—$R^{3b}$ or —$CMe_2$-O—C(═O)—$R^{3b}$ or —$CH_2$—O—C(═O)—O—$R^{3b}$ or —CHMe—O—C(═O)—O—$R^{3b}$ or —$CMe_2$-O—C(═O)—O—$R^{3b}$.

$R^{3b}$ represents an alkyl group having 1 to 11 carbon atoms, which is linear, branched, cyclic or a combination thereof, which $R^{3b}$ group may optionally be substituted by one or more groups independently selected from —OH, and —O—$C_{1-6}$-alkyl;

$R^4$ represents H, $C_{1-4}$-alkyl; and $R^5$ represents H, $C_{1-4}$-alkyl, $C_{1-4}$-alkylene-$OR^3$.

9. Compound according to item 6, wherein the compound is selected from the group of compounds represented by general formula VI

VI

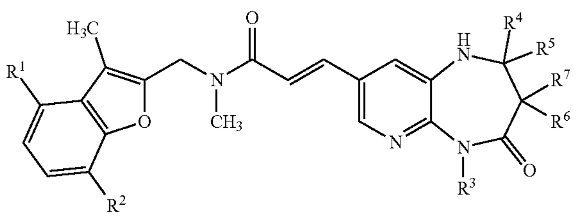

wherein $R^1$, $R^2$, $R^3$, $R^4$, $R^5$, $R^6$ and $R^7$ have the same meanings as specified in item 1, 2 or 3 above.

10. Compound according to item 9, wherein $R^1$ represents H, $NH_2$;

$R^2$ represents H;

$R^3$ represents a group selected from H, —$PO_3R^{3a}{}_2$, —$CH_2$—$OPO_3R^{3a}{}_2$ and —$CH_2$—O—C(═O)—$R^{3b}$.

$R^{3a}$ represents a hydrogen atom or a cation suitable for forming a pharmaceutically acceptable salt or —$CH_2$—O—C(═O)—$R^{3b}$ or —CHMe—O—C(═O)—$R^{3b}$ or —$CMe_2$-O—C(═O)—$R^{3b}$ or —$CH_2$—O—C(═O)—O—$R^{3b}$ or —CHMe—O—C(═O)—O—$R^{3b}$ or —$CMe_2$-O—C(═O)—O—$R^{3b}$.

$R^{3b}$ represents an alkyl group having 1 to 11 carbon atoms, which is linear, branched, cyclic or a combination thereof, which $R^{3b}$ group may optionally be substituted by one or more groups independently selected from —OH, and —O—$C_{1-6}$-alkyl;

$R^4$ represents H, $C_{1-4}$-alkyl; and $R^5$ represents H, $C_{1-4}$-alkyl, $C_{1-4}$-alkylene-$OR^3$;

$R^6$ represents H, $C_{1-4}$-alkyl, OH, —$OPO_3R^{3a}{}_2$; and $R^7$ represents H, $C_{1-4}$-alkyl, $C_{1-4}$-alkylene-OH, $C_{1-4}$-alkylene-$OR^3$, wherein $R^3$ is as specified above, $C_{1-4}$-alkylene-F.

11. Compound according to item 6, wherein the compound is selected from the group of compounds represented by general formula VII

VII

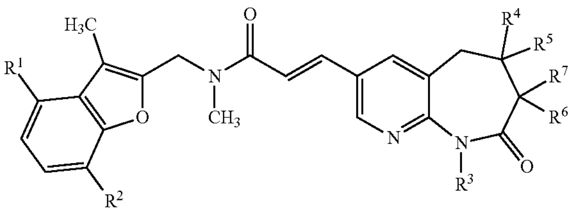

wherein $R^1$, $R^2$, $R^3$, $R^6$ and $R^7$ have the same meanings as specified in item 1, 2 or 3 above.

12. Compound according to item 11, wherein $R^1$ represents H, $NH_2$;

$R^2$ represents H;

$R^3$ represents a group selected from H, —$PO_3R^{3a}{}_2$, —$CH_2$—$OPO_3R^{3a}{}_2$ and —$CH_2$—O—C(═O)—$R^{31}$.

$R^{3a}$ represents a hydrogen atom or a cation suitable for forming a pharmaceutically acceptable salt or —$CH_2$—O—C(═O)—$R^{3b}$ or —CHMe—O—C(═O)—$R^{3b}$ or —$CMe_2$-O—C(═O)—$R^{3b}$ or —$CH_2$—O—C(═O)—O—$R^{3b}$ or —CHMe—O—C(═O)—O—$R^{3b}$ or —$CMe_2$-O—C(═O)—O—$R^{3b}$.

$R^{3b}$ represents an alkyl group having 1 to 11 carbon atoms, which is linear, branched, cyclic or a combination thereof, which $R^{3b}$ group may optionally be substituted by one or more groups independently selected from —OH, and —O—$C_{1-6}$-alkyl;

$R^4$ represents H, $C_{1-4}$-alkyl; and $R^5$ represents H, $C_{1-4}$-alkyl, $C_{1-4}$-alkylene-$OR^3$;

$R^6$ represents H, $C_{1-4}$-alkyl, OH, —$OPO_3R^{3a}{}_2$; and $R^7$ represents H, $C_{1-4}$-alkyl, $C_{1-4}$-alkylene-OH, $C_{1-4}$-alkylene-$OR^3$, wherein $R^3$ is as specified above, $C_{1-4}$-alkylene-F.

13. Compound according to item 4, wherein the compound is selected from the group of compounds represented by general formula VIII

VIII

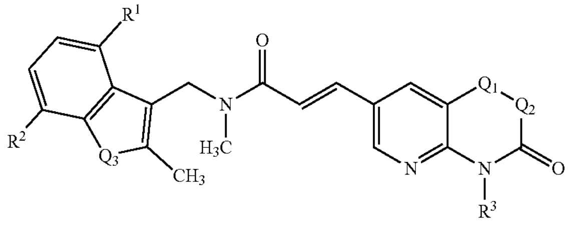

wherein $R^1$, $R^2$, $R^3$, $Q_1$, $Q_2$, $Q_3$ have the same meanings as specified in item 1, 2 or 3 above.

14. Compound according to item 13, wherein the compound is selected from the group of compounds represented by general formula IX

IX

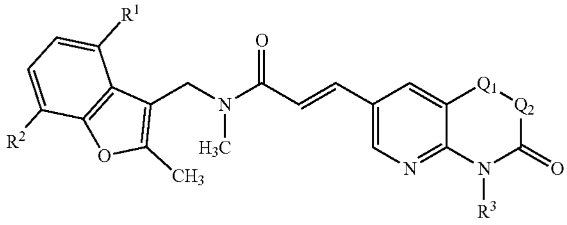

wherein $R^1$, $R^2$, $R^3$, $Q_1$, $Q_2$ have the same meanings as specified in item 1, 2 or 3 above.

15. Compound according to item 14, wherein the compound is selected from the group of compounds represented by general formula Xa and Xb Xa

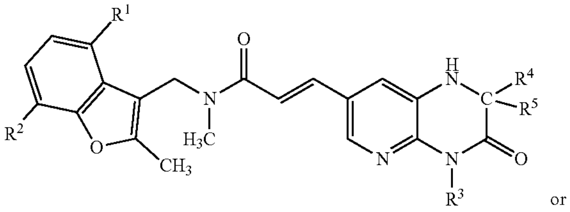

or

Xb

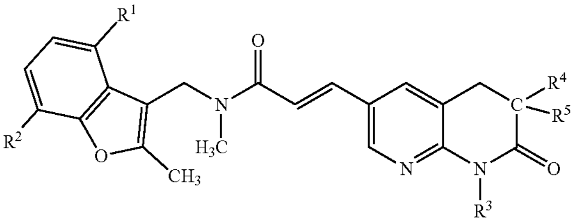

wherein $R^1$, $R^2$, $R^3$, $R^4$ and $R^5$ have the same meanings as specified in item 1 above.

16. Compound according to item 15, wherein $R^1$ represents H;

$R^2$ represents a group selected from H, —O—$Ar^1$, —O-$Het^1$, —$NH_2$, wherein $Ar^1$ represents a phenyl group that may optionally be substituted by one or more groups individually selected from —CN, —O—$C_{1-4}$-alkyl, or wherein the phenyl group may carry two substituent groups at adjacent ring atoms such that these adjacent substituent groups may be bonded together to form a 5-membered heterocycle having one or two heteroatoms individually selected from N and O, wherein $Het^1$ represents an aromatic heterocycle with 5 or 6 ring atoms including 1 or 2 heteroatoms individually selected from N, S and O, or a non-aromatic partially or fully saturated heterocycle with 6 ring atoms including 1 heteroatom selected from N, S and O, which $Het^1$ group may optionally be substituted by one or more groups individually selected from —$C_{1-4}$-alkyl, —O—$C_{1-4}$-alkyl, —CN;

$R^3$ represents H, —$CH_2$—$OPO_3R^{3a}{}_2$ wherein $R^{3a}$ represents a hydrogen atom or a cation suitable for forming a pharmaceutically acceptable salt;

$R^4$ represents H, $C_{1-4}$-alkyl, $C_{1-4}$-alkylene-F; and $R^5$ represents H, $C_{1-4}$-alkyl, $C_{1-4}$-alkylene-OH or $C_{1-4}$-alkylene-$OR^3$, wherein $R^3$ is as specified above.

17. Compound according to item 14, wherein the compound is selected from the group of compounds represented by general formula XI

XI

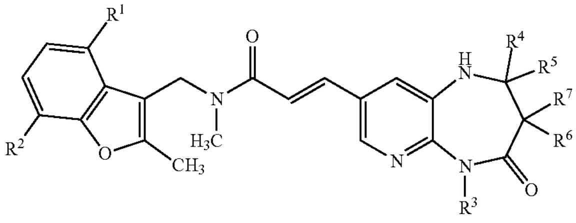

wherein $R^1$, $R^2$, $R^3$, $R^4$, $R^5$, $R^6$ and $R^7$ have the same meanings as specified in item 1, 2 or 3 above.

18. Compound according to item 17, wherein $R^1$ represents H;

$R^2$ represents a group selected from H, —O—$Ar^1$, —O-$Het^1$, —$NH_2$, wherein $Ar^1$ represents a phenyl group that may optionally be substituted by one or more groups individually selected from —CN, —O—$C_{1-4}$-alkyl, or wherein the phenyl group may carry two substituent groups at adjacent ring atoms such that these adjacent substituent groups may be bonded together to form a 5-membered heterocycle having one or two heteroatoms individually selected from N and O, wherein $Het^1$ represents an aromatic heterocycle with 5 or 6 ring atoms including 1 or 2 heteroatoms individually selected from N, S and O, or a non-aromatic partially or fully saturated heterocycle with 6 ring atoms including 1 heteroatom selected from N, S and O, which $Het^1$ group may optionally be substituted by one or more groups individually selected from —$C_{1-4}$-alkyl, —O—$C_{1-4}$-alkyl, —CN;

$R^3$ represents a group selected from H, —$PO_3R^{3a}{}_2$, —$CH_2$—$OPO_3R^{3a}{}_2$ and —$CH_2$—O—C(═O)—$R^{3b}$.

$R^{3a}$ represents a hydrogen atom or a cation suitable for forming a pharmaceutically acceptable salt or —$CH_2$—O—C(═O)—$R^{3b}$ or —CHMe—O—C(═O)—$R^{3b}$ or —$CMe_2$-O—C(═O)—$R^{3b}$ or —$CH_2$—O—C(═O)—O—$R^{3b}$ or —CHMe—O—C(═O)—O—$R^{3b}$ or —$CMe_2$-O—C(═O)—O—$R^{3b}$.

$R^{3b}$ represents an alkyl group having 1 to 11 carbon atoms, which is linear, branched, cyclic or a combination thereof, which $R^{3b}$ group may optionally be substituted by one or more groups independently selected from —OH, and —O—$C_{1-6}$-alkyl;

$R^4$ represents H, $C_{1-4}$-alkyl; and $R^6$ represents H, $C_{1-4}$-alkyl, $C_{1-4}$-alkylene-$OR^3$.

$R^6$ represents H, $C_{1-4}$-alkyl, OH, —$OPO_3R^{3a}{}_2$; and $R^7$ represents H, $C_{1-4}$-alkyl, $C_{1-4}$-alkylene-OH, $C_{1-4}$-alkylene-$OR^3$, wherein $R^3$ is as specified above, $C_{1-4}$-alkylene-F.

19. Compound according to item 14, wherein the compound is selected from the group of compounds represented by general formula XII

XII

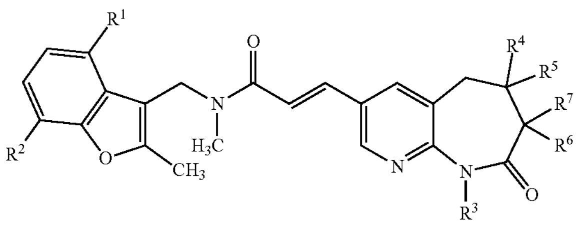

wherein $R^1$, $R^2$, $R^3$, $R^6$ and $R^7$ have the same meanings as specified in item 1, 2 or 3 above.

20. Compound according to item 19, wherein $R^1$ represents H;

$R^2$ represents a group selected from H, —O—$Ar^1$, —O-$Het^1$, —$NH_2$, wherein $Ar^1$ represents a phenyl group that may optionally be substituted by one or more groups individually selected from —CN, —O—$C_{1-4}$-alkyl, or wherein the phenyl group may carry two substituent groups at adjacent ring atoms such that these adjacent substituent groups may be bonded together to form a 5-membered heterocycle having one or two heteroatoms individually selected from N and O, wherein $Het^1$ represents an aromatic heterocycle with 5 or 6 ring atoms including 1 or 2 heteroatoms individually selected from N, S and O, or a non-aromatic partially or fully saturated heterocycle with 6 ring atoms including 1 heteroatom selected from N, S and O, which $Het^1$ group may optionally be substituted by one or more groups individually selected from —$C_{1-4}$-alkyl, —O—$C_{1-4}$-alkyl, —CN;

$R^3$ represents a group selected from H, —$PO_3R^{3a}{}_2$, —$CH_2$—$OPO_3R^{3a}{}_2$ and —$CH_2$—O—C(═O)—$R^{3b}$.

$R^{3a}$ represents a hydrogen atom or a cation suitable for forming a pharmaceutically acceptable salt or —$CH_2$—O—C(═O)—$R^{3b}$ or —CHMe—O—C(═O)—$R^{3b}$ or —$CMe_2$-O—C(═O)—$R^{3b}$ or —$CH_2$—O—C(═O)—O—$R^{3b}$ or —CHMe—O—C(═O)—O—$R^{3b}$ or —$CMe_2$-O—C(═O)—O—$R^{3b}$.

$R^{3b}$ represents an alkyl group having 1 to 11 carbon atoms, which is linear, branched, cyclic or a combination thereof, which $R^{3b}$ group may optionally be substituted by one or more groups independently selected from —OH, and —O—$C_{1-6}$-alkyl;

$R^4$ represents H, $C_{1-4}$-alkyl; and $R^6$ represents H, $C_{1-4}$-alkyl, $C_{1-4}$-alkylene-$OR^3$.

$R^6$ represents H, $C_{1-4}$-alkyl, OH, —$OPO_3R^{3a}{}_2$; and $R^7$ represents H, $C_{1-4}$-alkyl, $C_{1-4}$-alkylene-OH, $C_{1-4}$-alkylene-$OR^3$, wherein $R^3$ is as specified above, $C_{1-4}$-alkylene-F.

21. Compound according to item 1, wherein the compound is selected from the group of compounds represented by general formula XIII

XIII

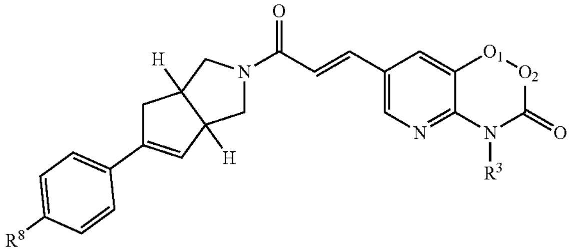

wherein $R^3$, $R^8$, $Q_1$, $Q_2$ have the same meanings as specified in item 1, 2 or 3 above.

22. Compound according to item 21, wherein the compound is selected from the group of compounds represented by general formula XIVa or XIVb XIVa

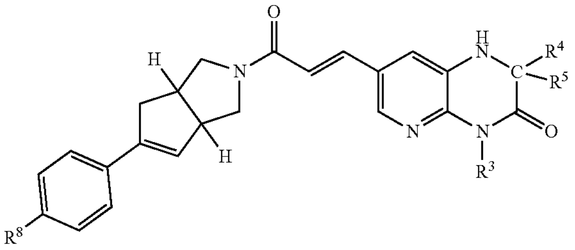

wherein $R^3$, $R^4$, $R^5$, $R^8$ have the same meanings as specified in item 1 above;

or

XIVb

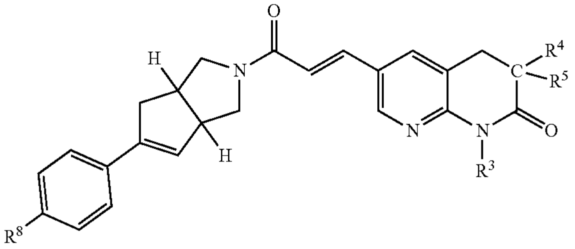

wherein $R^3$, $R^4$, $R^5$, $R^8$ have the same meanings as specified for general formula I above.

23. Compound according to item 22, wherein $R^3$ represents H, —$CH_2$—$OPO_3R^{3a}{}_2$ wherein $R^{3a}$ represents a hydrogen atom or a cation suitable for forming a pharmaceutically acceptable salt;

$R^4$ represents H, $C_{1-4}$-alkyl, $C_{1-4}$-alkylene-F;

$R^5$ represents H, $C_{1-4}$-alkyl, $C_{1-4}$-alkylene-OH or $C_{1-4}$-alkylene-$OR^3$, wherein $R^3$ is as specified above; and $R^8$ represents a group selected from —O—$Ar^2$ and —O-$Het^2$;

wherein $Ar^2$ represents a phenyl group that may optionally be substituted by one or more groups individually selected from —CN, —O—$C_{1-4}$-alkyl or wherein the phenyl group may carry two substituent groups at adjacent ring atoms such that these adjacent substituent groups may be bonded together to form a 5-membered heterocycle having one or two heteroatoms individually selected from N, S and O, wherein said heterocycle may optionally carry one or two substituents selected from oxo, F, —O—$C_{1-4}$-alkyl, $C_{1-4}$-alkyl, CN;

and wherein $Het^2$ represents an aromatic heterocycle with 5 or 6 ring atoms including 1 or 2 heteroatoms individually selected from N, S and O, which may optionally be substituted by one or more groups individually selected from —O—$C_{1-4}$-alkyl, —CN, F, $C_{1-4}$-alkyl.

24. Compound according to item 21, wherein the compound is selected from the group of compounds represented by general formula XV

XV

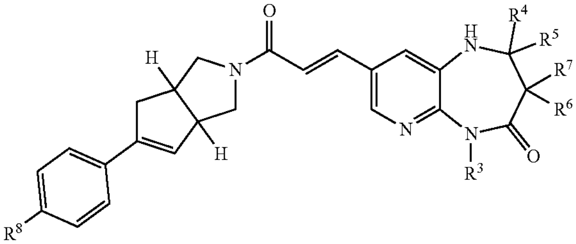

wherein $R^3$, $R^4$, $R^5$, $R^6$, $R^7$, $R^8$ have the same meanings as specified in item 1, 2 or 3 above.

25. Compound according to item 23, wherein $R^3$ represents a group selected from H, —$PO_3R^{3a}_2$, —$CH_2$—$OPO_3R^{3a}_2$ and —$CH_2$—O—C(═O)—$R^{3b}$.

$R^{3a}$ represents a hydrogen atom or a cation suitable for forming a pharmaceutically acceptable salt or —$CH_2$—O—C(═O)—$R^{3b}$ or —CHMe—O—C(═O)—$R^{3b}$ or —$CMe_2$-O—C(═O)—$R^{3b}$ or —$CH_2$—O—C(═O)—O—$R^{3b}$ or —CHMe—O—C(═O)—O—$R^{3b}$ or —$CMe_2$-O—C(═O)—O—$R^{3b}$.

$R^{3b}$ represents an alkyl group having 1 to 11 carbon atoms, which is linear, branched, cyclic or a combination thereof, which $R^{3b}$ group may optionally be substituted by one or more groups independently selected from —OH, and —O—$C_{1-6}$-alkyl;

$R^4$ represents H, $C_{1-4}$-alkyl; and $R^5$ represents H, $C_{1-4}$-alkyl, $C_{1-4}$-alkylene-$OR^3$;

$R^6$ represents H, $C_{1-4}$-alkyl, OH, —$OPO_3R^{3a}_2$; and $R^7$ represents H, $C_{1-4}$-alkyl, $C_{1-4}$-alkylene-OH, $C_{1-4}$-alkylene-$OR^3$, wherein $R^3$ is as specified above, $C_{1-4}$-alkylene-F;

and $R^8$ represents a group selected from —O—$Ar^2$ and —O-$Het^2$, wherein $Ar^2$ represents a phenyl group that may optionally be substituted by one or more groups individually selected from —CN, —O—$C_{1-4}$-alkyl or wherein the phenyl group may carry two substituent groups at adjacent ring atoms such that these adjacent substituent groups may be bonded together to form a 5-membered heterocycle having one or two heteroatoms individually selected from N, S and O, wherein said heterocycle may optionally carry one or two substituents selected from oxo, F, —O—$C_{1-4}$-alkyl, $C_{1-4}$-alkyl, CN and wherein $Het^2$ represents an aromatic heterocycle with 5 or 6 ring atoms including 1 or 2 heteroatoms individually selected from N, S and O, which may optionally be substituted by one or more groups individually selected from —O—$C_{1-4}$-alkyl, —CN, F, $C_{1-4}$-alkyl.

26. Compound according to item 21, wherein the compound is selected from the group of compounds represented by general formula XVI

XVI

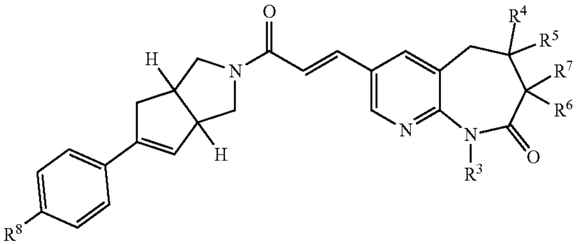

wherein $R^3$, $R^4$, $R^5$, $R^6$, $R^7$, $R^8$ have the same meanings as specified in item 1, 2 or 3 above.

27. Compound according to item 26, wherein $R^3$ represents a group selected from H, —$PO_3R^{3a}_2$, —$CH_2$—$OPO_3R^{3a}_2$ and —$CH_2$—O—C(═O)—$R^{3b}$.

$R^{3a}$ represents a hydrogen atom or a cation suitable for forming a pharmaceutically acceptable salt or —$CH_2$—O—C(═O)—$R^{3b}$ or —CHMe—O—C(═O)—$R^{3b}$ or —$CMe_2$-O—C(═O)—$R^{3b}$ or —$CH_2$—O—C(═O)—O—$R^{3b}$ or —CHMe—O—C(═O)—O—$R^{3b}$ or —$CMe_2$-O—C(═O)—O—$R^{3b}$.

$R^{3b}$ represents an alkyl group having 1 to 11 carbon atoms, which is linear, branched, cyclic or a combination thereof, which $R^{3b}$ group may optionally be substituted by one or more groups independently selected from —OH, and —O—$C_{1-6}$-alkyl;

$R^4$ represents H, $C_{1-4}$-alkyl; and $R^5$ represents H, $C_{1-4}$-alkyl, $C_{1-4}$-alkylene-$OR^3$;

$R^6$ represents H, $C_{1-4}$-alkyl, OH, —$OPO_3R^{3a}_2$; and $R^7$ represents H, $C_{1-4}$-alkyl, $C_{1-4}$-alkylene-OH, $C_{1-4}$-alkylene-$OR^3$, wherein $R^3$ is as specified above, $C_{1-4}$-alkylene-F;

$R^8$ represents a group selected from —O—$Ar^2$ and —O-$Het^2$, wherein $Ar^2$ represents a phenyl group that may optionally be substituted by one or more groups individually selected from —CN, —O—$C_{1-4}$-alkyl or wherein the phenyl group may carry two substituent groups at adjacent ring atoms such that these adjacent substituent groups may be bonded together to form a 5-membered heterocycle having one or two heteroatoms selected N, S and O, wherein said heterocycle may optionally carry one or two substituents individually selected from oxo, F, —O—$C_{1-4}$-alkyl, $C_{1-4}$-alkyl, CN and wherein $Het^2$ represents an aromatic heterocycle with 5 or 6 ring atoms including 1 or 2 heteroatoms individually selected from N, S and O, which may optionally be substituted by one or more groups individually selected from —O—$C_{1-4}$-alkyl, —CN, F, $C_{1-4}$-alkyl.

28. Pharmaceutical composition comprising the compound of anyone of items 1 to 27.

29. Compound according to anyone of items 1 to 27 or pharmaceutical composition according to item 26 for use in the treatment of a bacterial infection selected from infections by *N. gonorrhoeae, Bacillus* Spp., in particular *Bacillus cereus, Bacillus coagulans, Bacillus megaterium, Bacillus subtilis, Bacillus anthracis, Bartonella* Spp., *Brucella* Spp, in particular *Brucella abortus, Brucella melitensis, Campylobacter* Spp., in particular *Campylobacter jejuni, Chlamydia trachomatis, Enterococcus faecalis, Enterococcus faecium, Legionella pneumophila, Listeria* Spp., in particular *Listeria monocytogenes, Proteus mirabilis, Providencia stuartii Rickettsia* Spp., in particular *Rickettsia rickettsii, Bordetella pertussis, Bordetella parapertussis, Burkholderia* Spp., in particular *Burkholderia pseudomallei, Burkholderia mallei, Burkholderia cenocepacia, Haemophilus influenza, Kingella kingae, Moraxella catarrhalis, Streptomyces* Spp., *Nocardioides* Spp., *Frankia* Spp., *Propionibacterium acnes, Mycobacterium* Spp., in particular *Mycobacterium smegmatis, Mycobacterium abscessus, Mycobacterium leprae, Mycobacterium tuberculosis, Mycobacterium avium* and combinations thereof, preferably infections by *N. gonorrhoeae* alone or in combination with *Chlamydia trachomatis.*

31. Method of manufacturing a compound according to anyone of items 1 to 27, comprising the step of coupling a precursor compound of formula XVII

XVII

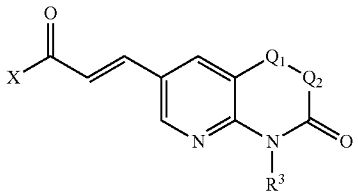

wherein $Q_1$, $Q_2$ and $R^3$ have the same meanings as specified in item 1, 2 or 3 above, and wherein X represents a leaving group, with an amine compound of formula $H\text{-}NA_1A_2$, wherein $A_1$ and $A_2$ have the same meanings as specified in item 1 above.

32. Method of manufacturing a compound according to anyone of items 1 to 27, comprising the step of coupling a precursor compound of formula XVIII

XVIII

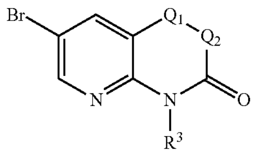

wherein $R^3$, $Q_1$ and $Q_2$ have the same meanings as specified in item 1, 2 or 3 above, with a precursor compound of formula XIX

XIX

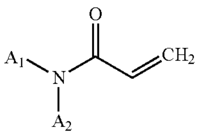

wherein $A_1$ and $A_2$ have the same meanings as specified in item 1 above.

Definitions

The following definitions are provided to assist the reader. Unless otherwise defined, all terms of art, notations, and other scientific or medical terms or terminology used herein are intended to have the meanings commonly understood by those of skill in the chemical and medical arts. In some cases, terms with commonly understood meanings are defined herein for clarity and/or for ready reference, and the inclusion of such definitions herein should not be construed as representing a substantial difference over the definition of the term as generally understood in the art.

In some embodiments, the term "about" refers to a deviation of ±10% from the recited value. When the word "about" is used herein in reference to a number, it should be understood that still another embodiment of the invention includes that number not modified by the presence of the word "about"

"Administering" or "administration of" a drug to a patient (and grammatical equivalents of this phrase) refers to direct administration, which may be administration to a patient by a medical professional or may be self-administration, and/or indirect administration, which may be the act of prescribing a drug. E.g., a physician who instructs a patient to self-administer a drug or provides a patient with a prescription for a drug is administering the drug to the patient.

"Dose" and "dosage" refer to a specific amount of active or therapeutic agents for administration. Such amounts are included in a "dosage form," which refers to physically discrete units suitable as unitary dosages for human subjects and other mammals, each unit containing a predetermined quantity of active agent calculated to produce the desired onset, tolerability, and therapeutic effects, in association with one or more suitable pharmaceutical excipients such as carriers.

The terms "treatment" and "therapy", as used in the present application, refer to a set of hygienic, pharmacological, surgical and/or physical means used with the intent to cure and/or alleviate a disease and/or symptoms with the goal of remediating the health problem. The terms "treatment" and "therapy" include preventive and curative methods, since both are directed to the maintenance and/or reestablishment of the health of an individual or animal. Regardless of the origin of the symptoms, disease and disability, the administration of a suitable medicament to alleviate and/or cure a health problem should be interpreted as a form of treatment or therapy within the context of this application.

"Unit dosage form" as used herein refers to a physically discrete unit of therapeutic formulation appropriate for the subject to be treated. It will be understood, however, that the total daily usage of the compositions of the present invention will be decided by the attending physician within the scope of sound medical judgment. The specific effective dose level for any particular subject or organism will depend upon a variety of factors including the disorder being treated and the severity of the disorder; activity of specific active agent employed; specific composition employed; age, body weight, general health, sex and diet of the subject; time of administration, and rate of excretion of the specific active agent employed; duration of the treatment; drugs and/or additional therapies used in combination or coincidental with specific compound(s) employed, and like factors well known in the medical arts.

The articles "a" and "an" are used herein to refer to one or to more than one (i.e., to at least one) of the grammatical object of the article. By way of example, "an element" means one element or more than one element.

The term "including" is used to mean "including but not limited to". "Including" and "including but not limited to" are used interchangeably. The term "comprising" is used to have the same meaning as "including". The term "consisting of" is used to indicate that the listed element(s) is/are present but no other unmentioned elements. The term "comprising" is used to include the meaning of "consisting of" as a preferred embodiment.

The term "FabI" is art-recognized and refers to the bacterial enzyme believed to function as an enoyl-acyl carrier protein (ACP) reductase in the final step of the four reactions involved in each cycle of bacterial fatty acid biosynthesis. This enzyme is believed to be widely distributed in bacteria and plants.

The term "enzyme inhibitor" refers to any compound that prevents an enzyme from effectively carrying out its respective biochemical roles. Therefore a "FabI inhibitor" is any compound that inhibits FabI from carrying out its biochemical role. The amount of inhibition of the enzyme by any such compound will vary and is described herein and elsewhere.

The term "antibiotic agent" or "antibacterial agent" shall mean any drug that is useful in treating, preventing, or otherwise reducing the severity of any bacterial disorder, or any complications thereof, including any of the conditions, disease, or complications arising therefrom and/or described herein. Antibiotic agents include, for example, cephalosporins, quinolones and fluoroquinolones, penicillins and beta lactamase inhibitors, carbapenems, monobactams, macrolides and lincosamides, glycopeptides, rifampin, oxazolidinones, tetracyclines, aminoglycosides, streptogramins, sulfonamides, and the like. Other antibiotic or antibacterial agents are disclosed herein, and are known to those of skill in the art. In certain embodiments, the term "antibiotic agent" does not include an agent that is a FabI inhibitor, so that the combinations of the present invention in certain instances will include one agent that is a FabI inhibitor and another agent that is not.

The term "drug" as used herein refers to any substance falling within at least one of the definitions given in Article 1, Items 2(a), 2(b) or 3a. of Directive 2001/83/EC of Nov. 6, 2001 in the version of Nov. 16, 2012 or in Article 1, Items 2(a) or 2(b) of Directive 2001/82/EC of Nov. 6, 2001 in the version of Aug. 7, 2009 and in Article 2 of Regulation (EC) No. 726/2004 of Mar. 31, 2004.

The term "illness" as used herein refers to any illness caused by or related to infection by an organism.

The term "bacterial illness" as used herein refers to any illness caused by or related to infection by bacteria.

The term "cis" is art-recognized and refers to the arrangement of two atoms or groups around a double bond such that the atoms or groups are on the same side of the double bond. Cis configurations are often labeled as (Z) configurations.

The term "trans" is art-recognized and refers to the arrangement of two atoms or groups around a double bond such that the atoms or groups are on the opposite sides of a double bond. Trans configurations are often labeled as (E) configurations.

The term "therapeutic effect" is art-recognized and refers to a local or systemic effect in animals, particularly mammals, and more particularly humans caused by a pharmacologically active substance. The term thus means any measurable effect in the diagnosis, cure, mitigation, treatment or prevention of disease or in the enhancement of desirable physical or mental development and/or conditions in an animal or human. The phrase "therapeutically-effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art. For example, certain compositions of the present invention may be administered in a sufficient amount to produce a therapeutic effect at a reasonable benefit/risk ratio applicable to such treatment.

The term "chiral" is art-recognized and refers to molecules which have the property of non-superimposability of the mirror image partner, while the term "achiral" refers to molecules which are superimposable on their mirror image partner. A "prochiral molecule" is a molecule which has the potential to be converted to a chiral molecule in a particular process.

The compounds of the disclosure may contain one or more chiral centers and/or double bonds and, therefore, exist as geometric isomers, enantiomers or diastereomers. The enantiomer and diastereomers may be designated by the symbols "(+)" "(−)", "R" or "S," depending on the configuration of substituents around the stereogenic carbon atom, but the skilled artisan will recognize that a structure may denote one or more chiral centers implicitly. Mixtures of enantiomers or diastereomers may be designated "(±)" in nomenclature, but the skilled artisan will recognize that a structure may denote a chiral center implicitly. Geometric isomers, resulting from the arrangement of substituents around a carbon-carbon double bond or arrangement of substituents around a cycloalkyl or heterocyclic ring, can also exist in the compounds of the present invention.

The symbol  denotes a bond that may be a single, double or triple bond as described herein.

Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans" or "Z/E."

The term "stereoisomers" when used herein consist of all geometric isomers, enantiomers or diastereomers. The present invention encompasses various stereoisomers of these compounds and mixtures thereof. Conformational isomers and rotamers of disclosed compounds are also contemplated.

The term "ED50" is art-recognized. In certain embodiments, ED50 means the effective dose of a drug which produces 50% of its maximum response or effect, or alternatively, the dose which produces a pre-determined response in 50% of test subjects or preparations. The term "LD50" is art-recognized. In certain embodiments, LD50 means the dose of a drug which is lethal in 50% of test subjects. The term "therapeutic index" is an art-recognized term that refers to the therapeutic index of a drug, defined as ED50/LD50.

The term "Ki" is art-recognized and refers to the dissociation constant of the enzyme-inhibitor complex.

The term "antimicrobial" is art-recognized and refers to the ability of the compounds disclosed herein to prevent, inhibit or destroy the growth of microbes such as bacteria, fungi, protozoa and viruses.

The term "antibacterial" is art-recognized and refers to the ability of the compounds disclosed herein to prevent, inhibit or destroy the growth of microbes of bacteria.

The term "microbe" is art-recognized and refers to a microscopic organism. In certain embodiments the term microbe is applied to bacteria. In other embodiments the term refers to pathogenic forms of a microscopic organism.

The term "alkyl" as used herein refers to a saturated straight or branched hydrocarbon, such as a straight or branched group of 1-8 or 1-6 carbon atoms referred to herein as $C_1$-$C_8$alkyl, or $C_1$-$C_6$alkyl, respectively. The term "lower alkyl" as used herein specifically refers to a saturated straight or branched hydrocarbon, such as a straight or branched group of 1-4 or 1-3 carbon atoms, referred to herein as $C_1$-$C_4$alkyl, and $C_1$-$C_3$alkyl, respectively. Exemplary alkyl groups and lower alkyl groups include, but are not limited to, methyl, ethyl, propyl, isopropyl, 2-methyl-1-propyl, 2-methyl-2-propyl, 2-methyl-1-butyl, 3-methyl-1-butyl, 3-methyl-2-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, and hexyl.

Moreover, the term "alkyl" (or "lower alkyl") includes "substituted alkyls", i.e. it should be understood as optionally carrying one or more substituents at one or more positions. That is, it refers also to alkyl moieties having one or more (e.g. two, three, four, five, six, etc.) substituents, each replacing a hydrogen on a carbon of the hydrocarbon backbone. Such substituents may include, for example, a hydroxyl, a carbonyl group (wherein the carbonyl group carries a hydrogen atom, an alkyl group or another group as defined in this paragraph, such as to yield a carboxyl, an alkoxycarbonyl, a formyl, or an acyl group), a thiocarbonyl-containing group (wherein the carbonyl group carries a hydrogen atom, an alkyl group or another group as defined in this paragraph, such as to yield a thioester, a thioacetate, or a thioformate), an alkoxyl, a phosphoryl, a phosphonate, a phosphinate, a phosphate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, a cycloalkyl, a heterocycle or an aromatic or heteroaromatic moiety. In all instances, wherein the above-mentioned groups have more than one valency, the further free valency can be saturated by a hydrogen atom, an alkyl group, a cycloalkyl group, a heterocyclic group, an aryl group or a heteroaryl group. It will further be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate, phosphinate and phosphate), sulfonyl (including sulfate, sulfonamido, sulfamoyl and sulfonate), and silyl groups, as well as ethers, alkylthios, carbonyls (including ketones, aldehydes, carboxylates, and esters), nitrile and isonitrile. For the avoidance of doubt, an alkyl group carrying another alkyl group should not be regarded as an alkyl group substituted with another alkyl group, but as a single branched alkyl group.

The term "alkenyl" is art-recognized and refers to a group corresponding to the alkyl group defined above, but carrying one or more carbon-carbon double bonds. Of course, the total number of double bonds is restricted by the number of carbon atoms in the alkenyl group and in order to allow for at least one double bond, the alkenyl group must have at least two carbon atoms. Except for this difference, the definitions and characterizations given for the alkyl group above apply equally to the alkenyl group.

The term "alkynyl" is art-recognized and refers to a group corresponding to the alkyl group defined above, but carrying one or more carbon-carbon triple bonds. Of course, the total number of double bonds is restricted by the number of carbon atoms in the alkenyl group and in order to allow for at least one triple bond, the alkynyl group must have at least two carbon atoms. Except for this difference, the definitions and characterizations given for the alkyl group above apply equally to the alkynyl group.

The term "aryl" is art-recognized and refers to 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryl" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, phosphate, carbonyl, carboxyl, silyl, ether, alkylthio, sulfonyl, sulfonamido, ketone, aldehyde, ester, heterocyclyl, aromatic or heteroaromatic moieties, $—CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The term "aralkyl" or "arylalkyl" is art-recognized and refers to an alkyl group substituted with an aryl group (e.g., an aromatic or heteroaromatic group).

The term "carbocycle" is art-recognized and refers to an aromatic or non-aromatic ring in which each atom of the ring is carbon.

The term "cycloalkyl" as used herein refers to a monocyclic saturated or partically unsatured alkyl or alkenyl group of for example 3-6, or 4-6 carbons, referred to herein, e.g., as "$C_{3-6}$cycloalkyl" or "$C_{4-6}$cycloalkyl," and derived from a cycloalkane. Exemplary cycloalkyl groups include, but are not limited to, cyclohexane, cyclohexene, cyclopentane, cyclobutane, cyclopropane or cyclopentene. Said cycloalkyl group may be substituted at one or more positions with one or more substituents as described above.

The terms "halo" or "halogen" as used herein refer to F, Cl, Br, or I. "Halide" designates the corresponding anion of the halogens, and "pseudohalide" has the definition set forth on page 560 of "Advanced Inorganic Chemistry" by Cotton and Wilkinson, Interscience Publishers, 1966.

The term "amino" as used herein refers to any group of the general structure —$NR_aR_b$, wherein, unless specified otherwise, $R_a$ and $R_b$ are independently selected from the group consisting of H, alkyl, cycloalkyl, alkenyl, alkynyl, aryl, heteroaryl, heterocyclic groups, as well as any other substituent group listed above with respect to the scope of substituted alkyl groups, with the exception of carbonyl groups, thiocarbonyl groups, imine groups, and substituent groups in which attachment to the remaining molecule is via a heteroatom selected from N, O, S and P. Alternatively, $R_a$ and $R_b$ may represent hydrocarbon groups that are linked to form a heterocycle together with the nitrogen atom to which they are attached.

The term "heteroaryl" as used herein refers to a monocyclic aromatic 4-6 membered ring system containing one or more heteroatoms, for example one to three heteroatoms, which may be the same or different, such as nitrogen, oxygen, and sulfur. Where possible, said heteroaryl ring may be linked to the adjacent radical through carbon or nitrogen. Examples of heteroaryl rings include but are not limited to furan, benzofuran, thiophene, pyrrole, thiazole, oxazole, isothiazole, isoxazole, imidazole, pyrazole, triazole, pyridine, and pyrimidine. Said heteroaryl group may be substituted with one or more substituents as described for the aryl group above. The term "heteroaryl" also includes polycyclic ring systems having two or more cyclic rings in which two or more carbons or heteroatoms are common to two adjoining rings (the rings are "fused rings") wherein at least one of the rings is a heteroaryl as defined above whereas the other cyclic rings may be cycloalkyls, cycloalkenyls, cycloalkynyls, aromatic rings and/or saturated, unsaturated or aromatic heterocycles.

The term "heterocycle" as used herein refers to a monocyclic ring containing one or more heteroatoms, for example one to three heteroatoms, which may be the same or different, such as nitrogen, oxygen, and sulfur. The remaining ring members are formed by carbon atoms. The heterocycle typically has 4 to 8 ring members and preferably 5 or 6 ring members. Unless specified otherwise, a heterocycle may be aromatic, partially or fully saturated. Unless specified otherwise, it may or may not contain permissible substituents as specified herein.

The terms "hydroxy" and "hydroxyl" as used herein refer to the radical —OH.

The term "nitro" is art-recognized and refers to —NO2; the term "sulfhydryl" is art-recognized and refers to —SH; and the term "sulfonyl" is art-recognized and refers to —SO2-.

The definition of each expression, when it occurs more than once in any structure, is intended to be independent of its definition elsewhere in the same structure.

The terms "triflyl", "tosyl", "mesyl", and "nonaflyl" are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate, p-toluenesulfonate, methanesulfonate, and nonafluorobutanesulfonate functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations.

The term "prodrug" refers to a derivative of an active compound (drug) that undergoes a transformation under the conditions of use, such as within the body, to release the active drug. Prodrugs are frequently, but not necessarily, pharmacologically inactive until converted into the active drug.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above, e.g. in connection with substituted alkyls. The permissible substituents may be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. In this context, the term "permissible substituents" means any substituent that can be bonded to the core molecule without contravening general principles of chemical bond formation such as the maximum number of valence electrons for an atom of interest, and without making the compound so toxic for the patient that inacceptable toxicity is found even at the minimum dosage required for achieving a therapeutic effect.

For purposes of this invention, the chemical elements are identified in accordance with the Periodic Table of the Elements, CAS version, Handbook of Chemistry and Physics, 67th Ed., 1986-87, inside cover. Also for purposes of the disclosure, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds that may be substituted or unsubstituted.

The term "pharmaceutically-acceptable salts" is art-recognized and refers to the relatively non-toxic, inorganic and organic acid addition salts, or inorganic or organic base addition salts of compounds, including, for example, those contained in compositions of the present invention, and including those present in other approved drugs (wherein approval may be by any competent authority in the EU, USA, CA, JP, CN or KR). Pharmaceutically acceptable salts are meant to be encompassed by the present invention. Hence, all references to compounds of the invention are to be understood as references not only to the compounds as such, but also to pharmaceutically acceptable salts of the respective compounds. According to one aspect, the pharmaceutically acceptable salts may be selected from the salts acknowledged as pharmaceutically acceptable in the literature at the filing date, and in particular as described in G. S. Paulekuhn et al. in J. Med. Chem. 2007, 50, 6665-6672 and references cited therein. If the compound of the invention is an acidic compound, and in particular a prodrug containing a phosphate group, said compound of the invention may be provided in the form of pharmaceutically acceptable salts, wherein the compound forms the anion part and the counterion is selected from Na, K, Mg, Ca, or the protonated forms of the organic bases ethanolamine, meglumine, tromethamine (i.e. 2-amino-2-(hydroxymethyl)propane-1,3-diol), and deanol (i.e. 2-(dimethylamino)ethanol). The stoichiometry of the salts is not particularly restricted. For instance, salts may be formed with the phosphate prodrugs of the invention (having 2 acidic protons) in any stoichiometric ratio of from 0 to 2 equivalents. Generally, pharmaceutically acceptable salts are formed such that the net charge of the salt is zero, i.e. that the total number of positive charges equals the total number of negative charges.

The term "treating" includes any significant effect, e.g., lessening, reducing, modulating, or eliminating, that results in the improvement of the condition, disease, disorder and the like.

The term "prophylactic" or "therapeutic" treatment is art-recognized and refers to administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

A "patient," "subject" or "host" to be treated by the subject method may mean either a human or non-human animal. Non human animals include companion animals (e.g. cats, dogs) and animals raised for consumption (i.e. food animals), such as cows, pigs, chickens. Non-human animals are preferably mammals.

The term "mammal" is known in the art, and exemplary mammals include humans, primates, bovines, porcines, canines, felines, and rodents (e.g., mice and rats).

The term "bioavailable" is art-recognized and refers to a form of the subject disclosure that allows for it, or a portion of the amount administered, to be absorbed by, incorporated to, or otherwise physiologically available to a subject or patient to whom it is administered.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof from one organ, or portion of the body, to another organ, or portion of the body. Each carrier must be "acceptable" in the sense of being compatible with the subject composition and its components and not injurious to the patient. Some examples of materials which may serve as pharmaceutically acceptable carriers include: (1) sugars, such as dextrose, lactose, glucose and sucrose; (2) starches, such as corn starch and potato starch as well as starch derivatives such as cyclodextrins and modified cyclodextrins including preferably (2-hydroxypropyl)-β-cyclodextrin and sulfobutylether-β-cyclodextrin; (3) cellulose, and its derivatives, such as microcrystalline cellulose, sodium carboxymethyl cellulose, methyl cellulose, ethyl cellulose, hydroxypropylmethyl cellulose (HPMC), and cellulose acetate; (4) powdered tragacanth; (5) malt; (6) gelatin; (7) talc; (8) matrix-forming polymeric excipients such as polyvinyl pyrrolidine (PVP), e.g. PVP K30, acrylic polymers and co-polymers such as the different grades of Eudragit and preferably Eurdragit L100, hydroxypropylmethyl cellulose acetate succinate (HPMCAS), other copolymers such as polyethylene glycol-based copolymers like Soluplus; (9) excipients, such as cocoa butter and suppository waxes; (10) oils, such as peanut oil, cottonseed oil, safflower oil, sesame oil, olive oil, corn oil and soybean oil; (11) glycols, such as propylene glycol; (12) polyols, such as glycerin, sorbitol, mannitol and polyethylene glycol; (13) esters, such as ethyl oleate, glyceryl behenate and ethyl laurate; (14) agar; (15) buffering agents, such as magnesium hydroxide and aluminum hydroxide; (16) alginic acid; (17) pyrogen-free water; (18) isotonic saline; (19) Ringer's solution; (20) ethyl alcohol; (21) phosphate buffer solutions; and (22) other non-toxic compatible substances employed in pharmaceutical formulations. The disclosed excipients may serve more than one function. For example, fillers or binders may also be disintegrants, glidants, anti-adherents, lubricants, sweeteners and the like.

The term "solvent" is used herein to mean a liquid chemical substance that is capable of dissolving a significant quantity of another substance of interest, the "solute", to thereby generate a clear homogeneous solution. The term "significant quantity" is determined by the intended use of the solution in such a manner that the intended use must be possible by the dissolved quantity of the solute. For instance, if it is intended to administer a compound of the present invention in the form of a solution by injection, the solvent must be capable of dissolving the compound in such amounts, to make administration of a therapeutic dose possible.

Unless specified otherwise, all reactions described herein are carried out at reaction temperatures that yield the desired target compound and that provide a reasonable compromise between reaction rate and selectivity. Typical reaction temperatures for Pd-based coupling reactions and Fe-based cyclization reactions are 80° C. to 90° C. while removal of protecting groups is typically accomplished at a temperature of from 0° C. to room temperature (25° C.).

Unless specified otherwise, all characterizations of variable groups as being the same as specified for the compound of formula I, or the like, are to be understood such that the more specific meanings and combinations of meanings, as embodied by the formulae I to XVI, are also possible and even preferred.

Unless specified otherwise, the term "protective group" is used herein to characterize a group that is bonded to a functional group to prevent this functional group from participating in a contemplated chemical reaction. The protective group must be inert under the conditions of the contemplated chemical reaction, but it must be possible to remove the protective group from the compound such that no further transformations take place in other parts of the molecule. Suitable protective groups are described for each functional group in "Greene's Protective Groups in Organic Synthesis", Peter G. M. Wuts, Theodora W. Greene, John Wiley & Sons, 20 Dec. 2012.

Compounds of the Invention

The present invention provides compounds, which exhibit favorable antibiotic activity via FabI inhibition. The compounds of the present invention are represented by the following general formula I

I

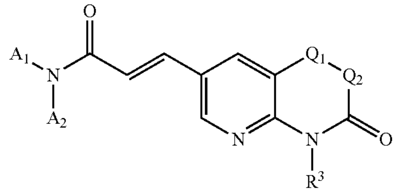

wherein $A_1$ represents a moiety selected from the groups $A_{11}$ and $A_{12}$ having the following structures $A_{11}$

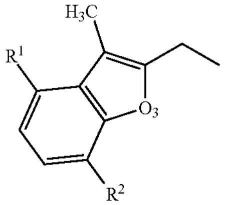

and $A_{12}$

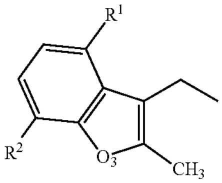

;

wherein the line connected to the exocyclic methylene group represents a single covalent bond formed with the nitrogen atom of formula I;

$A_2$ represents a methyl group;

or $A_1$ and $A_2$ together with the nitrogen atom to which they are bonded form the following moiety $A_3$:

$A_3$

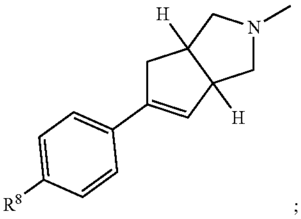

;

wherein moiety $A_3$ is not restricted in terms of its stereochemistry. It can be one enantiomer:

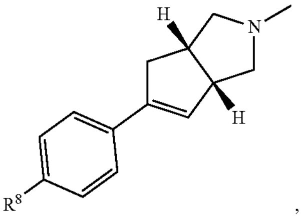

, or it can be the other enantiomer

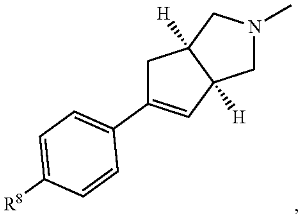

, or it can be any mixture thereof, including especially the racemic mixture of the above two enantiomers. Any of these moieties is referred to as moiety $A_3$;

wherein in moiety $A_3$ the exocyclic line connected to the nitrogen atom of the bicycle represents the covalent bond between nitrogen and carbonyl group in the left-hand side of formula I;

$Q_1$ represents —CH═CR$^7$—, $CH_2$ or NH;

$Q_2$ represents CR$^4$R$^5$, or CR$^4$R$^5$—CR$^6$R$^7$, wherein the CR$^4$R$^5$ group binds to $Q_1$;

or $Q_1$-$Q_2$ represents —N═CR$^7$—CHR$^7$— or its tautomer —NH—CR$^7$═CR$^7$—

$Q_3$ represents O or S;

$R^1$ represents a group selected from H, —$NH_2$;

$R^2$ represents a group selected from H, —O—Ar$^1$, —O-Het$^1$, —NR$^9$R$^{10}$, —O-Alk$^1$, wherein Ar$^1$ represents a phenyl group that may optionally be substituted by one or more groups individually selected from —CN, —O—$C_{1-4}$-alkyl, —O—$(CH_2)_{1-4}$—NR$^9$R$^{10}$, or wherein the phenyl group may carry two substituent groups at adjacent ring atoms such that these adjacent substituent groups, which may for instance be selected from alkylene groups and alkylene groups carrying one or two heteroatoms individually selected from N and O within their backbone, which substituent groups may be bonded together to form a 5-membered heterocycle having one or two heteroatoms individually selected from N and O wherein the N atom may carry a group selected from H and methyl, wherein Het$^1$ represents an aromatic heterocycle with 5 or 6 ring atoms including 1 or 2 heteroatoms individually selected from N, S and O, or a non-aromatic partially or fully saturated heterocycle with 6 ring atoms including 1 heteroatom selected from N and O, wherein said aromatic or non-aromatic heterocycle may optionally be substituted by one or more groups individually selected from —$C_{1-4}$-alkyl, —O—$C_{1-4}$-alkyl, —CN, —$(CH_2)_{0-4}$—OH, wherein $R^9$ is selected from H and —$C_{1-4}$-alkyl; wherein $R^{10}$ is selected from H, —$C_{1-4}$-alkyl and —C(═O)—$CH_3$; wherein Alk$^1$ represents an alkyl group having 1 to 6 carbon atoms, which is linear, branched, cyclic or a combination thereof, which Alk$^1$ group may optionally be substituted by one or more groups selected from —OH, —O-alkyl $R^3$ represents a group selected from H, —$PO_3R^{3a}{}_2$, —$CH_2$—$OPO_3R^{3a}{}_2$ and —$CH_2$—O—C(═O)—R$^{3b}$.

$R^{3a}$ represents a hydrogen atom or a cation suitable for forming a pharmaceutically acceptable salt or —$CH_2$—O—C(═O)—R$^{3b}$ or —CHMe—O—C(═O)—R$^{3b}$ or —$CMe_2$-O—C(═O)—R$^{3b}$ or —$CH_2$—O—C(═O)—O—R$^{3b}$ or —CHMe—O—C(═O)—O—R$^{3b}$ or —$CMe_2$-O—C(═O)—O—R$^{3b}$.

$R^{3b}$ represents an alkyl group having 1 to 11 carbon atoms, which is linear, branched, cyclic or a combination thereof, which R$^{3b}$ group may optionally be substituted by one or more groups independently selected from —OH, and —O—$C_{1-6}$-alkyl;

$R^4$ represents a group selected from H, $C_{1-4}$-alkyl, CN and $C_{1-4}$-alkylene-F;

$R^5$ represents a group selected from H, $C_{1-4}$-alkyl, $C_{1-4}$-alkylene-OH, $C_{1-4}$-alkylene-$OR^3$, —OH, —$OPO_3R^{3a}{}_2$;

or $R^4$ and $R^5$ together form a cyclic group having 4 to 6 ring members formed by methylene groups and optionally an oxygen atom;

$R^6$ represents a group selected from H, —OH, $C_{1-4}$-alkyl, or —$OPO_3R^{3a}{}_2$;

$R^7$ represents a group selected from H, $C_{1-4}$-alkyl, $C_{1-4}$-alkylene-OH, $C_{1-4}$-alkylene-$OR^3$, $C_{1-4}$-alkylene-F, —CN;

or $R^6$ and $R^7$ together form a cyclic group having 4 to 6 ring members formed by methylene groups and optionally an oxygen atom; the cyclic group may optionally carry a substituent selected from —OH, —O-alkyl;

$R^8$ represents a group selected from —O—$Ar^2$ and —O-$Het^2$;

wherein $Ar^2$ represents a phenyl group that may optionally be substituted by one or more groups individually selected from —CN, —O—$C_{1-4}$-alkyl or wherein the phenyl group may carry two substituent groups at adjacent ring atoms such that these adjacent substituent groups may be bonded together to form a 5-membered heterocycle having one or two heteroatoms individually selected from N, S and O, wherein said heterocycle may optionally carry one or two substituents selected from oxo, halogen, —O—$C_{1-4}$-alkyl, $C_{1-4}$-alkyl, and CN;

and wherein $Het^2$ represents an aromatic heterocycle with 5 or 6 ring atoms including 1 or 2 heteroatoms individually selected from N, S and O, which may optionally be substituted by one or more groups individually selected from —O—$C_{1-4}$-alkyl, —CN, F, $C_{1-4}$-alkyl.

In one embodiment, the compounds of the present invention are represented by general formula II

II

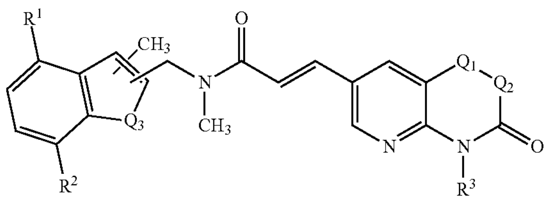

wherein $R^1$, $R^2$, $R^3$, $Q_1$, $Q_2$, $Q_3$ have the same meanings as specified for general formula I above;

and wherein the five-membered heterocycle comprising $Q_3$ is bonded to the methylene-amide moiety at the 2-position and to the methyl group at the 3-position or is bonded to the methylene-amide moiety at the 3-position and to the methyl group at the 2-position.

Preferably, the compounds of this embodiment are represented by general formula III

III

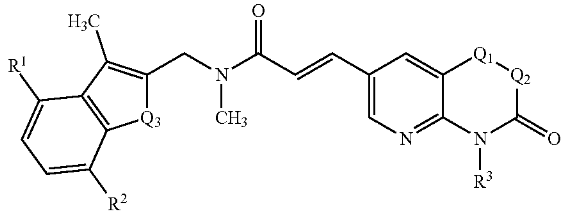

wherein $R^1$, $R^2$, $R^3$, $Q_1$, $Q_2$, $Q_3$ have the same meanings as specified for general formula I above.

In this embodiment, variable group $Q_3$ may especially represent an oxygen atom, such that the moiety at the left-hand side of the molecule is a benzofurane moiety. Such compounds are represented by general formula IV

IV

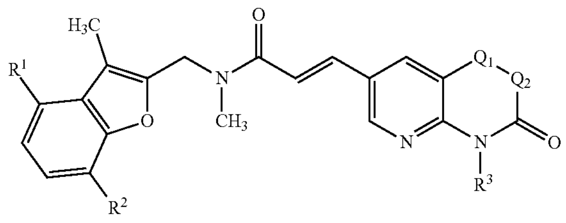

wherein $R^1$, $R^2$, $R^3$, $Q_1$, $Q_2$ have the same meanings as specified for general formula I above.

According to another preferred aspect of this embodiment, the variable groups $Q_1$ and $Q_2$ represent NH or $CH_2$ for $Q_1$ and $CR^4R^5$ for $Q_2$, respectively. The compounds of this aspect are represented by general formula Va or general formula Vb Va

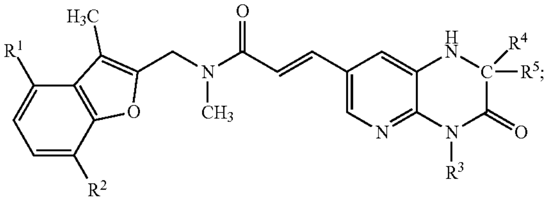

; or

Vb

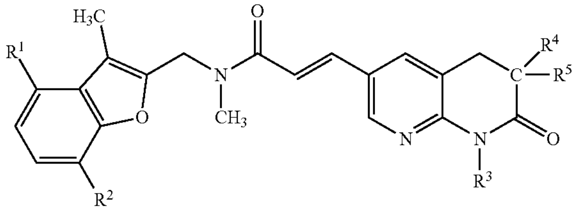

wherein $R^1$, $R^2$, $R^3$, have the same meanings as specified for general formula I above. In formula Va, $R^4$ represents a group selected from H, $C_{1-4}$-alkyl and $C_{1-4}$-alkylene-F and $R^5$ represents a group selected from H, $C_{1-4}$-alkyl, $C_{1-4}$-alkylene-OH, $C_{1-4}$-alkylene-$OR^3$. In formula Vb, $R^4$ represents a group selected from H, $C_{1-4}$-alkyl and $C_{1-4}$-alkylene-F and $R^5$ represents a group selected from H, $C_{1-4}$-alkyl, $C_{1-4}$-alkylene-OH, $C_{1-4}$-alkylene-$OR^3$, —OH; and —$OPO_3R^{3a}{}_2$.

The variable groups of general formula Va or Vb may preferably have the following meanings:

$R^1$ represents H, $NH_2$;

$R^2$ represents H;

$R^3$ represents a group selected from H, —$PO_3R^{3a}{}_2$, —$CH_2$—$OPO_3R^{3a}{}_2$ and —$CH_2$—O—C(═O)—$R^{3b}$.

$R^{3a}$ represents a hydrogen atom or a cation suitable for forming a pharmaceutically acceptable salt or —$CH_2$—O—C(═O)—$R^{3b}$ or —CHMe—O—C(═O)—$R^{3b}$ or —$CMe_2$-O—C(═O)—$R^{3b}$ or —$CH_2$—O—C(═O)—O—$R^{3b}$ or —CHMe—O—C(═O)—O—$R^{3b}$ or —$CMe_2$-O—C(═O)—O—$R^{3b}$.

$R^{3b}$ represents an alkyl group having 1 to 11 carbon atoms, which is linear, branched, cyclic or a combination thereof, which $R^{3b}$ group may optionally be substituted by one or more groups independently selected from —OH, and —O—$C_{1-6}$-alkyl;

$R^4$ represents H, $C_{1-4}$-alkyl; and $R^5$ represents H, $C_{1-4}$-alkyl, $C_{1-4}$-alkylene-$OR^3$.

According to another aspect of this embodiment, the variable groups $Q_1$ and $Q_2$ represent NH and $CR^4R^5$—$CR^6R^7$, respectively. The compounds of this aspect are represented by general formula VI

VI

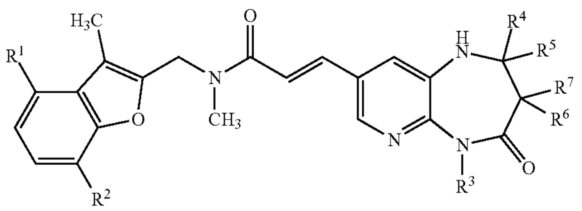

wherein $R^1$, $R^2$, $R^3$, $R^4$, $R^5$, $R^6$ and $R^7$ have the same meanings as specified for general formula I above.

In this aspect, the variable groups may preferably have the following meanings:

$R^1$ represents H, $NH_2$;

$R^2$ represents H;

$R^3$ represents a group selected from H, —$PO_3R^{3a}{}_2$, —$CH_2$—$OPO_3R^{3a}{}_2$ and —$CH_2$—O—C(═O)—$R^{3b}$.

$R^{3a}$ represents a hydrogen atom or a cation suitable for forming a pharmaceutically acceptable salt or —$CH_2$—O—C(═O)—$R^{3b}$ or —CHMe—O—C(═O)—$R^{3b}$ or —$CMe_2$-O—C(═O)—$R^{3b}$ or —$CH_2$—O—C(═O)—O—$R^{3b}$ or —CHMe—O—C(═O)—O—$R^{3b}$ or —$CMe_2$-O—C(═O)—O—$R^{3b}$.

$R^{3b}$ represents an alkyl group having 1 to 11 carbon atoms, which is linear, branched, cyclic or a combination thereof, which $R^{3b}$ group may optionally be substituted by one or more groups independently selected from —OH, and —O—$C_{1-6}$-alkyl;

$R^4$ represents H, $C_{1-4}$-alkyl; and $R^5$ represents H, $C_{1-4}$-alkyl, $C_{1-4}$-alkylene-$OR^3$.

$R^6$ represents H, $C_{1-4}$-alkyl, OH, —$OPO_3R^{3a}{}_2$; and $R^7$ represents H, $C_{1-4}$-alkyl, $C_{1-4}$-alkylene-OH, $C_{1-4}$-alkylene-$OR^3$, wherein $R^3$ is as specified above, $C_{1-4}$-alkylene-F.

According to yet another aspect of this embodiment, the variable group $Q_1$ represents a methylene group while $Q_2$ has the same meaning as in the preceding aspect, i.e. —$CR^4R^5$—$CR^6R^7$. The compounds of this aspect are represented by general formula VII

VII

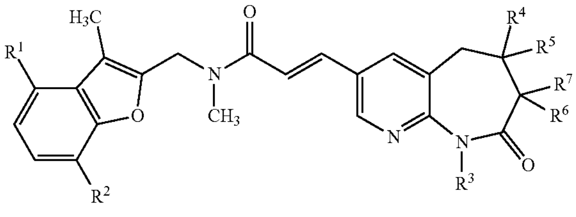

wherein $R^1$, $R^2$, $R^3$, $R^4$, $R^5$, $R^6$ and $R^7$ have the same meanings as specified for general formula I above.

In the compounds of this aspect, the variable groups have preferably the following meanings:

$R^1$ represents H, $NH_2$;

$R^2$ represents H;

$R^3$ represents a group selected from H, —$PO_3R^{3a}{}_2$, —$CH_2$—$OPO_3R^{3a}{}_2$ and —$CH_2$—O—C(═O)—$R^{3b}$.

$R^{3a}$ represents a hydrogen atom or a cation suitable for forming a pharmaceutically acceptable salt or —$CH_2$—O—C(═O)—$R^{3b}$ or —CHMe—O—C(═O)—$R^{3b}$ or —$CMe_2$-O—C(═O)—$R^{3b}$ or —$CH_2$—O—C(═O)—O—$R^{3b}$ or —CHMe—O—C(═O)—O—$R^{3b}$ or —$CMe_2$-O—C(═O)—O—$R^{3b}$.

$R^{3b}$ represents an alkyl group having 1 to 11 carbon atoms, which is linear, branched, cyclic or a combination thereof, which $R^{3b}$ group may optionally be substituted by one or more groups independently selected from —OH, and —O—$C_{1-6}$-alkyl;

$R^4$ represents H, $C_{1-4}$-alkyl; and $R^5$ represents H, $C_{1-4}$-alkyl, $C_{1-4}$-alkylene-$OR^3$;

$R^6$ represents H, $C_{1-4}$-alkyl, OH, —$OPO_3R^{3a}{}_2$; and $R^7$ represents H, $C_{1-4}$-alkyl, $C_{1-4}$-alkylene-OH, $C_{1-4}$-alkylene-$OR^3$, wherein $R^3$ is as specified above, $C_{1-4}$-alkylene-F.

In another embodiment of the present invention, the bicyclic moiety on the left-hand side of the molecule is bonded via the 3-position of the five-membered heterocycle. The compounds of this embodiment are represented by general formula VIII

VIII

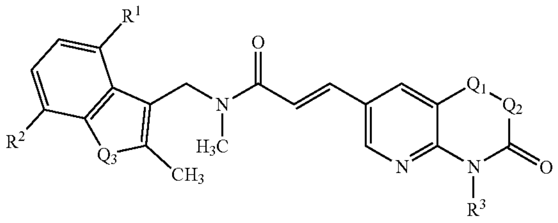

wherein $R^1$, $R^2$, $R^3$, $Q_1$, $Q_2$, $Q_3$ have the same meanings as specified for general formula I above.

In one specific aspect of this embodiment, the variable group $Q_3$ represents an oxygen atom, so that the bicyclic moiety on the left-hand side is a benzofurane moiety. The compounds of this aspect are represented by general formula IX

IX

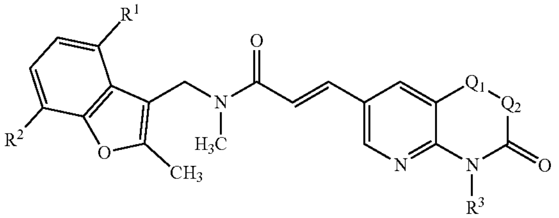

wherein $R^1$, $R^2$, $R^3$, $Q_1$, $Q_2$ have the same meanings as specified for general formula I above.

In this aspect, the variable groups $Q_1$ and $Q_2$ preferably represent NH or $CH_2$ for $Q_1$ and $CR^4R^5$ for $Q_2$, respectively. Preferred compounds of this aspect are thus represented by general formula Xa and Xb Xa

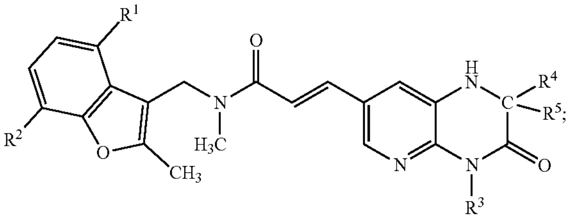

Xb

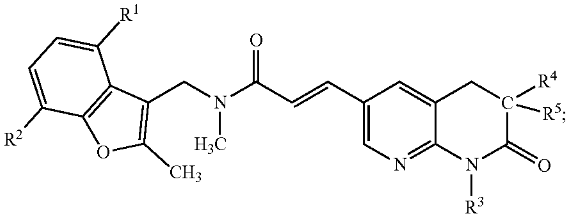

wherein $R^1$, $R^2$, $R^3$, $R^4$ and $R^5$ have the same meanings as specified for general formula I above.

The variable group meanings for the compounds of this aspect are preferably as follows:

$R^1$ represents H;

$R^2$ represents a group selected from H, —O—$Ar^1$, —O-$Het^1$, $NH_2$, wherein $Ar^1$ represents a phenyl group that may optionally be substituted by one or more groups individually selected from —CN, —O—$C_{1-4}$-alkyl, or wherein the phenyl group may carry two substituent groups at adjacent ring atoms such that these adjacent substituent groups may be bonded together to form a 5-membered heterocycle having one or two heteroatoms individually selected from N and O, wherein $Het^1$ represents an aromatic heterocycle with 5 or 6 ring atoms including 1 or 2 heteroatoms individually selected from N, S and O, or a non-aromatic partially or fully saturated heterocycle with 6 ring atoms including 1 heteroatom selected from N, S and O, which $Het^1$ group may optionally be substituted by one or more groups individually selected from —$C_{1-4}$-alkyl, —O—$C_{1-4}$-alkyl, —CN;

$R^3$ represents a group selected from H, —$PO_3R^{3a}{}_2$, —$CH_2$—$OPO_3R^{3a}{}_2$ and —$CH_2$—O—C(═O)—$R^{3b}$.

$R^{3a}$ represents a hydrogen atom or a cation suitable for forming a pharmaceutically acceptable salt or —$CH_2$—O—C(═O)—$R^{3b}$ or —CHMe—O—C(═O)—$R^{3b}$ or —$CMe_2$-O—C(═O)—$R^{3b}$ or —$CH_2$—O—C(═O)—O—$R^{3b}$ or —CHMe—O—C(═O)—O—$R^{3b}$ or —$CMe_2$-O—C(═O)—O—$R^{3b}$.

$R^{3b}$ represents an alkyl group having 1 to 11 carbon atoms, which is linear, branched, cyclic or a combination thereof, which $R^{3b}$ group may optionally be substituted by one or more groups independently selected from —OH, and —O—$C_{1-6}$-alkyl;

$R^4$ represents H, $C_{1-4}$-alkyl, $C_{1-4}$-alkylene-F; and $R^5$ represents H, $C_{1-4}$-alkyl, $C_{1-4}$-alkylene-OH or $C_{1-4}$-alkylene-$OR^3$, wherein $R^3$ is as specified above.

Another preferred sub-genus of compounds of this aspect of the invention is represented by general formula XI

XI

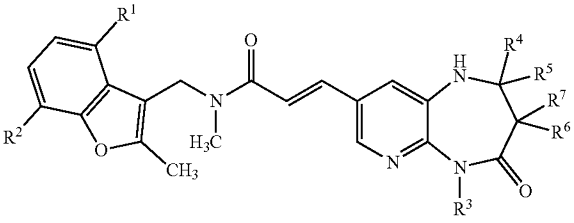

wherein $R^1$, $R^2$, $R^3$, $R^4$, $R^5$, $R^6$ and $R^7$ have the same meanings as specified for general formula I above.

For this sub-genus, the variable group meanings are preferably as follows:

$R^1$ represents H;

$R^2$ represents a group selected from H, —O—$Ar^1$, —O-$Het^1$, —$NH_2$, wherein $Ar^1$ represents a phenyl group that may optionally be substituted by one or more groups individually selected from —CN, —O—$C_{1-4}$-alkyl, or wherein the phenyl group may carry two substituent groups at adjacent ring atoms such that these adjacent substituent groups may be bonded together to form a 5-membered heterocycle having one or two heteroatoms individually selected from N and O, wherein $Het^1$ represents an aromatic heterocycle with 5 or 6 ring atoms including 1 or 2 heteroatoms individually selected from N, S and O, or a non-aromatic partially or fully saturated heterocycle with 6 ring atoms including 1 heteroatom selected from N, S and O, which $Het^1$ group may optionally be substituted by one or more groups individually selected from —$C_{1-4}$-alkyl, —O—$C_{1-4}$-alkyl, —CN;

$R^3$ represents a group selected from H, —$PO_3R^{3a}{}_2$, —$CH_2$—$OPO_3R^{3a}{}_2$ and —$CH_2$—O—C(═O)—$R^{3b}$.

$R^{3a}$ represents a hydrogen atom or a cation suitable for forming a pharmaceutically acceptable salt or —$CH_2$—O—C(═O)—$R^{3b}$ or —CHMe—O—C(═O)—$R^{3b}$ or —$CMe_2$-O—C(═O)—$R^{3b}$ or —$CH_2$—O—C(═O)—O—$R^{3b}$ or —CHMe—O—C(═O)—O—$R^{3b}$ or —$CMe_2$-O—C(═O)—O—$R^{3b}$.

$R^{3b}$ represents an alkyl group having 1 to 11 carbon atoms, which is linear, branched, cyclic or a combination thereof, which $R^{3b}$ group may optionally be substituted by one or more groups independently selected from —OH, and —O—$C_{1-6}$-alkyl;

$R^4$ represents H, $C_{1-4}$-alkyl; and $R^6$ represents H, $C_{1-4}$-alkyl, $C_{1-4}$-alkylene-$OR^3$.

$R^6$ represents H, $C_{1-4}$-alkyl, OH, —$OPO_3R^{3a}{}_2$; and $R^7$ represents H, $C_{1-4}$-alkyl, $C_{1-4}$-alkylene-OH, $C_{1-4}$-alkylene-$OR^3$, wherein $R^3$ is as specified above, $C_{1-4}$-alkylene-F.

Another preferred sub-genus of compounds of this aspect of the invention is represented by general formula XII

XII

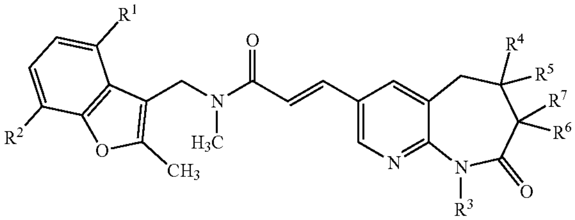

wherein $R^1$, $R^2$, $R^3$, $R^4$, $R^5$, $R^6$ and $R^7$ have the same meanings as specified for general formula I above.

The variable group meanings in this sub-genus of compounds are preferably as follows:

$R^1$ represents H;

$R^2$ represents a group selected from H, —O—$Ar^1$, —O-$Het^1$, —$NH_2$, wherein $Ar^1$ represents a phenyl group that may optionally be substituted by one or more groups individually selected from —CN, —O—$C_{1-4}$-alkyl, or wherein the phenyl group may carry two substituent groups at adjacent ring atoms such that these adjacent substituent groups may be bonded together to form a 5-membered heterocycle having one or two heteroatoms individually selected from N and O, wherein $Het^1$ represents an aromatic heterocycle with 5 or 6 ring atoms including 1 or 2 heteroatoms individually selected from N, S and O, or a non-aromatic partially or fully saturated heterocycle with 6 ring atoms including 1 heteroatom selected from N, S and O, which $Het^1$ group may optionally be substituted by one or more groups individually selected from —$C_{1-4}$-alkyl, —O—$C_{1-4}$-alkyl, —CN;

$R^3$ represents a group selected from H, —$PO_3R^{3a}{}_2$, —$CH_2$—$OPO_3R^{3a}{}_2$ and —$CH_2$—O—C(═O)—$R^{3b}$.

$R^{3a}$ represents a hydrogen atom or a cation suitable for forming a pharmaceutically acceptable salt or —$CH_2$—O—C(═O)—$R^{3b}$ or —CHMe—O—C(═O)—$R^{3b}$ or —$CMe_2$-O—C(═O)—$R^{3b}$ or —$CH_2$—O—C(═O)—O—$R^{3b}$ or —CHMe—O—C(═O)—O—$R^{3b}$ or —$CMe_2$-O—C(═O)—O—$R^{3b}$.

$R^{3b}$ represents an alkyl group having 1 to 11 carbon atoms, which is linear, branched, cyclic or a combination thereof, which $R^{3b}$ group may optionally be substituted by one or more groups independently selected from —OH, and —O—$C_{1-6}$-alkyl;

$R^4$ represents H, $C_{1-4}$-alkyl; and $R^6$ represents H, $C_{1-4}$-alkyl, $C_{1-4}$-alkylene-$OR^3$.

$R^6$ represents H, $C_{1-4}$-alkyl, OH, —$OPO_3R^{3a}{}_2$; and $R^7$ represents H, $C_{1-4}$-alkyl, $C_{1-4}$-alkylene-OH, $C_{1-4}$-alkylene-$OR^3$, wherein $R^3$ is as specified above, $C_{1-4}$-alkylene-F.

Another embodiment of the present invention pertains to compounds represented by general formula XIII

XIII

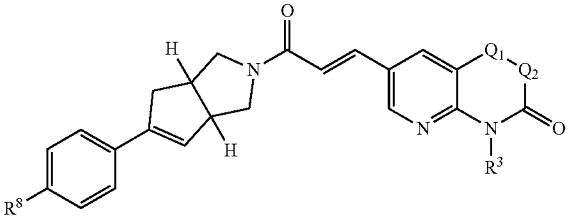

wherein $R^3$, $R^8$, $Q_1$, $Q_2$ have the same meanings as specified for general formula I above.

Among the compounds of this embodiment, a preferred aspect relates to compounds having an amino group NH or a methylene group $CH_2$ in the position of $Q_1$ and a group $CR^4R^5$ in the position of $Q_2$. These compounds are represented by general formula XIVa and XIVb XIVa

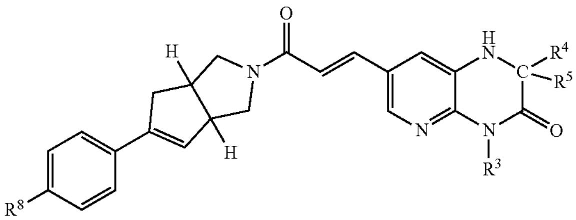

wherein $R^3$, $R^4$, $R^5$, $R^8$ have the same meanings as specified for general formula I above;

or

XIVb

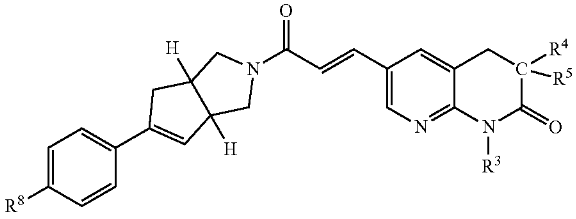

wherein $R^3$, $R^4$, $R^5$, $R^8$ have the same meanings as specified for general formula I above.

For this aspect of the invention, preferred variable group meanings are as follows:

$R^3$ represents a group selected from H, —$PO_3R^{3a}{}_2$, —$CH_2$—$OPO_3R^{3a}{}_2$ and —$CH_2$—O—C(═O)—$R^{3b}$.

$R^{3a}$ represents a hydrogen atom or a cation suitable for forming a pharmaceutically acceptable salt or —$CH_2$—O—C(═O)—$R^{3b}$ or —CHMe—O—C(═O)—$R^{3b}$ or —CMe$_2$-O—C(═O)—$R^{3b}$ or —$CH_2$—O—C(═O)—O—$R^{3b}$ or —CHMe—O—C(═O)—O—$R^{3b}$ or —CMe$_2$-O—C(═O)—O—$R^{3b}$.

$R^{3b}$ represents an alkyl group having 1 to 11 carbon atoms, which is linear, branched, cyclic or a combination thereof, which $R^{3b}$ group may optionally be substituted by one or more groups independently selected from —OH, and —O—$C_{1-6}$-alkyl;

$R^4$ represents H, $C_{1-4}$-alkyl, $C_{1-4}$-alkylene-F; and $R^5$ represents H, $C_{1-4}$-alkyl, $C_{1-4}$-alkylene-OH or $C_{1-4}$-alkylene-OR$^3$, wherein $R^3$ is as specified above;

$R^8$ represents a group selected from —O—$Ar^2$ and —O-Het$^2$;

wherein $Ar^2$ represents a phenyl group that may optionally be substituted by one or more groups individually selected from —CN, —O—$C_{1-4}$-alkyl or wherein the phenyl group may carry two substituent groups at adjacent ring atoms such that these adjacent substituent groups may be bonded together to form a 5-membered heterocycle having one or two heteroatoms individually selected from N, S and O, wherein said heterocycle may optionally carry one or two substituents selected from oxo, F, —O—$C_{1-4}$-alkyl, $C_{1-4}$-alkyl, CN;

and wherein Het$^2$ represents an aromatic heterocycle with 5 or 6 ring atoms including 1 or 2 heteroatoms individually selected from N, S and O, which may optionally be substituted by one or more groups individually selected from —O—$C_{1-4}$-alkyl, —CN, F, $C_{1-4}$-alkyl.

In another preferred aspect of this embodiment, an amino group NH is present in the position of $Q_1$ and a group —CR$^4$R$^5$—CR$^6$R$^7$ is present in the position of $Q_2$. The compounds are thus represented by general formula XV

XV

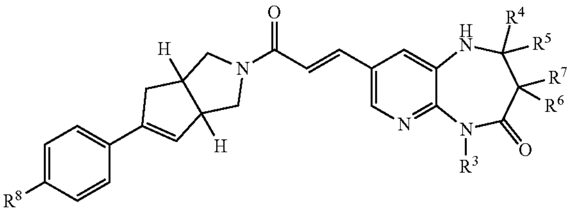

wherein $R^3$, $R^4$, $R^5$, $R^6$, $R^7$, $R^8$ have the same meanings as specified for general formula I above.

Preferred substituent meanings for the compounds of this aspect are as follows:

$R^3$ represents a group selected from H, —PO$_3$R$^{3a}{}_2$, —CH$_2$—OPO$_3$R$^{3a}{}_2$ and —CH$_2$—O—C(═O)—R$^{3b}$.

$R^{3a}$ represents a hydrogen atom or a cation suitable for forming a pharmaceutically acceptable salt or —CH$_2$—O—C(═O)—R$^{3b}$ or —CHMe—O—C(═O)—R$^{3b}$ or —CMe$_2$-O—C(═O)—R$^{3b}$ or —CH$_2$—O—C(═O)—O—R$^{3b}$ or —CHMe—O—C(═O)—O—R$^{3b}$ or —CMe$_2$-O—C(═O)—O—R$^{3b}$.

$R^{3b}$ represents an alkyl group having 1 to 11 carbon atoms, which is linear, branched, cyclic or a combination thereof, which $R^{3b}$ group may optionally be substituted by one or more groups independently selected from —OH, and —O—$C_{1-6}$-alkyl;

$R^4$ represents H, $C_{1-4}$-alkyl; and $R^5$ represents H, $C_{1-4}$-alkyl, $C_{1-4}$-alkylene-OR$^3$.

$R^6$ represents H, $C_{1-4}$-alkyl, OH, —OPO$_3$R$^{3a}{}_2$; and $R^7$ represents H, $C_{1-4}$-alkyl, $C_{1-4}$-alkylene-OH, $C_{1-4}$-alkylene-OR$^3$, wherein $R^3$ is as specified above, $C_{1-4}$-alkylene-F;

$R^8$ represents a group selected from —O—$Ar^2$ and —O-Het$^2$, wherein $Ar^2$ represents a phenyl group that may optionally be substituted by one or more groups individually selected from —CN, —O—$C_{1-4}$-alkyl or wherein the phenyl group may carry two substituent groups at adjacent ring atoms such that these adjacent substituent groups may be bonded together to form a 5-membered heterocycle having one or two heteroatoms individually selected from N, S and O, wherein said heterocycle may optionally carry one or two substituents selected from oxo, F, —O—$C_{1-4}$-alkyl, $C_{1-4}$-alkyl, CN and wherein Het$^2$ represents an aromatic heterocycle with 5 or 6 ring atoms including 1 or 2 heteroatoms individually selected from N, S and O, which may optionally be substituted by one or more groups individually selected from —O—$C_{1-4}$-alkyl, —CN, F, $C_{1-4}$-alkyl.

In a related aspect, variable group $Q_1$ represents a methylene group so that the compounds are represented by general formula XVI

XVI

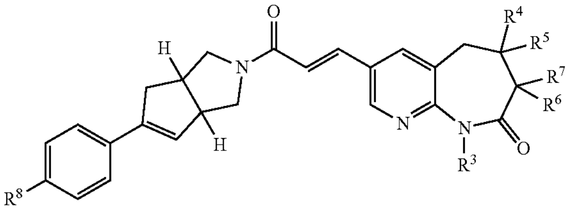

wherein $R^3$, $R^4$, $R^5$, $R^6$, $R^7$, $R^8$ have the same meanings as specified for general formula I above.

Preferred variable group meanings for this aspect are the following ones:

$R^3$ represents a group selected from H, —PO$_3$R$^{3a}{}_2$, —CH$_2$—OPO$_3$R$^{3a}{}_2$ and —CH$_2$—O—C(═O)—R$^{3b}$.

$R^{3a}$ represents a hydrogen atom or a cation suitable for forming a pharmaceutically acceptable salt or —CH$_2$—O—C(═O)—R$^{3b}$ or —CHMe—O—C(═O)—R$^{3b}$ or —CMe$_2$-O—C(═O)—R$^{3b}$ or —CH$_2$—O—C(═O)—O—R$^{3b}$ or —CHMe—O—C(═O)—O—R$^{3b}$ or —CMe$_2$-O—C(═O)—O—R$^{3b}$.

$R^{3b}$ represents an alkyl group having 1 to 11 carbon atoms, which is linear, branched, cyclic or a combination thereof, which $R^{3b}$ group may optionally be substituted by one or more groups independently selected from —OH, and —O—$C_{1-6}$-alkyl;

$R^4$ represents H, $C_{1-4}$-alkyl; and $R^5$ represents H, $C_{1-4}$-alkyl, $C_{1-4}$-alkylene-OR$^3$;

$R^6$ represents H, $C_{1-4}$-alkyl, OH, —OPO$_3$R$^{3a}{}_2$; and $R^7$ represents H, $C_{1-4}$-alkyl, $C_{1-4}$-alkylene-OH, $C_{1-4}$-alkylene-OR$^3$, wherein $R^3$ is as specified above, $C_{1-4}$-alkylene-F;

$R^8$ represents a group selected from —O—$Ar^2$ and —O-Het$^2$, wherein $Ar^2$ represents a phenyl group that may optionally be substituted by one or more groups individually selected from —CN, —O—$C_{1-4}$-alkyl or wherein the phenyl group may carry two substituent groups at adjacent ring atoms such that these adjacent substituent groups may be bonded together to form a 5-membered heterocycle having one or two heteroatoms selected N, S and O, wherein said heterocycle may optionally carry one or two substituents individually selected from oxo, F, —O—$C_{1-4}$-alkyl, $C_{1-4}$-alkyl, CN and wherein $Het^2$ represents an aromatic heterocycle with 5 or 6 ring atoms including 1 or 2 heteroatoms individually selected from N, S and O, which may optionally be substituted by one or more groups individually selected from —O—$C_{1-4}$-alkyl, —CN, F, $C_{1-4}$-alkyl.

The present disclosure contemplates all such compounds, including cis- and trans-isomers, R- and S-enantiomers, diastereomers, (d)-isomers, (l)-isomers, the racemic mixtures thereof, and other mixtures thereof, as falling within the scope of the invention. However, the carbon-carbon double bond between the pyridine ring and the amide group in the center of the molecule must be in trans configuration, as shown in the above formulae. Additional asymmetric carbon atoms may be present in a substituent such as an alkyl group. All such isomers, as well as mixtures thereof, are intended to be included in this invention.

If, for instance, a particular enantiomer of a compound disclosed herein is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Moreover, individual enantiomers and diastereomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well known methods, such as chiral-phase gas chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations. For examples, see Carreira and Kvaerno, Classics in Stereoselective Synthesis, Wiley-VCH: Weinheim, 2009.

The compounds disclosed herein can exist in solvated as well as unsolvated forms with pharmaceutically acceptable solvents such as water, ethanol, and the like, and it is intended that the invention embrace both solvated and unsolvated forms. The compounds disclosed here may exist in single or multiple crystalline forms or polymorphs. In one embodiment, the compound is amorphous. In one embodiment, the compound is a single polymorph. In another embodiment, the compound is a mixture of polymorphs. In another embodiment, the compound is in a crystalline form.

The invention also embraces isotopically labeled compounds of the invention which are as recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. For example, a compound of the invention may have one or more H atom replaced with deuterium.

Certain isotopically-labeled disclosed compounds (e.g., those labeled with 3H and 14C) are useful in compound and/or substrate tissue distribution assays. Tritiated (i.e., 3H) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the e.g., Examples herein by substituting an isotopically labeled reagent for a non-isotopically labeled reagent.

Prodrugs of the present invention contain at least one prodrug moiety, i.e. a moiety that is cleaved under physiologic conditions to thereby release the active species. Such prodrug moieties may be attached to the compounds of the present invention in all positions represented by variable group $R^3$. A suitable prodrug moiety is the methylene phosphate moiety, as described in WO 2013/190384 A1. Further suitable prodrug moieties are phospates or other solubilizing moieties as described in “Prodrugs: design and clinical applications” (Rautio et al. Nature Reviews Drug Discovery, 2008, 7, 255). One specific prodrug modification is the conversion of an amine group to an N-oxide group. The above chemical formulae illustrate suitable positions for prodrug modifications by means of the methylene phosphate moiety and the phosphate moiety. It should be understood that these prodrug moieties may be replaced by other prodrug moieties. According to a preferred embodiment of the present invention, the prodrugs of the invention contain exactly one prodrug moiety.

Methods of Manufacture

The compounds of the present invention can be prepared using established organic chemistry synthetic methods and procedures and/or information described hereinbelow. Starting materials may either be purchased (if commercially available) or synthesized using established organic chemistry synthetic methods and procedures and/or information described hereinbelow.

Final Step Amide Coupling

Compounds disclosed herein may be prepared by means of the following method, which comprises the step of coupling a precursor compound of formula XVII

XVII

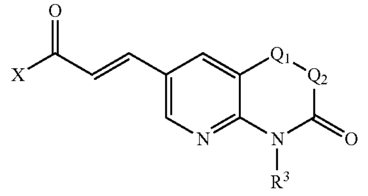

wherein $Q_1$, and $Q_2$ have the same meanings as specified hereinabove, wherein R3 represents a hydrogen atom, and wherein X represents a leaving group, with an amine compound of formula $H\text{-}NA_1A_2$, herein sometimes referred to as formula XXIII, wherein $A_1$ and $A_2$ have the same meanings as specified hereinabove for the compound of formula I.

The leaving group may be selected from a hydroxyl group, tosylate group, triflate group, mesylate group, iodide, bromide and the like.

Especially if the leaving group is a hydroxyl group, the coupling reaction is preferably carried out in a solvent and in the presence of a coupling agent and more preferably in the presence of a solvent, a coupling group and a base. The solvent is preferably selected from DMF, THF, DCM. The coupling agent is preferably selected from HATU, HBTU, HCTU, TBTU, COMU, TOMBU, COMBU and most preferably HATU. The reaction is typically carried out in the presence of a base. The base is preferably selected from DIPEA.

This reaction sequence is illustrated by the following Scheme 1.

Scheme 1

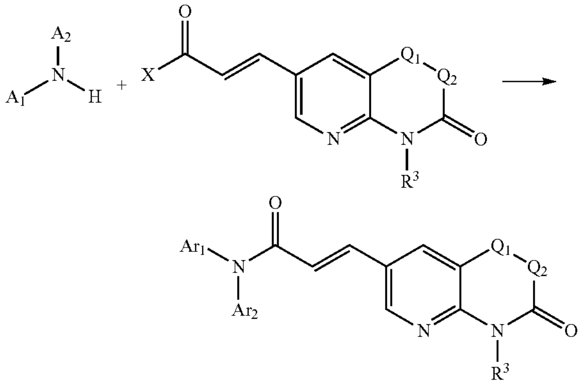

wherein $A_1$ and $A_2$ as well as $Q_1$ and $Q_2$ have the same meanings as specified for compound I hereinabove, and wherein $R^3$ represents a hydrogen atom.

Manufacture of Right-Hand Side Precursor

The precursor compound of formula XVII can be manufactured by reacting a compound of formula XVIII

XVIII

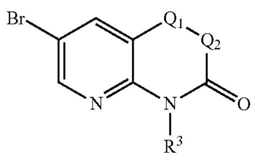

wherein $Q_1$ and $Q_2$ have the same meanings as specified for compound I hereinabove, and wherein $R^3$ represents a hydrogen atom, with a carboxyl-protected acrylic acid, such as a $C_{1-6}$-alkyl ester (preferably tert-butyl ester) of acrylic acid. This coupling reaction is carried out under Heck coupling conditions and preferably in the presence of a Pd(II)-salt such as Pd(OAc)2 and a phosphine ligand such as Xantphos, tri-(o-tolyl)phosphine or 1,1-Bis (diphenylphosphino)ferrocene (dppf). The reaction is typically carried out in the presence of a solvent such as DMF, proprionitrile or a combination thereof and also in the presence of a base such as DIPEA. The coupling reaction is followed by deprotection and optionally introduction of a leaving group other than hydroxyl. This reaction sequence is illustrated by the following Scheme 2.

Scheme 2

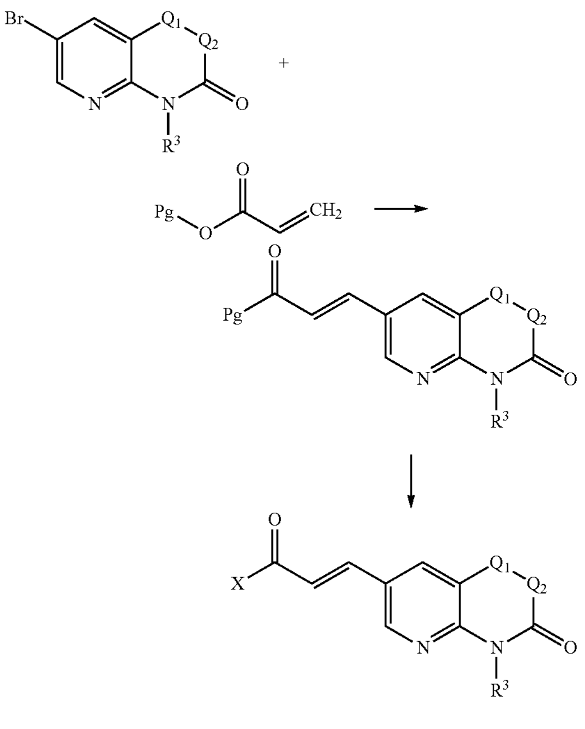

wherein Pg represents a protective group, $Q_1$ and $Q_2$ have the same meanings as specified for compound I hereinabove, and wherein $R^3$ represents a hydrogen atom.

Precursor compound XX can be synthesized by means of a cyclization reaction starting from a compound of formula XXI:

XXI

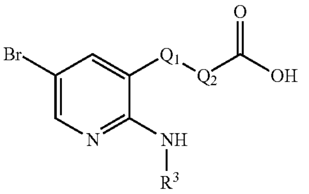

wherein $Q_1$ and $Q_2$ have the same meanings as specified for compound I hereinabove, and wherein $R^3$ represents a hydrogen atom. The cyclization is typically accomplished using coupling agents such as HATU in the presence of a base like DIPEA and in a solvent such as DMF. This reaction sequence is illustrated by the following Scheme 3.

Scheme 3

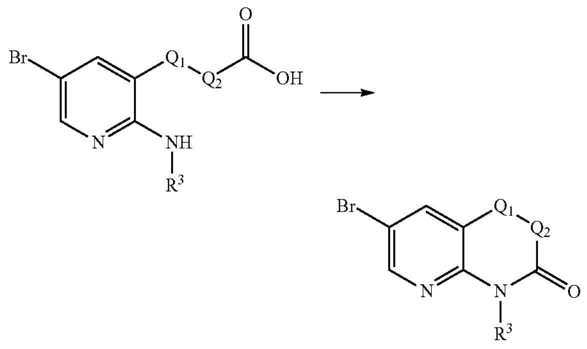

wherein $Q_1$ and $Q_2$ have the same meanings as specified hereinabove, and wherein $R^3$ represents a hydrogen atom.

Alternatively, precursor compound XX can be synthesized by means of a cyclization reaction starting from a compound of formula XXII:

XXII

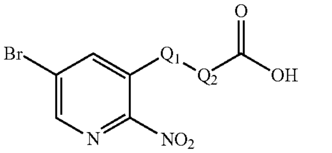

wherein $Q_1$ and $Q_2$ have the same meanings as specified for compound I hereinabove.

This variant of the cyclization reaction is typically carried out in the presence of a reducing agent such as Fe in acetic acid or a mixture of water, ethanol and ammonium chloride. This reaction step is illustrated by the following reaction scheme 4.

Scheme 4

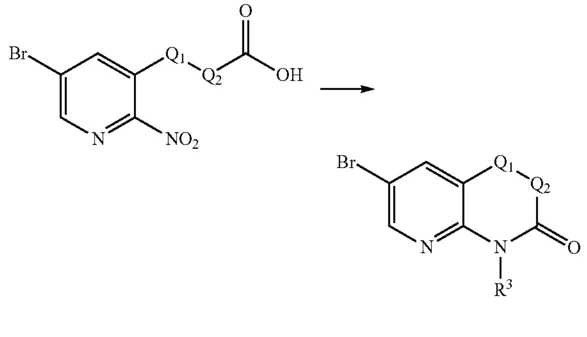

wherein $Q_1$ and $Q_2$ have the same meanings as specified for compound I hereinabove, and wherein $R^3$ represents a hydrogen atom.

Manufacture of $H\text{-}NA_1A_2$ Precursor

If variable group $A_1$ is a group selected from groups $A_{11}$ and $A_{12}$ and $A_2$ is a methyl group, the precursor compound $H\text{-}NA_1A_2$ may be obtained by means of the following procedures.

One option is to form an amide precursor XXIV that is subsequently reduced to the amine compound XXIII. The amide precursor XXIV has the following structure (wherein the structure XXIV permits the amide group to be bonded to the 2-position and the methyl group bonded to the 3-position or vice versa):

XXIV

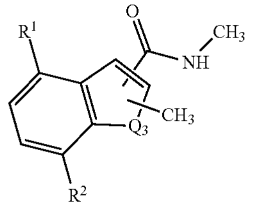

wherein $R^1$, $R^2$ and $Q_3$ have the same meanings as indicated for compound I above or wherein $R^1$ and/or $R^2$ may represent a functional group that can be converted to the desired substituent at a later stage of the reaction sequence. Said functional group must of course be inert under the reaction conditions specified for the conversions described herein (i.e. from compound XXV to compound XXIII), but be susceptible to subsequent conversion under different reaction conditions. This can be, for instance, a Br substituent.

Compound XXIV can be synthesized by reacting an activated carboxylic acid derivative XXV

XXV

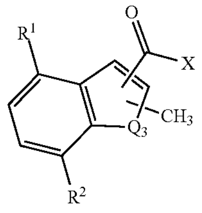

with methylamine. In formula XXV the variable group X represents a leaving group that can be, for instance, an alkoxy group, —OHet such as 1-hydroxybenzotriazole, carbamimidate, while $R^1$, $R^2$ and $Q_3$ have the same meanings as indicated for compound I above.

In a subsequent step, the amide group of compound XXIV is reduced to yield the amine XXIII. This can be done by means of a conventional reducing agent suitable for reducing carbonyl groups, such as $BH_3$. This reaction is typically performed in a solvent such as THF.

The sequence of reaction steps described above is illustrated by the following reaction scheme 5.

Scheme 5

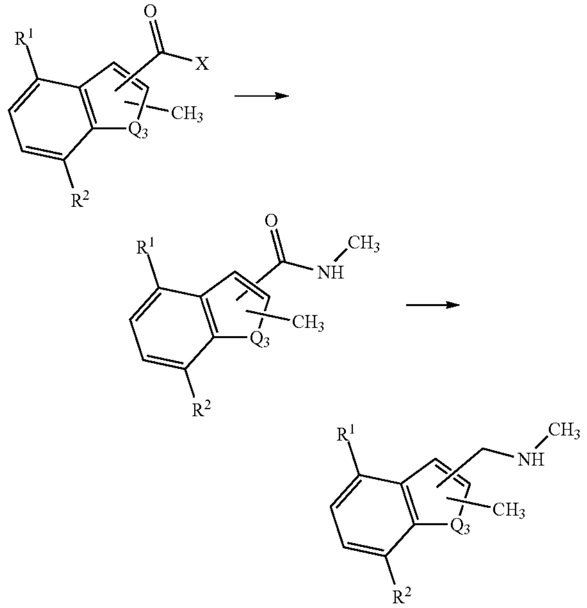

Alternatively, the amine compound XXIII can be prepared starting from the corresponding formyl derivative XXVI

XXVI

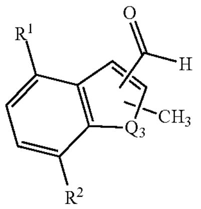

wherein $R^1$, $R^2$ and $Q_3$ have the same meanings as indicated for compound I above or wherein $R^1$ and/or $R^2$ may represent a functional group that can be converted to the desired substituent at a later stage of the reaction sequence, as described above.

Formyl compound XXVI is reacted with protected N-methyl amine in the presence of a borohydride compound such as $Na(OAc)_3BH$ in the presence of a solvent such as ethanol or 1,2-dichloroethane. Suitable protective groups are benzyl or p-methoxybenzyl. Intermediate compound XXVII is obtained.

XXVII

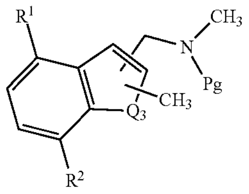

In formula XXVII Pg represents a protective group and $R^1$, $R^2$ and $Q_3$ have the same meanings as indicated for compound I above or $R^1$ and/or $R^2$ may represent a functional group that can be converted to the desired substituent at a later stage of the reaction sequence, as described above.

After the reaction, the protective group is removed, typically by hydrogenolysis, to yield amine compound XXIII. The reaction sequence is illustrated by the following Scheme 6.

Scheme 6

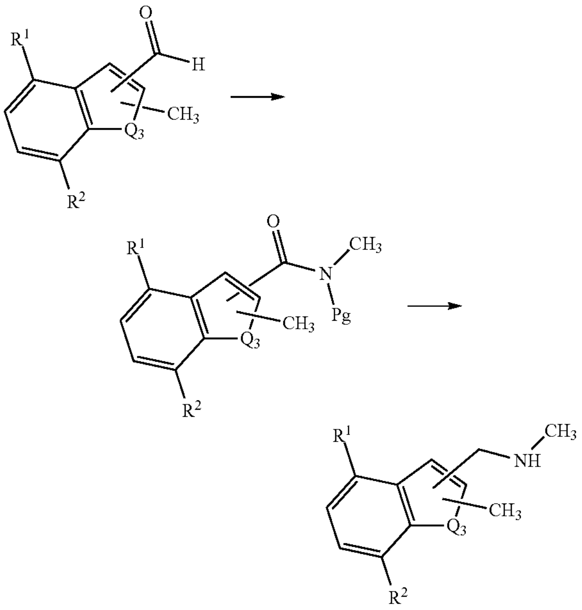

If variable groups A1 and A2 together form group A3, the precursor compound XXIII has the following structure XXIIIa:

XXIIIa

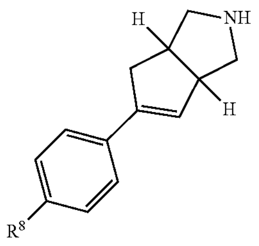

wherein $R^8$ has the same meaning as specified for compound I above.

Compound XXIIIa can be prepared by coupling precursor compound XXIV

XXIV

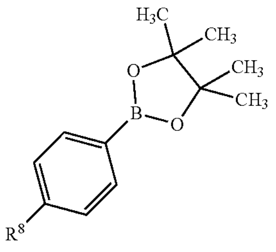

wherein $R^8$ has the same meaning as specified for compound I above, with precursor compound XXV

XXV

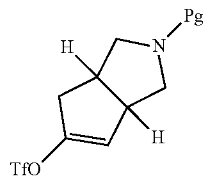

followed by deprotection, according to the following reaction scheme 7. The coupling reaction is typically carried out in the presence of a carbonate salt such as $Na_2CO_3$ or $K_2CO_3$ and a Pd-complex that is suitably selected from $Pd(PPh_3)_4$ and $PdCl_2(dppf)$. A suitable reaction solvent is a mixture of water and 1,4-dioxane. The preferred protective group is a BOC group.

Scheme 7

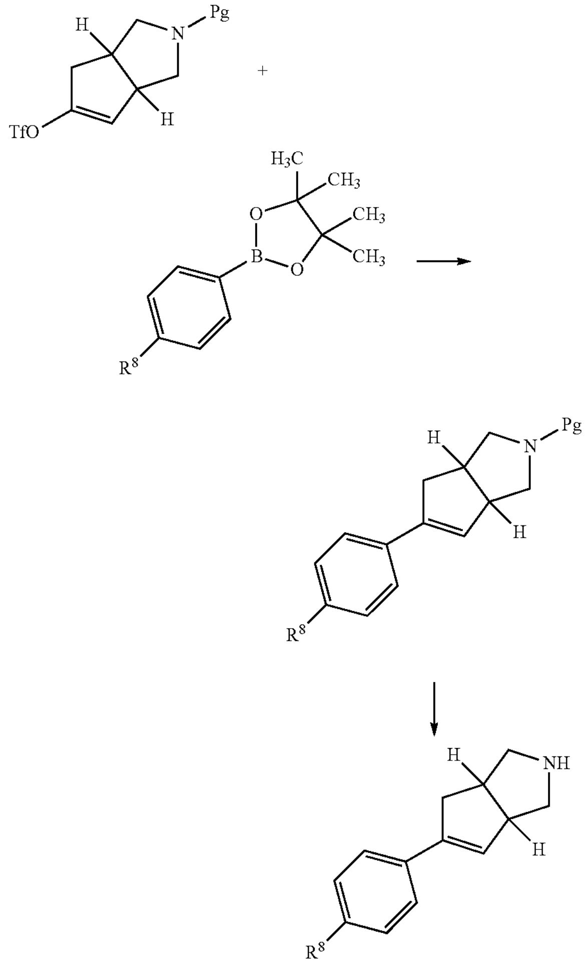

wherein Pg represents a protective group such as Boc, and $R^8$ has the same meaning as specified for compound I above.

Alternatively, target compound XXIIIa can be obtained by coupling precursor compound XXVI

XXVI

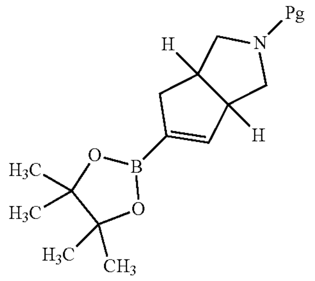

with precursor compound XXVII

XXVII

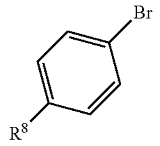

followed by deprotection, according to the following reaction scheme 8. The coupling reaction is typically carried out in the presence of a carbonate salt such as $K_2CO_3$ and a Pd-complex such as $PdCl_2(dppf)$. A suitable reaction solvent is 1,4-dioxane or a mixture of water and 1,4-dioxane. The preferred protecting group is a BOC group.

Scheme 8

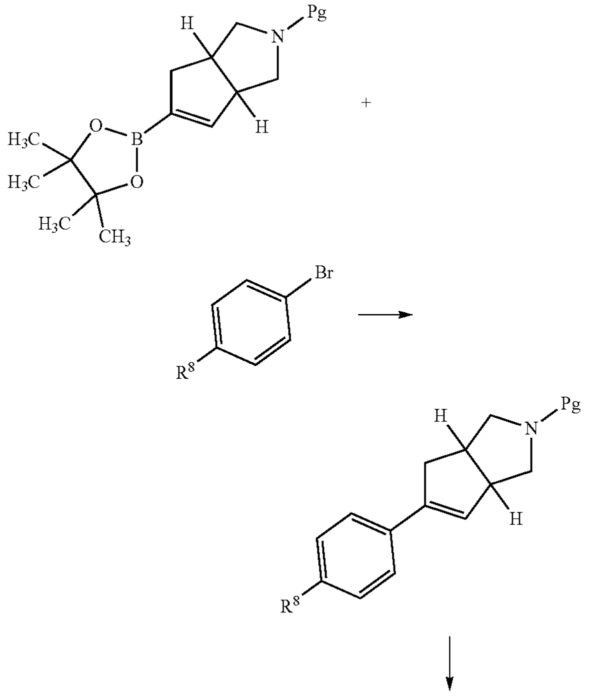

-continued

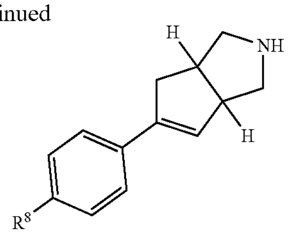

In the above reaction scheme, Pg represents a protective group and R8 is as specified for compound I above.

Final Step Heck Coupling

According to an alternative synthetic strategy, the compounds disclosed herein may be manufactured by means of the following method, which comprises the step of coupling a precursor compound of formula XVIII

XVIII

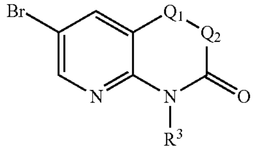

wherein $Q_1$ and $Q_2$ have the same meanings as specified for compound I hereinabove and wherein $R^3$ represents a hydrogen atom, with a precursor compound of formula XIX

XIX

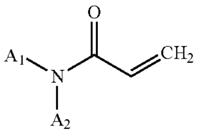

wherein $A_1$ and $A_2$ have the same meanings as specified hereinabove.

This coupling reaction is carried out under conditions of the Heck coupling. Typically, it is carried out in the presence of a Pd(II) complex such as Pd-162 (i.e. $[P(tBu)_3]Pd(crotyl)Cl$), tetrabutylammonium chloride, N-cyclohexyl-N-methylcyclohexanamine and dioxane. It is also possible to use a combination of a Pd(II)-salt such as $Pd(OAc)_2$ with a phosphine ligand such as tri-o-tolylphosphan, a base like DIPEA and a solvent such as a mixture of DMF and ACN. The reaction is illustrated by the following reaction scheme 9.

Scheme 9

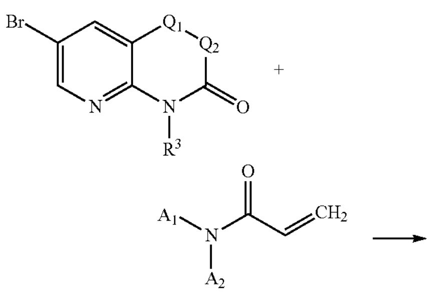

-continued

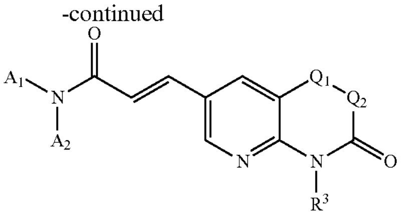

In the above reaction scheme, $Q_1$, $Q_2$, $A_1$ and $A_2$ have the same meanings as specified for compound I above and $R^3$ represents hydrogen.

The preparation of prodrugs of the compounds of the invention is typically accomplished by converting the respective compound of the invention with $R^3$ being hydrogen to a compound of the same structure except that $R^3$ represents a prodrug moiety that is cleavable under physiologic conditions for instance a phosphate-containing group as specified above. The prodrug moiety is preferably a methylene phosphate moiety. Such prodrug moieties and suitable reaction conditions for manufacturing methylene phosphate prodrugs are described in WO 2013/190384 A1.

Alternatively, the prodrug moiety may also be bonded to other parts of the molecule. In particular, it is contemplated to bind the prodrug moiety to the right-hand side of the molecule via variable groups $R^5$ or $R^7$, in which case these variable groups represent a group $C_{1-4}$-alkylene-$OR^3$. The method of preparing such prodrugs is analogous to the method described in WO 2013/190384 A1, but wherein the nitrogen atom carrying $R^3$ must of course be suitably protected.

Pharmaceutical Compositions

Administration Forms, Pharmaceutical Compositions and Formulations

Pharmaceutical compositions of the disclosure may be administered by various means, depending on their intended use, as is well known in the art. For example, if compositions of the disclosure are to be administered orally, they may be formulated as tablets, capsules, granules, powders or syrups. Alternatively, formulations disclosed herein may be administered parenterally as injections (intravenous, intramuscular or subcutaneous), drop infusion preparations or suppositories. For application by the ophthalmic mucous membrane route, the compositions disclosed herein may be formulated as eye drops or eye ointments. These formulations may be prepared by conventional means, and, if desired, the compositions may be mixed with any conventional additive, such as an excipient, a binder, a disintegrating agent, a lubricant, a corrigent, a solubilizing agent, a suspension aid, an emulsifying agent or a coating agent. The disclosed excipients may serve more than one function. For example, fillers or binders may also be disintegrants, glidants, anti-adherents, lubricants, sweeteners and the like.

In formulations of the disclosure, wetting agents, emulsifiers and lubricants, such as sodium lauryl sulfate and magnesium stearate, as well as coloring agents, release agents, coating agents, sweetening, flavoring and perfuming agents, preservatives and antioxidants may be present in the formulated agents.

Subject compositions may be suitable for oral, nasal (e.g., by inhalation using a dry powder formulation or a nebulized formulation), topical (including buccal and sublingual), pulmonary (including aerosol administration), rectal, vaginal, aerosol and/or parenteral (e.g., by injection, for example, intravenous, intramuscular, or subcutaneous injection) administration. The formulations may conveniently be presented in unit dosage form and may be prepared by any methods well known in the art of pharmacy. The amount of a compound disclosed herein that may be combined with a carrier material to produce a single dose may vary depending upon the identity of the compound, the subject being treated, and the particular mode of administration.

Methods of preparing these formulations include the step of bringing into association compositions of the disclosure with the carrier and, optionally, one or more accessory ingredients. In general, the formulations are prepared by uniformly and intimately bringing into association agents with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition thereof as an active ingredient. Compositions of the disclosure may also be administered as a bolus, electuary, or paste.

In solid dosage forms for oral administration (capsules, tablets, pills, dragees, powders, granules and the like), the subject composition is mixed with one or more pharmaceutically acceptable excipients selected from: (1) fillers or extenders, such as starches, dextrose, lactose, sucrose, glucose, mannitol, and/or silicic acid; (2) binders, such as, for example, celluloses (e.g., microcrystalline cellulose, methyl cellulose, hydroxypropylmethyl cellulose (HPMC) and carboxymethylcellulose), alginates, gelatin, polyvinyl pyrrolidone, sucrose and/or acacia; (3) humectants, such as glycerol; (4) disintegrating agents, such as croscarmellose sodium, sodium carboxymethyl starch (sodium starch glycolate), crosslinked polyvinylpurrolidone (crospovidone), gellan gum, xanthan gum, agar-agar, calcium carbonate, potato or tapioca starch, alginic acid and sodium alginate, certain silicates and especially calcium silicate, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such as talc, calcium stearate, magnesium stearate, solid polyethylene glycols, sodium lauryl sulfate, and mixtures thereof; (10) coloring agents; (11) complexing agents such as cyclodextrins and modified cyclodextrins including preferably (2-hydroxypropyl)-β-cyclodextrin and sulfobutylether-β-cyclodextrin; (12) matrix-forming polymeric excipients such as polyvinyl pyrrolidine (PVP), e.g. PVP K30, acrylic polymers and co-polymers such as the different grades of Eudragit and preferably Eudragit L100, hydroxypropylmethyl cellulose acetate succinate (HPMCAS), other copolymers such as polyethylene glycol-based copolymers like Soluplus; and (13) carriers, such as sodium citrate or dicalcium phosphate. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like. The disclosed excipients may serve more than one function. For example, fillers or binders may also be disintegrants, glidants, antiadherents, lubricants, sweeteners and the like. It is possible in accordance with the present invention to use two or more excipients, wherein said two or more excipients may belong to the same and/or different categories. There is no restriction in this respect.

Preferred Oral Formulations

Binders

A binder is advantageously used for increasing the particle size of active ingredient alone or with excipients and improve its handling properties. There is no particular limitation on the binder material that can be employed in the present invention.

Suitable binder materials include povidone (polyvinylpyrrolidone), copovidone (Poly(1-vinylpyrrolidone-co-vinyl acetate)), maltodextrin, poloxamer (a block copolymer with a first poly(ethylene oxide) block, a second and central poly(propylene oxide) block and a third poly(ethylene oxide) block), polyethylene glycol, polyethylene oxide, magnesium aluminosilicate, gelatin, acacia, alginic acid, carbomer (e.g. carbopol), dextrin, dextrates (a purified mixture of saccharides developed from the controlled enzymatic hydrolysis of starch), guar gum, hydrogenated vegetable oil, liquid glucose, wax, starch (pregelatinized and plain), sodium alginate and mixtures thereof.

The use of povidone and copovidone is preferred.

The binder may be present in a relative amount of from 0.5 wt % to 15 wt %, preferably from 1 wt % to 12 wt % and more preferably 4 wt % to 10 wt %.

Diluents

Diluents are advantageously used for increasing the bulk of the pharmaceutical composition and for facilitating handling of the composition. There is no particular limitation on the diluent material that can be employed in the present invention.

Suitable diluent materials include mannitol, isomalt, histidine, lactose (including anhydrous or monohydrate forms), calcium phosphate (including dibasic and tribasic calcium phosphate), calcium carbonate, calcium sulfate, sucrose, fructose, maltose, xylitol, sorbitol, maltitol, aluminium silicate, dextrose, starch (pregelatinized or plain), glucose, dextrates (a purified mixture of saccharides developed from the controlled enzymatic hydrolysis of starch), magnesium carbonate, and mixtures thereof.

The use of mannitol, xylitol, sorbitol, isomalt and/or histidine is preferred. Mannitol is particularly preferred.

The diluent may be present in a relative amount that is not particularly restricted. Suitable amounts may range from 2 wt % to 85 wt %, preferably from 8 wt % to 80 wt % and more preferably 10 wt % to 50 wt %.

Surfactant

A surfactant may advantageously be used for assisting wettability of the tablet and of the active ingredient. The surfactant is an optional but preferred component. There is no particular limitation on the surfactant material that can be employed in the present invention Suitable surfactant materials include sodium lauryl sulfate, poloxamer, sodium docusate, sorbitan esters, polyethylene oxide, polysorbate 20, polysorbate 40, polysorbate 60, polysorbate 80 (ethoxylated sorbitan esterified with fatty acids wherein the number indicates the number of repeating units of polyethylene glycol), and mixtures thereof.

The use of sodium lauryl sulfate is preferred.

The surfactant may be present in a relative amount that is not particularly restricted. Suitable amounts may range from 0 wt % or more to 7 wt %, preferably from 0.1 wt % to 6.5 wt % and more preferably 1 wt % to 6 wt %.

Disintegrant

A disintegrant is used for accelerating disintegration of the pharmaceutical composition to thereby assist in dissolution and uptake of the active ingredient. There is no particular limitation on the disintegrant material that can be employed in the present invention.

Suitable disintegrant materials include crosslinked polyvinylpurrolidone (crospovidone), sodium carboxymethyl starch (sodium starch glycolate), croscarmellose sodium, gellan gum, xanthan gum, magnesium aluminosilicate, sodium alginate, pregelatinized starch, alginic acid, guar gum, homo- and copolymers of (meth)acrylic acid and salts thereof such as polacrilin potassium, and mixtures thereof.

The use of crospovidone is preferred.

The disintegrant may be present in a relative amount that is not particularly restricted. Suitable amounts may range from 0 wt % or more to 20 wt %, preferably from 1 wt % to 15 wt % and more preferably 2 wt % to 10 wt %.

Glidant

A glidant is advantageously used for improving flowability of the pharmaceutical composition to thereby improve its handling properties. The glidant is an optional but preferred component. There is no particular limitation on the glidant material that can be employed in the present invention.

Suitable glidant materials include colloidal silica dioxide, magnesium oxide, magnesium silicate, tribasic calcium phosphate, and mixtures thereof.

The use of colloidal silica dioxide is preferred.

The glidant may be present in a relative amount that is not particularly restricted. Suitable amounts may range from 0 wt % or more to 5 wt %, preferably from 0.1 wt % to 4 wt % and more preferably 0.2 wt % to 1 wt %.

Lubricant

Lubricants are advantageously used to facilitate tableting, in particular by preventing sticking of the tablets to the tablet punch. The lubricant is an optional but preferred component. There is no particular limitation on the lubricant material that can be employed in the present invention.

Suitable lubricant materials include magnesium stearate, sodium stearyl fumarate, talc, stearic acid, leucine, poloxamer, polyethylene glycol, glyceryl behenate, glycerin monostearate, magnesium lauryl sulfate, sucrose esters of fatty acids, calcium stearate, aluminum stearate, hydrogenated castor oil, hydrogenated vegetable oil, mineral oil, sodium benzoate, zinc stearate, palmitic acid, carnauba wax, sodium lauryl sulfate, polyoxyethylene monostearates, calcium silicate, and mixtures thereof.

The use of a lubricant selected from magnesium stearate and sodium stearyl fumarate, and combinations thereof is preferred.

The lubricant may be present in a relative amount that is not particularly restricted. Suitable amounts may range from 0 wt % or more to 7 wt %, preferably from 0.1 wt % to 4 wt % and more preferably 0.5 wt % to 3.5 wt %.

Matrix Forming Polymers and Copolymers

Suitable matrix-forming polymers and copolymers include polyvinyl pyrrolidine (PVP), acrylic polymers and co-polymers such as the different grades of Eudragit, hydroxypropylmethyl cellulose acetate succinate (HPMCAS), as well as other copolymers such as polyethylene glycol-based copolymers like Soluplus.

Preferred matrix-forming polymers and copolymers are HPMC AS and Soluplus.

The matrix-forming polymers and copolymers may be present in a relative amount that is not particularly restricted. Suitable amounts may range from 0.1 g to 10 g, preferably from 0.2 g to 5 g and more preferably from 0.3 g to 4 g.

Complexing Agents

Suitable complexing agents include cyclodextrins and modified cyclodextrins.

Preferred complexing agents include (2-hydroxypropyl)-β-cyclodextrin and sulfobutylether-β-cyclodextrin.

The complexing agents may be present in a relative amount that is not particularly restricted. Suitable amounts may range from 0.1 g to 24 g, preferably from 0.1 g to 10 g and more preferably from 0.1 g to 5 g.

Other Types of Excipients

The composition of the present invention may contain further excipients that are commonly used in the art.

Such further excipients may include release rate modifiers, plasticizer, film forming agent, colorant, anti-tacking agent and/or pigment for coating the compositions of the present invention. Further types of excipients, which may be present, include flavoring agents, sweeteners, antioxidants, absorption accelerators and/or bulking agents. Relative amounts of such excipients are not particularly limited. They may be determined by the skilled person based on common general knowledge and routine procedures.

Film forming agents are advantageously used for providing the tablets of the invention with a coherent coating. Suitable film forming agents include isomalt, polyvinyl alcohol, polyethylene glycol, maltodextrin, sucrose, xylitol, maltitol, enteric coating agents such as materials selected from the group consisting of methyl acrylate-methacrylic acid copolymers, polyvinyl acetate phthalate (PVAP), methyl methacrylate-methacrylic acid copolymers, shellac, sodium alginate and zein. It is preferred to use a combination of film forming agents comprising polyvinyl alcohol and one or more second agents selected from isomalt, maltodextrin, sucrose, xylitol, and maltitol. It is particularly preferred to use a combination of film forming agents comprising at least polyvinyl alcohol and isomalt.

Suitable plasticizers include sorbitol, triacetin, poloxamer, polyethylene glycol, glycerin, propylene glycol, polyethylene glycol monomethyl ether, acetyl tributyl citrate, acetyl triethyl citrate, castor oil, glyceryl monostearate, diacetylated monoglyerides, dibutyl sebacate, diethyl phthalate, triethyl citrate, and tributyl citrate.

For each of the above-mentioned categories of excipients it is possible to use only a single substance or a combination of two or more substances belonging to the same category. Of course, it is not necessary that members of each and every category are present.

Formulations and compositions of the invention may include the compounds disclosed herein in the form of particles of amorphous substance or in any crystalline form. The particle size is not particularly limited. For instance, formulations and compositions may include micronized crystals of the disclosed compounds. Micronization may be performed on crystals of the compounds alone, or on a mixture of crystals and a part or whole of pharmaceutical excipients or carriers. Mean particle size of micronized crystals of a disclosed compound may be for example about 5 to about 200 microns, or about 10 to about 110 microns. The compounds of the invention may also be present in the form of a molecular dispersion within a polymeric matrix. In yet another embodiment, the compounds of the invention may be complexed with suitable complexing agents such as cyclodextrins.

A tablet may be made by compression or molding, optionally with one or more accessory ingredients. Compressed tablets may be prepared using binder (for example, gelatin, microcrystalline cellulose, or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art. The disclosed excipients may serve more than one function. For example, fillers or binders may also be disintegrants, glidants, anti-adherents, lubricants, sweeteners and the like.

It will be appreciated that a disclosed composition may include lyophilized or freeze dried compounds disclosed herein. For example, disclosed herein are compositions that disclosed compounds crystalline and/or amorphous powder forms. Such forms may be reconstituted for use as e.g., an aqueous composition.

Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent. Formulations which are suitable for vaginal administration also include pessaries, tampons, creams, gels, pastes, foams or spray formulations containing such carriers as are known in the art to be appropriate.

Dosage forms for transdermal administration of a subject composition includes powders, sprays, ointments, pastes, creams, lotions, gels, solutions, and patches. The active component may be mixed under sterile conditions with a pharmaceutically acceptable carrier, and with any preservatives, buffers, or propellants that may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the disclosure may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions.

Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

It should be noted that excipients given as examples may have more than one function. For example, fillers or binders can also be disintegrants, glidants, anti-adherents, lubricants, sweeteners and the like.

Pharmaceutical compositions of this disclosure suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. For example, provided herein is an aqueous composition that includes a disclosed compound, and may further include for example, dextrose (e.g., about 1 to about 10 weight percent dextrose, or about 5 weight percent dextrose in water (D5W).

Examples of suitable aqueous and non-aqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants.

It will be appreciated that contemplated formulations, such as oral formulations (e.g. a pill or tablet), may be formulated as controlled release formulation, e.g., an immediate release formulation, a delayed release formulation, or a combination thereof.

In certain embodiments, the subject compounds may be formulated as a tablet, pill, capsule or other appropriate ingestible formulation (collectively hereinafter "tablet"). In certain embodiments, a therapeutic dose may be provided in 10 tablets or fewer. In another example, a therapeutic dose is provided in 50, 40, 30, 20, 15, 10, 5 or 3 tablets.

In a certain embodiment, a disclosed compound is formulated for oral administration as a tablet, capsule, or an aqueous solution or suspension. In another embodiment of a tablet form the tablets are formulated such that the resulting amount of antibacterial agent (or antibacterial agents) provided in 20 tablets, if taken together (e.g., over time) once administered, would provide a therapeutically effective dose and/or a dose of at least the median effective dose (ED50), e.g., the dose at which at least 50% of individuals exhibited the quantal effect of inhibition of bacterial cell growth or protection (e.g., a statistically significant reduction in infection). In a further embodiment, tablets may be formulated such that the total amount of antibacterial agent (or antibacterial agents) provided upon administration in 10, 5, 2 or 1 tablets would provide a therapeutically effective dose and/or at least an ED50 dose to a patient (human or non-human mammal). In other embodiments, the amount of antibacterial agent (or antibacterial agents) provided, upon administration, in 20, 10, 5 or 2 tablets taken in a 24 hour time period would provide a dosage regimen providing, on average, a mean plasma level of the antibacterial agent(s) of a therapeutically effective dose and/or at least the ED50 concentration (the concentration for 50% of maximal effect of, e.g., inhibiting bacterial cell growth). In other embodiments less than 100 times, 10 times, or 5 times the ED50 is provided. In other embodiments, a single dose of tablets (1-20 tablets) provides about 40 mg to 3000 mg of compound(s). These specified unit dose amounts apply also for other oral dosage forms.

Likewise, compounds disclosed herein can be formulated for parenteral administration, as for example, for subcutaneous, intramuscular or intravenous injection, e.g., the antibacterial agent can be provided in a sterile solution or suspension (collectively hereinafter "injectable solution"). The injectable solution may be, in some embodiments, formulated such that the amount of antibacterial agent (or antibacterial agents) provided in, for example, in about 0.1 to about 200 cc bolus injection, or a dose administered intravenously, would provide a dose of at least the median effective dose, or less than 100 times the ED50, or less than 10 or 5 times the ED50. The injectable solution may be formulated such that the total amount of antibacterial agent (or antibacterial agents) provided (upon administration) in 100, 50, 25, 10, 5, 2.5, or 1 cc injections would provide a therapeutically effective amount and/or an ED50 dose to a patient, or less than 100 times the ED50, or less than 10 or 5 times the ED50. In other embodiments, the amount of antibacterial agent (or antibacterial agents) provided, upon administration, in a total volume of 100 cc, 50, 25, 5 or 2 cc to be injected at least twice in a 24 hour time period would provide a dosage regimen providing, on average, a mean plasma level of the antibacterial agent(s) of a therapeutically effective amount and/or at least the ED50 concentration, or less than 100 times the ED50, or less than 10 or 5 times the ED50. In other embodiments, a single dose injection provides about 40 mg to 3000 mg, or about 100 mg to about 1000 mg of antibacterial agent. In case of i.m. administration, the same amount indications apply, in principle, too. However, the upper end of the unit dose range may be lower depending on the solubility of the drug compound and the maximum tolerable amount for injection.

Unit Dosages

If treatment of the patient by the pharmaceutical compositions of the present invention is by means of oral administration, a single unit dose of the pharmaceutical composition of the present invention is typically administered one, two or three times a day. The daily dosage is determined by the physician in accordance with the above guidance taking severity of the infection, gender, weight, age and general condition of the patient into account. Preferred oral daily dosages range from 40 to 3000 mg, preferably 100 mg to 2000 mg. By consequence, typical unit dosages may range from 40 to 2000 mg, depending on the intended frequency of administration.

In case of parenteral administration (for instance in i.v. or i.m. administration), the pharmaceutical compositions of the present invention are typically administered two, three or more times a day. Preferred daily dosages are in the range of from 40 to 3000 mg, so that typical unit dosages are from 40 to 3000 mg and preferably 100 to 1000 mg. The upper limits of the specified ranges are subject to their feasibility. For instance, in case of i.m. administration, it may happen that the maximum dose that can be administered in a single shot is restricted due to low solubility and correspondingly increased volume of the drug solution. In such a case, the maximum unit dosages are limited by the maximum tolerated dose.

Drug Combinations

Compositions are also contemplated herein that include one or more of the disclosed compounds with a second component. Second components in such compositions of the present disclosure are usually an antibiotic agent other than a disclosed compound. Additional components may also be present, including FabI inhibitors or other antibiotic agents. The contemplated methods of treatment disclosed herein, in some embodiments, may further comprise administering another agent such as one described below. For example, a method of treating a bacterial infection is provided that comprises administering a disclosed compound and further comprises administering an antibiotic agent or antibacterial agent described below. The compound disclosed herein and the second component may be part of the same dosage form or may be formulated in two separate dosage forms. If they are formulated in two separate dosage forms, the dosage form with the second component may be administered at the same time, before or after the dosage form with the compound disclosed herein.

Non-limiting examples of antibiotic agents that may be used in the antibacterial compositions of the disclosure include cephalosporins, quinolones and fluoroquinolones, penicillins, penicillins and beta lactamase inhibitors, carbepenems, monobactams, macrolides and lincosamines, glycopeptides, rifampin, oxazolidonones, tetracyclines, aminoglycosides, streptogramins, sulfonamides, and others. Each family comprises many members.

Cephalosporins can be further categorized by generation. Non-limiting examples of cephalosporins by generation include the following. Examples of cephalosporins: First generation compounds include Cefadroxil, Cefazolin, Cephalexin, Cephalothin, Cephapirin, and Cephradine. Second generation compounds include Cefaclor, Cefamandol, Cefonicid, Cefotetan, Cefoxitin, Cefprozil, Ceftmetazole, Cefuroxime, Cefuroxime axetil, and Loracarbef. Third generation include Cefdinir, Ceftibuten, Cefditoren, Cefetamet, Cefpodoxime, Cefprozil, Cefuroxime (axetil), Cefuroxime (sodium), Cefoperazone, Cefixime, Cefotaxime, Cefpodoxime proxetil, Ceftazidime, Ceftizoxime, and Ceftriaxone. Fourth generation compounds include Cefepime.

Non-limiting examples of quinolones and fluoroquinolones include Cinoxacin, Ciprofloxacin, Enoxacin, Gatifloxacin, Grepafloxacin, Levofloxacin, Lomefloxacin, Moxifloxacin, Nalidixic acid, Norfloxacin, Ofloxacin, Sparfloxacin, Trovafloxacin, Oxolinic acid, Gemifloxacin, and Perfloxacin.

Non-limiting examples of penicillins include Amoxicillin, Ampicillin, Bacampicillin, Carbenicillin Indanyl, Mezlocillin, Piperacillin, and Ticarcillin.

Non-limiting examples of penicillins and beta lactamase inhibitors include Amoxicillin-Clavulanic Acid, Ampicillin-Sulbactam, Benzylpenicillin, Cloxacillin, Dicloxacillin, Methicillin, Oxacillin, Penicillin G (Benzathine, Potassium, Procaine), Penicillin V, Piperacillin+Tazobactam, Ticarcillin+Clavulanic Acid, and Nafcillin. Non-limiting examples of carbepenems include Imipenem-Cilastatin and Meropenem.

A non-limiting example of a monobactam includes Aztreonam. Non-limiting examples of macrolides and lincosamines include Azithromycin, Clarithromycin, Clindamycin, Dirithromycin, Erythromycin, Lincomycin, and Troleandomycin. Non-limiting examples of glycopeptides include Teicoplanin and Vancomycin. Non-limiting examples of rifampins include Rifabutin, Rifampin, and Rifapentine. A non-limiting example of oxazolidonones includes Linezolid. Non-limiting examples of tetracyclines include Demeclocycline, Doxycycline, Methacycline, Minocycline, Oxytetracycline, Tetracycline, and Chlortetracycline.

Non-limiting examples of aminoglycosides include Amikacin, Arbakacin, Gentamicin, Kanamycin, Sisomicin, Arbekacin, Neomycin, Netilmicin, Streptomycin, Tobramycin, and Paromomycin. A non-limiting example of streptogramins includes Quinopristin+Dalfopristin.

Non-limiting examples of sulfonamides include Mafenide, Silver Sulfadiazine, Sulfacetamide, Sulfadiazine, Sulfamethoxazole, Sulfasalazine, Sulfisoxazole, Trimethoprim-Sulfamethoxazole, and Sulfamethizole.

Non-limiting examples of other antibiotic agents include Bacitracin, Chloramphenicol, Colistimethate, Fosfomycin, Isoniazid, Methenamine, Metronidazole, Mupirocin, Nitrofurantoin, Nitrofurazone, Novobiocin, Polymyxin B, Spectinomycin, Tobramycin, Tigecycline, Trimethoprim, Colistin, Cycloserine, Capreomycin, Pyrazinamide, para-Aminosalicyclic acid, and Erythromycin ethylsuccinate+sulfisoxazole.

Therapeutic Uses

Medical Indications

The compounds of the present invention may be used for treating bacterial infections in a patient. They are in particular suitable for use in treating infections by *N. gonorrhoeae*. Other therapeutic indications for which the compounds of the present invention may be used are as follows:

*Bacillus* Spp, in particular *Bacillus cereus, Bacillus coagulans, Bacillus megaterium,*
*Bacillus subtilis, Bacillus anthacis*
*Bartonella* Spp.
*Brucella* Spp, in particular *Brucella abortus, Brucella melitensis.*
*Campylobacter* Spp., in particular *Campylobacter jejuni, Campylobacter coli*
*Enterococcus faecalis, Enterococcus faecium, Legionella pneumophila.*
*Listeria* Spp. In particular *Listeria monocytogenes.*
*Proteus mirabilis, Providencia stuartii.*
*Rickettsia* Spp., in particular *Rickettsia rickettsii.*
*Burkholderia* Spp., in particular *Burkholderia pseudomallei, Burkholderia mallei, Burkholderia cenocepacia.*
*Bordetella pertussis, Bordetella parapertussis. Haemophilus influenza, Kingella kingae, Moraxella catarrhalis.*
*Streptomyces* Spp.
*Nocardioides* Spp.
*Frankia* Spp.
*Propionibacterium acnes.*
*Mycobacterium* Spp., in particular *Mycobacterium smegmatis, Mycobacterium abscessus, Mycobacterium leprae, Mycobacterium tuberculosis, Mycobacterium avium.*

Patients

The compounds of the present invention may be used for treating bacterial infections in patients that are human patients or non-human animals, preferably humans and non-human mammals.

Daily Dosages

The dosage of any disclosed compound or composition will vary depending on the symptoms, age and body weight of the patient, the nature and severity of the disorder to be treated or prevented, the route of administration, and the form of the subject composition. Any of the subject formulations may be administered in a single dose or in divided doses. Dosages for the compositions may be readily determined by techniques known to those of skill in the art or as taught herein.

In certain embodiments, the dosage of the subject compounds will generally be in the range of about 0.01 ng to about 10 g per kg body weight, specifically in the range of about 1 ng to about 0.1 g per kg, and more specifically in the range of about 100 ng to about 10 mg per kg.

An effective dose or amount, and any possible effects on the timing of administration of the formulation, may need to be identified for any particular composition of the disclosure. This may be accomplished by routine experiment as described herein, using one or more groups of animals (preferably at least 5 animals per group), or in human trials if appropriate. The effectiveness of any subject composition and method of treatment or prevention may be assessed by administering the composition and assessing the effect of the administration by measuring one or more applicable indices, and comparing the post-treatment values of these indices to the values of the same indices prior to treatment.

The precise time of administration and amount of any particular subject composition that will yield the most effective treatment in a given patient will depend upon the activity, pharmacokinetics, and bioavailability of a subject composition, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during the treatment period. Treatment, including composition, amounts, times of administration and formulation, may be optimized according to the results of such monitoring. The patient may be periodically reevaluated to determine the extent of improvement by measuring the same parameters. Adjustments to the amount(s) of subject composition administered and possibly to the time of administration may be made based on these reevaluations.

Treatment may be initiated with smaller dosages which are less than the optimum dose of the compound. Thereafter, the dosage may be increased by small increments until the optimum therapeutic effect is attained.

The use of the subject compositions may reduce the required dosage for any individual agent contained in the compositions because the onset and duration of effect of the different agents may be complimentary.

Toxicity and therapeutic efficacy of subject compositions may be determined by standard pharmaceutical procedures in cell cultures or experimental animals, e.g., for determining the LD50 and the ED50.

The data obtained from the cell culture assays and animal studies may be used in formulating a range of dosage for use in humans. The dosage of any subject composition lies preferably within a range of circulating concentrations that include the ED50 with little or no toxicity and/or that give rise to a statistically significant reduction in infection in at least 50% e.g. 60%, 70%, 80%, 90%, 100%, of individuals with little or no toxicity, wherein little toxicity may for instance mean non serious and/or predictable and transient toxicity. For instance, the dosage of the subject composition may be chosen such that a reasonable benefit/risk ratio is accomplished by the treatment. The dosage may vary within this range depending upon the dosage form employed and the route of administration utilized. For compositions of the disclosure, the therapeutically effective dose may be estimated initially from cell culture assays.

Administration Frequency

The compounds and compositions disclosed herein may be administered once or multiple times a day, in particular once daily (qd), twice daily (bid), three times a day (tid) or four times a day (qid).

Duration of Treatment

The compounds and compositions disclosed herein may be administered for an unlimited period of time. It is advantageous that they are administered for a period of time to eradicate the bacterial infection completely or at least to such an extent that the patient's immune system can cope with any remaining pathologic bacteria. Typical durations of administration are from 1 day to 2 weeks and especially from 1 to 5 days. In case of i.m. administration, typical durations of administration may range from 1 shot to 4 shots and preferably 1 shot. Multiple shots may be administered on the same day, on consecutive days or on in intervals with days of no administration in between.

Methods of Treatment

In another aspect, disclosed herein are methods of treating a bacterial infection, comprising administering to a patient in need thereof the pharmaceutical composition comprising a disclosed compound.

In certain embodiments, disclosed herein are methods of treating a *N. gonorrhoeae* infection in a patient in need thereof, comprising administering a compound of the invention as disclosed herein. Other contemplated methods include treating infections by one or more of the bacteria or microbes listed above in a patient in need thereof.

For example, disclosed here is a method of treating an *N. gonorrhoeae* or other bacterial infection in a patient in need thereof comprising administering a composition comprising a disclosed compound, which method further comprises administering, in the same or a separate dosage form, an additional antibacterial or antibiotic agent as disclosed herein.

Abbreviations

The following abbreviations are used in the present disclosure.

CC Column chromatography
DCM Dichloromethane
N Normal
g Gram
pH Potential of Hydrogen
mol Mole
v/v Volume/volume
vol Volume
m/z Mass to charge ratio
° C. degree Celsius
TEA Triethylamine
$Et_2O$ Diethyl ether
HPLC High performance liquid chromatography
Boc tert-butyloxycarbonyl
h hour
mL milliliter
eq. Equivalent
M Mass
Me Methyl, $CH_3$
MeOH Methanol
AcOH Acetic acid
THF Tetrahydrofuran
DIPEA N,N-Diisopropylethylamine
$Pd(OAc)_2$ Palladium(II) acetate
EtOH Ethanol
DCE 1,2-Dichloroethane
EtOAc Ethyl acetate
$Et_3N$ Triethylamine
Aq. Aqueous
RT, rt Room temperature
$R^t$, $t_{ret}$ Retention time
DMF Dimethylformamide
ACN Acetonitrile
$NH_4OAc$ Ammonium acetate
TFA Trifluoroacetic acid
HOBT/HOBt 1-Hydroxybenzotriazole
TLC Thin layer chromatography
$H_2O$ Water
sat. Saturated
sol. Solution
EDCl 1-Ethyl-3-(3-dimethylaminopropyl)carbodiimide
NMR Nuclear Magnetic Resonance
s singlet
d doublet
t triplet
m multiplet
dd double of doublet
MHz Megahertz
ppm parts per million
H Proton
J Coupling constant
UPLC-MS Ultra-performance liquid chromatography-tandem mass spectrometry
DMSO Dimethyl sulfoxide
$CDCl_3$ Deuterated chloroform
ML Mother liquor
SCX Strong Cation Exchange Chromatography
LCMS Liquid Chromatography Mass Spectrometry
HATU 1-[Bis(dimethylamino)methylene]-1H-1,2,3-triazolo[4,5-b]pyridinium 3-oxid hexafluorophosphate
HPLC High-performance liquid chromatography
HBTU (2-(1H-benzotriazol-1-yl)-1,1,3,3-tetramethyluronium hexafluorophosphate, Hexafluorophosphate Benzotriazole Tetramethyl Uronium
HCTU 2-(6-Chlor-1H-benzotriazol-1-yl)-1,1,3,3-tetramethylaminium-hexafluorophosphate
TBTU O-(Benzotriazol-1-yl)-N,N,N',N'-tetramethyluronium tetrafluoroborate
COMU (1-Cyano-2-ethoxy-2-oxoethylideneaminooxy)dimethylamino-morpholino-carbenium-hexafluorophosphate
TOMBU N-{[1,3-Dimethyl-2,4,6-trioxotetrahydropyrimidine-5(6H)-ylideneaminooxy](dimethylamino)methylene}-N-methylmethaneaminium hexafluorophosphate
COMBU 4-{[1,3-Dimethyl-2,4,6-trioxotetrahydropyrimidine-5(6H)ylideneaminooxy](dimethylamino)methylene}morpholin-4-ium hexafluorophosphate
$Cy_2NCH_3$ N-Cyclohexyl-N-methylcyclohexanamine
PMB p-Methoxybenzyl
STAB Sodium triacetoxyborohydride
IM or i.m. Intramuscular administration
IV or i.v. Intravenous administration The following examples are in no way intended to limit the scope of the present invention, but are provided only to illustrate the inventive compounds and their preparation.

EXAMPLES

General Procedures

All starting materials and solvents were obtained either from commercial sources or prepared according to the literature citation. Unless otherwise stated all reactions were stirred. Organic solutions were routinely dried over anhydrous magnesium sulfate or sodium sulfate Column chromatography was performed on pre-packed silica (230-400 mesh, 40-63 μm) cartridges using the eluent indicated. SCX was purchased from Silicycle and treated with 1M hydrochloric acid prior to use. Unless stated otherwise the reaction mixture to be purified was first diluted with MeOH and made acidic with a few drops of AcOH. This solution was loaded directly onto the SCX and washed with MeOH. The desired material was then eluted by washing with 0.7 M NH3 in MeOH.

Analytical Methods

Analytical LCMS

Analytical LCMS was carried out using either acidic or basic methods as follows:

Method 1a:

Waters X-Select CSH C18, 2.5 μm, 4.6×30 mm column eluting with a gradient of 0.1% Formic acid in MeCN in 0.1% Formic acid in water. The gradient from 5-95% 0.1% Formic acid in MeCN occurs between 0.00-3.00 minutes at 2.5 mL/min with a flush from 3.01-3.5 minutes at 4.5 mL/min. A column re-equilibration to 5% MeCN is from 3.60-4.00 minutes at 2.5 mL/min. UV spectra of the eluted peaks were measured using an Agilent 1260 Infinity or Agilent 1200 VWD at 254 nm. Mass spectra were measured using an Agilent 6120 or Agilent 1956 MSD running with positive/negative switching or an Agilent 6100 MSD running in either positive or negative mode.

Method 1b:

Waters X-Select BEH C18, 2.5 μm, 4.6×30 mm column eluting with a gradient of MeCN in aqueous 10 mM ammonium bicarbonate. The gradient from 5-95% MeCN occurs between 0.00-3.00 minutes at 2.5 mL/min with a flush from 3.01-3.5 minutes at 4.5 mL/min. A column re-equilibration to 5% MeCN is from 3.60-4.00 minutes at 2.5 mL/min. UV spectra of the eluted peaks were measured using an Agilent 1260 Infinity or Agilent 1200 VWD at 254 nm. Mass spectra were measured using an Agilent 6120 or Agilent 1956 MSD running with positive/negative switching or an Agilent 6100 MSD running in either positive or negative mode.

Method 1c:

The product was analysed by UPLC (Acquity and SQD Waters system, Water (HPLC grade) UPLC® BEH C18, 50×2.1 mm, 1.7 μm, (0.1% HCOOH in water, 0.1% HCOOH in acetonitrile) 3 min method, 5-95% MeCN/water).

All UPLC-MS analyses were performed on a UPLC Acquity and SQD Waters system. Masslynx software was used to launch and analyse experiments using OALogin and automatic or manual integrations. Details of the method used are listed below.

Chemicals: Water (HPLC grade)

Acetonitrile ACN (HPLC grade)

Formic acid 98% (for LC-MS)

Mobile Phase Description:

| | |
|---|---|
| Solution A1: | 0.06% HCOOH in water |
| Solution B1: | 0.06% HCOOH in acetonitrile |
| Solution A2: | Water |
| Solution B2: | Acetonitrile |
| Weak Wash | Water-ACN (7:3) |

-continued

| | |
|---|---|
| Strong Wash | Water-ACN (1:9) |
| Seal Wash | Water-ACN (1:1) |

UPLC Parameters:

| | |
|---|---|
| Column: | UPLC ® BEH C18, 50 × 2.1 mm, 1.7 μm |
| Mobile phase: | A1: 0.06% HCOOH in water<br>B1: 0.06% HCOOH in acetonitrile |

| Gradient: | Time [min] | FlowRate [mL/min] | A1 [%] | B1 [%] |
|---|---|---|---|---|
| | 0.00 | 0.9 | 95 | 5 |
| | 0.10 | 0.9 | 95 | 5 |
| | 3.00 | 0.9 | 0 | 100 |
| | 3.10 | 0.9 | 95 | 5 |

| | |
|---|---|
| Column Temperature: | 40° C. |
| UV Detection: | 210-400 nm |
| Injection volume: | 1 to 10 μL (on demand) |

MASS SPECTROSCOPY Method: Performed based on MS Tune parameters: Routine.ipr as shown below.

| AS+ Source | |
|---|---|
| Voltages | |
| Capillary (kV) | 3.50 |
| Cone (V) | 30 |
| Extractor (V) | 3 |
| RF Lens (V) | 0.1 |
| Temperatures | |
| Source Temp (° C.) | 150 |
| Dessolvation Temp (° C.) | 350 |

| AS+ Source | |
|---|---|
| Analyser | |
| LM resolution | 15.0 |
| HM resolution | 15.0 |
| Ion energy | 0.6 |
| Gain | 1.00 |

The method is carried out based on the information "MS Method: pos_neg_3mn_30v". Points per peak: 3.846. Total run time: 3.0 min. MS scan, Time 0.00 to 3.00, Mass 100.00 to 900.00 $ES^+$.

UPLC-MS mass spectra were recorded on a SQ detector Acquity Waters (Waters Corporation, Waters Milford, 34 Maple St., Milford, USA) equipped with software Empower 2 pro in a positive ionization mode. Ionization conditions: Capilary 2.25 KV, Cone 160 V, Source 100° C., Desolvation 150° C.; Gas flow→Desolvation 500 L/h, Cone 50 L/h.

Analytical UPLC/MS

Alternatively analytical UPLC/MS was carried out using either acidic or basic methods as follows:

Method 2a: Waters Acquity CSH C18, 1.7 μm, 2.1×30 mm column eluting with a gradient of 0.1% Formic acid in MeCN in 0.1% Formic acid in water. The gradient is structured with a starting point of 5% MeCN held from 0.0-0.11 minutes. The gradient from 5-95% occurs between 0.11-2.15 minutes with a flush from 2.15-2.56 minutes. A column re-equilibration to 5% MeCN is from 2.56-2.83 minutes. UV spectra of the eluted peaks were measured using an Acquity PDA and mass spectra were recorded using an Acquity QDa detector with ESI pos/neg switching.

Method 2b: Waters Acquity BEH C18, 1.7 μm, 2.1×30 mm column eluting with a gradient of MeCN in aqueous 10 mM Ammonium Bicarbonate. The gradient is structured with a starting point of 5% MeCN held from 0.0-0.11 minutes. The gradient from 5-95% occurs between 0.11-2.15 minutes with a flush from 2.15-2.56 minutes. A column re-equilibration to 5% MeCN is from 2.56-2.83 minutes. UV spectra of the eluted peaks were measured using an Acquity PDA and mass spectra were recorded using an Acquity QDa detector with ESI pos/neg switching.

Preparative HPLC

Preparative HPLC was carried out using a Waters Xselect CSH C18, 5 μm, 19×50 mm column using either a gradient of either 0.1% Formic Acid in MeCN in 0.1% aqueous Formic Acid or a gradient of MeCN in aqueous 10 mM Ammonium Bicarbonate; or a Waters Xbridge BEH C18, 5 μm, 19×50 mm column using a gradient MeCN in aqueous 10 mM Ammonium Bicarbonate. Fractions were collected following detection by UV at a single wavelength measured by a variable wavelength detector on a Gilson 215 preparative HPLC or Varian PrepStar preparative HPLC; by mass and UV at a single wavelength measured by a ZQ single quadrupole mass spectrometer, with positive and negative ion electrospray, and a dual wavelength detector on a Waters FractionLynx LCMS.

Preparative Chiral High Performance Liquid Chromatography

Method 3a: Chiralpak® IA (Daicel Ltd.) column (2×25 cm), flow rate 13.5 mL $min^{-1}$ eluting with a mixture of (% of ethanol) ethanol in a 4:1 mixture of heptane+0.2% TFA and chloroform, UV detection at 254 nm. Samples were loaded onto the column via an at-column dilution pump, pumping chloroform (1.5 mL $min^{-1}$) for the duration of the run, giving a combined flow rate of 15 mL $min^{-1}$.

Method 3b: Chiralpak® IC (Daicel Ltd.) column (2×25 cm), flow rate 13.5 mL $min^{-1}$ eluting with a mixture of (% of ethanol) ethanol in heptane+0.2% diethylamine, UV detection at 254 nm. Samples were loaded onto the column via an at-column dilution pump, pumping chloroform (1.5 mL $min^{-1}$) for the duration of the run, giving a combined flow rate of 15 m L $min^{-1}$.

Analytical Chiral High Performance Liquid Chromatography

Method 4a: Chiralpak® IA (Daicel Ltd.) column (4.6 mm×25 mm), flow rate 1 mL $min^{-1}$ eluting with a mixture of (% of ethanol) ethanol in a 4:1 mixture of isohexane+0.2% TFA and chloroform, UV detection at 254 nm.

Method 4b: Chiralpak® IC (Daicel Ltd.) column (4.6 mm×25 mm), flow rate 1 mL $min^{-1}$ eluting with a mixture of (% of ethanol) ethanol in isohexane+0.2% diethylamine, UV detection at 254 nm.

$^1$H NMR Spectroscopy $^1$H NMR Spectra were acquired on a Bruker Avance III spectrometer at 400 MHz using residual undeuterated solvent as reference.

Example 1. Synthesis of (E)-N-((4-amino-3-methylbenzofuran-2-yl)methyl)-N-methyl-3-(8-oxo-6,7,8,9-tetrahydro-5H-pyrido[2,3-b]azepin-3-yl)acrylamide (Compound 5)

General Synthetic Scheme.

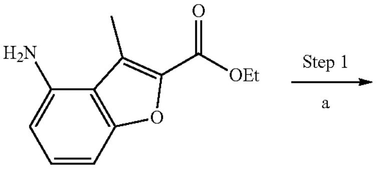

1

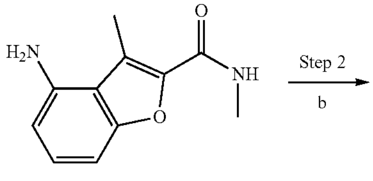

2

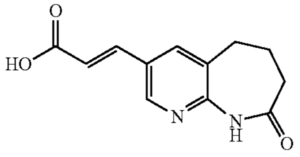

4

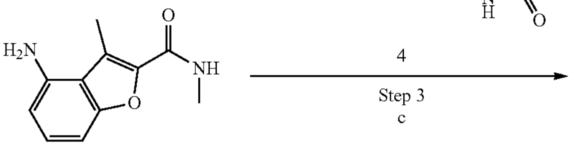

3

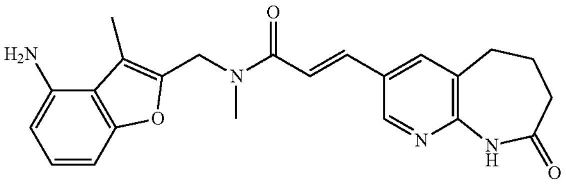

5

Reaction conditions: a) $MeNH_2$, EtOH; b) $BH_3$ THF, reflux; c) HATU, DIPEA, DMF The synthesis of (E)-3-(8-oxo-6,7,8,9-tetrahydro-5H-pyrido[2,3-b]azepin-3-yl)acrylic acid (compound 4) was previously reported by AFFINIUM PHARMECEUTICALS, INC: WO2007/67416, 2007, A2.

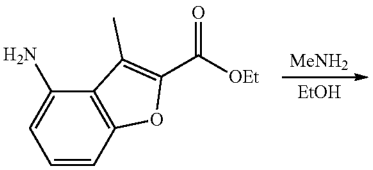

1

-continued

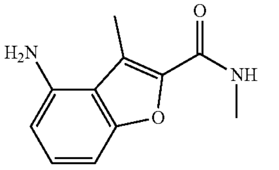

2

Step 1. 4-Amino-N,3-dimethylbenzofuran-2-carboxamide (compound 2). Ethyl 4-amino-3-methylbenzofuran-2-carboxylate 1 (0.1 g, 0.46 mmol) was dissolved in methanamine (10 mL, 80 mmol, 33% in EtOH) and the reaction was stirred at RT for ~36 h. The solvent was removed in vacuo to give the desired product 2 as a pale brown crystalline solid (0.097 g, quantitative). $R^t$ 1.25 min (Method 1a); m/z 205 $[M+H]^+$ $(ES^+)$. $^1H$ NMR (400 MHz, DMSO-$d_6$): δ, ppm 8.24 (q, J=4.6 Hz, 1H), 7.07 (t, J=8.0 Hz, 1H), 6.68 (dd, J=8.2, 0.8 Hz, 1H), 6.43 (dd, J=7.9, 0.8 Hz, 1H), 5.41 (s, 2H), 2.74 (d, J=4.7 Hz, 3H), 2.72 (s, 3H).

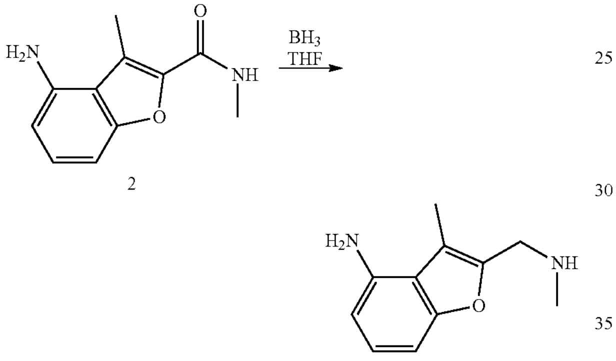

2

3

Step 2. 3-Methyl-2-((methylamino)methyl)benzofuran-4-amine (compound 3). To a suspension of compound 2 (300 mg, 1.47 mmol) in dry THF (30 mL) at 0° C. was added borane tetrahydrofuran complex (7.34 mL, 7.34 mmol, 1 M in THF). After warming to RT the reaction mixture was heated under reflux for 3 h. The mixture was quenched with methanol (20 mL) whilst still at reflux, then 1 N hydrochloric acid (2 mL) was added and the mixture continued to heat at reflux for 30 mins. The mixture was cooled to RT then evaporated to dryness. The residue was taken up into methanol (50 mL) and applied to an SCX column. The column was washed with methanol (50 mL) and the product eluted with 10% methanolic ammonia. The solvent was removed in vacuo to afford the desired product 3 as a yellow oil (0.20 g, 68%). $R^t$ 0.17 min (Method 1a); m/z 160 $[M-NHCH_3]^+$ $(ES^+)$. $^1H$ NMR (400 MHz, DMSO-$d_6$): δ, ppm 6.88 (t, J=7.9 Hz, 1H), 6.63 (dd, J=8.1 Hz, 0.8 Hz, 1H), 6.36 (dd, J=7.8 Hz, 0.8 Hz, 1H), 5.10 (s, 2H), 3.66 (s, 2H), 2.34 (s, 3H), 2.24 (s, 3H).

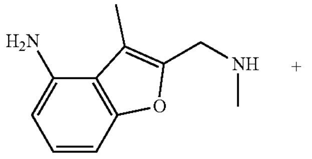

3

-continued

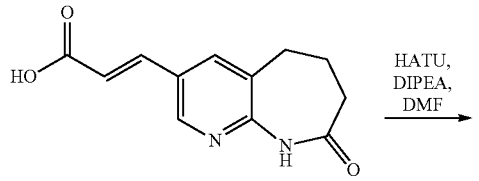

4

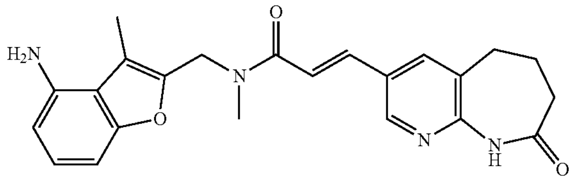

5

Step 3. (E)-N-((4-Amino-3-methylbenzofuran-2-yl)methyl)-N-methyl-3-(8-oxo-6,7,8,9-tetrahydro-5H-pyrido[2,3-b]azepin-3-yl)acrylamide (compound 5). A solution of 3-methyl-2-((methylamino)methyl)benzofuran-4-amine 3 (0.07 g, 0.35 mmol), (E)-3-(8-oxo-6,7,8,9-tetrahydro-5H-pyrido[2,3-b]azepin-3-yl)acrylic acid 4 (0.07 g, 0.29 mmol) and DIPEA (0.26 mL, 1.47 mmol) in DMF (2 mL) was stirred for 10 mins. Then HATU (0.17 g, 0.44 mmol) was added in one portion and the reaction mixture stirred for 2 h. Water (20 mL) was added to the mixture and the resulting precipitate collected by filtration. The solid was washed with water (10 mL) and dried on the filter paper before being dissolved in the minimum amount of DMSO possible and precipitated by addition of water. The solid was collected then the crude material was further purified by chromatography (0-10% MeOH in DCM) to give the compound 5 as a tan solid (0.04 g, 29%). $R^t$ 1.54 min (Method 1a); m/z 405 $[M+H]^+$ $(ES^+)$. $^1H$ NMR (400 MHz, DMSO-$d_6$, 363 K): δ, ppm 9.56 (s, 1H), 8.48 (d, J=2.2 Hz, 1H), 8.02 (d, J=2.2 Hz, 1H), 7.51 (d, J=15.4 Hz, 1H), 7.27 (d, J=15.6 Hz, 1H), 6.92 (t, J=8.0 Hz, 1H), 6.66 (dd, J=8.2 Hz, 0.9 Hz, 1H), 6.41 (dd, J=7.8 Hz, 0.8 Hz, 1H), 4.93 (s, 2H), 4.77 (s, 2H), 3.07 (s, 3H), 2.77 (t, J=7.1 Hz, 2H), 2.43 (s, 3H), 2.32 (t, J=7.2 Hz, 2H), 2.15 (p, J=7.7, 7.3 Hz, 2H).

Example 2. Synthesis of (E)-N-((4-amino-3-methylbenzofuran-2-yl)methyl)-N-methyl-3-(4-oxo-2,3,4,5-tetrahydro-1H-pyrido[2,3-b][1,4]diazepin-8-yl)acrylamide (Compound 7)

General Synthetic Scheme.

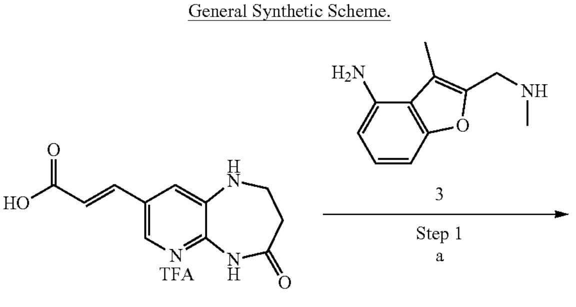

3

6

-continued

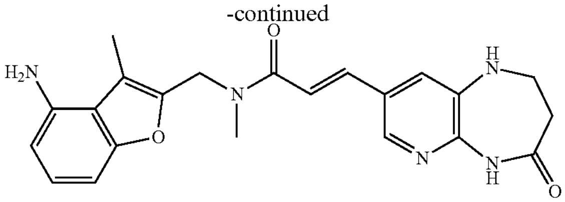

7

Reaction conditions: a) HATU, DIPEA, DMF

The synthesis of (E)-3-(4-oxo-2,3,4,5-tetrahydro-1H-pyrido[2,3-b][1,4]diazepin-8-yl)acrylic acid hydrochloride (compound 6) was previously reported by AFFINIUM PHARMECEUTICALS, INC: WO2007/67416, 2007, A2; AURIGENE DISCOVERY TECHNOLOGIES LIMITED: WO2013/80222, 2013, A1; Ramnauth Jailall and co-workers, Bioorg. Med. Chem. Lett., 2009, 19, pp. 5359-5362.

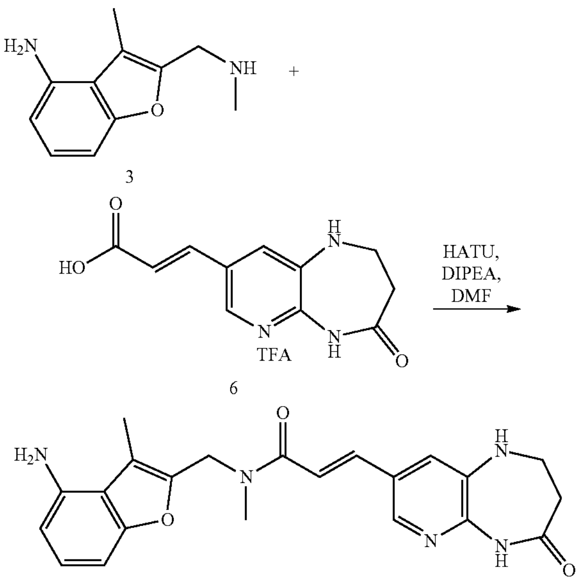

3

6

7

Step 1. (E)-N-((4-Amino-3-methylbenzofuran-2-yl)methyl)-N-methyl-3-(4-oxo-2,3,4,5-tetrahydro-1H-pyrido[2,3-b][1,4]diazepin-8-yl)acrylamide (compound 7). A solution of 3-methyl-2-((methylamino)methyl)benzofuran-4-amine 3 (0.05 g, 0.26 mmol), (E)-3-(4-oxo-2,3,4,5-tetrahydro-1H-pyrido[2,3-b][1,4]diazepin-8-yl)acrylic acid TFA salt 6 (0.05 g, 0.22 mmol) and DIPEA (0.38 mL, 2.19 mmol) in DMF (2 mL) was stirred for 10 mins. Then 2-(3H-[1,2,3]triazolo[4,5-b]pyridin-3-yl)-1,1,3,3-tetramethylisouronium hexafluorophosphate (0.13 g, 0.33 mmol) was added in one portion and the reaction mixture stirred for 2 hours. Water (20 mL) was added to the mixture and the resulting precipitate collected by filtration. The solid was washed with water (10 mL) and dried on the filter paper before being dissolved in the minimum amount of DMSO possible and precipitated by addition of water. The solid was collected then the crude material was further purified by chromatography (0-10% MeOH in DCM) to give the desired product 7 as a yellow solid (0.05 g, 53%). $R^t$ 1.43 min (Method 1a); m/z 406 $[M+H]^+$ ($ES^+$). $^1H$ NMR (400 MHz, DMSO-$d_6$, 363 K): δ, ppm 9.14 (s, 1H), 7.97 (d, J=1.9 Hz, 1H), 7.45-7.34 (m, 2H), 7.09 (d, J=15.7 Hz, 1H), 6.92 (t, J=8.0 Hz, 1H), 6.66 (dd, J=8.2 Hz, 0.8 Hz, 1H), 6.41 (dd, J=7.8 Hz, 0.8 Hz, 1H), 5.82 (d, J=4.6 Hz, 1H), 4.93 (s, 2H), 4.74 (s, 2H), 3.48-3.40 (m, 2H), 3.05 (s, 3H), 2.69-2.62 (m, 2H), 2.43 (s, 3H).

Example 3. Synthesis of (E)-N-methyl-N-((3-methylbenzofuran-2-yl)methyl)-3-(3-oxo-1,2,3,4-tetrahydropyrido[2,3-b]pyrazin-7-yl)acrylamide (Compound 10)

General Synthetic Scheme.

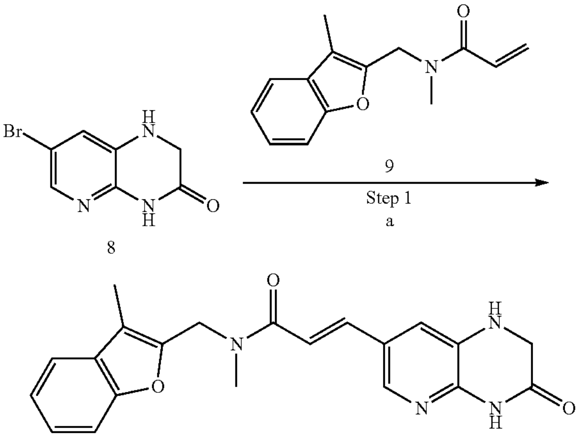

9

8

10

Reaction conditions: a) Pd-162, $Bu_4N^+Cl^-$, $Cy2NCH_3$ Dioxane 80 deg C., 2 h The synthesis of 7-bromo-1,4-dihydropyrido[2,3-b]pyrazin-3(2H)-one (compound 8) was previously reported by CEPHALON, INC—WO2007/130468, 2007, A2.

N-Methyl-N-((3-methylbenzofuran-2-yl)methyl)acrylamide (compound 9) was prepared as described in the patents of AFFINIUM PHARMACEUTICALS, INC.—WO2007/67416, 2007, A2 and VITAS PHARMA RESEARCH PRIVATE LIMITED, WO2013/42035, 2013, A1.

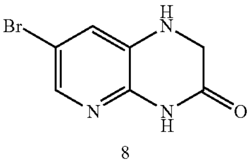

8

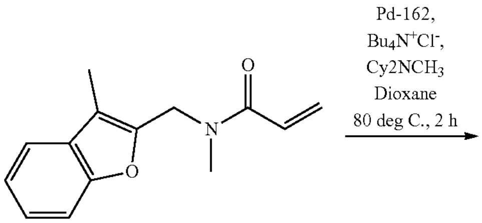

9

-continued

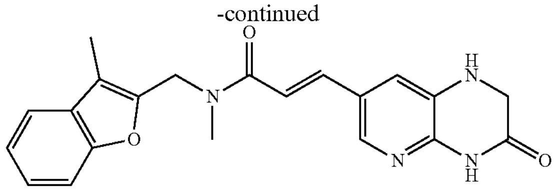

10

Step 1. (E)-N-Methyl-N-((3-methylbenzofuran-2-yl)methyl)-3-(3-oxo-1,2,3,4-tetrahydropyrido[2,3-b]pyrazin-7-yl)acrylamide (compound 10). A reaction vial was charged with N-methyl-N-((3-methylbenzofuran-2-yl)methyl)acrylamide 9 (23.12 mg, 0.101 mmol), 7-bromo-1,2-dihydropyrido[2,3-b]pyrazin-3(4H)-one 8 (23 mg, 0.10 mmol), tetrabutylammonium chloride hydrate (2.98 mg, 10.09 μmol), [P(tBu)3]Pd(crotyl)Cl (Pd-162) (4.03 mg, 10.09 μmmol). The vial was flushed with nitrogen (5 mins). 1,4-Dioxane (3 mL) and N-cyclohexyl-N-methylcyclohexanamine (43.2 μmL, 0.20 mmol) were added and the reaction mixture was purged with nitrogen (5 mins). The mixture was heated to 80° C. for 2 h and allowed to cool to room temperature. The solvent was evaporated to dryness. The residue was taken up in DCM (5 mL) and sat. $NaHCO_3$ (5 mL) was added. The aqueous phase was separated and extracted with DCM (2×5 mL). The combined organic phases were passed through a phase separator and concentrated in vacuo. The crude product was purified by silica chromatography (0-10% MeOH/DCM) to afford the title compound 10 as a yellow solid (6.2 mg, 0.016 mmol, 16% yield). $R^t$ 1.20 min (Method 2a); 377.0 $[M+H]^+$ $(ES^+)$. $^1H$ NMR Acquired at 360K (400 MHz, DMSO-$d_6$): δ, ppm 10.49 (s, 1H), 7.83 (d, J=1.9 Hz, 1H), 7.58-7.54 (m, 1H), 7.47 (dt, J=8.2, 0.8 Hz, 1H), 7.42 (d, J=15.4 Hz, 1H), 7.31-7.23 (m, 3H), 7.07 (d, J=15.9 Hz, 1H), 5.99 (s, 1H), 4.84 (s, 2H), 3.85 (d, J=1.9 Hz, 2H), 3.10 (s, 3H), 2.28 (s, 3H).

Example 4. Synthesis of (E)-3-(2,2-dimethyl-3-oxo-1,2,3,4-tetrahydropyrido[2,3-b]pyrazin-7-yl)-N-methyl-N-((3-methylbenzofuran-2-yl)methyl)acrylamide (Compound 19)

General Synthetic Scheme.

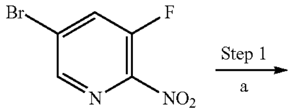

11

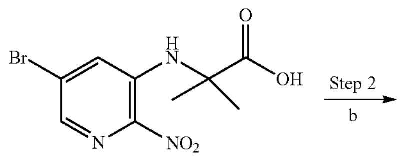

13

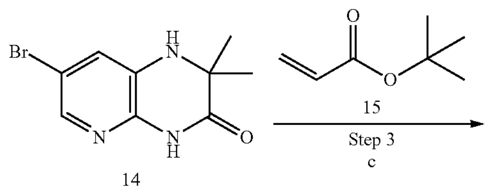

14

-continued

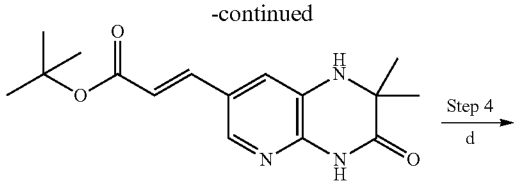

16

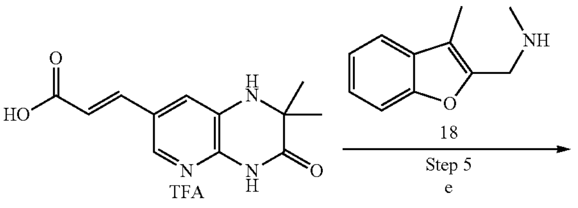

17

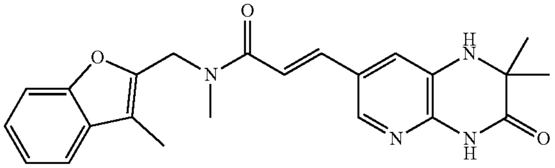

19

Reaction conditions: a) 2-Amino-2-methylpropanoic acid 12, $K_2CO_3$/THF Reflux, overnight; b) Fe, water, EtOH, $NH_4Cl$; c) tri-(o-tolyl)phosphine, $Pd(AcO)_2$, DIPEA, DMF: propionitrile (1:4 V/V); d) TFA/DCM; e) $T_3P$, DIPEA, DMF

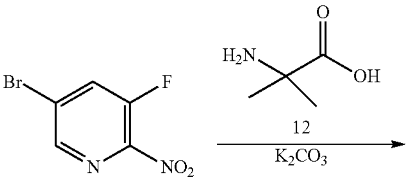

11

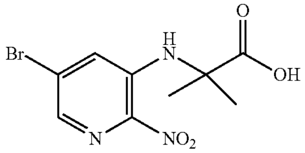

13

Step 1. 2-((5-Bromo-2-nitropyridin-3-yl)amino)-2-methylpropanoic acid (compound 13). A mixture of 5-bromo-3-fluoro-2-nitropyridine 11 (30.0 g, 135.7 mmol), $K_2CO_3$ (38.96 g, 282.31 mmol) and 2-amino-2-methylpropanoic acid 12 (20.9 g, 203.6 mmol) in THF (500 mL) was heated at 90° C. for 16 hours. The progress of reaction was monitored by TLC. The reaction mixture was allowed to cool to RT and concentrated to dryness. The crude product was dissolved in water (500 mL) and washed with ethyl acetate (100 mL). The aqueous layer was acidified with 1N HCl solution to pH 2 and extracted with ethyl acetate (2×250 mL). The organic layer was dried over $NaSO_4$, filtered, and concentrated in vacuo to afford the crude compound. To the crude compound was added 50 mL diethyl ether and stirred for 30 min, filtered the solid mass and dried under vacuum to afford the title compound 13 as a yellow solid (26.0 g, 63% yield). m/z 304/306 $[M+H]^+$ $(ES^+)$. $^1H$ NMR (400 MHz, DMSO-$d_6$): δ, ppm 13.48 (s, 1H), 7.90 (s, 1H), 8.10 (s, 1H), 7.97 (s, 1H), 7.39 (s, 1H), 1.60 (s, 6H).

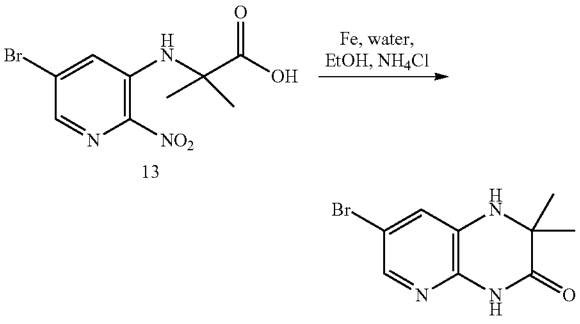

13

14

Step 2. 7-Bromo-2,2-dimethyl-1,4-dihydropyrido[2,3-b]pyrazin-3(2H)-one (compound 14). To a stirred solution of 2-((5-bromo-2-nitropyridin-3-yl)amino)-2-methylpropanoic acid 13 (26.0 g, 85.4 mmol) in EtOH:water (1:1, 520 mL) and was added $NH_4Cl$ (10.42 g, 194 mmol) followed by iron powder (10.31 g, 184.6 mmol). The reaction mixture was stirred at 80° C. for 2 h. The progress of reaction was monitored by TLC. The reaction mixture was allowed to cool to RT and diluted with ethyl acetate (500 mL), filtered through Celite® and washed with THF (200 mL), MeOH (200 mL). The filtrate was concentrated in vacuo to afford the crude compound. To the crude compound was added 50 mL diethyl ether and stirred for 30 min, filtered the solid mass and dried under vacuum to afford the title compound 14 as an off white solid (12.5 g, 57% yield). m/z 256/258 $[M+H]^+$ $(ES^+)$. $^1H$ NMR (400 MHz, DMSO-$d_6$): δ, ppm 10.83 (s, 1H), 7.63 (d, J=2.0 Hz, 1H), 7.09 (d, J=2.0 Hz, 1H), 6.54 (s, 1H), 1.25 (s, 6H).

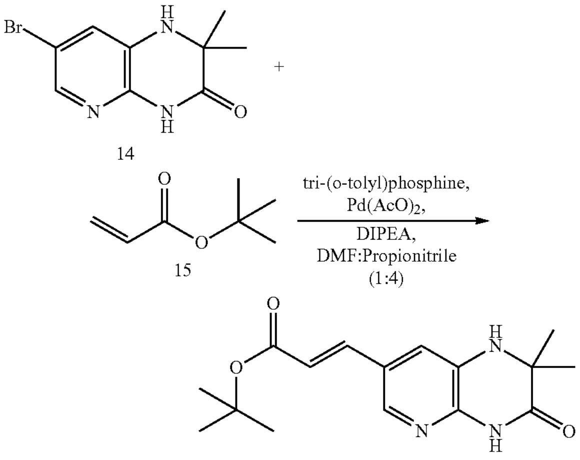

14

15

16

Step 3. tert-Butyl (E)-3-(2,2-dimethyl-3-oxo-1,2,3,4-tetrahydropyrido[2,3-b]pyrazin-7-yl)acrylate (compound 16). In a seal tube, a stirred solution of 7-bromo-2,2-dimethyl-1,4-dihydropyrido[2,3-b]pyrazin-3(2H)-one 14 (5.0 g, 19.5 mmol) and DIPEA (14.3 g, 78.12 mmol) in DMF:propionitrile (1:4, 75 mL) was purged with nitrogen gas for 10 min. Then added tert-butyl acrylate 15 (7.5 g, 58.5 mmol), tri-(o-tolyl)phosphine (1.18 g, 3.9 mmol) and palladium(II) acetate (4.37 g, 1.95 mmol) to the reaction mixture and again purged with nitrogen gas for 5 min. The reaction mixture was heated at 90° C. for 18 h. The progress of reaction was monitored by TLC and LCMS. The reaction mixture was cooled to RT and diluted with 10% MeOH in DCM (50 mL), filtered through Celite®, washed 10% MeOH in DCM (50 mL) and filtrate was concentrated in vacuo to afford the crude material, which was triturated with diethyl ether (20 mL) and n-pentane (20 mL), filtered and dried under vacuum to give the title compound 16. Note: Reaction was performed in one more batch (each of 5 g, total 10.0 g) to yield total 6.5 g, 55% as a yellow solid. m/z 304.41 $[M+H]^+$ $(ES^+)$. $^1H$ NMR (400 MHz, DMSO-$d_6$): δ, ppm 10.88 (s, 1H), 7.87 (s, 1H), 7.45-7.41 (d, J=16.0 Hz, 1H), 7.18 (s, 1H), 6.32-6.27 (m, 2H), 1.47 (s, 9H), 1.26 (s, 6H).

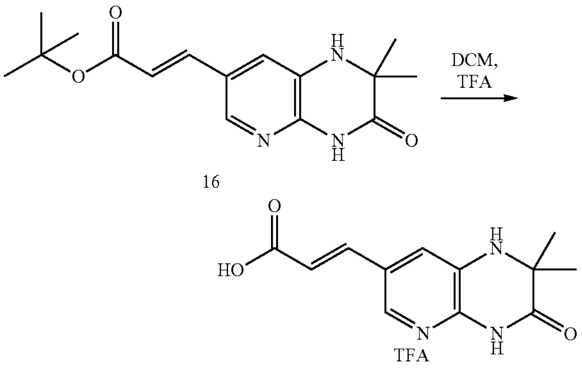

16

17

Step 4. ((E)-3-(2,2-Dimethyl-3-oxo-1,2,3,4-tetrahydropyrido[2,3-b]pyrazin-7-yl)acrylic acid trifluoroacetate (compound 17). Trifluoroacetic acid (30.0 mL) was added to a cool suspension of tert-butyl (E)-3-(2,2-dimethyl-3-oxo-1,2,3,4-tetrahydropyrido[2,3-b]pyrazin-7-yl)acrylate 16 (6.0 g, 19.8 mmol) in DCM (60 mL) at 0° C. The reaction mixture was stirred at RT for 3 h. The progress of reaction was monitored by TLC and LCMS, then concentrated in vacuo. The residue was triturated with diethyl ether (2×50 mL) and the solid collected by filtration to afford the title compound 17 as a yellow solid (4.5 g, 92% yield). m/z 248.05 $[M+H]^+$ $(ES^+)$. $^1H$ NMR (400 MHz, DMSO-$d_6$): δ, ppm 12.33 (s, 1H), 10.89 (s, 1H), 9.78 (s, 1H), 7.86 (d, J=1.6 Hz, 1H), 7.50-7.46 (d, J=16.0 Hz, 1H), 7.19 (d, J=1.2 Hz, 1H), 6.36 (s, 1H), 6.32-6.28 (d, J=16.0 Hz, 1H), 1.26 (s, 6H).

The synthesis of N-methyl-1-(3-methylbenzofuran-2-yl)methanamine (compound 18) was described previously by AFFINIUM PHARMACEUTICALS, INC.—WO2008/98374, 2008, A1 and/or VITAS PHARMA RESEARCH PRIVATE LIMITED, WO2013/42035, 2013, A1.

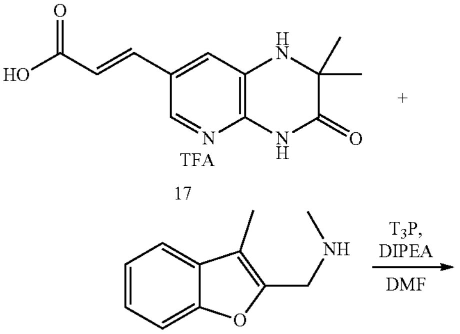

17

18

-continued

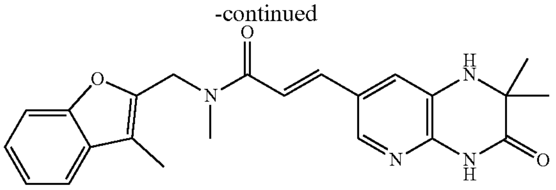

19

Step 5. (E)-3-(2,2-Dimethyl-3-oxo-1,2,3,4-tetrahydropyrido[2,3-b]pyrazin-7-yl)-N-methyl-N-((3-methylbenzofuran-2-yl)methyl)acrylamide (compound 19). DIPEA (16.7.0 mL, 91.0 mmol) was added dropwise to a stirred solution of N-methyl-1-(3-methylbenzofuran-2-yl)methanamine 18 (3.8 g, 18.21 mmol) and (E)-3-(2,2-dimethyl-3-oxo-1,2,3,4-tetrahydropyrido[2,3-b]pyrazin-7-yl)acrylic acid trifluoroacetate 17 (4.5 g, 13.04 mmol) in DMF (25 mL) and THF (25 mL). The reaction was stirred for 5 mins then T3P 50% in ethyl acetate (34.7 mL, 54.6 mmol) was added at 0° C. and the reaction was stirred for a further 4 h at rt. The progress of reaction was monitored by TLC. The reaction mixture was diluted with water (500 mL) and the solid collected, washed with water (2×50 mL) and dried under vacuum. The crude compound was taken in diethyl ether (50 mL), and stirred for 15 min at rt. Filtered the solid mass and washed with diethyl ether (25 mL), dried under vacuum to give (E)-3-(2,2-dimethyl-3-oxo-1,2,3,4-tetrahydropyrido[2,3-b]pyrazin-7-yl)-N-methyl-N-((3-methylbenzofuran-2-yl)methyl)acrylamide 19 as a light yellow solid (3.55 g, 67.5% yield). The filtrate was concentrated to give 3.5 g mixture. m/z 405.21 $[M+H]^+$ $(ES^+)$. $^1H$ NMR (400 MHz, DMSO-$d_6$): δ, ppm 10.84 (s, 1H), 7.90 (s, 1H), 7.57-7.55 (d, J=7.2 Hz, 1H), 7.50-7.42 (m, 2H), 7.30-7.22 (m, 3H), 7.03-6.99 (d, J=15.2 Hz, 1H), 6.35-6.33 (d, J=9.6, Hz, 1H), 4.94-4.78 (d, J=64.8 Hz, 2H), 3.16-2.94 (d, 3H), 2.26 (s, 3H), 1.25 (s, 6H).

Example 5. Synthesis of 2-hydroxyethan-1-aminium (e)-(8-(3-(methyl((3-methylbenzofuran-2-yl)methyl)amino)-3-oxoprop-1-en-1-yl)-4-oxo-1,2,3,4-tetrahydro-5h-pyrido[2,3-b][1,4]diazepin-5-yl)methyl phosphate (Compound 23)

General Synthetic Scheme.

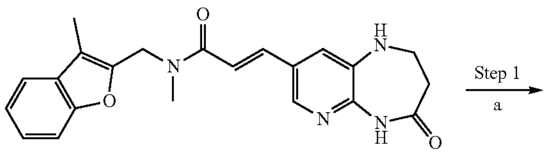

20

-continued

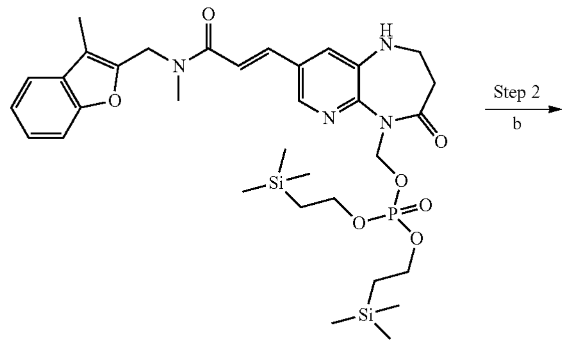

22

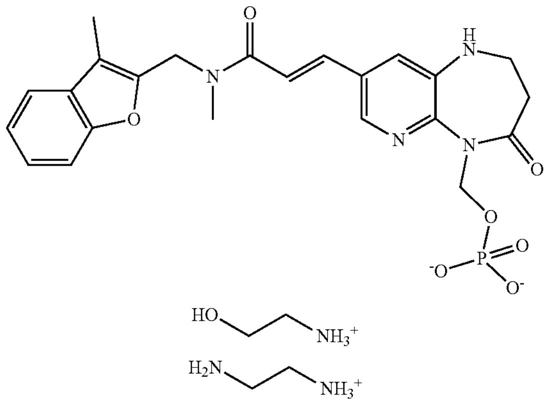

23

Reaction conditions: a) 1. 18-crown-6, NMP/N-ethylpyrrolidone, RT 2. t-BuOK at -20° C. to -35° C., then chloromethyl bis[2-(trimethylsilyl)ethyl] phosphate 21; b) TFA/DCM, long work-up The full synthesis of (E)-N-methyl-N-((3-methylbenzofuran-2-yl)methyl)-3-(4-oxo-2,3,4,5-tetrahydro-1H-pyrido[2,3-b][1,4]diazepin-8-yl)acrylamide (compound 20) was described previously in Bioorganic & Medicinal Chemistry Letters (2009), 19(18), 5359-5362 and WO 2007067416.

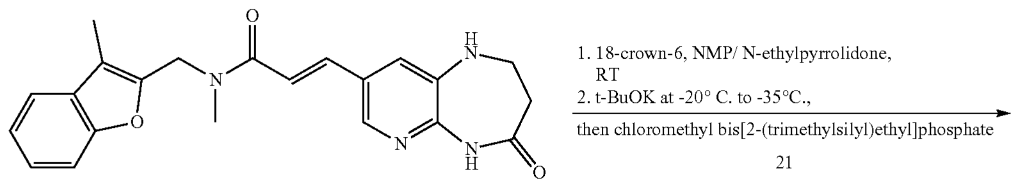

20

-continued

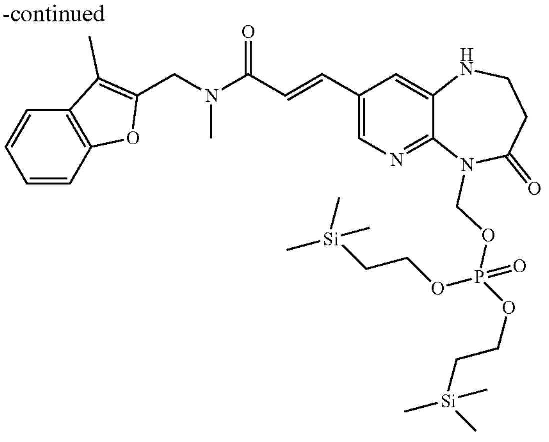

22

Step 1. (E)-(8-(3-(Methyl((3-methylbenzofuran-2-yl)methyl)amino)-3-oxoprop-1-en-1-yl)-4-oxo-1,2,3,4-tetrahydro-5H-pyrido[2,3-b][1,4]diazepin-5-yl)methyl bis(2-(trimethylsilyl)ethyl) phosphate (compound 22). To a sealed 10 mL vial under nitrogen containing (E)-N-methyl-N-((3-methylbenzofuran-2-yl)methyl)-3-(4-oxo-2,3,4,5-tetrahydro-1H-pyrido[2,3-b][1,4]diazepin-8-yl)acrylamide 20 (250 mg; 1 eq; previously milled under dry stirring for 10 minutes) and 18-crown-6 (208 mg; 1.24 eq) was added N-methyl-2-pyrrolidone (1.0 mL; 4 vols) and N-ethylpyrrolidone (0.275 mL; 1.10 vols). Then mixture was stirred at 25° C. for 10 minutes, and submitted to degassing cycles (5 cycles; vacuum/nitrogen). Reaction mixture was then cooled down to −20° C. (not measured; bath temp at −30° C.) and potassium tert-butoxide (82 mg; 1.1 eq) was added portion-wise over 2 minutes. Reaction mixture was again submitted to degassing cycles (3 cycles; vacuum/nitrogen) and was then stirred at −20° C. (temperature bath: −30° C.) for 1 h 30 min until nearly complete solubilisation (dark green mixture). Reaction mixture was cooled down to −35° C. (not measured; bath temp at −45° C.) and a degassed (5 cycles; vacuum/nitrogen) solution of chloromethyl bis[2-(trimethylsilyl)ethyl]phosphate 21(Carbogen Amcis) (1.058 g; 1.4 eq; 29.1% w/w in heptane) was added over 4 minutes keeping temperature at −35° C. (not measured; bath temp at −45° C.). Reaction mixture (biphasic) was stirred at −35° C. for 16 h until nearly completion as indicated by UPLC/MS: (Starting material: $R_t$=1.62 min; 34.5% (AUC); $ES^+$: 391.5. Product: $R_t$=2.50 min; 34.25% (AUC); $ES^+$: 701.79). N-Methyl-2-pyrrolidone (0.64 mL), methyl cyclohexane (1.25 mL), toluene (0.35 mL) and water (0.37 mL) were added to the reaction mixture keeping temperature at −20° C. (not measured; bath temp at −30° C.). Then after stirring and phase separation, lower phase was extracted with MTBE (3×2 mL) keeping temperature at −20° C. All upper phases were then combined and washed with half saturated sodium chloride solution (2×6 mL). All washing were done keeping temperature at −10° C. (not measured; bath temp at −20° C.). Organic phase was then dried over sodium sulfate, filtered and rinsed with MTBE (2×3 mL) at 25° C. Concentration to dryness was done keeping bath temperature below 25° C. to give crude compound as orange foam (m=150.73 mg; purity: 88.36% (AUC)). Stored overnight under nitrogen at −25° C. The crude compound was purified by normal phase chromatography ($SiO_2$; 40-63 μm). Conditioning was done with n-heptane, then crude compound was solubilised in a mixture of n-heptane/MTBE/DIPEA: 2/1/0.75% (3 mL) and MTBE (2 mL) and injected. Elution was done with cold eluents (stored few hours in ice maker). First eluent (n-heptane/MTBE/DIPEA: 2/1/0.75%), second eluent (MTBE/DIPEA: 100/0.2%), third eluent (methyl acetate/DIPEA: 100/0.2%). Product was finally eluted with the third eluent. Fractions were combined and concentrated to dryness (temperature bath: 25° C.) to give title compound 22 as yellow oil (m=122.5 mg; purity: 96% (AUC); $ES^+$: 701.7; yield: 26.5%). Stored at −25° C. until next step.

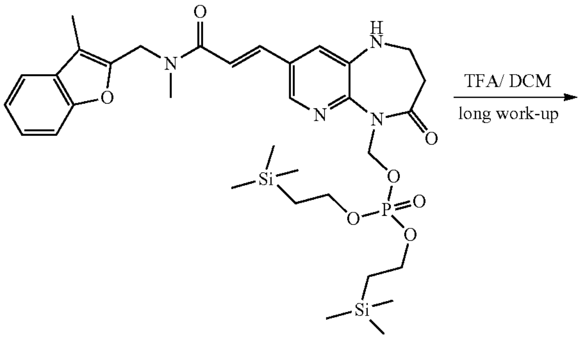

22

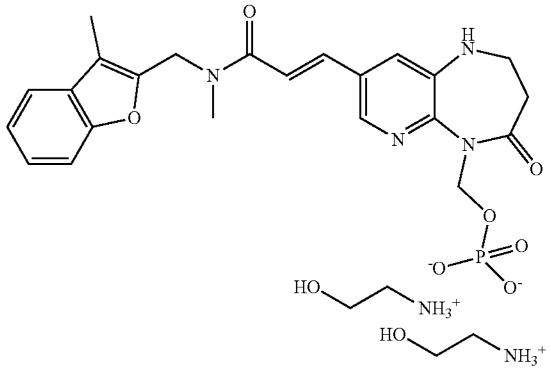

23

Step 2. 2-Hydroxyethan-1-aminium (E)-(8-(3-(methyl((3-methylbenzofuran-2-yl)methyl)amino)-3-oxoprop-1-en-1-yl)-4-oxo-1,2,3,4-tetrahydro-5H-pyrido[2,3-b][1,4]diazepin-5-yl)methyl phosphate (compound 23). In a sealed 2.5 mL vial under nitrogen was prepared a solution of TFA (0.369 mL; 19.3 eq) in anhydrous dichloromethane (0.32 mL; 2.6 vols) at −20° C., this solution was called solution No 1. In a sealed 2.5 mL vial under nitrogen was prepared a solution of (E)-(8-(3-(methyl((3-methylbenzofuran-2-yl)methyl)amino)-3-oxoprop-1-en-1-yl)-4-oxo-1,2,3,4-tetrahydro-5H-pyrido[2,3-b][1,4]diazepin-5-yl)methyl bis(2-(trimethylsilyl)ethyl) phosphate 22 (123 mg; 1 eq) in anhydrous toluene (0.408 mL; 3.33 vols) at −10° C., this solution was called solution No 2. Then solution No 2 was added to solution No 1 under stirring over 10 minutes keeping temperature at −20° C. (not measured; bath temp at −30° C.). Then vial containing solution No 2 was rinsed with anhydrous dichloromethane (0.404 mL; 3.3 vols) which was then added to solution No 1. Reaction mixture was then stirred for 25 minutes under nitrogen keeping temperature at −20° C. (not measured; temperature was adjusted keeping yellowish reaction mixture at the freezing limit (TFA): slight trouble). Completion of hydrolysis was confirmed by UPLC/MS (Product: $R_t$=1.34 min; $ES^-$: 499.3. Starting material: $R_t$=2.49 min; 0% (AUC)). In a sealed 20 mL vial under nitrogen was prepared a solution of ethanolamine (274 mg; 26.5 eq) in a mixture of acetone (1.814 mL; 14.8 vols) and water (0.050 mL; 0.41 vols) at 0° C. (not measured; bath temperature: −5° C.), this solution was called solution No 3. Then previous reaction mixture was cooled down to −20° C. (not measured; just slightly above freezing point) and added through cannula to solution No 3 under gentle stirring (100 rpm; can be increased to have an homogeneous solution (biphasic)) over 10 minutes keeping temperature at 0° C. (bath temp at −5° C.). Then vial containing reaction mixture was rinsed with dichloromethane (0.208 mL; 1.7 vols) which was then added to solution No 3. Then final reaction mixture was stirred at 200 rpm at 0° C. (measured internally) for 30 minutes and stored at 4° C. for 14 h in the fridge until precipitation was observed. Reaction mixture was allowed to warm up to 25° C. and was filtered through a glass filter. Resulting cake was washed with ethanol (2×2 mL) but complete dissolution was observed. Filtrate was concentrated to dryness (bath temperature at 25° C.) and resulting oil was dissolved in a mixture of acetone (1.5 mL), toluene (1.5 mL) and MTBE (3 mL). Resulting solution was stored at −25° C. for 1 h 30 min until complete precipitation. Suspension was filtered through a glass filter, and resulting solid was washed with a mixture of 1-butanol (2 mL) and MTBE (4 mL) then with MTBE(2×2 mL) and finally with 2-butanone (1×3 mL and 1×2 mL). However, after drying NMR analysis on isolated solid showed only TFA-ethanolamine salt. Filtrate was stored at −25° C. for 16 h until precipitation was observed. Suspension was filtered through a glass filter and resulting yellow solid was washed several time with 2-butanone (2 mL) until acceptable amount of TFA-ethanolamine salt was measured by NMR. Finally, after drying at 25° C. under vacuum, title compound 23 was obtained as yellow powder (m=42.41 mg; purity: 100% (AUC); $ES^-$: 499.3; 2 eq of ethanolamine by NMR; 2.4% w/w of TFA-ethanolamine salt; yield: 40.6%). $^1H$ NMR (400 MHz, $D_2O$): δ, ppm 8.13 (d, J=1.7 Hz, 1H), 7.47 (dd, J=1.8 Hz, 6.6 Hz, 1H), 7.43-7.08 (m, 5H), 6.87 (d, J=15.8 Hz, 1H), 5.46 (d, J=5.6 Hz, 2H), 4.68 (s, 1H), 4.60 (s, 1H), 3.72 (t, J=5.2 Hz, 4H), 3.65-3.55 (m, 2H), 3.05 (t, J=5.2 Hz, 4H), 3.05 (s, 1.8H), 2.92 (s, 1.2H), 2.53-2.42 (m, 2H, m), 2.09 (s, 1.8H), 2.08 (s, 1.2H) (rotamers).

Example 6. Synthesis of (E)-3-(3-(hydroxymethyl)-3-methyl-4-oxo-2,3,4,5-tetrahydro-1H-pyrido[2,3-b][1,4]diazepin-8-yl)-N-methyl-N-((3-methylbenzofuran-2-yl)methyl)acrylamide (Compound 31) as Well as Two Enantiomers (S,E)-3-(3-(hydroxymethyl)-3-methyl-4-oxo-2,3,4,5-tetrahydro-1H-pyrido[2,3-b][1,4]diazepin-8-yl)-N-methyl-N-((3-methylbenzofuran-2-yl)methyl)acrylamide (compound 32) and (R,E)-3-(3-(hydroxymethyl)-3-methyl-4-oxo-2,3,4,5-tetrahydro-1H-pyrido[2,3-b][1,4]diazepin-8-yl)-N-methyl-N-((3-methylbenzofuran-2-yl)methyl)acrylamide (Compound 33)

General Synthetic Scheme.

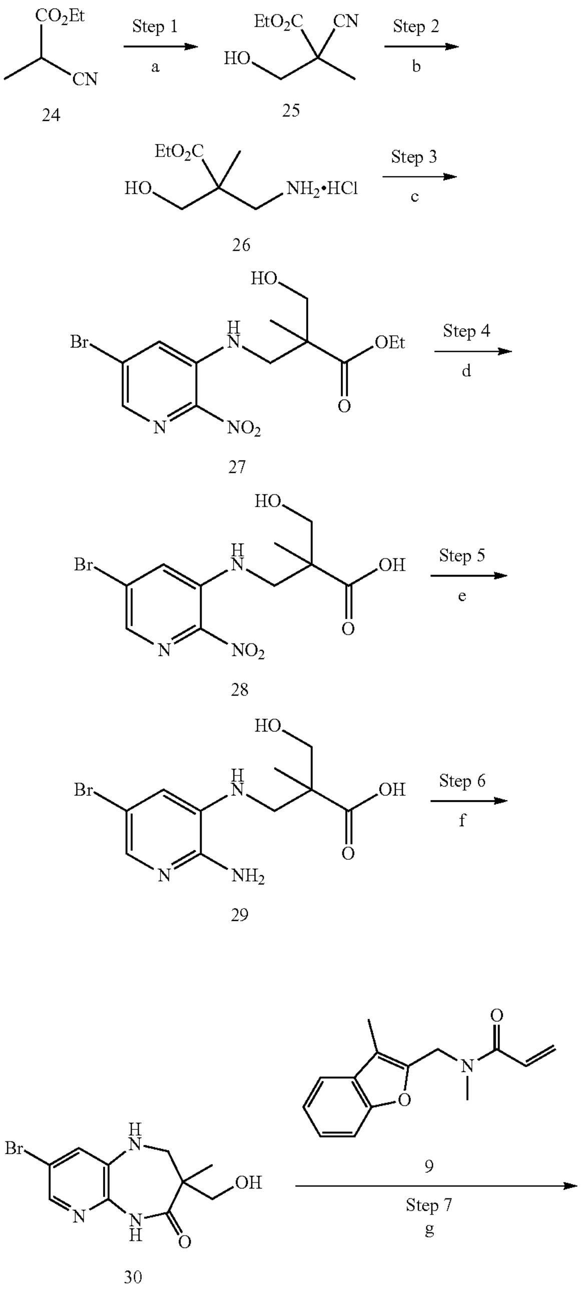

-continued

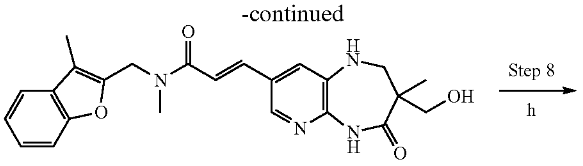

31

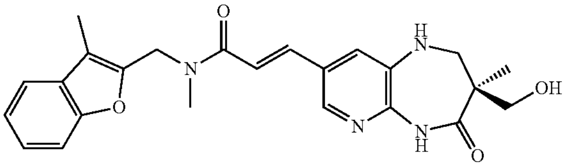

32

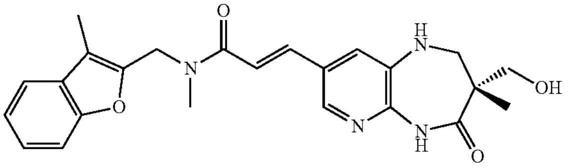

33

Reaction conditions: a) $K_2CO_3$, $(HCHO)_n$, EtOH; b) HCl in 1,4-dioxane, $PtO_2$•$H_2O$, EtOH; c) 5-bromo-3-fluoro-2-nitropyridine 11, TEA, EtOH, Δ; d) LiOH, water/THF; e) Fe, $NH_4Cl$, EtOH, $H_2O$, 90° C.; f) HATU, DIPEA, DMF; g) Pd-162, $Cy_2NMe$, $NBu_4Cl$, 1,4-dioxane, 80° C.; h) chiral separation

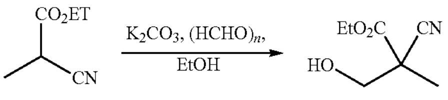

24 25

Step 1. Ethyl 2-cyano-3-hydroxy-2-methylpropanoate (compound 25). A mixture of paraformaldehyde (3.54 g, 118 mmol), ethyl 2-cyanopropanoate 24 (TCI—Tokyo Chemical Industry) (10 g, 79 mmol) and potassium carbonate (32.6 g, 236 mmol) in ethanol (500 mL) was stirred for 18 hours. The solid was removed by filtration through a plug of Celite® and the filtrate evaporated to dryness. The crude product was purified by silica chromatography (0-50% EtOAc/isohexane) to afford the title compound 25 as a clear colourless oil (6.01 g, 48%). $^1$H NMR (400 MHz, $CDCl_3$): δ, ppm 4.30 (q, J=7.1 Hz, 2H), 3.98-3.83 (m, 2H), 2.59 (s, 1H), 1.58 (s, 3H), 1.34 (t, J=7.1 Hz, 3H).

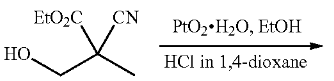

25

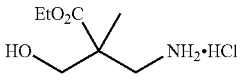

26

Step 2. Ethyl 3-amino-2-(hydroxymethyl)-2-methylpropanoate hydrochloride (compound 26). A mixture of platinum(IV) oxide (0.14 g, 0.64 mmol), ethyl 2-cyano-3-hydroxy-2-methylpropanoate 25 (1.00 g, 6.36 mmol) and HCl (4M in 1,4-dioxane, 3.18 mL, 12.73 mmol) in a solvent of ethanol (12 mL) was stirred under an atmosphere of hydrogen at 5 bar for 18 hours. The catalyst was removed by filtration and the filtrate evaporated to dryness. The residue was dissolved in acetonitrile (10 mL) and evaporated to dryness to give the title compound 26 as a colourless gum (1.38 g, quant. yield). $^1$H NMR (400 MHz, DMSO-$d_6$) δ 8.11 (s, 3H), 5.31 (s, 1H), 4.13-4.07 (m, 2H), 3.64-3.44 (m, 2H), 3.09-2.91 (m, 2H), 1.21 (t, J=7.1 Hz, 3H), 1.13 (s, 3H).

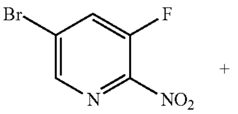

11

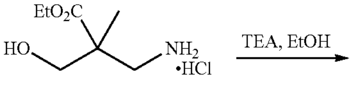

26

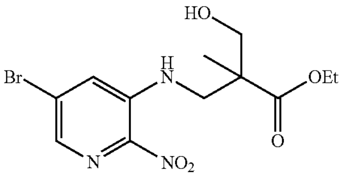

27

Step 3. Ethyl 3-((5-bromo-2-nitropyridin-3-yl)amino)-2-(hydroxymethyl)-2-methylpropanoate (compound 27). A mixture of ethyl 3-amino-2-(hydroxymethyl)-2-methylpropanoate hydrochloride 26 (322 mg, 1.63 mmol), triethylamine (757 μmL, 5.43 mmol) and 5-bromo-3-fluoro-2-nitropyridine 11 (300 mg, 1.36 mmol) in a solvent of ethanol (20 mL) was heated and stirred under reflux for 1 hours. The reaction mixture was evaporated to dryness. The crude product was purified by silica chromatography (0-100% EtOAc/isohexane) to afford the title compound 27 as a yellow gum (485 mg, 94%). $R^t$ 1.17 min (Method 2b) m/z 362/364 $[M+H]^+$ ($ES^+$). $^1$H NMR (DMSO-$d_6$): δ, ppm 8.24 (t, J=6.0 Hz, 1H), 8.05 (d, J=1.9 Hz, 1H), 7.87 (d, J=1.9 Hz, 1H), 5.19 (t, J=5.2 Hz, 1H), 4.08 (qd, J=7.1 Hz, 2.2 Hz, 2H), 3.66-3.60 (m, 3H), 3.54 (dd, J=10.6 Hz, 5.0 Hz, 1H), 1.19-1.16 (m, 3H).

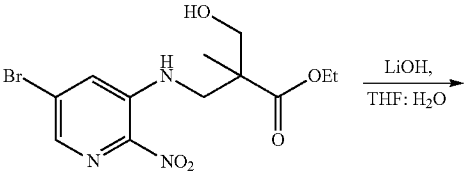

27

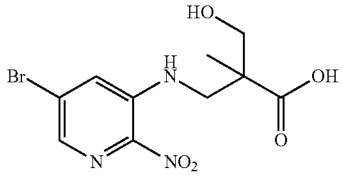

28

Step 4. 3-((5-Bromo-2-nitropyridin-3-yl)amino)-2-(hydroxymethyl)-2-methylpropanoic acid (compound 28). A mixture of ethyl 3-((5-bromo-2-nitropyridin-3-yl)amino)-2-

(hydroxymethyl)-2-methylpropanoate 27 (480 mg, 1.38 mmol) and lithium hydroxide monohydrate (49.5 mg, 2.07 mmol) in a solvent mixture of THF (20 mL) and water (5 mL) was stirred for 1 hour at RT. The mixture was acidified to pH ~3 by the addition of an aqueous solution of 1M HCl and the mixture evaporated to dryness to give the title compound 28 (501 mg, quant. yield) which was used in the next step without further purification. R$^t$ 0.59 min (Method 2b) 332/334 $[M-H]^-$ ($ES^-$).

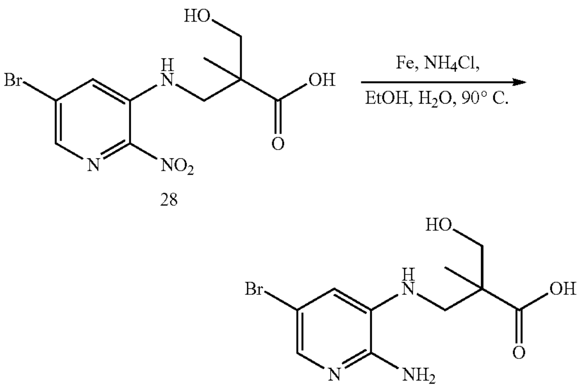

28

29

Step 5. 3-((2-Amino-5-bromopyridin-3-yl)amino)-2-(hydroxymethyl)-2-methylpropanoic acid (compound 29). A mixture of 3-((5-bromo-2-nitropyridin-3-yl)amino)-2-(hydroxymethyl)-2-methylpropanoic acid 28 (460 mg, 1.38 mmol), iron powder (615 mg, 11.01 mmol) and ammonium chloride (147 mg, 2.75 mmol) in a solvent mixture of ethanol (30 mL) and water (8 mL) was heated and stirred under reflux for 1 hour. The reaction mixture was filtered through a plug of Celite® and the filtrate evaporated to dryness. The residue was triturated with ice water (10 mL), the solid collected and dried in vacuo to give the title compound 29 as grey solid (180 mg, 41% yield). R$^t$ 0.71 min (Method 1b) m/z 304/306 $[M+H]^+$ ($ES^+$); 302/304 $[M-H]^-$ ($ES^-$). $^1H$ NMR (400 MHz, DMSO-$d_6$): δ, ppm 7.32 (s, 1H), 7.17 (s, 2H), 6.79 (s, 1H), 5.78 (s, 2H), 4.79 (d, J=59.7 Hz, 2H), 3.54 (q, J=10.6 Hz, 2H), 3.25-3.12 (m, 2H), 1.13 (s, 3H).

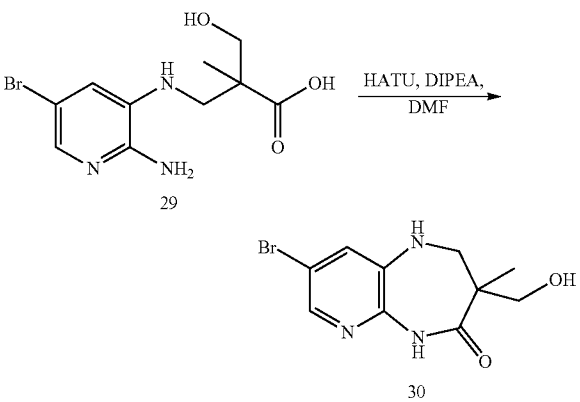

29

30

Step 6. 8-Bromo-3-(hydroxymethyl)-3-methyl-2,3-dihydro-1H-pyrido[2,3-b][1,4]diazepin-4(5H)-one (compound 30). To a solution of 3-((2-amino-5-bromopyridin-3-yl)amino)-2-(hydroxymethyl)-2-methylpropanoic acid 29 (165 mg, 0.54 mmol) and DIPEA (284 µmL, 1.63 mmol) in DMF (5 mL) was added HATU (309 mg, 0.81 mmol) and the mixture stirred for 1 hour. The reaction mixture was evaporated to dryness and the crude product was purified by silica chromatography (0-100% EtOAc/isohexane) to afford the title compound 30 as a tan solid (31 mg, 20% yield). R$^t$ 1.33 min (Method 1b) m/z 286/288 $[M+H]^+$ ($ES^+$). $^1H$ NMR (400 MHz, DMSO-$d_6$): δ, ppm 9.51 (s, 1H), 7.67 (d, J=2.1 Hz, 1H), 7.25 (d, J=2.1 Hz, 1H), 6.38 (t, J=4.5 Hz, 1H), 4.79 (t, J=5.5 Hz, 1H), 3.60 (dd, J=10.5 Hz, 5.7 Hz, 1H), 3.44 (dd, J=10.6 Hz, 5.3 Hz, 1H), 3.20 (dd, J=13.8 Hz, 3.7 Hz, 1H), 3.07 (dd, J=13.8 Hz, 5.3 Hz, 1H), 1.08 (s, 3H).

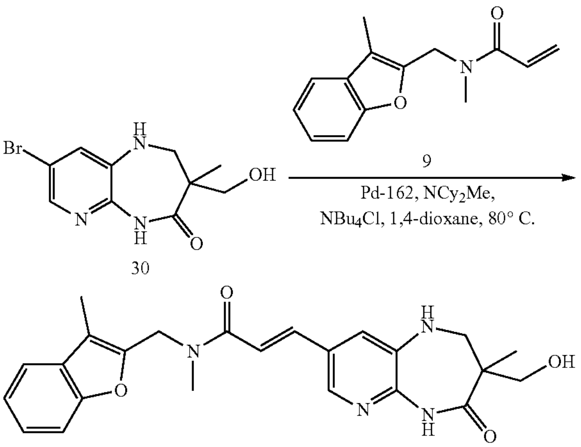

30

31

Step 7. (E)-3-(3-(Hydroxymethyl)-3-methyl-4-oxo-2,3,4,5-tetrahydro-1H-pyrido[2,3-b][1,4]diazepin-8-yl)-N-methyl-N-((3-methylbenzofuran-2-yl)methyl)acrylamide (compound 31). A reaction vial was charged with N-methyl-N-((3-methylbenzofuran-2-yl)methyl)acrylamide 9 (61.7 mg, 0.27 mmol), 8-bromo-3-(hydroxymethyl)-3-methyl-2,3-dihydro-1H-pyrido[2,3-b][1,4]diazepin-4(5H)-one 30 (70 mg, 0.25 mmol), tetrabutylammonium chloride hydrate (7.24 mg, 0.02 mmol), $[P(tBu)_3]Pd(crotyl)Cl$ (Pd-162) (Johnson Matthey) (9.77 mg, 0.02 mmol). The reaction vial was flushed with nitrogen for 5 mins. 1,4-Dioxane (10 mL) and N-cyclohexyl-N-methylcyclohexanamine (0.11 mL, 0.49 mmol) were added and the reaction mixture was purged with nitrogen for a further 5 mins. The mixture was heated to 80° C. for 30 mins. The reaction mixture was evaporated to dryness and the crude product was purified by silica chromatography (0-10% MeOH/DCM) to afford the title compound 31 as a yellow solid (71.2 mg, 66% yield). R$^t$ 1.85 min (Method 1b) m/z 435 $[M+H]^+$ $(ES)^+$. $^1H$ NMR (400 MHz, DMSO-$d_6$, 363 K): δ, ppm 8.88 (s, 1H), 7.95 (d, J=2.0 Hz, 1H), 7.58-7.54 (m, 1H), 7.49-7.36 (m, 3H), 7.32-7.22 (m, 2H), 7.17-7.04 (m, 1H), 5.90 (s, 1H), 4.84 (s, 2H), 3.67 (d, J=10.5 Hz, 1H), 3.51 (d, J=10.6 Hz, 1H), 3.27 (d, J=13.9 Hz, 1H), 3.15-3.07 (m, 4H), 2.28 (s, 3H), 1.15 (s, 3H).

Step 8. Chiral separation of compound 31.

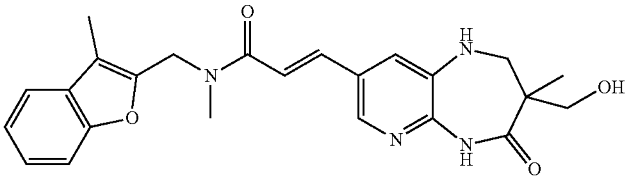

31

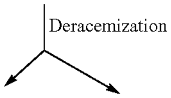

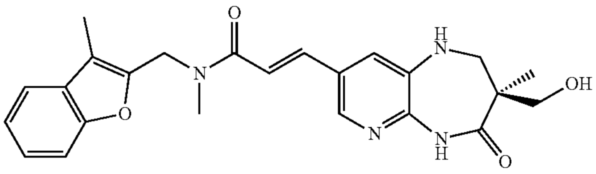

32

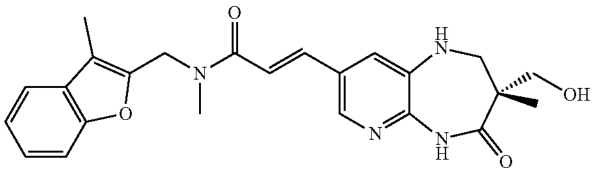

33

Chiral method separation: Apparatus: Isolera (Biotage). Chiralpak® IA (Daicel Ltd.) glass column (20 μmm; 250 mm×25 mm), flow rate 40 mL $min^{-1}$ eluting with a mixture of Acetonitrile/Ethanol (8/2 v/v). UV detection at 254 nm. Temperature: 30° C. Run time: 25 min. Samples were loaded after filtration through 0.2 um PTFE filter directly onto the column. Amount injected: 46.4 mg of 31 in 10 mL of eluent (polishing filtration through a 0.2 μm PTFE filter).

(S,E)-3-(3-(Hydroxymethyl)-3-methyl-4-oxo-2,3,4,5-tetrahydro-1H-pyrido[2,3-b][1,4]diazepin-8-yl)-N-methyl-N-((3-methylbenzofuran-2-yl)methyl)acrylamide (compound 32). Pure fractions of first enantiomer were collected and concentrated. The first enantiomer was obtained as a yellow solid (m=12.95 mg; chiral purity: 99.66%). $R^t$ 1.53 min (Method 1c) m/z 435.5 $(M+H)^+$ $(ES^+)$. The stereochemistry of obtained enantiomer was randomly assigned.

(R,E)-3-3-(3-(Hydroxymethyl)-3-methyl-4-oxo-2,3,4,5-tetrahydro-1H-pyrido[2,3-b][1,4]diazepin-8-yl)-N-methyl-N-((3-methylbenzofuran-2-yl)methyl)acrylamide (compound 33). Pure fractions of second enantiomer were collected and concentrated. The second enantiomer was obtained as yellow solid (m=8.97 mg; chiral purity: 98.20%). $R^t$ 1.53 min (Method 1c) m/z 435.5 $[M+H]^+$ $(ES^+)$. The stereochemistry of obtained enantiomers was randomly assigned.

Example 7. Synthesis of (E)-3-(3-(hydroxymethyl)-3-methyl-4-oxo-2,3,4,5-tetrahydro-1H-pyrido[2,3-b][1,4]diazepin-8-yl)-N-methyl-N-((2-methylbenzofuran-3-yl)methyl)acrylamide (Compound 39) as Well as Two Enantiomers (S,E)-3-(3-(hydroxymethyl)-3-methyl-4-oxo-2,3,4,5-tetrahydro-1H-pyrido[2,3-b][1,4]diazepin-8-yl)-N-methyl-N-((2-methylbenzofuran-3-yl)methyl)acrylamide (Compound 40) and (R,E)-3-(3-(hydroxymethyl)-3-methyl-4-oxo-2,3,4,5-tetrahydro-1H-pyrido[2,3-b][1,4]diazepin-8-yl)-N-methyl-N-((2-methylbenzofuran-3-yl)methyl)acrylamide (Compound 41)

General Synthetic Scheme.

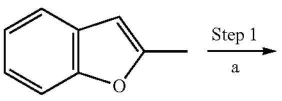

34

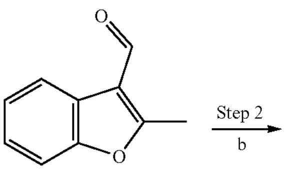

35

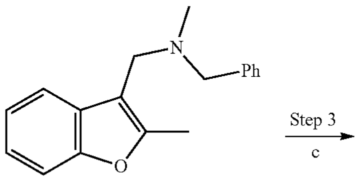

36

-continued

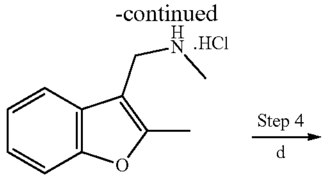

37

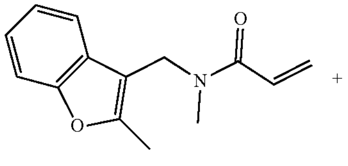

38

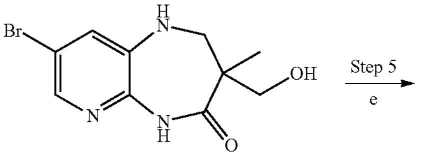

30

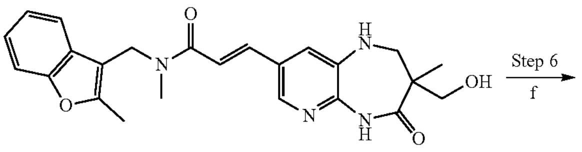

39

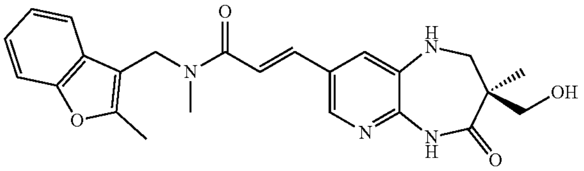

40

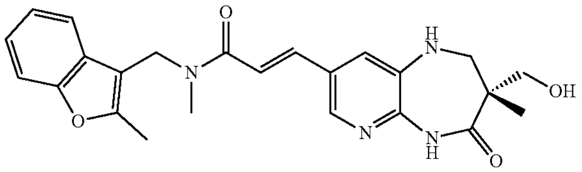

41

Reaction conditions: a) $Cl_2CHOMe$, $TiCl_4$, DCM; b) $PhCH_2NHMe$, $Na(OAc)_3BH$, DCE; c) Pd/C, $H_2$, MeOH, Aq. HCl; d) Acryloyl chloride, TEA, THF; e) Pd-162, $NCy_2Me$, $NBu_4Cl$, 1,4-dioxane, 80° C;f) chiral seperation

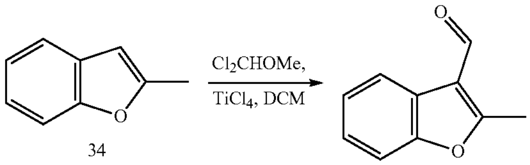

34 35

Step 1. 2-Methylbenzofuran-3-carbaldehyde (compound 35). To a solution of dichloro(methoxy)methane (5.1 mL, 56.7 mmol) and 2-methylbenzofuran 34 (5.0 g, 37.8 mmol) in DCM (100 mL) stirred at 0° C. was added dropwise tin(IV) chloride (1M in DCM) (60.5 mL, 60.5 mmol) over 30 mins. Upon completion of addition the mixture was allowed to warm to RT over 30 mins, then poured onto ice cold saturated sodium hydrogen carbonate solution (500 mL). The mixture was extracted into DCM (2×100 mL) and the organics separated and dried. Filtration and evaporation gave the crude product which was purified by silica chromatography (0-50% EtOAc/isohexane) to afford the title compound 35 as a yellow solid (5.30 g, 86%). $^1H$ NMR (400 MHz, $CDCl_3$): δ, ppm 10.16 (s, 1H), 8.06-8.01 (m, 1H), 7.41-7.35 (m, 1H), 7.34-7.23 (m, 2H), 2.70 (s, 3H).

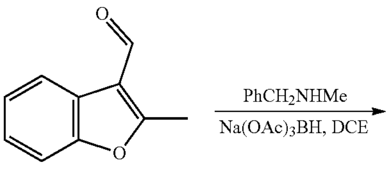

35

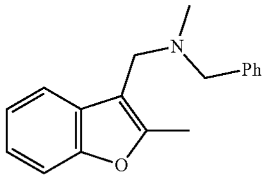

36

Step 2. N-Benzyl-N-methyl-1-(2-methylbenzofuran-3-yl) methanamine (compound 36). To a solution of 2-methylbenzofuran-3-carbaldehyde 35 (1.00 g, 6.24 mmol) and N-methyl-1-phenylmethanamine (0.98 mL, 7.49 mmol) in DCE (20 mL) was added sodium triacetoxyborohydride (1.99 g, 9.37 mmol) and the mixture stirred for 72 hours. The reaction mixture was washed with saturated sodium bicarbonate solution (20 mL) and dried over sodium sulfate. Filtration and evaporation gave the title compound 36 as a pale yellow oil (1.60 g, 94% yield) which was used without further purification. $^1H$ NMR (400 MHz, DMSO-$d_6$): δ, ppm 7.63-7.58 (m, 1H), 7.48-7.43 (m, 1H), 7.33 (d, J=4.8 Hz, 4H), 7.28-7.20 (m, 3H), 3.56 (s, 2H), 3.52 (s, 2H), 2.42 (s, 3H), 2.08 (s, 3H).

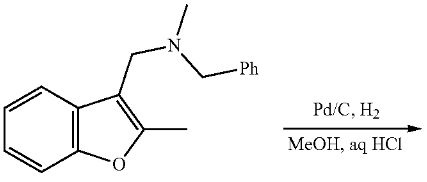

36

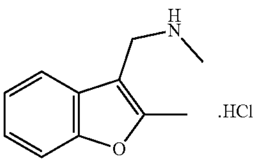

37

Step 3. N-Methyl-1-(2-methylbenzofuran-3-yl)methanamine hydrochloride (compound 37). A mixture of N-benzyl-N-methyl-1-(2-methylbenzofuran-3-yl)methanamine 36 (1.60 g, 6.03 mmol) and Pd—C 87 L 5% on carbon (0.64 g, 6.03 mmol) in methanol (20 mL) acidified to pH 1 with 1M hydrochloric acid was hydrogenated at 5 bar and left to stir at RT for 18 hours. The catalyst was removed by filtration and the filtrate evaporated to dryness to give the title compound 37 as a white solid (737 mg, 56%). $^1$H NMR (400 MHz, DMSO-$d_6$): δ, ppm 9.24 (s, 2H), 7.89-7.80 (m, 1H), 7.59-7.49 (m, 1H), 7.34-7.23 (m, 2H), 4.24 (s, 2H), 2.57 (s, 3H), 2.55 (s, 3H).

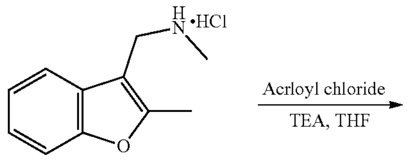

37

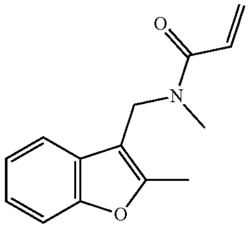

38

Step 4. N-Methyl-N-((2-methylbenzofuran-3-yl)methyl) acrylamide (compound 38). To a suspension of N-methyl-1-(2-methylbenzofuran-3-yl)methanamine hydrochloride 37 (300 mg, 1.42 mmol) and triethylamine (600 μmL, 4.25 mmol) in dry THF (10 mL) was added acryloyl chloride (154 mg, 1.70 mmol) dropwise at RT over 15 mins. The mixture was allowed to stir for 1 hour and then poured onto water (30 mL). The organic solvent was removed by rotary evaporation to give a solid. This solid was collected by filtration, washed with water (10 mL) and dried to give the title compound 38 (316 mg, 95%) as a colourless solid. $R^t$ 1.94 min (Method 1b) m/z 230 $[M+H]^+$ ($ES^+$).

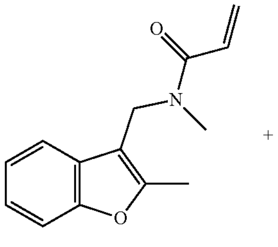

38

-continued

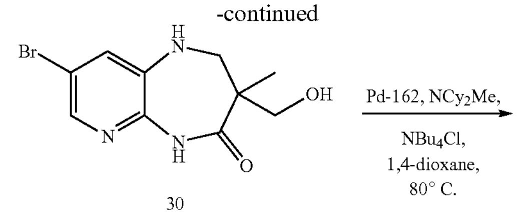

30

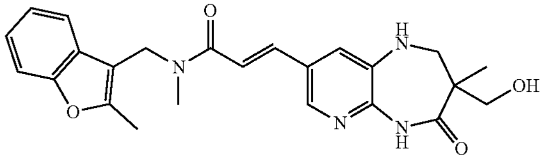

39

Step 5. (E)-3-(3-(Hydroxymethyl)-3-methyl-4-oxo-2,3,4,5-tetrahydro-1H-pyrido[2,3-b][1,4]diazepin-8-yl)-N-methyl-N-((2-methylbenzofuran-3-yl)methyl)acrylamide (compound 39). A reaction vial was charged with N-methyl-N-((2-methylbenzofuran-3-yl)methyl)acrylamide 38 (72.0 mg, 0.32 mmol), 8-bromo-3-(hydroxymethyl)-3-methyl-2,3-dihydro-1H-pyrido[2,3-b][1,4]diazepin-4(5H)-one 30 (90.0 mg, 0.32 mmol), tetrabutylammonium chloride hydrate (9.3 mg, 0.031 mmol), $[P(tBu)_3]Pd(crotyl)Cl$ (Pd-162) (12.6 mg, 0.03 mmol). The reaction vial was flushed with nitrogen for 5 mins. 1,4-Dioxane (10 mL) and N-cyclohexyl-N-methylcyclohexanamine (0.14 mL, 0.63 mmol) were added and the reaction mixture was purged with nitrogen for a further 5 mins. The mixture was heated to 80° C. for 30 mins. The reaction mixture was evaporated to dryness and the crude product was purified by silica chromatography (0-10% MeOH/DCM) to afford the title compound 39 as a yellow solid (94.3 mg, 68% yield). $R^t$ 1.21 min (Method 2a) m/z 435 $[M+H]^+$ ($ES^+$). $^1$H NMR (400 MHz, DMSO-$d_6$, 363 K): δ, ppm 8.88 (s, 1H), 7.95 (d, J=2.0 Hz, 1H), 7.58-7.36 (m, 4H), 7.28-7.04 (m, 3H), 5.88 (t, J=4.7 Hz, 1H), 4.77 (s, 2H), 4.45 (t, J=5.5 Hz, 1H), 3.67 (dd, J=10.6 Hz, 5.7 Hz, 1H), 3.54-3.48 (m, 1H), 3.26 (dd, J=13.9 Hz, 3.9 Hz, 1H), 3.11 (dd, J=13.9 Hz, 5.3 Hz, 1H), 3.01 (bs, 3H), 1.14 (s, 3H). Note: Methyl group at the benzofuran underneath solvent peak.

Step 6. Chiral separation of compound 39.

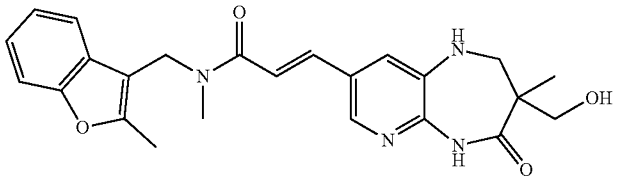

39

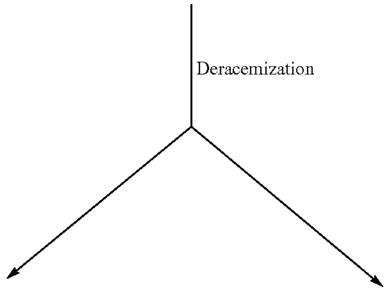

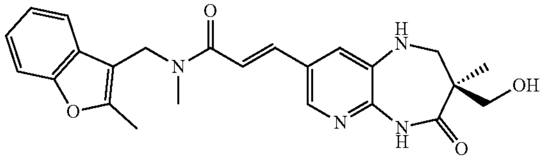

40

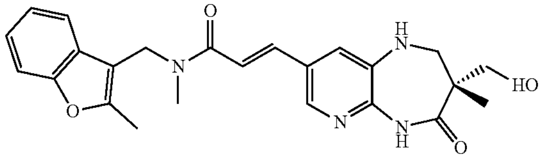

41

Chiral method separation: Apparatus: Isolera (Biotage). Chiralpak® IA (Daicel Ltd.) glass column (20 μm; 250 mm×25 mm), flow rate 40 mL $min^{-1}$ eluting with a mixture of Acetonitrile/Ethanol (8/2 v/v). UV detection at 254 nm. Temperature: 30° C. Run time: 25 min. Samples were loaded after filtration through 0.2 um PTFE filter directly onto the column. Amount injected: 56.1 mg of 39 in 10 mL of eluent (polishing filtration through a 0.2 μm PTFE filter).

(S,E)-3-(3-(Hydroxymethyl)-3-methyl-4-oxo-2,3,4,5-tetrahydro-1H-pyrido[2,3-b][1,4]diazepin-8-yl)-N-methyl-N-((2-methylbenzofuran-3-yl)methyl)acrylamide (compound 40). Pure fractions of first enantiomer were collected and concentrated. The first enantiomer was obtained as a yellow solid (m=21.11 mg; chiral purity: 98.82%). $R^t$ 1.50 min (Standard) m/z 435.5 $[M+H]^+$ ($ES^+$). The stereochemistry of obtained enantiomer was randomly assigned (R,E)-3-(3-(Hydroxymethyl)-3-methyl-4-oxo-2,3,4,5-tetrahydro-1H-pyrido[2,3-b][1,4]diazepin-8-yl)-N-methyl-N-((2-methylbenzofuran-3-yl)methyl)acrylamide (compound 41). Pure fractions of second enantiomer were collected and concentrated. The second enantiomer was obtained as a yellow solid (m=18.22 mg; chiral purity: 99.49%). $R^t$ 1.50 min (Standard) m/z 435.5 $[M+H]^+$ ($ES^+$). The stereochemistry of obtained enantiomer was randomly assigned.

Example 8. Synthesis of (R,E)-3-(3-Hydroxy-3-methyl-4-oxo-2,3,4,5-tetrahydro-1H-pyrido[2,3-b][1,4]diazepin-8-yl)-N-methyl-N-((3-methylbenzofuran-2-yl)methyl)acrylamide (Compound 49) and (S,E)-3-(3-hydroxy-3-methyl-4-oxo-2,3,4,5-tetrahydro-1H-pyrido[2,3-b][1,4]diazepin-8-yl)-N-methyl-N-((3-methylbenzofuran-2-yl)methyl)acrylamide (Compound 50)

General Synthetic Scheme

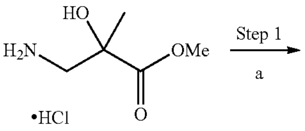

42

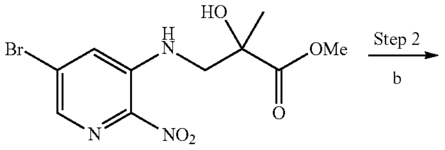

43

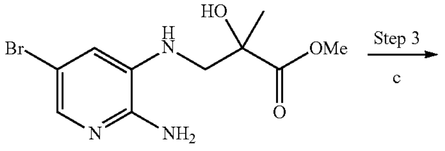

44

-continued

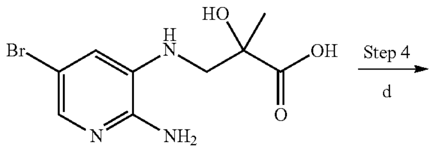

45

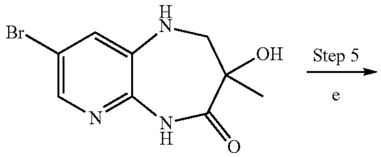

Racemic mixture

46

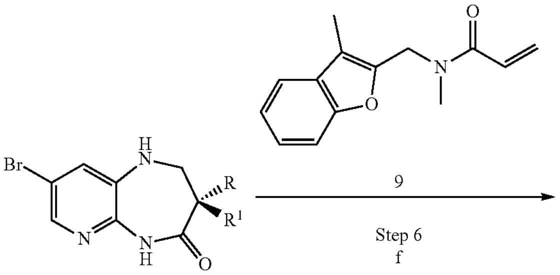

isomer 1: R = Me, $R^1$ = OH 47
isomer 2: R = OH, $R^1$ = Me 48

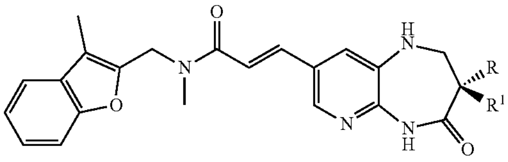

isomer 1: R = Me, $R^1$ = OH 49
isomer 2: R = OH, $R^1$ = Me 50

Reaction conditions: a) 5-bromo-3-fluoro-2-nitropyridine 11, $K_2CO_3$, reflux; b) Fe, AcOH, 90° C.; c) LiOH, THF:$H_2O$, RT: d) HATU, Hunig's base, DMF, RT; e) chiralpak IA, EtOH/heptane/$CHCl_3$; f) Pd-162, $Bu_4NCl$, $Cy_2NMe$, 80° C.

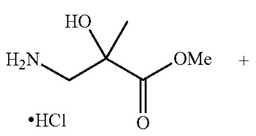

42

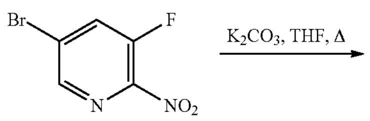

11

-continued

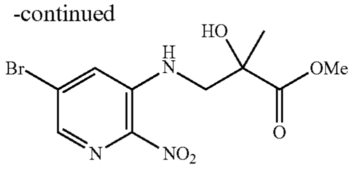

43

Step 1. Methyl 3-((5-bromo-2-nitropyridin-3-yl)amino)-2-hydroxy-2-methylpropanoate (compound 43). To a stirred solution of 5-bromo-3-fluoro-2-nitropyridine 11 (0.33 g, 1.47 mmol) in THF (5 mL) was added methyl 3-amino-2-hydroxy-2-methylpropanoate hydrochloride 42 (Enamine) (0.25 g, 1.47 mmol) followed by potassium carbonate (0.41 g, 2.95 mmol). The reaction mass was stirred at reflux for 2 h. The reaction mixture was allowed to cool to room temperature. The solvent was removed in vacuo to afford the title compound 43 as a yellow oil (0.48 g, 94% yield). $R^t$ 1.03 min (Method 2a) m/z 334/336 $[M+H]^+$ $(ES^+)$.

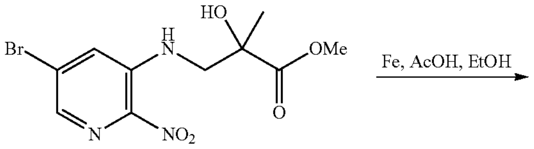

43

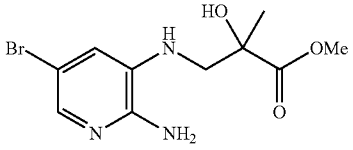

44

Step 2. 3-((2-Amino-5-bromopyridin-3-yl)amino)-2-hydroxy-2-methylpropanoate (compound 44). To a stirred solution of methyl 3-((5-bromo-2-nitropyridin-3-yl)amino)-2-hydroxy-2-methylpropanoate 43 (0.48 g, 1.44 mmol) in EtOH (6 mL) was added acetic acid (1.64 mL, 28.7 mmol) followed by iron powder (0.80 g, 14.4 mmol). The reaction mixture was stirred at 90° C. for 30 min. The reaction mixture was allowed to cool to room temperature and neutralised to pH 8 with solid $NaHCO_3$. The resulting reaction mixture was diluted with $H_2O$ (10 mL) and EtOAc (10 mL). The aqueous phase was separated and extracted with EtOAc (2×10 mL). The combined organic phases were washed with $H_2O$ (10 mL), passed through a hydrophobic frit, and concentrated in vacuo to afford the title compound 44 (0.43 g, 50%). $R^t$ 0.58 min (Method 2a) m/z 304/306 $[M+H]^+$ $(ES^+)$.

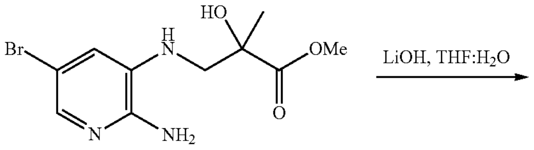

44

-continued

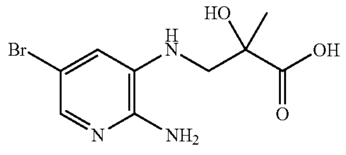

45

Step 3. 3-((2-Amino-5-bromopyridin-3-yl)amino)-2-hydroxy-2-methylpropanoic acid (compound 45). To a stirred solution of methyl 3-((2-amino-5-bromopyridin-3-yl)amino)-2-hydroxy-2-methylpropanoate 44 (0.35 g, 1.15 mmol) in THF (1.5 mL) was added a solution of LiOH (0.14 g, 5.8 mmol) in $H_2O$ (1.5 mL). The reaction mixture was stirred at room temperature overnight. The solvent was evaporated to dryness to give the title compound 45 as a colourless solid (320 mg, 34% yield) which was used in the next step without further purification. $R^t$ 0.73 min (Method 2a) m/z 290/292 $[M+H]^+$ $(ES^+)$.

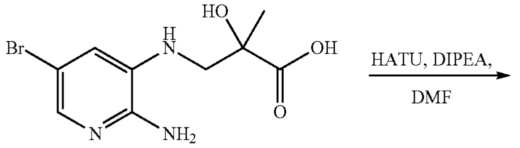

45

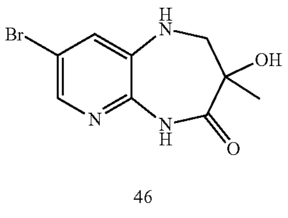

46

Step 4. 8-Bromo-3-hydroxy-3-methyl-1,2,3,5-tetrahydro-4H-pyrido[2,3-b][1,4]diazepin-4-one (compound 46). To a stirred solution of 3-((2-amino-5-bromopyridin-3-yl)amino)-2-hydroxy-2-methylpropanoic acid 45 (0.32 g, 1.1 mmol) in DMF (4 mL) was added DIPEA (0.58 mL, 3.3 mmol) followed by HATU (0.63 g, 1.65 mmol). The reaction mixture was stirred at room temperature for 1 h. Water (4 mL) was added. The aqueous phase was separated and extracted with EtOAc (2×5 mL). The combined organic phases were washed with $H_2O$ (3×5 mL), passed through a hydrophobic frit, and concentrated in vacuo to afford the title compound 46 as a colourless solid (41 mg, 14% yield). $R^t$ 0.83 min (Method 2a) m/z 272/274 $[M+H]^+$ $(ES^+)$. $^1H$ NMR (400 MHz, DMSO-$d_6$): δ, ppm 9.92 (s, 1H), 7.65 (d, J=2.1 Hz, 1H), 7.24 (d, J=2.1 Hz, 1H), 6.50 (t, J=4.6 Hz, 1H), 5.34 (s, 1H), 3.28-3.05 (m, 2H), 1.22 (s, 3H).

Step 5. Chiral separation of racemate 46.

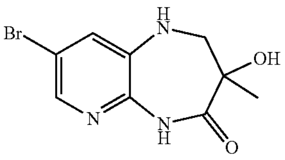

46

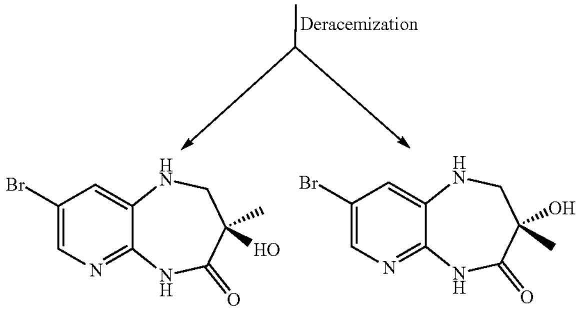

47 48

The enantiomers were separated by chiral prep HPLC using Method 3a. Chirality was arbitrarily assigned.

(R)-8-Bromo-3-hydroxy-3-methyl-1,2,3,5-tetrahydro-4H-pyrido[2,3-b][1,4]diazepin-4-one (compound 47). First eluting isomer: $R^t$ 6.4 min (Method 4a); $R^t$ 0.83 min (Method 2a) m/z 272/274 $[M+H]^+$ $(ES^+)$.

(S)-8-Bromo-3-hydroxy-3-methyl-1,2,3,5-tetrahydro-4H-pyrido[2,3-b][1,4]diazepin-4-one (compound 48). Second eluting enantiomer: $R^t$ 11.7 min (Method 4a); $R^t$ 0.83 min (Method 2a) m/z 272/274 $[M+H]^+$ $(ES^+)$.

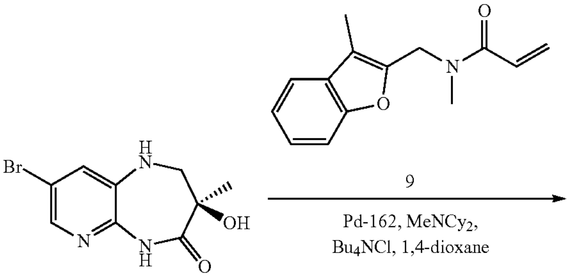

47

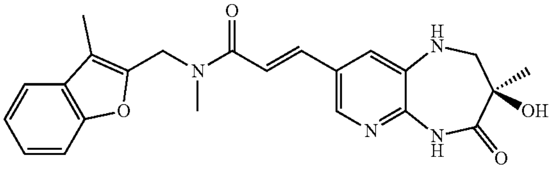

49

Step 6a. (R,E)-3-(3-Hydroxy-3-methyl-4-oxo-2,3,4,5-tetrahydro-1H-pyrido[2,3-b][1,4]diazepin-8-yl)-N-methyl-N-((3-methylbenzofuran-2-yl)methyl)acrylamide (compound 49). A reaction vial was charged with N-methyl-N-((3-methylbenzofuran-2-yl)methyl)acrylamide 9 (22 mg, 0.1 mmol), (R)-8-bromo-3-hydroxy-3-methyl-2,3-dihydro-1H-pyrido[2,3-b][1,4]diazepin-4(5H)-one 47 (27 mg, 0.1 mmol), tetrabutylammonium chloride hydrate (3 mg, 0.01 mmol), $[P(tBu)_3]Pd(crotyl)Cl$ (Pd-162) (4 mg, 0.01 mmol). The vial was flushed with nitrogen for 5 mins. 1,4-Dioxane (2 mL) and N-cyclohexyl-N-methylcyclohexanamine (42 μL, 0.20 mmol) were added and the reaction mixture was purged with nitrogen for a further 5 mins. The mixture was heated to 80° C. for 3 h and allowed to cool to room temperature. The solvent was evaporated to dryness. The crude product was purified by silica chromatography (0-10% MeOH/DCM) to afford the title compound 49 as a yellow solid (20 mg, 48%). $R^t$ 19 min (Method 4a). $R^t$ 1.23 min (Method 2a) m/z 421 $[M+H]^+$ $(ES^+)$. $^1H$ NMR (400 MHz, DMSO-$d_6$): δ, ppm 9.37 (s, 1H), 7.95 (d, J=1.9 Hz, 1H), 7.60-7.53 (m, 1H), 7.49-7.45 (m, 1H), 7.42 (d, J=15.4 Hz, 1H), 7.36 (d, J=2.0 Hz, 1H), 7.30-7.24 (m, 2H), 7.18-7.07 (m, 1H), 6.06 (s, 1H), 4.92 (s, 1H), 4.84 (s, 2H), 3.20 (dd, J=6.7 Hz, 4.7 Hz, 2H), 3.10 (s, 3H), 2.28 (s, 3H), 1.29 (s, 3H).

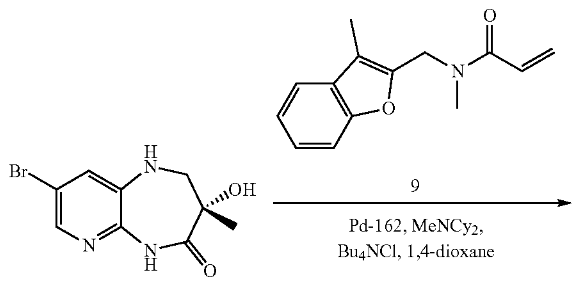

-continued

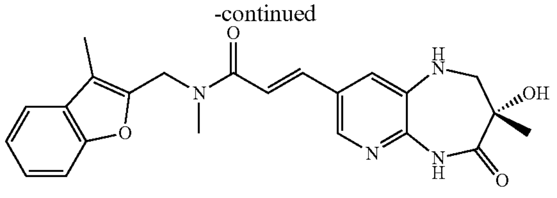

50

Step 6b. (S,E)-3-(3-Hydroxy-3-methyl-4-oxo-2,3,4,5-tetrahydro-1H-pyrido[2,3-b][1,4]diazepin-8-yl)-N-methyl-N-((3-methylbenzofuran-2-yl)methyl)acrylamide (compound 50). A reaction vial was charged with N-methyl-N-((3-methylbenzofuran-2-yl)methyl)acrylamide 9 (23 mg, 0.1 mmol), (S)-8-bromo-3-hydroxy-3-methyl-2,3-dihydro-1H-pyrido[2,3-b][1,4]diazepin-4(5H)-one 48 (27 mg, 0.1 mmol), tetrabutylammonium chloride hydrate (3 mg, 0.01 mmol), $[P(tBu)_3]Pd(crotyl)Cl$ (Pd-162) (4 mg, 0.01 mmol). The vial was flushed with nitrogen for 5 mins. 1,4-Dioxane (2 mL) and N-cyclohexyl-N-methylcyclohexanamine (43 μL, 0.20 mmol) were added and the reaction mixture was purged with nitrogen for a further 5 mins. The mixture was heated to 80° C. for 3 h and allowed to cool to room temperature. The solvent was evaporated to dryness. The crude product was purified by silica chromatography (0-10% MeOH/DCM) to afford the title compound 50 as a yellow solid (34 mg, 80% yield). $R^t$ 33 min (Method 4a). $R^t$ 1.23 min (Method 2a) m/z 421 $[M+H]^+$ $(ES^+)$. $^1H$ NMR (400 MHz, DMSO-$d_6$): δ, ppm 9.37 (s, 1H), 7.95 (d, J=1.9 Hz, 1H), 7.60-7.53 (m, 1H), 7.49-7.45 (m, 1H), 7.42 (d, J=15.4 Hz, 1H), 7.36 (d, J=2.0 Hz, 1H), 7.30-7.24 (m, 2H), 7.18-7.07 (m, 1H), 6.06 (s, 1H), 4.92 (s, 1H), 4.84 (s, 2H), 3.20 (dd, J=6.7, 4.7 Hz, 2H), 3.10 (s, 3H), 2.28 (s, 3H), 1.29 (s, 3H).

Example 9. Synthesis of 8-((E)-3-oxo-3-((3aS,6aR)-5-(4-(pyrimidin-2-yloxy)phenyl)-3,3a,4,6a-tetrahydrocyclopenta[c]pyrrol-2(1H)-yl)prop-1-en-1-yl)-1,2,3,5-tetrahydro-4H-pyrido[2,3-b][1,4]diazepin-4-one (Compound 60)

General Synthetic Scheme.

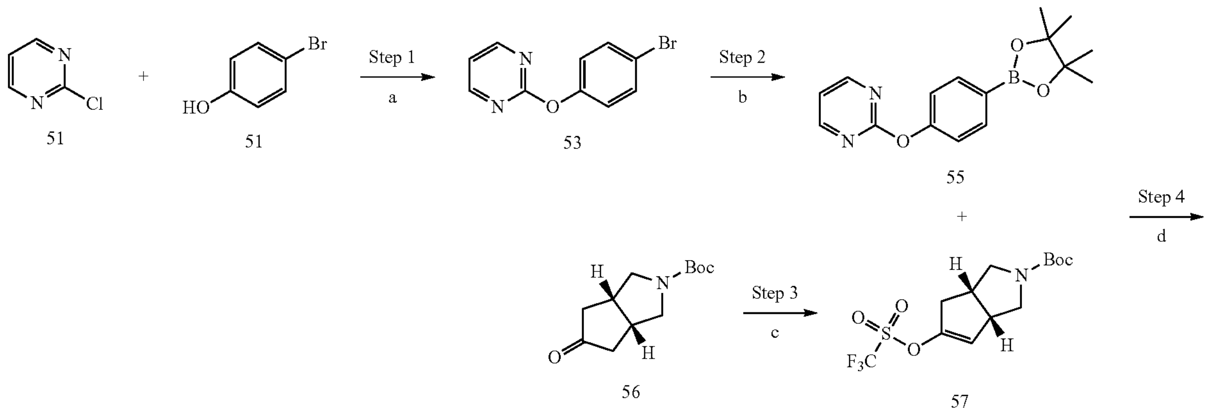

-continued

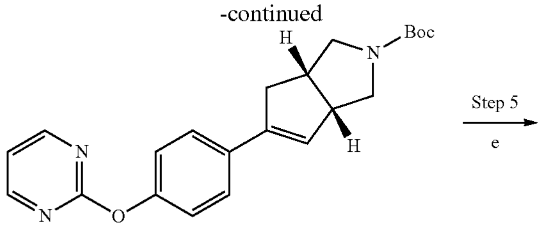

58

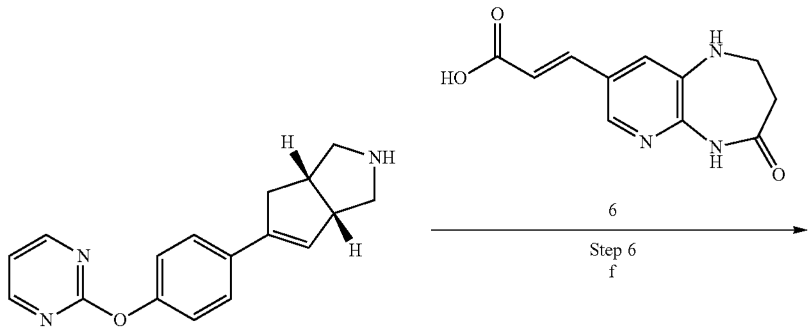

6

59

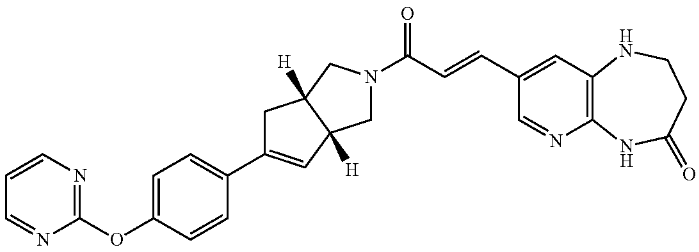

60

Reaction conditions: a) $Cs_2CO_3$, NMP, 80° C., 2 h; b) Bis(pinacolato)diboron 54, Pd(dppf)$Cl_2$, AcOK, 1,4-dioxane; c) LHMDS, Comins' reagent, THF, -78° C. to rt; d) $Na_2CO_3$, $Pd(PPh_3)_4$, $H_2O$, 1,4-dioxane, 90° C; e) TFA, DCM; f) DIPEA, HATU, DMF

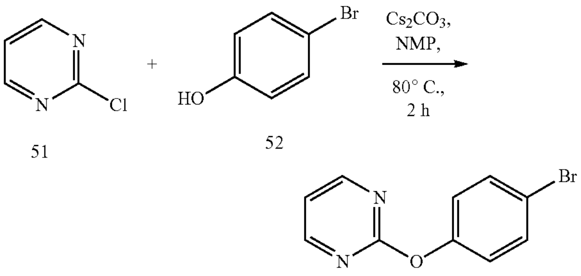

51 52

53

Step 1. 2-(4-Bromophenoxy)pyrimidine (compound 53). A mixture of 2-chloropyrimidine 51 (Alfa Aesar) (2 g, 17 mmol), 4-bromophenol 52 (Sigma-Aldrich) (3.6 g, 21 mmol) and $Cs_2CO_3$ (17 g, 52 mmol) in N-methyl-2-pyrrolidone (50 mL) was heated at 80° C. for 2 hours. The reaction mixture was allowed to cool to room temperature, and poured into water (200 mL). The mixture was extracted with EtOAc (2×100 mL). The organics were combined and washed with brine (2×100 mL), passed through an hydrophobic frit, and concentrated in vacuo. The crude product was purified by chromatography (0-50% EtOAc/isohexane) to afford the title compound 53 as a colourless crystalline solid (3.95 g, 90% yield). $R^t$ 1.86 min (Method 1a) m/z 251/253 $[M+H]^+$ ($ES^+$). $^1H$ NMR (400 MHz, $CDCl_3$): δ, ppm 8.59 (d, J=4.7 Hz, 2H), 7.59-7.53 (m, 2H), 7.15-7.10 (m, 2H), 7.08 (t, J=4.8 Hz, 1H).

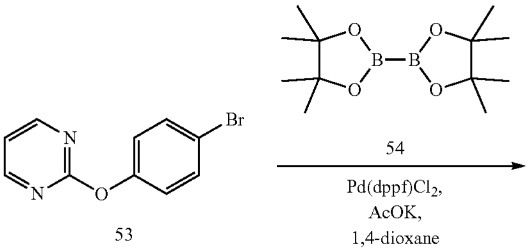

54

53

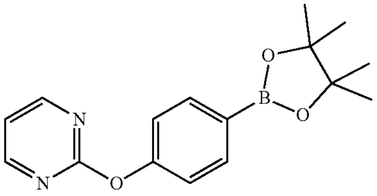

55

Step 2. 2-(4-(4,4,5,5-Tetramethyl-1,3,2-dioxaborolan-2-yl)phenoxy)pyrimidine. Step 2 (compound 55). A mixture of 2-(4-bromophenoxy)pyrimidine 53 (0.5 g, 2.0 mmol), 4,4, 4',4',5,5,5',5'-octamethyl-2,2'-bi(1,3,2-dioxaborolane) 54 (Fluorochem) (0.7 g, 2.8 mmol), potassium acetate (0.6 g, 6.0 mmol) and $PdCl_2$(dppf) (0.07 g, 0.1 mmol) in 1,4-dioxane (20 mL) was stirred at 85° C. for 16 h. The reaction mixture was allowed to cool to room temperature, filtered through Celite®, and concentrated in vacuo. The crude residue was partitioned between EtOAc (50 mL) and water (50 mL). The aqueous phase was extracted with EtOAc (2×50 mL). The combined organic layers were passed through a phase separator and evaporated to dryness to give the crude product 55 as a dark brown solid (0.6 g, 2.0 mmol, quant. yield). $R^t$ 2.23 min (Method 1a) m/z 299 $[M+H]^+$ ($ES^+$).

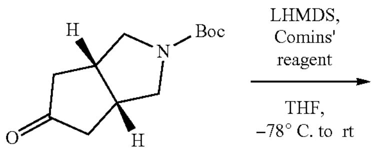

56

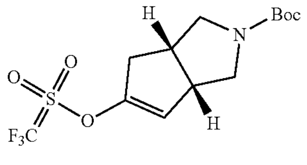

57

Step 3. Preparation of tert-butyl (3aS,6aS)-5-(((trifluoromethyl)sulfonyl)oxy)-3,3a,4,6a-tetrahydrocyclopenta[c]pyrrole-2(1H)-carboxylate (compound 57). To a stirred solution of tert-butyl 5-oxohexahydrocyclopenta[c]pyrrole-2(1H)-carboxylate 56 (Ark Pharm) (3 g, 13.3 mmol) in THF (60 mL) was slowly added a solution of LHMDS (1M in THF) (17 mL, 17.3 mmol) at −78° C. The reaction mixture was stirred at −78° C. for 30 min, then a solution of N-(5-chloropyridin-2-yl)-1,1,1-trifluoro-N-((trifluoromethyl)sulfonyl)methanesulfonamide (7.3 g, 18.6 mmol) in THF (20 mL) was slowly added. The mixture was stirred for an additional 1 h at −78° C., allowed to warm up to room temperature and stirred for 2 h. The reaction mixture was concentrated in vacuo. The crude residue was purified by chromatography (0-50% EtOAc/isohexane) to afford the title compound 57 as a pale yellow oil (4.4 g, 91% yield). $R^t$ 1.29 min (Method 1a) m/z 302 $[M+H-{}^tBu]^+$ ($ES^+$). $^1H$ NMR (400 MHz, $CDCl_3$): δ, ppm 5.58 (d, J=1.9 Hz, 1H), 3.72 (dd, J=11.4 Hz, 8.5 Hz, 1H), 3.53 (dd, J=11.8 Hz, 8.3 Hz, 1H), 3.40 (ddt, J=8.6 Hz, 6.0 Hz, 2.7 Hz, 2H), 3.16 (dd, J=11.4, 6.5 Hz, 1H), 3.04-2.80 (m, 2H), 2.51-2.33 (m, 1H), 1.46 (s, 9H).

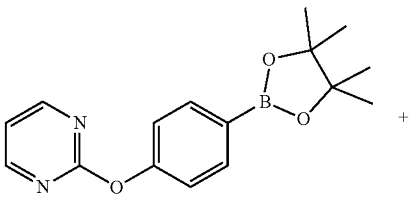

55

-continued

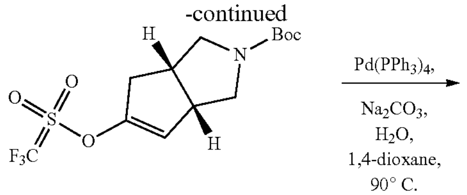

57

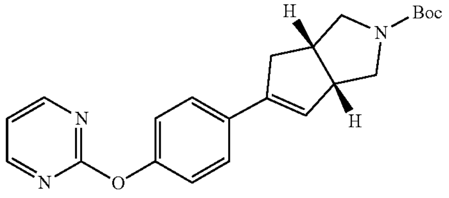

58

Step 4. tert-Butyl (3aS,6aR)-5-(4-(pyrimidin-2-yloxy)phenyl)-3,3a,4,6a-tetrahydrocyclopenta[c]pyrrole-2(1H)-carboxylate (compound 58). To a stirred suspension of (3aS,6aS)-tert-butyl 5-(((trifluoromethyl)sulfonyl)oxy)-3,3a,6,6a-tetrahydrocyclopenta[c]pyrrole-2(1H)-carboxylate 57 (0.28 g, 0.77 mmol), 2-(4-(4,4,5,5-tetramethyl-1,3,2-dioxaborolan-2-yl)phenoxy)pyrimidine 55 (0.30 g, 1.00 mmol), $Pd(Ph_3P)_4$ (0.09 g, 0.08 mmol) in 1,4-dioxane (20 mL) was added a solution of $Na_2CO_3$ (0.5 g, 5.0 mmol) in $H_2O$ (2.5 mL). The reaction mixture was stirred at 85° C. for 16 h. The reaction mass was allowed to cool to room temperature, filtered through Celite®, and concentrated in vacuo. The crude residue was diluted with water (50 mL), extracted with EtOAc (2×50 mL). The combined organic layers were passed through a phase separator and evaporated to dryness. The crude product was purified by chromatography (0-100% EtOAc/isohexane) to afford the title compound 58 as a clear colourless oil (0.18 g, 60% yield). $R^t$ 2.44 min (Method 1a) m/z 324 $[M+H-{}^tBu]^+$ ($ES^+$). $^1H$ NMR (400 MHz, $CDCl_3$): δ, ppm 8.59 (d, J=4.8 Hz, 2H), 7.50 (d, J=8.7 Hz, 2H), 7.21-7.15 (m, 2H), 7.06 (t, J=4.8 Hz, 1H), 6.03 (s, 1H), 3.72 (dd, J=10.7 Hz, 8.4 Hz, 1H), 3.61-3.47 (m, 3H), 3.14-2.93 (m, 3H), 2.62 (d, J=15.5 Hz, 1H), 1.47 (s, 9H).

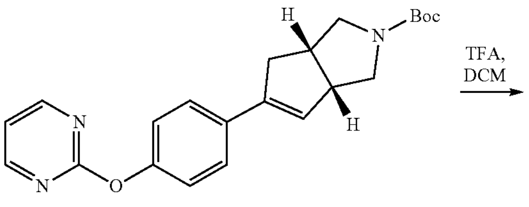

58

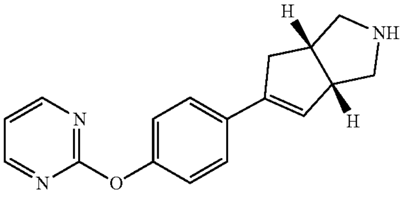

59

Step 5. (3aS,6aR)-5-(4-(Pyrimidin-2-yloxy)phenyl)-1,2,3,3a,4,6a-hexahydrocyclopenta[c]pyrrole (compound 59).

To a stirred solution of (3aR,6aS)-tert-butyl 5-(4-(pyrimidin-2-yloxy)phenyl)-3,3a,6,6a-tetrahydrocyclopenta[c]pyrrole-2(1H)-carboxylate 58 (0.18 g, 0.47 mmol) in DCM (1 mL) was added TFA (1 mL). The reaction mixture was stirred at room temperature for 2 h. The solvent was removed in vacuo. The resulting oil was taken up in MeOH (5 mL) and applied to an SCX column. The column was washed with methanol (5 mL) and the product eluted with 10% methanolic ammonia (5 mL) to afford the title compound 59 as a colourless crystalline solid (0.09 g, 69%). $R^t$ 0.92 min (Method 1a) m/z 280 $[M+H]^+$ $(ES^+)$.

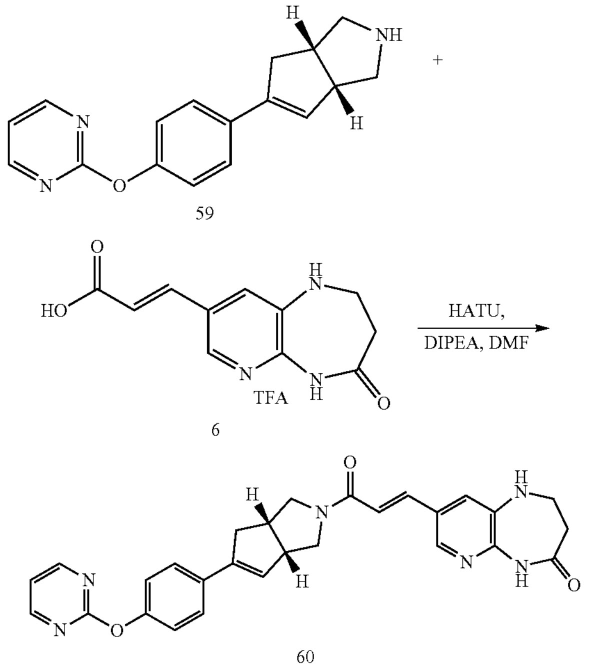

59

6

60

Step 6. 8-((E)-3-Oxo-3-((3aS,6aR)-5-(4-(pyrimidin-2-yloxy)phenyl)-3,3a,4,6a-tetrahydrocyclopenta[c]pyrrol-2(1H)-yl)prop-1-en-1-yl)-1,2,3,5-tetrahydro-4H-pyrido[2,3-b][1,4]diazepin-4-one (compound 60). To a stirred solution of (3aS,6aR)-5-(4-(pyrimidin-2-yloxy)phenyl)-1,2,3,3a,4,6a-hexahydrocyclopenta[c]pyrrole 59 (0.09 g, 0.31 mmol) in DMF (2 mL) was added (E)-3-(4-oxo-2,3,4,5-tetrahydro-1H-pyrido[2,3-b][1,4]diazepin-8-yl)acrylic acid trifluoroacetate 6 (79 mg, 0.34 mmol) and N-ethyl-N-isopropylpropan-2-amine (0.27 mL, 1.54 mmol). The reaction mixture was stirred at rt for 5 min and HATU (0.14 g, 0.37 mmol) was added. The reaction mixture was stirred at room temperature for 2 h. $H_2O$ (1 mL) was added and the reaction mixture sonicated. The solid was filtered and washed with $H_2O$ (2×2 mL). The filtrate was discarded. The crude solid was purified by chromatography (0-10% MeOH/DCM) to afford the title compound 60 as a yellow solid (0.13 g, 79% yield). $R^t$ 1.65 min (Method 1a) m/z 495 $[M+H]^+$ $(ES^+)$. $^1H$ NMR (400 MHz, DMSO-$d_6$): δ, ppm 9.74 (d, J=7.3 Hz, 1H), 8.64 (dd, J=4.8 Hz, 1.5 Hz, 2H), 7.98 (dd, J=9.3 Hz, 1.9 Hz, 1H), 7.58-7.51 (m, 2H), 7.38-7.30 (m, 2H), 7.27 (td, J=4.8 Hz, 0.8 Hz, 1H), 7.21-7.14 (m, 2H), 6.87 (dd, J=15.5 Hz, 9.4 Hz, 1H), 6.22-6.15 (m, 1H), 6.03 (d, J=14.4 Hz, 1H), 4.06-3.77 (m, 2H), 3.72-3.50 (m, 2H), 3.45-3.39 (m, 2H), 3.24-2.84 (m, 3H), 2.69-2.55 (m, 3H).

Example 10. Preparation of (E)-N-methyl-N-((2-methylbenzofuran-3-yl)methyl)-3-(3'-oxo-2,3,3',4',5,6-hexahydro-1'H-spiro[pyran-4,2'-pyrido[2,3-b]pyrazin]-7'-yl)acrylamide (Compound 64)

General Synthetic Scheme.

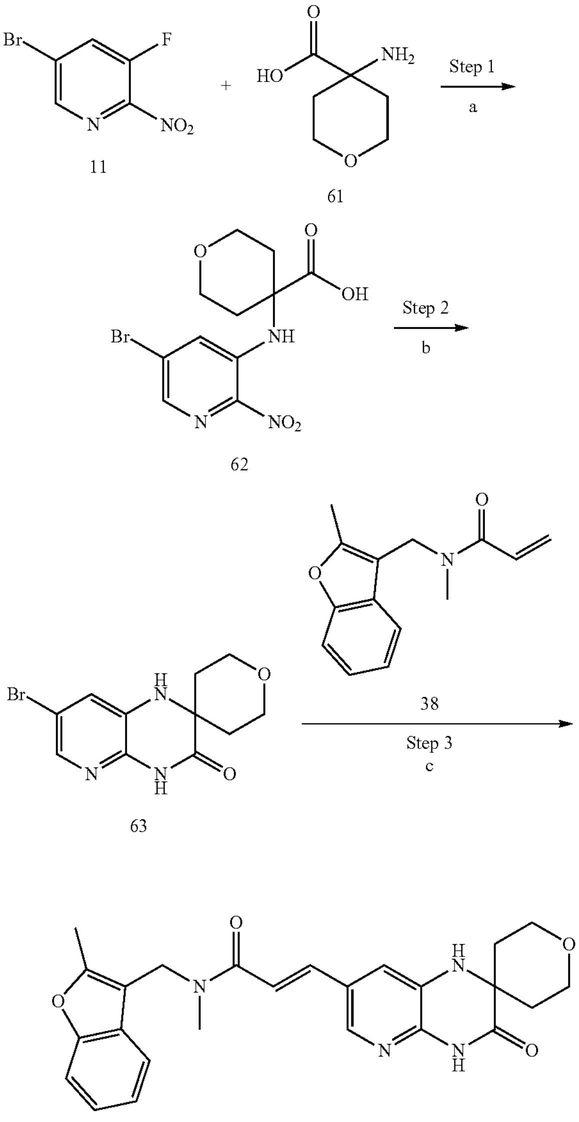

11

61

62

38

63

64

Reaction conditions: a) $K_2CO_3$, THF; b) $NH_4Cl$, Fe, EtOH/Water; c) $Pd(OAc)_2$, Tri-o-tolylphosphan, DIPEA in DMF/ACN

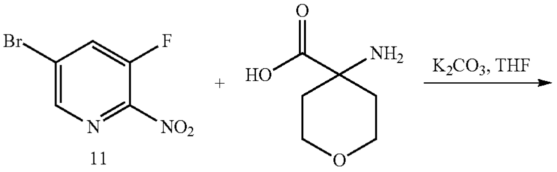

11

61

-continued

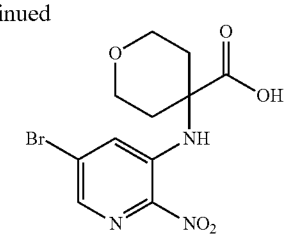

62

Step 1. 4-((5-Bromo-2-nitropyridin-3-yl)amino)tetrahydro-2H-pyran-4-carboxylic acid (compound 62). 5-Bromo-3-fluoro-2-nitropyridine 11 (800 mg, 3.62 mmol, 1.0 eq) and 4-aminotetrahydro-2H-pyran-4-carboxylic acid 61 (Combi-Blocks) (735 mg, 5.06 mmol, 1.4 eq) were dissolved in THF (10 mL), then $K_2CO_3$ (1 g) was added. The resulting reaction mixture was heated to 90° C. overnight in a sealed tube. The UPLC analysis showed almost complete conversion of the SM with the formation of the expected product ($R_t$=1.11 min; $ES^+$=348.1). The solvent was removed under vacuum and the residue was dissolved in a mixture of water/EtOAc. An aqueous phase was acidified with aq. 1M HCl to pH 1 and extracted twice with EOAc. The combined organic layers were washed with brine, dried over $MgSO_4$ and concentrated to dryness. The resulting yellow solid was diluted with EtOAc. The precipitate, thus formed, was filtered off to afford the product 62 as a yellow solid with a purity of 99% (535 mg, 42% yield). The filtrate was concentrated to dryness to yield less pure product 62 as a brown solid with a purity of 93% (550 mg, 43.8% yield). Both batches were used in the next step without further purification. $R^t$ 1.09 min (Method 1c) m/z 346.1/348.1 $[M+H]^+$ ($ES^+$) (isotop effect)

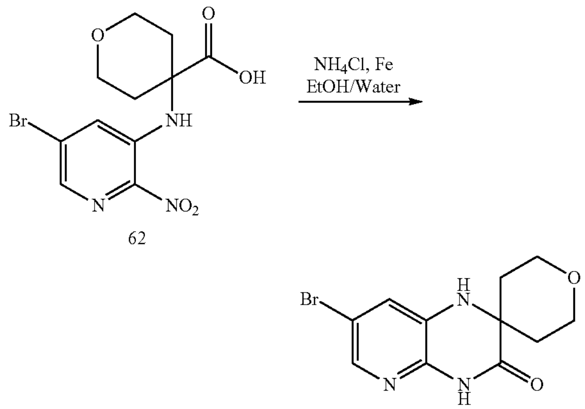

62

63

Step 2. 7'-Bromo-1',2,3,4',5,6-hexahydro-3'H-spiro[pyran-4,2'-pyrido[2,3-b]pyrazin]-3'-one (compound 63). To a stirred solution of 4-((5-bromo-2-nitropyridin-3-yl)amino)tetrahydro-2H-pyran-4-carboxylic acid 62 (535 mg, 1.5 mmol, 1.0 eq), $NH_4Cl$ (165 mg, 3.1 mmol, 2.0 eq) and iron (170 mg, 3.1 mmol, 2.0 eq) was suspended in a mixture of EtOH/Water (1:1 v/v, 10 mL). The resulting suspension was heated to 80° C. for 1.5 h. The UPLC analysis showed formation of the product (Rt=1.09 min; $ES^+$=300.1) with complete conversion of the starting material. The reaction mass was diluted with EtOAc (and small amount of MeOH), filtered through 0.22 μM filter and washed with acetonitrile. The solution was concentrated to dryness and diluted with AcOEt and washed with water. The organic phase was dried ($MgSO_4$), filtered and concentrated to dryness. The residue was purified on silica gel using SNAP Ultra cartridge 25 g and DCM/MeOH 99:1 to 95:5 v/v as an eluent. Fractions containing the product were combined to afford the 7'-bromo-1',2,3,4',5,6-hexahydro-3'H-spiro[pyran-4,2'-pyrido[2,3-b]pyrazin]-3'-one 63 as a grey-green powder with a purity of 99% (220 mg, 48% yield). UPLC-MS m/z: 300.1 $[M+H]^+$ ($ES^+$). $^1H$ NMR (400 MHz, DMSO-$d_6$): δ, ppm 10.94 (s, 1H), 7.69 (d, J=2.1 Hz, 1H), 7.33 (d, J=2.0 Hz, 1H), 6.77 (s, 1H), 3.75-3.70 (m, 4H), 2.00-1.90 (m, 2H), 1.46 (d, J=13.6 Hz, 2H).

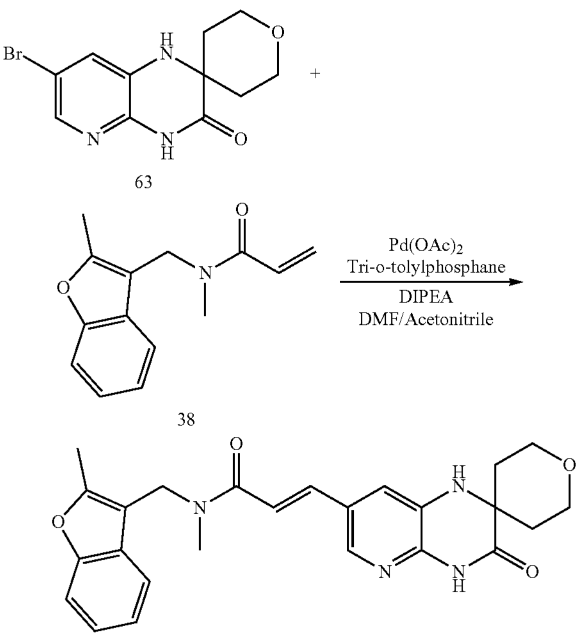

63

+

38

64

Step 3. (E)-N-Methyl-N-((2-methylbenzofuran-3-yl)methyl)-3-(3'-oxo-2,3,3',4',5,6-hexahydro-1'H-spiro[pyran-4,2'-pyrido[2,3-b]pyrazin]-7'-yl)acrylamide (compound 64). An oven dried vial was charged with 7'-bromo-1',2,3,4',5,6-hexahydro-3'H-spiro[pyran-4,2'-pyrido[2,3-b]pyrazin]-3'-one 63 (50 mg, 0.16 mmol), anhydrous DMF (0.9 mL) and acetonitrile (0.1 mL) were added. The reaction mixture was degassed with nitrogen for 5 min. Then, N-methyl-N-((2-methylbenzofuran-3-yl)methyl)acrylamide 38 (58 mg, 0.25 mmol) and DIPEA (109 uL) were added and the mixture was degassed for the second time for 10 min. Finally, $Pd(OAc)_2$ (0.4 mg) and tri-o-tolylphosphane (1.0 mg) were added in one portion and the nitrogen was bubbled through the mixture for 1 min and the solution and heated at 100° C. overnight. The reaction was cooled to RT and filtered on a Celite® bed. The cake was rinsed with MeOH/AcOEt mixture and the filtrate concentrated under high vacuum to give the crude brown solid (250 mg) which was purified by Isolera (DCM 100% to DCM/AcOEt 0/100%). All fractions containing the product were evaporated to give the title molecule 64 as a white solid with a purity of 97%(46 mg, 0.10 mmol, 64% yield). $R^t$ 1.55 min (Method 1c). UPLC-MS m/z: 447.1 $[M+H]^+$ ($ES^+$). $^1H$ NMR (400 MHz, DMSO-$d_6$): δ, ppm 10.97 (s, 1H), 8.00 (s, 1H), 7.96 (s, 1H), 7.57 (d, J=7.3 Hz, 1H), 7.52 (d, J=15.4 Hz, 1H), 7.49-7.44 (m, 2H), 7.27-7.15 (m, 2H), 6.99 (d, J=15.3 Hz, 1H), 6.63-6.56 (m, 1H), 4.89 (s, 2H), 4.75 (s, 2H), 3.79-3.66 (m, 4H), 3.05 (s, 2H), 2.83 (s, 1H), 1.99-1.89 (m, 2H), 1.46 (d, J=14.3 Hz, 2H), 1.24 (s, 3H) (rotamers).

Example 11. Synthesis of (E)-N-((7-Amino-2-methylbenzofuran-3-yl)methyl)-N-methyl-3-(4-oxo-2,3,4,5-tetrahydro-1H-pyrido[2,3-b][1,4]diazepin-8-yl) acrylamide (Compound 75)

General Synthetic Scheme.

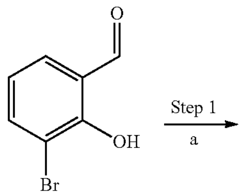

65

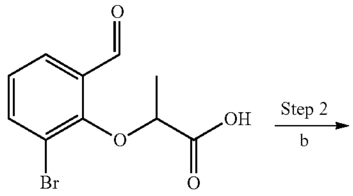

67

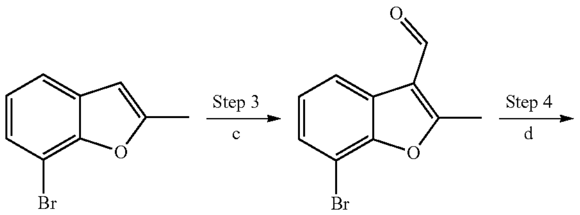

68 69

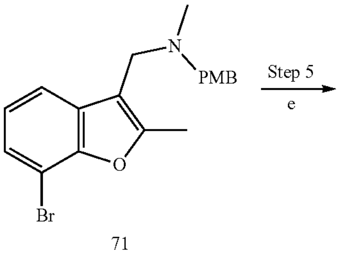

71

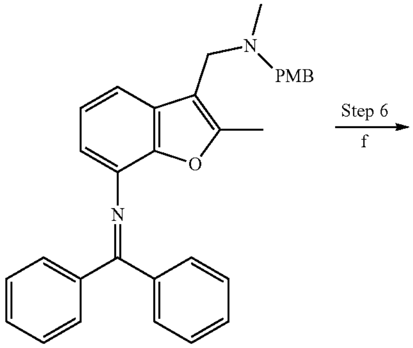

73

-continued

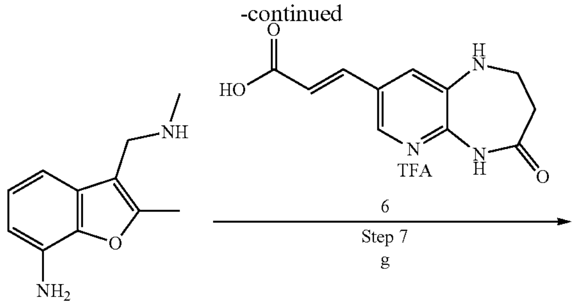

74

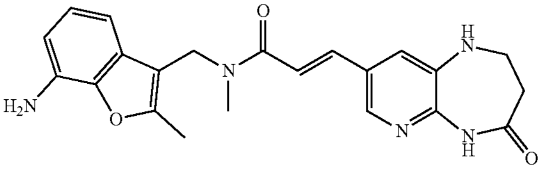

75

Reaction conditions: a) Ethyl 2-bromopropanoate 66, $K_2CO_3$, MeCN, reflux, then aq. NaOH, THF, reflux; b) NaOAc, $Ac_2O$, reflux; c) dichloro(methoxy)methane, $SnCl_4$ 1M in DCM, DCM, 0° C. to RT; d) 1-(4-methoxyphenyl)-N-methylmethanamine 70, $Na(OAc)_3BH$, DCE; e) $Pd_2(dba)_3$, Xantphos, Benzophenone imine 72, $Cs_2CO_3$, $PhCh_3$, 100° C.; f) 1-chloroethyl chloroformate, DCM, 0° C. - rt; g) HATU, DIPEA, DMF, rt.

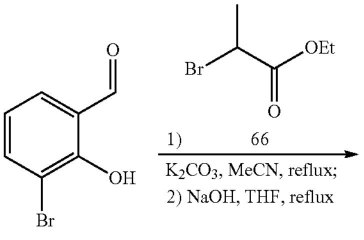

65

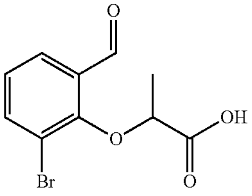

67

Step 1. 2-(2-Bromo-6-formylphenoxy)propanoic acid (compound 67). $K_2CO_3$ (13.8 g, 99 mmol) was added in one portion to a stirred solution of 3-bromo-2-hydroxybenzaldehyde 65 (10 g, 49.7 mmol) and ethyl 2-bromopropanoate 66 (5.9 mL, 45.2 mmol) in MeCN (80 mL) and the reaction was heated to reflux for 3 h. The reaction mixture was allowed to cool to RT, was filtered to remove $K_2CO_3$ and then concentrated in vacuo. The resulting residue was dissolved in THF (50 mL) and a solution of NaOH (2M in $H_2O$, 57 mL, 113 mmol) was added. The mixture was heated to reflux for 2 h, then cooled to RT and concentrated in vacuo. The remaining aqueous material was acidified to pH 1 by dropwise addition of concentrated HCl and the product precipitated. The product was collected by filtration and dried by azeotroping with MeCN (2×50 mL) to give the desired product 67 as an orange oil which crystallised on standing to give an off-white solid (13.5 g, 99% yield). $R^t$1.19 min (Method 2a) m/z 273/275 $[M+H]^+$ $(ES^+)$. $^1H$ NMR (400 MHz, $DMSO-d_6$): δ, ppm 13.23 (s, 1H), 10.41

(d, J=0.8 Hz, 1H), 7.97 (dd, J=7.9, 1.7 Hz, 1H), 7.74 (dd, J=7.7 Hz, 1.7 Hz, 1H), 7.25 (td, J=7.8 Hz, 0.9 Hz, 1H), 4.93 (q, J=6.8 Hz, 1H), 1.60 (d, J=6.8 Hz, 3H).

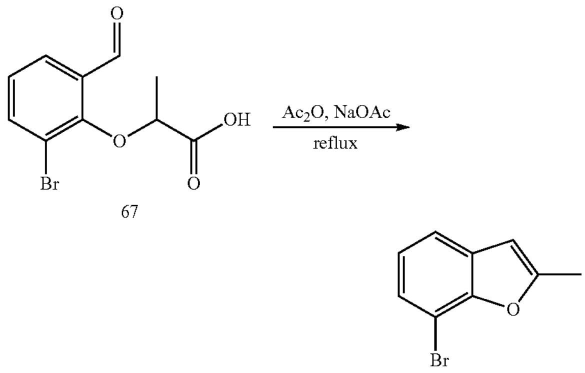

67

68

Step 2. 7-Bromo-2-methylbenzofuran (compound 68). A mixture of 2-(2-bromo-6-formylphenoxy)propanoic acid 67 (13 g, 48 mmol) and sodium acetate (39 g, 48 mmol) in acetic anhydride (70 mL) was heated to reflux for 2 h. The mixture was allowed to cool to RT, then poured onto ice water (800 mL). The mixture was then extracted with DCM (3×300 mL) and the combined organic layers were washed with NaOH (2M aq, 2×200 mL) then brine (200 mL). The organic layer was dried by passing through a phase separator then concentrated in vacuo. The crude product was purified by column chromatography (5-10% EtOAc/isohexane) to give the desired product 68 as a colourless oil (6.72 g, 66% yield). R$^t$1.67 min (Method 2a) no m/z observed. $^1$H NMR (400 MHz, DMSO-$d_6$): δ, ppm 7.53 (dd, J=7.7 Hz, 1.0 Hz, 1H), 7.43 (dd, J=7.8 Hz, 1.0 Hz, 1H), 7.13 (t, J=7.8 Hz, 1H), 6.71 (q, J=1.1 Hz, 1H), 2.48 (d, J=1.1 Hz, 3H).

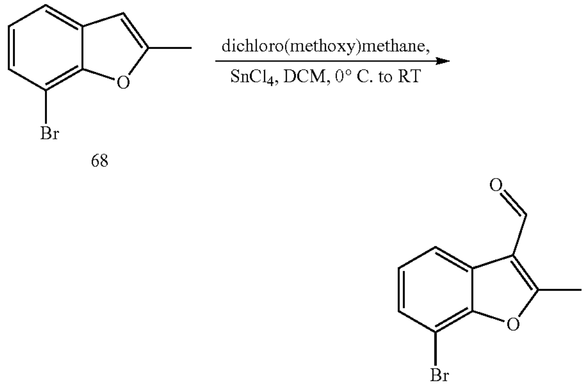

68

69

Step 3. 7-Bromo-2-methylbenzofuran-3-carbaldehyde (compound 69). Tin (IV) chloride (38 mL, 38 mmol, 1M in DCM) was added dropwise over ~30 min to a stirred solution of dichloro(methoxy)methane (3.2 mL, 35 mmol) and 7-bromo-2-methylbenzofuran 68 (6.7 g, 32 mmol) in DCM (120 mL) at 0° C. The reaction was allowed to return to RT over ~90 mins then poured into ice cold saturated sodium hydrogen carbonate solution (500 mL). The organic material was separated and the aqueous phase was extracted again with DCM (3×150 mL). The combined organic layers were washed with brine (200 mL) then dried by passing through a phase separation cartridge and concentrated in vacuo. The crude material was purified by recrystallisation from EtOAc/Hexane (1:1) to yield the desired product 69 as a pale yellow solid (4.5 g, 59% yield). R$^t$ 1.48 min (Method 2a) m/z 239/241 $[M+H]^+$ ($ES^+$). $^1$H NMR (400 MHz, DMSO-$d_6$): δ, ppm 10.20 (s, 1H), 7.98 (dd, J=7.7 Hz, 1.1 Hz, 1H), 7.59 (dd, J=7.9 Hz, 1.1 Hz, 1H), 7.29 (t, J=7.8 Hz, 1H), 2.84 (s, 3H).

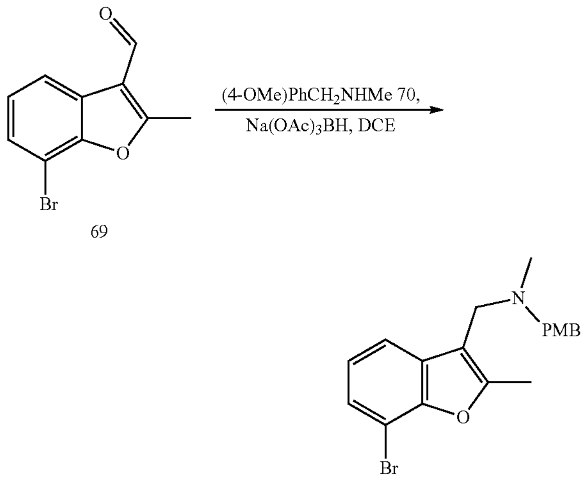

69

71

Step 4. 1-(7-Bromo-2-methylbenzofuran-3-yl)-N-(4-methoxybenzyl)-N-methylmethanamine (compound 71). Sodium triacetoxyborohydride (4.4 g, 21 mmol) was added in one portion to a stirred solution of 7-bromo-2-methylbenzofuran-3-carbaldehyde 69 (2 g, 8.37 mmol) and 1-(4-methoxyphenyl)-N-methylmethanamine 70 (1.3 mL, 8.37 mmol) in DCE (40 mL) at RT. The reaction mixture was stirred for ~16 h then the solvent was concentrated in vacuo and the resulting residue was taken up in $NaHCO_3$ (100 mL, sat aq). The aqueous material was extracted with DCM (3×100 mL) and the combined organic layers were washed with brine (100 mL) before being dried by passing through a phase separation cartridge. The crude material was purified by column chromatography (0-5% MeOH/DCM) to give the desired product 71 as a colourless oil (3.11 g, 92%). R$^t$ 0.98 min (Method 2a) m/z 374/376 $[M+H]^+$ ($ES^+$). $^1$H NMR (400 MHz, DMSO-$d_6$): δ, ppm 7.59 (dd, J=7.7 Hz, 1.0 Hz, 1H), 7.44 (dd, J=7.8 Hz, 1.0 Hz, 1H), 7.25-7.19 (m, 2H), 7.16 (t, J=7.8 Hz, 1H), 6.92-6.84 (m, 2H), 3.73 (s, 3H), 3.52 (s, 2H), 3.44 (s, 2H), 2.45 (s, 3H), 2.04 (s, 3H).

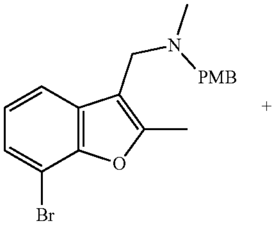

71

-continued

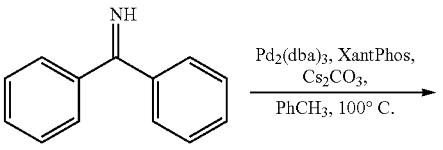

72

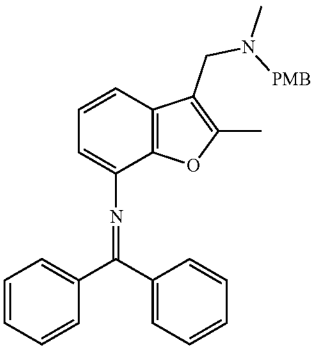

73

Step 5. N-(Diphenylmethylene)-3-(((4-methoxybenzyl)(methyl)amino)methyl)-2-methylbenzofuran-7-amine (compound 73). A 20 mL vial was evacuated and back filled with $N_2$ three times, then 1-(7-bromo-2-methylbenzofuran-3-yl)-N-(4-methoxybenzyl)-N-methylmethanamine 71 (0.3 g, 0.80 mmol), tris(dibenzylideneacetone)dipalladium(0) (75 mg, 0.08 mmol), cesium carbonate (0.52 g, 1.60 mmol) and Xantphos (70 mg, 0.12 mmol) were added and the vial was again evacuated and back filled with $N_2$ three times. Toluene (5 mL) and benzophenone imine 72 (0.14 ml, 0.80 mmol) were then added and the reaction mixture was heated to 100° C. and stirred for ~16 h. The reaction mixture was allowed to cool to rt, was filtered through Celite® and the cake was washed with DCM (100 mL). The filtrate was concentrated in vacuo and purified by column chromatography (0-50% EtOAc/isohexane) to give the desired product 73 as a yellow oil (0.36 g, 70% yield). $R^t$ 1.97 min (Method 1a); m/z 475 $[M+H]^+$ $(ES^+)$. $^1H$ NMR (500 MHz, DMSO-d6): δ, ppm 7.74-7.69 (m, 2H), 7.60-7.53 (m, 1H), 7.53-7.48 (m, 2H), 7.25-7.21 (m, 3H), 7.21-7.17 (m, 2H), 7.14-7.07 (m, 3H), 6.94 (t, J=7.7 Hz, 1H), 6.91-6.85 (m, 2H), 6.48 (dd, J=7.6 Hz, 1.1 Hz, 1H), 3.73 (s, 3H), 3.43 (s, 2H), 3.38 (s, 2H), 2.32 (s, 3H), 1.99 (s, 3H).

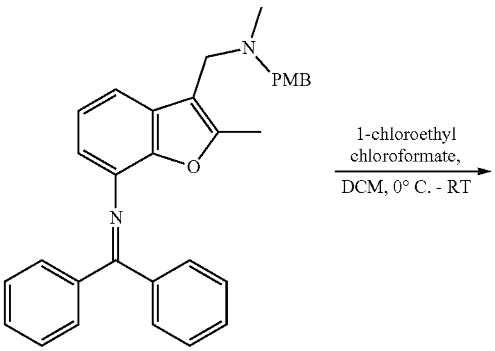

73

-continued

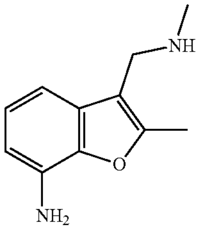

74

Step 6. 2-Methyl-3-((methylamino)methyl)benzofuran-7-amine (compound 74). 1-Chloroethyl chloroformate (0.12 ml, 1.14 mmol) was added dropwise to a stirred solution of N-(diphenylmethylene)-3-(((4-methoxybenzyl)(methyl)amino)methyl)-2-methylbenzofuran-7-amine 73 (0.36 g, 0.76 mmol) in DCM (5 mL) at 0° C. under $N_2$. The reaction was allowed to warm to room temperature and was stirred for ~16 h. The reaction mixture was concentrated in vacuo then taken up in MeOH (15 mL) and heated to reflux for 1 h. The reaction mixture was allowed to cool to RT then was concentrated in vacuo and purified by column chromatography (0-10% MeOH (0.7M $NH_3$)/DCM) to give the desired product 74 as a yellow oil (78 mg, 46% yield). $R^t$ 0.77 min (Method 1b); m/z 191 $[M+H]^+$ $(ES^+)$. $^1H$ NMR (500 MHz, DMSO-d6): δ, ppm 6.86-6.83 (m, 1H), 6.78 (dd, J=7.7 Hz, 1.2 Hz, 1H), 6.46 (dd, J=7.6, 1.2 Hz, 1H), 5.09 (s, 2H), 3.65 (s, 2H), 2.39 (s, 3H), 2.25 (s, 3H). Amine proton not assigned.

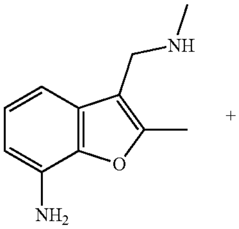

+

74

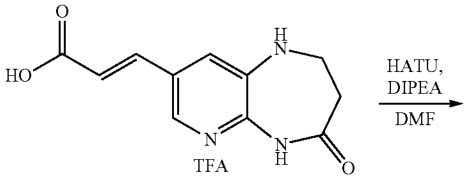

TFA

6

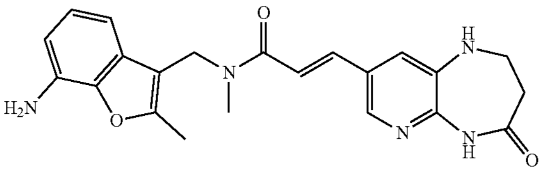

75

Step 7. (E)-N-((7-Amino-2-methylbenzofuran-3-yl)methyl)-N-methyl-3-(4-oxo-2,3,4,5-tetrahydro-1H-pyrido[2,3-b][1,4]diazepin-8-yl)acrylamide (compound 75). DIPEA (0.2 mL, 1.15 mmol) was added dropwise to a stirred solution of 2-methyl-3-((methylamino)methyl)benzofuran-7-amine 74 (78 mg, 0.41 mmol) and (E)-3-(4-oxo-2,3,4,5-tetrahydro-1H-pyrido[2,3-b][1,4]diazepin-8-yl)acrylic acid trifluoroacetate 6 (50 mg, 0.14 mmol) in DMF (2 mL) at rt. The reaction was stirred for 10 mins then HATU (70 mg, 0.18 mmol) was added and the reaction was stirred for 2 h. The reaction mixture was diluted with water (10 ml) and the precipitate collected by filtration. The crude material was purified by column chromatography (0-4% MeOH/DCM) to give the desired product 75 as a pale yellow solid (18 mg, 31% yield). R$^t$ 1.30 min (Method 1a); m/z 406 $[M+H]^+$ ($ES^+$). $^1H$ NMR (500 MHz, DMSO-d6, 363K): δ, ppm 9.13 (s, 1H), 7.97 (d, J=1.9 Hz, 1H), 7.44 (d, J=15.4 Hz, 1H), 7.37 (d, J=2.0 Hz, 1H), 7.08 (d, J=15.4 Hz, 1H), 6.87 (t, J=7.7 Hz, 1H), 6.74 (d, J=7.7 Hz, 1H), 6.53 (dd, J=7.7, 1.1 Hz, 1H), 5.79 (s, 1H), 4.86 (s, 2H), 4.71 (s, 2H), 3.46-3.40 (m, 2H), 2.98 (s, 3H), 2.68-2.61 (m, 2H), 2.46 (s, 3H).

Example 12. Synthesis of (E)-N-((7-(4-cyanophenoxy)-2-methylbenzofuran-3-yl)methyl)-N-methyl-3-(4-oxo-2,3,4,5-tetrahydro-1H-pyrido[2,3-b][1,4]diazepin-8-yl)acrylamide (Compound 80)

General Synthetic Scheme

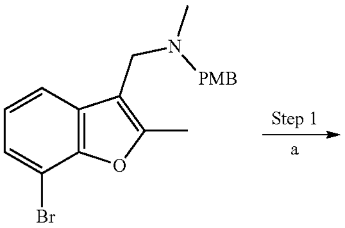

71

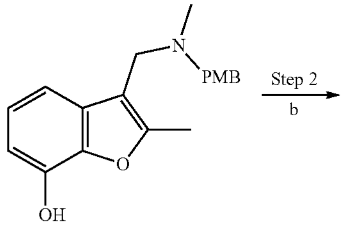

76

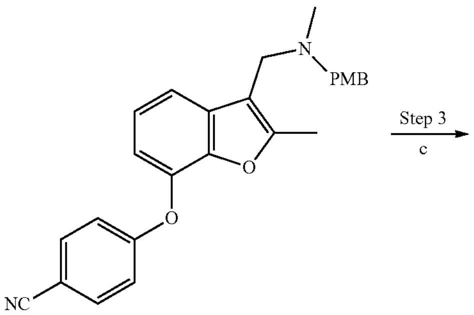

78

-continued

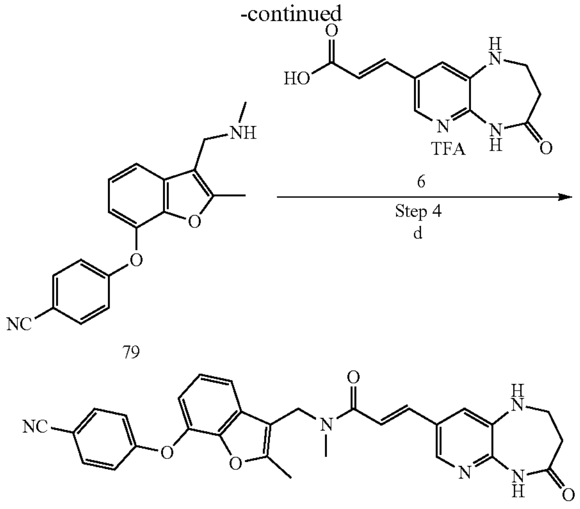

79 6 80

Reaction conditions: a) Pd-175, tBuBrettPhos, KOH, $H_2O$, dioxane, 80° C.; b) 4-Fluorobenzonitrile 77, $K_2CO_3$, NMP, 100° C.; c) 1-chloroethyl chloroformate, DCM, 0° C. to RT; d) HATU, DIPEA, DMF

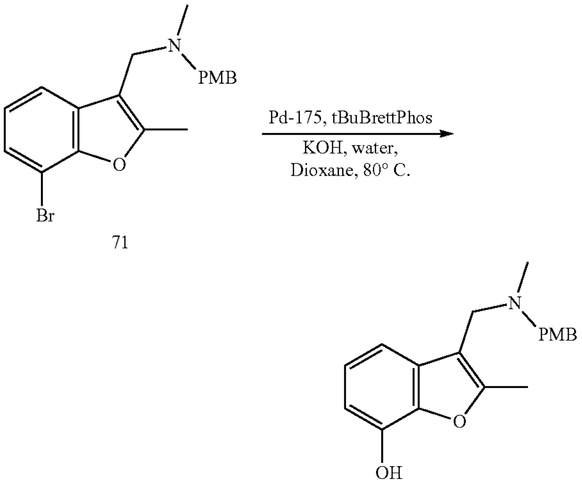

71 76

Step 1. 3-(((4-Methoxybenzyl)(methyl)amino)methyl)-2-methylbenzofuran-7-ol (compound 76). A 100 mL round bottom flask was charged with 1-(7-bromo-2-methylbenzofuran-3-yl)-N-(4-methoxybenzyl)-N-methylmethanamine 71 (2.7 g, 7.21 mmol), Pd-175 (Johnson Matthey) (0.11 g, 0.14 mmol), tBuBrettPhos (0.07 g, 0.14 mmol) and potassium hydroxide (1.21 g, 21.6 mmol). It was then evacuated and backfilled with nitrogen three times and subsequently were added degassed 1,4-dioxane (15 mL) and degassed water (2.6 mL). The resulting mixture was heated to 80° C. and stirred for 2 h. The mixture was cooled to rt and diluted with EtOAc (20 mL), then acidified with 1M HCl (20 mL) and stirred for 5 min until all the solid dissolved. The reaction mixture was neutralized with $NaHCO_3$ (25 mL, sat. aq.) and the phases were separated. The aqueous phase was extracted with EtOAc (2x25 mL) and the combined organic phases were washed with brine (25 mL), dried over $MgSO_4$, filtered and concentrated in vacuo. The crude product was purified by chromatography (0-5% MeOH/DCM) to afford the title compound 76 as a beige solid (1.80 g, 80%). $R^t$ 1.12 min (Method 1a) m/z 312 $[M+H]^+$ $(ES^+)$.

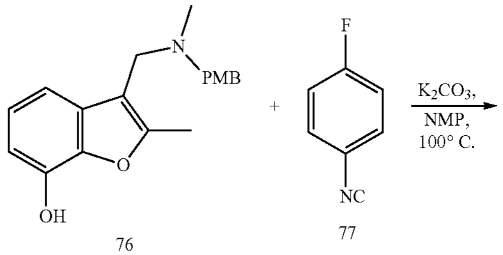

76

77

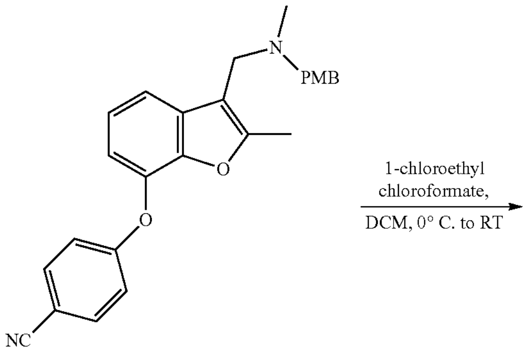

78

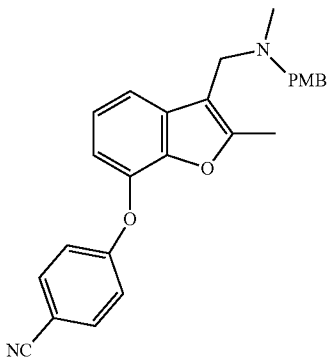

78

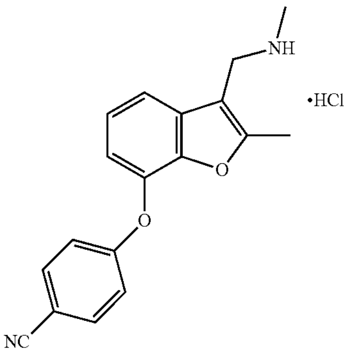

79

Step 2. 4-((3-(((4-Methoxybenzyl)(methyl)amino)methyl)-2-methylbenzofuran-7-yl)oxy)benzonitrile (compound 78). A mixture of 3-(((4-methoxybenzyl)(methyl)amino)methyl)-2-methylbenzofuran-7-ol 76 (150 mg, 0.48 mmol), 4-fluorobenzonitrile 77 (70 mg, 0.58 mmol) and potassium carbonate (133 mg, 0.96 mmol) in a solvent of N-methyl-2-pyrrolidone (6 mL) was heated at 100° C. for 12 h. The reaction mixture was cooled to RT and the mixture poured onto water (20 mL). The aqueous phase was extracted with ethyl acetate (2×30 mL) and the combined organic layers were washed with brine (30 mL), dried over $Na_2SO_4$ and concentrated in vacuo. The crude product was purified by chromatography (1% MeOH/DCM) to afford the title compound 78 as a colourless oil (170 mg, 86%). $R^t$ 1.65 min (Method 1a) m/z 413 $[M+H]^+$ $(ES^+)$.

Step 3. 4-((2-Methyl-3-((methylamino)methyl)benzofuran-7-yl)oxy)benzonitrile hydrochloride (compound 79). To an ice cooled solution of 4-((3-(((4-methoxybenzyl)(methyl)amino)methyl)-2-methylbenzofuran-7-yl)oxy)benzonitrile 78 (185 mg, 0.45 mmol) in DCM (2 mL) was added 1-chloroethyl carbonochloridate (0.10 mL, 0.90 mmol) at 0° C. The reaction mixture was warmed to RT and stirred for 1 h, and then concentrated in vacuo. The residue was dissolved in methanol (5 mL) and heated under reflux for 1 h. The reaction mixture was evaporated to dryness and triturated with TBME (10 mL) to afford the title compound 79 as a yellow solid (185 mg, 47%). $R^t$ 1.31 min (Method 1a) m/z 293 $[M+H]^+$ $(ES^+)$.

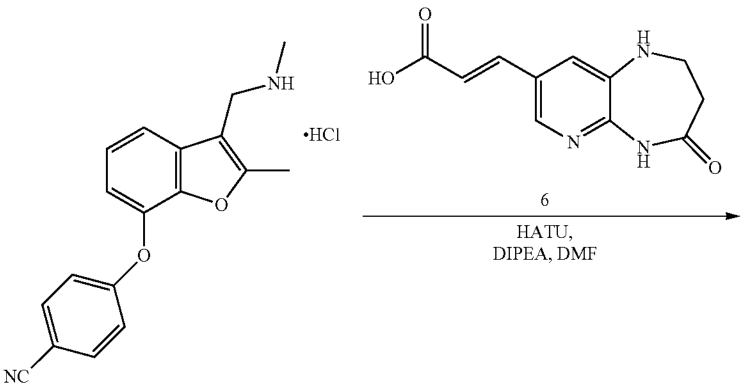

79

-continued

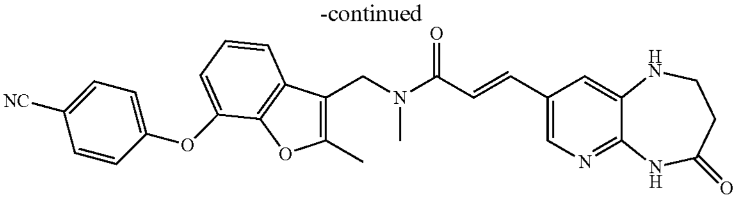

80

Step 4. (E)-N-((7-(4-Cyanophenoxy)-2-methylbenzofuran-3-yl)methyl)-N-methyl-3-(4-oxo-2,3,4,5-tetrahydro-H-pyrido[2,3-b][1,4]diazepin-8-yl)acrylamide (compound 80). A solution of 4-((2-methyl-3-((methylamino)methyl) benzofuran-7-yl)oxy)benzonitrile hydrochloride 79 (69 mg, 0.20 mmol) in DMF (4 mL) was treated with (E)-3-(4-oxo-2,3,4,5-tetrahydro-1H-pyrido[2,3-b][1,4]diazepin-8-yl) acrylic acid trifluoroacetate 6 (80 mg, 0.23 mmol), Hunig's Base (180 μL, 1.05 mmol) and HATU (96 mg, 0.25 mmol) and then stirred at rt for 1 h. The reaction mixture was quenched with water (10 mL) and the solid was collected by filtration and dried. The crude product was purified by column chromatography (0-10% MeOH/DCM) to afford the title compound 80 as a pale yellow solid (23 mg, 21% yield). $R^t$ 2.01 min (Method 1a) m/z 508 $[M+H]^+$ $(ES^+)$. $^1H$ NMR (500 MHz, DMSO-$d_6$, 363 K): δ, ppm 9.15 (s, 1H), 7.99 (d, J=1.9 Hz, 1H), 7.83-7.77 (m, 2H), 7.50-7.44 (m, 2H), 7.38 (d, J=2.0 Hz, 1H), 7.25 (t, J=7.9 Hz, 1H), 7.15-7.06 (m, 3H), 7.06-7.01 (m, 1H), 5.81 (s, 1H), 4.79 (s, 2H), 3.47-3.40 (m, 2H), 3.04 (s, 3H), 2.69-2.62 (m, 2H), 2.46 (s, 3H).

Example 13. Synthesis of (E)-3-(2-(hydroxymethyl)-2-methyl-3-oxo-1,2,3,4-tetrahydropyrido[2,3-b]pyrazin-7-yl)-N-methyl-N-((3-methylbenzofuran-2-yl)methyl)acrylamide (Compound 84)

General Synthetic Scheme.

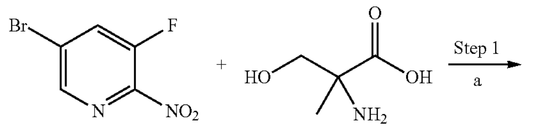

11 81

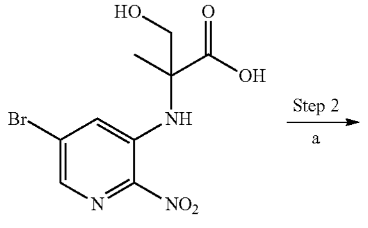

82

-continued

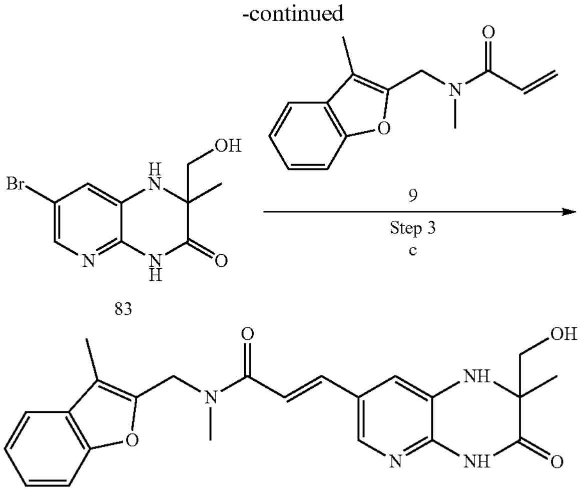

83

84

Reaction conditions: a) $K_2CO_3$, THF; b) $NH_4Cl$, Fe, EtOH/Water; c) $Pd(OAc)_2$, Tri-o-tolylphosphane, DIPEA in DMF/ACN

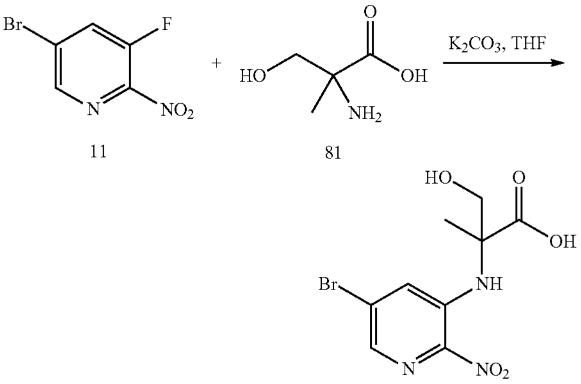

11 81

82

Step 1. 2-((5-Bromo-2-nitropyridin-3-yl)amino)-3-hydroxy-2-methylpropanoic acid (compound 82). 5-Bromo-3-fluoro-2-nitropyridine 11 (800 mg, 3.62 mmol, 1.0 eq) and 2-amino-3-hydroxy-2-methylpropanoic acid 81 (Sigma-Aldrich) (736 mg, 5.07 mmol, 1.4 eq) were dissolved in THF (16.0 mL), then $K_2CO_3$ (999 mg) was added. The resulting reaction mixture was heated to 90° C. overnight in a sealed tube. The UPLC-MS analysis showed almost full conversion of the SM with formation of a good product (Rt=0.94 min; $ES^+$=322.0). The solvent was removed under vacuum. The residue was dissolved in a mixture of water and EtOAc. An aq. layer was acidified with 1M HCl to pH 1-2. The phases were separated and the aq. phase was re-extracted with EtOAc. The combined organic phases were washed with brine, dried over $MgSO_4$ and concentrated to dryness. The crude product (800 mg) was purified by Isolera system using AcOEt/MeOH (100% to 80/20 v/v) to afford the title compound 82 as an orange solid with a purity of 60% (320 mg, 17% yield). The second batch with a purity of 80% was also isolated (40 mg, 3.45% yield). $R^t$ 0.94 min (Method 1c). UPLC-MS m/z: 322.0 $[M+H]^+$ ($ES^+$).

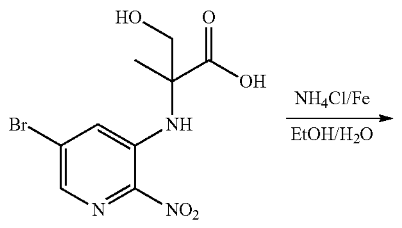

82

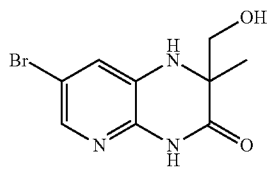

83

Step 2. 7-Bromo-2-(hydroxymethyl)-2-methyl-1,4-dihydropyrido[2,3-b]pyrazin-3(2H)-one (compound 83). To a stirred solution of 2-((5-bromo-2-nitropyridin-3-yl)amino)-3-hydroxy-2-methylpropanoic acid 82 (40 mg, 0.124 mmol, 1.0 eq), $NH_4Cl$ (13.4 mg, 0.25 mmol, 2.0 eq) and iron (14 mg, 0.25 mmol, 2.0 eq) was suspended in a mixture of EtOH/Water (1:1 v/v, 2 mL). The resulting suspension was heated to 80° C. for 1.5 h. The UPLC analysis showed the formation of the product (Rt=0.89 min; $ES^+$=272.1) with complete conversion of the starting material. The reaction was diluted with EtOAc/MeOH, filtered through 0.22 μM filter and the filter was rinsed with acetonitrile. The resulting solution was evaporated to dryness, then diluted with AcOEt, washed with water, dried ($MgSO_4$) and concentrated. The crude product 83 (37 mg, 0.136 mmol) as a red solid with a purity of 60% was isolated. The resulting material was used in the next step without further purification. $R^t$ 0.89 min (Method 1c). LCMS: m/z: 272.1 $[M+H]^+$ ($ES^+$). $^1H$ NMR (400 MHz, DMSO-$d_6$): δ, ppm 10.80 (s, 1H), 7.52 (s, 1H), 7.07 (s, 1H), 6.47 (s, 1H), 5.12 (t, J=5.6 Hz, 1H), 3.58 (dd, J=6.1 Hz, 10.4 Hz, 1H), 3.29 (s, 1H), 1.25 (s, 3H).

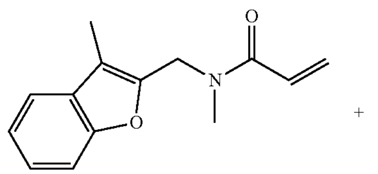

9

+

-continued

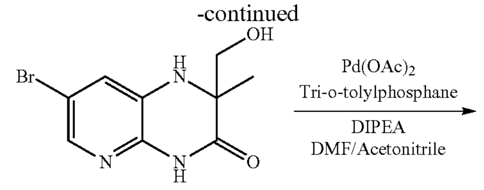

83

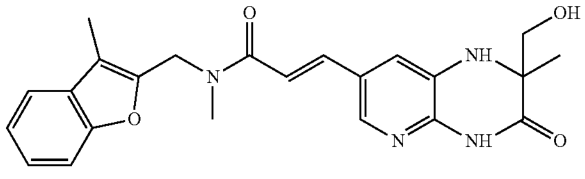

84

Step 3. (E)-3-(2-(Hydroxymethyl)-2-methyl-3-oxo-1,2,3,4-tetrahydropyrido[2,3-b]pyrazin-7-yl)-N-methyl-N-((3-methylbenzofuran-2-yl)methyl)acrylamide (compound 84). An oven dried vial was charged with 7-bromo-2-(hydroxymethyl)-2-methyl-1,4-dihydropyrido[2,3-b]pyrazin-3(2H)-one 83 (37 mg, 0.13 mmol), anhydrous DMF (0.9 mL) and ACN (0.1 mL) were added and the reaction mixture was degassed with nitrogen for 5 min. Then, N-methyl-N-((2-methylbenzofuran-3-yl)methyl)acrylamide 9 (47 mg, 0.204 mmol) and DIPEA (93 uL) were added and the mixture was degassed for the second time for 10 min. Finally, $Pd(OAc)_2$ (0.3 mg) and tri-o-tolylphosphane (0.83 mg) were added in one portion and the nitrogen was bubbled through the mixture for 1 min and the solution was heated at 100° C. overnight. The reaction mass was cooled to RT, filtered on a 0.22 μM filter, washed with MeOH/AcOEt mixture and concentrated under high vacuum. The crude brownish oil was purified by Isolera (n-Heptane/AcOEt 7/3 v/v→100% AcOEt→AcOEt/MeOH 8/2 v/v) and then re-purified 2 more times with DCM/MeOH (100% to 95/5 v/v). The targeted molecule 84 as a beige solid with a purity of 94% was isolated (4.9 mg, 8.6% yield). $R^t$ 1.47 min (Method 1c). LCMS: m/z: 421.3 $[M+H]^+$ ($ES^+$). $^1H$ NMR (400 MHz, DMSO-$d_6$): δ, ppm 10.85 (s, 1H), 7.80 (s, 1H), 7.58 (d, J=7.4 Hz, 1H), 7.51 (d, J=7.4 Hz, 1H), 7.43 (d, J=16.1 Hz, 1H), 7.32-7.22 (m, 4H), 6.99 (d, J=14.4 Hz, 1H), 6.20 (d, J=13.1 Hz, 1H), 5.06 (t, J=5.5 Hz, 1H), 4.95 (s, 2H), 4.80 (s, 2H), 3.62-3.53 (m, 1H), 2.96 (s, 1H), 2.28 (s, 3H), 1.25 (s, 6H) (rotamers).

Example 14. Synthesis of 8-((E)-3-oxo-3-((3rS,6rR)-5-(4-(pyridin-4-yloxy)phenyl)-3,3r,4,6r-tetrahydrocyclopenta[c]pyrrol-2(1H)-yl)prop-1-en-1-yl)-1,2,3,5-tetrahydro-4H-pyrido[2,3-b][1,4]diazepin-4-one (Compound 90)

General Synthetic Scheme.

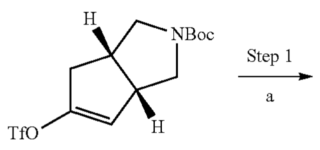

57

-continued

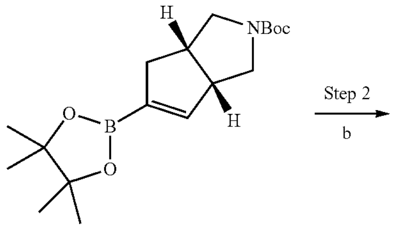

86

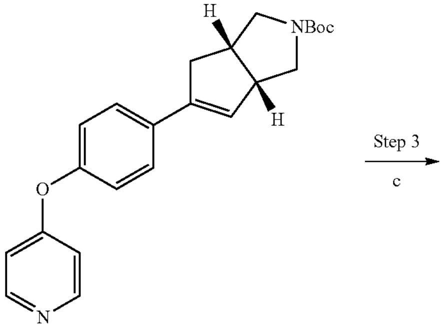

88

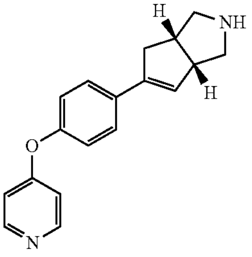

89

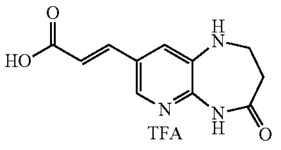

6

Step 4
d

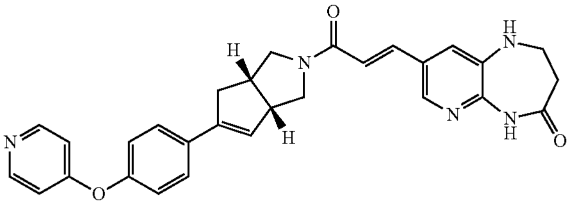

90

Reaction conditions: a) $B_2(pin)_2$ 85, KOAc, $PdCl_2(dppf)$, 1,4-dioxane, 100° C.; b) 4-(4-bromophenoxy)pyridine 87, $K_2CO_3$, $H_2O$, $PdCl_2(dppf)$, 1,4-dioxane, 80° C.; c) TFA, DCM; d) HATU, DIPEA, DMF

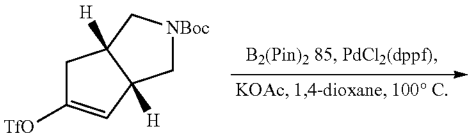

57

-continued

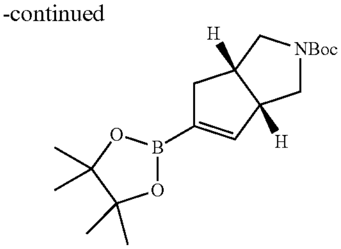

86

Step 1. tert-Butyl(3rR,6rS)-5-(4,4,5,5-tetramethyl-1,3,2-dioxaborolan-2-yl)-3,3r,4,6r-tetrahydrocyclopenta[c]pyrrole-2(1H)-carboxylate (compound 86). A mixture of tert-butyl 5-(((trifluoromethyl)sulfonyl)oxy)-3,3r,6,6r-tetrahydrocyclopenta[c]pyrrole-2(1H)-carboxylate 57 (2 g, 5.6 mmol), 4,4,4',4',5,5,5',5'-octamethyl-2,2'-bi(1,3,2-dioxaborolane) 85 (2.42 g, 9.5 mmol), potassium acetate (1.65 g, 16.8 mmol) and $PdCl_2(dppf)$-$CH_2Cl_2$ adduct (0.46 g, 0.6 mmol) in 1,4-dioxane (20 mL) was degassed with nitrogen and then heated at 100° C. overnight. The mixture was diluted with water (30 mL), extracted with ethyl acetate (2×30 mL). The combined organic layers were washed with brine (30 mL), dried over $MgSO_4$, filtered and evaporated to dryness. The crude product was purified by column chromatography (0-50% EtOAc/isohexane) to afford the title compound 86 as a colourless oil (1.97 g, 94%). $^1H$ NMR (400 MHz, $CDCl_3$): δ, ppm 6.35 (q, J=2.0 Hz, 1H), 3.66-3.61 (m, 1H), 3.54-3.44 (m, 2H), 3.39 (ddt, J=8.0 Hz, 5.7 Hz, 2.5 Hz, 1H), 2.97 (dd, J=10.9 Hz, 7.2 Hz, 1H), 2.89 (ddd, J=9.0 Hz, 7.3 Hz, 1.6 Hz, 1H), 2.65 (ddt, J=16.5 Hz, 7.2 Hz, 2.6 Hz, 1H), 2.38 (dq, J=16.5 Hz, 1.8 Hz, 1H), 1.46 (s, 9H), 1.29 (s, 12H), 1.28 (s, 3H).

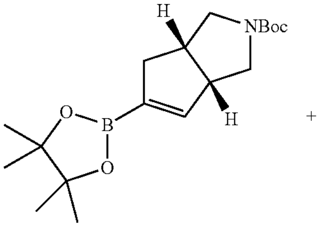

86

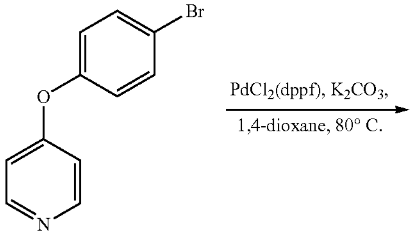

87

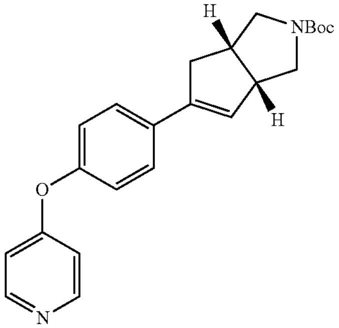

88

Step 2. tert-Butyl (3rR,6rS)-5-(4-(pyridin-4-yloxy)phenyl)-3,3r,4,6r-tetrahydrocyclopenta[c]pyrrole-2(1H)-carboxylate (compound 88). A mixture of 4-(4-bromophenoxy) pyridine 87 (Enamine) (149 mg, 0.60 mmol), tert-butyl 5-(4,4,5,5-tetramethyl-1,3,2-dioxaborolan-2-yl)-3,3r,6,6r-tetrahydrocyclopenta[c]pyrrole-2(1H)-carboxylate 86 (200 mg, 0.6 mmol), $K_2CO_3$ (247 mg, 1.8 mmol) and $PdCl_2$ (dppf)-$CH_2Cl_2$ adduct (49 mg, 0.06 mmol) in 1,4-dioxane (3 mL) was degassed with nitrogen and then heated at 80° C. for 5 h. The mixture was diluted with water (30 mL), extracted with ethyl acetate (2×30 mL). The combined organic layers were washed with brine (30 mL), dried over $MgSO_4$, filtered and evaporated to dryness. The crude product was purified by chromatography (0-5% MeOH/DCM) to afford the title compound 88 as a brown oil (193 mg, 77%). $R^t$ 2.49 min (Method 1b); m/z 379 $[M+H]^+$ ($ES^+$). $^1H$ NMR (400 MHz, $CDCl_3$): δ, ppm 8.47 (d, J=5.6 Hz, 2H), 7.53-7.46 (m, 2H), 7.09-7.04 (m, 2H), 6.90-6.81 (m, 2H), 6.03 (s, 1H), 3.71-3.45 (m, 4H), 3.14-2.93 (m, 3H), 2.60 (s, 2H), 1.46 (s, 9H).

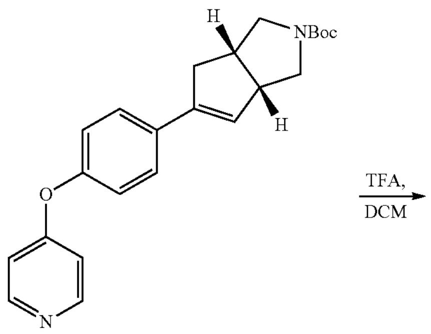

88

-continued

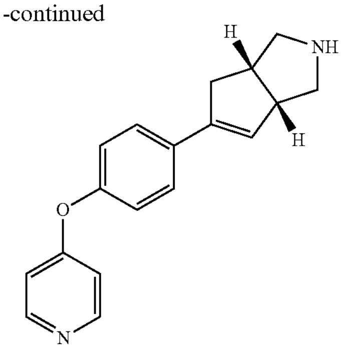

89

Step 3. (3rR,6rS)-5-(4-(Pyridin-4-yloxy)phenyl)-1,2,3,3r,4,6r-hexahydrocyclopenta[c]pyrrole (compound 89). Trifluoroacetic acid (1.5 mL) was added dropwise to a stirred solution of tert-butyl 5-(4-(pyridin-4-yloxy)phenyl)-3,3r,6,6r-tetrahydrocyclopenta[c]pyrrole-2(1H)-carboxylate 88 (193 mg, 0.5 mmol) in DCM (1.5 mL) at RT. The reaction mixture was stirred for 2 h then the solvent was concentrated in vacuo and the resulting residue was taken up in methanol (30 mL) and applied to an SCX column. The column was washed with methanol (50 mL) and the product eluted with 10% methanolic ammonia. The mixture was then evaporated affording the title compound 89 as a yellow oil (115 mg, 73%). $R^t$ 1.36 min (Method 1b); m/z 279 $[M+H]^+$ ($ES^+$). $^1H$ NMR (400 MHz, $CDCl_3$): δ, ppm 8.48-8.41 (m, 2H), 7.44 (d, J=8.3 Hz, 2H), 7.02 (d, J=8.3 Hz, 2H), 6.87-6.76 (m, 2H), 5.95-5.94 (m, 1H), 3.78 (s, 2H), 3.51 (d, J=7.4 Hz, 1H), 3.10-2.80 (m, 5H), 2.51 (dd, J=15.6, 2.6 Hz, 1H).

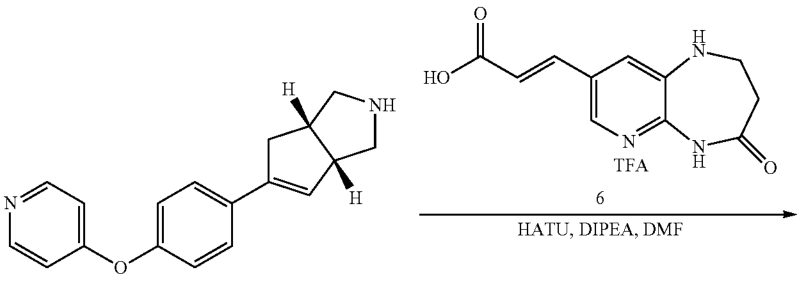

89

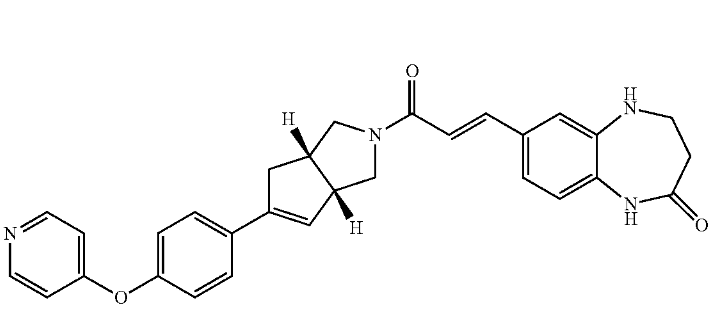

90

Step 4. 8-((E)-3-Oxo-3-((3rS,6rR)-5-(4-(pyridin-4-yloxy)phenyl)-3,3r,4,6r-tetrahydrocyclopenta[c]pyrrol-2(1H)-yl)prop-1-en-1-yl)-1,2,3,5-tetrahydro-4H-pyrido[2,3-b][1,4]diazepin-4-one (compound 90). A suspension of (3rS,6rR)-5-(4-(pyridin-4-yloxy)phenyl)-1,2,3,3r,4,6r-hexahydrocyclopenta[c]pyrrole 89 (115 mg, 0.4 mmol), (E)-3-(4-oxo-2,3,4,5-tetrahydro-1H-pyrido[2,3-b][1,4]diazepin-8-yl)acrylic acid trifluoroacetate 6 (136 mg, 0.4 mmol), N-ethyl-N-isopropylpropan-2-amine (0.28 mL, 1.6 mmol) in DMF (2 mL) was stirred for 10 min. HATU (157 mg, 0.4 mmol) was added in one portion and the reaction mixture was left to stir at RT for 1 h. The mixture was diluted with water (10 mL) and the precipitate was collected by filtration. The crude product was purified by column chromatography (0-5% MeOH/DCM) to afford the title compound 90 as a yellow solid (92 mg, 45% yield). $R^t$ 1.74 min (Method 1b); m/z 494 $[M+H]^+$ $(ES^+)$. $^1H$ NMR (400 MHz, DMSO-$d_6$): δ, ppm 9.73 (d, J=6.6 Hz, 1H), 8.47-8.43 (m, 2H), 7.98 (dd, J=8.2 Hz, 2.0 Hz, 1H), 7.61-7.56 (m, 2H), 7.38-7.30 (m, 2H), 7.18-7.13 (m, 2H), 6.93-6.83 (m, 3H), 6.22 (d, J=3.6 Hz, 1H), 6.05-5.98 (m, 1H), 4.00 (t, J=9.9 Hz, 1H), 3.88-3.78 (m, 1H), 3.70 (m, 1H), 3.65-3.52 (m, 1H), 3.45-3.39 (m, 2H), 3.21-3.13 (m, 1H), 3.04-2.88 (m, 2H), 2.68-2.57 (m, 3H).

Example 15. Synthesis of 8-((E)-3-oxo-3-((3rS,6rR)-5-(4-(thiazol-5-yloxy)phenyl)-3,3r,4,6r-tetrahydrocyclopenta[c]pyrrol-2(1H)-yl)prop-1-en-1-yl)-1,2,3,5-tetrahydro-4H-pyrido[2,3-b][1,4]diazepin-4-one (Compound 96)

General Synthetic Scheme.

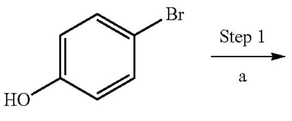

91

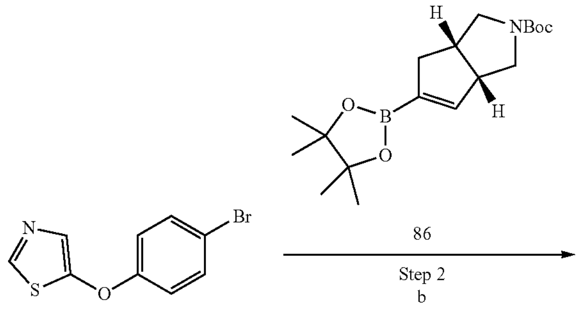

93 86

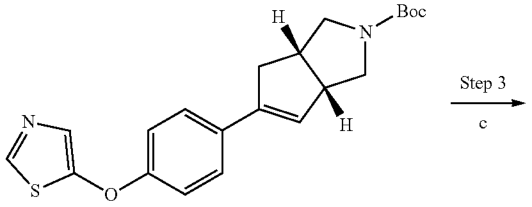

94

-continued

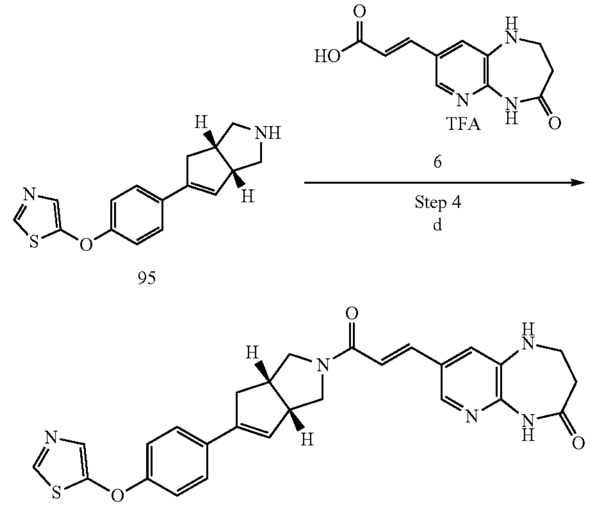

6 95 96

Reaction conditions: a) 5-Bromothiazole, 92, $Cs_2CO_3$, CuI, DMF, 110° C.; b) Pd(dppf)$Cl_2$, $K_2CO_3$, 1,4-dioxane, 90° C.; c) TFA, DCM; d) HATU, DIPEA, DMF

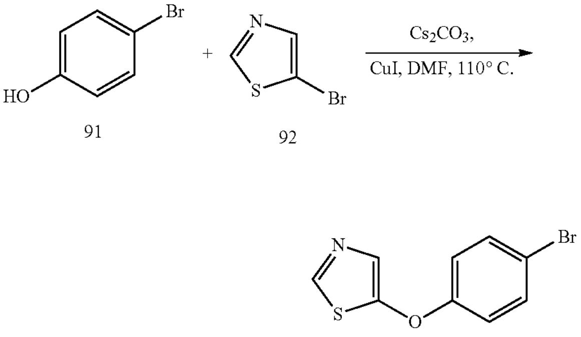

91 92 93

Step 1. 5-(4-Bromophenoxy)thiazole (compound 93). To a stirred solution of 5-bromothiazole 92 (Fluorochem) (0.2 g, 1.2 mmol) in DMF (6 mL) was added 4-bromophenol 91 (0.25 g, 1.5 mmol), copper(I) iodide (0.23 g, 1.2 mmol), followed by cesium carbonate (1.19 g, 3.7 mmol). The reaction mixture was stirred at 110° C. for 5 h and allowed to cool to room temperature. The reaction mixture was partitioned between water (5 mL) and EtOAc (5 mL). The phases were separated and the aqueous phase was extracted with EtOAc (2×10 mL). The combined organic phases were washed with brine (15 mL), dried over $MgSO_4$ and concentrated in vacuo to afford the title compound 93 as a white solid (0.26 g, 84%). $R^t$ 2.19 min (Method 1a) m/z 256/258 $[M+H]^+$ $(ES^+)$.

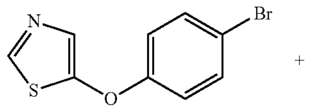

93

-continued

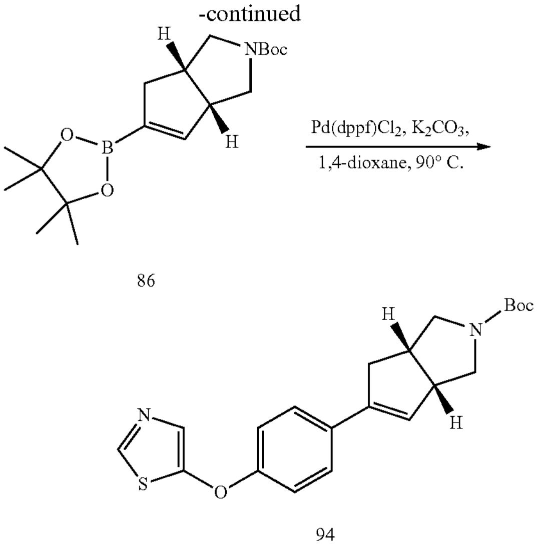

86

94

Step 2. tert-Butyl (3rS,6rR)-5-(4-(thiazol-5-yloxy)phenyl)-3,3r,4,6r-tetrahydrocyclopenta[c]pyrrole-2(1H)-carboxylate (compound 94). A mixture of 5-(4-bromophenoxy) thiazole 93 (0.17 g, 0.7 mmol), tert-butyl 5-(4,4,5,5-tetramethyl-1,3,2-dioxaborolan-2-yl)-3,3r,6,6r-tetrahydrocyclopenta[c]pyrrole-2(1H)-carboxylate 86 (0.22 g, 0.7 mmol), $K_2CO_3$ (0.28 g, 2.0 mmol) and $PdCl_2$(dppf)-$CH_2Cl_2$ adduct (0.05 g, 0.07 mmol) in 1,4-dioxane (4 mL) was degassed with nitrogen and then stirred at 90° C. overnight. The reaction mixture was allowed to cool to room temperature, diluted with water (10 mL) and extracted with ethyl acetate (2×10 mL). The combined organic layers were washed with brine (20 mL), dried ($MgSO_4$), filtered and concentrated in vacuo. The crude product was purified by column chromatography (0-50% EtOAc/isohexane) to afford the title compound 94 as a thick colourless oil (0.06 g, 23% yield). $R^t$ 2.68 min (Method 1a) m/z 329 $[M+H-tBu]^+$ ($ES^+$). $^1$H NMR (400 MHz, DMSO-$d_6$): δ, ppm 8.77 (s, 1H), 7.63 (s, 1H), 7.51 (d, J=8.7 Hz, 2H), 7.12 (d, J=8.7 Hz, 2H), 6.13 (s, 1H), 3.62-3.53 (m, 1H), 3.49-3.35 (m, 3H), 3.11-2.81 (m, 4H), 1.37 (s, 9H).

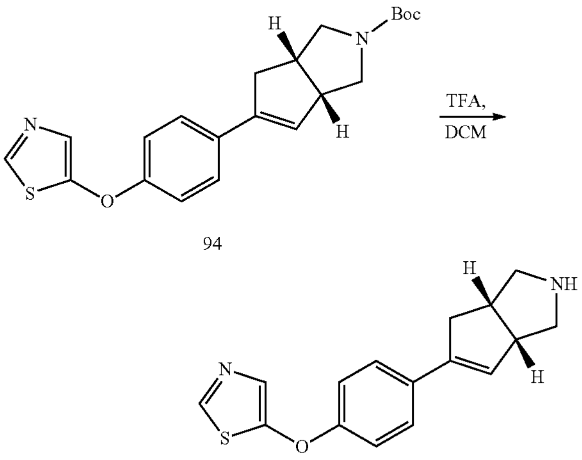

94

95

Step 3. 5-(4-((3rS,6rR)-1,2,3,3r,4,6r-Hexahydrocyclopenta[c]pyrrol-5-yl)phenoxy)thiazole (compound 95). To a stirred solution of (3rS,6rR)-tert-butyl 5-(4-(thiazol-5-yloxy)phenyl)-3,3r,6,6r-tetrahydrocyclopenta[c]pyrrole-2(1H)-carboxylate 94 (0.06 g, 0.2 mmol) in DCM (1 mL) was added TFA (1 mL). The reaction mixture was stirred at room temperature for 2 h. The solvent was removed in vacuo. The resulting oil was taken up in MeOH (5 mL) and applied to an SCX column. The column was washed with methanol (5 mL) and the product eluted with 10% methanolic ammonia (5 mL) to afford the title compound 95 as a colourless crystalline solid (34 mg, 74%). The crude product was used in the next step without further purification. $R^t$ 1.17 min (Method 1a) m/z 285 $[M+H]^+$ ($ES^+$).

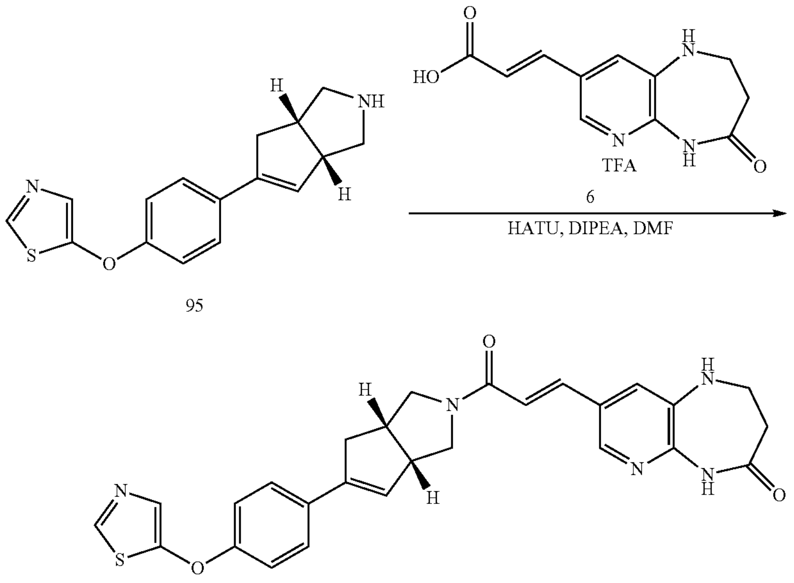

95

6

96

Step 4. 8-((E)-3-Oxo-3-((3aS,6aR)-5-(4-(thiazol-5-yloxy)phenyl)-3,3a,4,6a-tetrahydrocyclopenta[c]pyrrol-2(1H)-yl)prop-1-en-1-yl)-1,2,3,5-tetrahydro-4H-pyrido[2,3-b][1,4]diazepin-4-one (compound 96). To a stirred solution of 5-(4-((3rS,6rR)-1,2,3,3r,4,6r-hexahydrocyclopenta[c]pyrrol-5-yl)phenoxy)thiazole 95 (34 mg, 0.1 mmol) in DMF (2 mL) was added (E)-3-(4-oxo-2,3,4,5-tetrahydro-1H-pyrido[2,3-b][1,4]diazepin-8-yl)acrylic acid trifluoroacetate 6 (31 mg, 0.13 mmol) and N-ethyl-N-isopropylpropan-2-amine (0.1 mL, 0.6 mmol). The reaction mixture was stirred at RT for 5 min and HATU (55 mg, 0.1 mmol) was added. The resulting mixture was stirred for 3 h. Water (1 mL) was added and the reaction mixture sonicated. The solid was filtered and washed with $H_2O$ (2×2 mL). The filtrate was discarded. The crude solid was purified by column chromatography (0-10% MeOH/DCM) to afford the title compound 96 as a yellow solid (25 mg, 40%). $R^t$ 1.85 min (Method 1a) m/z 500 $[M+H]^+$ ($ES^+$). $^1H$ NMR (400 MHz, DMSO-$d_6$): δ, ppm 9.74 (d, J=7.3 Hz, 1H), 8.76 (d, J=1.3 Hz, 1H), 7.98 (dd, J=9.1 Hz, 1.9 Hz, 1H), 7.63 (t, J=1.2 Hz, 1H), 7.53 (d, J=8.7 Hz, 2H), 7.39-7.28 (m, 2H), 7.20-7.09 (m, 2H), 6.86 (dd, J=15.5 Hz, 9.6 Hz, 1H), 6.17 (s, 1H), 6.02 (d, J=14.0 Hz, 1H), 4.02-3.78 (m, 2H), 3.68 (d, J=12.1 Hz, 1H), 3.64-3.49 (m, 2H), 3.45-3.35 (m, 2H), 3.19-3.08 (m, 1H), 3.03-2.87 (m, 2H), 2.64-2.58 (m, 2H).

Example 16. Synthesis of (E)-N-methyl-N-((2-methyl-7-(thiazol-5-yloxy)benzofuran-3-yl)methyl)-3-(4-oxo-2,3,4,5-tetrahydro-1H-pyrido[2,3-b][1,4]diazepin-8-yl)acrylamide (Compound 101)

General Synthetic Scheme.

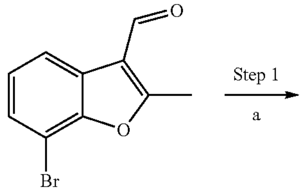

69

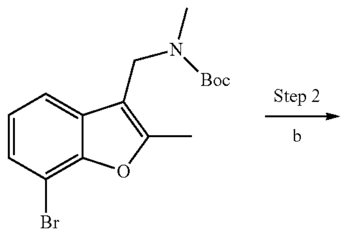

97

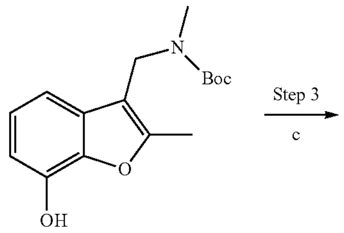

98

-continued

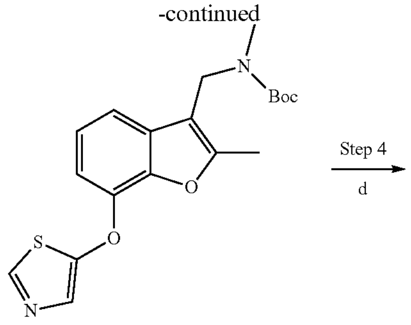

99

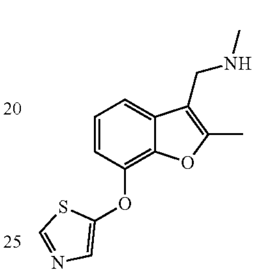

100

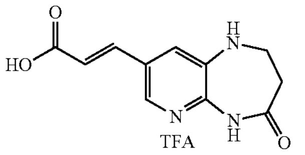

6

Step 5
e

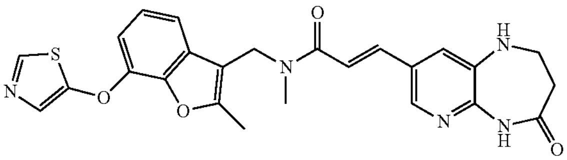

101

Reaction conditions: a) i) $NH_2Me$, STAB, EtOH; ii) $Boc_2O$, DMAP, DCM; b) Pd-175, tBuBrettPhos, KOH, 1,4-dioxane, $H_2O$; c) 5-Bromothiazole 92, CuI, N,N-dimethyl glycine, $Cs_2CO_3$, DMF; d) TFA, DCM; e) HATU, DIPEA, DMF

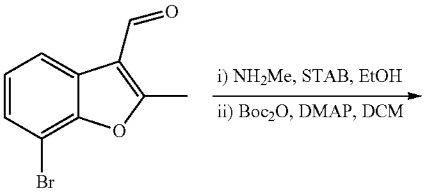

69

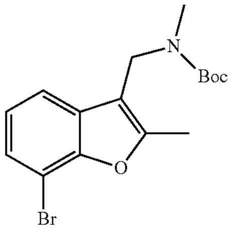

97

Step 1. tert-Butyl ((7-bromo-2-methylbenzofuran-3-yl)methyl)(methyl)carbamate (compound 97). Methanamine (33% in EtOH, 0.5 mL, 4.4 mmol) was added dropwise to a stirred solution of 7-bromo-2-methylbenzofuran-3-carbaldehyde 69 (2.8 g, 3.7 mmol) and sodium triacetoxyborohydride (STAB) (1.9 g, 9.2 mmol) in EtOH (100 mL) at 0° C.

The reaction mixture was allowed to return to RT and stirred for 5 h. The reaction mixture was then concentrated in vacuo and the resulting residue was taken up in EtOAc (100 mL) and $NaHCO_3$ (aq. sat. 100 mL). The organic material was separated and the aqueous phase was extracted with EtOAc (2×100 mL). The combined organic layers were washed with brine (100 mL), dried using $MgSO_4$ and concentrated in vacuo. The resulting residue was dissolved in DCM (80 mL), followed by addition of DMAP (0.6 g, 4.6 mmol) and di-tert-butyl dicarbonate (1.6 g, 7.3 mmol) and the reaction mixture was stirred at RT for 16 h. The crude reaction mixture was concentrated in vacuo and purified by column chromatography (0-50% EtOAc/isohexane) to afford the title compound 97 as a yellow oil which crystallised on standing (1.0 g, 69% yield). $R^t$ 1.86 min (Method 1a) m/z 376/378 $[M+Na]^+$ ($ES^+$). $^1H$ NMR (400 MHz, DMSO-$d_6$): δ, ppm 7.55 (br s, 1H), 7.46 (d, J=7.8 Hz, 1H), 7.17 (br s, 1H), 4.48 (s, 2H), 2.67 (s, 3H), 2.51 (s, 3H), 1.44 (s, 9H).

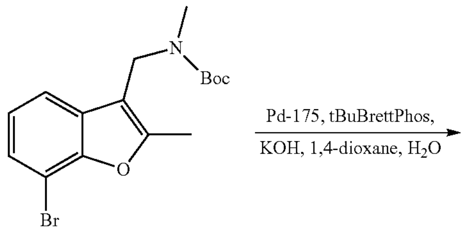

97

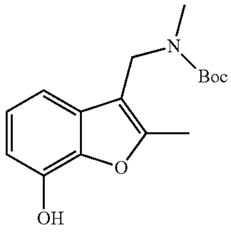

98

Step 2. tert-Butyl ((7-hydroxy-2-methylbenzofuran-3-yl)methyl)(methyl)carbamate (compound 98). 1,4-Dioxane (5 mL) and degassed $H_2O$ (1.5 mL) were added to a mixture of tert-butyl ((7-bromo-2-methylbenzofuran-3-yl)methyl)(methyl)carbamate 97 (1.0 g, 2.9 mmol), Pd-175 (0.06 g, 0.07 mmol), tBuBrettPhos (0.03 g, 0.07 mmol) and KOH (0.5 g, 8.8 mmol) under an atmosphere of nitrogen and the reaction mixture was stirred at 80° C. for 2 h. The reaction mixture was allowed to cool to RT then was poured into water (50 mL). The aqueous mixture was adjusted to pH 6 using 1 M HCl and extracted with EtOAc (3×50 mL). The combined organic extracts were washed with brine (50 mL), dried using $MgSO_4$ and concentrated in vacuo. The crude material was purified by column chromatography (0-50% EtOAc/isohexane) to afford the title compound 98 as a pale brown solid (0.58 g, 67% yield). $R^t$ 2.18 min (Method 1a) m/z 314 $[M+Na]^+$ ($ES^+$). $^1H$ NMR (400 MHz, DMSO-$d_6$): δ, ppm 9.85 (s, 1H), 6.96 (br s, 2H), 6.76-6.56 (m, 1H), 4.44 (s, 2H), 2.65 (s, 3H), 2.44 (s, 3H), 1.44 (s, 9H).

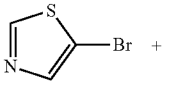

92

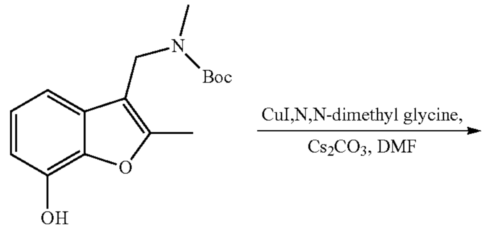

98

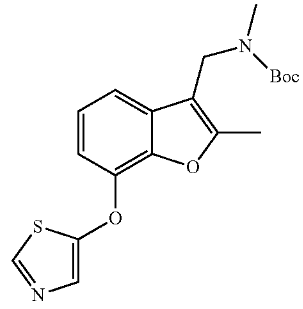

99

Step 3. tert-Butyl methyl((2-methyl-7-(thiazol-5-yloxy)benzofuran-3-yl)methyl)carbamate (compound 99). DMF (5 mL) was added to a mixture of $Cs_2CO_3$ (0.9 g, 2.8 mmol), 5-bromothiazole 92 (0.17 g, 1.03 mmol), tert-butyl ((7-hydroxy-2-methylbenzofuran-3-yl)methyl)(methyl)carbamate 98 (0.2 g, 0.686 mmol), 2-(dimethylamino)acetic acid (0.07 g, 0.69 mmol) and CuI (0.13 g, 0.69 mmol) under an atmosphere of $N_2$ and the reaction mixture was heated to 110° C. The reaction was stirred at this temperature for 24 h then a further equivalent of 5-bromothiazole (0.17 g, 1.03 mmol) was added and the reaction was stirred for a further 16 h at the same temperature. The reaction mixture was allowed to cool to RT then was stirred over the weekend. The crude mixture was dry loaded onto Celite® and purified by column chromatography (0-100% EtOAc/isohexane) to afford the title compound 99 as a yellow oil (54 mg, 20% yield). $R^t$ 2.51 min (Method 1a) m/z 375 $[M+H]^+$ ($ES^+$).

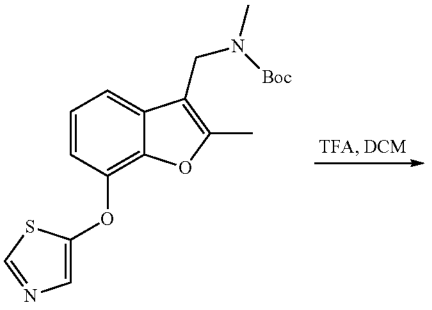

99

-continued

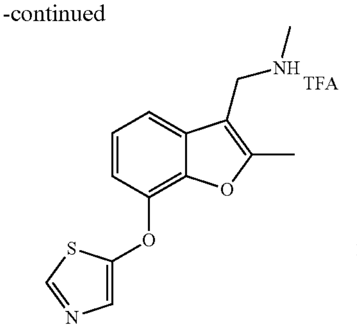

100

Step 4. N-Methyl-1-(2-methyl-7-(thiazol-5-yloxy)benzofuran-3-yl)methanamine trifluoroacetate (compound 100). Trifluoroacetic acid (2.5 mL) was added dropwise to a stirred solution of tert-butyl methyl((2-methyl-7-(thiazol-5-yloxy)benzofuran-3-yl)methyl)carbamate 99 (0.05 g, 0.13 mmol) in DCM (2.5 mL) at RT. The reaction was stirred for 30 min then was concentrated in vacuo to give 100 as an yellow oil which was used in the next step without further purification. $R^t$ 1.39 min (Method 1a) m/z 275 $[M+H]^+$ ($ES^+$).

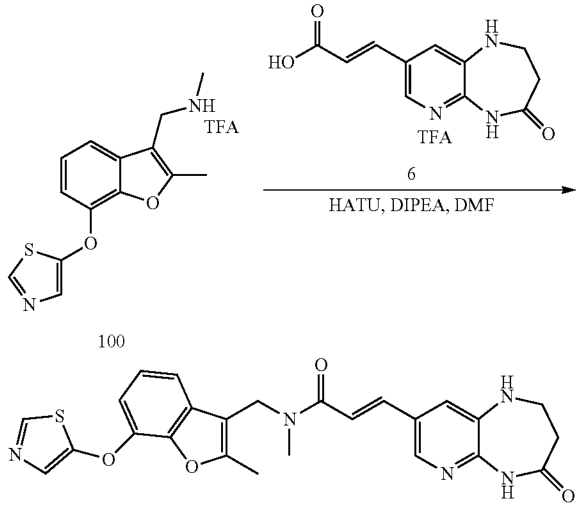

100

101

Step 5. (E)-N-Methyl-N-((2-methyl-7-(thiazol-5-yloxy)benzofuran-3-yl)methyl)-3-(4-oxo-2,3,4,5-tetrahydro-1H-pyrido[2,3-b][1,4]diazepin-8-yl)acrylamide (compound 101). DIPEA (0.5 mL, 2.86 mmol) was added dropwise to a stirred solution of N-methyl-1-(2-methyl-7-(thiazol-5-yloxy)benzofuran-3-yl)methanamine trifluoroacetate 100 (0.05 g, 0.13 mmol) and (E)-3-(4-oxo-2,3,4,5-tetrahydro-1H-pyrido[2,3-b][1,4]diazepin-8-yl)acrylic acid trifluoroacetate 6 (0.06 g, 0.16 mmol) in DMF (2 mL) at RT. The reaction was stirred for 10 mins then HATU (0.08 g, 0.20 mmol) was added and the reaction was stirred for 16 h. The reaction mixture was diluted with water (10 mL) and the precipitate collected by filtration. The crude material was purified by column chromatography (0-5% MeOH/DCM) to give the title compound 101 as a pale yellow solid (57 mg, 73% yield). $R^t$ 1.78 min (Method 1a) m/z 490 $[M+H]^+$ ($ES^+$). $^1H$ NMR (400 MHz, DMSO-$d_6$): δ, ppm 9.14 (s, 1H), 8.66 (s, 1H), 7.98 (d, J=1.9 Hz, 1H), 7.58 (s, 1H), 7.46 (d, J=15.4 Hz, 1H), 7.43-7.35 (m, 2H), 7.19 (t, J=7.9 Hz, 1H), 7.08 (d, J=15.5 Hz, 1H), 7.02 (d, J=8.1 Hz, 1H), 5.79 (t, J=4.2 Hz, 1H), 4.78 (s, 2H), 3.48-3.39 (m, 2H), 3.02 (s, 3H), 2.67-2.62 (m, 2H), 2.51 (s, 3H).

Example 17. Synthesis of (E)-N-((7-amino-2-methylbenzofuran-3-yl)methyl)-3-(3,3-dimethyl-4-oxo-2,3,4,5-tetrahydro-1H-pyrido[2,3-b][1,4]diazepin-8-yl)-N-methylacrylamide (Compound 109)

General Synthetic Scheme.

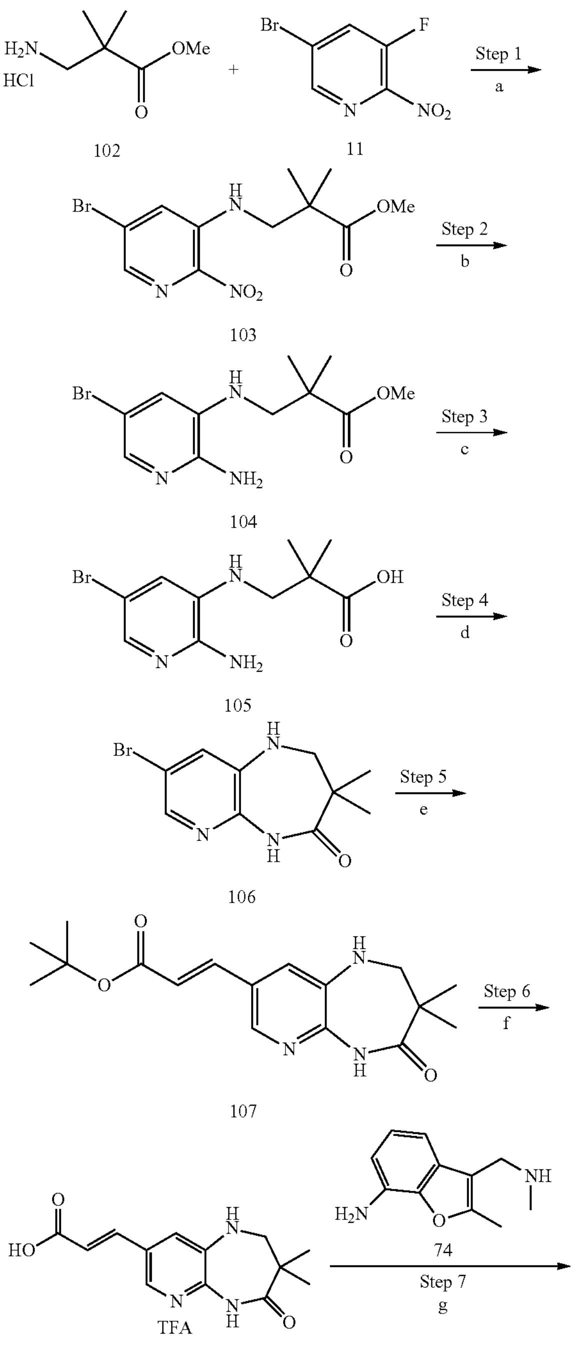

102 11 103 104 105 106 107 108

-continued

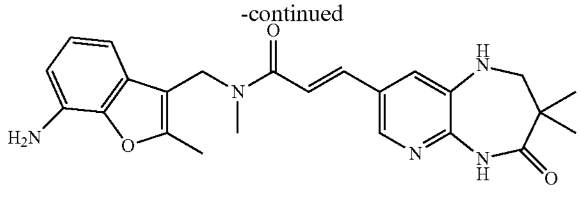

109

Reaction conditions: (a) $K_2CO_3$, THF, reflux; (b) Fe, AcOH, EtOH, 90° C.; (c) LiOH, THF:$H_2O$, RT; (d) HATU, DIPEA, DMF, RT; e) tert-butyl acrylate, Pd-116, DIPEA, $NBu_4Cl$, 1,4-dioxane, 90° C.; f) TFA, DCM; g) HATU, DIPEA, DMF

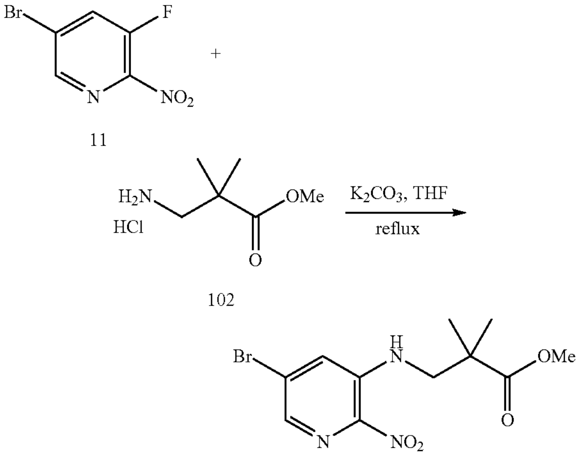

11

102

103

Step 1. Methyl 3-((5-bromo-2-nitropyridin-3-yl)amino)-2,2-dimethylpropanoate (compound 103). To a solution of 5-bromo-3-fluoro-2-nitropyridine 11 (0.34 g, 1.55 mmol) in THF (5 mL) was added methyl 3-amino-2,2-dimethylpropanoate hydrochloride 102 (0.20 g, 1.55 mmol) and $K_2CO_3$ (0.43 g, 3.10 mmol). The reaction mass was stirred at reflux overnight. The reaction mixture was allowed to cool to room temperature, diluted with water (15 mL), and extracted with EtOAc (3×15 mL). The organic layers were combined, dried over $MgSO_4$, filtered, and concentrated in vacuo to afford the title compound 103 (0.51 g, 82% yield) as a yellow oil. The crude product was used in the next step without further purification. $R^t$ 2.15 min (Method 1a); m/z 332/334 $[M+H]^+$ ($ES^+$).

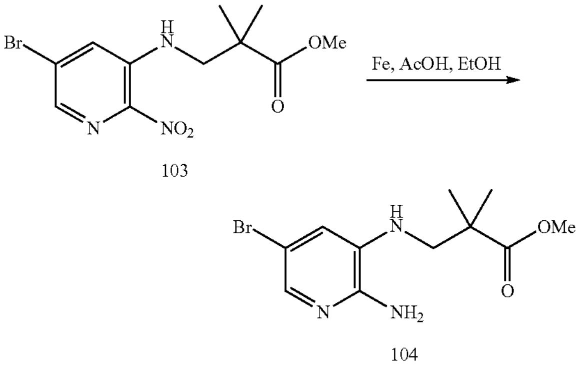

103

104

Step 2. Methyl 3-((2-amino-5-bromopyridin-3-yl)amino)-2,2-dimethylpropanoate (compound 104). To a stirred solution of methyl 3-((5-bromo-2-nitropyridin-3-yl)amino)-2,2-dimethylpropanoate 103 (0.51 g, 1.55 mmol) in EtOH (8 mL) was added acetic acid (1.80 mL, 30.9 mmol) followed by iron (0.86 g, 15.5 mmol). The reaction mixture was stirred at 90° C. for 2 h. The resulting mixture was allowed to cool to room temperature and neutralised to pH 8 with solid $NaHCO_3$. The stirring was continued until the effervescence ceased. The reaction mixture was diluted with $H_2O$ (5 mL) and EtOAc (5 mL). The aqueous phase was extracted with EtOAc (2×5 mL). The combined organic phases were washed with $H_2O$ (10 mL), dried over $MgSO_4$, filtered, and concentrated in vacuo to afford the title compound 104 (424 mg, 84% yield) as a brown solid. The crude product was used in the next step without further purification. $R^t$ 1.25 min (Method 1a); m/z 302/304 $[M+H]^+$ ($ES^+$).

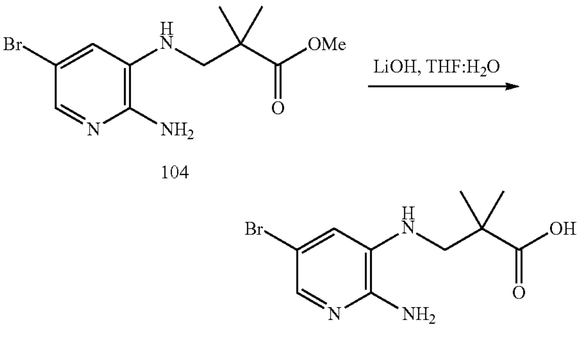

104

105

Step 3. 3-((2-Amino-5-bromopyridin-3-yl)amino)-2,2-dimethylpropanoic acid (compound 105). To a stirred solution of methyl 3-((2-amino-5-bromopyridin-3-yl)amino)-2,2-dimethylpropanoate 104 (424 mg, 1.40 mmol) in THF (1 mL) was added a solution of lithium hydroxide (170 mg, 7.01 mmol) in $H_2O$ (1 mL). The reaction mixture was stirred at room temperature for 3 h. Solvent was removed in vacuo to afford the title compound 105 (404 mg, 1.40 mmol, quant. yield) as a brown solid. The crude product was used in the next step without further purification. $R^t$ 1.10 min (Method 1a); m/z 288/290 $[M+H]^+$ ($ES^+$).

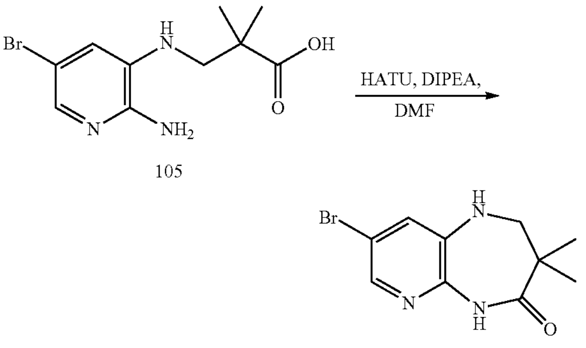

105

106

Step 4. 8-Bromo-3,3-dimethyl-2,3-dihydro-1H-pyrido[2,3-b][1,4]diazepin-4(5H)-one (compound 106). To a stirred solution of 3-((2-amino-5-bromopyridin-3-yl)amino)-2,2-dimethylpropanoic acid 105 (404 mg, 1.40 mmol) in DMF (3 mL) was added DIPEA (730 μL, 4.21 mmol) followed by HATU (800 mg, 2.10 mmol). The reaction mixture was stirred at room temperature for 1 h and then aq. 1M HCl (3 mL) was added. The aqueous phase was extracted with DCM (2×5 mL). The combined organic extracts were washed with $H_2O$ (3×5 mL), dried over $MgSO_4$, filtered, and concentrated in vacuo. The crude product was purified by silica chromatography (0-5% MeOH in DCM) to afford 8-bromo-3,3-dimethyl-2,3-dihydro-1H-pyrido[2,3-b][1,4]diazepin-4(5H)-one 106 (317 mg, 84% yield) as a white solid. $R^t$ 1.68 min (Method 1a); m/z 270/272 $[M+H]^+$ $(ES^+)$. $^1H$ NMR (400 MHz, $CDCl_3$): δ, ppm 7.97 (s, 1H), 7.72 (d, J=2.0 Hz, 1H), 7.04 (d, J=2.0 Hz, 1H), 3.09 (s, 2H), 1.23 (s, 6H).

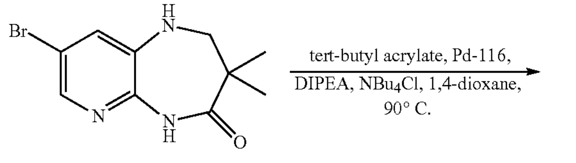

106

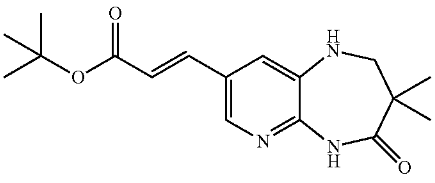

107

Step 5. tert-Butyl (E)-3-(3,3-dimethyl-4-oxo-2,3,4,5-tetrahydro-1H-pyrido[2,3-b][1,4]diazepin-8-yl)acrylate (compound 107). DIPEA (1.3 mL, 7.4 mmol) and tert-butyl acrylate (1.1 mL, 7.5 mmol) were added dropwise to a stirred solution of 8-bromo-3,3-dimethyl-2,3-dihydro-1H-pyrido[2,3-b][1,4]diazepin-4(5H)-one 106 (1 g, 3.7 mmol), $Bu_4NCl$ (0.1 g, 0.4 mmol) and $[P(tBu)_3]_2Pd$ (Pd-116, Johnson Matthey) (0.1 g, 0.2 mmol) in 1,4-dioxane (20 mL) under $N_2$. The reaction mixture was heated to 90° C. and stirred for 2 h. The reaction mixture was cooled to RT and concentrated in vacuo. The crude material was purified by column chromatography (0-100% EtOAc/isohexane) to afford the title compound 107 as a yellow oil (0.97 g, 80% yield). $R^t$ 2.07 min (Method 1a); m/z 318 $[M+H]^+$ $(ES^+)$. $^1H$ NMR (400 MHz, DMSO-$d_6$): δ, ppm 9.51 (s, 1H), 7.93 (d, J=2.0 Hz, 1H), 7.43 (d, J=16.0 Hz, 1H), 7.33 (d, J=2.0 Hz, 1H), 6.34 (d, J=16.0 Hz, 1H), 6.21 (s, 1H), 3.05 (d, J=4.4 Hz, 2H), 1.48 (s, 9H), 1.15 (s, 6H).

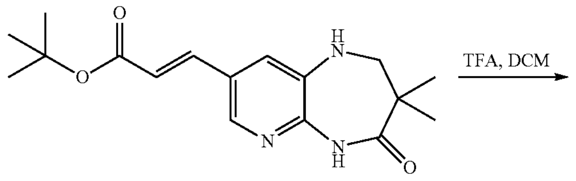

107

-continued

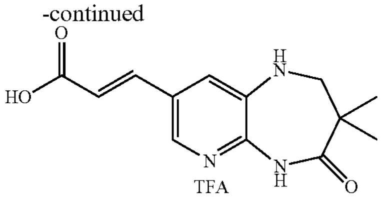

108

Step 6. (E)-3-(3,3-Dimethyl-4-oxo-2,3,4,5-tetrahydro-1H-pyrido[2,3-b][1,4]diazepin-8-yl)acrylic acid TFA salt (compound 108). Trifluoroacetic acid (5 mL) was added dropwise to a stirred solution of (E)-tert-butyl 3-(3,3-dimethyl-4-oxo-2,3,4,5-tetrahydro-1H-pyrido[2,3-b][1,4]diazepin-8-yl)acrylate 107 (0.97 g, 3.1 mmol) in $CH_2Cl_2$ (10 mL) at RT and the reaction was stirred for 2 h. The reaction mixture was concentrated in vacuo and the resulting solid was triturated with MTBE (50 mL) then collected by filtration to give the desired product 108 as a yellow solid (0.81 g, 70%). $R^t$ 1.25 min (Method 1a); m/z 262 $[M+H]^+$ $(ES^+)$. $^1H$ NMR (400 MHz, DMSO-$d_6$): δ, ppm 12.38 (br s, 1H), 9.51 (s, 1H), 7.91 (d, J=1.8 Hz, 1H), 7.47 (d, J=16.0 Hz, 1H), 7.33 (d, J=1.9 Hz, 1H), 6.33 (d, J=16.0 Hz, 1H), 6.25 (s, 1H), 3.08-3.00 (m, 2H), 1.15 (s, 6H).

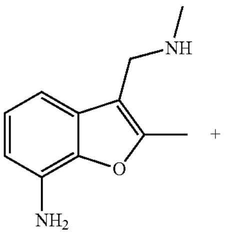

74

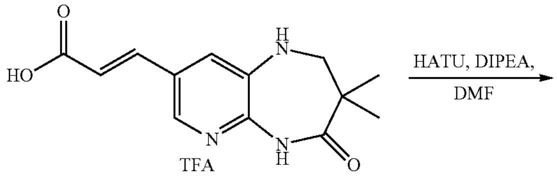

108

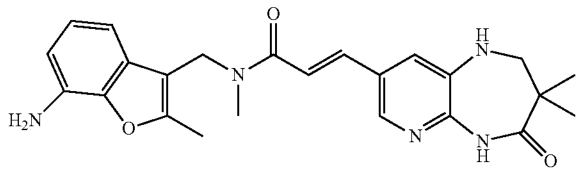

109

Step 7. (E)-N-((7-Amino-2-methylbenzofuran-3-yl)methyl)-3-(3,3-dimethyl-4-oxo-2,3,4,5-tetrahydro-1H-pyrido[2,3-b][1,4]diazepin-8-yl)-N-methylacrylamide (compound 109). DIPEA (0.5 mL, 2.9 mmol) was added dropwise to a stirred solution of 2-methyl-3-((methylamino)methyl)benzofuran-7-amine 74 (0.04 g, 0.2 mmol) and (E)-3-(3,3-dimethyl-4-oxo-2,3,4,5-tetrahydro-1H-pyrido[2,3-b][1,4]diazepin-8-yl)acrylic acid trifluoroacetate 108 (0.07 g, 0.2 mmol) in DMF (2 mL) at RT. The reaction was stirred for 10 min then HATU (0.09 g, 0.2 mmol) was added and the reaction was stirred for 16 h. The reaction mixture was diluted with water (10 mL) and the precipitate collected by filtration. The crude material was purified by column chromatography (0-5% MeOH/DCM) to afford the title compound 109 as a yellow solid (19 mg, 24% yield). R$^t$ 1.57 min (Method 1a); m/z 434 $[M+H]^+$ $(ES^+)$. $^1H$ NMR (400 MHz, DMSO-d6, 363 K): δ, ppm 8.77 (s, 1H), 7.92 (d, J=1.9 Hz, 1H), 7.44 (d, J=15.4 Hz, 1H), 7.35 (d, J=2.0 Hz, 1H), 7.07 (d, J=15.6 Hz, 1H), 6.87 (t, J=7.7 Hz, 1H), 6.74 (d, J=7.3 Hz, 1H), 6.53 (d, J=7.6 Hz, 1H), 6.03-5.91 (m, 1H), 4.86 (s, 2H), 4.71 (s, 2H), 3.07 (d, J=4.6 Hz, 2H), 2.97 (s, 3H), 2.47 (s, 3H), 1.18 (s, 6H).

Example 18. Synthesis of (E)-3-(3-hydroxy-4'-oxo-1',2',4',5'-tetrahydrospiro[cyclobutane-1,3'-pyrido[2,3-b][1,4]diazepin]-8'-yl)-N-methyl-N-((3-methylbenzofuran-2-yl)methyl)acrylamide (Compound 115)

General Synthetic Scheme.

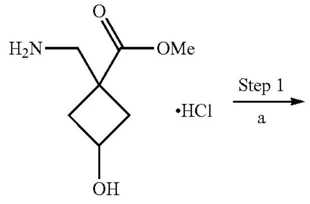

110

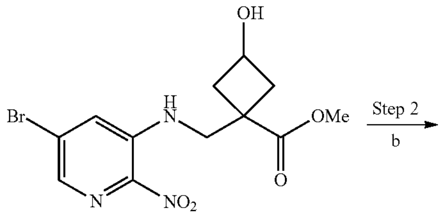

111

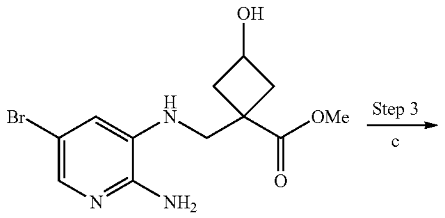

112

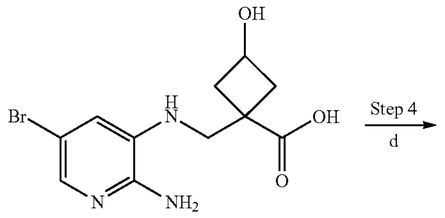

113

-continued

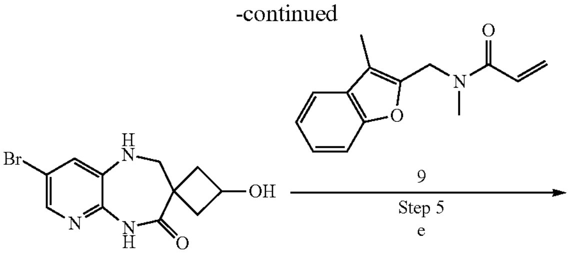

114

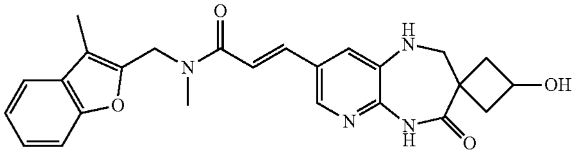

115

Reaction conditions: a) 5-Bromo-3-fluoro-2-nitropyridine 11, TEA, EtOH, reflux; b) Fe, $NH_4Cl$, EtOH, $H_2O$, reflux; c) LiOH, $H_2O$, THF; d) HATU, DIPEA, DMF; e) Pd-162, $MeNCy_2$, $NBu_4Cl$, 1,4-dioxane, 80° C.

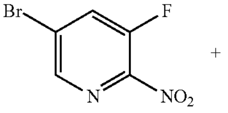

11

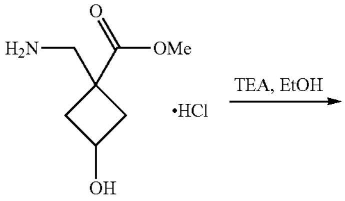

110

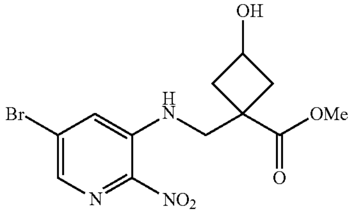

111

Step 1. Methyl 1-(((5-bromo-2-nitropyridin-3-yl)amino)methyl)-3-hydroxycyclobutanecarboxylate (compound 111). To a solution of 5-bromo-3-fluoro-2-nitropyridine 11 (230 mg, 1.0 mmol) in ethanol (10 mL) was added methyl 1-(aminomethyl)-3-hydroxycyclobutanecarboxylate hydrochloride 110 (Enamine) (200 mg, 1.0 mmol) and TEA (0.6 mL, 4.1 mmol). The reaction mixture was heated under reflux overnight. The solvent was removed in vacuo and the reaction was partitioned between water (2 mL) and ethyl acetate (2 mL). The organic extract was separated, dried with $MgSO_4$, filtered and concentrated in vacuo. The crude product was purified by chromatography (0-100% EtOAc/isohexane) to give the title compound 111 as a yellow oil (250 mg, 61% yield). R$^t$ 1.58 min (Method 1a); m/z 360/362 $[M+H]^+$ $(ES^+)$. $^1H$ NMR (400 MHz, $CDCl_3$): δ, ppm 8.10 (s, 1H), 7.91 (d, J=1.9 Hz, 1H), 7.63 (d, J=1.9 Hz, 1H), 4.58 (tt, J=7.2 Hz, 5.8 Hz, 1H), 3.81 (s, 3H), 3.72 (d, J=5.6 Hz, 2H), 2.93-2.88 (m, 2H), 2.10-2.06 (m, 2H) (missing OH).

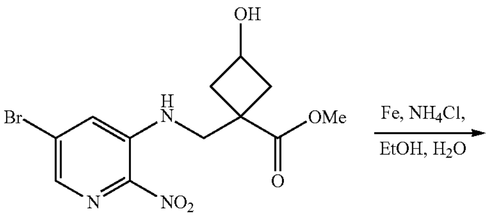

111

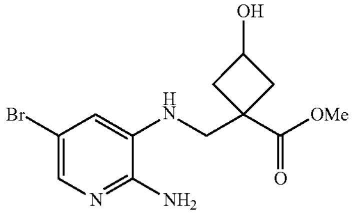

112

Step 2. Methyl 1-(((2-amino-5-bromopyridin-3-yl)amino)methyl)-3-hydroxycyclobutane carboxylate (compound 112). A mixture of methyl 1-(((5-bromo-2-nitropyridin-3-yl)amino)methyl)-3-hydroxycyclobutanecarboxylate 111 (245 mg, 0.7 mmol), iron powder (152 mg, 2.7 mmol) and ammonium chloride (364 mg, 6.8 mmol) in a solvent mixture of ethanol (12 mL) and water (3 mL) was heated under reflux for 1 hour. The mixture was filtered hot through a pad of Celite® before being concentrated in vacuo. The residue was partitioned between water (20 mL) and DCM (20 mL) and the aqueous layer was extracted with DCM (2×20 mL). The combined organic layers were dried with $MgSO_4$, filtered and concentrated in vacuo. The crude product was purified by chromatography (0-10% MeOH/DCM) to give the title compound 112 as a yellow oil (180 mg, 76%). $R^t$ 0.91 min (Method 1a); m/z 330/332 $[M+H]^+$ ($ES^+$).

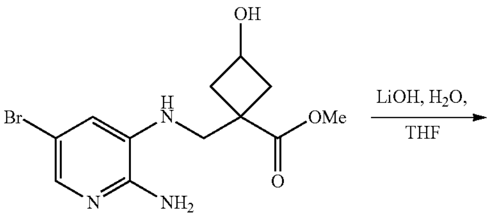

112

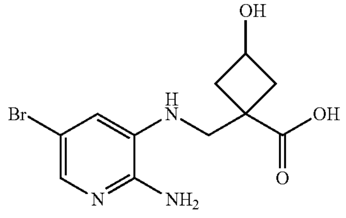

113

Step 3. 1-(((2-Amino-5-bromopyridin-3-yl)amino)methyl)-3-hydroxycyclobutanecarboxylic acid (compound 113). A mixture of methyl 1-(((2-amino-5-bromopyridin-3-yl)amino)methyl)-3-hydroxycyclobutanecarboxylate 112 (175 mg, 0.5 mmol) and lithium hydroxyde (66 mg, 2.7 mmol) in a solvent mixture of THF (4.5 mL) and water (1.5 mL) was stirred at RT for 3 h. The reaction was then acidified to pH 3 by the addition of acetic acid (~0.4 mL). The solvent was removed in vacuo to give the title compound 113 as a yellow solid (190 mg, 98% yield) which was used in the next step without further purification. $R^t$ 0.53 min (Method 1a); m/z 316/318 $[M+H]^+$ ($ES^+$).

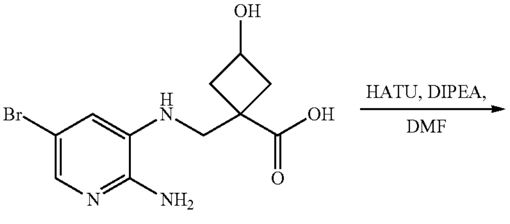

113

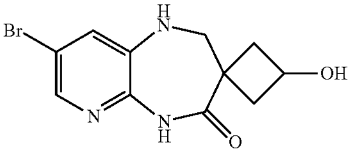

114

Step 4. 8'-Bromo-3-hydroxy-1',2'-dihydrospiro[cyclobutane-1,3'-pyrido[2,3-b][1,4]diazepin]-4'(5'H)-one (compound 114). To a stirred solution of 1-(((2-amino-5-bromopyridin-3-yl)amino)methyl)-3-hydroxycyclobutanecarboxylic acid 113 (172 mg, 0.5 mmol) in DMF (2.5 mL) was added N-ethyl-N-isopropylpropan-2-amine (0.5 mL, 2.7 mmol) followed by HATU (250 mg, 0.7 mmol). The reaction mixture was stirred at RT for 1 h. Water (4 mL) was then added and the resulting mixture extracted with DCM (3×5 mL). The combined organic phases were washed with brine (5 mL), dried with $MgSO_4$, filtered and concentrated in vacuo. The crude product was purified by chromatography (0-10% MeOH/DCM) to give the title compound 114 as a colourless solid (30 mg, 17% yield). $R^t$ 1.20 min (Method 1a); m/z 298/300 $[M+H]^+$ ($ES^+$). $^1H$ NMR (400 MHz, $CD_3OD$): δ, ppm 7.72 (d, J=2.0 Hz, 1H), 7.27 (d, J=2.0 Hz, 1H), 4.28 (p, J=7.2 Hz, 1H), 3.46 (s, 2H), 2.85-2.66 (m, 2H), 1.94-1.79 (m, 2H).

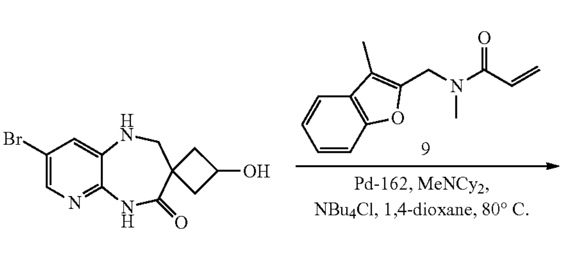

114

-continued

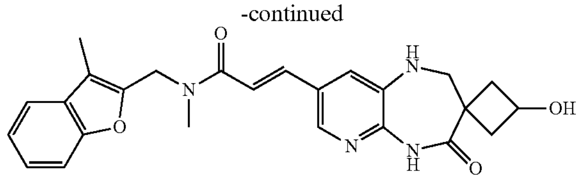

115

Step 5. (E)-3-(3-Hydroxy-4'-oxo-1',2',4',5'-tetrahydrospiro[cyclobutane-1,3'-pyrido[2,3-b][1,4]diazepin]-8'-yl)-N-methyl-N-((3-methylbenzofuran-2-yl)methyl)acrylamide (compound 115). A reaction vial was charged with N-methyl-N-((3-methylbenzofuran-2-yl)methyl)acrylamide 9 (25 mg, 0.1 mmol), 8'-bromo-3-hydroxy-1',2'-dihydrospiro[cyclobutane-1,3'-pyrido[2,3-b][1,4]diazepin]-4'(5'H)-one 114 (28 mg, 0.1 mmol), $Bu_4NCl$ (3 mg, 9.4 μmol), $[P(tBu)_3]Pd(crotyl)Cl$ (Pd-162) (4 mg, 9.4 μmol). The vial was flushed with nitrogen for 5 min. 1,4-Dioxane (2.5 mL) and N-cyclohexyl-N-methylcyclohexanamine (41 μL, 0.2 mmol) were added and the reaction mixture was purged with nitrogen for a further 5 mins. The mixture was heated to 80° C. for 1 h and allowed to cool to room temperature. Ethyl acetate (5 mL) was added and the resulting solution was washed with $H_2O$ (5 mL), brine (5 mL), dried over $MgSO_4$, filtered and concentrated in vacuo. The crude product was purified by column chromatography (0-10% MeOH/DCM) to give the title compound 115 as a pale yellow solid (22 mg, 49%). $R^t$ 1.79 min (Method 1a); m/z 447 $[M+H]^+$ ($ES^+$). $^1H$ NMR (400 MHz, DMSO-$d_6$): δ, ppm 9.05 (s, 1H), 7.94 (d, J=1.9 Hz, 1H), 7.56 (dd, J=7.6, 1.4 Hz, 1H), 7.47 (d, J=8.0 Hz, 1H), 7.45-7.34 (m, 2H), 7.33-7.19 (m, 2H), 7.10 (d, J=15.6 Hz, 1H), 5.97 (d, J=4.7 Hz, 1H), 4.84 (s, 3H), 4.21-4.03 (m, 1H), 3.41 (d, J=3.9 Hz, 2H), 3.10 (s, 3H), 2.64-2.54 (m, 2H), 2.28 (s, 3H), 1.83-1.74 (m, 2H).

Example 19. Synthesis of (E)-N-((7-(benzo[d][1,3]dioxol-5-yloxy)-2-methylbenzofuran-3-yl)methyl)-N-methyl-3-(4-oxo-2,3,4,5-tetrahydro-1H-pyrido[2,3-b][1,4]diazepin-8-yl)acrylamide (Compound 119)

General Synthetic Scheme.

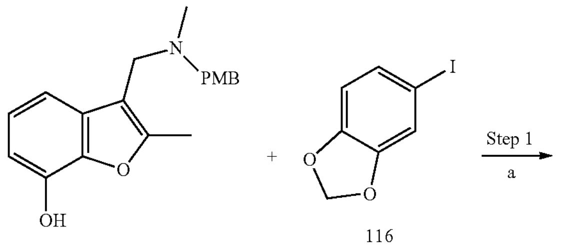

76 116

-continued

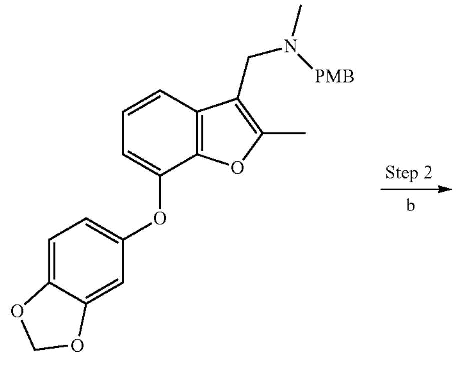

117

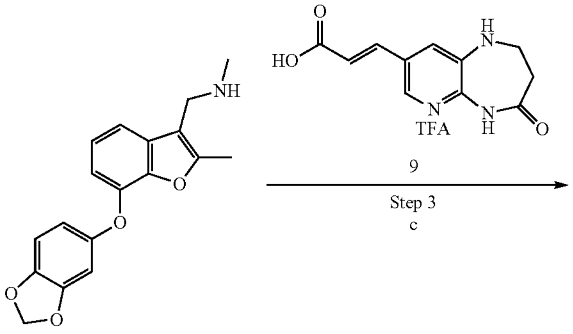

118

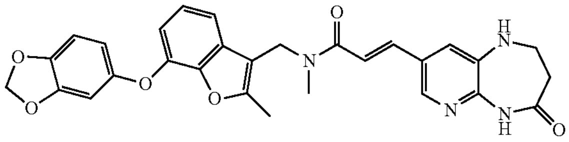

119

Reaction conditions: a) CuI, 2-(dimethylamino)acetic acid, $Cs_2CO_3$ DMF, 110° C.; b) 1-chloroethyl chloroformate, DCM, 0° C. to RT; c) HATU, DIPEA, DMF

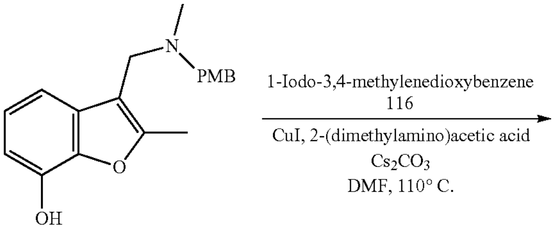

76

-continued

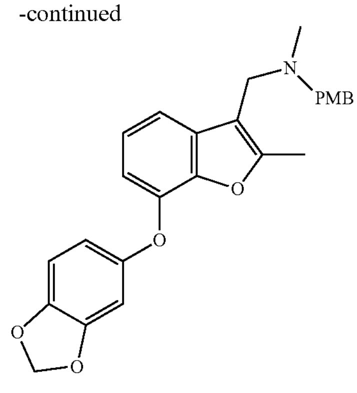

117

Step 1. 1-(7-(Benzo[d][1,3]dioxol-5-yloxy)-2-methylbenzofuran-3-yl)-N-(4-methoxybenzyl)-N-methylmethanamine (compound 117). A mixture of 3-(((4-methoxybenzyl)(methyl)amino)methyl)-2-methylbenzofuran-7-ol 76 (150 mg, 0.48 mmol), 1-iodo-3,4-methylenedioxybenzene 116 (Fluorochem) (358 mg, 1.45 mmol), 2-(dimethylamino) acetic acid (50 mg, 0.48 mmol), copper(I) iodide (92 mg, 0.48 mmol) and cesium carbonate (942 mg, 2.89 mmol) was evacuated and backfilled with nitrogen (3 times). DMF (3 mL) was added and the mixture was heated to 110° C. overnight. The reaction mixture was allowed to cool to RT, poured onto water (30 mL) and the crude product extracted into ethyl acetate (2×30 mL). The organic extracts were combined and dried over $Na_2SO_4$. The crude product was purified by chromatography[0-10% (0.7M Ammonia/MeOH)/DCM] to afford the title compound 117 as a clear yellow gum (85 mg, 38% yield). $R^t$ 1.69 min (Method 1a) m/z 432 $[M+H]^+$ $(ES^+)$.

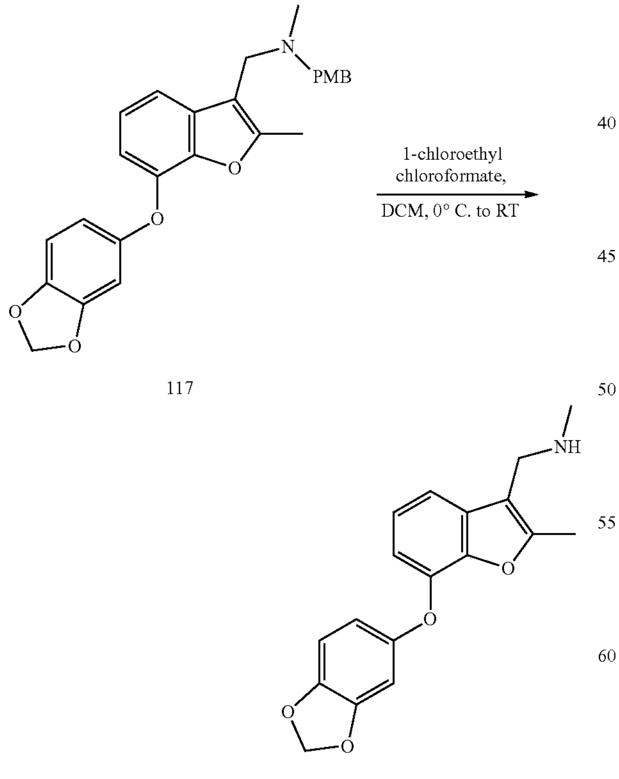

117

118

Step 2. 1-(7-(Benzo[d][1,3]dioxol-5-yloxy)-2-methylbenzofuran-3-yl)-N-methylmethanamine (compound 118). To a solution of 1-(7-(benzo[d][1,3]dioxol-5-yloxy)-2-methylbenzofuran-3-yl)-N-(4-methoxybenzyl)-N-methylmethanamine 117 (85 mg, 0.20 mmol) in DCM (2 mL) was added 1-chloroethyl carbonochloridate (0.031 mL, 0.29 mmol) at 0° C. and the mixture allowed to attain RT then stirred for 1 hour. The mixture was evaporated to dryness and the residue was taken up into methanol (5 mL) and the mixture was heated under reflux for 1 hour. The reaction mixture was allowed to cool to RT and the solution applied directly to an SCX column (1 g). The column was washed with methanol (10 mL) and the crude product was eluted with 10% methanolic ammonia solution (10 mL) to give the title compound 118 as a yellow oil (60 mg, 90% yield). $R^t$ 1.38 min (Method 1a) m/z 281$[M+H]^+$ $(ES^+)$.

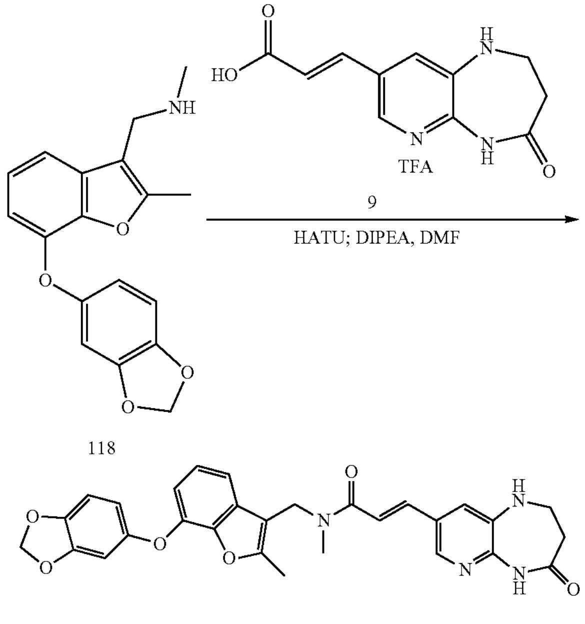

118

9

119

Step 3. (E)-N-((7-(Benzo[d][1,3]dioxol-5-yloxy)-2-methylbenzofuran-3-yl)methyl)-N-methyl-3-(4-oxo-2,3,4,5-tetrahydro-1H-pyrido[2,3-b][1,4]diazepin-8-yl)acrylamide (compound 119). A solution of 1-(7-(benzo[d][1,3]dioxol-5-yloxy)-2-methylbenzofuran-3-yl)-N-methylmethanamine 118 (60 mg, 0.19 mmol), (E)-3-(4-oxo-2,3,4,5-tetrahydro-1H-pyrido[2,3-b][1,4]diazepin-8-yl)acrylic acid trifluoroacetate 9 (67 mg, 0.19 mmol) and DIPEA (135 μl, 0.77 mmol) in DMF (3 mL) was added HATU (73 mg, 0.19 mmol) and the mixture was stirred at RT for 1 hour. The reaction mixture was quenched by the addition of water (10 mL). The solid was collected by filtration and dried. The crude product was initially purified by chromatography (0-10% MeOH/DCM) to afford the title compound 119 as a pale yellow solid (LCMS purity 93%). This solid was further purified by trituration with acetonitrile (10 mL) followed by further trituration with DMF (2 mL) and washing the collected solid with TBME (10 mL) to afford the title compound 119 as a pale yellow solid (14 mg, 13% yield). $R^t$ 2.12 min (Method 1a) m/z 527$[M+H]^+$ $(ES^+)$. $^1H$ NMR (500 MHz, DMSO-$d_6$, 363 K): δ, ppm 9.14 (s, 1H), 7.98 (d, J=1.9 Hz, 1H), 7.46 (d, J=15.4 Hz, 1H), 7.38 (d, J=1.9 Hz, 1H), 7.30 (d, J=7.8 Hz, 1H), 7.15-7.06 (m, 2H), 6.85 (d, J=8.4 Hz, 1H), 6.78 (dd, J=8.0, 1.0 Hz, 1H), 6.69 (d, J=2.5 Hz, 1H), 6.50 (dd, J=8.4, 2.5 Hz, 1H), 6.01 (s, 2H), 5.80 (s, 1H), 4.77 (s, 2H), 3.44 (dd, J=6.9, 3.5 Hz, 2H), 2.67-2.62 (m, 2H), 1.20 (s, 1H). Both $CH_3$ protons obscured by solvent and water

Example 20. Synthesis of 3-(4-((3rS,6rR)-2-((E)-3-(4-oxo-2,3,4,5-tetrahydro-1H-pyrido[2,3-b][1,4]diazepin-8-yl)acryloyl)-1,2,3,3r,4,6r-hexahydrocyclopenta[c]pyrrol-5-yl)phenoxy)benzonitrile (Compound 123)

General Synthetic Scheme.

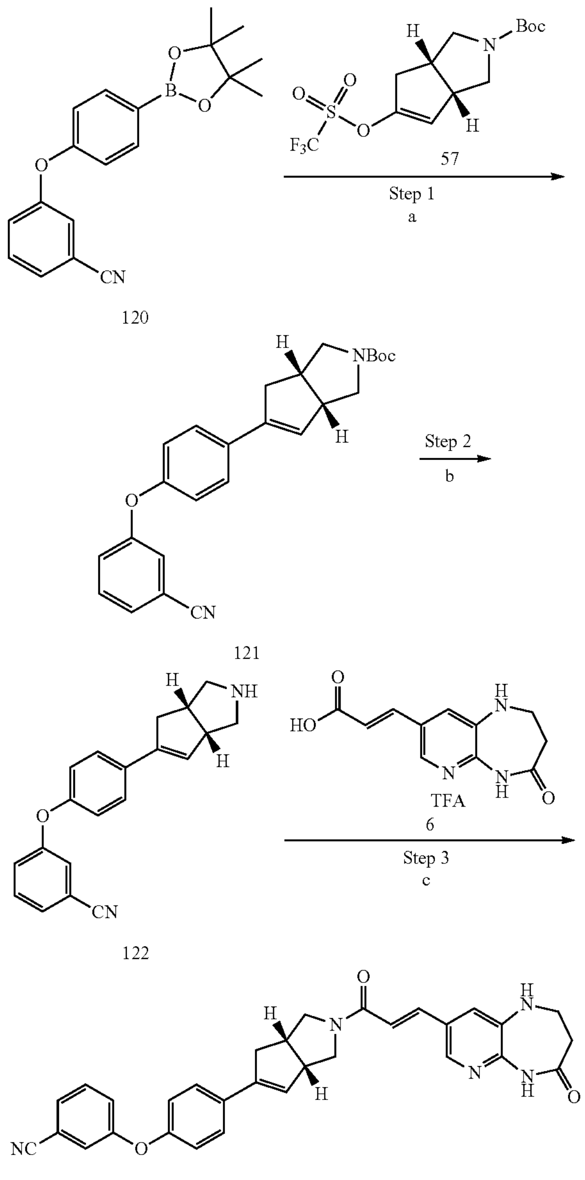

Reaction conditions: a) $K_2CO_3$, $H_2O$, $PdCl_2$(dppf), 1,4-dioxane, 80° C.; b) TFA, DCM; c) HATU, DIPEA, DMF The synthesis of 3-(4-(4,4,5,5-tetramethyl-1,3,2-dioxaborolan-2-yl)phenoxy)benzonitrile (compound 120) was previously reported by Abbott Laboratories-US2002/156081, 2002, A1. This compound is also commercially available from Fluorochem (CAS: 330792-98-8).

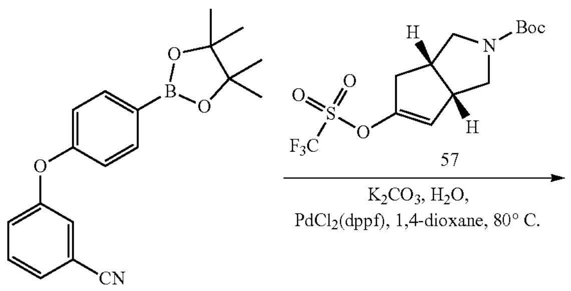

120

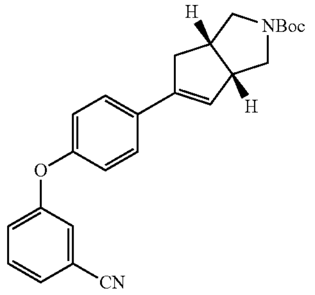

121

Step 1. tert-Butyl (3rS,6rR)-5-(4-(3-cyanophenoxy)phenyl)-3,3r,4,6r-tetrahydro-cyclopenta[c]pyrrole-2(1H)-carboxylate (compound 121). A mixture of 3-(4-(4,4,5,5-tetramethyl-1,3,2-dioxaborolan-2-yl)phenoxy)benzonitrile 120 (250 mg, 0.78 mmol), tert-butyl 5-(((trifluoromethyl)sulfonyl)oxy)-3,3r,6,6r-tetrahydrocyclopenta[c]pyrrole-2(1H)-carboxylate) 57 (278 mg, 0.8 mmol), $PdCl_2$(dppf)-$CH_2Cl_2$ adduct (64 mg, 0.08 mmol), potassium carbonate (323 mg, 2.3 mmol) and water (1.5 mL) in 1,4-dioxane (4 mL) was stirred at 80° C. overnight. The reaction was cooled to RT, filtered through Celite®, and washed with EtOAc (50 mL). The mixture was then evaporated under vacuum to afford the title compound 121 as a brown oil (396 mg, quant. yield) which was used in the following step without further purification. $R^t$ 2.86 min (Method 1b); m/z 347 $[M+H-tBu]^+$ $(ES^+)$.

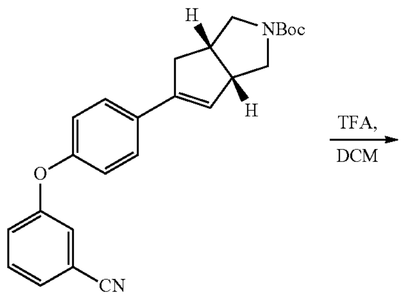

121

-continued

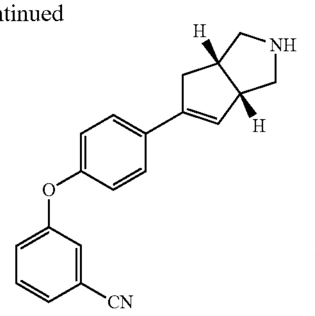

122

Step 2. 3-(4-((3rS,6rR)-1,2,3,3r,4,6r-Hexahydrocyclopenta[c]pyrrol-5-yl)phenoxy)benzonitrile (compound 122). Trifluoroacetic acid (2.5 mL) was added dropwise to a stirred solution of tert-butyl 5-(4-(3-cyanophenoxy)phenyl)-3,3r,6,6r-tetrahydrocyclopenta[c]pyrrole-2(1H)-carboxylate 121 (313 mg, 0.8 mmol) in DCM (2.5 mL) at RT. The reaction mixture was stirred for 2 h then the solvent was concentrated in vacuo and the resulting residue was taken up in methanol (30 mL) and applied to an SCX column. The column was washed with methanol (50 mL) and the product eluted with a solution of 10% methanolic ammonia. The mixture was then evaporated affording the title compound 122 as a yellow oil (154 mg, 64% yield). $R^t$ 1.75 min (Method 1b); m/z 303 $[M+H]^+$ ($ES^+$). $^1H$ NMR (400 MHz, $CDCl_3$): δ, ppm 7.44-7.39 (m, 3H), 7.34 (d, J=7.6 Hz, 1H), 7.24-7.18 (m, 2H), 6.97 (d, J=8.5 Hz, 2H), 5.93 (d, J=2.6 Hz, 1H), 3.50-3.45 (m, 1H), 3.06-2.98 (m, 2H), 2.97-2.90 (m, 2H), 2.90-2.84 (m, 1H), 2.82-2.75 (m, 1H), 2.49 (m, 1H), 2.41 (br s, 1H).

Step 3. 3-(4-((3rS,6rR)-2-((E)-3-(4-Oxo-2,3,4,5-tetrahydro-1H-pyrido[2,3-b][1,4]diazepin-8-yl)acryloyl)-1,2,3,3r,4,6r-hexahydrocyclopenta[c]pyrrol-5-yl)phenoxy)benzonitrile (compound 123). A suspension of 3-(4-((3rS,6rR)-1,2,3,3r,4,6r-hexahydrocyclopenta[c]pyrrol-5-yl)phenoxy) benzonitrile 122 (70 mg, 0.2 mmol), (E)-3-(4-oxo-2,3,4,5-tetrahydro-1H-pyrido[2,3-b][1,4]diazepin-8-yl)acrylic acid trifluoroacetate 6 (76 mg, 0.2 mmol), N-ethyl-N-isopropylpropan-2-amine (0.20 mL, 1.2 mmol) in DMF (1 mL) was stirred for 10 min. HATU (88 mg, 0.2 mmol) was added in one portion and the reaction mixture was left to stir at room temperature for 1 h. The mixture was diluted with water (10 mL) and the precipitate was collected by filtration. The crude product was purified by column chromatography (0-5% MeOH/DCM) to afford the title compound 123 as a yellow solid (87 mg, 72% yield). $R^t$ 2.08 min (Method 1b); m/z 518 $[M+H]^+$ ($ES^+$). $^1H$ NMR (400 MHz, DMSO-$d_6$): δ, ppm 9.74 (d, J=6.9 Hz, 1H), 7.98 (dd, J=8.4 Hz, 1.9 Hz, 1H), 7.60-7.53 (m, 4H), 7.50-7.47 (m, 1H), 7.37-7.31 (m, 3H), 7.09-7.04 (m, 2H), 6.87 (dd, J=15.5 Hz, 9.0 Hz, 1H), 6.18 (d, J=4.7 Hz, 1H), 6.05-6.00 (m, 1H), 4.00 (t, J=9.9 Hz, 1H), 3.87-3.79 (m, 2H), 3.69-3.51 (m, 2H), 3.43-3.37 (m, 2H), 3.19-3.12 (m, 1H), 3.03-2.90 (m, 2H), 2.66-2.59 (m, 3H).

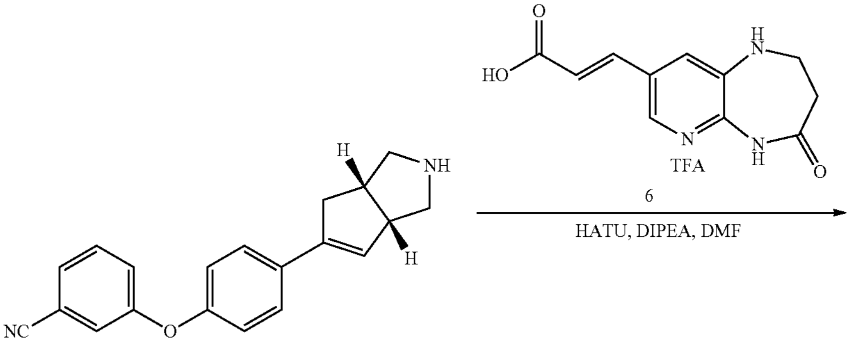

6

122

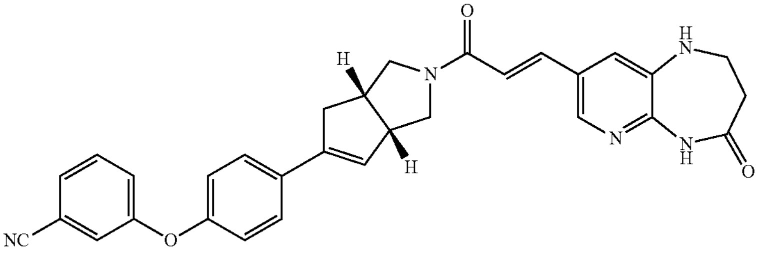

123

Example 21. Synthesis of 8-((E)-3-((3rS,6rR)-5-(4-(3-methoxyphenoxy)phenyl)-3,3r,4,6r-tetrahydrocyclopenta[c]pyrrol-2(1H)-yl)-3-oxoprop-1-en-1-yl)-1,2,3,5-tetrahydro-4H-pyrido[2,3-b][1,4]diazepin-4-one (Compound 129)
General Synthetic Scheme.
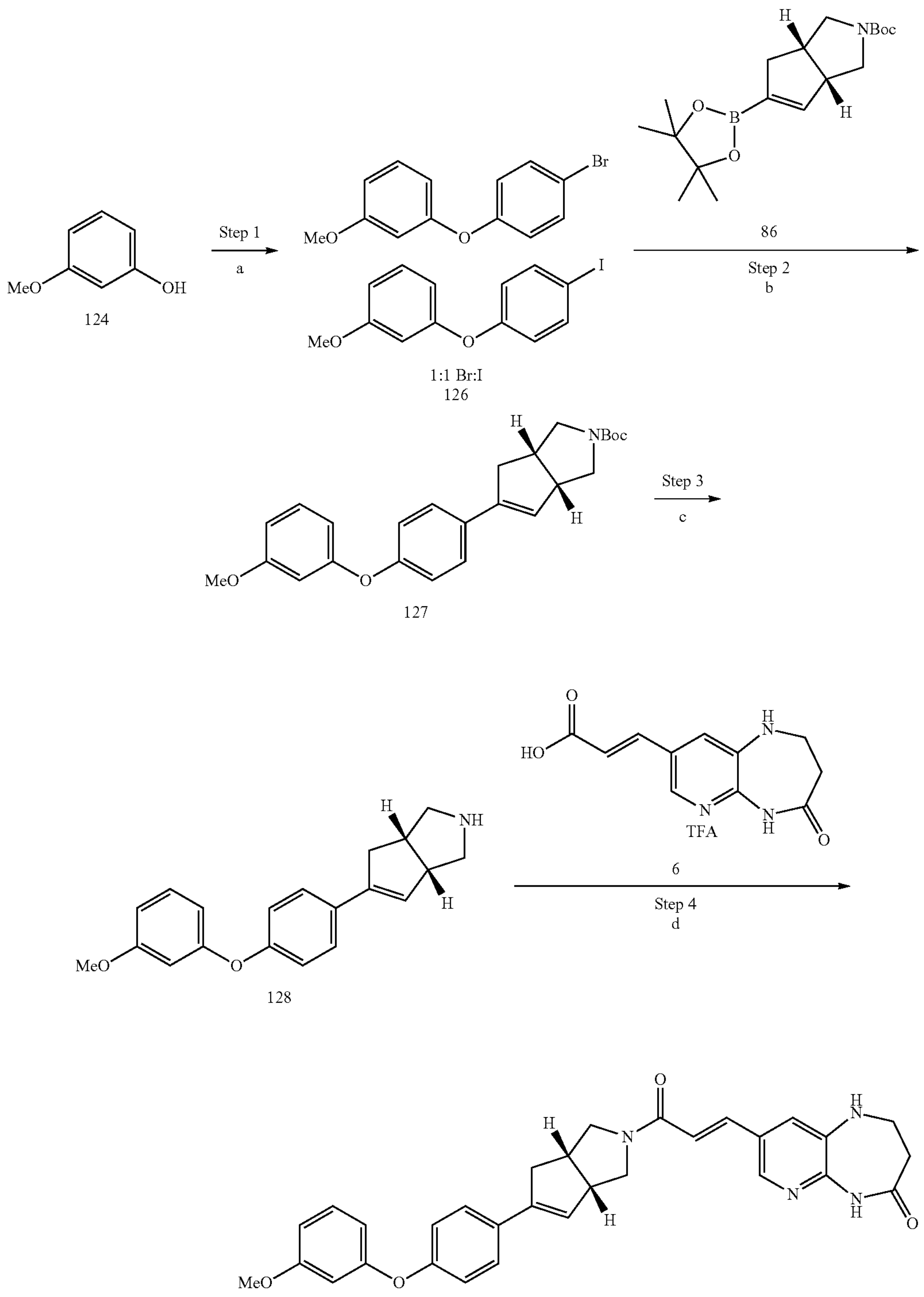
124, 126, 86, 127, 128, 6, 96
Reaction conditions: a) 1-bromo-4-iodobenzene 125, CuI, N,N-diemethyl glycine, $Cs_2CO_3$, DMF, 110° C.; b) $K_2CO_3$, $H_2O$, $PdCl_2$(dppf), 1,4-dioxane, 80° C.; c) TFA, DCM; d) HATU, DIPEA, DMF

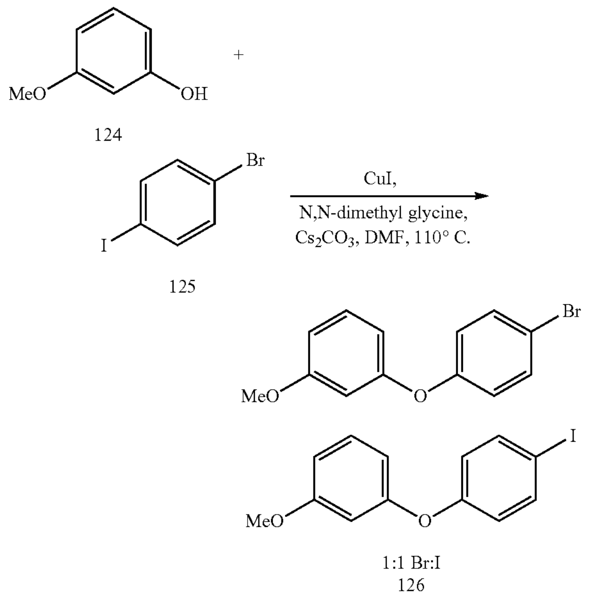

124

125

1:1 Br:I
126

Step 1. 1-(4-Bromophenoxy)-3-methoxybenzene and 1-(4-Iodophenoxy)-3-methoxybenzene (compound 126). A mixture of 1-bromo-4-iodobenzene 125 (Sigma Aldrich) (500 mg, 1.8 mmol), copper(I)iodide (337 mg, 1.8 mmol), N,N-dimethylglycine (182 mg, 1.8 mmol), cesium carbonate (2.30 g, 7.1 mmol) and 3-methoxyphenol 124 (Sigma Aldrich) (0.19 mL, 1.8 mmol) was evacuated and backfilled with nitrogen (3 times). DMF (10 mL) was added and the mixture was heated to 110° C. overnight. The mixture was filtered through a pad of Celite® washing with EtOAc (50 mL) and then evaporated to dryness. The crude product was purified by column chromatography (0-10% EtOAc/isohexane) to afford a mixture of the title compounds 126 as a dark oil (338 mg, 53% yield) which was used in the following step without further purification. $^1$H NMR (400 MHz, $CDCl_3$): δ, ppm 7.66-7.62 (m, 1H), 7.51-7.43 (m, 3H), 7.28-7.24 (m, 2H), 6.96-6.89 (m, 3H), 6.82-6.79 (m, 1H), 6.71 (ddt, J=8.3 Hz, 2.2 Hz, 1.3 Hz, 2H), 6.60 (dq, J=9.4 Hz, 1.3 Hz, 4H), 3.81 (s, 6H).

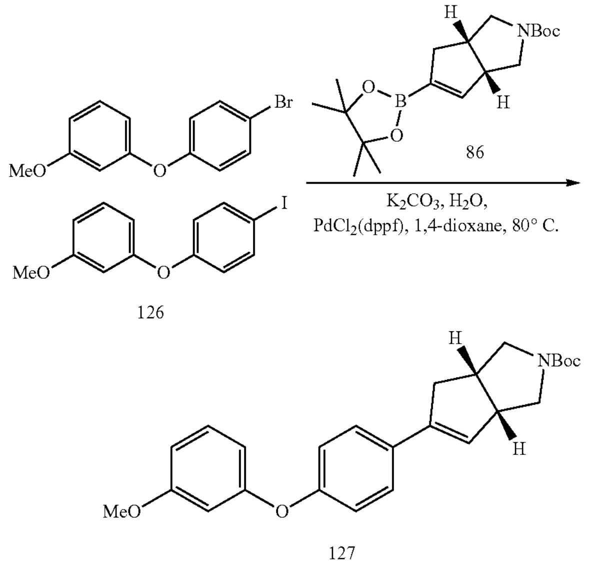

86

126

127

Step 2. tert-Butyl(3rS,6rR)-5-(4-(3-methoxyphenoxy)phenyl)-3,3r,4,6r-tetrahydrocyclopenta[c]pyrrole-2(1H)-carboxylate (compound 127). A mixture of 1-(4-iodophenoxy)-3-methoxybenzene 126 (169 mg, 0.51 mmol), 1-(4-bromophenoxy)-3-methoxybenzene 126 (169 mg, 0.6 mmol), tert-butyl 5-(4,4,5,5-tetramethyl-1,3,2-dioxaborolan-2-yl)-3,3r,6,6r-tetrahydrocyclopenta[c]pyrrole-2(1H)-carboxylate 86 (375 mg, 1.1 mmol), $PdCl_2$(dppf)-$CH_2Cl_2$ adduct (91 mg, 0.1 mmol), potassium carbonate (464 mg, 3.4 mmol) and water (2 mL) in 1,4-dioxane (6 mL) was stirred at 80° C. for 4 h. The reaction was cooled to RT, filtered through Celite®, and washed with EtOAc (50 mL). The mixture was then evaporated under vacuum. The crude product was purified by column chromatography (0-50% EtOAc/isohexane) to afford the title compound 127 as a white solid (209 mg, 45% yield). $R^t$ 3.00 min (Method 1b); m/z 352 $[M+H-tBu]^+$ ($ES^+$). $^1$H NMR (400 MHz, $CDCl_3$): δ, ppm 7.44-7.38 (m, 2H), 7.23 (td, J=8.2 Hz, 7.4 Hz, 1.2 Hz, 1H), 7.03-6.96 (m, 2H), 6.69-6.66 (m, 1H), 6.63-6.57 (m, 2H), 5.97 (br s, 1H), 3.79 (d, J=2.1 Hz, 3H), 3.75-3.69 (m, 1H), 3.59-3.48 (m, 3H), 3.11 (dd, J=11.0 Hz, 6.9 Hz, 1H), 3.06-2.99 (m, 1H), 2.97-2.90 (m, 1H), 2.59 (d, J=15.7 Hz, 1H), 1.47 (s, 9H).

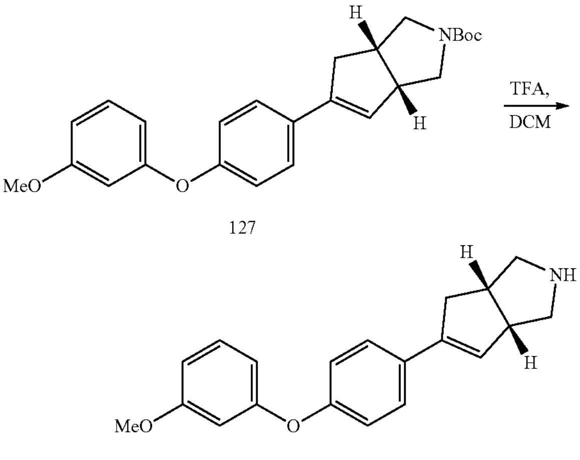

127

128

Step 3. (3rS,6rR)-5-(4-(3-Methoxyphenoxy)phenyl)-1,2,3,3r,4,6r-hexahydrocyclopenta[c]pyrrole (compound 128). Trifluoroacetic acid (1 mL) was added dropwise to a stirred solution of tert-butyl 5-(4-(3-methoxyphenoxy)phenyl)-3,3r,6,6r-tetrahydrocyclopenta[c]pyrrole-2(1H)-carboxylate 127 (209 mg, 0.5 mmol) in DCM (1 mL) at RT. The reaction mixture was stirred for 1 h then the solvent was concentrated in vacuo. The resulting residue was taken up in methanol (30 mL) and applied to an SCX column. The column was washed with methanol (50 mL) and the product eluted with a solution of 10% methanolic ammonia. The mixture was then evaporated to afford the title compound 128 as a yellow oil (157 mg, 96% yield). $R^t$ 1.91 min (Method 1b); m/z 308 $[M+H]^+$ ($ES^+$). $^1$H NMR ($CDCl_3$): δ, ppm 7.37 (d, J=8.5 Hz, 2H), 7.23-7.17 (m, 1H), 6.99-6.93 (m, 2H), 6.67-6.62 (m, 1H), 6.59-6.55 (m, 2H), 5.89-5.87 (m, 1H), 3.75 (s, 3H), 3.47-3.42 (m, 3H), 3.05-2.78 (m, 5H), 2.50-2.46 (m, 1H), 1.36 (d, J=8.3 Hz, 1H).

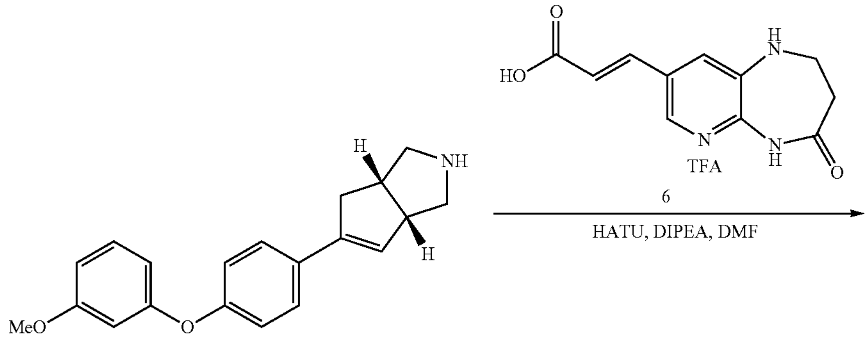

128

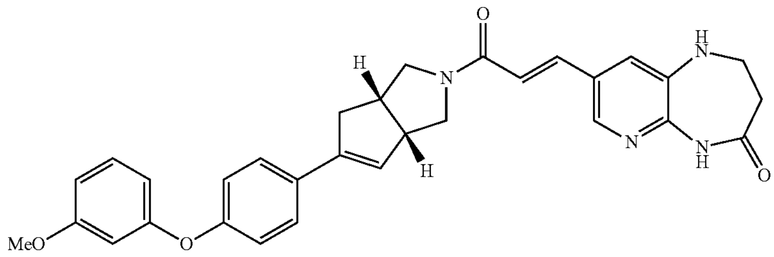

129

Step 4. (3rS,6rR)-5-(4-(3-Methoxyphenoxy)phenyl)-1,2,3,3r,4,6r-hexahydrocyclopenta[c]pyrrole (compound 129). A suspension of (3rS,6rR)-5-(4-(3-methoxyphenoxy)phenyl)-1,2,3,3r,4,6r-hexahydrocyclopenta[c]pyrrole 128 (70 mg, 0.3 mmol), (E)-3-(4-oxo-2,3,4,5-tetrahydro-1H-pyrido[2,3-b][1,4]diazepin-8-yl)acrylic acid trifluoroacetate 6 (75 mg, 0.3 mmol), N-ethyl-N-isopropylpropan-2-amine (0.2 ml, 1.2 mmol) in DMF (1.5 mL) was stirred for 10 min. HATU (87 mg, 0.3 mmol) was added in one portion and the reaction mixture was left to stir at room temperature for 1 h. The mixture was diluted with water (10 mL) and the precipitate was collected by filtration. The crude product was purified by column chromatography (0-5% MeOH/DCM) to afford the title compound 129 as a yellow solid (86 mg, 70% yield). $R^t$ 2.19 min (Method 1b); m/z 523 $[M+H]^+$ ($ES^+$). $^1H$ NMR (400 MHz, DMSO-$d_6$): δ, ppm 9.74 (d, J=6.8 Hz, 1H), 7.98 (dd, J=8.4 Hz, 1.9 Hz, 1H), 7.50 (d, J=8.5 Hz, 2H), 7.38-7.26 (m, 3H), 7.01-6.97 (m, 2H), 6.89-6.84 (m, 1H), 6.72 (dd, J=8.3 Hz, 2.4 Hz, 1H), 6.59-6.58 (m, 1H), 6.56-6.53 (m, 1H), 6.14-6.13 (m, 1H), 6.05-5.98 (m, 1H), 3.99 (t, J=9.8 Hz, 1H), 3.87-3.78 (m, 1H), 3.73 (d, J=0.8 Hz, 3H), 3.68-3.51 (m, 2H), 3.42 (td, J=6.1 Hz, 3.4 Hz, 2H), 3.20-3.11 (m, 1H), 3.02-2.87 (m, 2H), 2.61 (dt, J=10.9 Hz, 6.0 Hz, 3H).

Example 22. Synthesis of (E)-N-methyl-N-((2-methyl-7-((1-methylindolin-6-yl)oxy)benzofuran-3-yl)methyl)-3-(4-oxo-2,3,4,5-tetrahydro-1H-pyrido[2,3-b][1,4]diazepin-8-yl)acrylamide (Compound 134)

General Synthetic Scheme.

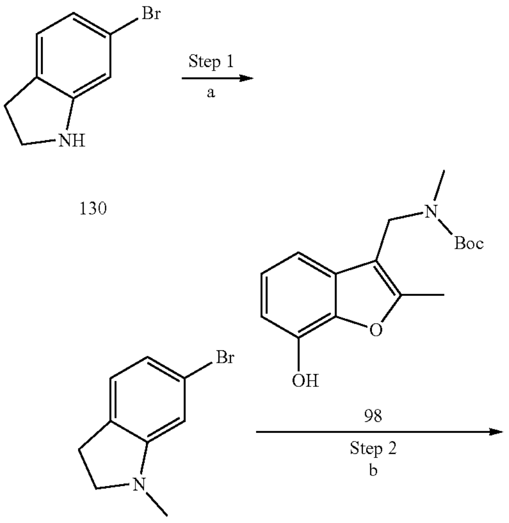

130

98

131

-continued

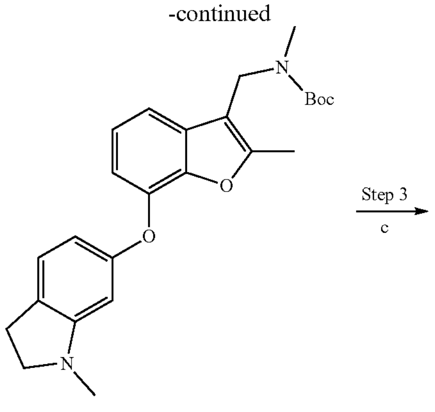

132

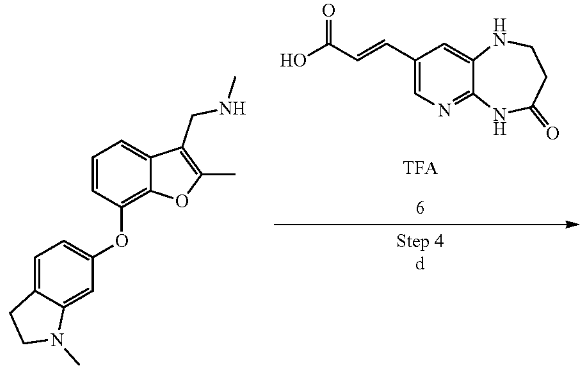

133

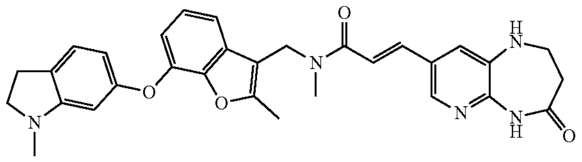

134

Reaction conditions: a) NaH, MeI, THF, 0° C.; b) CuI, N,N-dimethyl glycine, $Cs_2CO_3$, DMF, 110° C.; c) TFA, DCM; d) HATU, DIPEA, DMF

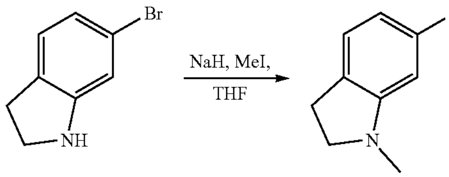

Step 1. 6-Bromo-1-methylindoline (compound 131). Sodium hydride (60% in mineral oil, 0.15 g, 3.8 mmol) was added in small portions to a stirred solution of 6-bromoindoline 130 (0.5 g, 2.5 mmol) in THF (20 mL) at 0° C. under $N_2$. The reaction mixture was stirred for 30 min then iodomethane (0.2 mL, 2.5 mmol) was added and the reaction mixture was allowed to warm to RT. The reaction mixture was stirred at RT over the weekend then chilled to 0° C. and quenched by addition of sat. $NH_4Cl$ (50 mL). The aqueous mixture was extracted with EtOAc (3×50 mL) and the combined organic extracts were washed with brine (50 mL), dried with $MgSO_4$, and concentrated in vacuo. The crude material was purified by column chromatography (0-20% EtOAc/isohexane) to afford the title compound 131 as a brown oil (0.44 g, 76%). $R^t$ 2.39 min (Method 1a) m/z 212/214 $[M+H]^+$ ($ES^+$). $^1H$ NMR (400 MHz, DMSO-$d_6$): δ, ppm 6.97-6.91 (m, 1H), 6.69 (dd, J=7.6 Hz, 1.8 Hz, 1H), 6.62 (d, J=1.7 Hz, 1H), 3.28 (t, J=8.3 Hz, 2H), 2.82 (t, J=8.5 Hz, 2H), 2.69 (s, 3H).

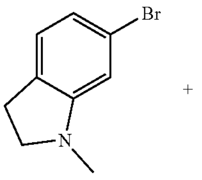

131

+

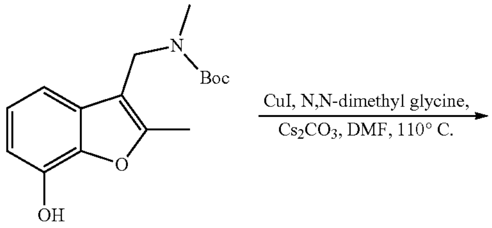

98

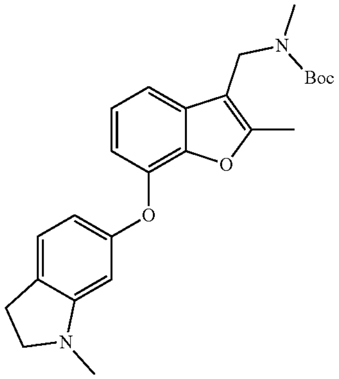

132

Step 2. tert-Butyl methyl((2-methyl-7-((1-methylindolin-6-yl)oxy)benzofuran-3-yl)methyl)carbamate (compound 132). DMF (5 mL) was added to a mixture of $Cs_2CO_3$ (0.67 g, 2.1 mmol), 6-bromo-1-methylindoline 131 (Fluorochem) (0.4 g, 1.9 mmol), tert-butyl ((7-hydroxy-2-methylbenzofuran-3-yl)methyl)(methyl)carbamate 98 (0.15 g, 0.5 mmol), 2-(dimethylamino)acetic acid (0.05 g, 0.5 mmol) and CuI (0.1 g, 0.5 mmol) under an atmosphere of $N_2$ and the reaction mixture was heated to 110° C. The reaction mixture was stirred at this temperature for 16 h then the reaction mixture was allowed to cool to RT. The crude mixture was dry loaded onto Celite® and purified by column chromatography (0-50% EtOAc/isohexane) to afford the title compound 132 as a colourless oil (41 mg, 19% yield). $R^t$3.02 min (Method 1a) m/z 423 $[M+H]^+$ ($ES^+$).

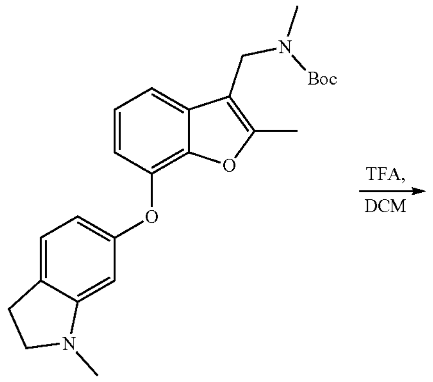

132

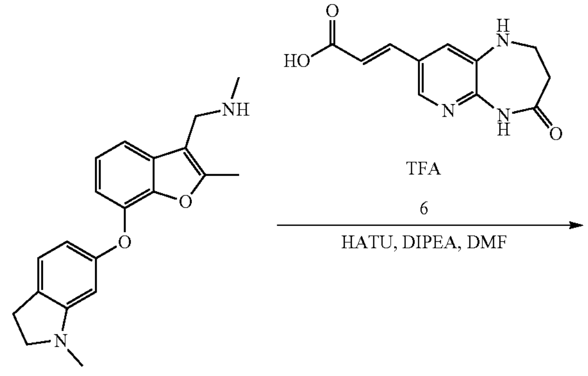

133

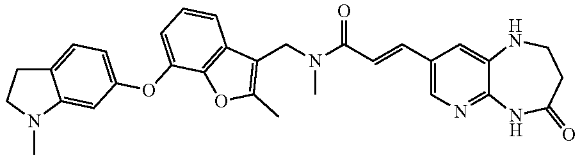

134

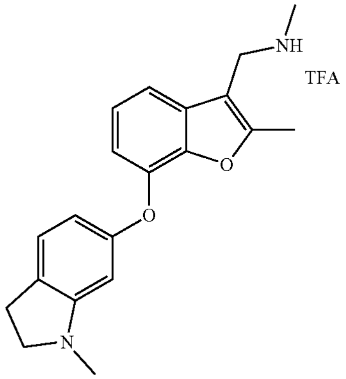

133

Step 3. N-Methyl-1-(2-methyl-7-((1-methylindolin-6-yl)oxy)benzofuran-3-yl)methanamine trifluoroacetate (compound 133). Trifluoroacetic acid (2 mL) was added dropwise to a stirred solution of tert-butyl methyl((2-methyl-7-((1-methylindolin-6-yl)oxy)benzofuran-3-yl)methyl)carbamate 132 (0.04 g, 0.1 mmol) in DCM (2 mL) at RT. The reaction was stirred for 30 min then was concentrated in vacuo to afford the title compound 133 as a brown oil which was used in the next step without further purification. $R^t$ 2.02 min (Method 1a) m/z 323 $[M+H]^+$ $(ES^+)$.

Step 4. (E)-N-Methyl-N-((2-methyl-7-((1-methylindolin-6-yl)oxy)benzofuran-3-yl)methyl)-3-(4-oxo-2,3,4,5-tetrahydro-1H-pyrido[2,3-b][1,4]diazepin-8-yl)acrylamide (compound 134). DIPEA (0.5 mL, 2.9 mmol) was added dropwise to a stirred solution of N-methyl-1-(2-methyl-7-((1-methylindolin-6-yl)oxy)benzofuran-3-yl)methanamine trifluoroacetate 133 (0.07 g, 0.2 mmol) and (E)-3-(4-oxo-2,3,4,5-tetrahydro-1H-pyrido[2,3-b][1,4]diazepin-8-yl)acrylic acid trifluoroacetate 6 (0.06 g, 0.2 mmol) in DMF (2 mL) at RT. The reaction was stirred for 10 min then HATU (0.08 g, 0.2 mmol) was added and the reaction was stirred for 2 h. The reaction mass was diluted with $H_2O$ (10 mL) and the precipitate collected by filtration. The crude material was purified by column chromatography (0-3% MeOH/DCM) to afford the title compound 134 as a pale yellow solid (20 mg, 23% yield). $R^t$ 2.13 min (Method 1a) m/z 538 $[M+H]^+$ $(ES^+)$. $^1H$ NMR (400 MHz, 363 K, DMSO-$d_6$): δ, ppm 9.14 (s, 1H), 7.98 (d, J=1.9 Hz, 1H), 7.46 (d, J=15.4 Hz, 1H), 7.38 (d, J=1.9 Hz, 1H), 7.28 (d, J=7.8 Hz, 1H), 7.16-7.04 (m, 2H), 6.95 (dt, J=7.8, 1.1 Hz, 1H), 6.78 (dd, J=8.0, 1.1 Hz, 1H), 6.21-6.13 (m, 2H), 5.79 (s, 1H), 4.77 (s, 2H), 3.46-3.41 (m, 2H), 3.33 (t, J=8.2 Hz, 2H), 3.02 (s, 3H), 2.87 (t, J=8.2 Hz, 2H), 2.67 (s, 3H), 2.66-2.62 (m, 2H), 2.49 (s, 3H).

Example 23. Synthesis of 2-methoxy-4-(4-((3rS, 6rR)-2-((E)-3-(4-oxo-2,3,4,5-tetrahydro-1H-pyrido [2,3-b][1,4]diazepin-8-yl)acryloyl)-1,2,3,3r,4,6r-hexahydrocyclopenta[c]pyrrol-5-yl)phenoxy) benzonitrile (Compound 140)

General Synthetic Scheme.

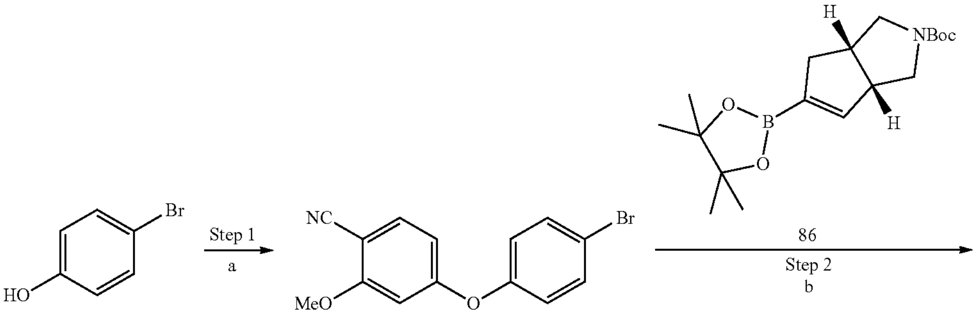

135

137

-continued

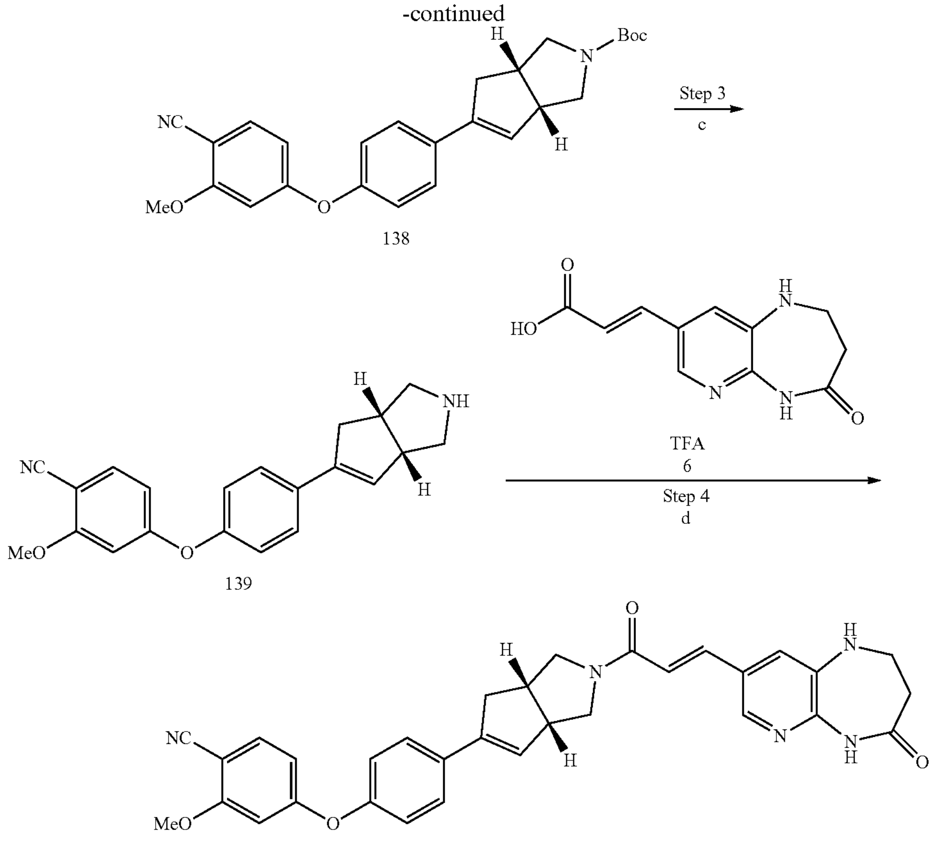

138

139

140

Reaction conditions: a) 4-Fluoro-2-methoxybenzonitrile 136, $Cs_2CO_3$, NMP, 80° C.; b) $Pd(dppf)Cl_2$, $K_2CO_3$, 1,4-dioxane, 90° C.; c) TFA, DCM; d) HATU, DIPEA, DMF

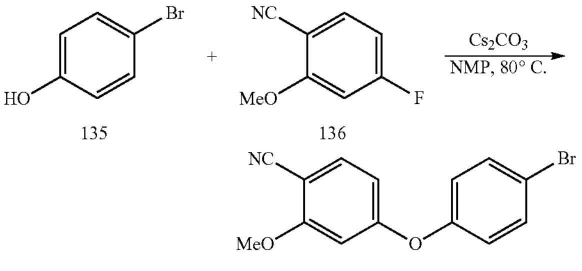

135 + 136

137

Step 1. 4-(4-Bromophenoxy)-2-methoxybenzonitrile (compound 137). A mixture of 4-fluoro-2-methoxybenzonitrile 136 (Fluorochem) (1 g, 6.6 mmol), 4-bromophenol 135 (1.37 g, 7.94 mmol) and $Cs_2CO_3$ (6.47 g, 19.9 mmol) in N-methyl-2-pyrrolidon (20 mL) was heated at 80° C. for 2 h. The reaction mixture was allowed to cool to room temperature, and was poured into water (50 mL). The mixture was extracted with ethyl acetate (2×50 mL). The organics were combined and washed with brine (2×50 mL), passed through a hydrophobic frit, and concentrated in vacuo. The crude product was purified by column chromatography (0-50% EtOAc/isohexane) to afford the title compound 137 as a clear colourless oil which crystallised upon standing (2.02 g, 70% yield). $R^t$ 2.56 min (Method 1a) m/z 304/306 $[M+H]^+$ $(ES^+)$.

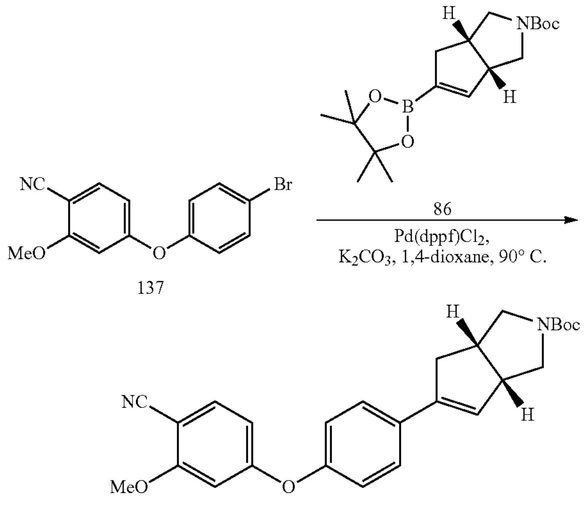

137

138

Step 2. tert-Butyl (3rS,6rR)-5-(4-(4-cyano-3-methoxyphenoxy)phenyl)-3,3r,4,6r-tetrahydrocyclopenta[c]pyrrole-2(1H)-carboxylate (compound 138). A mixture of 4-(4-bromophenoxy)-2-methoxybenzonitrile 137 (0.18 g, 0.6 mmol), (3rR,6rS)-tert-butyl 5-(4,4,5,5-tetramethyl-1,3,2-dioxaborolan-2-yl)-3,3r,6,6r-tetrahydrocyclopenta[c]pyrrole-2(1H)-carboxylate 86 (0.2 g, 0.6 mmol), $K_2CO_3$ (0.25 g, 1.8 mmol) in water (1 mL) and $PdCl_2$(dppf)-$CH_2Cl_2$ adduct (0.05 g, 0.06 mmol) in 1,4-dioxane (4 mL) was degassed with nitrogen and then stirred at 80° C. overnight. The reaction mixture was allowed to cool to room temperature, diluted with water (10 mL), extracted with ethyl acetate (2×10 mL). The combined organic layers were washed with brine (20 mL), dried ($MgSO_4$), filtered and concentrated in vacuo. The crude product was purified by column chromatography (0-50% EtOAc/isohexane) to afford the title compound 138 as a thick colourless oil (0.23 g, 73% yield). $R^t$ 2.93 min (Method 1a) m/z 377 $[M+H-tBu]^+$ ($ES^+$). $^1H$ NMR (400 MHz, $CDCl_3$): δ, ppm 7.51-7.44 (m, 3H), 7.07-7.02 (m, 2H), 6.59 (d, J=2.2 Hz, 1H), 6.53 (dd, J=8.6 Hz, 2.2 Hz, 1H), 6.06-6.01 (m, 1H), 3.88 (s, 3H), 3.77-3.68 (m, 1H), 3.59-3.48 (m, 3H), 3.12 (dd, J=11.0 Hz, 6.9 Hz, 1H), 3.10-2.93 (m, 2H), 2.62 (d, J=15.7 Hz, 1H), 1.47 (s, 9H).

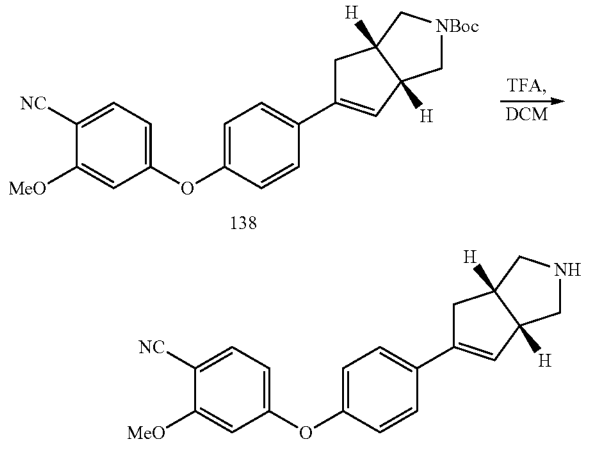

138

139

Step 3. 4-(4-((3rS,6rR)-1,2,3,3r,4,6r-Hexahydrocyclopenta[c]pyrrol-5-yl)phenoxy)-2-methoxybenzonitrile (compound 139). To a stirred solution of (3rR,6rS)-tert-butyl 5-(4-(4-cyano-3-methoxyphenoxy)phenyl)-3,3r,6,6r-tetrahydrocyclopenta[c]pyrrole-2(1H)-carboxylate 138 (0.23 g, 0.5 mmol) in DCM (2 mL) was added TFA (1.6 mL). The reaction mixture was stirred at room temperature for 1 h. The solvent was removed in vacuo. The resulting oil was taken up in MeOH (5 mL) and applied to an SCX column. The column was washed with methanol (5 mL) and the product eluted with 10% methanolic ammonia (5 mL) to afford the title compound 139 as a colourless crystalline solid (0.1 g, 56%). $R^t$ 1.50 min (Method 1a) m/z 333 $[M+H]^+$ ($ES^+$).

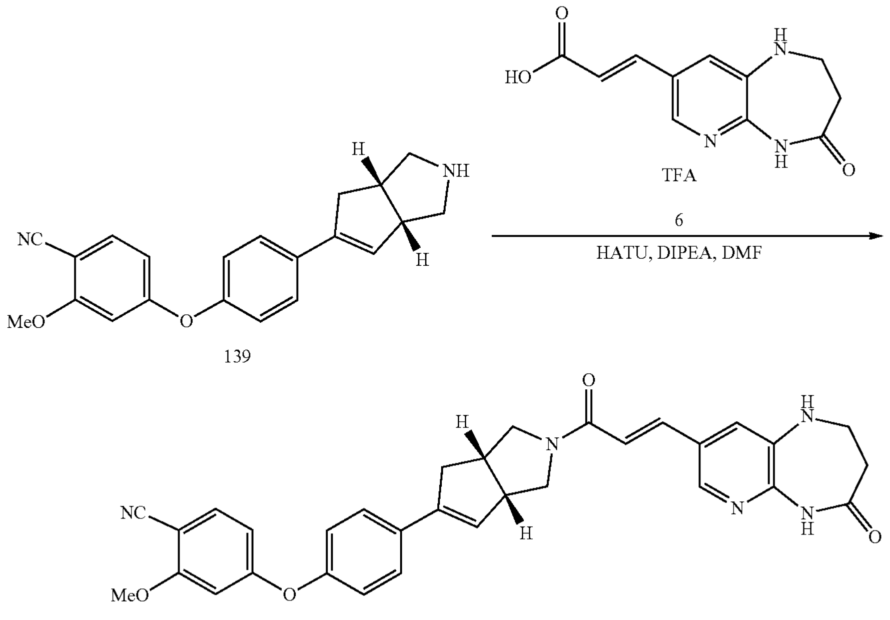

139

140

Step 4. 2-Methoxy-4-(4-((3rS,6rR)-2-((E)-3-(4-oxo-2,3,4,5-tetrahydro-1H-pyrido[2,3-b][1,4]diazepin-8-yl)acryloyl)-1,2,3,3r,4,6r-hexahydrocyclopenta[c]pyrrol-5-yl)phenoxy)benzonitrile (compound 140). To a stirred solution of 4-(4-((3rS,6rR)-1,2,3,3r,4,6r-hexahydrocyclopenta[c]pyrrol-5-yl)phenoxy)-2-methoxybenzonitrile (0.1 g, 0.29 mmol) in DMF (2 mL) was added (E)-3-(4-oxo-2,3,4,5-tetrahydro-1H-pyrido[2,3-b][1,4]diazepin-8-yl)acrylic acid trifluoroacetate (75 mg, 0.32 mmol) and N-ethyl-N-isopropylpropan-2-amine (0.26 mL, 1.46 mmol). The reaction mixture was stirred at RT for 5 min and HATU (0.1 g, 0.35 mmol) was added. The reaction mixture was stirred for 1 h. Water (2 mL) was added and the aqueous phase extracted with DCM (3×5 mL). The combined organic phases were washed with $H_2O$ (2×5 mL), brine (5 mL), dried ($MgSO_4$), filtered, and concentrated in vacuo. The crude solid was purified by column chromatography (0-10% MeOH/DCM) to afford the title compound 140 as a yellow solid (0.1 g, 62% yield). $R^t$ 2.11 min (Method 1a) m/z 548 $[M+H]^+$ ($ES^+$). $^1H$ NMR (400 MHz, DMSO-$d_6$): δ, ppm 9.74 (d, J=6.7 Hz, 1H), 7.98 (dd, J=8.3, 1.9 Hz, 1H), 7.69 (d, J=8.6 Hz, 1H), 7.60-7.55 (m, 2H), 7.39-7.29 (m, 2H), 7.15-7.11 (m, 2H), 6.91-6.83 (m, 2H), 6.53 (ddd, J=8.5 Hz, 6.1 Hz, 2.2 Hz, 1H), 6.20 (t, J=3.2 Hz, 1H), 6.02 (d, J=13.2 Hz, 1H), 4.05-3.96 (m, 0.5H), 3.90-3.76 (m, 4H), 3.70 (d, J=12.0 Hz, 0.5H), 3.67-3.48 (m, 2H), 3.45-3.39 (m, 2H), 3.20-2.92 (m, 3H), 2.70-2.57 (m, 3H) (rotamers).

Example 24. Synthesis of (R,E)-N-((4-amino-3-methylbenzofuran-2-yl)methyl)-3-(3-hydroxy-3-methyl-4-oxo-2,3,4,5-tetrahydro-1H-pyrido[2,3-b][1,4]diazepin-8-yl)-N-methylacrylamide (Compound 143)

General Synthetic Scheme

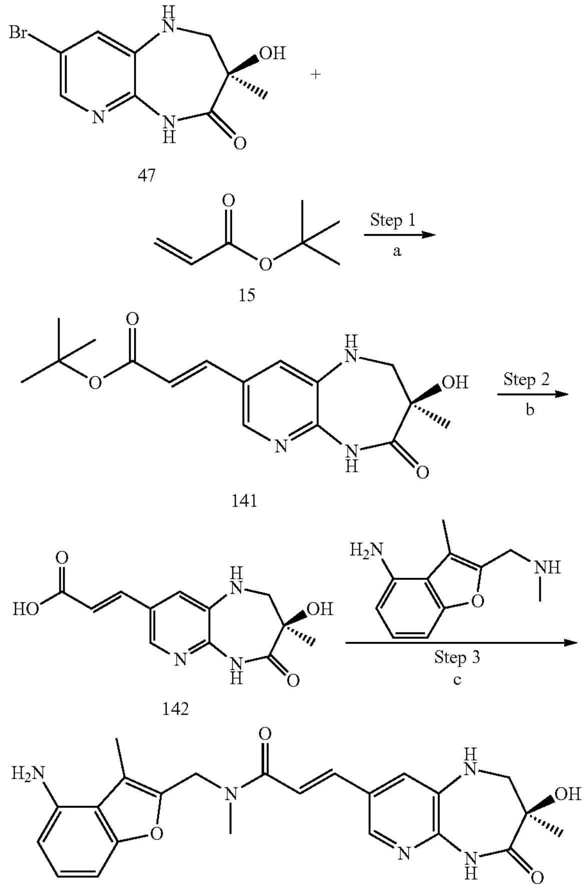

Reaction conditions: a) Chloro(crotyl)(tri-tert-butylphosphine)palladium(II), $[CH_3(CH_2)_3]_4NCl$, DIPEA, 1,4-dioxane, 90° C., 18 h; b) TFA, DCM, 0° C. to RT; c) HOBT•$H_2O$, EDC•HCl, DIPEA, DMF

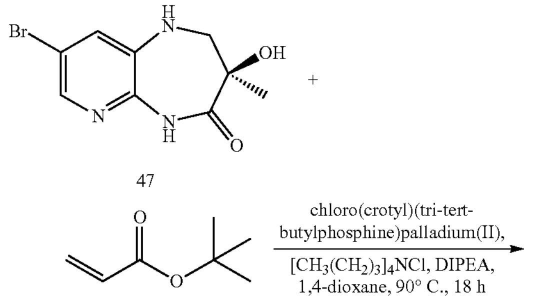

15

-continued

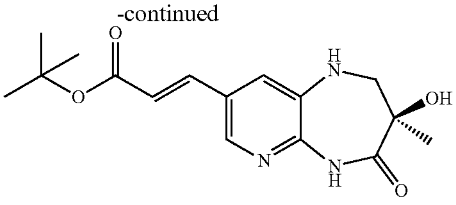

141

Step 1. tert-Butyl (R,E)-3-(3-hydroxy-3-methyl-4-oxo-2,3,4,5-tetrahydro-1H-pyrido[2,3-b][1,4]diazepin-8-yl)acrylate (compound 141). A 100 mL flask vial was charged with (R)-8-bromo-3-hydroxy-3-methyl-1,2,3,5-tetrahydro-4H-pyrido[2,3-b][1,4]diazepin-4-one 47 (ChiralTek; chirality arbitrarily assigned; 2.0 g, 7.2 mmol), n-$Bu_4NCl$ (0.240 mg, 0.86 mmol), chloro(crotyl)(tri-tert-butylphosphine)palladium(II) (0.144 g, 0.36 mmol) and the mixture was purged with nitrogen for 10 mins. Then, tert-butyl acrylate 15 (1.57 mL, 10.8 mmol), 1,4-dioxane (52 mL) and DIPEA (2.45 mL, 14.4 mmol) were added and the nitrogen bubbled through the mixture for an additional 5 mins. The reaction mixture was heated at 90° C. for 18 h and cooled to RT. The reaction mass was filtered using 0.22 uM filters, washed with MeCN and concentrated to dryness in vacuo. Acetonitrile was added to the crude material, sonicated and the yellow precipitate was filtered off to afford 141 (2.1 g, 6.5 mmol, 91.3% yield) as a yellow solid. $R^t$ 1.45 min; LCMS: m/z: 321.3 $[M+H]^+$. $^1H$ NMR (400 MHz, DMSO-$d_6$): δ, ppm 9.97 (s, 1H), 7.93 (d, J=1.7 Hz, 1H), 7.42 (d, J=16.1 Hz, 1H), 7.32 (d, J=1.7 Hz, 1H), 6.34 (d, J=16.1 Hz, 1H), 6.26 (s, 1H), 5.31 (s, 1H), 3.15 (d, J=53.8 Hz, 2H), 1.47 (s, 9H), 1.23 (s, 3H).

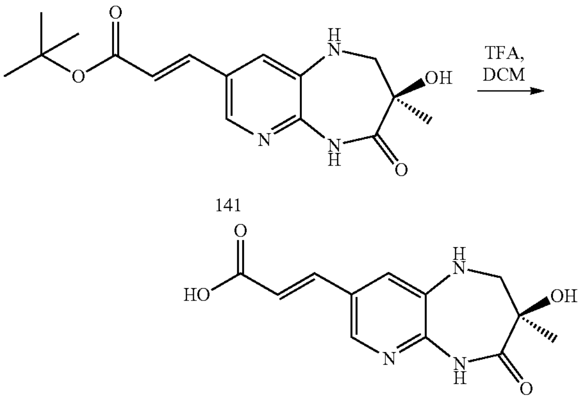

142

Step 2. (R,E)-3-(3-Hydroxy-3-methyl-4-oxo-2,3,4,5-tetrahydro-1H-pyrido[2,3-b][1,4]diazepin-8-yl)acrylic acid (compound 142). To a solution of tert-butyl (R,E)-3-(3-hydroxy-3-methyl-4-oxo-2,3,4,5-tetrahydro-1H-pyrido[2,3-b][1,4]diazepin-8-yl)acrylate 141 (0.364 g, 1.03 mmol) in DCM (9.1 mL) 2,2,2-trifluoroacetic acid (0.117 g, 1.03 mmol) was added at 0° C. After completion of reaction (UPLC-MS control) all solvents were removed under vacuum. Then, DCM was added and the resulting mixture was added into a cold $Et_2O$. The yellow precipitate was filtered off and washed with $Et_2O$ to afford the title compound 142 (0.287 g, 1.09 mmol, 106% yield) as a yellow solid. $R^t$ 0.68 min; LCMS: m/z: 264.2 $[M+H]^+$. $^1H$ NMR (400 MHz, DMSO-$d_6$): δ, ppm 12.39 (s, 1H), 9.98 (s, 1H), 7.92 (d, J=1.7 Hz, 1H), 7.47 (d, J=15.6 Hz, 1H), 7.32 (d, J=1.8 Hz, 1H), 6.35 (d, J=16.3 Hz, 1H), 3.23-3.09 (m, 3H), 1.23 (s, 3H).

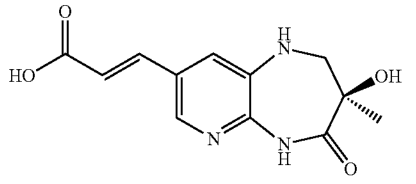

142

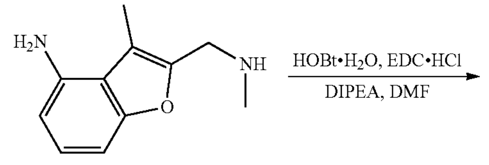

3

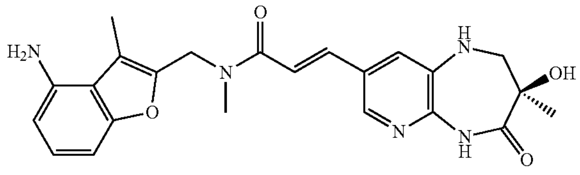

143

Step 3. (E)-N-[(4-Amino-3-methyl-benzofuran-2-yl) methyl]-3-[(3R)-3-hydroxy-3-methyl-4-oxo-2,5-dihydro-1H-pyrido[2,3-b][1,4]diazepin-8-yl]-N-methyl-prop-2-enamide (compound 143). In a microwave vial covered with aluminium foil, a mixture of (E)-3-[(3R)-3-hydroxy-3-methyl-4-oxo-2,5-dihydro-1H-pyrido[2,3-b][1,4]diazepin-8-yl]prop-2-enoic acid 142 (35 mg, 0.13 mmol) and 3-methyl-2-(methylaminomethyl)benzofuran-4-amine 3 (42.93 mg, 0.16 mmol) was dissolved in DMF (0.22 mL). HOBt-$H_2O$ (31.83 mg, 0.20 mmol) and EDC-HCl (39.84 mg, 0.20 mmol) were added to the reaction mixture and after 2 mins of stirring at room temperature, DIPEA (0.08 mL, 0.46 mmol) was added. The resulting mixture was stirred in the dark overnight at room temperature. The reaction mass was diluted with acetonitrile, no precipitation was observed but after few additional minutes very thin solid was present. The mixture was diluted with DMF and purified by preparative HPLC and lyophilized to afford 143 (25.7 mg, 0.0575 mmol, 43.72% yield) as a yellow solid. $R^t$ 1.11 min; LCMS: m/z: 436.4 $[M+H]^+$. $^1$H NMR (400 MHz, DMSO-$d_6$)): δ, ppm 9.93 (s, 1H), 7.98 (d, J=11.6 Hz, 1H), 7.46-7.31 (m, 2.5H), 7.10-7.00 (m, 0.5H), 6.91 (t, J=7.9 Hz, 1H), 6.67-6.61 (m, 1H), 6.38 (d, J=7.9 Hz, 1H), 6.27-6.22 (m, 1H), 5.28 (s, 1H), 5.17 (br s, 2H), 4.83 (s, 0.8H, rotamer), 4.69 (s, 1.2H, rotamer), 3.23-3.07 (m, 4H), 2.92 (s, 1H), 2.46-2.38 (m, 3H), 1.23 (s, 3H).

Example 25. Synthesis of (E)-3-((2R,3S)-3-hydroxy-2-methyl-4-oxo-2,3,4,5-tetrahydro-1H-pyrido[2,3-b][1,4]diazepin-8-yl)-N-methyl-N-((3-methylbenzofuran-2-yl)methyl)acrylamide (Compound 150)

General Synthetic Scheme.

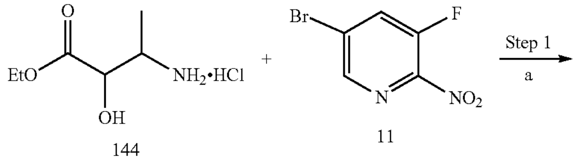

144 11

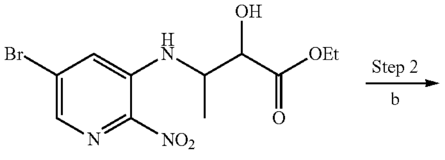

145

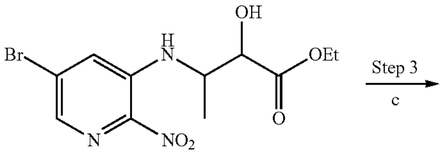

146

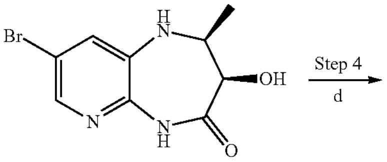

cis regioisomer

147

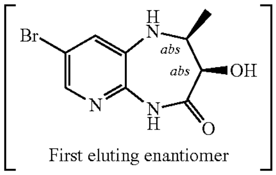

First eluting enantiomer

148

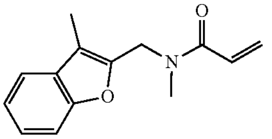

9

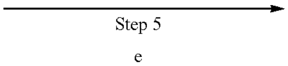

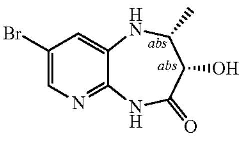

Second eluting enantiomer

149

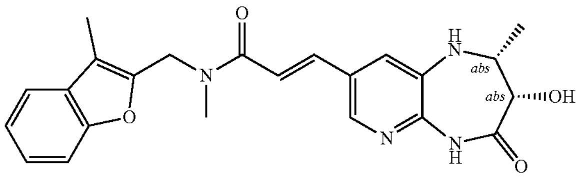

150

Reaction conditions: a) TEA, EtOH, reflux; b) Fe, $NH_4Cl$, EtOH, $H_2O$, reflux; c) NaH, THF, 0° C. to RT; d) Chiral Sep; e) Pd-162, $MeNCy_2$, $NBu_4Cl$, 1,4-dioxane, 80° C.

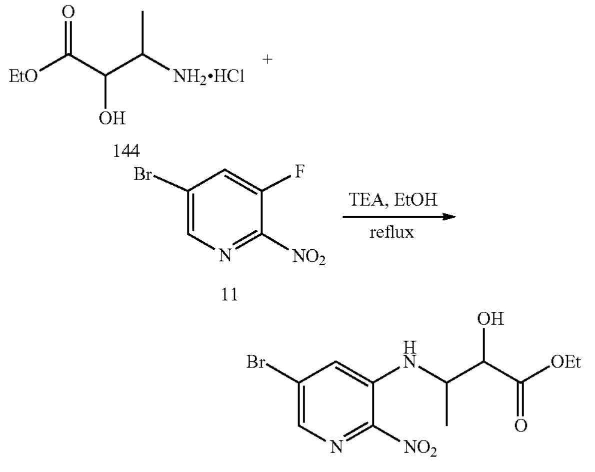

144 + 11 → 145

Step 1. Ethyl 3-((5-bromo-2-nitropyridin-3-yl)amino)-2-hydroxybutanoate (compound 145). TEA (2.8 mL, 20.1 mmol) was added to a stirred solution of 5-bromo-3-fluoro-2-nitropyridine 11 (1.1 g, 5.0 mmol) and ethyl 3-amino-2-hydroxybutanoate hydrochloride 144 (0.9 g, 4.9 mmol) in EtOH (20 mL) and the reaction mixture was heated to reflux for 4 h. The reaction mixture was allowed to cool to RT then was concentrated in vacuo and the crude material was purified by column chromatography (DCM, then 0-10% MeOH/DCM) to give diasteromer 1 as a yellow solid (0.55 g, 32%) and diastereomer 2 as a yellow oil (0.50 g, 26%) along with a further portion which contained both diastereomers in the form of a yellow oil (0.22 g, 13%).

Diastereomer 1: $R^t$ 1.76 min (Method 1a) m/z 348/350 $[M+H]^+$ $(ES^+)$. $^1H$ NMR (400 MHz, DMSO-$d_6$): δ, ppm 8.04 (d, J=1.9 Hz, 1H), 7.97 (d, J=9.2 Hz, 1H), 7.88 (d, J=1.8 Hz, 1H), 6.12 (d, J=4.8 Hz, 1H), 4.39-4.30 (m, 1H), 4.24 (dd, J=4.8 Hz, 2.8 Hz, 1H), 4.04 (q, J=7.1 Hz, 2H), 1.24 (d, J=6.5 Hz, 3H), 1.09 (t, J=7.1 Hz, 3H).

Diastereomer 2: $R^t$ 1.80 min (Method 1a) m/z 348/350 $[M+H]^+$ $(ES^+)$. $^1H$ NMR (400 MHz, DMSO-$d_6$): δ, ppm 8.01 (d, J=1.9 Hz, 1H), 7.99 (d, J=8.9 Hz, 1H), 7.90 (d, J=1.8 Hz, 1H), 6.09 (d, J=5.8 Hz, 1H), 4.28 (dd, J=5.9 Hz, 4.2 Hz, 1H), 4.26-4.19 (m, 1H), 4.14 (q, J=7.1 Hz, 2H), 1.21 (t, J=7.1 Hz, 3H), 1.14 (d, J=6.3 Hz, 3H).

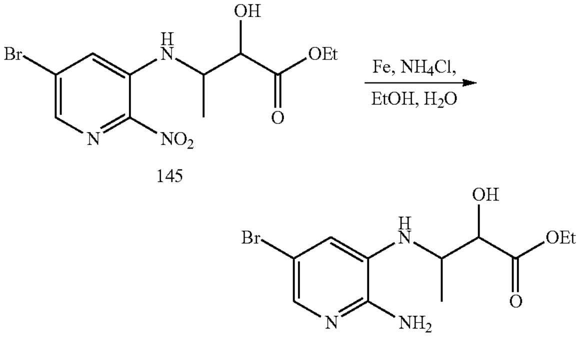

145 → 146

Step 2. Ethyl 3-((2-amino-5-bromopyridin-3-yl)amino)-2-hydroxybutanoate (compound 146). A mixture of ethyl 3-((5-bromo-2-nitropyridin-3-yl)amino)-2-hydroxybutanoate 145 (Diastereomer 1) (0.55 g, 1.6 mmol), iron powder (0.71 g, 12.6 mmol) and ammonium chloride (0.34 g, 6.3 mmol) in a solvent mixture of EtOH (50 mL) and $H_2O$ (10 mL) was stirred at reflux for 1 hour. The reaction mixture was dry loaded on Celite® and purified by column chromatography (0-100% EtOAc/iso-hexane) to give the desired product 146 as a brown solid (0.28 g, 56%). $R^t$ 0.99 min (Method 1a) m/z 318/320 $[M+H]^+$ $(ES^+)$. $^1H$ NMR (400 MHz, DMSO-$d_6$): δ, ppm 7.28 (d, J=2.0 Hz, 1H), 6.72 (d, J=2.1 Hz, 1H), 5.72 (s, 2H), 5.46 (d, J=6.7 Hz, 1H), 4.64 (d, J=9.2 Hz, 1H), 4.11 (dd, J=6.7 Hz, 3.4 Hz, 1H), 4.08-3.95 (m, 2H), 3.88-3.76 (m, 1H), 1.21-1.05 (m, 6H).

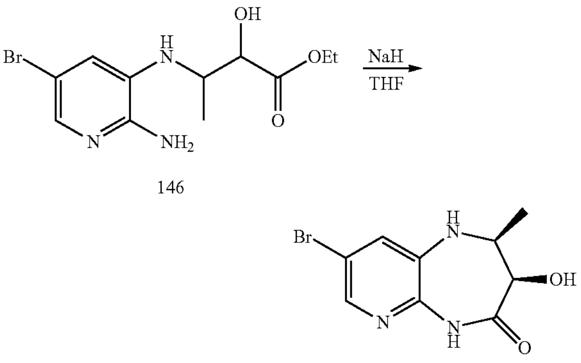

146 → 147

Step 3. 8-Bromo-3-hydroxy-2-methyl-2,3-dihydro-1H-pyrido[2,3-b][1,4]diazepin-4(5H)-one (compound 147). Sodium hydride (60% in mineral oil, 0.2 g, 5.00 mmol) was added in small portions to a stirred solution of ethyl 3-((2-amino-5-bromopyridin-3-yl)amino)-2-hydroxybutanoate 146 (1.0 g, 3.14 mmol) in THF (5.0 mL) at 0° C. The reaction was allowed to warm to RT and was stirred for 4 h. The reaction was quenched by careful addition of $NH_4Cl$ (50 mL) and the aqueous mixture was extracted with EtOAc (3×100 mL). The combined organic layers were washed with brine (1×100 mL), dried with $MgSO_4$, concentrated in vacuo and purified by column chromatography (0-50% EtOAc/iso-hexane) to give the desired product 147 as a brown solid (0.34 g, 37%). $R^t$ 1.18 min (Method 1a) m/z 272/274 $[M+H]^+$ $(ES^+)$. $^1H$ NMR (500 MHz, DMSO-$d_6$): δ, ppm 10.23 (s, 1H), 7.70 (d, J=2.1 Hz, 1H), 7.29 (d, J=2.1 Hz, 1H), 6.36 (d, J=5.6 Hz, 1H), 5.18 (d, J=4.9 Hz, 1H), 4.18 (dd, J=4.8 Hz, 3.2 Hz, 1H), 3.79-3.65 (m, 1H), 1.08 (d, J=6.5 Hz, 3H).

Chiral separation of compound 147.

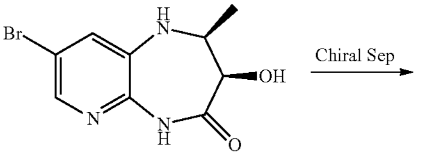

147

-continued

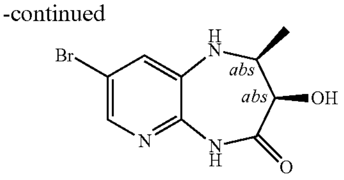

First eluting enantiomer

148

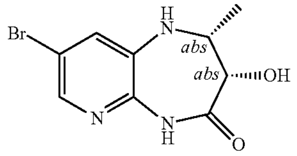

Second eluting enantiomer

149

Step 4. (2S,3R)-8-Bromo-3-hydroxy-2-methyl-2,3-dihydro-1H-pyrido[2,3-b][1,4]diazepin-4(5H)-one (compound 148) and (2R,3S)-8-bromo-3-hydroxy-2-methyl-2,3-dihydro-1H-pyrido[2,3-b][1,4]diazepin-4(5H)-one (compound 149). Enantiomers were separated by chiral prep HPLC using a Chiralpak© IC (Daicel Ltd.) column (2×25 cm), flow rate 13.5 mL $min^{-1}$ eluting with a mixture of 10% ethanol in heptane+0.2% diethylamine, UV detection at 254 nm. Samples were loaded onto the column via an at-column dilution pump, pumping ethanol (1.5 mL $min^{-1}$) for the duration of the run, giving a combined flow rate of 15 mL $min^{-1}$. Chirality was arbitrarily assigned.

First eluting enantiomer (compound 148). $R^t$ 9.6 min (Method 4b). Second eluting enantiomer (compound 149). $R^t$ 13.5 min (Method 4b).

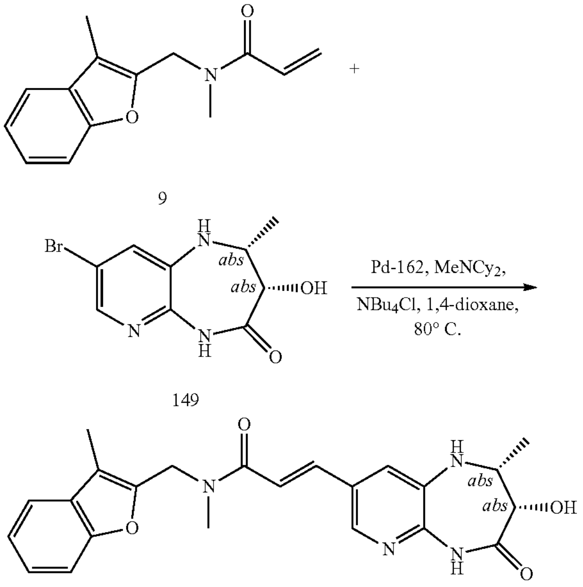

9

149

150

Step 5. (E)-3-((2R,3S)-3-Hydroxy-2-methyl-4-oxo-2,3,4,5-tetrahydro-1H-pyrido[2,3-b][1,4]diazepin-8-yl)-N-methyl-N-((3-methylbenzofuran-2-yl)methyl)acrylamide (compound 150). A reaction vial was charged with N-methyl-N-((3-methylbenzofuran-2-yl)methyl)acrylamide 9 (42 mg, 0.18 mmol), (2R,3S)-8-bromo-3-hydroxy-2-methyl-2,3-dihydro-1H-pyrido[2,3-b][1,4]diazepin-4(5H)-one 149 (50 mg, 0.18 mmol), $NBu_4Cl$ (5.0 mg, 0.02 mmol) and $[P(tBu)_3]Pd(crotyl)Cl$ (Pd-162) (7.0 mg, 0.02 mmol) and the vial was evacuated and backfilled with $N_2$ three times. 1,4-Dioxane (5.0 mL) and N-cyclohexyl-N-methylcyclohexanamine (79 μl, 0.37 mmol) were added and the reaction mixture was heated to 80° C. and stirred for ~16 h. The reaction was allowed to cool to RT, the solvent was removed in vacuo and the solid was washed with isohexane. The crude material was then purified by column chromatography (0-3% MeOH/DCM) to give the desired product as a pale yellow solid. The solid was partially dissolved in MeCN and water was added until the product precipitated. The precipitate was collected by filtration and dried by azeotroping with MeCN (2×2 mL) to give the desired product 150 as a pale yellow solid (35 mg, 45%). $R^t$1.83 min (Method 1a) m/z 421 $[M+H]^+$ $(ES^+)$. $^1H$ NMR (500 MHz, DMSO-$d_6$, 363 K): δ, ppm 9.80 (s, 1H), 7.98 (d, J=1.9 Hz, 1H), 7.59-7.52 (m, 1H), 7.49-7.37 (m, 3H), 7.31-7.22 (m, 2H), 7.12 (d, J=15.7 Hz, 1H), 5.91 (d, J=5.7 Hz, 1H), 4.84 (s, 2H), 4.76 (d, J=4.7 Hz, 1H), 4.22 (dd, J=4.7 Hz, 3.4 Hz, 1H), 3.82-3.71 (m, 1H), 3.10 (s, 3H), 2.27 (s, 3H), 1.12 (d, J=6.5 Hz, 3H).

Example 26. Synthesis of (E)-3-((2R,3S)-3-hydroxy-2-methyl-4-oxo-2,3,4,5-tetrahydro-1H-pyrido[2,3-b][1,4]diazepin-8-yl)-N-methyl-N-((2-methylbenzofuran-3-yl)methyl)acrylamide (Compound 151)

General Synthetic Scheme.

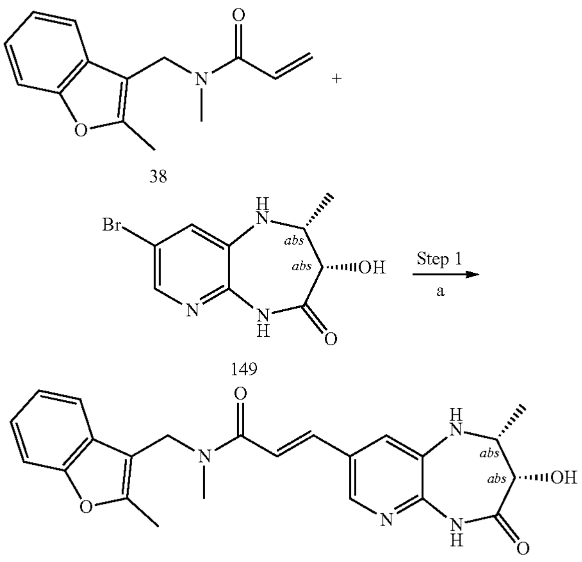

38

149

151

Reactions conditions: a) Pd-162, $MeNCy_2$, $NBu_4Cl$, 1,4-dioxane, 80° C.

Step 1. (E)-3-((2R,3S)-3-Hydroxy-2-methyl-4-oxo-2,3,4,5-tetrahydro-1H-pyrido[2,3-b][1,4]diazepin-8-yl)-N-methyl-N-((2-methylbenzofuran-3-yl)methyl)acrylamide (compound 151). A reaction vial was charged with N-methyl-N-((2-methylbenzofuran-3-yl)methyl)acrylamide 38 (42 mg, 0.18 mmol), (2R,3S)-8-bromo-3-hydroxy-2-methyl-2,3-dihydro-1H-pyrido[2,3-b][1,4]diazepin-4(5H)-one 149 (50 mg, 0.18 mmol), $NBu_4Cl$ (5.0 mg, 0.02 mmol) and $[P(tBu)_3]Pd(crotyl)Cl$ (Pd-162) (7.0 mg, 0.02 mmol) and the vial was evacuated and backfilled with $N_2$ three times. 1,4-Dioxane (5.0 mL) and N-cyclohexyl-N-methylcyclohexanamine (79 μL, 0.37 mmol) were added and the reaction mixture was heated to 80° C. and stirred for 3 h. The reaction was allowed to cool to RT, the solvent was removed in vacuo and the solid was washed with isohexane. The crude material was then purified by column chromatography (0-3% MeOH/DCM) to give the desired product as a pale yellow solid. The solid was partially dissolved in MeCN and water was added until the product precipitated. The precipitate was collected by filtration and dried by azeotroping with MeCN (2×2 mL) to give the desired product 151 as a pale yellow solid (14 mg, 17%). R$^t$1.80 min (Method 1a) m/z 421 $[M+H]^+$ ($ES^+$). $^1H$ NMR (500 MHz, DMSO-$d_6$, 363 K): δ, ppm 9.80 (s, 1H), 7.98 (d, J=1.9 Hz, 1H), 7.54 (d, J=7.6 Hz, 1H), 7.49-7.42 (m, 2H), 7.39 (d, J=2.0 Hz, 1H), 7.26-7.15 (m, 2H), 7.10 (d, J=15.9 Hz, 1H), 5.89 (d, J=5.8 Hz, 1H), 4.80-4.73 (m, 3H), 4.21 (dd, J=4.7 Hz, 3.4 Hz, 1H), 3.81-3.71 (m, 1H), 3.00 (s, 3H—obscured by solvent peak), 2.50 (s, 3H, —obscured by solvent peak), 1.11 (d, J=6.5 Hz, 3H).

Example 27. Synthesis of (R,E)-N-((7-(4-cyanophenoxy)-2-methylbenzofuran-3-yl)methyl)-3-(3-hydroxy-3-methyl-4-oxo-2,3,4,5-tetrahydro-1H-pyrido[2,3-b][1,4]diazepin-8-yl)-N-methylacrylamide (Compound 152)

General Synthetic Scheme.

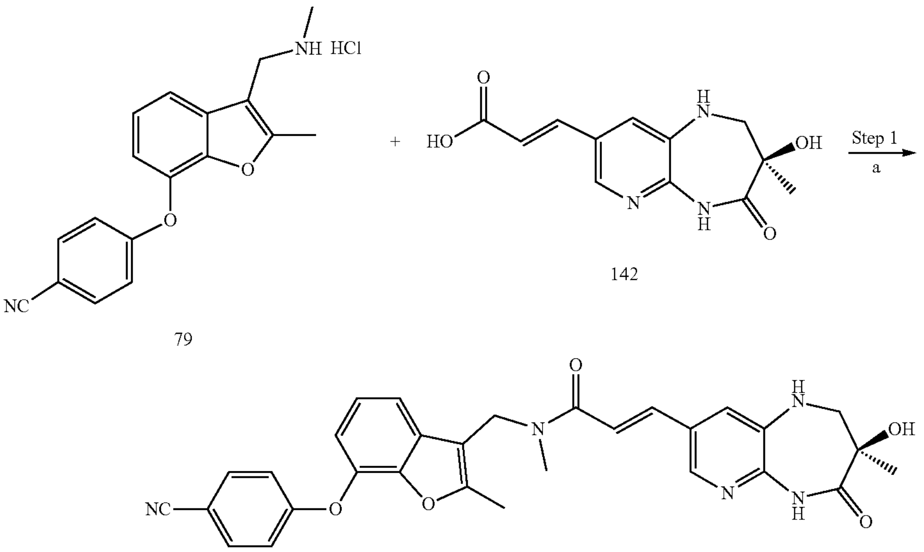

79

142

152

Reaction condtitions: a) HOBt•$H_2O$, EDC•HCl, DIPEA, DMF

Step 1. (R,E)-N-((7-(4-Cyanophenoxy)-2-methylbenzofuran-3-yl)methyl)-3-(3-hydroxy-3-methyl-4-oxo-2,3,4,5-tetrahydro-1H-pyrido[2,3-b][1,4]diazepin-8-yl)-N-methylacrylamide (compound 152) was obtained from the amine 79 and the acid 142 as a yellow solid in standard amine to amide coupling reaction described e.g. for compound 143 (Purity=95%; Yield=38%). R$^t$ 1.72 min; LCMS: m/z: 538.5 $[M+H]^+$. $^1H$ NMR (400 MHz, DMSO-$d_6$): δ, ppm 9.93 (s, 1H), 7.98 (s, 1H), 7.83 (d, J=8.9 Hz, 2H), 7.57-7.19 (m, 4H), 7.15-6.99 (m, 4H), 6.24 (br s, 1H), 5.28 (br s, 1H), 4.91 (s, 0.3H, rotamer), 4.76 (s, 1.7H, rotamer), 3.22-3.09 (m, 2H), 3.07 (s, 2.3H, rotamer), 2.87 (s, 0.7H, rotamer), 2.48 (s, 3H, partially under DMSO peak), 1.23 (s, 3H).

Example 28. Synthesis of (E)-N-((7-(3-methoxyphenoxy)-2-methylbenzofuran-3-yl)methyl)-N-methyl-3-(4-oxo-2,3,4,5-tetrahydro-1H-pyrido[2,3-b][1,4]diazepin-8-yl)acrylamide (Compound 155)

General Synthetic Scheme .

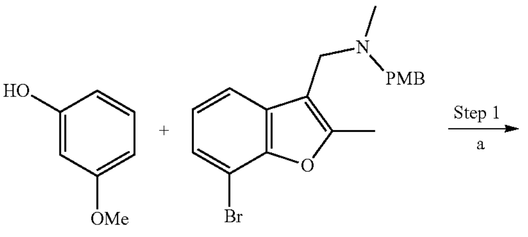

124

76

-continued

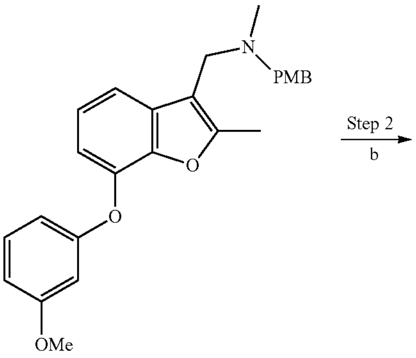

153

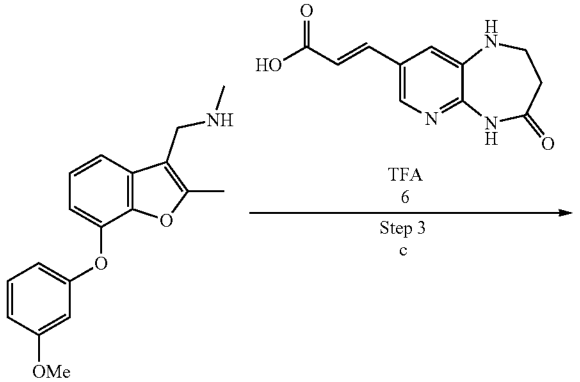

154

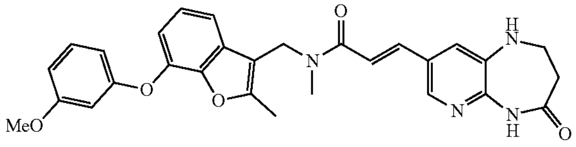

155

Reaction conditions: a) N,N-Dimethylglycine, CuI, $K_3PO_4$, DMSO, 110° C.; b) 1-chloroethyl chloroformate, DCM, 0° C. to RT; c) HATU, DIPEA, DMF

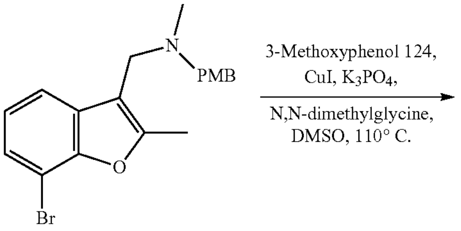

76

-continued

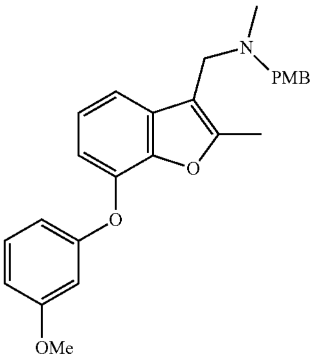

153

Step 1. N-(4-Methoxybenzyl)-1-(7-(3-methoxyphenoxy)-2-methylbenzofuran-3-yl)-N-methylmethanamine (compound 153). A mixture of 1-(7-bromo-2-methylbenzofuran-3-yl)-N-(4-methoxybenzyl)-N-methylmethanamine 76 (200 mg, 0.53 mmol), 3-methoxyphenol 124 (Sigma-Aldrich) (80 mg, 0.64 mmol), 2-(dimethylamino)acetic acid (11 mg, 0.11 mmol), copper(I) iodide (10 mg, 0.05 mmol) and potassium phosphate tribasic (230 mg, 1.1 mmol) was evacuated and backfilled with nitrogen (3×). DMSO (2 mL) was added and the mixture was heated to 110° C. overnight. Further aliquots of copper(I) iodide (10 mg, 0.05 mmol) and 3-methoxyphenol 124 (80 mg, 0.64 mmol) were added and heating continued for a further 3 hours. The reaction mixture was allowed to cool to RT, was filtered through Celite® and the filtrate was diluted with brine (20 mL). The crude mixture was extracted with ethyl acetate (2×10 mL) and the combined organic phases were dried over $Na_2SO_4$ and concentrated in vacuo. The crude product was purified by chromatography (0-100% EtOAc/iso-hexane) to afford the title compound 153 as a light orange oil (103 mg, 43%). $R^t$ 1.76 min (Method 1a) m/z 418 $[M+H]^+$ $(ES^+)$.

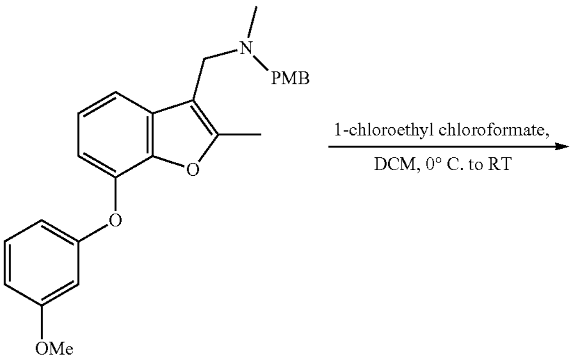

153

-continued

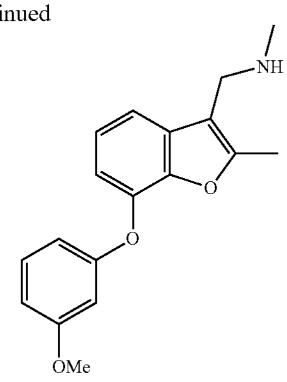

154

Step 2. 1-(7-(3-Methoxyphenoxy)-2-methylbenzofuran-3-yl)-N-methylmethanamine (compound 154). To an ice cooled solution of N-(4-methoxybenzyl)-1-(7-(3-methoxyphenoxy)-2-methylbenzofuran-3-yl)-N-methylmethanamine 153 (100 mg, 0.24 mmol) in DCM (2 mL) was added 1-chloroethyl chloroformate (0.031 mL, 0.29 mmol). The mixture was allowed to attain RT and stirred for a further 20 mins, then was evaporated to dryness. The residue was taken up into methanol (5 mL) and heated under reflux for 1 hour. The mixture was evaporated to dryness and the residue was dissolved in methanol (4 mL) and applied to an SCX column (2 g). The column was washed with methanol (20 mL) and the product eluted with a solution of 10% methanolic ammonia (10 mL) to give the title compound 154 as a colourless gum (42 mg, 47%), which was used in the next step without further purification. R$^t$ 1.40 min (Method 1b) m/z 267 $[M-NHCH_3]^+$ ($ES^+$).

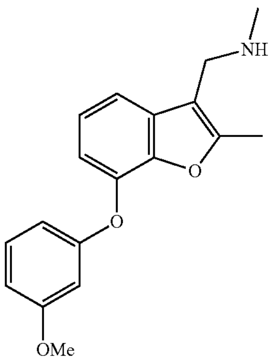

154

+

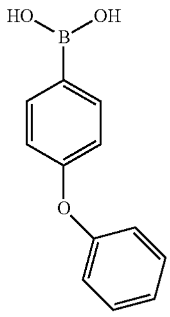

+

156

-continued

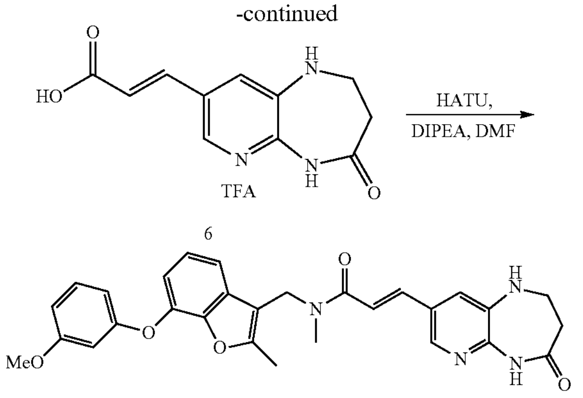

6

155

Step 3. (E)-N-((7-(3-Methoxyphenoxy)-2-methylbenzofuran-3-yl)methyl)-N-methyl-3-(4-oxo-2,3,4,5-tetrahydro-1H-pyrido[2,3-b][1,4]diazepin-8-yl)acrylamide (compound 155). To a solution of 1-(7-(3-methoxyphenoxy)-2-methylbenzofuran-3-yl)-N-methylmethanamine 154 (40 mg, 0.11 mmol), (E)-3-(4-oxo-2,3,4,5-tetrahydro-1H-pyrido[2,3-b][1,4]diazepin-8-yl)acrylic acid trifluoroacetate 6 (31 mg, 0.09 mmol) and DIPEA (78 μL, 0.45 mmol) in DMF (2 mL) was added HATU (41 mg, 0.11 mmol) and the mixture was stirred at RT for 1 hour. The reaction mixture was quenched by the addition of water (10 mL) and the solid was collected and dried. The crude product was purified by chromatography (0-10% MeOH/DCM) to afford the title compound 155 as a pale yellow solid (25 mg, 54%). R$^t$ 2.17 min (Method 1a) m/z 513 $[M+H]^+$ ($ES^+$). $^1H$ NMR (500 MHz, DMSO-$d_6$, 363 K): δ, ppm 9.13 (s, 1H), 7.99 (d, J=2.0 Hz, 1H), 7.47 (d, J=15.5 Hz, 1H), 7.41-7.34 (m, 2H), 7.26 (t, J=8.2 Hz, 1H), 7.17 (t, J=7.9 Hz, 1H), 7.10 (d, J=15.6 Hz, 1H), 6.88 (dd, J=7.9 Hz, 1.0 Hz, 1H), 6.72 (ddd, J=8.3 Hz, 2.4 Hz, 0.8 Hz, 1H), 6.61 (t, J=2.4 Hz, 1H), 6.57 (ddd, J=8.1 Hz, 2.3 Hz, 0.8 Hz, 1H), 5.80 (s, 1H), 4.78 (s, 2H), 3.76 (s, 3H), 3.47-3.42 (m, 2H), 3.03 (s, 3H), 2.70-2.63 (m, 2H), 2.48 (s, 3H).

Example 29. Synthesis of (R)-3-hydroxy-3-methyl-8-((E)-3-oxo-3-((3aS,6aR)-5-(4-phenoxyphenyl)-3,3a,4,6a-tetrahydrocyclopenta[c]pyrrol-2(1H)-yl)prop-1-en-1-yl)-1,2,3,5-tetrahydro-4H-pyrido[2,3-b][1,4]diazepin-4-one (Compound 159)

-continued
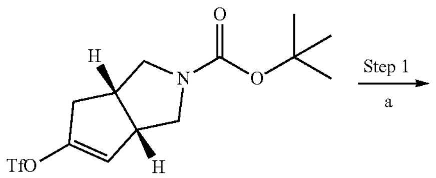
57
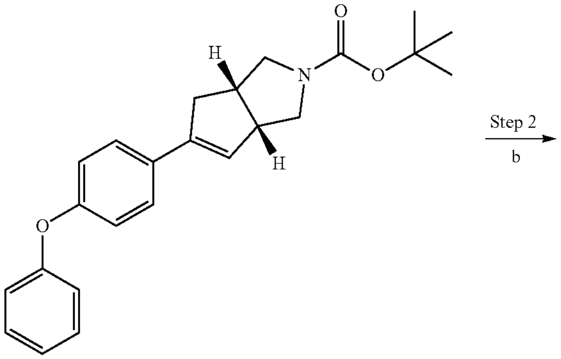
157
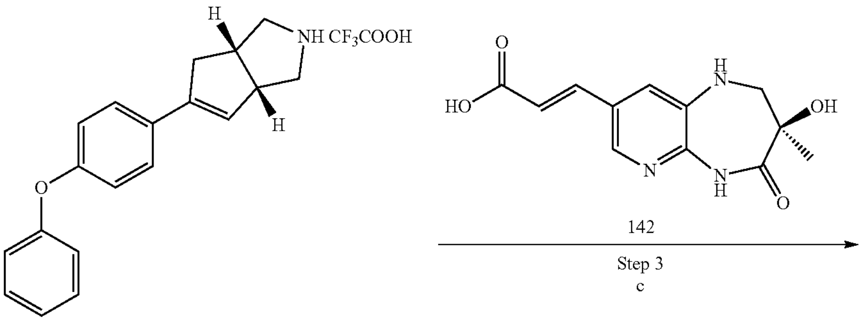
158
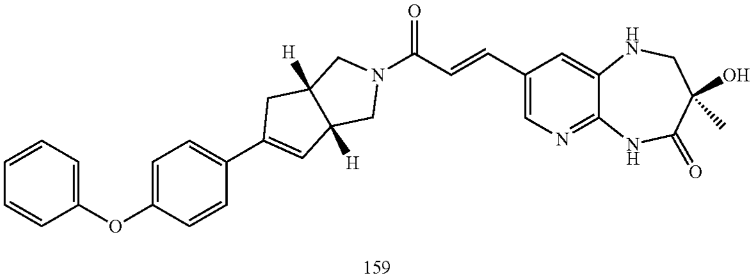
159
Reaction conditions: a) aq. 2M $K_2CO_3$, DME, $Pd(PPh_3)_4$; b) TFA/DCM, 0° C. to RT; c) HOBT, EDC, DIPEA, DMF

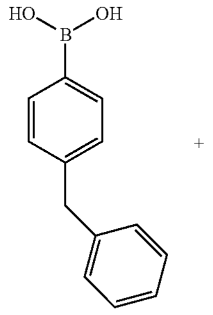

156

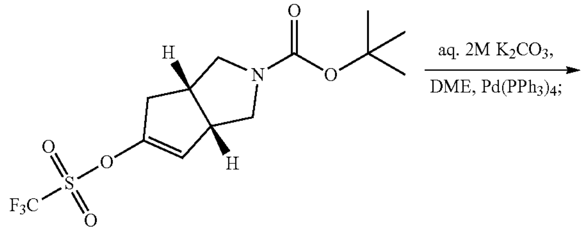

57

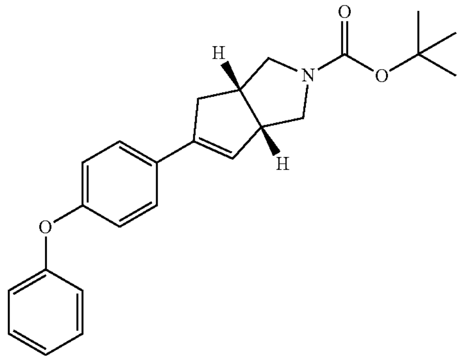

157

Step 1. tert-Butyl (3aS,6aR)-5-(4-phenoxyphenyl)-3,3a,4,6a-tetrahydrocyclopenta[c]pyrrole-2(1H)-carboxylate (compound 157) was synthetized following the procedure described in US2017/0174683 A1. In a microwave vial was added, tert-butyl (3aR,6aR)-5-(((trifluoromethyl)sulfonyl)oxy)-3,3a,4,6a-tetrahydrocyclopenta[c]pyrrole-2(1H)-carboxylate 57 (104 mg, 0.276 mmol), (4-phenoxyphenyl) boronic acid 156 (96 mg, 0.448 mmol) and a solution of 2 M $K_2CO_3$ (276 μL, 0.552 mmol) in ethylene glycol dimethyl ether (1 mL) was purged with nitrogen for 10 mins in ultrasound bath. Then tetrakisphenyl-phosphinepalladium (30 mg, 0.025 mmol) was added. The resulting suspension was stirred at 100° C. for 30 min under microwave irradiation. The resulting solution was cooled down to RT. Water and EtOAc were added, the organic layer was separated, washed with water then brine and dried ($MgSO_4$) and evaporated till dryness to afford a brown oil which was purified on silica gel using SNAP ultra column (10 g) and n-Hept/AcOEt 95/5 to 50/50 as an eluent. Good fractions were collected and concentrated to dryness to afford tert-butyl (3aR,6aS)-5-(4-phenoxyphenyl)-3,3a,4,6a-tetrahydrocyclopenta[c]pyrrole-2(1H)-carboxylate 157 as a colourless oil which crystallised as a white solid upon standing (85 mg, Purity=99%, Yield=85%). $R^t$ 2.65 min; LCMS: m/z: 322.2 $[M+H]^+$.

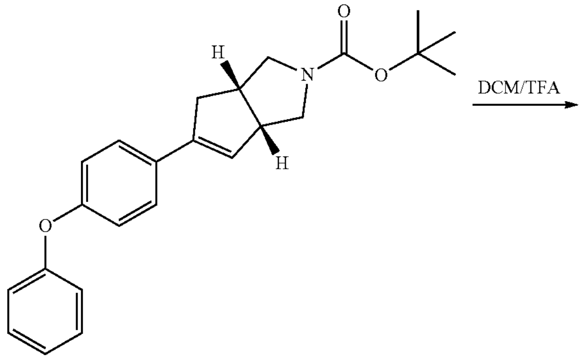

157

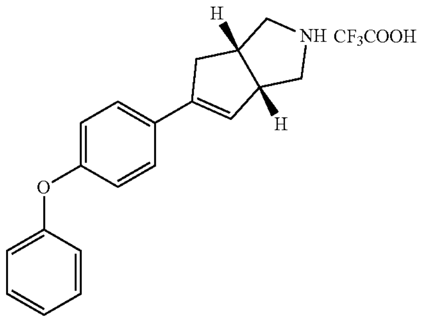

158

Step 2. (3aS,6aR)-5-(4-Phenoxyphenyl)-1,2,3,3a,4,6a-hexahydrocyclopenta[c]pyrrole 2,2,2-trifluoroacetate (compound 158). To a solution of tert-butyl (3aR,6aS)-5-(4-phenoxyphenyl)-3,3a,6,6a-tetrahydro-1H-cyclopenta[c]pyrrole-2-carboxylate 157 (85 mg, 0.23 mmol) in DCM (1.0 mL) was added dropwise 2,2,2-trifluoroacetic acid (25.67 mg, 0.23 mmol). The reaction was stirred at room temperature until complete conversion of the starting material was detected. After completion of reaction solvents were removed by vacuum to afford the title compound 158 (88 mg) as a yellow oil. $R^t$ 1.29 min (Method 1b); m/z 278.6 $[M+H]^+$ $(ES^+)$.

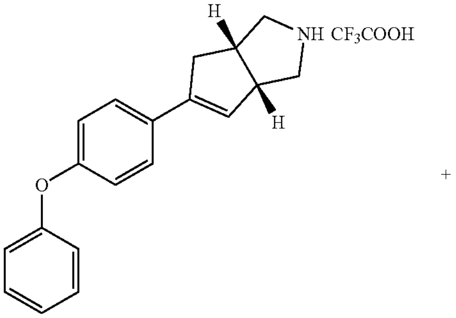

158

-continued

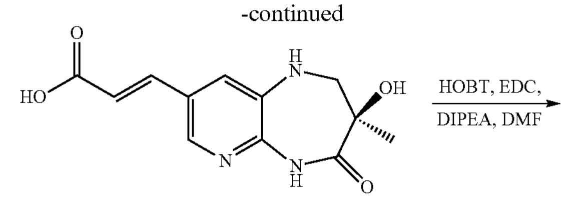

142

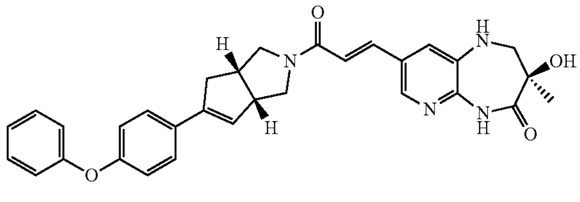

159

Step 3. (R)-3-Hydroxy-3-methyl-8-((E)-3-oxo-3-((3aS,6aR)-5-(4-phenoxyphenyl)-3,3a,4,6a-tetrahydrocyclopenta[c]pyrrol-2(1H)-yl)prop-1-en-1-yl)-1,2,3,5-tetrahydro-4H-pyrido[2,3-b][1,4]diazepin-4-one (compound 159). To a microwave vial covered with aluminium foil, (3aR,6aS)-5-(4-phenoxyphenyl)-1,2,3,3a,6,6a-hexahydrocyclopenta[c]pyrrole 2,2,2-trifluoroacetate 158 (44.6 mg, 0.11 mmol), HOBt-$H_2O$ (26.18 mg, 0.17 mmol, 1.5 eq.), EDC-HCl (32.77 mg, 0.17 mmol) and (E)-3-[(3R)-3-hydroxy-3-methyl-4-oxo-2,5-dihydro-1H-pyrido[2,3-b][1,4]diazepin-8-yl]prop-2-enoic acid 142 (30 mg, 0.11 mmol) were added and the solid was dissolved in DMF (0.2 mL). After 2 mins of stirring at RT, DIPEA (0.07 mL, 0.40 mmol) was added. The reaction mixture was stirred in the dark overnight at the same temperature. After completion of the reaction, water and acetonitrile were added to the mixture, the suspension was sonicated, the precipitate was filtered off and washed with MTBE. The crude material (18 mg) was further purified by autoprep. The title compound 159 (6.6 mg) as a yellow foam was isolated. $R^t$ 1.91 min (Method 1b); m/z 523.5 $[M+H]^+$ ($ES^+$). $^1H$ NMR (400 MHz, DMSO-$d_6$): δ, ppm $^1H$ NMR (400 MHz, DMSO-$d_6$): δ, ppm 9.95 (d, J=5.3 Hz, 1H), 7.92 (m, 1H), 9.50 (d, J=8.3 Hz, 2H), 7.42-7.28 (m, 4H), 7.14 (t, J=6.2 Hz, 1H), 7.03-6.95 (m, 4H), (dd, J=6.8 Hz, 15.5 Hz, 1H), 6.28-6.21 (m, 1H), 6.13 (br s, 1H), 5.30 (d, J=4.4 Hz, 1H), 4.05-3.75 (m, 2H), 3.73-3.49 (m, 2H), 3.22-3.10 (m, 2H), 3.10-2.91 (m, 2H), 2.69-2.55 (m, 2H), 1.23 (d, J=4.1 Hz, 3H). Note: Aliphatic signals partially obscured by water and solvent peaks.

Example 30. Synthesis of (E)-N-((7-((2,3-dihydrobenzofuran-6-yl)oxy)-2-methylbenzofuran-3-yl)methyl)-3-(2,2-dimethyl-3-oxo-1,2,3,4-tetrahydropyrido[2,3-b]pyrazin-7-yl)-N-methylacrylamide (Compound 164)

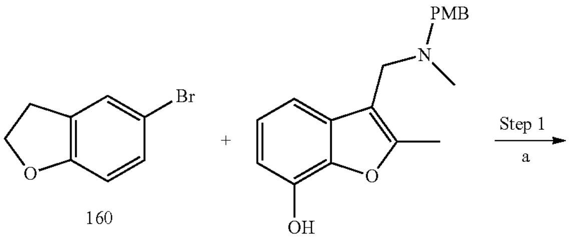

160

76

-continued

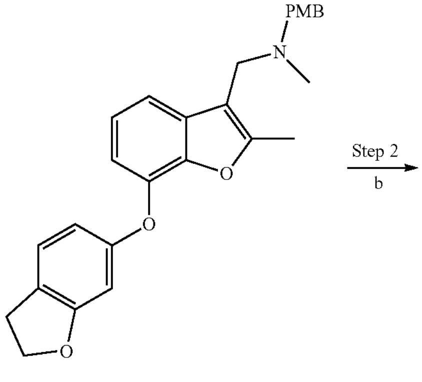

161

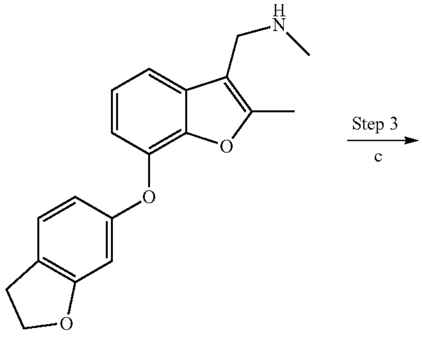

162

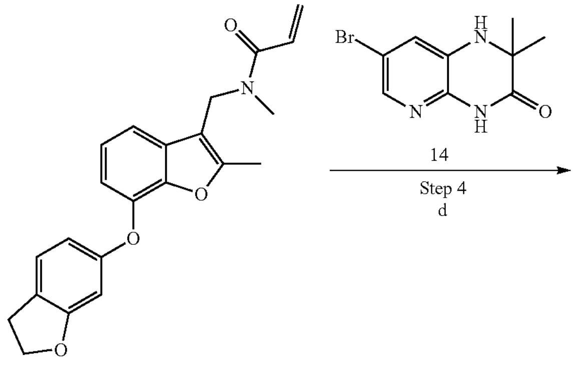

14

163

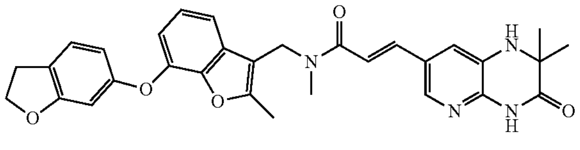

164

Reaction conditions: a) CuI, N,N-dimethyl glycine, $K_3PO_4$, 1,4-dioxane, 110° C.; b) Pd/C, MeOH, $H_2$, 45° C.; c) acryloyl chloride, TEA, DCM, 0° C. to RT; d) Pd-116, DIPEA $Bu_4NCl$, 1,4-dioxane, 80° C.

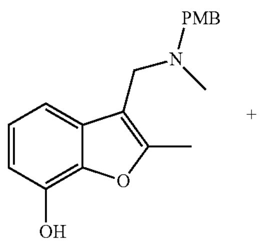

76

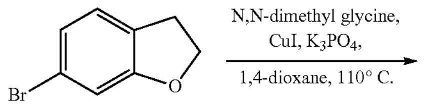

160

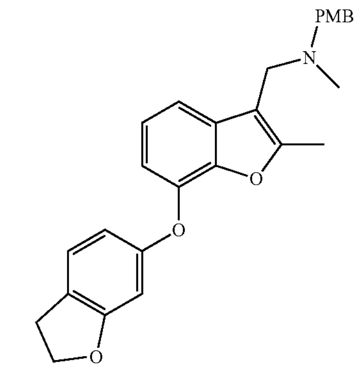

161

Step 1. 1-(7-((2,3-Dihydrobenzofuran-6-yl)oxy)-2-methylbenzofuran-3-yl)-N-(4-methoxybenzyl)-N-methylmethanamine (compound 161). A mixture of 3-(((4-methoxybenzyl)(methyl)amino)methyl)-2-methylbenzofuran-7-ol 76 (200 mg, 0.64 mmol), 6-bromo-2,3-dihydrobenzofuran 160 (153 mg, 0.77 mmol), N,N-dimethyl glycine (66 mg, 0.64 mmol), CuI (122 mg, 0.64 mmol) and $K_3PO_4$ (273 mg, 1.3 mmol) was evacuated and backfilled with nitrogen three times. DMSO (3 mL) was added and the mixture was heated to 110° C. and stirred for 16 h. The reaction mixture was cooled to RT. Ethyl acetate (10 mL) was added and the mixture was filtered through Celite®. The resulting solution was washed with water (10 mL) and brine (10 mL), dried over $MgSO_4$, filtered and concentrated in vacuo. The crude product was purified by column chromatography (0-10% MeOH/DCM) to give the title compound 161 as a colourless oil (80 mg, 27%). $R^t$ 1.77 min (Method 1a) m/z 430 $[M+H]^+$ $(ES^+)$.

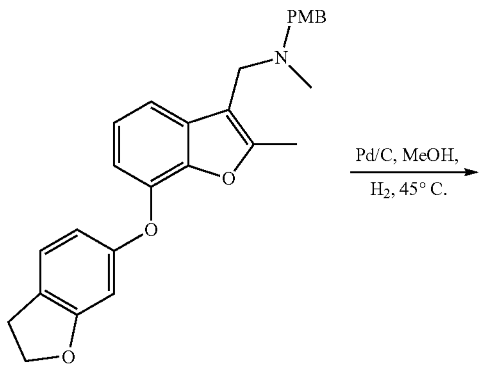

161

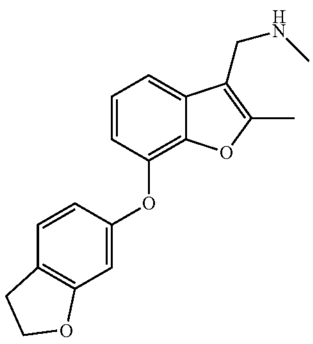

162

Step 2. 1-(7-((2,3-Dihydrobenzofuran-6-yl)oxy)-2-methylbenzofuran-3-yl)-N-methylmethanamine (compound 162). A solution of 1-(7-((2,3-dihydrobenzofuran-6-yl)oxy)-2-methylbenzofuran-3-yl)-N-(4-methoxybenzyl)-N-methylmethanamine 161 (80 mg, 0.19 mmol) in methanol (5 mL) was passed through a H-cube with a 10% Pd/C catalytic cartridge and using 'Full $H_2$' mode at 45° C. The solvent was concentrated in vacuo to give the title compound 162 as a colourless oil (43 mg, 70%). $R^t$ 1.45 min (Method 1a) m/z 279 $[M-MeNH]^+$ $(ES^+)$.

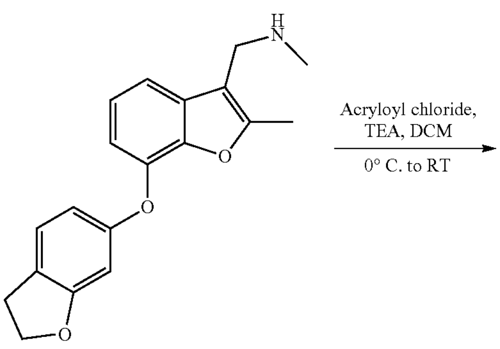

162

-continued

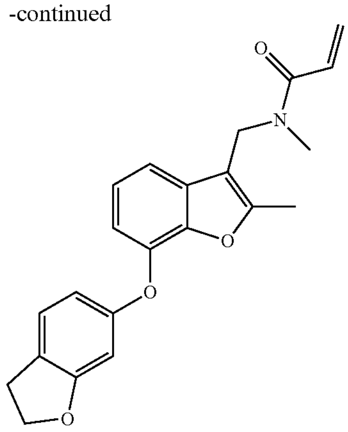

163

Step 3. N-((7-((2,3-Dihydrobenzofuran-6-yl)oxy)-2-methylbenzofuran-3-yl)methyl)-N-methylacrylamide (compound 163). To an ice cooled solution of 1-(7-((2,3-dihydrobenzofuran-6-yl)oxy)-2-methylbenzofuran-3-yl)-N-methylmethanamine 160 (160 mg, 0.52 mmol) and TEA (300 μL, 2.07 mmol) in DCM (10 mL) was added dropwise a solution of acryloyl chloride (42 μL, 0.52 mmol) in DCM (1.0 mL). The reaction mixture was allowed to warm to RT and stirred for 1 h. The reaction was quenched with water (5.0 mL) and the two phases separated. The organic phase was dried with $MgSO_4$, filtered and concentrated in vacuo. The crude product was purified by chromatography (0-100% EtOAc/iso-hexane) to give the title compound 163 as a colourless oil (120 mg, 60%). $R^t$ 2.36 min (Method 1a); m/z 364 $[M+H]^+$ ($ES^+$).

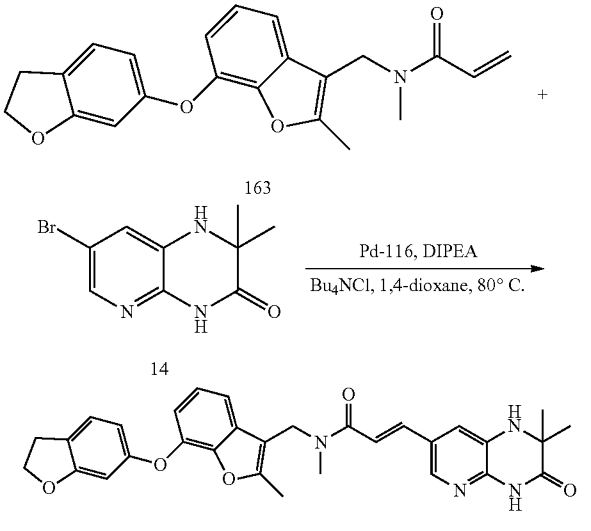

163

14

164

Step 4. (E)-N-((7-((2,3-Dihydrobenzofuran-6-yl)oxy)-2-methylbenzofuran-3-yl)methyl)-3-(2,2-dimethyl-3-oxo-1,2,3,4-tetrahydropyrido[2,3-b]pyrazin-7-yl)-N-methylacrylamide (compound 164). A reaction vial was charged with N-((7-((2,3-dihydrobenzofuran-6-yl)oxy)-2-methylbenzofuran-3-yl)methyl)-N-methylacrylamide 163 (60 mg, 0.16 mmol), 7-bromo-2,2-dimethyl-1,2-dihydropyrido[2,3-b]pyrazin-3(4H)-one 14 (42 mg, 0.16 mmol), tetrabutylammonium chloride hydrate (5.0 mg, 0.02 mmol) and $Pd[P(tBu)_3]_2$ (Pd-116) (9.0 mg, 0.02 mmol) and the vial was evacuated and backfilled with $N_2$ three times. 1,4-Dioxane (4.0 mL) and DIPEA (58 μL, 0.33 mmol) were added and the reaction mixture was heated to 80° C. and stirred overnight. The reaction was allowed to cool to RT, the solvent was removed in vacuo. The crude material was then purified by column chromatography (0-3% MeOH/DCM) to give the desired product 164 as a pale yellow solid (66 mg, 74%). $R^t$ 2.72 min (Method 1b); m/z 539 $[M+H]^+$ ($ES^+$). $^1H$ NMR (500 MHz, DMSO-$d_6$, VT NMR): δ, ppm 10.42 (s, 1H), 7.89 (d, J=1.9 Hz, 1H), 7.48 (d, J=15.4 Hz, 1H), 7.34 (d, J=7.8 Hz, 1H), 7.25 (d, J=1.9 Hz, 1H), 7.18-7.13 (m, 2H), 7.04 (d, J=15.4 Hz, 1H), 6.83 (dd, J=7.9 Hz, 1.0 Hz, 1H), 6.47 (dd, J=8.1 Hz, 2.3 Hz, 1H), 6.42 (d, J=2.2 Hz, 1H), 6.04 (s, 1H), 4.78 (s, 2H), 4.57 (t, J=8.6 Hz, 2H), 3.15 (t, J=8.6 Hz, 2H), 3.03 (s, 3H), 2.49 (s, 3H), 1.31 (s, 6H).

Example 31. Synthesis of (R,E)-N-((7-amino-2-methylbenzofuran-3-yl)methyl)-3-(3-hydroxy-3-methyl-4-oxo-2,3,4,5-tetrahydro-1H-pyrido[2,3-b][1,4]diazepin-8-yl)-N-methylacrylamide (Compound 167)

General Synthetic Scheme.

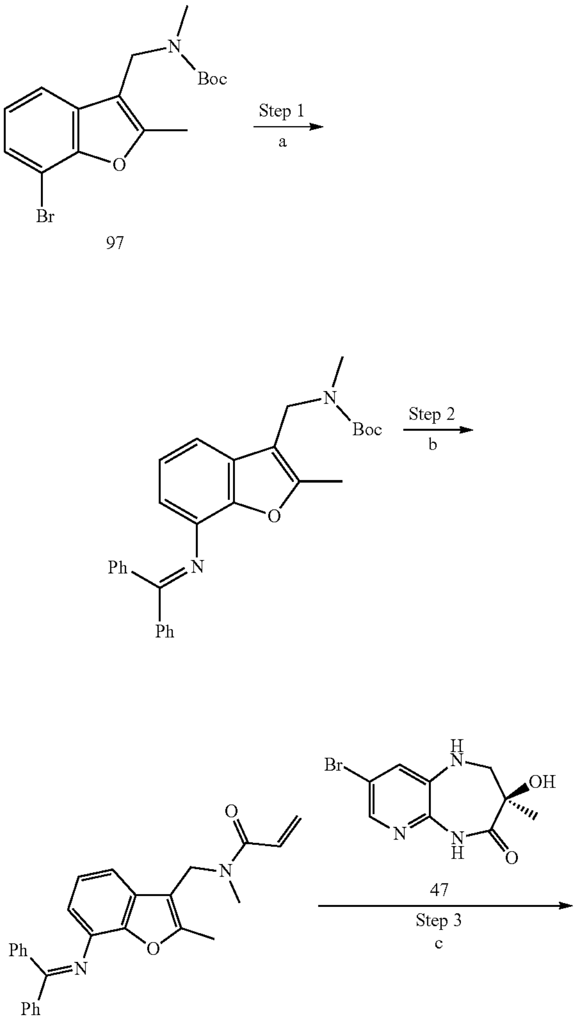

97

47

166

-continued

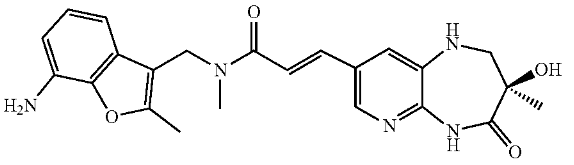

167

Reaction conditions: a) $Pd_2(dba)_3$, Xantphos, benzophenone imine 72, $Cs_2CO_3$, $PhCh_3$, 110° C.; b) i) TFA, DCM; ii) Acryloyl chloride, TEA, DCM, 0° C. to rt; b) i) Pd-116, NBu4Cl, DIPEA, 1,4-Dioxane, 80° C.; ii) 1M HCl, DCM.

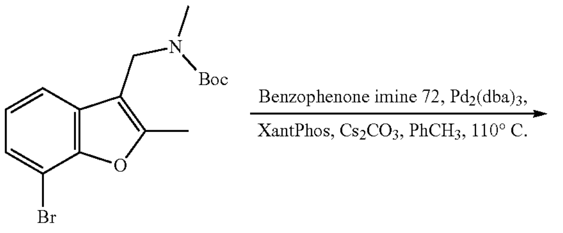

97

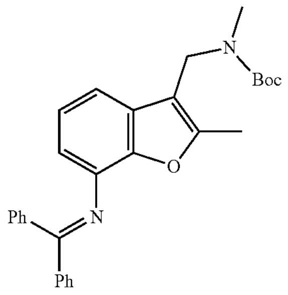

165

Step 1. tert-Butyl ((7-((diphenylmethylene)amino)-2-methylbenzofuran-3-yl)methyl)(methyl)carbamate (compound 165). tert-Butyl ((7-bromo-2-methylbenzofuran-3-yl)methyl)(methyl)carbamate 97 (2.0 g, 5.65 mmol), tris(dibenzylideneacetone)dipalladium (0.52 g, 0.57 mmol), $Cs_2CO_3$ (3.68 g, 11.3 mmol) and Xantphos (0.49 g, 0.85 mmol) were added to a flask and the flask was evacuated and back filled with $N_2$ three times. Toluene (40 mL) was added and $N_2$ was bubbled through the reaction mixture for 10 mins. Benzophenone imine 72 (1.1 mL, 6.78 mmol) was then added and the reaction mixture was heated to reflux for ~24 h. The reaction mixture was allowed to cool to RT, was stirred over the weekend and then was concentrated in vacuo. The crude material was purified by column chromatography (DCM) to give the desired product 165 as a yellow oil which crystallised on standing (1.67 g, 65%). $R^t$ 3.09 min (Method 1b); m/z 455 $[M+H]^+$ ($ES^+$). $^1H$ NMR (500 MHz, DMSO-$d_6$): δ, ppm 7.76-7.65 (m, 2H), 7.63-7.55 (m, 1H), 7.55-7.46 (m, 2H), 7.33-7.21 (m, 3H), 7.16-7.04 (m, 3H), 7.01-6.88 (m, 1H), 6.49 (d, J=7.6 Hz, 1H), 4.40 (s, 2H), 2.61 (s, 3H), 2.37 (s, 3H), 1.43 (s, 9H).

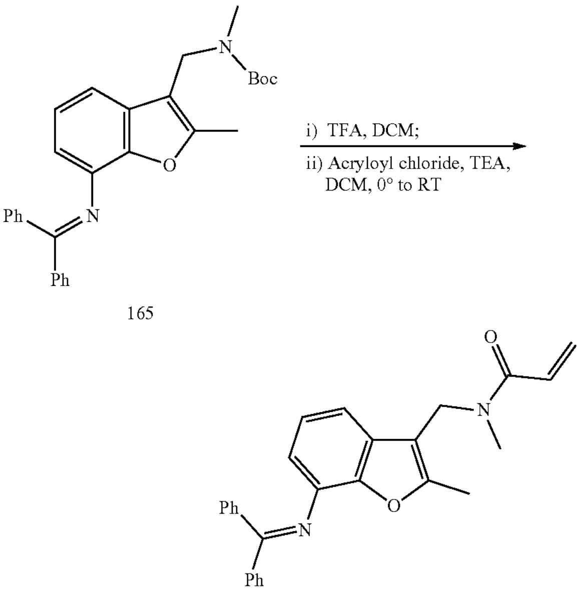

165

166

Step 2. N-((7-((Diphenylmethylene)amino)-2-methylbenzofuran-3-yl)methyl)-N-methylacrylamide (compound 166). TFA (15 mL, 195 mmol) was added dropwise to a stirred solution of tert-butyl ((7-((diphenylmethylene)amino)-2-methylbenzofuran-3-yl)methyl)(methyl)carbamate 165 (0.8 g, 1.76 mmol) in DCM (30 mL) and the reaction mixture was stirred at RT for 1 h. The reaction mixture was concentrated in vacuo and the resulting residue was taken up in DCM (30 mL), cooled to 0° C. and TEA (5.0 mL, 35.9 mmol) followed by acryloyl chloride (0.17 mL, 2.11 mmol) were added. The reaction was allowed to return to RT and was stirred for ~16 h. The reaction mixture was quenched with water (50 mL), then the organic phase was separated and the aqueous phase was extracted again with DCM (2×50 mL). The combined organic layers were dried by passing through a phase separation cartridge and concentrated in vacuo. The crude material was purified by column chromatography (0-3% MeOH/DCM) to give impure material which was purified again by column chromatography (0-30% EtOAc/iso-hexane) to give the desired product 166 as a yellow oil (0.16 g, 21% over 2 steps).

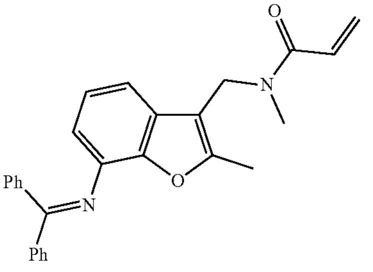

+

166

-continued

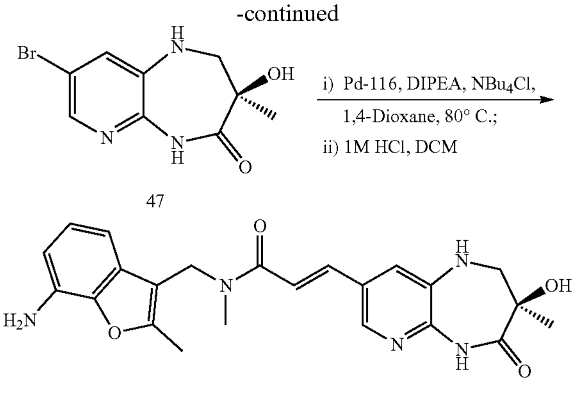

47

167

Step 3. (R,E)-N-((7-Amino-2-methylbenzofuran-3-yl) methyl)-3-(3-hydroxy-3-methyl-4-oxo-2,3,4,5-tetrahydro-1H-pyrido[2,3-b][1,4]diazepin-8-yl)-N-methylacrylamide (compound 167). A reaction vial was charged with N-((7-((diphenylmethylene)amino)-2-methylbenzofuran-3-yl) methyl)-N-methylacrylamide 166 (0.12 g, 0.29 mmol), (R)-8-bromo-3-hydroxy-3-methyl-2,3-dihydro-1H-pyrido[2,3-b][1,4]diazepin-4(5H)-one 47 (80 mg, 0.29 mmol), $NBu_4Cl$ (9 mg, 0.03 mmol) and Pd-116 (15 mg, 0.03 mmol) and the vial was evacuated and backfilled with $N_2$ three times. 1,4-Dioxane (5 mL) and DIPEA (0.10 mL, 0.59 mmol) were added and the reaction mixture was heated to 80° C. and stirred for 3 h. The reaction mass was allowed to cool to RT, then was diluted with HCl (10 mL, 1M Aq) and the aqueous mixture was extracted with DCM (3×20 mL). The combined organic extracts were washed with aq. 1 M HCl (2×20 mL), then the combined aqueous layers were neutralised with sat. aq. $NaHCO_3$. The resulting precipitate was collected by filtration and purified by column chromatography (0-5% MeOH/DCM) to give the desired product 167 as a pale yellow solid (42 mg, 33% over 2 steps). $R^t$ 1.32 min (Method 1a); m/z 436 $[M+H]^+$ ($ES^+$). $^1H$ NMR (500 MHz, DMSO-$d_6$, 363 K): δ, ppm 9.36 (s, 1H), 7.94 (d, J=1.8 Hz, 1H), 7.44 (d, J=15.4 Hz, 1H), 7.36 (d, J=2.0 Hz, 1H), 7.08 (d, J=15.3 Hz, 1H), 6.87 (t, J=7.7 Hz, 1H), 6.74 (d, J=7.7 Hz, 1H), 6.53 (d, J=7.6 Hz, 1H), 6.03 (t, J=4.6 Hz, 1H), 4.91 (s, 1H), 4.87 (s, 2H), 4.71 (s, 2H), 3.21 (dd, J=13.4, 3.7 Hz, 1H), 3.16 (dd, J=13.4, 5.6 Hz, 1H), 2.98 (s, 3H), 2.47 (s, 3H), 1.28 (s, 3H).

Example 32. Synthesis of (E)-N-((7-amino-2-methylbenzofuran-3-yl)methyl)-N-methyl-3-(8-oxo-6,7,8,9-tetrahydro-5H-pyrido[2,3-b]azepin-3-yl)acrylamide (Compound 168)

General Synthetic Scheme.

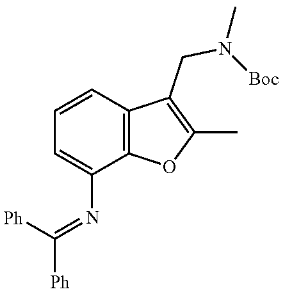

165

-continued

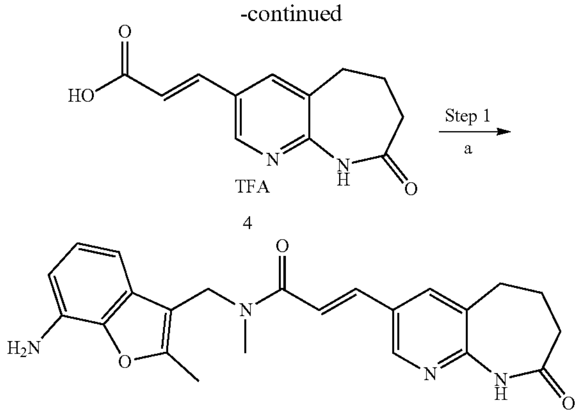

4

168

Reaction conditions: a) i) TFA, DCM; ii) HATU, DIPEA, DMF; iii) 1M HCl, DCM.

Step 1. (E)-N-((7-Amino-2-methylbenzofuran-3-yl) methyl)-N-methyl-3-(8-oxo-6,7,8,9-tetrahydro-5H-pyrido [2,3-b]azepin-3-yl)acrylamide (compound 168). TFA (2.5 mL, 32.4 mmol) was added dropwise to a stirred solution of tert-butyl ((7-((diphenylmethylene)amino)-2-methylbenzofuran-3-yl)methyl)(methyl)carbamate 165 (0.15 g, 0.21 mmol) in DCM (5.0 mL) and the reaction mixture was stirred at RT for 1 h. The reaction mixture was concentrated in vacuo and the resulting residue was taken up in DMF (2.0 mL) and (E)-3-(8-oxo-6,7,8,9-tetrahydro-5H-pyrido[2,3-b] azepin-3-yl)acrylic acid trifluoroacetate 4 (75 mg, 0.21 mmol) followed by DIPEA (1.0 mL, 5.73 mmol) were added. The reaction was stirred for 10 mins then HATU (0.12 g, 0.32 mmol) was added and the reaction was stirred for a further ~16 h at RT. The reaction mixture was diluted with aq. 1 M HCl (10 mL) and extracted with DCM (3×20 mL). The combined organic extracts were washed with HCl (2×20 mL, 1 M aq.) and the combined aqueous layers were neutralised with sat. aq. $NaHCO_3$. The resulting precipitate was collected by filtration and purified by column chromatography (0-5% MeOH/DCM) to give the desired product 168 as an off-white solid (40 mg, 43% over 3 steps). $R^t$ 1.41 min (Method 1a); m/z 405 $[M+H]^+$ ($ES^+$). $^1H$ NMR (500 MHz, DMSO-$d_6$, 363 K): δ, ppm 9.55 (s, 1H), 8.47 (d, J=2.2 Hz, 1H), 8.02 (d, J=2.2 Hz, 1H), 7.54 (d, J=15.4 Hz, 1H), 7.34-7.20 (m, 1H), 6.87 (t, J=7.6 Hz, 1H), 6.75 (d, J=7.7 Hz, 1H), 6.53 (dd, J=7.6 Hz, 1.1 Hz, 1H), 4.86 (s, 2H), 4.73 (s, 2H), 2.97 (s, 3H), 2.76 (t, J=7.2 Hz, 2H), 2.47 (s, 3H), 2.31 (t, J=7.2 Hz, 2H), 2.14 (p, J=7.2 Hz, 2H).

Example 33. Synthesis of (E)-N-methyl-N-((2-methylbenzofuran-3-yl)methyl)-3-(4-oxo-2,3,4,5-tetrahydro-1H-pyrido[2,3-b][1,4]diazepin-8-yl)acrylamide (Compound 169)

General Synthetic Scheme.

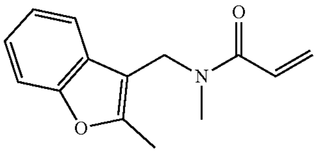
+

38

-continued

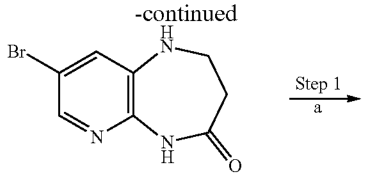

169

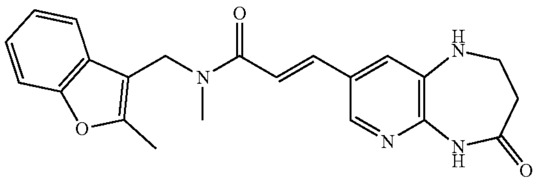

170

Reaction conditions: a) Pd-162, $NCy_2NMe$, $NBu_4Cl$, 1,4-dioxane, 80° C.

The 8-bromo-1,2,3,5-tetrahydro-4H-pyrido[2,3-b][1,4]diazepin-4-one (compound 169) was synthesized according to the literature procedures described by AFFINIUM PHARMECEUTICALS, INC: WO2007/67416, 2007, A2 and AURIGENE DISCOVERY TECHNOLOGIES LIMITED; WO2013/80222, 2013, A1.

Step 1. (E)-N-Methyl-N-((2-methylbenzofuran-3-yl)methyl)-3-(4-oxo-2,3,4,5-tetrahydro-1H-pyrido[2,3-b][1,4]diazepin-8-yl)acrylamide (compound 170). A reaction vial was charged with N-methyl-N-((2-methylbenzofuran-3-yl)methyl)acrylamide 38 (150 mg, 0.65 mmol), 8-bromo-2,3-dihydro-1H-pyrido[2,3-b][1,4]diazepin-4(5H)-one 169 (158 mg, 0.65 mmol), tetra butylammonium chloride hydrate (19.36 mg, 0.07 mmol), $[P(tBu)_3]Pd(crotyl)Cl$ (Pd-162) (26.1 mg, 0.07 mmol). The reaction vial was flushed with nitrogen for 5 mins. 1,4-Dioxane (10 mL) and N-cyclohexyl-N-methylcyclohexanamine (280 μL, 1.31 mmol) were added and the reaction mixture was purged with nitrogen for a further 5 mins. The mixture was heated to 80° C. for 1 h. The reaction mixture was allowed to cool to RT and the solid collected by filtration, washed with 1,4-dioxane (10 mL), followed by acetonitrile (10 mL) and the solid dried in vacuo to give the title compound 170 as a pale yellow solid (192 mg, 74%). $R^t$ 1.83 min (Method 1b) m/z 391 $[M+H]^+$ ($ES^+$). $^1H$ NMR (400 MHz, DMSO-$d_6$, 363 K): δ, ppm 9.17 (s, 1H), 7.98 (d, J=2.0 Hz, 1H), 7.54 (d, J=7.5 Hz, 1H), 7.50-7.43 (m, 2H), 7.38 (d, J=2.0 Hz, 1H), 7.26-7.16 (m, 2H), 7.10 (d, J=15.5 Hz, 1H), 5.81 (d, J=4.8 Hz, 1H), 4.77 (s, 2H), 3.47-3.41 (m, 2H), 2.69-2.62 (m, 2H). Note: Both $CH_3$ signals obscured by water and solvent peaks.

Example 34. Synthesis of 2-hydroxyethan-1-aminium (E)-(2,2-dimethyl-7-(3-(methyl((3-methylbenzofuran-2-yl)methyl)amino)-3-oxoprop-1-en-1-yl)-3-oxo-2,3-dihydropyrido[2,3-b]pyrazin-4(1H)-yl) methyl phosphate (Compound 172)

General Synthetic Scheme.

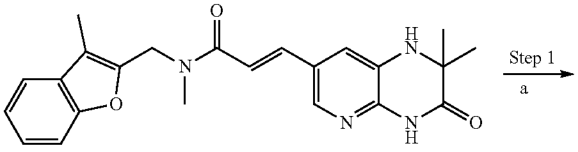

19

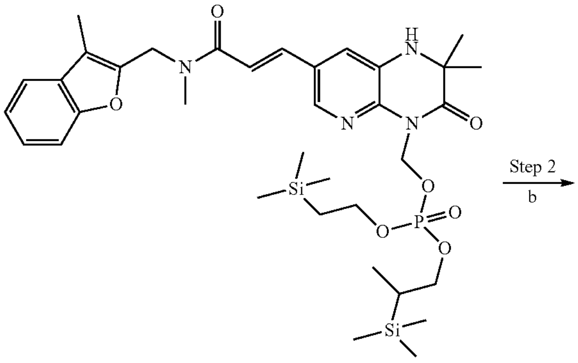

171

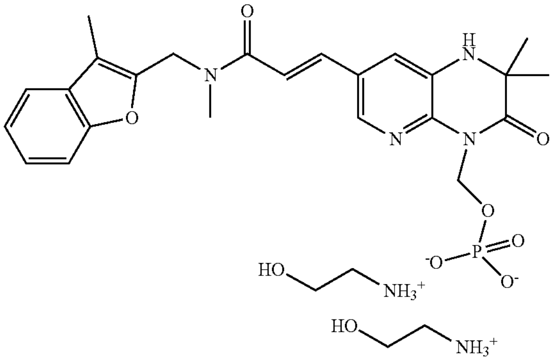

172

Reaction conditions: a) 1. 18-crown-6, NMP/N-ethylpyrrolidone, RT 2. t-BuOK at 10° C., then chloromethyl bis[2-(trimethylsilyl)ethyl] phosphate 21, 24 h, RT; b) TFA/DCM, long work-up

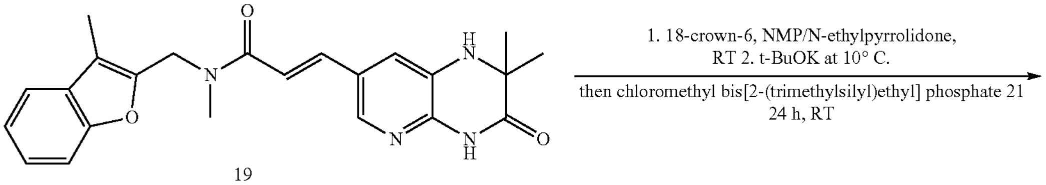

19

-continued

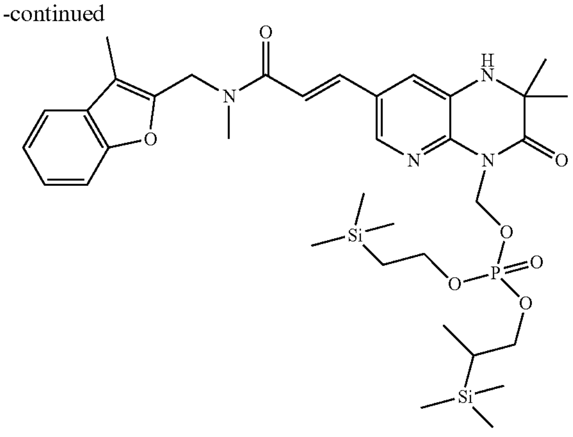

171

Step 1. (E)-(3,3-Dimethyl-6-(3-(methyl((3-methylbenzofuran-2-yl)methyl)amino)-3-oxoprop-1-en-1-yl)-2-oxo-3,4-dihydroquinoxalin-1(2H)-yl)methyl bis(2-(trimethylsilyl)ethyl) phosphate (compound 171). In a sealed 6 mL microwave vial under $N_2$, (E)-3-(2,2-dimethyl-3-oxo-1,4-dihydropyrido[2,3-b]pyrazin-7-yl)-N-methyl-N-[(3-methylbenzofuran-2-yl)methyl]prop-2-enamide 19 (500 mg, 1.23 mmol, 1.00 eq.) and 1,4,7,10,13,16-hexaoxacyclooctadecane (408.37 mg, 1.53 mmol, 1.24 eq.) were put in suspension in N-ethylpyrrolidone (3.0 mL) at RT. Then resulting yellow suspension was stirred at RT for 5 minutes, and submitted to degassing cycles (5 cycles; vacuum/nitrogen). Then reaction mixture was cooled down to 10° C. and potassium 2-methylpropan-2-olate (1.3 mL, 1.3 mmol, 1.05 eq, 1 M in THF) was added dropwise over 5 minutes. Resulting yellow solution was again submitted to degassing cycles (3 cycles; vacuum/nitrogen) and was then stirred at RT for 20 minutes. Then, chloromethyl bis(2-(trimethylsilyl)ethyl)phosphate 21 (1997.1 mg, 1.73 mmol, 1.4 eq., 30% w/w in Heptane) was added dropwise to the reaction mixture at RT over 5 minutes. Reaction mixture was then stirred at RT for 22 hrs (UPLC/MS: Starting material: Rt=1.64 min; 41% (AUC); ES+: 405.4. Product: Rt=2.68 min; 44% (AUC); ES+: 715.6). A mixture of saturated solution of ammonium acetate (7 mL; pH=9) and THF (5 mL) was added to the reaction mixture. After shaking, phase were separated and second washing was done with a mixture of brine (7 mL) and THF (5 mL). The third washing was done with brine (7 mL) and methyl cyclohexane (7 mL) was then added to the organic phase. Resulting suspension was filtered through a glass filter and solid was then washed with methyl cyclohexane (7 mL). Filtrate was concentrated to dryness at 25° C. under vacuum to give yellow oil which was purified by flash chromatography ($SiO_2$) eluting first with MTBE 99.8%-DIEA 0.2% then with MTBE 89.8%-Acetonitrile 10%-DIEA 0.2%. Fractions of interest were combined and concentrated to dryness at RT under vacuum to give the title compound 171 as an yellow oil (m=440.6 mg; UPLC purity: 98% (AUC); ES+: 715.6; 48.9% yield).

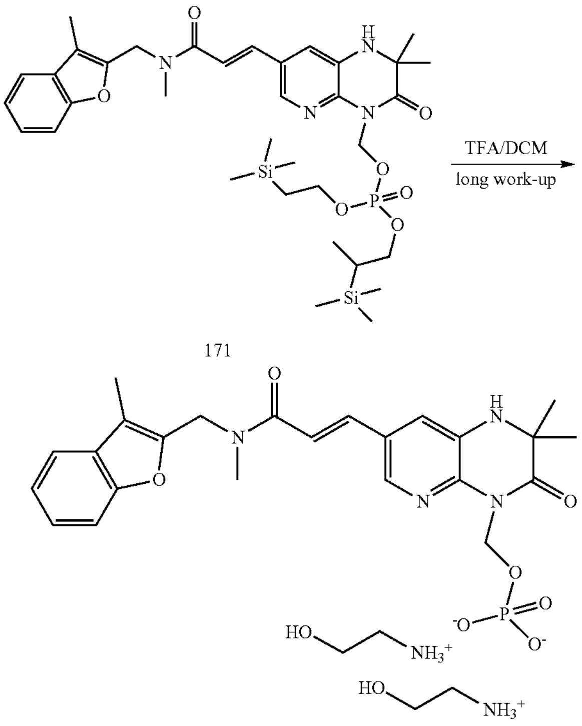

171

172

Step 2. 2-Hydroxyethan-1-aminium (E)-(3,3-dimethyl-6-(3-(methyl((3-methylbenzofuran-2-yl) methyl)amino)-3-oxoprop-1-en-1-yl)-2-oxo-3,4-dihydroquinoxalin-1(2H)-yl) methyl phosphate (compound 172). In the 50 mL flask containing [2,2-dimethyl-7-[(E)-3-[methyl-[(3-methylbenzofuran-2-yl)methyl]amino]-3-oxo-prop-1-enyl]-3-oxo-1H-pyrido[2,3-b]pyrazin-4-yl]methyl bis(2-trimethylsilylethyl) phosphate (440.6 mg, 0.60 mmol, 1 eq.) under $N_2$ was added anhydrous toluene (4 mL). The reaction mixture was stirred at 0° C. until complete solubilisation and a solution of TFA (0.93 mL, 12.08 mmol, 20 eq.) in anhydrous DCM (2 mL) at 0° C. was added dropwise over 1 minute under stirring. The reaction mixture was then stirred at 0° C. for 1 minute maximum and it was then immediately concentrated under deep vacuum in a rotavapor (bath temperature: 1° C.) until 2 mL was left. Then, anhydrous toluene (4 mL) was added and reaction mixture was concentrated until 2 mL was left. This co-evaporation was repeated 4 times. Then, a second co-evaporation cycle to dryness was done twice using each time anhydrous toluene (4 mL). Final residue was obtained as thick yellow oil. Completion of hydrolysis was confirmed by UPLC/MS (Product: $R^t$ 1.40 min; $ES^-$: 513.5. Starting material: $R^t$ 2.68 min; 0% (AUC)). Stored in dry ice during preparation for the next step. In a 50 mL flask under $N_2$ was prepared a solution of ethanolamine (186.31 mg, 3.02 mmol, 5 eq.) in acetone (10 mL) at 0° C. which was then added in one shot to a solution of previous intermediate in dichloromethane (5 mL) at 0° C. Immediate precipitation was observed and resulting milky clear yellow suspension was stirred at 0° C. for 10 minutes. After filtration through a glass filter, sticky solid was washed with acetone (1×5 mL; 2×10 mL) then with diethyl ether (2×10 mL). Suspension must be not filtered completely and each time a layer of solvent should be present before proceeding to the next washing, excepted for the last one. Then, the resulting nice cream solid was sucked dry for only 2-3 seconds and final drying was done under vacuum at RT to give the title compound 172 as yellow powder (m=253.7 mg; UPLC purity: 99% (AUC); $ES^-$: 513.5; 2 eq of ethanolamine by NMR; 1.3% w/w of TFA-ethanolamine salt; 65.3% yield). $^1$H NMR (400 MHz, $D_2O$): δ, ppm 7.72 (d, J=3.8 Hz, 1H), 7.27-6.92 (m, 7H), 6.65 (d, J=15.6 Hz, 1H), 5.58 (dd, J=3.3 Hz, 11.2 Hz, 2H), 4.55 (s, 1H, rotamer), 4.49 (s, 1H, rotamer), 3.74-3.70 (m, 4H), 3.06-3.02 (m, 4H), 2.90 (s, 2H, rotamer), 2.84 (s, 1H, rotamer), 1.98 (s, 2H, rotamer), 1.96 (s, 1H, rotamer), 1.26-1.20 (m, 6H).

Example 35. Synthesis of 2-hydroxyethan-1-aminium (E)-(8-(3-(((7-(3-methoxyphenoxy)-2-methylbenzofuran-3-yl)methyl)(methyl)amino)-3-oxoprop-1-en-1-yl)-4-oxo-1,2,3,4-tetrahydro-5H-pyrido[2,3-b][1,4]diazepin-5-yl)methyl phosphate (Compound 174)

General Synthetic Scheme.

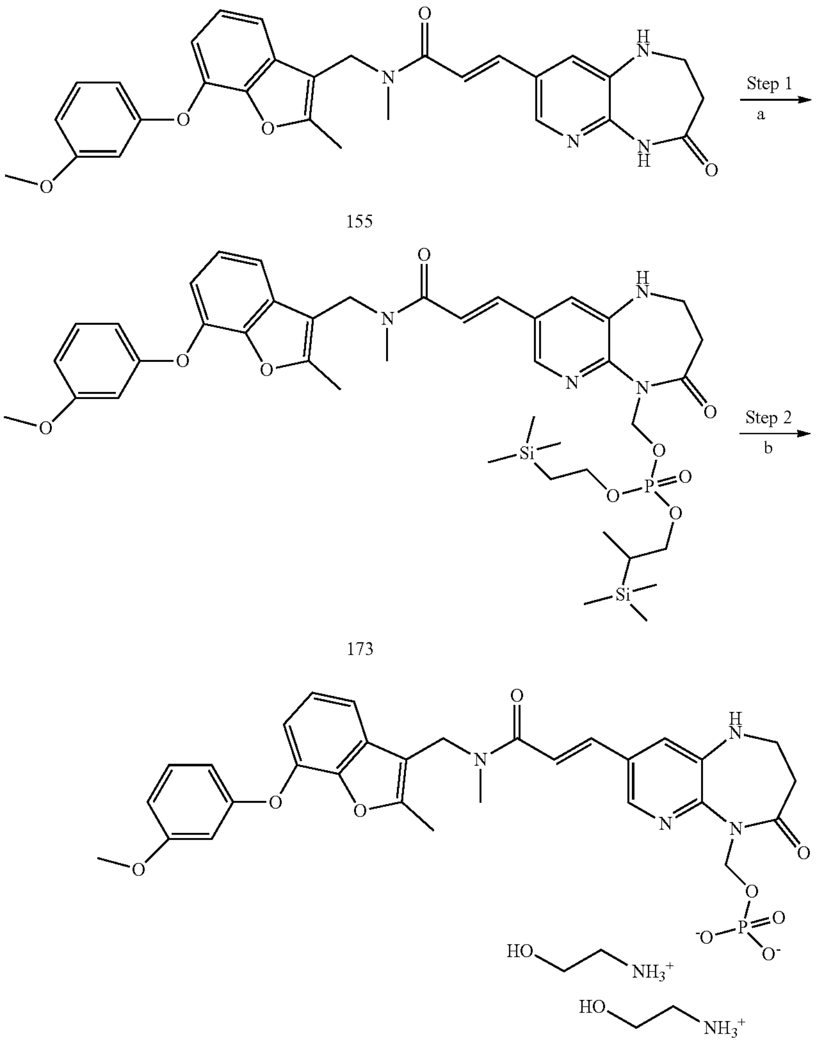

155

173

174

Reaction conditions: a) 1. 1M t-BuOK/THF, DMSO, RT, 2. chloromethyl bis[2-(trimethylsilyl)ethyl] phosphate 21; b) TFA/DCM, long work-up

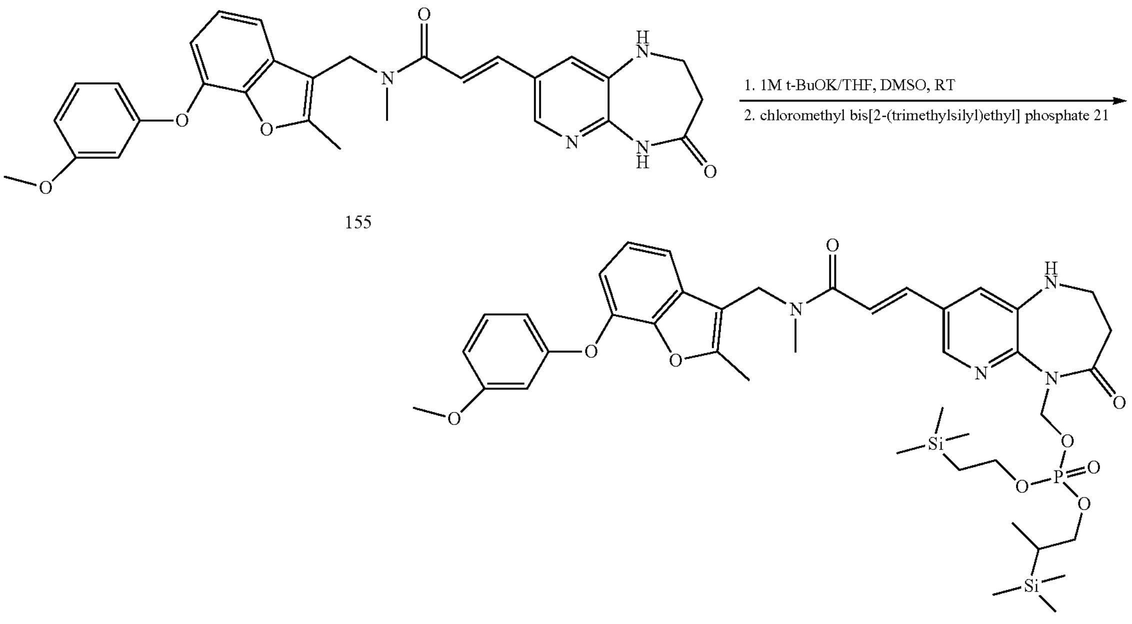

155

173

Step 1. (E)-(8-(3-(((7-(3-methoxyphenoxy)-2-methylbenzofuran-3-yl)methyl)(methyl)amino)-3-oxoprop-1-en-1-yl)-4-oxo-1,2,3,4-tetrahydro-5H-pyrido[2,3-b][1,4]diazepin-5-yl)methyl bis(2-(trimethylsilyl)ethyl) phosphate (compound 173). In a sealed 6 mL microwaves vial under nitrogen, containing (E)-N-((7-(3-methoxyphenoxy)-2-methylbenzofuran-3-yl)methyl)-N-methyl-3-(4-oxo-2,3,4,5-tetrahydro-1H-pyrido[2,3-b][1,4]diazepin-8-yl)acrylamide 155 (400 mg, 0.76 mmol, 1.00 eq.) in suspension in anhydrous DMSO (3.2 mL) at RT was added dropwise potassium 2-methylpropan-2-olate (0.83 mL, 0.83 mmol, 1.10 eq.; 1 M in THF) over 2 minutes. Then the resulting dark yellow solution was submitted to degassing cycles (5 cycles; vacuum/nitrogen) and was then stirred at RT for 20 minutes. Then reaction mixture was added dropwise over 13 minutes to a solution of chloromethyl bis(2-(trimethylsilyl)ethyl) phosphate 21 (1.47 mL, 1.06 mmol, 1.4 eq.; 30% in hexane) under vigorous stirring, then reaction mixture (orange biphasic solution) was stirred vigorously for 45 minutes to show good conversion by UPLC/MS (starting material: R$^{t}$ 1.82 min; 14% (AUC at 254 nm); ES+: 513.6). Product: R$^{t}$ 2.66 min; 65% (AUC at 254 nm); ES+: 823.8). The reaction mixture was quenched with a sat. solution of $AcONH_4$ (6 mL) and extracted four times with MTBE (4×6 mL). Combined organic phases were washed with brine and dried over $Na_2SO_4$ to give after concentration under vacuum at 20° C. a thick orange oil (m=643 mg; UPLC/MS: 72% (AUC at 254 nm)).

Purification was done by flash chromatography ($SiO_2$; eluting first with MTBE 99.5%-DIEA 0.5% then MTBE 93%-Acetonitrile 6.5%-DIEA 0.5% and finally MTBE 85%-Acetonitrile 14.5%-DIEA 0.5%). Fractions of interest were combined and concentrated to dryness at RT under vacuum to give the title compound as yellow foam (m=219.5 mg; UPLC purity: 96% (AUC at 254 nm); 33.82% yield). Medium yield was explained by some degradation during flash chromatography (confirmed by TLC 2D experiments).

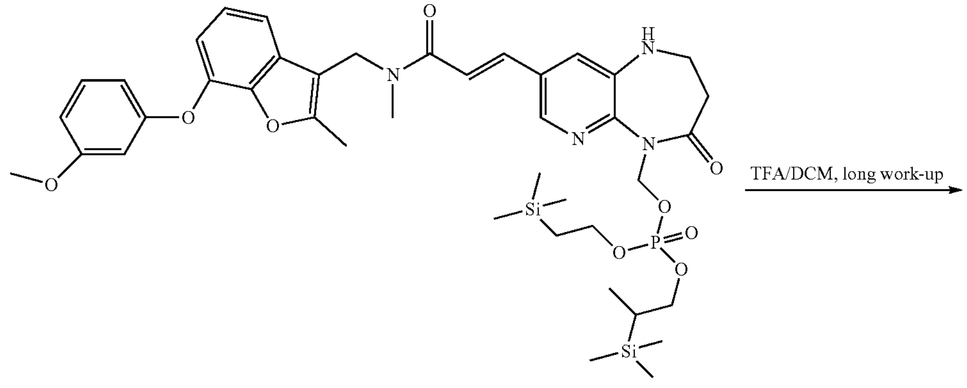

173

-continued

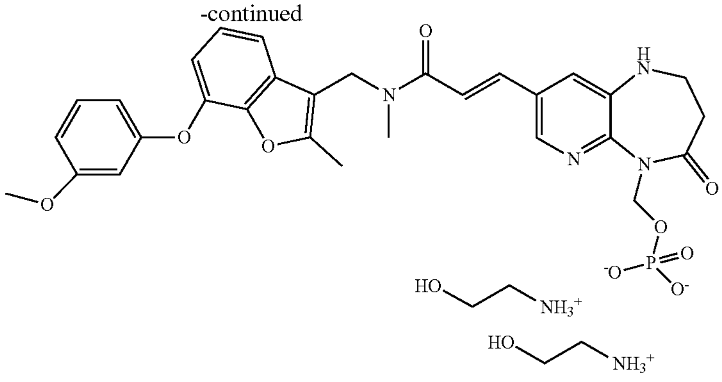

174

Step 2. 2-Hydroxyethan-1-aminium (E)-(8-(3-(((7-(3-methoxyphenoxy)-2-methylbenzofuran-3-yl)methyl)(methyl)amino)-3-oxoprop-1-en-1-yl)-4-oxo-1,2,3,4-tetrahydro-5H-pyrido[2,3-b][1,4]diazepin-5-yl)methyl phosphate (compound 174). In a 100 mL flask containing [8-[(E)-3-[[7-(3-methoxyphenoxy)-2-methyl-benzofuran-3-yl]methyl-methyl-amino]-3-oxo-prop-1-enyl]-4-oxo-2,3-dihydro-1H-pyrido[2,3-b][1,4]diazepin-5-yl]methyl bis(2-trimethylsilylethyl) phosphate 173 (219.5 mg, 0.26 mmol, 1.0 eq.) under $N_2$ was added anhydrous toluene (4 mL). The resulting mixture was then stirred at 0° C. until full dissolution and a solution of 2,2,2-trifluoroacetic acid (0.93 mL, 12.08 mmol, 20 eq.) in anhydrous DCM (2.0 mL) at 0° C. was added dropwise over 30 seconds. The reaction mixture was stirred at 0° C. for 3 minutes and reaction mass was then immediately concentrated under deep vacuum with a rotavapor (bath temperature: 1° C.) until 2 mL was left. Then anhydrous toluene (4 mL) was added and reaction mixture was concentrated until 2 mL was left. This co-evaporation was repeated four times to remove all residual TFA (yellow foam). UPLC/MS (expected product: $R^t$ 1.58 min; $ES^-$: 621.6; 92% (AUC at 254 nm). API: $R^t$ 1.81 min; 2% (AUC at 254 nm)). No starting material left.

In a 50 mL flask under $N_2$ was prepared a solution of ethanolamine (186.31 mg, 3.02 mmol, 5.0 eq.) in THF (10 mL) at 0° C. which was then added in one shot to a solution of previous intermediate in THF (5 mL) at 0° C. Precipitation was observed after few minutes under stirring at 0-5° C. and suspension was then filtered through a glass filter (solid was apparently hydroscopic and filtration was stopped before cake went dry). Thick suspension was washed with THF (2×10 mL; filtration was stopped each time just before completion). UPLC/MS of the filtrate showed the API as major product and only traces of the expected prodrug). Finally thick suspension was washed with diethyl ether (2×4 mL), and solid was sucked dry for few seconds only. Then resulting yellow solid was dried under vacuum at RT overnight to give the title compound (135.37 mg; 69.2% yield). UPLC/MS; method: 3 min acid_standard; 254 nm; purity 97.50% (max plot AUC), ES−: 621.58. $^1H$ NMR (400 MHz, $D_2O$, 333K): δ, ppm 78.62 (s, 1H), 7.92 (bs, 1H), 7.85 (d, J=15.7 Hz, 1H), 7.55 (m, 1H), 7.31 (m, 3H), 6.94 (m, 1H), 6.84 (m, 1H), 6.75 (s, 1H), 6.66 (d, J=7.6 Hz, 1H), 5.97 (s, 1H, rotamer), 5.96 (s, 1H, rotamer), 5.10 (s, 1H, rotamer), 5.01 (s, 1H, rotamer), 4.22 (t, J=5.3 Hz, 4H), 4.03 (m, 2H), 3.91 (s, 1H, rotamer), 3.89 (s, 2H, rotamer), 3.54 (t, J=5.2 Hz, 4H), 3.31 (s, 3H), 2.88 (m, 1H), 2.78 (m, 1H), 2.64 (s, 3H). TFA-ethanolamine salt content: 7.6% w/w.

Example 36. Synthesis of (R,E)-N-((7-(benzo[d][1,3]dioxol-5-yloxy)-2-methylbenzofuran-3-yl)methyl)-3-(3-hydroxy-3-methyl-4-oxo-2,3,4,5-tetrahydro-1H-pyrido[2,3-b][1,4]diazepin-8-yl)-N-methylacrylamide (Compound 176)

General Synthetic Scheme.

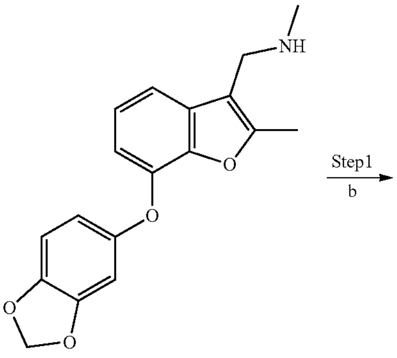

118

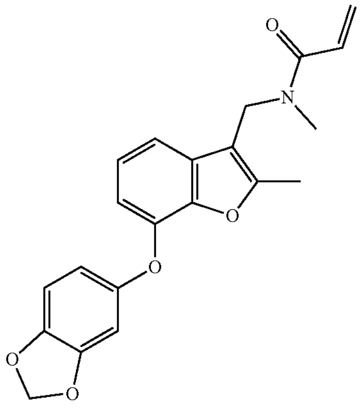

+

175

-continued

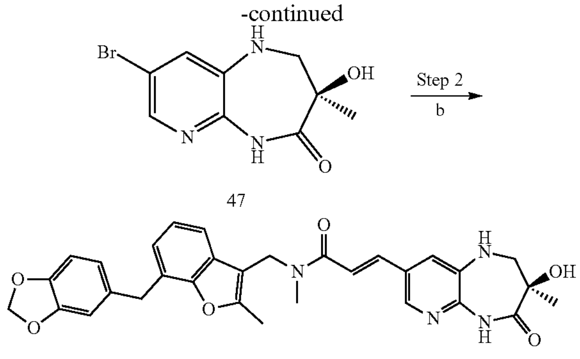

47

176

Reaction conditions: a) Acryloyl chloride, TEA, 0° C. to RT; b) Pd-162, $MeNCy_2$, $NBu_4Cl$, 1,4-dioxane, 80° C.

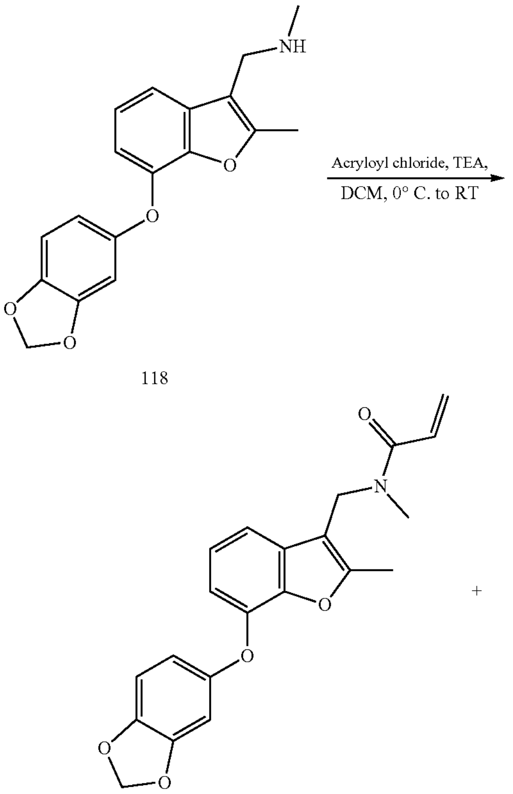

118

175

Step 1. N-((7-(Benzo[d][1,3]dioxol-5-yloxy)-2-methylbenzofuran-3-yl)methyl)-N-methylacrylamide (compound 175). To an ice cooled solution of 1-(7-(benzo[d][1,3]dioxol-5-yloxy)-2-methylbenzofuran-3-yl)-N-methylmethanamine 118 (196 mg, 0.63 mmol) and TEA (350 μL, 2.52 mmol) in DCM (10 mL) was added dropwise a solution of acryloyl chloride (51 μL, 0.63 mmol) in DCM (1.0 mL). Upon completion of addition the mixture was allowed to warm to RT. The mixture was washed with water (5.0 mL) and the organics separated through a phase separation cartridge and evaporated to dryness. The crude product was purified by column chromatography (0-50% EtOAc/iso-hexane) to afford the title compound 175 as a clear colourless oil (120 mg, 51%). $R^t$ 2.29 min (Method 1a) m/z 366 $[M+H]^+$ ($ES^+$). $^1H$ NMR (500 MHz, DMSO-$d_6$, 363 K): δ, ppm 7.27 (d, J=7.7 Hz, 1H), 7.13 (td, J=7.9, 0.9 Hz, 1H), 6.90-6.76 (m, 3H), 6.70 (dd, J=2.6 Hz, 0.9 Hz, 1H), 6.51 (ddd, J=8.4 Hz, 2.4 Hz, 0.9 Hz, 1H), 6.18 (ddd, J=16.7 Hz, 2.4 Hz, 0.9 Hz, 1H), 6.02 (d, J=0.9 Hz, 2H), 5.71 (dd, J=10.5 Hz, 2.4 Hz, 1H), 4.71 (s, 2H), 2.94 (s, 3H), 2.47 (s, 3H).

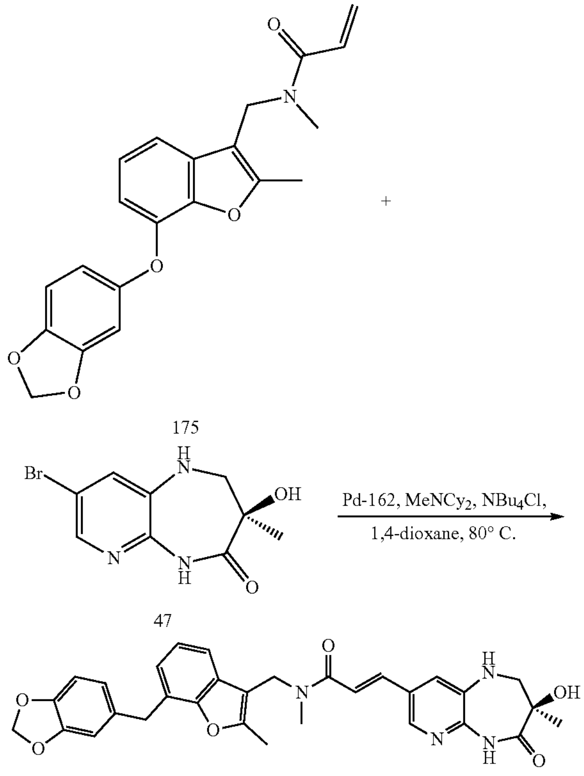

175

47

176

Step 2. (R,E)-N-((7-(Benzo[d][1,3]dioxol-5-yloxy)-2-methylbenzofuran-3-yl)methyl)-3-(3-hydroxy-3-methyl-4-oxo-2,3,4,5-tetrahydro-1H-pyrido[2,3-b][1,4]diazepin-8-yl)-N-methylacrylamide (compound 176). A reaction vial was charged with N-((7-(benzo[d][1,3]dioxol-5-yloxy)-2-methylbenzofuran-3-yl)methyl)-N-methylacrylamide 175 (50 mg, 0.14 mmol), (R)-8-bromo-3-hydroxy-3-methyl-2,3-dihydro-1H-pyrido[2,3-b][1,4]diazepin-4(5H)-one 47 (37 mg, 0.14 mmol), $NBu_4Cl$ (4.0 mg, 0.01 mmol) and [P$(tBu)_3$]Pd(crotyl)Cl (Pd-162) (6.0 mg, 0.01 mmol) and the vial was flushed with $N_2$ (5 mins). 1,4-Dioxane (2.0 mL) and N-cyclohexyl-N-methylcyclohexanamine (59 μL, 0.27 mmol) were added and the reaction mixture was purged again with $N_2$ (5 mins). The reaction mixture was heated to 80° C. for 1 h, then was allowed to cool to RT and evaporated to dryness. The residue was triturated with iso-hexane (10 mL) and the crude solid was purified by chromatography (0-5% MeOH/DCM) to afford the title compound 176 as a pale yellow solid (41 mg, 53%). Rt 2.15 min (Method 1a); m/z 557 $[M+H]^+$ ($ES^+$). $^1H$ NMR (500 MHz, DMSO-$d_6$, 363 K): δ, ppm 9.37 (s, 1H), 7.96 (d, J=1.9 Hz, 1H), 7.47 (d, J=15.4 Hz, 1H), 7.37 (d, J=2.0 Hz, 1H), 7.31 (d, J=7.8 Hz, 1H), 7.13 (t, J=7.9 Hz, 2H), 6.86 (d, J=8.4 Hz, 1H), 6.79 (dd, J=8.0 Hz, 0.9 Hz, 1H), 6.70 (d, J=2.4 Hz, 1H), 6.51 (dd, J=8.4 Hz, 2.5 Hz, 1H), 6.06-6.02 (m, 1H), 6.02 (s, 2H), 4.92 (d, J=1.1 Hz, 1H), 4.78 (s, 2H), 3.25-3.13 (m, 2H), 3.00 (d, J=1.1 Hz, 3H), 2.49 (s, 3H), 1.29 (s, 3H).

Example 37. Synthesis of (E)-N-((7-(indolin-5-yloxy)-2-methylbenzofuran-3-yl)methyl)-N-methyl-3-(8-oxo-6,7,8,9-tetrahydro-5H-pyrido[2,3-b]azepin-3-yl)acrylamide (Compound 180)
General Synthetic Scheme.
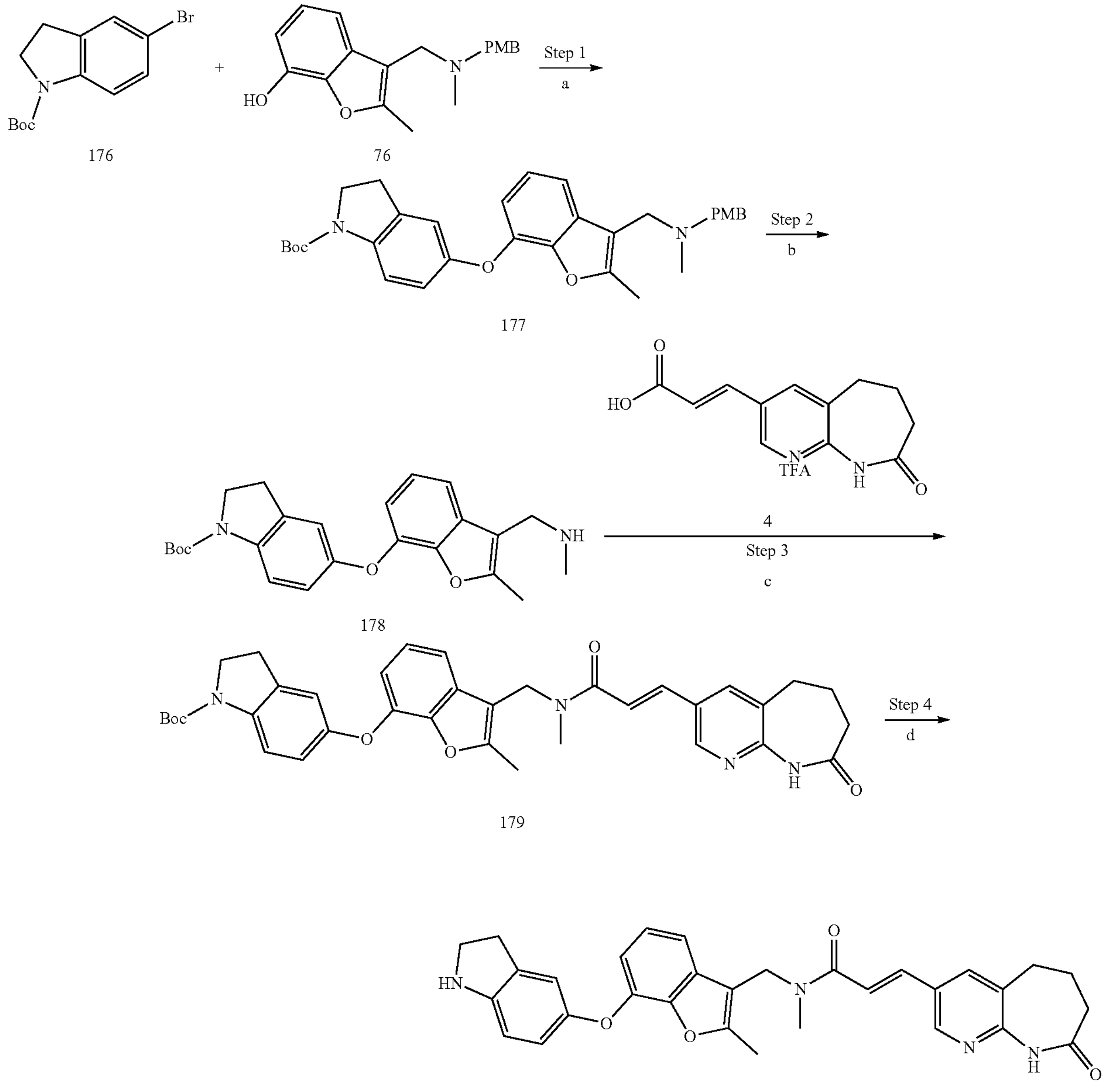
180
Reaction conditions: a) CuI, N,N-dimethylglycine, $Cs_2CO_3$, DMF, 110° C.; b) Pd/C, MeOH, $H_2$, 50° C.; c) HATU, DIPEA, DMF; d) TFA, DCM.
-continued
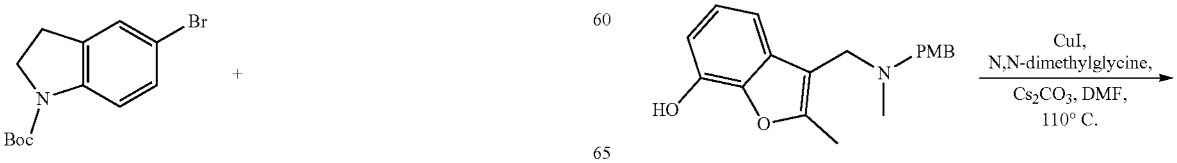
176 76

-continued

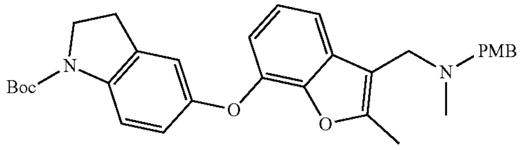

177

Step 1. tert-Butyl 5-((3-(((4-methoxybenzyl)(methyl) amino)methyl)-2-methylbenzofuran-7-yl)oxy)indoline-1-carboxylate (compound 177). A mixture of 3-(((4-methoxy-benzyl)(methyl)amino)methyl)-2-methylbenzofuran-7-ol 76 (150 mg, 0.48 mmol), copper(I) iodide (92 mg, 0.48 mmol), N,N-dimethylglycine (50 mg, 0.48 mmol), $Cs_2CO_3$ (628 mg, 1.9 mmol) and tert-butyl 5-bromoindoline-1-carboxylate 176 (144 mg, 0.48 mmol) was evacuated and backfilled with nitrogen (3×). DMF (3 mL) was added and the mixture was heated to 110° C. overnight. The mixture was diluted with water (5 mL) and EtOAc (5 mL). The phases were separated and the aqueous phase was extracted with EtOAc (2×10 mL). The combined organic phases were washed with brine (15 mL), dried over $MgSO_4$, filtered and concentrated under vacuum. The crude product was purified by chromatography (0-100% EtOAc/iso-hexane) to afford the title compound 177 as a dark yellow oil (129 mg, 49%). $R^t$ 3.21 min (Method 1b); m/z 529 $[M+H]^+$ ($ES^+$). $^1H$ NMR (500 MHz, $CDCl_3$): δ, ppm 7.47-7.24 (m, 4H), 7.09 (t, J=7.8 Hz, 1H), 6.97-6.87 (m, 4H), 6.71 (d, J=7.9 Hz, 1H), 4.02 (br s, 2H), 3.83 (s, 3H), 3.56 (s, 2H), 3.52 (s, 2H), 3.08 (t, J=8.6 Hz, 2H), 2.46 (s, 3H), 2.21 (s, 3H), 1.59 (s, 9H).

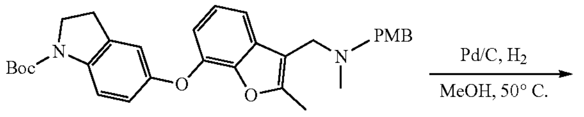

177

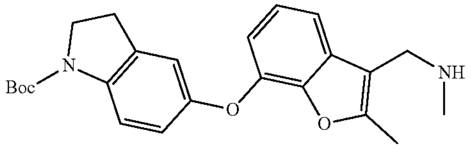

178

Step 2. tert-Butyl 5-((2-methyl-3-((methylamino)methyl) benzofuran-7-yl)oxy)indoline-1-carboxylate (compound 178). A solution of tert-butyl 5-((3-(((4-methoxybenzyl) (methyl)amino)methyl)-2-methylbenzofuran-7-yl)oxy)indoline-1-carboxylate 177 (129 mg, 0.24 mmol) in MeOH (5 mL) was hydrogenated in the H-Cube (10% Pd/C, 30×4 mm, Full hydrogen, 50° C., 1 mL/min). The solvent was removed in vacuo, then the residue was redissolved in MeOH and was loaded onto a SCX column (1 g). The column was washed with MeOH (50 mL) and then the product was eluted with 0.7 M methanolic ammonia and concentrated in vacuo. The crude product was purified by chromatography (0-10% (0.7 M $NH_3$/MeOH)/DCM) to afford the title compound 178 as a colourless oil (54 mg, 52%). $R^t$ 2.41 min (Method 1b); m/z 322 $(M-tBu-NHCH_3)^+$ ($ES^+$).

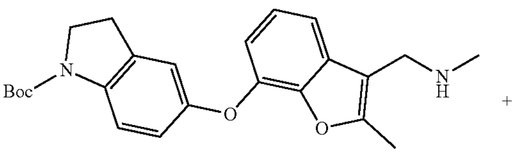

178

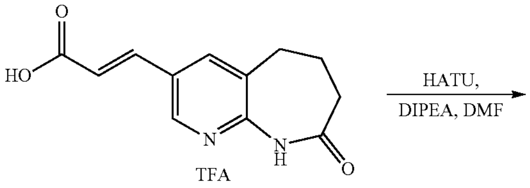

4

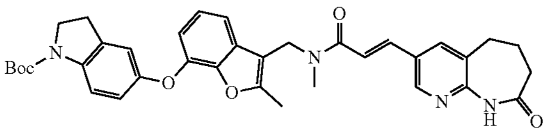

179

Step 3. (E)-tert-Butyl 5-((2-methyl-3-((N-methyl-3-(8-oxo-6,7,8,9-tetrahydro-5H-pyrido[2,3-b]azepin-3-yl)acrylamido)methyl)benzofuran-7-yl)oxy)indoline-1-carboxylate (compound 179). To a suspension of tert-butyl 5-((2-methyl-3-((methylamino)methyl)benzofuran-7-yl)oxy)indoline-1-carboxylate 178 (100 mg, 0.24 mmol), (E)-3-(8-oxo-6,7,8,9-tetrahydro-5H-pyrido[2,3-b]azepin-3-yl)acrylic acid trifluoroacetate 4 (109 mg, 0.24 mmol) and DIPEA (0.21 mL, 1.22 mmol) in DMF (2.0 mL) was added HATU (102 mg, 0.27 mmol) and the reaction mixture was stirred for 2 h. Water (3.0 mL) was then added and the solid was collected by filtration. The crude solid was purified by chromatography (0-10% MeOH/DCM) to give the title compound 179 as a yellow solid (100 mg, 62%). $R^t$ 2.63 min (Method 1a); m/z 623 $[M+H]^+$ ($ES^+$).

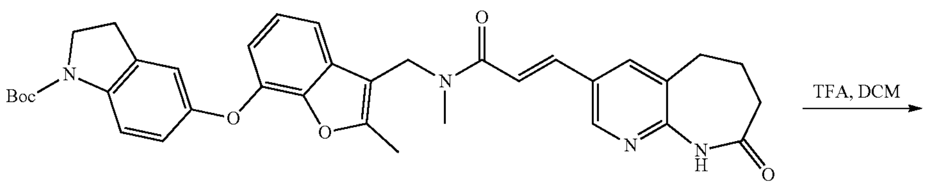

179

-continued

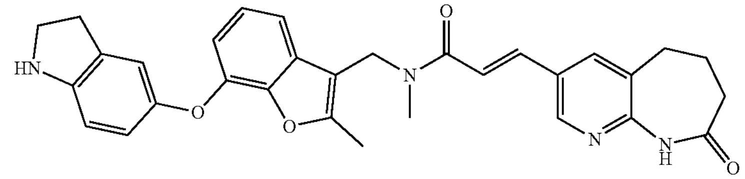

180

Step 4. (E)-N-((7-(Indolin-5-yloxy)-2-methylbenzofuran-3-yl)methyl)-N-methyl-3-(8-oxo-6,7,8,9-tetrahydro-5H-pyrido[2,3-b]azepin-3-yl)acrylamide (compound 180). TFA (2 mL, 25 mmol) was added dropwise to a stirred solution of (E)-tert-butyl 5-((2-methyl-3-((N-methyl-3-(8-oxo-6,7,8,9-tetrahydro-5H-pyrido[2,3-b]azepin-3-yl)acrylamido)methyl)benzofuran-7-yl)oxy)indoline-1-carboxylate 179 (100 mg, 0.16 mmol) in DCM (4.0 mL). The reaction was stirred for 30 min before being concentrated in vacuo. The resulting yellow oil was suspended in $NaHCO_3$ (10 mL) and stirred for 30 mins. The aqueous mixture was extracted with DCM (3×10 mL) and the combined organic layers were dried with $MgSO_4$, filtered and concentrated in vacuo to give the title compound 180 as a beige solid (50 mg, 56%). $R^t$ 1.36 min (Method 1a); m/z 523 $[M+H]^+$ $(ES^+)$. $^1H$ NMR (500 MHz, DMSO-$d_6$): δ, ppm 9.57 (s, 1H), 8.49 (d, J=2.2 Hz, 1H), 8.03 (d, J=2.2 Hz, 1H), 7.57 (d, J=15.4 Hz, 1H), 7.36-7.18 (m, 2H), 7.07 (t, J=7.9 Hz, 1H), 6.87-6.79 (m, 1H), 6.67 (dd, J=8.4 Hz, 2.5 Hz, 2H), 6.50 (d, J=8.3 Hz, 1H), 5.12 (s, 1H), 4.79 (s, 2H), 3.46 (t, J=8.5 Hz, 2H), 3.01 (s, 3H), 2.93 (t, J=8.5 Hz, 2H), 2.77 (t, J=7.2 Hz, 2H), 2.50 (s, 3H), 2.32 (t, J=7.2 Hz, 2H), 2.15 (p, J=7.2 Hz, 2H).

Example 38. Synthesis of (R,E)-N-((7-((2,3-dihydrobenzofuran-6-yl)oxy)-2-methylbenzofuran-3-yl)methyl)-3-(3-hydroxy-3-methyl-4-oxo-2,3,4,5-tetrahydro-1H-pyrido[2,3-b][1,4]diazepin-8-yl)-N-methylacrylamide (Compound 182)

General Synthetic Scheme.

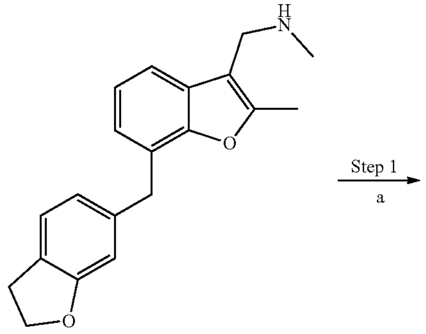

162

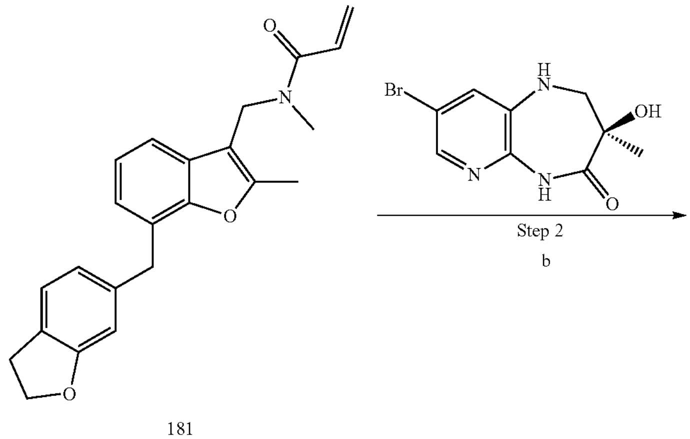

181

-continued

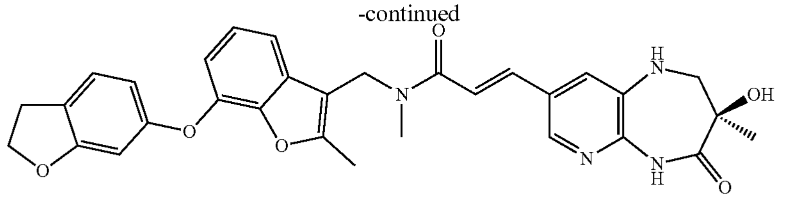

182

Reagents and conditions: a) Acryloyl chloride, TEA, DCM, 0° C. to RT, b) Pd-162, $MeNCy_2$, $NBu_4Cl$, 1,4-dioxane, 80° C.

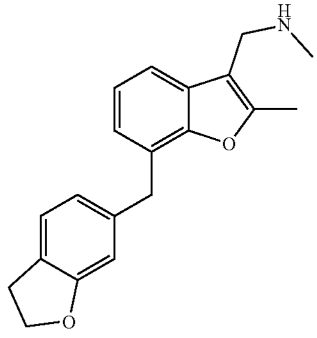

162

Acryloyl chloride,
TEA, DCM
0° C. to RT

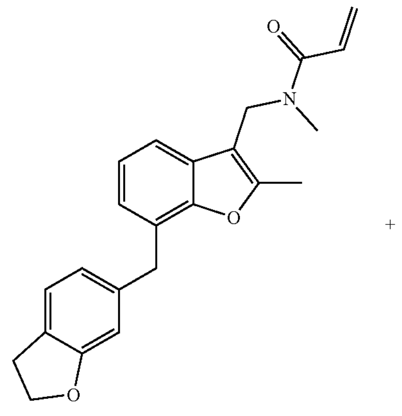

181

+

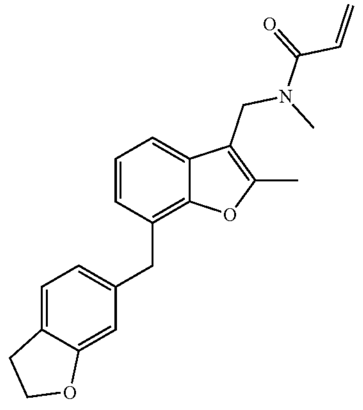

181

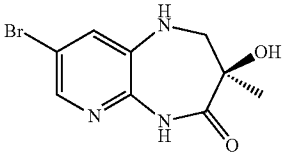

47

Pd-162, $MeNCy_2$,
$NBu_4Cl$,
1,4-dioxane, 80° C.

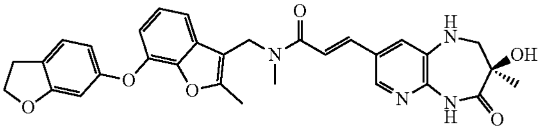

182

Step 1. N-((7-((2,3-Dihydrobenzofuran-6-yl)oxy)-2-methylbenzofuran-3-yl)methyl)-N-methylacrylamide (compound 181). To an ice cooled solution of 1-(7-((2,3-dihydrobenzofuran-6-yl)oxy)-2-methylbenzofuran-3-yl)-N-methylmethanamine 162 (160 mg, 0.52 mmol) and TEA (300 μL, 2.07 mmol) in DCM (10 mL) was added dropwise a solution of acryloyl chloride (42 μL, 0.52 mmol) in DCM (1.0 mL). The reaction mixture was allowed to warm to RT and stirred for 1 h. The reaction was quenched with water (5.0 mL) and the two phases separated. The organic phase was dried with $MgSO_4$, filtered and concentrated in vacuo. The crude product was purified by chromatography (0-100% EtOAc/iso-hexane) to give the title compound 181 as a colourless oil (120 mg, 60%). $R^t$ 2.36 min (Method 1a); m/z 364 $[M+H]^+$ $(ES^+)$.

Step 2. (R,E)-N-((7-((2,3-Dihydrobenzofuran-6-yl)oxy)-2-methylbenzofuran-3-yl)methyl)-3-(3-hydroxy-3-methyl-4-oxo-2,3,4,5-tetrahydro-1H-pyrido[2,3-b][1,4]diazepin-8-yl)-N-methylacrylamide (compound 182). A reaction vial was charged with N-((7-((2,3-dihydrobenzofuran-6-yl)oxy)-2-methylbenzofuran-3-yl)methyl)-N-methylacrylamide 181 (60 mg, 0.17 mmol), (R)-8-bromo-3-hydroxy-3-methyl-2,3-dihydro-1H-pyrido[2,3-b][1,4]diazepin-4(5H)-one 47 (45 mg, 0.17 mmol), $NBu_4Cl$ (5 mg, 0.02 mmol), $[P(tBu)_3]Pd$ (crotyl)Cl (Pd-162) (7 mg, 0.02 mmol) and the vial was flushed with $N_2$ for 5 mins. 1,4-Dioxane (3.0 mL) and N-cyclohexyl-N-methylcyclohexanamine (75 μL, 0.35 mmol) were added and the reaction mixture was purged with $N_2$ for a further 5 mins. The mixture was heated to 80° C. for 1 h and then allowed to cool to RT. Ethyl acetate (5.0 mL) was added and the resulting solution was washed with water (5.0 mL) and brine (5.0 mL), dried over $MgSO_4$, filtered and concentrated in vacuo. The crude product was purified by chromatography (0-10% MeOH/DCM) to give the title compound 182 as a pale yellow solid (29 mg, 36%). $R^t$ 2.12 min (Method 1a); m/z 555 $[M+H]^+$ $(ES^+)$. $^1H$ NMR (500

MHz, DMSO-$d_6$, 363 K): δ, ppm 9.38 (s, 1H), 7.96 (d, J=1.9 Hz, 1H), 7.47 (d, J=15.4 Hz, 1H), 7.41-7.25 (m, 2H), 7.25-7.03 (m, 3H), 6.83 (dd, J=7.9 Hz, 1.1 Hz, 1H), 6.47 (dd, J=8.0 Hz, 1.6 Hz, 1H), 6.42 (d, J=2.2 Hz, 1H), 6.05 (s, 1H), 4.93 (s, 1H), 4.78 (s, 2H), 4.57 (t, J=8.6 Hz, 2H), 3.25-3.11 (m, 4H), 3.03 (s, 3H), 2.48 (s, 3H), 1.29 (s, 3H).

Example 39. Synthesis of (R,E)-3-(3-hydroxy-3-methyl-4-oxo-2,3,4,5-tetrahydro-1H-pyrido[2,3-b][1,4]diazepin-8-yl)-N-((7-(3-methoxyphenoxy)-2-methylbenzofuran-3-yl)methyl)-N-methylacrylamide (Compound 183)

General Synthetic Scheme.

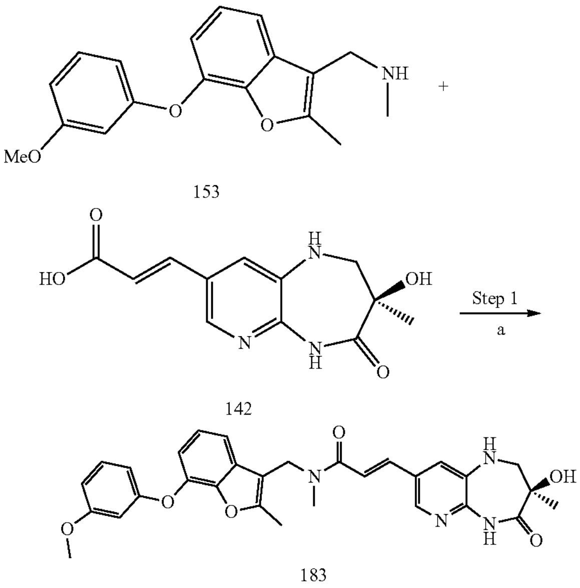

Reagents and conditions: a) HOBt•$H_2O$, EDC•HCl, DIPEA, DMF

Step 1. (R,E)-3-(3-Hydroxy-3-methyl-4-oxo-2,3,4,5-tetrahydro-1H-pyrido[2,3-b][1,4]diazepin-8-yl)-N-((7-(3-methoxyphenoxy)-2-methylbenzofuran-3-yl)methyl)-N-methylacrylamide (compound 183). A microwave vial covered by a aluminium foil was charged with HOBt-$H_2O$ (8.04 mg, 0.05 mmol) and (E)-3-[(3R)-3-hydroxy-3-methyl-4-oxo-2,5-dihydro-1H-pyrido[2,3-b][1,4]diazepin-8-yl] prop-2-enoic acid 142 (9.21 mg, 0.04 mmol) and DMF (0.3 mL). 1-[7-(3-methoxyphenoxy)-2-methyl-benzofuran-3-yl]-N-methyl-methanamine 153 (10.41 mg, 0.04 mmol) and EDCl-HCl (10.06 mg, 0.05 mmol) were added and after 2 mins of stirring at RT DIPEA (0.02 mL, 0.12 mmol) was added. The reaction mixture was stirred in the dark overnight at RT. Then, water and acetonitrile were added, the mixture was sonicated and the precipitate was filtered off. The crude product (24 mg) was purified by preparative HPLC using a gradient water/ACN 100% to 100% to afford the title compound 183 as an yellow oil (3.7 mg, 19.4% yield). $R^t$ 1.83 min (Method 1b); m/z 543.5 $[M+H]^+$ ($ES^+$). $^1H$ NMR (400 MHz, DMSO-$d_6$): δ, ppm 9.93 (s, 1H), 7.98 (s, 1H), 7.52-7.17 (m, 5H), 7.06 (d, J=15.5 Hz, 1H), 6.88 (d, J=8.2 Hz, 1H), 6.71 (dd, J=1.7 Hz, 7.9 Hz, 1H), 6.61-6.56 (m, 1H), 6.51 (dd, J=1.8 Hz, 8.4 Hz, 1H), 6.28-6.19 (m, 1H), 5.28 (s, 1H), 4.90, 4.75 (2 s, 2H), 3.73 (s, 3H), 3.21-3.08 (m, 2H), 3.06, 2.96 (2 s, 3H), 2.45 (s, 3H), 1.23 (s, 3H) (rotamers).

Example 40. Synthesis of (E)-N-((7-(3-methoxyphenoxy)-2-methylbenzofuran-3-yl)methyl)-N-methyl-3-(8-oxo-6,7,8,9-tetrahydro-5H-pyrido[2,3-b]azepin-3-yl)acrylamide (Compound 186)

General Synthetic Scheme.

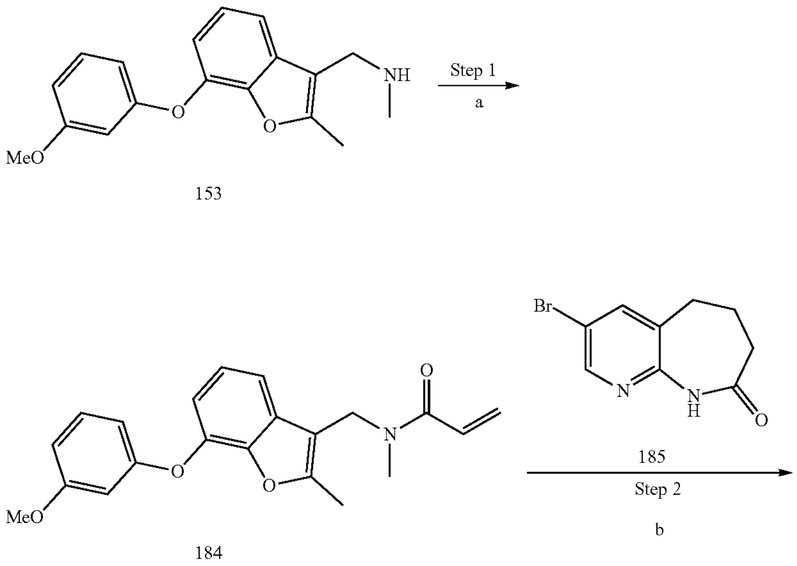

-continued

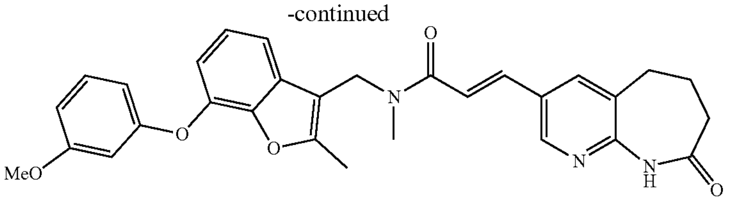

186

Reagents and conditions: a) Acryloyl chloride, TEA, DCM, 0° C.; b) Pd-116, DIPEA, $NBu_4Cl$, dioxane, 80° C.

The synthesis of 3-bromo-6,7-dihydro-5H-pyrido[2,3-b]azepin-8(9H)-one (compound 185) was previously reported by AFFINIUM PHARMECEUTICALS, INC: WO2007/67416, 2007, A2.

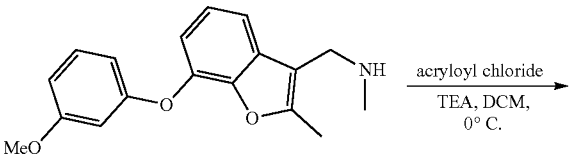

153

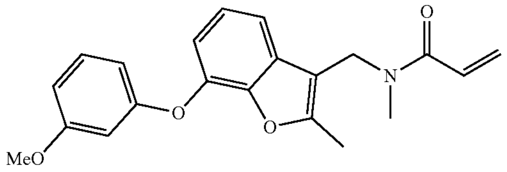

184

Step 1. N-((7-(3-Methoxyphenoxy)-2-methylbenzofuran-3-yl)methyl)-N-methylacrylamide (compound 184). To a stirred solution of 1-(7-(3-methoxyphenoxy)-2-methylbenzofuran-3-yl)-N-methylmethanamine 153 (155 mg, 0.52 mmol) in DCM (1.5 mL) was added TEA (0.22 mL, 1.58 mmol) and acryloyl chloride (0.051 mL, 0.63 mmol) at 0° C. The reaction mixture was stirred at 0° C. for 1 h then allowed to warm at RT. The reaction mixture was quenched with water (5.0 mL) followed by extraction into DCM (20 mL). The organics separated and dried by passing through an hydrophobic frit, and then concentrated in vacuo. The crude product was purified by silica chromatography (0-100% EtOAc/iso-hexane) to afford the title compound 184 as an yellow oil (122 mg, 67%). $R^t$ 2.32 min (Method 1b); m/z 352 $[M+H]^+$ $(ES^+)$.

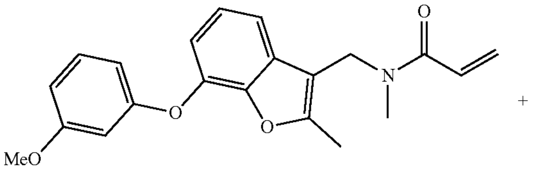

184

-continued

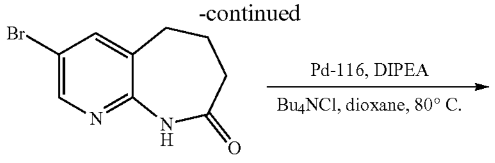

185

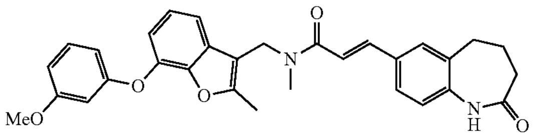

186

Step 2. (E)-N-((7-(3-Methoxyphenoxy)-2-methylbenzofuran-3-yl)methyl)-N-methyl-3-(8-oxo-6,7,8,9-tetrahydro-5H-pyrido[2,3-b]azepin-3-yl)acrylamide (compound 186). A reaction vial was charged with N-((7-(3-methoxyphenoxy)-2-methylbenzofuran-3-yl)methyl)-N-methylacrylamide 184 (55 mg, 0.16 mmol), 3-bromo-6,7-dihydro-5H-pyrido[2,3-b]azepin-8(9H)-one 185 (38 mg, 0.16 mmol), $n-Bu_4NCl—H_2O$ (5.0 mg, 0.02 mmol) and $Pd[P(^tBu)_3]_2$ (Pd-116) (8.00 mg, 0.02 mmol) and the vial was evacuated and backfilled with $N_2$ (3×). 1,4-Dioxane (4.0 mL) and DIPEA (55 μl, 0.30 mmol) were added and the reaction mixture was heated to 80° C. for 30 mins. The reaction mixture was evaporated to dryness and the crude product was purified by chromatography (0-10% MeOH/DCM) to afford the title compound 186 as a pale yellow solid (42 mg, 52%). $R^t$ 2.26 min (Method 1a); m/z 512 $[M+H]^+$ $(ES^+)$. $^1H$ NMR (500 MHz, DMSO-$d_6$, 363K): δ, ppm 9.57 (s, 1H), 8.49 (d, J=2.2 Hz, 1H), 8.04 (d, J=2.2 Hz, 1H), 7.57 (d, J=15.5 Hz, 1H), 7.37 (d, J=7.8 Hz, 1H), 7.26 (t, J=8.2 Hz, 2H), 7.17 (t, J=7.9 Hz, 1H), 6.88 (d, J=7.9 Hz, 1H), 6.72 (dd, J=8.3 Hz, 2.3 Hz, 1H), 6.60 (d, J=2.5 Hz, 1H), 6.56 (dd, J=8.3 Hz, 2.2 Hz, 1H), 4.80 (s, 2H), 3.76 (s, 3H), 3.00 (s, 3H), 2.77 (t, J=7.2 Hz, 2H), 2.48 (s, 3H), 2.32 (t, J=7.2 Hz, 2H), 2.16 (t, J=7.2 Hz, 2H).

Example 41. Synthesis of (E)-N-((7-(3-methoxyphenoxy)-2-methylbenzo[b]thiophen-3-yl)methyl)-N-methyl-3-(8-oxo-6,7,8,9-tetrahydro-5H-pyrido[2,3-b]azepin-3-yl)acrylamide (Compound 194)

General Synthetic Scheme.

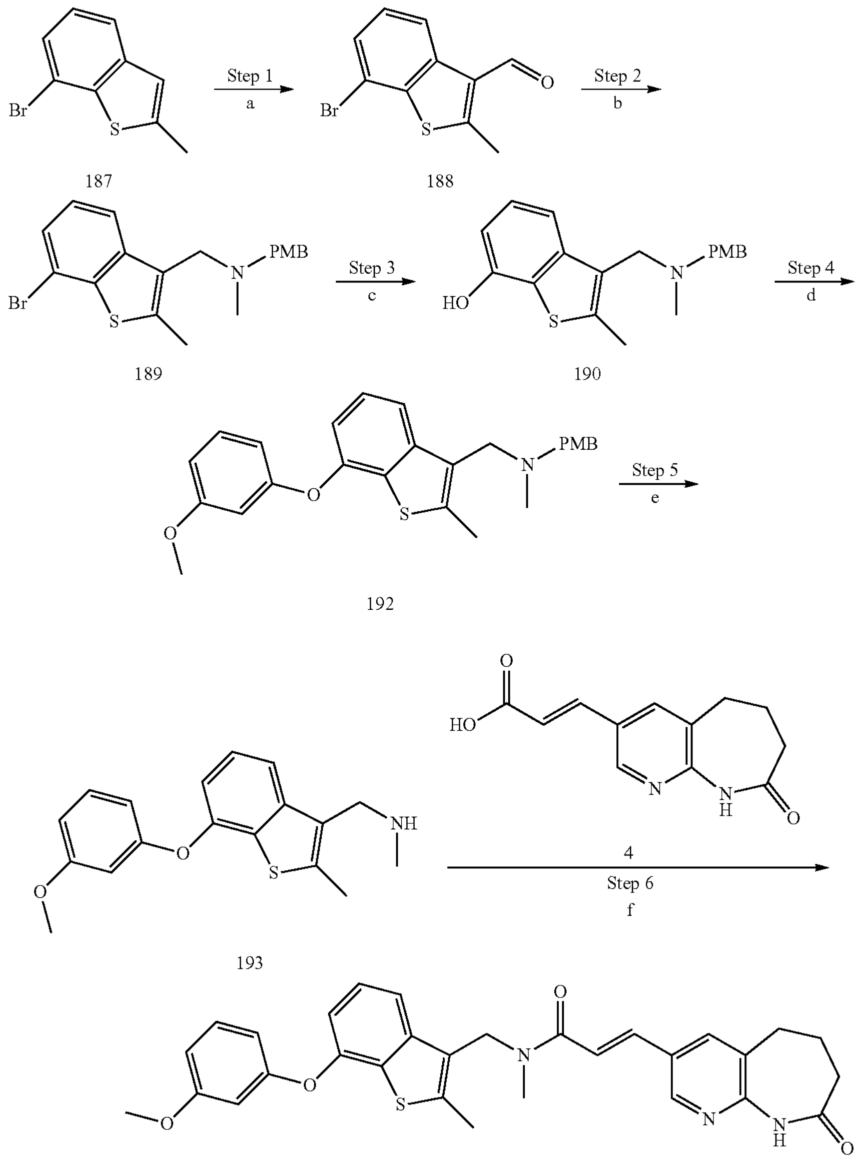

187 188 189 190 192 193 194

Reaction conditions: a) Dichloro(methoxy)methane, tin(IV) chloride, DCM, 0° C.; b)1-(4-methoxyphenyl)-N-methylmethanamine, $Na(OAc)_3BH$, DCE c) Pd-175, tBuBrettPhos, KOH 1,4-dioxane, $H_2O$, 80° C.; d) 3-bromoanisole 191, CuI, N,N-dimethyl glycine, $Cs_2CO_3$, DMF, 110° C.;ACE—Cl, MeOH, 0° C. to RT; f) HATU, DIPEA, DMF -continued

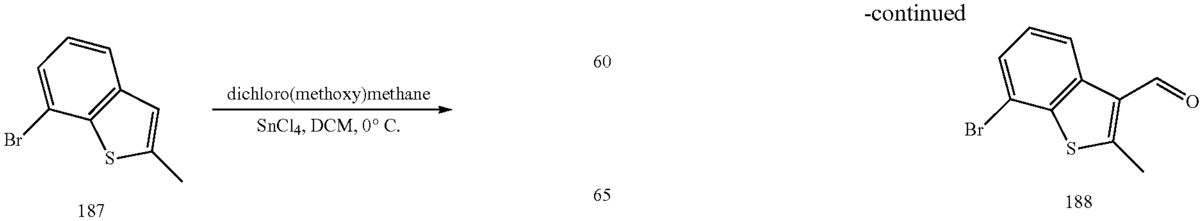

187 188

Step 1. 7-Bromo-2-methylbenzo[b]thiophene-3-carbaldehyde (compound 188). To a solution of 7-bromo-2-methylbenzo[b]thiophene 187 (950 mg, 4.18 mmol) and dichloro(methoxy)methane (0.42 mL, 4.64 mmol) in DCM (20 mL) at 0° C. was added dropwise a solution of tin(IV) chloride (1M in DCM, 5 mL, 5.00 mmol) over 15 mins. Upon completion of addition the mixture was allowed to warm to RT over 1 hour, then poured onto ice cold sat. $NaHCO_3$ solution (50 mL). The mixture was extracted into DCM (2×100 mL), the organic extracts were combined, dried over $Na_2SO_4$, filtered and concentrated under vacuum. The crude product was purified by chromatography (0-10% EtOAc/iso-hexane) to afford the title compound 188 as a white solid (780 mg, 69%). $^1H$ NMR (500 MHz, $CDCl_3$): δ, ppm 10.37 (s, 1H), 8.58 (dd, J=8.2 Hz, 1.1 Hz, 1H), 7.55 (dd, J=7.6 Hz, 1.1 Hz, 1H), 7.39-7.35 (m, 1H), 2.97 (s, 3H).

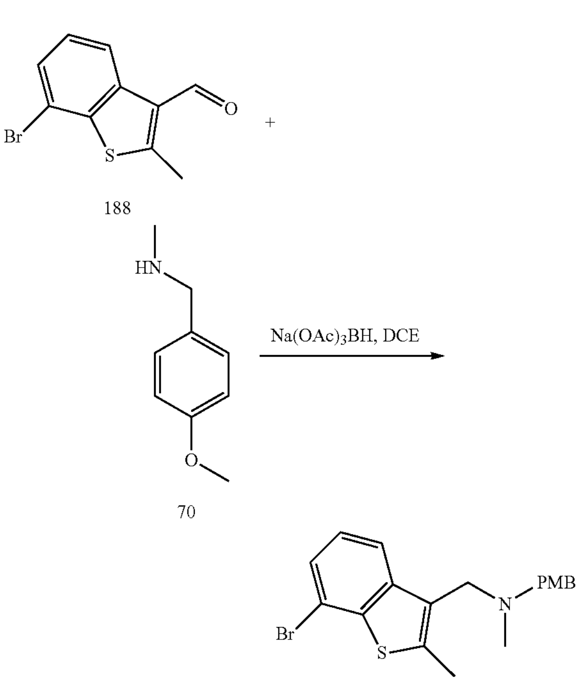

188

70

189

Step 2. 1-(7-Bromo-2-methylbenzo[b]thiophen-3-yl)-N-(4-methoxybenzyl)-N-methylmethanamine (compound 189). Sodium triacetoxyborohydride (1.61 g, 7.74 mmol) was added in one portion to a stirred solution of 7-bromo-2-methylbenzo[b]thiophene-3-carbaldehyde 188 (790 mg, 3.10 mmol) and 1-(4-methoxyphenyl)-N-methylmethanamine 70 (0.46 mL, 3.07 mmol) in DCE (12 mL) at RT. The reaction mixture was stirred for ~16 h then the solvent was concentrated in vacuo and the resulting residue was taken up in $NaHCO_3$ (25 mL, sat aq.). The aqueous material was extracted with DCM (3×30 mL) and the combined organic layers were washed with brine (30 mL) before being dried by passing through a phase separation cartridge. The crude material was purified by chromatography (0-50% EtOAc/iso-hexane) to give the title compound 189 as a brown oil (1.05 g, 86%). $R^t$ 3.18 min (Method 1b); m/z 390/392 $[M+H]^+$ $(ES^+)$.

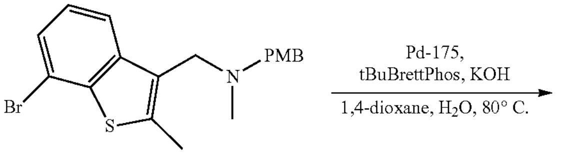

189

-continued

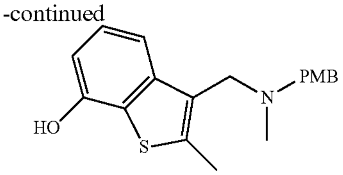

190

Step 3. 3-(((4-Methoxybenzyl)(methyl)amino)methyl)-2-methylbenzo[b]thiophen-7-ol (compound 190). A flask was charged with 1-(7-bromo-2-methylbenzo[b]thiophen-3-yl)-N-(4-methoxybenzyl)-N-methylmethanamine 189 (1.05 g, 2.69 mmol), Pd-175 (0.04 g, 0.05 mmol), tBuBrettPhos (0.03 g, 0.05 mmol) and KOH (0.45 g, 8.08 mmol). It was evacuated/backfilled with nitrogen (3 times) and subsequently were added 1,4-dioxane (5.0 mL) and degassed water (0.8 mL). The resulting mixture was heated to 80° C. and stirred for 3 hours. The mixture was cooled to RT and diluted with EtOAc (20 mL), then acidified with 1M HCl (20 mL). The mixture was stirred for 5 min until all solid was dissolved. The mixture was treated with sat. aq. $NaHCO_3$ (50 mL) and the phases were separated. The aqueous phase was extracted with EtOAc (2×50 mL). The combined organic extracts were dried over $MgSO_4$, filtered and concentrated. The crude product was purified by chromatography (0-50% EtOAc/iso-hexane) to afford the title compound 190 as a brown oil (879 mg, 99%). $R^t$ 2.51 min (Method 1b); m/z 328 $[M+H]^+$ $(ES^+)$.

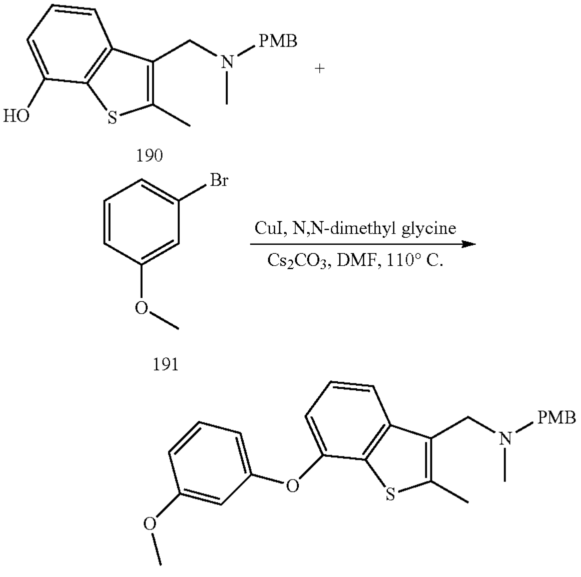

190

191

192

Step 4. N-(4-Methoxybenzyl)-1-(7-(3-methoxyphenoxy)-2-methylbenzo[b]thiophen-3-yl)-N-methylmethanamine (compound 192). A mixture of 3-(((4-methoxybenzyl)(methyl)amino)methyl)-2-methylbenzo[b]thiophen-7-ol 190 (250 mg, 0.76 mmol), copper(I) iodide (150 mg, 0.76 mmol),2-(dimethylamino)acetic acid (80 mg, 0.76 mmol) and $Cs_2CO_3$ (1.0 g, 3.05 mmol) was evacuated and backfilled with nitrogen (3 times). DMF (5.0 mL) and 1-bromo-3-methoxybenzene 191 (0.12 mL, 0.92 mmol) were added and the mixture was heated to 110° C. overnight. The mixture was filtered through a pad of Celite® washing with EtOAc (40 mL). The filtrate was evaporated to dryness. The crude product was purified by chromatography (0-30% EtOAc/iso-hexane) to afford the title compound 192 as a colourless oil (287 mg, 86%). $R^t$ 3.15 min (Method 1b); m/z 434 $[M+H]^+$ ($ES^+$).

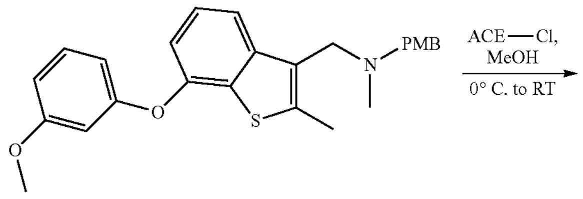

192

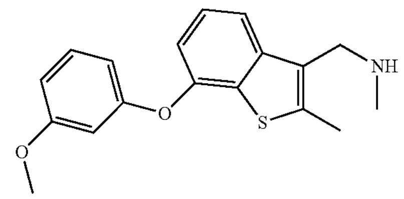

193

Step 5. 1-(7-(3-Methoxyphenoxy)-2-methylbenzo[b]thiophen-3-yl)-N-methylmethanamine (compound 193). 1-Chloroethyl chloroformate (0.15 mL, 1.37 mmol) was added dropwise to a stirred solution of N-(4-methoxybenzyl)-1-(7-(3-methoxyphenoxy)-2-methylbenzo[b]thiophen-3-yl)-N-methylmethanamine 192 (290 mg, 0.66 mmol) in DCM (9.0 mL) at 0° C. under $N_2$. The reaction was allowed to warm to RT and stirred overnight. The solvent was then concentrated in vacuo and the residue was redissolved in MeOH (15 mL) and heated to reflux for 1 h. The mixture was cooled to RT and applied onto a SCX column. The column was washed with methanol (50 mL), the product eluted with 10% methanolic ammonia and evaporated affording the title compound 193 as a dark oil (122 mg, 51%). $R^t$2.11 min (Method 1b); m/z 283 $[M-NHCH_3]^+$ ($ES^+$).

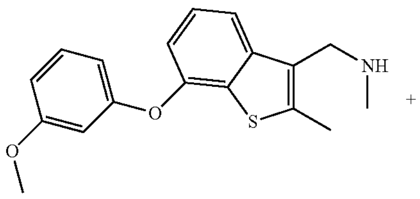

193

-continued

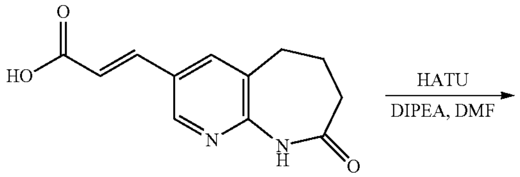

4

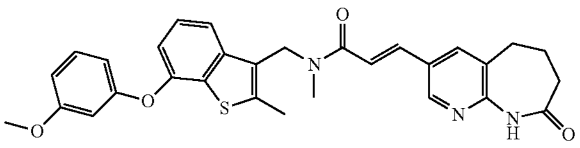

194

Step 6. (E)-N-((7-(3-Methoxyphenoxy)-2-methylbenzo[b]thiophen-3-yl)methyl)-N-methyl-3-(8-oxo-6,7,8,9-tetrahydro-5H-pyrido[2,3-b]azepin-3-yl)acrylamide (compound 194). A suspension of 1-(7-(3-methoxyphenoxy)-2-methylbenzo[b]thiophen-3-yl)-N-methylmethanamine 193 (64 mg, 0.20 mmol), (E)-3-(8-oxo-6,7,8,9-tetrahydro-5H-pyrido[2,3-b]azepin-3-yl)acrylic acid 4 (91 mg, 0.20 mmol), DIPEA (0.18 mL, 1.03 mmol) in DMF (1.0 mL) was stirred for 10 mins. HATU (78 mg, 0.20 mmol) was added in one portion and the reaction mixture stirred for 1 hour. The mixture was diluted with water (10 mL), extracted with DCM (3×20 mL), washed with brine, passed through a phase separator and evaporated. The crude product was purified by chromatography (0-3% MeOH/DCM). The fractions collected were then evaporated and the solid was triturated with MeCN to afford the title compound 194 as a white solid (21 mg, 19%). $R^t$ 2.36 min (Method 1b); m/z 528 $[M+H]^+$ ($ES^+$). $^1H$ NMR (500 MHz, DMSO-$d_6$): δ, ppm 9.57 (s, 1H), 8.49 (d, J=2.1 Hz, 1H), 8.03 (d, J=2.2 Hz, 1H), 7.62 (d, J=8.0 Hz, 1H), 7.58 (d, J=15.4 Hz, 1H), 7.35 (t, J=7.9 Hz, 1H), 7.30-7.27 (m, 2H), 6.90 (d, J=7.8 Hz, 1H), 6.76 (dd, J=8.3 Hz, 2.3 Hz, 1H), 6.64-6.63 (m, 1H), 6.60 (dd, J=8.2 Hz, 2.3 Hz, 1H), 4.94 (s, 2H), 3.76 (s, 3H), 2.96 (s, 3H), 2.77 (t, J=7.2 Hz, 2H), 2.59 (s, 3H), 2.32 (t, J=7.2 Hz, 2H), 2.18-2.12 (m, 2H).

Example 42. Synthesis of 4-(4-((3aR,6aS)-2-((E)-3-(4-oxo-2,3,4,5-tetrahydro-1H-pyrido[2,3-b][1,4]diazepin-8-yl)acryloyl)-1,2,3,3a,4,6a-hexahydrocyclopenta[c]pyrrol-5-yl)phenoxy)benzonitrile (Compound 198)

General Synthetic Scheme.

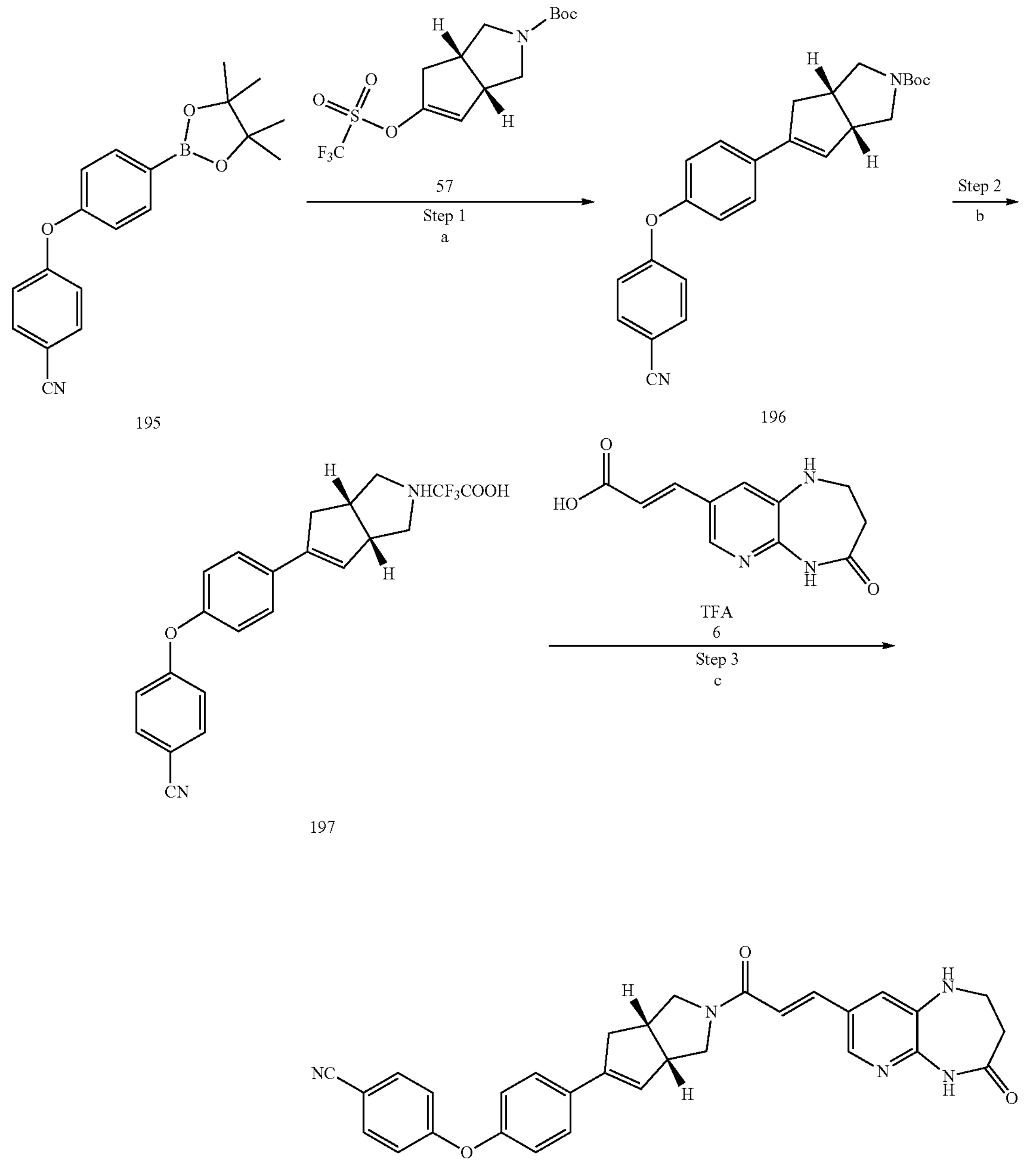

195 196 197 198

Reaction conditions: a) $K_2CO_3$, $H_2O$, $PdCl_2(dppf)$, 1,4-dioxane, 80° C.; b) TFA, DCM; c) HATU, DIPEA, DMF The synthesis of 4-(4-(4,4,5-trimethyl-1,3,2-dioxaborolan-2-yl)phenoxy)benzonitrile (compound 195) was previously reported by Abbott Laboratories; US2002/156081, 2002, A1 and X—RX DISCOVERY, INC.; WO2015/48662, 2015, A2. The pinacol ester 195 was prepared in 90% yield with a purity of 93% ($R^t$=2.40 min (standard); m/z 321.1 $[M+H]^+$ ($ES^+$)).

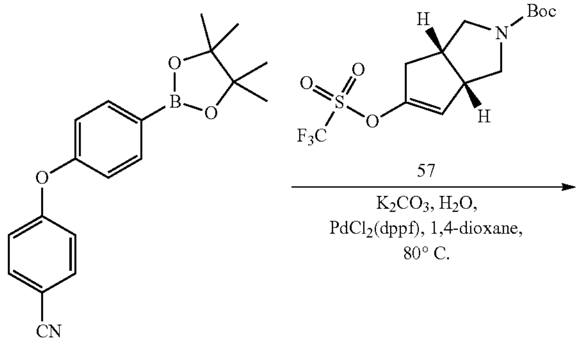
195
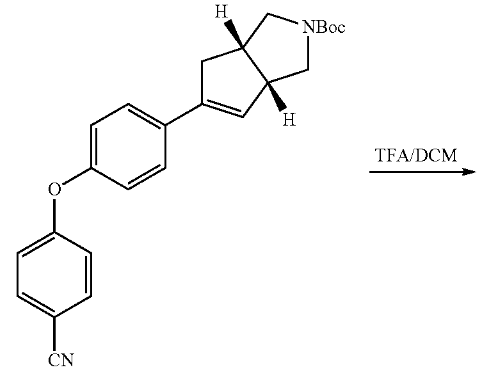
196
-continued
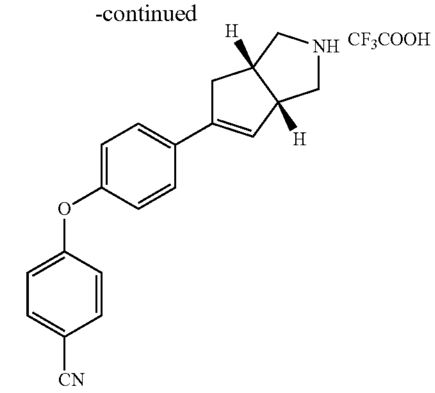
197
Steps 1 and 2. 4-(4-((3aS,6aR)-1,2,3,3a,4,6a-Hexahydrocyclopenta[c]pyrrol-5-yl)phenoxy)benzonitrile 2,2,2-trifluoroacetate (compound 197) was synthesized from compounds 57 and 195 via the intermediate 196 in 2 steps following the procedure described in Example 20 and US2017/0174683 A1. The crude product (TFA salt) 197 was used in the next step without further purification ($R^t$=1.26 min (standard); m/z 303.6 $[M+H]^+$ $(ES^+)$).
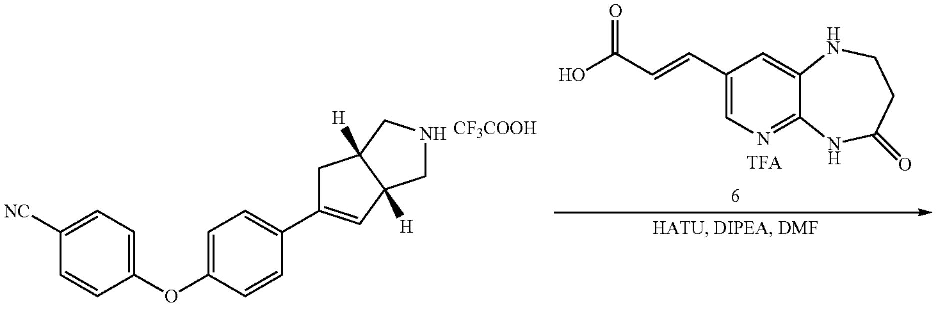
197
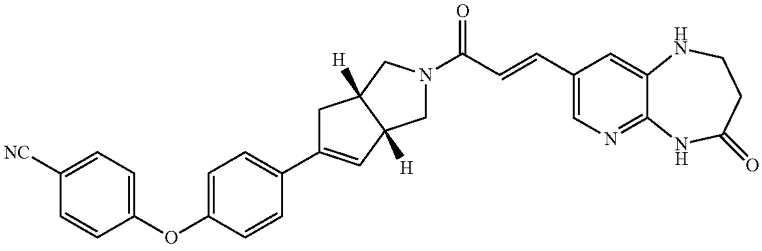
198

Step 3. 4-(4-((3aR,6aS)-2-((E)-3-(4-Oxo-2,3,4,5-tetrahydro-1H-pyrido[2,3-b][1,4]diazepin-8-yl)acryloyl)-1,2,3,3a,4,6a-hexahydrocyclopenta[c]pyrrol-5-yl)phenoxy)benzonitrile (compound 198) was obtained from the acid 6 and the amine 197 as a yellow solid with a purity of 99% (19% yield) in standard amine to amide coupling reaction described in Example 20. $R^t$=1.78 min (standard); m/z 518.3 $[M+H]^+$ ($ES^+$)). $^1H$ NMR (400 MHz, DMSO-$d_6$): δ, ppm 9.73 (d, J=4.9 Hz, 1H), 7.98 (d, J=6.2 Hz, 1H), 7.84 (d, J=8.8 Hz, 2H), 7.58 (d, J=8.3 Hz, 2H), 7.39-7.28 (m, 2H), 7.16-7.05 (4H, m), 6.86 (dd, J=6.7 Hz, 15.5 Hz, 1H), 6.20 (s, 1H), 6.05-6.00 (m, 1H), 4.05-3.75 (m, 2H), 3.73-3.49 (m, 2H), 3.47-3.36 (m, 3H), 3.22-3.10 (m, 1H), 3.10-2.91 (m, 1H), 2.69-2.55 (m, 3H).

Example 43. Synthesis of (E)-3-(3-hydroxy-2,3-dimethyl-4-oxo-2,3,4,5-tetrahydro-1H-pyrido[2,3-b][1,4]diazepin-8-yl)-N-methyl-N-((3-methylbenzofuran-2-yl)methyl)acrylamide (Compound 207)

General Synthetic Scheme.

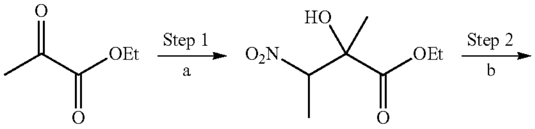

199

200
mix of diastereomers

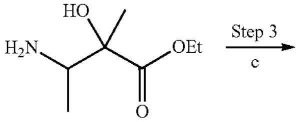

201
mix of diastereomers

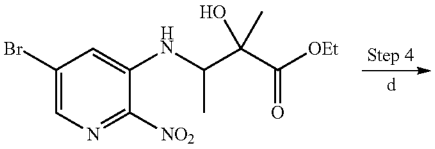

202
3:2 ratio
of diastereomers

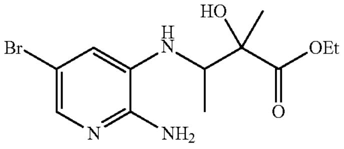

First eluting diastereomer
203

+

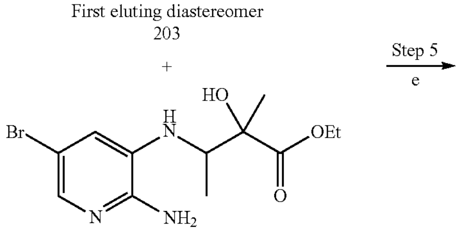

Second eluting diastereomer
204

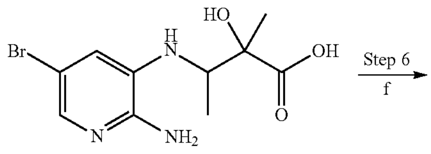

HCl
205

-continued

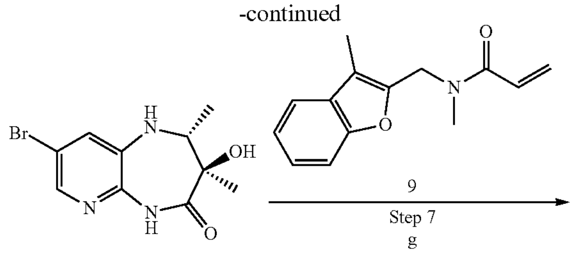

206
racemic cis
regioisomer

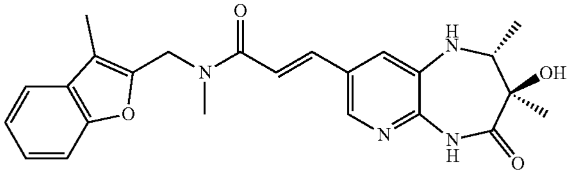

207

Reaction conditions: a) Nitroethane, Amberlyst A-21, 0° C. to RT; b) Zn, Acetic Acid; c) 5-Bromo-3-fluoro-2-nitropyridine 11, TEA, EtOH, reflux; d) Fe, $NH_4Cl$, EtOH, $H_2O$, reflux, separation of diastereomers; e) LiOH, $H_2O$, THF, MeOH; f) HATU, DIPEA, DMF; g) Pd-116, DIPEA, $NBu_4Cl$, 1,4-dioxane, 80° C.

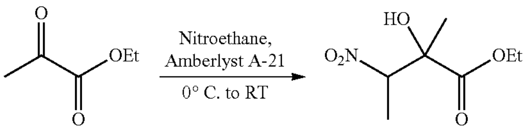

199

200
mix of
diasteromers

Step 1. Ethyl 2-hydroxy-2-methyl-3-nitrobutanoate (compound 200). Ethyl 2-oxopropanoate 199 (15.6 mL, 140 mmol) was added dropwise to a stirred suspension of Amberlyst A-21 (14 g, 140 mmol) in nitroethane (10.0 ml, 140 mmol) at 0° C. The reaction mixture was allowed to warm to RT and was stirred for ~16 h. The resin was removed by filtration and washed with DCM (3×100 mL). The filtrate was concentrated in vacuo to give the desired product 200 as a yellow oil (20.6 g, 73%) in an approximately 2:1 ratio of diastereomers.

Major Diastereomer: $^1H$ NMR (500 MHz, DMSO-$d_6$): δ, ppm 5.94 (s, 1H), 5.04 (q, J=6.8 Hz, 1H), 4.17 (q, J=7.1 Hz, 2H), 1.46 (d, J=6.8 Hz, 3H), 1.31 (s, 3H), 1.22 (t, J=7.1 Hz, 3H).

Minor Diastereomer: $^1H$ NMR (500 MHz, DMSO-$d_6$): δ, ppm 6.08 (s, 1H), 4.88 (q, J=6.8 Hz, 1H), 4.17 (q, J=7.1 Hz, 2H), 1.47 (d, J=6.8 Hz, 3H), 1.36 (s, 3H), 1.22 (t, J=7.1 Hz, 3H).

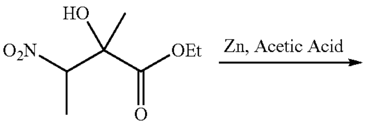

200
mix of
diasteromers

-continued

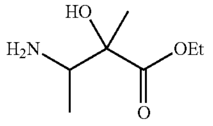

201
mix of
diastereomers

Step 2. Ethyl 3-amino-2-hydroxy-2-methylbutanoate (compound 201). To a solution of ethyl 2-hydroxy-2-methyl-3-nitrobutanoate 200 (5 g, 26.2 mmol) in acetic acid (300 mL), Zinc powder was added by portion (68.4 g, 1046 mmol). The mixture was stirred at RT for 4 h, then was filtered over a Celite® pad. The filtrate was neutralized by addition of sat. aq. $Na_2CO_3$ (~700 mL) and extracted with EtOAc (2×700 mL). The combined organic layers were dried over $Na_2SO_4$, filtered and evaporated under reduced pressure affording the title compound 201 as a yellow oil. The aqueous layer was then evaporated and the residue was divided into two portions and each of these were solubilised again in water (300 mL). The aqueous material was filtered to remove the salts formed, extracted with EtOAc (2×400 mL) and DCM (2×400 mL), and the combined organic layers were dried over $MgSO_4$, filtered and evaporated to dryness. $^1$H NMR analysis of the three fractions were consistent with product structure at 100% purity and they were combined affording the title compound 201 as a yellow oil (1.12 g, 27%). $^1$H NMR (DMSO-$d_6$): δ, ppm δ 4.12-4.07 (m, 2H), 2.94-2.84 (m, 1H), 1.24-1.15 (m, 6H), 0.94-0.91 (m, 3H). $NH_2$ and OH not observed (mix of isomers).

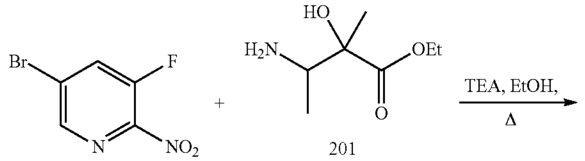

11

201
mix of
isomers

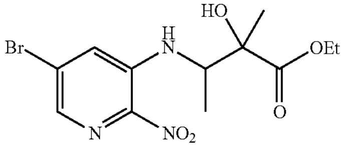

202
2:3 ratio of
diastereomers

Step 3. Ethyl 3-((5-bromo-2-nitropyridin-3-yl)amino)-2-hydroxy-2-methylbutanoate (compound 202). Triethylamine (1.8 mL, 12.8 mmol) was added to a stirred solution of 5-bromo-3-fluoro-2-nitropyridine 11 (1.3 g, 5.88 mmol) and ethyl 3-amino-2-hydroxy-2-methylbutanoate 201 (1.06 g, 4.27 mmol) in EtOH (20 mL) and the reaction mixture was heated to reflux for ~16 h. The reaction mixture was allowed to cool to RT, then was concentrated in vacuo and the crude material was purified by column chromatography (0-10% MeOH/DCM) to give the desired product 202 as a yellow oil (1.24 g, 79%) in an approximately 3:2 ratio of diastereomers.

Diastereomer 1: $R^t$ 1.90 min (Method 1a) m/z 362/364 $[M+H]^+$ ($ES^+$). $^1$H NMR (400 MHz, DMSO-$d_6$): δ, ppm 8.11-8.02 (m, 2H), 7.91-7.84 (m, 1H), 5.96 (s, 1H), 4.31-4.23 (m, 1H), 4.00 (q, J=7.1 Hz, 2H), 1.34 (s, 3H), 1.17 (d, J=6.4 Hz, 3H), 1.01 (t, J=7.1 Hz, 3H).

Diastereomer 2: $R^t$ 1.96 min (Method 1a) m/z 362/364 $[M+H]^+$ ($ES^+$). $^1$H NMR (400 MHz, DMSO-$d_6$) δ 8.13-8.00 (m, 2H), 7.89-7.85 (m, 1H), 5.98 (s, 1H), 4.18 (q, J=7.1 Hz, 2H), 4.15-4.08 (m, 1H), 1.34 (s, 3H), 1.25 (t, J=7.1 Hz, 3H), 1.09 (d, J=6.4 Hz, 3H).

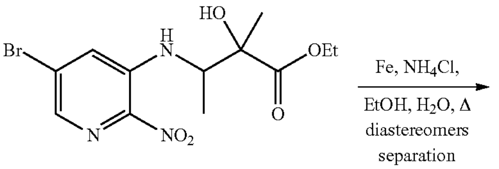

202
2:3 ratio of
diastereomers

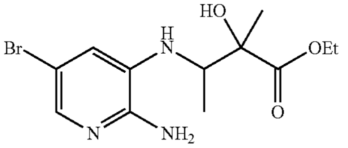

203
First Eluting
Disatereomer

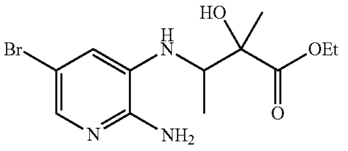

204
Second Eluting
Disatereomer

Step 4. Ethyl 3-((2-amino-5-bromopyridin-3-yl)amino)-2-hydroxy-2-methylbutanoate (compounds 203 and 204). A mixture of ethyl 3-((5-bromo-2-nitropyridin-3-yl)amino)-2-hydroxy-2-methylbutanoate 202 (1.2 g, 3.31 mmol), iron (1.48 g, 26.5 mmol) and $NH_4Cl$ (0.71 g, 13.3 mmol) in a mixture of EtOH (20 mL) and $H_2O$ (5 mL) was heated and stirred under reflux for ~16 h. The reaction mass was allowed to cool to RT, then was dry loaded on Celite® and purified by column chromatography (0-50% EtOAc/iso-hexane) to give the desired product as a brown solid: Diastereomer 1 203 (154 mg, 14%) and Diastereomer 2 204 (280 mg, 25%).

Diastereomer 1 203: $R^t$ 1.14 min (Method 1a) m/z 332/334 $[M+H]^+$ ($ES^+$). $^1$H NMR (400 MHz, DMSO-$d_6$): δ, ppm 7.28 (d, J=2.1 Hz, 1H), 6.80 (d, J=2.1 Hz, 1H), 5.63 (s, 2H), 5.11 (s, 1H), 4.39 (d, J=10.1 Hz, 1H), 3.96 (q, J=7.0 Hz, 2H), 3.86-3.78 (m, 1H), 1.28 (s, 3H), 1.07 (d, J=6.5 Hz, 3H), 1.03 (t, J=7.1 Hz, 3H).

Diastereomer 2 204: $R^t$ 1.13 min (Method 1a) m/z 332/334 $[M+H]^+$ ($ES^+$). $^1$H NMR (400 MHz, DMSO-$d_6$): δ, ppm 7.27 (d, J=2.0 Hz, 1H), 6.71 (d, J=2.0 Hz, 1H), 5.77 (s, 2H), 5.44 (s, 1H), 4.48 (d, J=9.7 Hz, 1H), 4.05 (q, J=7.1 Hz, 2H), 3.76-3.67 (m, 1H), 1.29 (s, 3H), 1.16 (t, J=7.1 Hz, 3H), 1.06 (d, J=6.6 Hz, 3H).

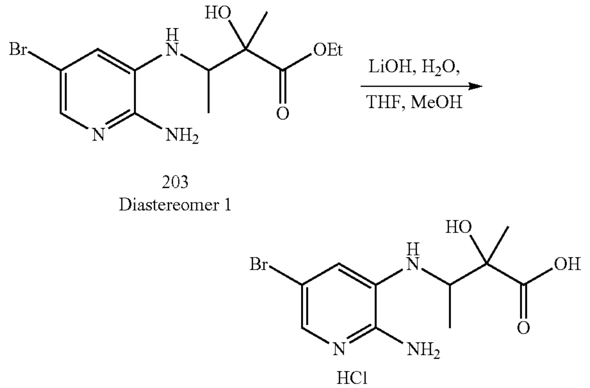

203
Diastereomer 1

HCl
205

Step 5. 3-((2-Amino-5-bromopyridin-3-yl)amino)-2-hydroxy-2-methylbutanoic acid hydrochloride (compound 205). Lithium hydroxide (1 M aq., 0.6 mL, 0.6 mmol) was added dropwise to a stirred solution of ethyl 3-((2-amino-5-bromopyridin-3-yl)amino)-2-hydroxy-2-methylbutanoate 203 (65 mg, 0.20 mmol) in THF (5 mL) and MeOH (1 mL) at RT and the reaction mixture was stirred for 4 h. The mixture was acidified to ~pH 5 by the addition of 1 M HCl (aq.) and the reaction mixture was concentrated in vacuo. The residue was azeotroped with MeCN (5 mL) to give the desired product 205 as a brown solid (68 mg, quant). R$^t$ 0.84 min (Method 1a) m/z 304/306 $[M+H]^+$ ($ES^+$).

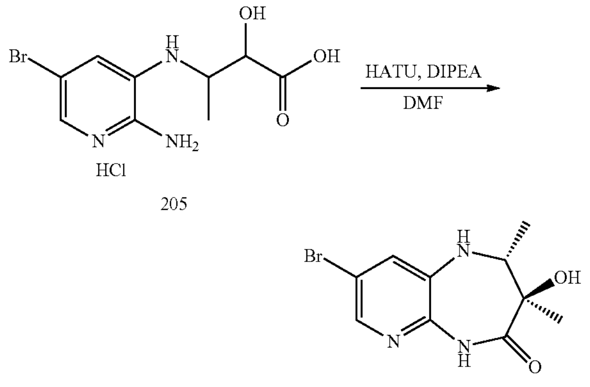

HCl
205

206
racemic
cis diastereomer

Step 6. 8-Bromo-3-hydroxy-2,3-dimethyl-2,3-dihydro-1H-pyrido[2,3-b][1,4]diazepin-4(5H)-one (compound 206). DIPEA (0.13 mL, 0.76 mmol) was added to a stirred solution of 3-((2-amino-5-bromopyridin-3-yl)amino)-2-hydroxy-2-methylbutanoic acid hydrochloride 205 (65 mg, 0.19 mmol) in DMF (2 mL) at RT. After 10 mins, HATU (75 mg, 0.20 mmol) was added and the reaction mixture was stirred for ~16 h. The reaction mixture was quenched with MeOH (5 mL) and $H_2O$ (30 mL). The aqueous mixture was extracted with EtOAc (3×50 mL) and the combined organic layers were washed with brine (2×50 mL), dried with $MgSO_4$, and concentrated in vacuo. The crude material was purified by column chromatography (0-50% EtOAc/isohexane) to give the desired product 206 as a white solid (21 mg, 38%). R$^t$ 1.21 min (Method 2a) m/z 286/288 $[M+H]^+$ ($ES^+$). $^1H$ NMR ($DMSO-d_6$): δ, ppm 10.25 (s, 1H), 7.66 (d, J=2.1 Hz, 1H), 7.26 (d, J=2.1 Hz, 1H), 6.79 (d, J=6.4 Hz, 1H), 5.12 (s, 1H), 3.31-3.24 (m, 1H), 1.16 (s, 3H), 1.03 (d, J=6.7 Hz, 3H). The cis stereochemistry of obtained diastereomer was assigned by the NMR studies including NOE and ROESY experiments.

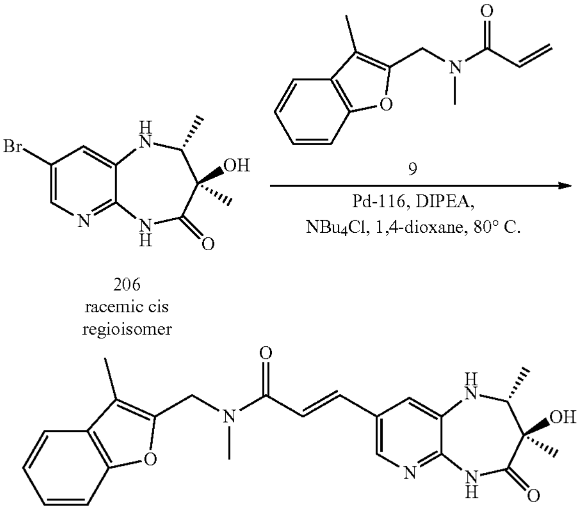

206
racemic cis
regioisomer

207

Step 7. (E)-3-(3-Hydroxy-2,3-dimethyl-4-oxo-2,3,4,5-tetrahydro-1H-pyrido[2,3-b][1,4]diazepin-8-yl)-N-methyl-N-((3-methylbenzofuran-2-yl)methyl)acrylamide (compound 207). A flask was charged with 8-bromo-3-hydroxy-2,3-dimethyl-2,3-dihydro-1H-pyrido[2,3-b][1,4]diazepin-4(5H)-one 206 (40 mg, 0.14 mmol), N-methyl-N-((3-methylbenzofuran-2-yl)methyl)acrylamide 9 (32 mg, 0.140 mmol), $NBu_4Cl$ (4 mg, 0.01 mmol) and Pd-116 (7 mg, 0.01 mmol) and the flask was evacuated and backfilled with $N_2$ three times. 1,4-Dioxane (2.5 mL) and DIPEA (0.05 mL, 0.28 mmol) were added and the reaction mixture was heated to 80° C. and stirred for 3 h. The solvent was removed in vacuo and the crude material was purified by column chromatography (0-5% MeOH/DCM) to give the desired product 207 as a yellow solid (36 mg, 59%). R$^t$ 1.93 min (Method 1a) m/z 435 $[M+H]^+$ ($ES^+$). $^1H$ NMR ($DMSO-d_6$, 363 K): δ, ppm 9.72 (s, 1H), 7.95 (d, J=1.9 Hz, 1H), 7.59-7.53 (m, 1H), 7.49-7.35 (m, 3H), 7.32-7.21 (m, 2H), 7.12 (d, J=15.4 Hz, 1H), 6.32 (d, J=6.4 Hz, 1H), 4.84 (s, 2H), 4.79 (d, J=1.1 Hz, 1H), 3.39-3.30 (m, 1H), 3.09 (s, 3H), 2.27 (s, 3H), 1.24 (s, 3H), 1.08 (d, J=6.7 Hz, 3H).

Example 44. Synthesis of (S,E)-3-(2-(hydroxymethyl)-2-methyl-3-oxo-1,2,3,4-tetrahydropyrido[2,3-b]pyrazin-7-yl)-N-methyl-N-((3-methylbenzofuran-2-yl)methyl)acrylamide (Compound 208) and (R,E)-3-(2-(hydroxymethyl)-2-methyl-3-oxo-1,2,3,4-tetrahydropyrido[2,3-b]pyrazin-7-yl)-N-methyl-N-((3-methylbenzofuran-2-yl)methyl)acrylamide (Compound 209)

Chiral separation of compound 84

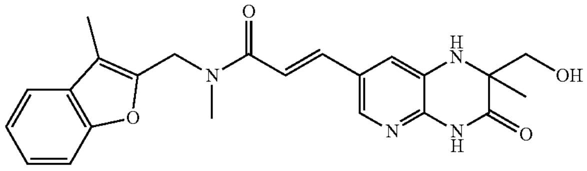

84

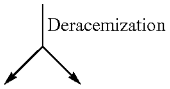

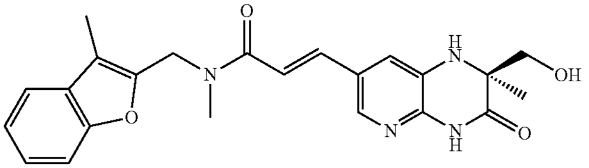

208

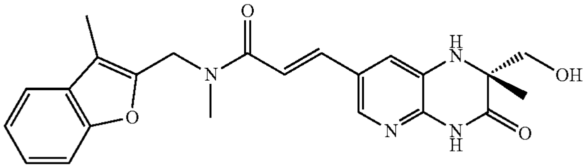

209

Chiral method separation: Apparatus: Isolera (Biotage). Column: Chiralpak IA (201 μm; glass column; 250 mm×25 mm). Eluent: Acetonitrile/Ethanol (8/2 v/v). Flow 40 mL/min. Temperature: 25° C. Run time: 25 min.

Amount injected: 30 mg of compound 84 in 20 mL of eluent (dissolution under reflux, followed by cooling and quick injection). Some degradation of the product during hot dissolution was observed, but by-products were not present in fractions of interest.

(S,E)-3-(2-(Hydroxymethyl)-2-methyl-3-oxo-1,2,3,4-tetrahydropyrido[2,3-b]pyrazin-7-yl)-N-methyl-N-((3-methylbenzofuran-2-yl)methyl)acrylamide (compound 208). Pure fractions of first enantiomer were collected and concentrated until precipitation was observed. Then evaporation to dryness was done under nitrogen flux at RT. The first enantiomer was obtained as a cream powder (m=8.6 mg; chiral purity: 99.84%). The stereochemistry of obtained enantiomer was randomly assigned.

(R,E)-3-(2-(Hydroxymethyl)-2-methyl-3-oxo-1,2,3,4-tetrahydropyrido[2,3-b]pyrazin-7-yl)-N-methyl-N-((3-methylbenzofuran-2-yl)methyl)acrylamide (compound 209). Pure fractions of second enantiomer were collected and concentrated until precipitation was observed. Then evaporation to dryness was done under nitrogen flux at RT. The second enantiomer was obtained as cream powder (m=6.9 mg; chiral purity: 99.59%). The stereochemistry of obtained enantiomer was randomly assigned.

Example 45. Synthesis of (R,E)-N-methyl-3-(2-methyl-4-oxo-2,3,4,5-tetrahydro-1H-pyrido[2,3-b][1,4]diazepin-8-yl)-N-((3-methylbenzofuran-2-yl)methyl)acrylamide (Compound 214)

General Synthetic Scheme.

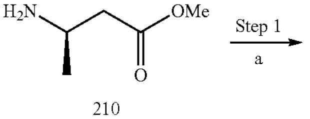

210

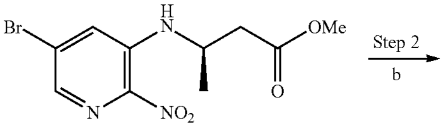

211

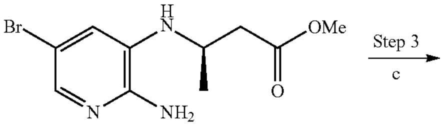

211

-continued

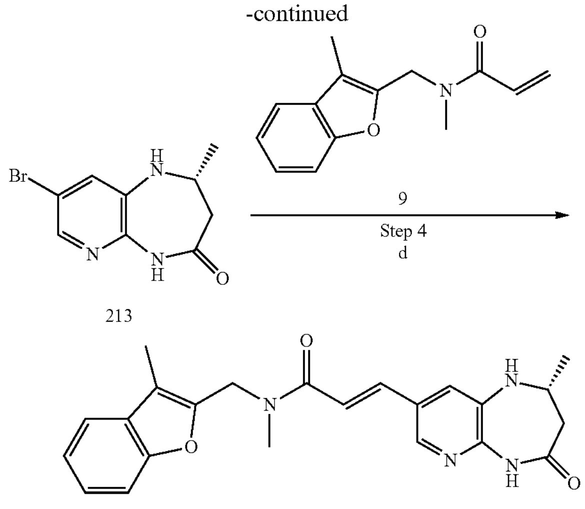

9

213

214

Reaction conditions: a) 5-Bromo-3-fluoro-2-nitropyridine 11, TEA, EtOH, 80° C.; b) Fe, $NH_4Cl$, EtOH, Water, 90° C.; c) NaH, THF, 0° C. to RT; d) Pd-116, $Bu_4NCl$, DIPEA, 1,4-Dioxane, 80° C.

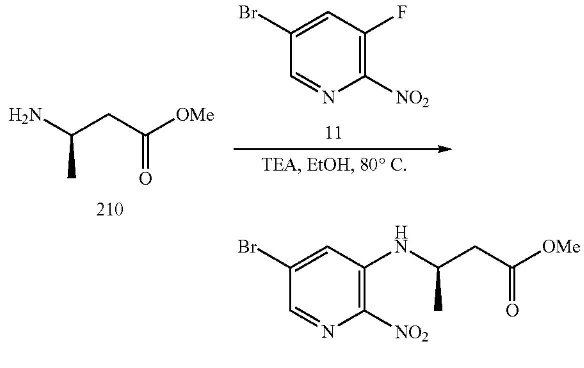

11

210

211

Step 1. (R)-Methyl 3-((5-bromo-2-nitropyridin-3-yl)amino)butanoate (compound 211). To a stirred solution of 5-bromo-3-fluoro-2-nitropyridine 11 (430 mg, 1.95 mmol) in MeCN (10 mL) was added (R)-methyl 3-aminobutanoate hydrochloride 210 (300 mg, 1.95 mmol) followed by TEA (700 μL, 4.88 mmol). The reaction mixture was stirred at reflux for 2 h and then was allowed to cool to RT. The reaction mixture was concentrated in vacuo, then the crude material was dissolved in ethyl acetate (10 mL) and washed with water (10 mL). The organic layer was dried with $MgSO_4$, filtered and concentrated in vacuo. The crude product was purified by chromatography (0-100% EtOAc/isohexane) to afford the title compound 211 as a yellow solid (590 mg, 90%). $R^t$ 1.89 min (Method 1a) m/z 318/320 $[M+H]^+$ $(ES^+)$.

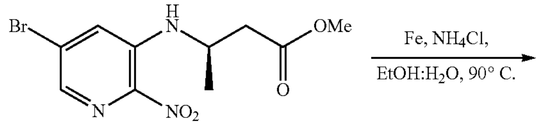

211

-continued

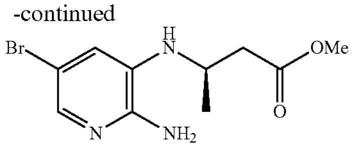

212

Step 2. (R)-Methyl 3-((2-amino-5-bromopyridin-3-yl)amino)butanoate (compound 212). To a mixture of methyl 3-((5-bromo-2-nitropyridin-3-yl)amino)butanoate 211 (570 mg, 1.85 mmol) in EtOH (35 mL) and water (8.75 mL) was added iron (415 mg, 7.42 mmol) and ammonia hydrochloride (400 mg, 7.42 mmol). The resulting reaction was heated and stirred at 90° C. for 1 h, before being filtered through a plug of Celite® while still hot. The filtrate was evaporated to dryness and the crude product was purified by chromatography (0-10% MeOH/DCM) to give the title compound 212 as a colourless solid (430 mg, 76%). $R^t$1.00 min (Method 1a) m/z 288/290 $[M+H]^+$ $(ES^+)$.

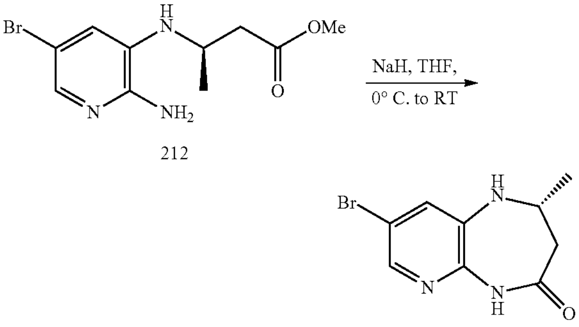

212

213

Step 3. (R)-8-Bromo-2-methyl-2,3-dihydro-1H-pyrido[2,3-b][1,4]diazepin-4(5H)-one (compound 213). Sodium hydride (60% in mineral oil, 83 mg, 2.08 mmol) was added in small portions to a stirred solution of methyl 3-((2-amino-5-bromopyridin-3-yl)amino)butanoate 212 (400 mg, 1.39 mmol) in THF (20 mL) at 0° C. The reaction was allowed to warm to RT and was stirred for 2 h. The reaction was quenched by careful addition of sat. aq. $NH_4Cl$ (20 mL) and the aqueous mixture was extracted with EtOAc (3x25 mL). The combined organic layers were dried with $MgSO_4$ and concentrated in vacuo. The crude product was purified by chromatography (0-10% MeOH/DCM) to give the title compound 213 as a colourless solid (170 mg, 45%). $R^t$ 1.30 min (Method 1a) m/z 256/258 $[M+H]^+$ $(ES^+)$.

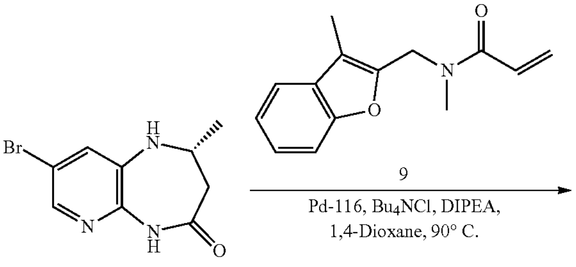

9

213

-continued

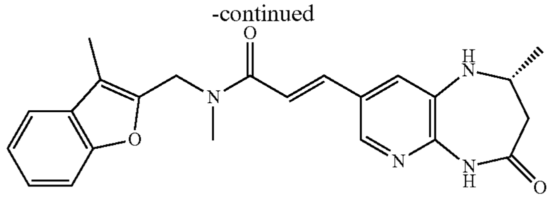

213

Step 4. (R,E)-N-Methyl-3-(2-methyl-4-oxo-2,3,4,5-tetrahydro-1H-pyrido[2,3-b][1,4]diazepin-8-yl)-N-((3-methylbenzofuran-2-yl)methyl)acrylamide (compound 214). A flask was charged with (R)-8-bromo-2-methyl-2,3-dihydro-1H-pyrido[2,3-b][1,4]diazepin-4(5H)-one 213 (80 mg, 0.31 mmol), N-methyl-N-((3-methylbenzofuran-2-yl)methyl) acrylamide (9) (70 mg, 0.31 mmol), tetrabutylammonium chloride hydrate (9.2 mg, 0.03 mmol) and Pd-116 (16 mg, 0.03 mmol) and the flask was evacuated and backfilled with $N_2$ three times. 1,4-Dioxane (2.5 mL) and DIPEA (0.11 mL) were added and the reaction mixture was heated to 90° C. for 2 h. Water (10 mL) was then added and the aqueous mixture was extracted with DCM (3×10 mL). The combined organic layers were dried by passing through a phase separation cartridge and concentrated in vacuo. The crude product was purified by chromatography (0-10% MeOH/DCM) to give the tile compound 214 as a yellow solid (68 mg, 52%). $R^t$ 1.89 min (Method 1a) m/z 405 $[M+H]^+$ $(ES^+)$. $^1H$ NMR (DMSO-$d_6$, 363K): δ, ppm 9.42-9.22 (m, 1H), 8.02 (d, J=1.9 Hz, 1H), 7.56 (dd, J=7.4 Hz, 1.5 Hz, 1H), 7.53-7.38 (m, 3H), 7.27 (dtd, J=20.7 Hz, 7.3 Hz, 1.3 Hz, 2H), 7.12 (d, J=15.4 Hz, 1H), 5.57-5.38 (m, 1H), 4.85 (s, 2H), 3.81 (ddt, J=7.7 Hz, 6.3 Hz, 3.2 Hz, 1H), 3.10 (s, 3H), 2.61 (dd, J=14.3 Hz, 3.1 Hz, 1H), 2.45 (dd, J=14.4 Hz, 7.7 Hz, 1H), 2.28 (s, 3H), 1.25 (d, J=6.4 Hz, 3H).

Example 46. Synthesis of (R,E)-3-(3-hydroxy-4-oxo-2,3,4,5-tetrahydro-1H-pyrido[2,3-b][1,4]diazepin-8-yl)-N-methyl-N-((3-methylbenzofuran-2-yl)methyl)acrylamide (Compound 229) and (S,E)-3-(3-hydroxy-4-oxo-2,3,4,5-tetrahydro-1H-pyrido[2,3-b][1,4]diazepin-8-yl)-N-methyl-N-((3-methylbenzofuran-2-yl)methyl)acrylamide (Compound 230)

General Synthetic Scheme.

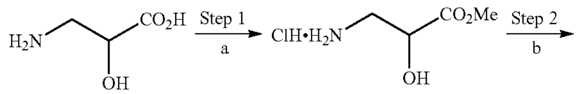

215 216

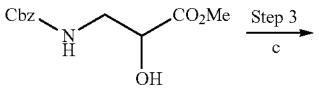

218

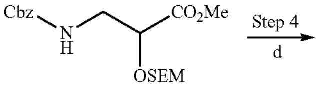

220

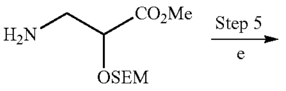

221

-continued

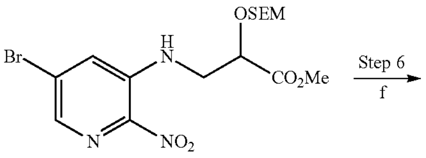

222

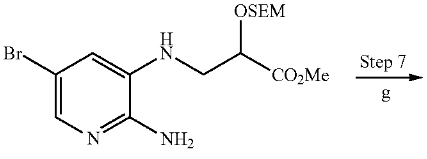

223

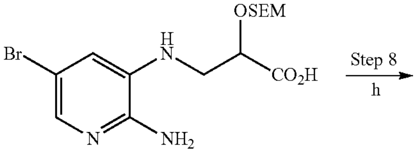

224

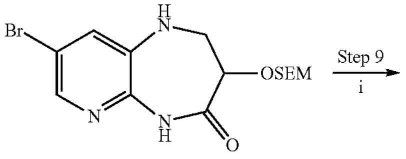

225

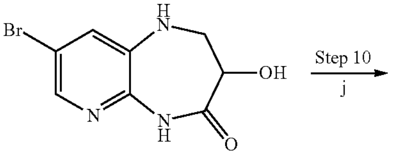

226

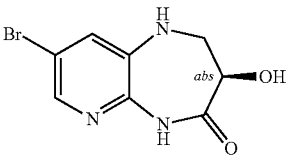

First eluting isomer
227

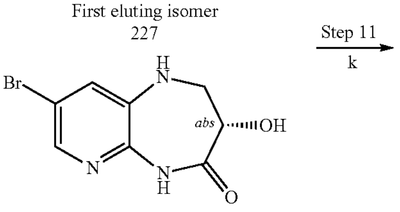

Second eluting isomer
228

-continued

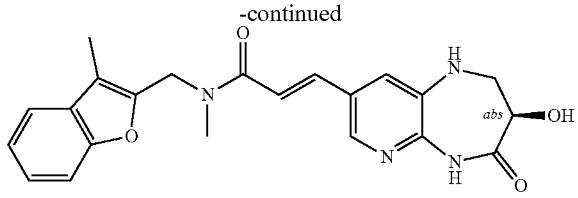

229

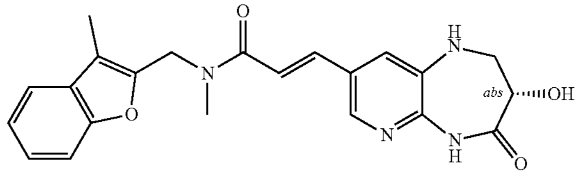

230

Reaction conditions: a) MeOH, $SOCl_2$, 0° C. - RT; b) CBZ-Cl 217, TEA, THF, 0° C.; c) SEM-Cl 219, DIPEA, DCE, 60° C.; d) Pd/C, $H_2$ 5 bar; e) 5-bromo-3-fluoro-2-nitropyridine 11, TEA, EtOH, reflux; f) Fe, $NH_4Cl$, EtOH, $H_2O$, reflux; g) LiOH, $H_2O$, THF, MeOH; h) HATU, DIPEA, DMF; i) a) TFA, b) $Na_2CO_3$; j) Chiralpak IA Column (25% Acetonitrile: 75% water); k) 9, Pd-116, DIPEA, $NBu_4Cl$, 1,4-dioxane, 80° C.

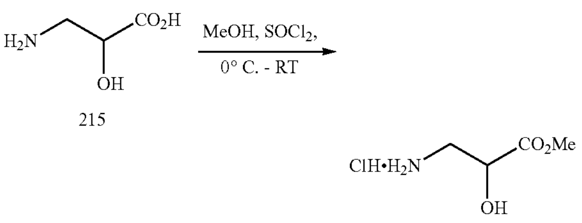

215

216

Step 1. Methyl 3-amino-2-hydroxypropanoate hydrochloride (compound 216). To a suspension of 3-amino-2-hydroxypropanoic acid 215 (4.0 g, 38 mmol) in methanol (154 mL) stirred in ice water was added dropwise thionyl chloride (8.3 mL, 114 mmol). Upon completion of addition, the mixture was stirred at RT overnight. The reaction mixture was evaporated to dryness to give the title compound 216 as a colourless gum, (6.1 g, quant.). $^1$H NMR (DMSO-$d_6$): δ, ppm 8.25 (br s, 3H), 6.07 (br s, 1H), 4.41 (dd, J=8.7 Hz, 3.8 Hz, 1H), 3.68 (s, 3H), 3.12-3.06 (m, 1H), 2.96-2.86 (m, 1H).

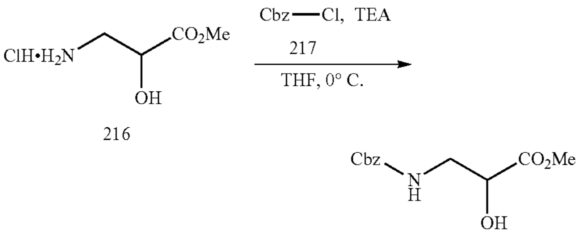

216

218

Step 2. Methyl 3-(((benzyloxy)carbonyl)amino)-2-hydroxypropanoate (compound 218). To an ice cooled mixture of methyl 3-amino-2-hydroxypropanoate hydrochloride 216 (5.92 g, 38 mmol) and triethylamine (22 mL, 152 mmol) in THF (100 mL) was added dropwise benzyl chloroformate 217 (5.4 mL, 38 mmol). The mixture was allowed to warm to RT and stirred for a further 2 h. The mixture was evaporated to dryness and the residue was redissolved in ethyl acetate (100 mL), washed with water (2×100 mL) and the organic phase was dried over sodium sulfate. The crude product was purified by silica chromatography (0-50% EtOAc/isohexane) to afford the title compound 218 as a clear colourless oil (5.50 g, 56%). $^1$H NMR ($CDCl_3$): δ, ppm 7.40-7.28 (m, 5H), 5.15-5.10 (m, 3H), 4.28 (d, J=4.8 Hz, 1H), 3.78 (s, 3H), 3.66-3.49 (m, 2H), 3.19 (s, 1H).

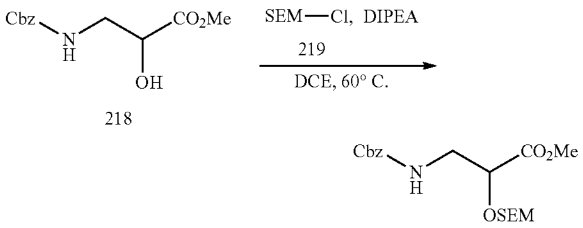

218

220

Step 3. Methyl 3-(((benzyloxy)carbonyl)amino)-2-((2-trimethylsilyl)ethoxy)methoxy)propanoate (compound 220). A mixture of 2-(trimethylsilyl)ethoxymethyl chloride 219 (2.3 mL, 13.2 mmol), DIPEA (3.4 mL, 19.7 mmol) and methyl 3-(((benzyloxy)carbonyl)amino)-2-hydroxypropanoate 218 (3.30 g, 13.2 mmol) in DCE (100 mL) was stirred at 60° C. for 24 h. The mixture was allowed to cool to RT, the solvent was removed in vacuo, and the crude product was purified by silica chromatography (0-50% EtOAc/isohexane) to afford the title compound 220 as a clear colourless oil (4.40 g, 83%). $^1$H NMR ($CDCl_3$): δ, ppm 7.41-7.32 (m, 5H), 5.19 (br s, 1H), 5.18-5.09 (m, 2H), 4.78 (s, 2H), 4.29 (dd, J=6.3 Hz, 4.3 Hz, 1H), 3.76 (s, 3H), 3.66 (m, 3H), 3.54 (m, 1H), 0.92 (m, 2H), 0.03 (s, 9H).

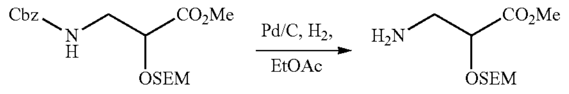

220 221

Step 4. Methyl 3-amino-2-((2-(trimethylsilyl)ethoxy)methoxy)propanoate (compound 221). A mixture of methyl 3-(((benzyloxy)carbonyl)amino)-2-((2-(trimethylsilyl)ethoxy)methoxy)propanoate 220 (4.40 g, 11.5 mmol) and 10% Pd/C (1.2 g, Type 87L) in a solvent of ethyl acetate (100 mL) was stirred under $H_2$ at 5 bar pressure for 1 h. The catalyst was removed by filtration and the filtrate evaporated to dryness to afford the title compound 221 as a yellow oil (2.6 g, 89%). $^1$H NMR (DMSO-$d_6$): δ, ppm 4.66 (dd, J=13.2 Hz, 4.7 Hz, 2H), 4.01 (dd, J=6.5 Hz, 4.7 Hz, 1H), 3.64 (s, 3H), 3.63-3.50 (m, 2H), 2.82 (m, 1H), 2.75 (m, 1H), 1.45 (s, 2H), 0.91-0.77 (m, 2H), 0.01 (s, 9H).

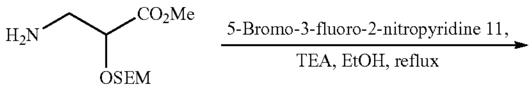

221

-continued

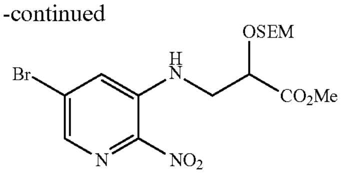

222

Step 5. Methyl 3-((5-bromo-2-nitropyridin-3-yl)amino)-2-((2-(trimethylsilyl)ethoxy)methoxy) propanoate (compound 222). A mixture of methyl 3-amino-2-((2-(trimethylsilyl)ethoxy)methoxy)propanoate 221 (2.60 g, 10.4 mmol), TEA (7.3 mL, 52.1 mmol) and 5-bromo-3-fluoro-2-nitropyridine 11 (2.30 g, 10.4 mmol) in a solvent of EtOH (80 mL) was heated under reflux for 2 h. The reaction mixture was evaporated to dryness and the residue was purified by silica chromatography (0-50% EtOAc/isohexane) to afford the title compound 222 as a yellow oil (4.30 g, 90%). $R^t$ 2.67 min (Method 1a); m/z 448/450 $[M+H]^+$ $(ES^+)$. $^1H$ NMR (DMSO-$d_6$): δ, ppm 8.08 (t, J=6.1 Hz, 1H), 8.00 (d, J=1.9 Hz, 1H), 7.91 (d, J=1.8 Hz, 1H), 4.76-4.62 (m, 2H), 4.44 (dd, J=7.2 Hz, 4.6 Hz, 1H), 3.77 (q, J=7.3 Hz, 6.2 Hz, 2H), 3.69 (s, 3H), 3.55-3.43 (m, 2H), 0.81-0.70 (m, 2H), −0.06 (s, 9H).

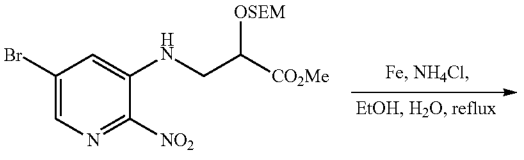

222

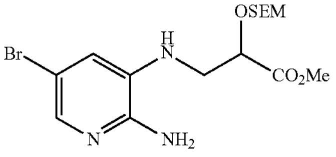

223

Step 6. Methyl 3-((2-amino-5-bromopyridin-3-yl)amino)-2-((2-(trimethylsilyl)ethoxy)methoxy)propanoate (compound 223). A mixture of methyl 3-((5-bromo-2-nitropyridin-3-yl)amino)-2-((2-(trimethylsilyl)ethoxy)methoxy) propanoate 222 (4.30 g, 9.5 mmol), iron powder (2.67 g, 47.7 mmol) and ammonium chloride (5.1 g, 95.0 mmol) in a solvent of ethanol (100 mL) and water (30 mL) was heated and stirred under reflux for 1 h. The mixture was allowed to cool to RT and was filtered through a plug of Celite®. The filtrate was evaporated to dryness and the residue taken up into DCM (130 mL). The organics were washed with water (200 mL) and dried over sodium sulfate. Filtration and evaporation gave the title compound 223 as a yellow oil (3.01 g, 74%). $R^t$ 1.76 min (Method 1a); m/z 420/422 $[M+H]^+$ $(ES^+)$.

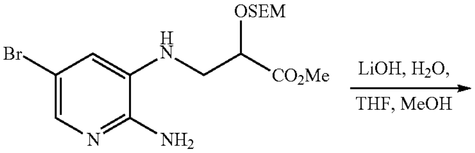

223

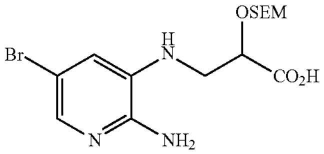

224

Step 7. 3-((2-Amino-5-bromopyridin-3-yl)amino)-2-((2-trimethylsilyl)ethoxy)methoxy)propanoic acid (compound 224). To a stirred solution of methyl 3-((2-amino-5-bromopyridin-3-yl)amino)-2-((2-(trimethylsilyl)ethoxy) methoxy)propanoate 223 (3.30 g, 7.85 mmol) in THF (200 mL) and MeOH (50 mL) was added a solution of LiOH monohydrate (0.23 g, 9.42 mmol) in water (30 mL) and the reaction mixture was stirred at RT for 1 h. The mixture was evaporated to dryness and the residue taken up into water (30 mL) and the pH was adjusted to ~pH 5 by the addition of acetic acid (~1 mL). The solid was collected by filtration, washed with water (4 mL) and dried to give the title compound 224 as a beige solid (2.75 g, 84%). $R^t$ 1.58 min (Method 1a); m/z 406/408 $[M+H]^+$ $(ES^+)$. $^1H$ NMR (DMSO-$d_6$): δ, ppm 7.31 (d, J=2.1 Hz, 1H), 6.75 (d, J=2.1 Hz, 1H), 5.75 (d, J=6.1 Hz, 2H), 5.37 (s, 1H), 4.67-4.64 (m, 2H), 4.22 (m, 1H), 3.55-3.31 (m, 4H), 0.78-0.74 (m, 2H), −0.06 (s, 9H). Acidic proton not observed.

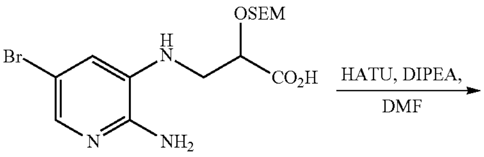

224

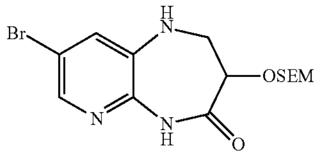

225

Step 8. 8-Bromo-3-((2-(trimethylsilyl)ethoxy)methoxy)-2,3-dihydro-1H-pyrido[2,3-b][1,4]diazepin-4(5H)-one (compound 225). To a solution of 3-((2-amino-5-bromopyridin-3-yl)amino)-2-((2-(trimethylsilyl)ethoxy)methoxy)propanoic acid 224 (2.75 g, 6.77 mmol) and DIPEA (6.0 mL, 33.8 mmol) in DMF (3 mL) was added HATU (3.0 g, 8.12 mmol) and the mixture was stirred at RT for 30 mins. The mixture was poured onto ice water (30 mL) and the solid collected and dried to give the title compound 225 as a beige solid (2.50 g, 93%). $R^t$ 2.27 min (Method 1b); m/z 388/390 $[M+H]^+$ $(ES^+)$. $^1H$ NMR (DMSO-$d_6$): δ, ppm 10.05 (s, 1H), 7.71 (s, 1H), 7.28 (s, 1H), 6.21 (d, J=4.5 Hz, 1H), 4.65 (q, J=6.9 Hz, 2H), 4.23 (d, J=5.4 Hz, 1H), 3.56-3.45 (m, 4H), 0.88-0.82 (m, 2H), −0.02 (s, 9H).

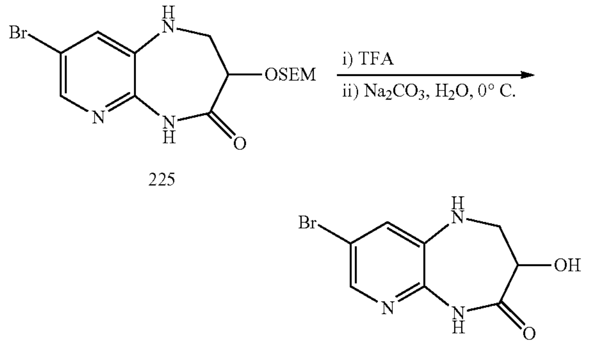

225

226

Step 9. 8-Bromo-3-hydroxy-2,3-dihydro-1H-pyrido[2,3-b][1,4]diazepin-4(5H)-one (compound 226). TFA (10 mL) was added in one portion to 8-bromo-3-((2-(trimethylsilyl)ethoxy)methoxy)-2,3-dihydro-1H-pyrido[2,3-b][1,4]diazepin-4(5H)-one 225 (800 mg, 2.1 mmol) and the solution was allowed to stand at RT for 5 mins before being carefully poured onto crushed ice (100 g). The resultant mixture was carefully neutralised by the addition of solid sodium carbonate and extracted with ethyl acetate (2×100 mL). The organics were combined and dried over sodium sulfate. Filtration and evaporation gave a gum which was triturated with acetonitrile (10 mL) to give the title compound 226 as an off white solid (310 mg, 57%). R$^t$ 1.04 min (Method 1a); m/z 258/260 $[M+H]^+$ ($ES^+$). $^1H$ NMR (DMSO-$d_6$): δ, ppm 10.12 (s, 1H), 7.70 (d, J=2.0 Hz, 1H), 7.28 (d, J=2.1 Hz, 1H), 6.37 (dd, J=6.2 Hz, 2.8 Hz, 1H), 5.24 (d, J=4.7 Hz, 1H), 4.16 (ddd, J=8.4 Hz, 4.8 Hz, 3.1 Hz, 1H), 3.45 (ddd, J=12.3 Hz, 6.1 Hz, 3.1 Hz, 1H), 3.29 (td, J=9.1 Hz, 4.5 Hz, 1H).

Step 10. Chiral separation of racemate 226.

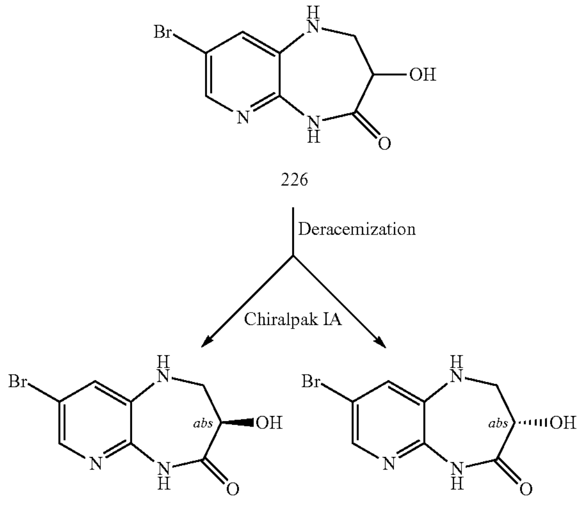

226

First eluting isomer
227

Second eluting isomer
228

The enantiomers were separated by chiral prep HPLC using Chiralpak® IA (Daicel Ltd.) column (2×25 cm), flow rate 13.5 mL $min^{-1}$ eluting with a mixture of 25% Acetonitrile:75% water, UV detection at 254 nm. Samples were loaded onto the column via an at-column dilution pump, pumping acetonitrile (1.5 mL $min^{-1}$) for the duration of the run, giving a combined flow rate of 15 mL $min^{-1}$. Chirality was arbitrarily assigned.

(R)-8-Bromo-3-hydroxy-2,3-dihydro-1H-pyrido[2,3-b][1,4]diazepin-4(5H)-one (compound 227). First eluting isomer: R$^t$ 7.98 min (Analytical Method: Chiralpak® IA, column (4.6 mm×25 mm), flow rate 1 mL $min^{-1}$, eluent: 30% acetonitrile: 70% 10 mmol aqueous ammonium bicarbonate solution).

(S)-8-Bromo-3-hydroxy-2,3-dihydro-1H-pyrido[2,3-b][1,4]diazepin-4(5H)-one (compound 228). Second eluting isomer: R$^t$ 13.09 min (Analytical Method: Chiralpak® IA, column (4.6 mm×25 mm), flow rate 1 mL $min^{-1}$, eluent: 30% acetonitrile: 70% 10 mmol aqueous ammonium bicarbonate solution).

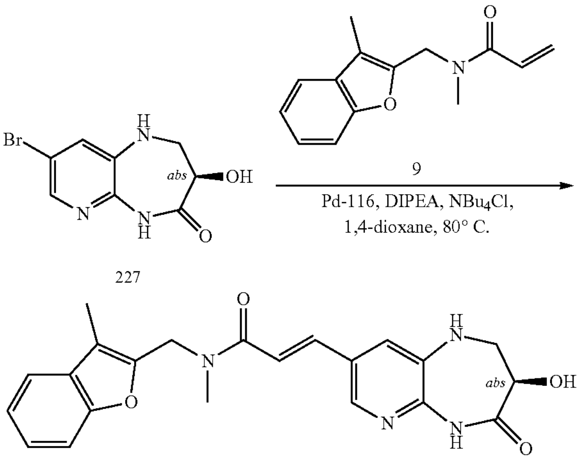

227

229

Step 11a. (R,E)-3-(3-Hydroxy-4-oxo-2,3,4,5-tetrahydro-1H-pyrido[2,3-b][1,4]diazepin-8-yl)-N-methyl-N-((3-methylbenzofuran-2-yl)methyl)acrylamide (compound 229). A reaction vial was charged with (R)-8-bromo-3-hydroxy-2,3-dihydro-1H-pyrido[2,3-b][1,4]diazepin-4(5H)-one 227 (50 mg, 0.19 mmol), DIPEA (70 μL, 0.39 mmol), tetrabutylammonium chloride hydrate (6 mg, 0.02 mmol), and $Pd[P(^tBu)_3]_2$ (Pd-116) (10 mg, 0.02 mmol) and the vial was flushed with nitrogen (5 mins). 1,4-Dioxane (5 mL) and N-methyl-N-((3-methylbenzofuran-2-yl)methyl)acrylamide 9 (49 mg, 0.21 mmol) were added, the reaction mixture was purged with nitrogen again (5 mins), and then the reaction mixture was heated and stirred at 80° C. for 30 mins. The reaction mixture was allowed to cool to RT, then was evaporated to dryness and the crude product was purified by column chromatography (0-10% MeOH/DCM) to afford the title compound 229 as a pale yellow solid (61 mg, 77%). R$^t$ 1.77 min (Method 1b); m/z 407 $[M+H]^+$ ($ES^+$). $^1H$ NMR (DMSO-$d_6$, 363K): δ, ppm 9.65 (s, 1H), 7.99 (d, J=1.8 Hz, 1H), 7.56 (d, J=7.5 Hz, 1H), 7.49-7.37 (m, 3H), 7.33-7.21 (m, 2H), 7.13 (d, J=14.6 Hz, 1H), 5.89 (d, J=5.5 Hz, 1H), 4.91-4.77 (m, 3H), 4.22-4.16 (m, 1H), 3.52 (ddd, J=12.4 Hz, 6.0 Hz, 3.3 Hz, 1H), 3.27 (ddd, J=12.1 Hz, 8.8 Hz, 2.8 Hz, 1H), 3.10 (s, 3H), 2.28 (s, 3H).

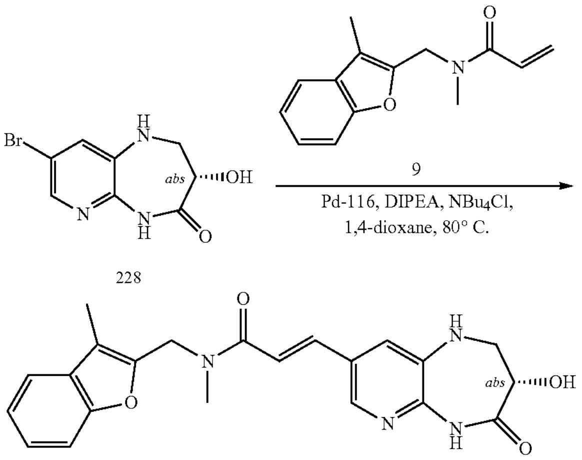

228 9 230

Step 11b. (S,E)-3-(3-Hydroxy-4-oxo-2,3,4,5-tetrahydro-1H-pyrido[2,3-b][1,4]diazepin-8-yl)-N-methyl-N-((3-methylbenzofuran-2-yl)methyl)acrylamide (compound 230). A reaction vial was charged with (S)-8-bromo-3-hydroxy-2,3-dihydro-1H-pyrido[2,3-b][1,4]diazepin-4(5H)-one 228 (50 mg, 0.19 mmol), DIPEA (70 μL, 0.39 mmol), tetrabutylammonium chloride hydrate (6 mg, 0.02 mmol) and $Pd[P(^tBu)_3]_2$ (Pd-116) (10 mg, 0.02 mmol) and the vial was flushed with nitrogen (5 mins). 1,4-Dioxane (5 mL) and N-methyl-N-((3-methylbenzofuran-2-yl)methyl)acrylamide 9 (50 mg, 0.21 mmol) were added, the reaction mixture was purged with nitrogen again (5 mins), and then the reaction mixture was heated and stirred at 80° C. for 30 mins. The reaction mixture was allowed to cool to RT, then was evaporated to dryness and the crude product was purified by silica chromatography (0-10% MeOH/DCM) to afford the title compound 230 as a pale yellow solid (58 mg, 73%). $R^t$ 1.76 min (Method 1b); m/z 407 $[M+H]^+$ $(ES^+)$. $^1H$ NMR (DMSO-$d_6$, 363K): δ, ppm 9.65 (s, 1H), 7.99 (d, J=1.8 Hz, 1H), 7.56 (d, J=7.5 Hz, 1H), 7.49-7.36 (m, 3H), 7.27 (dt, J=21.1 Hz, 7.4 Hz, 2H), 7.13 (d, J=15.7 Hz, 1H), 5.93-5.84 (m, 1H), 4.90-4.80 (m, 3H), 4.18 (dt, J=8.5 Hz, 3.8 Hz, 1H), 3.52 (ddd, J=12.3 Hz, 6.1 Hz, 3.4 Hz, 1H), 3.27 (ddd, J=12.2 Hz, 8.9 Hz, 2.8 Hz, 1H), 3.10 (s, 3H), 2.28 (s, 3H).

Example 47. Synthesis of (R,E)-3-methyl-8-(3-(methyl((3-methylbenzofuran-2-yl)methyl)amino)-3-oxoprop-1-en-1-yl)-4-oxo-2,3,4,5-tetrahydro-1H-pyrido[2,3-b][1,4]diazepin-3-yl dihydrogen phosphate (Compound 232)

General Synthetic Scheme.

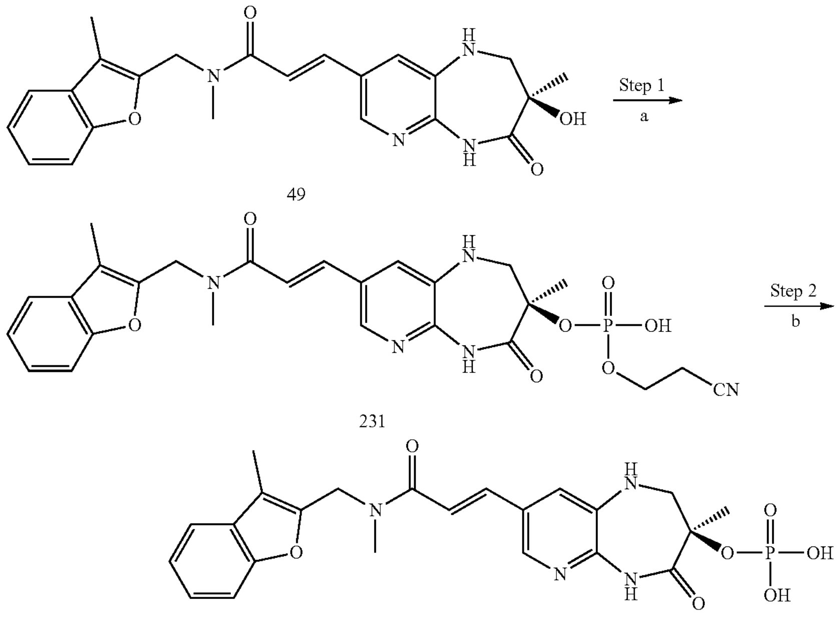

49 231 232

Reaction conditions: a) i. bis(2-cyanoethyl) diisopropylphosphoramidite, 1H-tetrazole, 1 day RT; ii. 0.1 M iodine solution (water/2,6-lutidine/THF, 1/19/80) at 0° C., 20% w/w $Na_2S_2O_3$; b) BSTFA, ACN, Barton's base, 35 min at 0° C. then HCOOH.

Step 1. 2-Cyanoethyl ((R)-3-methyl-8-((E)-3-(methyl((3-methylbenzofuran-2-yl)methyl)amino)-3-oxoprop-1-en-1-yl)-4-oxo-2,3,4,5-tetrahydro-1H-pyrido[2,3-b][1,4]diazepin-3-yl) hydrogen phosphate (compound 231). To a solution of the substrate 49 (250 mg, 0.59 mmol, 1 equiv.) in dry DCM (5.95 mL) were added bis(2-cyanoethyl) diisopropylphosphoramidite (645 mg, 2.38 mmol, 4 equiv.) and 1H-tetrazole (5.29 mL, 2.38 mmol, 4 equiv., 0.45 M in MeCN) under $N_2$ at rt. The mixture was stirred at rt for 1 day, then evaporated partially. The resulting phosphite was oxydized by treatment with a 0.1 M iodine solution (water/

2,6-lutidine/THF, 1/19/80) at 0° C. until persistence of iodine coloration. The mixture was allowed to return at rt, then after 1 h, the mixture was quenched using sodium thiosulfate 20% w/w under stirring until disappearance of iodine coloration. The aqueous phase was removed and the organic phase was dried over $Na_2SO_4$, diluted with MeOH and DCM and filtered. After evaporation, the crude was purified eluting with 5-100% MeCN (0.1% TFA) in water (0.1% TFA) to afford, after lyophilisation, the desired product 231 (165 mg, 0.30 mmol, 50%) as a yellow solid. The product was directly engaged in the next step.

Step 2. (R,E)-3-Methyl-8-(3-(methyl((3-methylbenzofuran-2-yl)methyl)amino)-3-oxoprop-1-en-1-yl)-4-oxo-2,3,4,5-tetrahydro-1H-pyrido[2,3-b][1,4]diazepin-3-yl dihydrogen phosphate (compound 232). To a solution of 231 (2.65 g, 4.79 mmol, 1 eq.) in MeCN (28.5 mL) were added N,O-bis(trimethylsilyl)trifluoroacetamide (BSTFA) (6.36 mL, 23.9 mmol, 5 eq.), then 2-tert-butyl-1,1,3,3-tetramethylguanidine (Barton's base) (4.14 mL, 19.9 mmol, 4.1 eq.). The mixture was at 0° C. for 35 min, then formic acid was added to quench the reaction. After evaporation, the crude was purified eluting with 5-100% MeCN (0.1% $HCO_2H$) in water (0.1% $HCO_2H$) and lyophilized to obtain the desired compound 232 (1.26 g, 250 mmol, 52%). $^1H$ NMR (400 MHz, DMSO-$d_6$): δ, ppm 9.89 (s, 1h), 8.05-7.96 (m, 1H), 7.61-7.53 (m, 1H), 7.52-7.02 (m, 6H), 6.20 (m, 1H), 4.95 (s, 0.8H), 4.79 (s, 1.2H), 3.62-3.41 (m, 2H), 3.17 (s, 2H), 2.95 (s, 1H), 2.31-2.21 (s, 3H). $^{31}P$ NMR (162 MHz, DMSO-$d_6$) δ−4.8. MS (Method 1c): m/z=501.1 $[M+H]^+$.

Example 48. Synthesis of [(2R,3S)-2-methyl-8-[(E)-3-[methyl-[(3-methylbenzofuran-2-yl)methyl]amino]-3-oxo-prop-1-enyl]-4-oxo-1,2,3,5-tetrahydropyrido[2,3-b][1,4]diazepin-3-yl]dihydrogen phosphate-(2R,3R,4R,5S)-6-(methylamino)hexane-1,2,3,4,5-pentol salt (Compound 235)

General Synthetic Scheme.

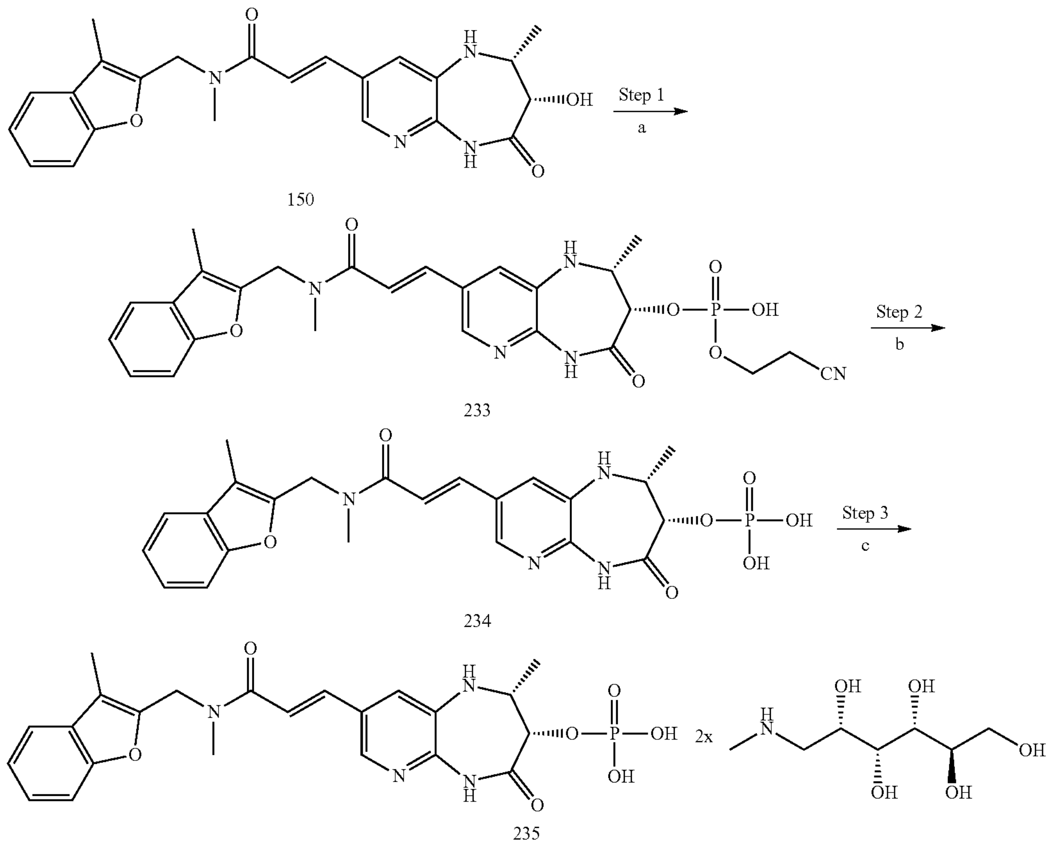

150

233

234

235

Reaction conditions: a) i. bis(2-cyanoethyl) diisopropylphosphoramidite, 1H-tertazole, 1 day, RT; ii 0.1M iodine solution (water/2,6-lutidine/THF, 1/19/80) at 0° C., 20% w/w $Na_2S_2O_3$; b) BSTFA, ACN, 2-tert-butyl-1,1,3,3-tetramethylguanidine, 35 min at 0° C. then HCOOH; c) $H_2O$ and MeCN (60 mL, 1/1), meglumine, 2 eq Step 1. 2-Cyanoethyl ((2R,3S)-2-methyl-8-((E)-3-(methyl((3-methylbenzofuran-2-yl)methyl)amino)-3-oxo-prop-1-en-1-yl)-4-oxo-2,3,4,5-tetrahydro-1H-pyrido[2,3-b][1,4]diazepin-3-yl) hydrogen phosphate (compound 233). To a mixture of 150 (129 mg, 0.31 mmol, 1 eq.) in dry $CH_2Cl_2$ (2.80 mL) were added bis(2-cyanoethyl)diisopropylphosphoramidite (0.24 mL, 0.92 mmol, 3 equiv.) and 1H-tetrazole (1.36 mL, 0.61 mmol, 2 equiv., 0.45 M in MeCN). The mixture was stirred at rt for 16 h. After completion of the reaction, a solution of 0.2 M iodine solution ($I_2$ in water/pyridine/THF, 1/19/80) was added at 0° C. until persistence of iodine coloration. The mixture was allowed to return at rt, then after 2 h, the mixture was quenched using sodium thiosulfate (20% w/w) under stirring until disappearance of iodine coloration. The aqueous phase was removed and the organic phase was dried over $Na_2SO_4$, diluted with MeOH and $CH_2Cl_2$ and filtered. After evaporation, the crude was purified eluting with 5-100% MeCN (0.1% TFA) in water (0.1% TFA) to afford, after lyophilization, the desired compound 233 (159 mg) as a yellow solid. The product was directly engaged in the next step.

Step 2. (2R,3S)-2-Methyl-8-((E)-3-(methyl((3-methylbenzofuran-2-yl)methyl)amino)-3-oxoprop-1-en-1-yl)-4-oxo-2,3,4,5-tetrahydro-1H-pyrido[2,3-b][1,4]diazepin-3-yl dihydrogen phosphate (compound 234). To a mixture of 233 (159 mg, 0.29 mmol, 1 equiv.) in dry MeCN (14.4 mL) were added N,O-bis(trimethylsilyl)trifluoroacetamide (0.31 mL, 1.15 mmol, 4 equiv.), then 2-tert-butyl-1,1,3,3-tetramethylguanidine (0.20 mL, 0.96 mmol, 3.3 equiv.). The mixture was stirred at 0° C. for 10 min, then formic acid (0.11 mL, 2.87 mmol, 10 eq.) was added to quench the reaction. After evaporation, the crude was purified eluting with 5-100% MeCN (0.1% TFA) in water (0.1% TFA) to afford, after lyophilization, the desired compound 234 (33 mg, 0.06 mmol, 22%) as a yellow solid. The desired compound was used to make meglumine salt.

Step 3. [(2R,3S)-2-Methyl-8-[(E)-3-[methyl-[(3-methylbenzofuran-2-yl)methyl]amino]-3-oxo-prop-1-enyl]-4-oxo-1,2,3,5-tetrahydropyrido[2,3-b][1,4]diazepin-3-yl]dihydrogen phosphate-(2R,3R,4R,5S)-6-(methylamino)hexane-1,2,3,4,5-pentol salt (compound 235). To a solution of the substrate 234 (1 equiv.) in water and MeCN (60 mL, 1/1) at rt was added the corresponding base (meglumine, 2 eq.). The mixture was stirred, sonicated and lyophilized to afford the desired product 235. $^1H$ NMR (400 MHz, $D_2O$): δ, ppm 7.80-7.65 (m, 1H), 7.25-7.46 (m, 7H), 4.52-4.25 (m, 2H), 4.18-4.02 (m, 3H), 3.83-3.69 (m, 6H), 3.67-3.56 (m, 4H), 3.26-3.04 (m, 4H), 2.89-2.75 (m, 6H), 2.72 (s, 6H), 1.84 (s, 3H), 1.25-1.16 (m, 6H). $^{31}P$ NMR (162 MHz, $D_2O$) δ 3.1. MS (Method 1c): m/z=501.1 [M+H]$^+$.

Example 49. Synthesis of 2-aminoethanol; (R,E)-8-(3-(((7-amino-2-methylbenzofuran-3-yl)methyl)(methyl)amino)-3-oxoprop-1-en-1-yl)-3-methyl-4-oxo-2,3,4,5-tetrahydro-1H-pyrido[2,3-b][1,4]diazepin-3-yl dihydrogen phosphate (Compound 237)

General Synthetic Scheme.

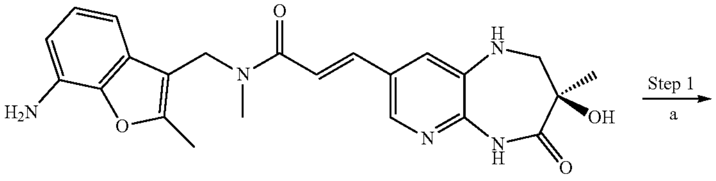

167

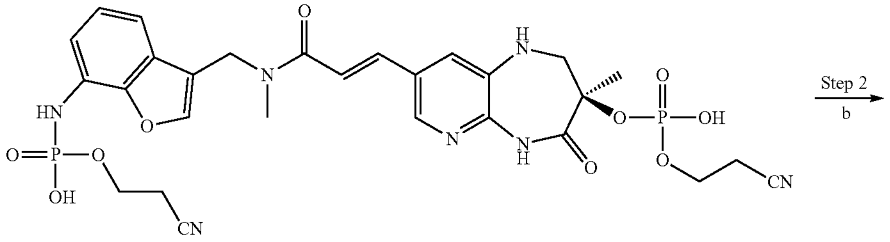

236

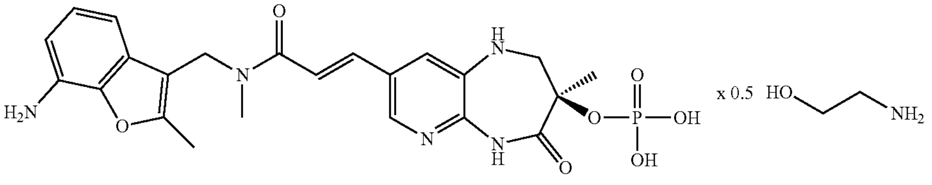

237

Reaction conditions: a) i. bis(2-cyanoethyl) diispropylphosphoramidite, 1H-tetrazole, 1 day RT; ii. 0.1 M iodine solution (water/2,6-lutidine/THF, 1/19/80) at 0° C., 20% w/w $Na_2S_2O_3$; b) i) BSTFA, ACN, Barton's base, 35 min at 0° C. then HCOOH; ii. water, $HOCH_2CH_2NH_2$ (5.0 eq.)

Step 1. 2-Cyanoethyl hydrogen (3-(((E)-3-((3R)-3-(((2-cyanoethoxy)(hydroxy)phosphoryl)oxy)-3-methyl-4-oxo-2,3,4,5-tetrahydro-1H-pyrido[2,3-b][1,4]diazepin-8-yl)-N-methylacrylamido)methyl)-2-methylbenzofuran-7-yl) phosphoramidate (compound 236). To a mixture of 167 (200 mg, 0.46 mmol, 1 eq.) in dry $CH_2Cl_2$ (4.59 mL) were added bis(2-cyanoethyl)diisopropylphosphoramidite (0.48 mL, 1.84 mmol, 4 eq.) and 1H-tetrazole (4.08 mL, 1.84 mmol, 4 eq., 0.45 M in MeCN). The mixture was stirred at rt for 16 h, then partially evaporated and a solution of 0.2 M iodine solution (water/pyridine/THF, 1/19/80) was added at 0° C. until persistence of iodine coloration. The mixture was allowed to return at rt. After 2 h, the mixture was quenched using sodium thiosulfate 20% w/w under stirring until disappearance of iodine coloration. The aqueous phase was removed and the organic phase was dried over $Na_2SO_4$, diluted with MeOH and $CH_2Cl_2$ and filtered. After evaporation, the crude was purified eluting with 5-100% MeCN (0.1% TFA) in water (0.1% TFA) to afford, after lyophilization, the desired compound 236 (245 mg) as a yellow solid.

Step 2. 2-Aminoethanol; (R,E)-8-(3-(((7-amino-2-methylbenzofuran-3-yl)methyl)(methyl)amino)-3-oxoprop-1-en-1-yl)-3-methyl-4-oxo-2,3,4,5-tetrahydro-1H-pyrido[2,3-b][1,4]diazepin-3-yl dihydrogen phosphate (compound 237).

To a mixture of 236 (240 mg, 0.34 mmol, 1 eq.) in dry MeCN (18.9 mL) were added BSTFA (0.91 mL, 3.42 mmol, 10 eq.), then 2-tert-butyl-1,1,3,3-tetramethylguanidine (Barton's base) (0.59 mL, 2.85 mmol, 8.3 eq.). The mixture was stirred at 0° C. for 5/10 min, then HCOOH was added to quench the reaction and water (1 mL). After evaporation, the crude was purified eluting with 5-100% MeCN (0.1% TFA) in water (0.1% TFA) to afford a powder containing the desired dihydrogen phosphate. The residue was dissolved in water+ethanolamine in excess (>5 equiv.). The mixture was purified eluting with 5-100% MeCN in water to afford, after lyophilization, the desired compound 237 (89 mg, 0.15 mmol, 45%) as a yellow solid. $^{1}$H NMR (400 MHz, $D_2O$): δ, ppm 7.88-7.78 (m, 1H), 7.44-7.26 (m, 2H), 7.21-6.61 (m, 4H), 4.76-4.59 (m, 2H), 3.59 (t, J=5.5 Hz, 1H), 3.55-3.46 (m, 2H), 3.00-2.81 (m, 3H), 2.77 (t, J=5.5 Hz, 1H), 2.46-2.28 (m, 3H), 1.59-1.46 (m, 3H). $^{31}$P NMR (162 MHz, $D_2O$) δ 0.0. MS (Method 1c): m/z=516.1 $[M+H]^+$.

Example 50. Synthesis of (R)-3-methyl-4-oxo-8-((E)-3-oxo-3-((3aS,6aR)-5-(4-phenoxyphenyl)-3,3a,4,6a-tetrahydrocyclopenta[c]pyrrol-2(1H)-yl)prop-1-en-1-yl)-2,3,4,5-tetrahydro-1H-pyrido[2,3-b][1,4]diazepin-3-yl dihydrogen phosphate (Compound 239)

clopenta[c]pyrrol-2(1H)-yl)prop-1-en-1-yl)-2,3,4,5-tetrahydro-1H-pyrido[2,3-b][1,4]diazepin-3-yl) hydrogen phosphate (compound 238). To a mixture of 159 (400 mg, 0.77 mmol, 1 eq.) in dry $CH_2Cl_2$ (7.65 mL) were added bis(2-cyanoethyl)diisopropylphosphoramidite (831 mg, 3.06 mmol, 4 eq.) and 1H-tetrazole (6.80 mL, 3.07 mmol, 4 eq., 0.45 M in MeCN). The mixture was stirred at rt for 16 h, then evaporated and a solution of 0.2 M iodine solution (water/pyridine/THF, 1/19/80) was added at 0° C. until persistence of iodine coloration. The mixture was allowed to return at rt, then after 2 h, the mixture was quenched using aqueous sodium thiosulfate 20% w/w until disappearance of iodine coloration. The aqueous phase was removed and the organic phase was dried over $Na_2SO_4$, diluted with MeOH and $CH_2Cl_2$ and filtered. After evaporation, the crude was purified eluting with 5-100% MeCN (0.1% TFA) in water (0.1% TFA) to afford the desired compound 238 (421 mg) as a yellow solid. The product was directly used in the next step.

Step 2. (R)-3-Methyl-4-oxo-8-((E)-3-oxo-3-((3aS,6aR)-5-(4-phenoxyphenyl)-3,3a,4,6a-tetrahydrocyclopenta[c]pyrrol-2(1H)-yl)prop-1-en-1-yl)-2,3,4,5-tetrahydro-1H-pyrido[2,3-b][1,4]diazepin-3-yl dihydrogen phosphate (compound 239). To a mixture of 238 (421 mg, 0.64 mmol, 1 eq.) in dry MeCN (35.54 mL) were added BSTFA (1.71 mL, 6.42

General Synthetic Scheme.

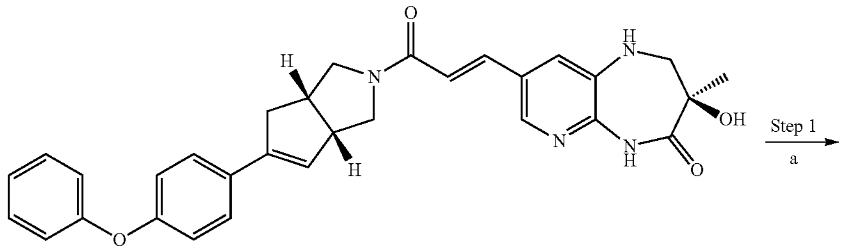

159

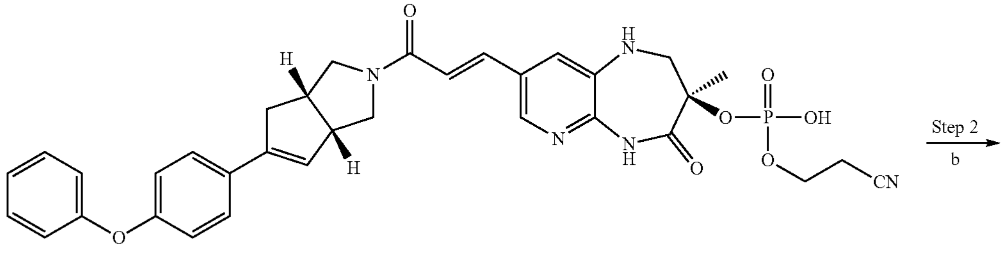

238

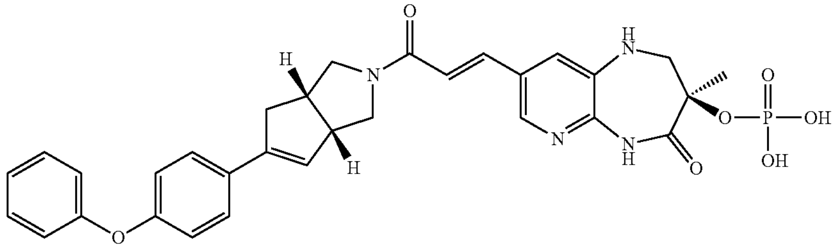

239

Reaction conditions: a) i. bis(2-cyanoethyl) diisopropylphosphoramidite, 1H-tertazole, 1 day, RT; ii. 0.1M iodine solution (water/2,6-lutidine/THF, 1/19/80) at 0° C., 20% w/w $Na_2S_2O_3$; b) BSTFA, ACN, Barton's base, 35 min at 0° C. then HCOOH.

Step 1. 2-Cyanoethyl ((R)-3-methyl-4-oxo-8-((E)-3-oxo-3-((3aS,6aR)-5-(4-phenoxyphenyl)-3,3a,4,6a-tetrahydrocymmol, 10 eq.), then Barton's base (1.11 mL, 5.35 mmol, 8.3 eq.). The mixture was stirred at rt for 5/10 min, then formic acid was added to quench the reaction. After evaporation, the residue was purified eluting with 5-100% MeCN (0.1% TFA) in water (0.1% TFA). The precipitate was recovered and lyophilized to afford the desired compound 239 (123 mg, 0.20 mmol, 32%) as a yellow solid. $^{1}$H NMR (400 MHz, DMSO-$d_6$): δ, ppm 9.89 (d, J=5.6 Hz, 1H), 8.11-7.90 (m, 1H), 7.59-7.27 (m, 7H), 7.15 (t, J=7.4 Hz, 1H), 7.09-6.93 (m, 5H), 6.86 (dd, J=15.5, 6.4 Hz, 1H), 6.13 (s, 1H), 4.15-2.78 (m, 9H), 2.62 (d, J=15.9 Hz, 1H), 1.61-1.49 (m, 3H). $^{19}$F NMR (376 MHz, DMSO-$d_6$) δ−73.6 (residual traces of TFA). $^{31}$P NMR (162 MHz, DMSO-$d_6$) δ−4.8. MS (Method 1c): m/z=603.2 $[M+H]^+$.

Example 51. Synthesis of (S,E)-8-(3-(methyl((3-methylbenzofuran-2-yl)methyl)amino)-3-oxoprop-1-en-1-yl)-4-oxo-2,3,4,5-tetrahydro-1H-pyrido[2,3-b][1,4]diazepin-3-yl dihydrogen phosphate 2,2,2-trifluoroacetate (Compound 241)

2 h, the mixture was quenched using sodium thiosulfate 20% w/w under stirring until disappearance of iodine coloration. The aqueous phase was removed and the organic phase was dried over $Na_2SO_4$, diluted with MeOH and $CH_2Cl_2$ and filtered. After evaporation, the crude was purified eluting with 5-100% MeCN (0.1% TFA) in water (0.1% TFA) to afford the desired compound 240 (199 mg) after lyophilization. The product was directly engaged in the next step.

Step 2. (S,E)-8-(3-(Methyl((3-methylbenzofuran-2-yl)methyl)amino)-3-oxoprop-1-en-1-yl)-4-oxo-2,3,4,5-tetrahydro-1H-pyrido[2,3-b][1,4]diazepin-3-yl dihydrogen phosphate 2,2,2-trifluoroacetate (compound 241). To a mixture of 240 (120 mg, 0.22 mmol, 1 eq.) in dry MeCN (12.3 mL) were added BSTFA (0.59 mL, 1.85 mmol, 8.3 eq.), then Barton's base (0.39 mL, 2.22 mmol, 10 eq.). The mixture was stirred at rt for 10 min, then formic acid (0.08 mL, 2.22 mmol, 10 eq.) was added to quench the reaction and MeOH (1 mL). After evaporation, the crude was purified eluting General Synthetic Scheme.

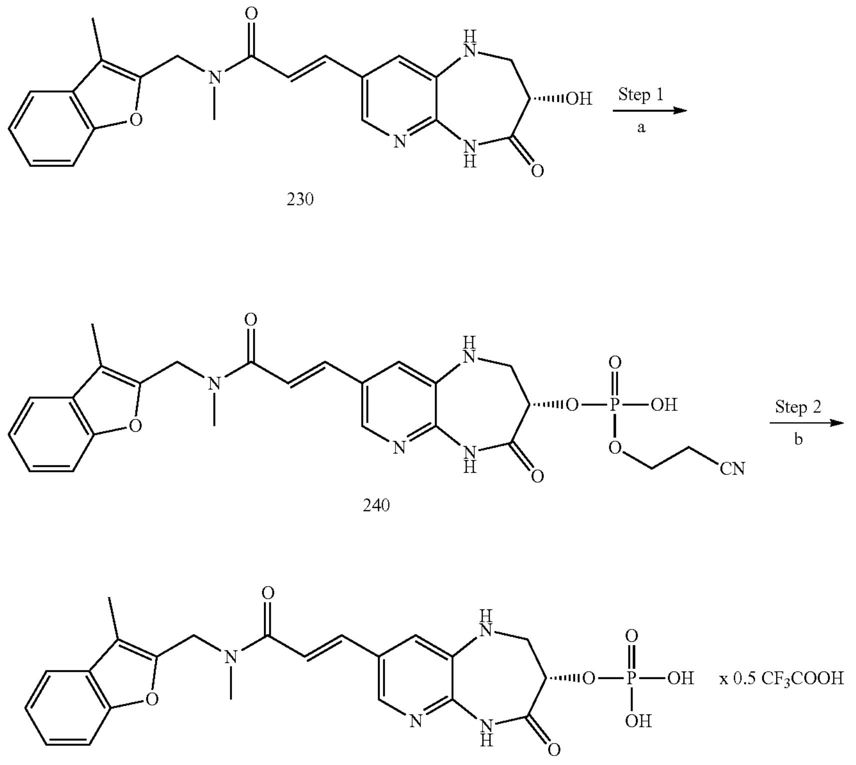

230

240

241

Reaction conditions: a) i. bis(2-cyanoethyl) diisopropylphosphoramidite, 1H-tertazole, 1 day, RT; ii. 0.1M iodine solution (water/2,6-lutidine/THF, 1/19/80) at 0° C., 20% w/w $Na_2S_2O_3$; b) BSTFA, ACN, Barton's base, 35 min at 0° C. then HCOOH.

Step 1. 2-Cyanoethyl ((S)-8-((E)-3-(methyl((3-methylbenzofuran-2-yl)methyl)amino)-3-oxoprop-1-en-1-yl)-4-oxo-2,3,4,5-tetrahydro-1H-pyrido[2,3-b][1,4]diazepin-3-yl) hydrogen phosphate (compound 240). To a mixture of 230 (200 mg, 0.49 mmol, 1 equiv.) in dry DMF (4.92 mL) were added bis(2-cyanoethyl)diisopropylphosphoramidite (0.51 mL, 1.97 mmol, 4 equiv.) and 1H-tetrazole (4.37 mL, 1.97 mmol, 4 equiv., 0.45 M in MeCN). The mixture was stirred at 60° C. for 4 hours, then MeCN was evaporated and a solution of 0.2 M iodine solution ($I_2$ in water/pyridine/THF, 1/19/80) was added at 0° C. until persistence of iodine coloration. The mixture was allowed to return at rt, then after with 5-100% MeCN (0.1% TFA) in water (0.1% TFA) to afford, after lyophilization, the desired compound (42 mg, 0.07 mmol, 31%) as a yellow solid. $^{1}$H NMR (400 MHz, DMSO-$d_6$): δ, ppm 10.23 (s, 1H), 8.18-8.04 (m, 1H), 7.57 (d, J=7.4 Hz, 1H), 7.54-7.35 (m, 4H), 7.31-7.07 (m, 3H), 6.10 (s, 1H), 4.96 (s, 0.8H), 4.80 (s, 1.2H), 4.74-4.57 (m, 1H), 3.69 (dd, J=12.3, 3.3 Hz, 1H), 3.51 (dd, J=12.3, 8.5 Hz, 1H), 3.18 (s, 1.7H), 2.95 (s, 1.3H), 2.28 (d, J=4.4 Hz, 3H). $^{31}$P NMR (162 MHz, DMSO-$d_6$) δ−1.9. $^{19}$F NMR (376 MHz, DMSO-$d_6$) δ−74.1 (traces of TFA)

MS (Method 1c): m/z=487.0 $[M+H]^+$.

Example 52. Synthesis of (R,E)-3-(6-hydroxy-6-methyl-7-oxo-5,6,7,8-tetrahydro-1,8-naphthyridin-3-yl)-N-methyl-N-((3-methylbenzofuran-2-yl)methyl) acrylamide (Compound 247)

General Synthetic Scheme.

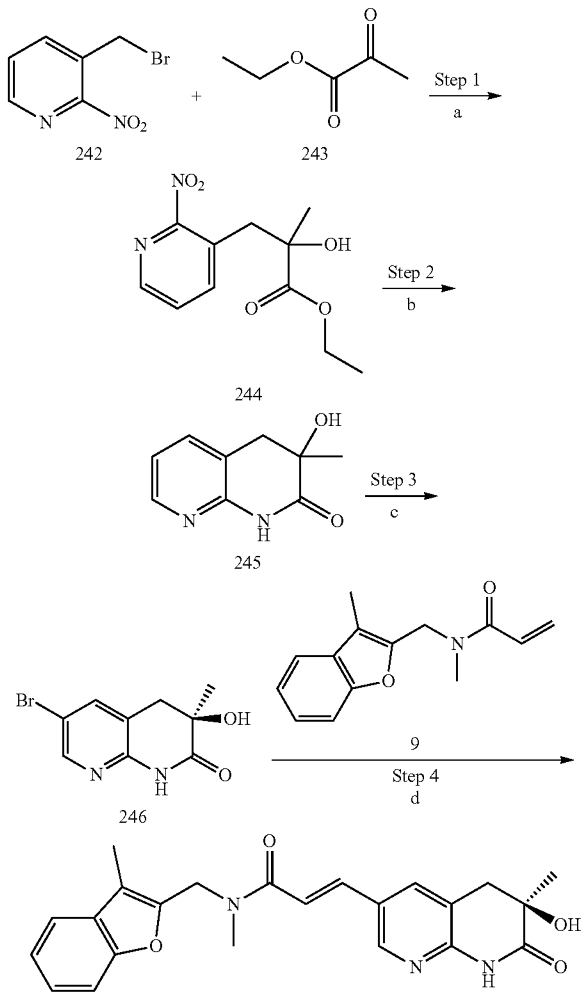

242 243 244 245 246 247

Reaction Conditions: a) N1,N2,N'1,N'1,N2,N2,N'2,N'2-octamethylethene-1,1,2,2-tetraamine, DMF, -20° C. to RT; b) Fe, $NH_4Cl$, EtOH, water, 90° C.; c) NBS, $K_2CO_3$, MeCN, followed by chiral separation; d) Pd-116, DIPEA, $NBu_4Cl$, 1,4-dioxane, 80° C.

Step 1. Ethyl 2-hydroxy-2-methyl-3-(2-nitropyridin-3-yl) propanoate (compound 244). To a stirring solution of 3-(bromomethyl)-2-nitropyridine 242 (850 mg, 3.92 mmol) in anhydrous DMF (15 mL), was added ethyl pyruvate 243 (1.3 mL, 11.8 mmol) at −20° C. The resulting solution was stirred and maintained at this temperature for 30 min. N1,N1,N'1, N'1,N2,N2,N'2,N'2-octamethylethene-1,1,2,2-tetraamine (1.0 mL, 4.31 mmol) was then added. A red colour immediately developed with the formation of a fine white precipitate. The solution was vigorously stirred at −20° C. for 1 h and then warmed up to RT for 2 h. The orange-red turbid solution was filtered and water (80 mL) was added. The aqueous layer was extracted with ethyl acetate (3×40 mL) and the combined organic extracts were washed with water (3×40 mL), dried over $MgSO_4$, filtered and concentrated in vacuo. The crude product was purified by chromatography (0-10% MeOH/DCM) to give title compound 244 as a colourless solid (630 mg, 57%). $R^t$ 1.48 min (Method 1a) m/z 255 $[M+H]^+$ $(ES^+)$.

Step 2. 3-Hydroxy-3-methyl-3,4-dihydro-1,8-naphthyridin-2(1H)-one (compound 245). To a solution of ethyl 2-hydroxy-2-methyl-3-(2-nitropyridin-3-yl)propanoate 244 (630 mg, 2.48 mmol) in ethanol (35 mL) and water (8.8 mL) were added iron (554 mg, 9.9 mmol) and ammonium chloride (530 mg, 9.91 mmol). The resulting mixture was heated under reflux for 1 h. The reaction mixture was filtered through a plug of Celite® when still hot. The filtrate was then evaporated to dryness. The crude product was purified by chromatography (0-10% MeOH/DCM) to give title compound 245 as a colourless solid (350 mg, 75%). $R^t$ 0.56 min (Method 1a) m/z 179 $[M+H]^+$ $(ES^+)$.

Step 3. (R)-6-Bromo-3-hydroxy-3-methyl-3,4-dihydro-1,8-naphthyridin-2(1H)-one (compound 246). N-Bromosuccinimide (619 mg, 3.48 mmol) and $K_2CO_3$ (962 mg, 6.96 mmol) were added in one portion to a stirred solution of 3-hydroxy-3-methyl-3,4-dihydro-1,8-naphthyridin-2(1H)-one 245 (310 mg, 1.74 mmol) in acetonitrile (20 mL) at 0° C. The reaction was allowed to warm up to RT and then stirred overnight. After this time more N-bromosuccinimide (619 mg, 3.48 mmol) and $K_2CO_3$ (962 mg, 6.96 mmol) were added and the resulting mixture was stirred for 3 h. The reaction was quenched by addition of $H_2O$ (10 mL) then extracted with DCM (3×10 mL). The combined organic layers were dried by passing through a phase separation cartridge and concentrated in vacuo. The crude product was purified by chromatography (0-100% EtOAc/isohexane) to afford the racemate as a white solid (200 mg, 42%). The racemate was submitted for a chiral separation giving first peak (R)-6-bromo-3-hydroxy-3-methyl-3,4-dihydro-1,8-naphthyridin-2(1H)-one 246 (60 mg). $R^t$ 1.19 min (Method 1a) m/z 257/259 $[M+H]^+$ $(ES^+)$. The absolute configuration arbitrarily assigned.

Step 4. (R,E)-3-(6-Hydroxy-6-methyl-7-oxo-5,6,7,8-tetrahydro-1,8-naphthyridin-3-yl)-N-methyl-N-((3-methylbenzofuran-2-yl)methyl)acrylamide (compound 247). A flask was charged with (R)-6-bromo-3-hydroxy-3-methyl-3,4-dihydro-1,8-naphthyridin-2(1H)-one 246 (60 mg, 0.23 mmol), N-methyl-N-((3-methylbenzofuran-2-yl)methyl) acrylamide 9 (54 mg, 0.23 mmol), $NBu_4Cl$ (7 mg, 0.03 mmol) and Pd-116 (12 mg, 0.03 mmol) and the flask was evacuated and backfilled with $N_2$ three times. 1,4-Dioxane (2 mL) and DIPEA (85 μL, 0.46 mmol) were added and the reaction mixture was heated to 80° C. for 2 h. Water (2 mL) was then added and the aqueous mixture was extracted with DCM (3×5 mL). The combined organic extracts were dried by passing through a phase separation cartridge and concentrated in vacuo. The crude material was purified by column chromatography (0-5% MeOH/DCM). The resulting product was triturated with MeCN (2 mL). The precipitate was collected by filtration and dried to give the title compound 247 as a pale yellow solid (30 mg, 32%). $R^t$ 1.83 min (Method 1a) m/z 406 $[M+H]^+$ $(ES^+)$. $^1H$ NMR (DMSO-$d_6$): δ, ppm 10.29 (s, 1H), 8.36 (d, J=2.2 Hz, 1H), 7.97 (d, J=2.1 Hz, 1H), 7.61-7.43 (m, 3H), 7.34-7.14 (m, 3H), 5.19 (d, J=1.5 Hz, 1H), 4.86 (s, 2H), 3.11 (s, 3H), 2.94 (s, 2H), 2.28 (s, 3H), 1.29 (s, 3H).

Example 53. Synthesis of (E)-3-(6-ethyl-6-hydroxy-7-oxo-5,6,7,8-tetrahydro-1,8-naphthyridin-3-yl)-N-methyl-N-((3-methylbenzofuran-2-yl)methyl)acrylamide (Compound 252)

General Synthetic Scheme.

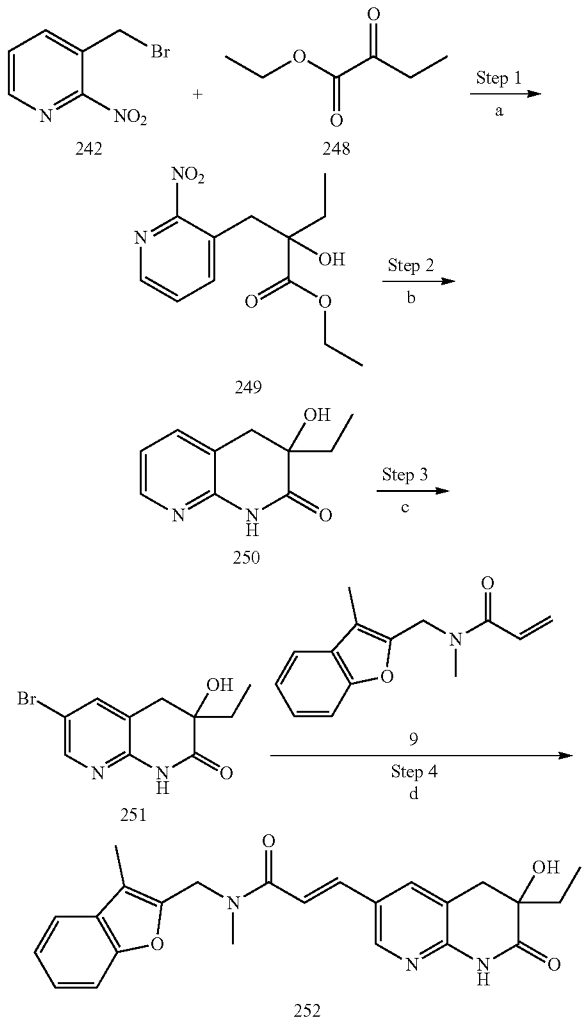

Reaction Conditions: a) N1,N2,N'1,N'1,N2,N2,N'2,N'2-octamethylethene-1,1,2,2-tetraamine, DMF, -20° C.; b) Fe, $NH_4Cl$, EtOH, water, 90° C.; c) NBS, $K_2CO_3$, ACN, 0° C.-RT; d) Pd-116, DIPEA, $NBu_4Cl$, 1,4-dioxane, 80° C.

Step 1. Ethyl 2-hydroxy-2-ethyl-3-(2-nitropyridin-3-yl) propanoate (compound 249). To a stirring solution of 3-(bromomethyl)-2-nitropyridine 242 (425 mg, 1.96 mmol) in anhydrous DMF (7.5 mL) was added ethyl 2-oxobutanoate 248 (765 mg, 5.88 mmol) at −20° C. The resulting solution was stirred for 30 min. After this time N1,N1,N'1,N'1,N2,N2,N'2,N'2-octamethylethene-1,1,2,2-tetraamine (0.5 mL, 2.15 mmol) was added. The solution was vigorously stirred at −20° C. for 1 h and then warmed up to RT and stirred for 2 h. The orange-red turbid solution was filtered and hydrolyzed with water (40 mL). The aqueous solution was extracted with ethyl acetate (3×20 mL), the combined organic layers were washed with water (3×20 mL), dried over $MgSO_4$, filtered and concentrated in vacuo. The crude product was purified by chromatography (0-10% MeOH/DCM) to afford the title compound 249 as a colourless solid (380 mg, 66%). $R^t$ 1.75 min (Method 1a) m/z 269 $[M+H]^+$ ($ES^+$).

Step 2. 3-Hydroxy-3-ethyl-3,4-dihydro-1,8-naphthyridin-2(1H)-one (compound 250). To a stirred solution of ethyl 2-hydroxy-2-((2-nitropyridin-3-yl)methyl)butanoate 249 (370 mg, 1.38 mmol) in ethanol (18 mL) and water (5 mL) was added iron (308 mg, 5.52 mmol) and ammonia hydrochloride (295 mg, 5.52 mmol). The reaction mixture was heated at 90° C. for 1 hour. The reaction mixture was allowed to cool to room temperature and was filtered through a plug of Celite®. The filtrate was evaporated to dryness and the crude product was purified by chromatography (0-10% MeOH/DCM) to afford the title compound 250 as a colourless solid (200 mg, 72%). $R^t$ 0.89 min (Method 1a) m/z 193 $[M+H]^+$ ($ES^+$).

Step 3. 6-Bromo-3-hydroxy-3-ethyl-3,4-dihydro-1,8-naphthyridin-2(1H)-one (compound 251). N-Bromosuccinimide (361 mg, 2.03 mmol) and $K_2CO_3$ (561 mg, 4.06 mmol) were added in one portion to a stirred solution of 3-ethyl-3-hydroxy-3,4-dihydro-1,8-naphthyridin-2(1H)-one 250 (195 mg, 1.01 mmol) in acetonitrile (15 mL) at 0° C. The reaction was allowed to return to RT and was stirred overnight. The reaction was filtered over a celite pad, and the solids rinsed with acetonitrile (20 mL). The filtrate was evaporated in vacuo and the crude product was purified by chromatography (0-100% EtOAc/isohexane) to afford the title compound 251 as a white solid (142 mg, 51%). $R^t$ 1.20 min (Method 2a) m/z 271/273 $[M+H]^+$ ($ES^+$). $^1H$ NMR (400 MHz, $CDCl_3$): δ, ppm 9.21 (s, 1H), 8.32 (dd, J=2.3 Hz, 1.1 Hz, 1H), 7.69 (t, J=1.7 Hz, 1H), 3.72 (s, 1H), 3.14 (d, J=16.1 Hz, 1H), 3.07 (d, J=16.1 Hz, 1H), 1.68-1.50 (m, 2H), 0.96 (t, J=7.4 Hz, 3H).

Step 4. (E)-3-(6-Ethyl-6-hydroxy-7-oxo-5,6,7,8-tetrahydro-1,8-naphthyridin-3-yl)-N-methyl-N-((3-methylbenzofuran-2-yl)methyl)acrylamide (compound 252). A reaction vial was charged with N-methyl-N-((3-methylbenzofuran-2-yl)methyl)acrylamide 9 (118 mg, 0.52 mmol), 6-bromo-3-ethyl-3-hydroxy-3,4-dihydro-1,8-naphthyridin-2(1H)-one 251 (140 mg, 0.52 mmol), tetrabutylammonium chloride hydrate (15 mg, 0.05 mmol) and Pd-116 (26 mg, 0.05 mmol) and the vial was flushed with nitrogen (5 mins). 1,4-Dioxane (8 mL) and DIPEA (180 μL, 1.03 mmol) were added to the vial, and the reaction mixture was heated to 80° C. for 50 minutes. The crude material was evaporated in vacuo and purified by chromatography (0-10% MeOH/DCM). The product was re-crystallized in DCM/hexanes (5 mL), then triturated with acetonitrile (2 mL) to give the title compound 252 as a white solid (144 mg, 66%). $R^t$ 1.59 min (Method 2a) m/z 420 $[M+H]^+$ ($ES^+$). $^1H$ NMR (400 MHz, DMSO-$d_6$, 363K): δ, ppm 10.33 (s, 1H), 8.35 (d, J=2.1 Hz, 1H), 8.01-7.97 (m, 1H), 7.61-7.53 (m, 1H), 7.53-7.44 (m, 2H), 7.32-7.20 (m, 3H), 4.95 (s, 1H), 4.86 (s, 2H), 3.11 (s, 3H), 2.97 (s, 2H), 2.28 (s, 3H), 1.66-1.48 (m, 2H), 0.89 (t, J=7.4 Hz, 3H).

Example 54. Synthesis of (R,E)-3-(7-hydroxy-7-methyl-8-oxo-8,9-dihydro-7H-pyrido[2,3-b]azepin-3-yl)-N-methyl-N-((3-methylbenzofuran-2-yl)methyl)acrylamide (Compound 260)

General Synthetic Scheme.

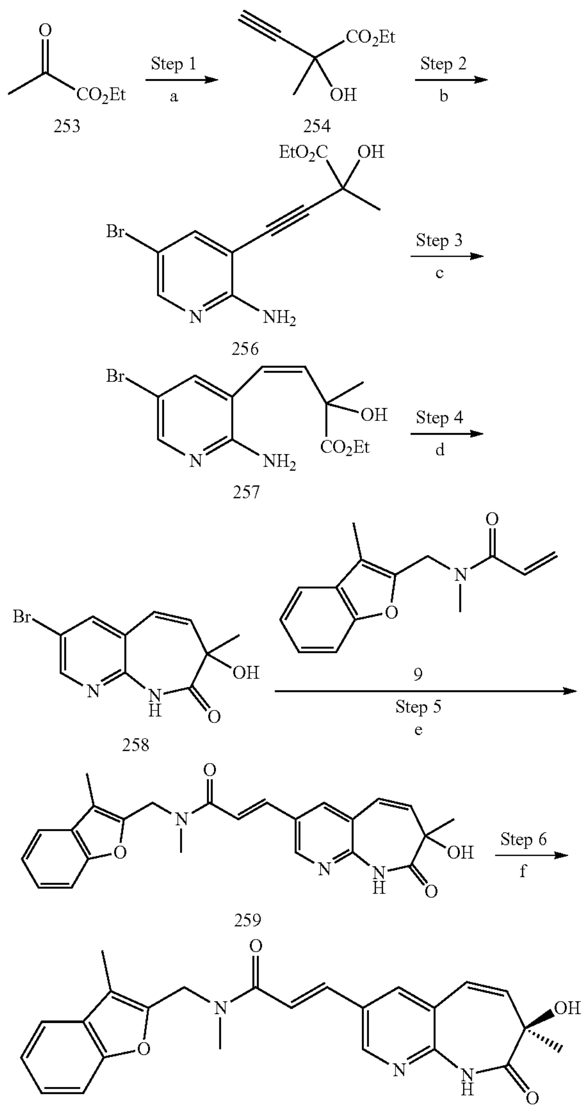

Reaction conditions: a) ethynyl magnesium bromide, -78° C. to RT; b) bis(triphenylphosphine)palladium(II)chloride, 5-bromo-3-iodo-pyridyl-2-amine 255, CuI, TEA, THF, 80° C.; c) $H_2$, Pd/C, EtOAc; d) NaH, THF, 0° C.-RT; e) Pd-116, DIPEA, $NBu_3Cl$, 1,4-Dioxane, 80° C.; f) chiral separation.

Step 1. Ethyl 2-hydroxy-2-methylbut-3-ynoate (compound 254). A solution of ethynylmagnesium bromide (0.5 M in THF, 99 ml, 49.6 mmol) was added dropwise, over ~1 h, to a solution of ethyl 2-oxopropanoate 253 (4.6 mL, 41.3 mmol) in THF (60 mL) at −78° C. The mixture was stirred at this temperature for an additional 15 mins then allowed to warm to RT. The reaction mixture was then poured onto saturated ammonium chloride solution (50 mL) and the mixture was extracted with TBME (2×30 mL). The combined organic extracts were dried over sodium sulfate, concentrated in vacuo and the crude product was purified by silica chromatography (0-40% MTBE/isohexane) to give the title compound 254 as a pale yellow oil (0.85 g, 14%). $^1$H NMR (400 MHz, DMSO-$d_6$): δ, ppm 6.28 (s, 1H), 4.15 (qd, J=7.1 Hz, 1.5 Hz, 2H), 3.46 (s, 1H), 1.51 (s, 3H), 1.21 (t, J=7.1 Hz, 3H).

Step 2. Ethyl 4-(2-amino-5-bromopyridin-3-yl)-2-hydroxy-2-methylbut-3-ynoate (compound 256). A vial was charged with copper iodide (31 mg, 0.16 mmol), bis(triphenylphosphine)palladium chloride (94 mg, 0.13 mmol) and 5-bromo-3-iodopyridin-2-amine 255 (0.80 g, 2.7 mmol) and the vial was evacuated and backfilled with $N_2$ three times. Ethyl 2-hydroxy-2-methylbut-3-ynoate 254 (0.42 g, 2.95 mmol), TEA (1.1 mL, 8.1 mmol) and THF (10 mL) were added and the mixture was degassed with $N_2$ for 10 mins before being heated to reflux for 2 h. The reaction mixture was allowed to cool to RT, filtered through a plug of Celite® and which was washed with EtOAc (20 mL). The filtrate was concentrated in vacuo and the crude product was purified by silica chromatography (0-100% EtOAc/isohexane) to afford the title compound 256 as a clear yellow oil (810 mg, 91%). R$^t$1.66 min (Method 1a); m/z 313/315 $[M+H]^+$ ($ES^+$). $^1$H NMR (400 MHz, DMSO-$d_6$): δ, ppm 8.03 (d, J=2.4 Hz, 1H), 7.66 (d, J=2.4 Hz, 1H), 6.57 (s, 1H), 6.45 (s, 2H), 4.19 (q, J=7.1 Hz, 2H), 1.61 (s, 3H), 1.23 (t, J=7.1 Hz, 3H).

Step 3. (Z)-Ethyl 4-(2-amino-5-bromopyridin-3-yl)-2-hydroxy-2-methylbut-3-enoate (compound 257). A mixture of ethyl 4-(2-amino-5-bromopyridin-3-yl)-2-hydroxy-2-methylbut-3-ynoate 256 (0.45 g, 1.44 mmol) and 5% Pd/C (0.15 g, 1.44 mmol) in EtOAc (50 mL) was stirred under $H_2$ at 1 bar for 30 min. The catalyst was removed by filtration, then the filtrate was concentrated in vacuo and purified by column chromatography (0-100% EtOAc/isohexane) to give the desired product 257 as a colourless oil (0.17 g, 27%). R$^t$ 0.98 min (Method 1a); m/z 315/317 $[M+H]^+$ ($ES^+$). $^1$H NMR (400 MHz, DMSO-$d_6$): δ, ppm 7.87 (d, J=2.5 Hz, 1H), 7.66 (d, J=2.5 Hz, 1H), 6.21 (d, J=12.1 Hz, 1H), 5.97 (s, 2H), 5.81 (d, J=12.1 Hz, 1H), 5.74 (s, 1H), 3.83-3.68 (m, 2H), 1.41 (s, 3H), 1.03 (t, J=7.1 Hz, 3H).

Step 4. 3-Bromo-7-hydroxy-7-methyl-7H-pyrido[2,3-b]azepin-8(9H)-one (compound 258). Sodium hydride (60% in mineral oil, 0.03 g, 0.79 mmol) was added in small portions to a stirred solution of (Z)-ethyl 4-(2-amino-5-bromopyridin-3-yl)-2-hydroxy-2-methylbut-3-enoate 257 (0.17 g, 0.52 mmol) in THF (15 mL) at 0° C. The reaction was allowed to warm to RT and was stirred for 2 h. The reaction was quenched by careful addition of sat. aq. $NH_4Cl$ (50 mL) and the aqueous mixture was extracted with EtOAc (3×100 mL). The combined organic layers were washed with brine (1×100 mL), dried with $MgSO_4$ and concentrated in vacuo to give the desired product 258 as an off white solid (0.17 g, quant) which was used in the next step without further purification. R$^t$ 1.38 min (Method 1a); m/z 269/271 $[M+H]^+$ ($ES^+$). $^1$H NMR (400 MHz, DMSO-$d_6$): δ, ppm 10.93 (s, 1H), 8.42 (d, J=2.4 Hz, 1H), 8.10 (d, J=2.4 Hz, 1H), 6.73 (d, J=10.9 Hz, 1H), 6.04 (d, J=10.9 Hz, 1H), 5.39 (s, 1H), 1.23 (s, 3H).

Step 5. (E)-3-(7-Hydroxy-7-methyl-8-oxo-8,9-dihydro-7H-pyrido[2,3-b]azepin-3-yl)-N-methyl-N-((3-methylbenzofuran-2-yl)methyl)acrylamide (compound 259). A flask was charged with 3-bromo-7-hydroxy-7-methyl-7H-pyrido[2,3-b]azepin-8(9H)-one 258 (0.08 g, 0.30 mmol), N-methyl-N-((3-methylbenzofuran-2-yl)methyl)acrylamide 9 (0.07 g, 0.31 mmol), $Bu_4NCl$ (9 mg, 0.03 mmol) and Pd-116 (15 mg, 0.03 mmol) and the flask was evacuated and backfilled with $N_2$ three times. 1,4-Dioxane (2.5 mL) and DIPEA (0.2 mL, 1.15 mmol) were added and the reaction mixture was heated to 80° C. and stirred for 2 h. The reaction was allowed to cool to RT, was concentrated in vacuo and purified by column chromatography (0-3% MeOH/DCM) to give the desired product 259 as a white solid (71 mg, 56%). R$^t$ 1.96 min (Method 1a); m/z 418 $[M+H]^+$ ($ES^+$). $^1H$ NMR (400 MHz, DMSO-$d_6$, 363 K): δ, ppm 10.52 (s, 1H), 8.60 (d, J=1.9 Hz, 1H), 8.14 (d, J=2.2 Hz, 1H), 7.58-7.50 (m, 2H), 7.46 (d, J=8.0 Hz, 1H), 7.39-7.17 (m, 3H), 6.72 (d, J=10.9 Hz, 1H), 6.04 (d, J=11.1 Hz, 1H), 5.08 (s, 1H), 4.87 (s, 2H), 3.11 (s, 3H), 2.27 (s, 3H), 1.22 (s, 3H).

Step 6. Chiral separation of compound 259. Chiral method separation: Apparatus: Isolera (Biotage). Column: Chiralpak IA (20 μm; glass column; 250 mm×25 mm). Eluent: CH3CN 90-Ethyl Acetate 10. Flow: 50 mL/min. Temperature: 25° C. Amount injected: 38.4 mg of 259 in 10 mL of CH3CN 90-Ethyl Acetate 10 and 2 mL of MeOH (dissolution at 50° C. in ultrasonic bath), followed by cooling and quick injection).

(R,E)-3-(7-Hydroxy-7-methyl-8-oxo-8,9-dihydro-7H-pyrido[2,3-b]azepin-3-yl)-N-methyl-N-((3-methylbenzofuran-2-yl)methyl)acrylamide (compound 260). Pure fractions of the first enantiomer were collected and concentrated to dryness. Solid was then slurried in diethyl ether, transferred in a registration vial and concentrated first under nitrogen flux then under vacuum at RT. First enantiomer was obtained as white solid (m=13.04 mg; chiral purity: 100%). The absolute configuration arbitrarily assigned.

Example 55. Synthesis of (E)-3-(3-(hydroxymethyl)-4-oxo-2,3,4,5-tetrahydro-1H-pyrido[2,3-b][1,4]diazepin-8-yl)-N-methyl-N-((3-methylbenzofuran-2-yl)methyl)acrylamide (Compound 270)

General Synthetic Scheme.

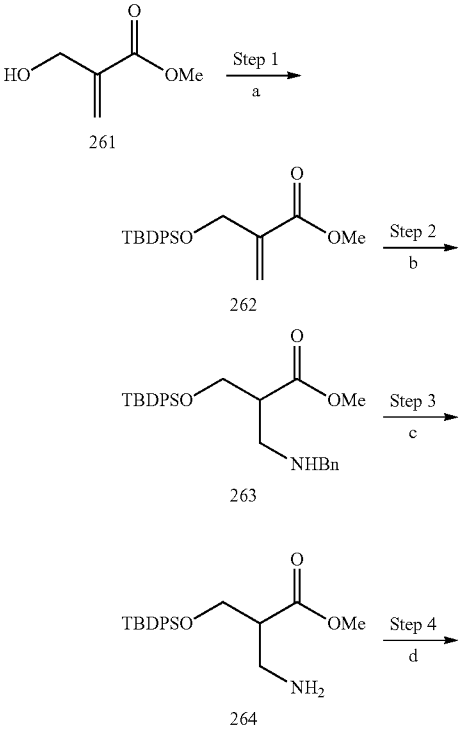

261

262

263

264

-continued

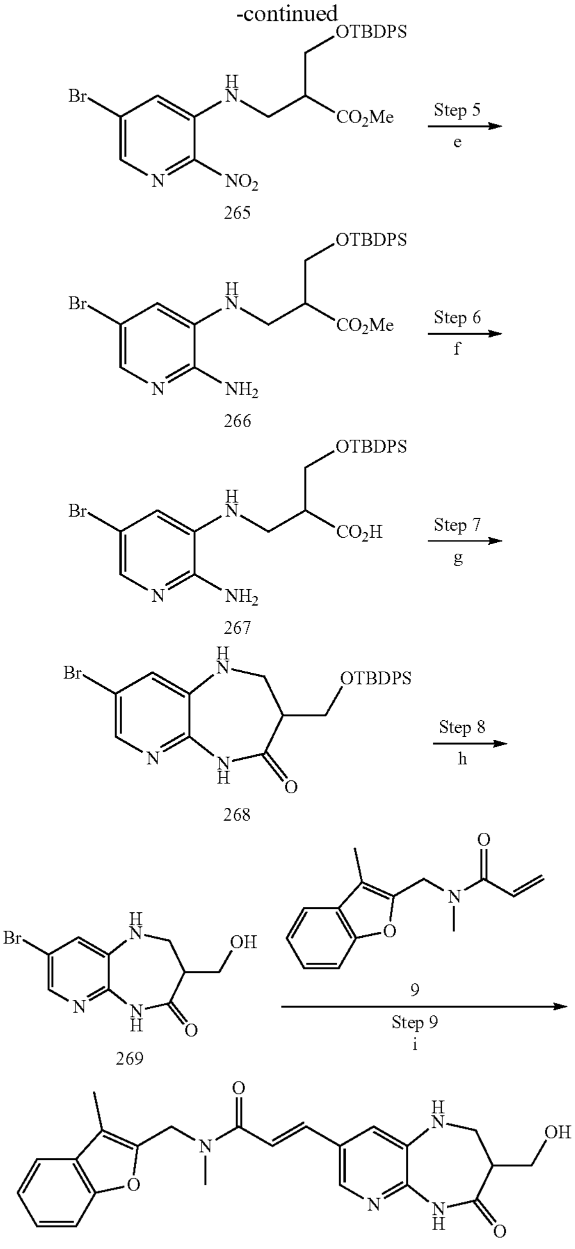

265

266

267

268

269

270

Reaction conditions: a) TBDPSCl, iimidazole, DMF, 0° C.-RT; b) Benzylamine, MeOH, 0° C.-RT; c) $H_2$, Pd/C, MeOH, 50° C.; d) 5-Bromo-3-fluoro-2-nitropyridine 11, TEA, EtOH, reflux; e) Fe, $NH_4Cl$, EtOH, $H_2O$, reflux; f) LiOH, $H_2O$, THF, MeOH; g) HATU, DIPEA, DMF; h) TBAF, THF; i) Pd-116, DIPEA, $NBu_4Cl$, 1-4-dioxane, 80° C.

Step 1. Methyl 2-(((tert-butyldiphenylsilyl)oxy)methyl) acrylate (compound 262). Imidazole (1.29 g, 19.0 mmol) and tert-butylchlorodiphenylsilane (4.95 mL, 19.0 mmol) were added to a stirred solution of methyl 2-(hydroxymethyl)acrylate 261 (1.77 mL, 17.2 mmol) in DMF (20 mL) at 0° C. The reaction was allowed to warm to RT and was stirred for ~16 h. The reaction mixture was diluted with EtOAc (30 mL) and $NaHCO_3$ (30 mL, Sat Aq) was added. The organic phase was separated and the aqueous phase was extracted again with EtOAc (3×30 mL). The combined organic fractions were washed with water (3×50 mL) and brine (2×50 mL), dried using $MgSO_4$ and concentrated in vacuo. The crude material was purified by column chromatography (0-50% EtOAc/isohexane) to give the desired product 262 as colourless oil (5.34 g, 87%). $R^t$ 3.16 min (Method 1a) m/z 377 $[M+Na]^+$ ($ES^+$). $^1H$ NMR (500 MHz, DMSO-$d_6$): δ, ppm 7.66-7.59 (m, 4H), 7.52-7.41 (m, 6H), 6.25 (q, J=1.8 Hz, 1H), 6.03 (q, J=2.0 Hz, 1H), 4.36 (s, 2H), 3.64 (s, 3H), 1.01 (s, 9H).

Step 2. Methyl 3-(benzylamino)-2-(((tert-butyldiphenylsilyl)oxy)methyl)propanoate (compound 263). Benzylamine (10% solution in MeOH, 7.4 ml, 6.77 mmol) was added dropwise to a stirred solution of methyl 2-(((tert-butyldiphenylsilyl)oxy)methyl)acrylate 262 (2.4 g, 6.77 mmol) in MeOH (30 mL) at 0° C. and the reaction was allowed to return to RT. The reaction was stirred for ~16 h, then was concentrated in vacuo and the crude material was purified by column chromatography (0-20% EtOAc/isohexane) to give the desired compound 263 as a colourless oil (0.99 g, 31%). $R^t$2.11 min (Method 1a) m/z 462 $[M+H]^+$ ($ES^+$). $^1H$ NMR (500 MHz, DMSO-$d_6$): δ, ppm 7.62-7.56 (m, 4H), 7.50-7.38 (m, 6H), 7.31-7.17 (m, 5H), 3.88-3.79 (m, 2H), 3.63 (s, 2H), 3.62 (s, 3H), 2.83 (p, J=6.6 Hz, 1H), 2.72 (dd, J=11.7 Hz, 7.0 Hz, 1H), 2.64 (dd, J=11.7 Hz, 6.8 Hz, 1H), 2.17 (s, 1H), 0.94 (s, 9H).

Step 3. Methyl 3-amino-2-(((tert-butyldiphenylsilyl)oxy)methyl)propanoate (compound 264). A solution of methyl 3-(benzylamino)-2-(((tert-butyldiphenylsilyl)oxy)methyl) propanoate 263 (1.5 g, 3.25 mmol) and palladium on carbon (0.35 g, 3.25 mmol) in MeOH (65 mL) was hydrogenated at 5 bar and 50° C. for 24 h. The palladium was removed by filtration through Celite® and the filtrate was concentrated in vacuo to give the desired product 264 as a mixture pale yellow oil (1.05 g, 87%) which was used in the next step without further purification.

Step 4. Methyl-3-((5-bromo-2-nitropyridin-3-yl)amino)-2-(((tert-butyldiphenylsilyl)oxy)methyl) propanoate (compound 265). To a stirred solution of 5-bromo-3-fluoro-2-nitropyridine 11 (630 mg, 2.83 mmol) in EtOH (15 mL) was added methyl 3-amino-2-(((tert-butyldiphenylsilyl)oxy)methyl)propanoate 264 (1.0 g, 2.83 mmol) followed by TEA (1.0 mL, 7.07 mmol). The reaction mixture was stirred at reflux for 2 h, before being concentrated in vacuo. The crude material was purified by column chromatography (0-100% ethyl acetate/isohexane) to give the title compound 265 as a brown oil (490 mg, 29%). $R^t$ 3.15 min (Method 1a) m/z 572/574 $[M+H]^+$ ($ES^+$).

Step 5. Methyl-3-((2-amino-5-bromopyridin-3-yl)amino)-2-(((tert-butyldiphenylsilyl)oxy)methyl) propanoate (compound 266). To a mixture of methyl 3-((5-bromo-2-nitropyridin-3-yl)amino)-2-(((tert-butyldiphenylsilyl)oxy)methyl)propanoate 265 (500 mg, 0.85 mmol) were added iron (190 mg, 3.42 mmol) and ammonium chloride (185 mg, 3.42 mmol) in ethanol (35 mL) and water (8.8 mL). The resulting reaction mixture was heated at 90° C. for 1 hour, before being filtered through a plug of Celite® when still hot. The filtrate was then evaporated to dryness. The crude product was purified by (0-10% MeOH/DCM) to give the title compound 266 as a colourless solid (300 mg, 64%). $R^t$ 2.59 min (Method 1a) m/z 542/544 $[M+H]^+$ ($ES^+$).

Step 6. 3-((2-Amino-5-bromopyridin-3-yl)amino)-2-(((tert-butyldiphenyl silyl)oxy)methyl)propanoic acid (compound 267). Lithium hydroxide (1 M aq., 618 μL, 0.618 mmol) was added dropwise to a stirred solution of methyl-3-((2-amino-5-bromopyridin-3-yl)amino)-2-(((tert-butyldiphenylsilyl)oxy)methyl) propanoate 266 (305 mg, 0.56 mmol) in THF (8.0 mL) and MeOH (1.5 mL). The reaction was stirred at the same temperature for 80 minutes then stored at −20° C. overnight. The mixture was quenched with AcOH (0.5 mL) and solvents evaporated in vacuum. The resulting crude material was purified by chromatography (0-10% MeOH/DCM) to give the title compound 267 as a white solid (76 mg, 25%). Rt 1.77 min (Method 2a) m/z 528/530 $[M+H]^+$ ($ES^+$).

Step 7. 8-Bromo-3-(((tert-butyldiphenylsilyl)oxy)methyl)-2,3-dihydro-1H-pyrido[2,3-b][1,4]diazepin-4(5H)-one (compound 268). DIPEA (0.13 mL, 0.72 mmol) was added to a stirred solution of 3-((2-amino-5-bromopyridin-3-yl)amino)-2-(((tert-butyldiphenylsilyl)oxy)methyl) propanoic acid 267 (76 mg, 0.14 mmol) in DMF (2.0 mL). HATU (66 mg, 0.17 mmol) was added to the mixture and the reaction mixture was stirred for 1 hour. The mixture was quenched with MeOH (4.0 mL) and partitioned between water (65 mL) and EtOAc (50 mL). The aqueous layer was extracted with EtOAc (2×50 mL) and the combined organic extracts were washed with brine (100 mL), dried with $MgSO_4$ and evaporated in vacuo to give the title compound 268 as an amber oil (101 mg, 85%) which was used in the following step without further purification. $R^t$ 2.33 min (Method 2a) m/z 510/512 $[M+H]^+$ ($ES^+$).

Step 8. 8-Bromo-3-(hydroxymethyl)-2,3-dihydro-1H-pyrido[2,3-b][1,4]diazepin-4(5H)-one (compound 269). A solution of 8-bromo-3-(((tert-butyldiphenylsilyl)oxy)methyl)-2,3-dihydro-1H-pyrido[2,3-b][1,4]diazepin-4(5H)-one 268 (101 mg, 0.12 mmol) in THF (4.0 mL) was treated TBAF (1 M in THF, 0.2 mL, 0.2 mmol). After 20 minutes the solvent was evaporated in vacuo and the crude product was purified by chromatography on silica gel (0-100% EtOAc/isohexane) to afford the title compound 269 as a white solid (26 mg, 78%). $R^t$ 0.93 min (Method 2a) m/z 272/274 $[M+H]^+$ ($ES^+$).

Step 9. (E)-3-(3-(Hydroxymethyl)-4-oxo-2,3,4,5-tetrahydro-1H-pyrido[2,3-b][1,4]diazepin-8-yl)-N-methyl-N-((3-methylbenzofuran-2-yl)methyl)acrylamide (compound 270). A vial was charged with N-methyl-N-((3-methylbenzofuran-2-yl)methyl)acrylamide 9 (22 mg, 0.096 mmol), 8-bromo-3-(hydroxymethyl)-2,3-dihydro-1H-pyrido[2,3-b][1,4]diazepin-4(5H)-one 269 (26 mg, 0.096 mmol), tetrabutylammonium chloride hydrate (2.8 mg, 9.56 μmol), Pd-116 (4.9 mg, 9.56 μmol). The vial was flushed with nitrogen for 5 min. 1,4-Dioxane (2.0 mL) and DIPEA (33 μL, 0.19 mmol) were added and the reaction mixture was heated to 80° C. for 1 hour then allowed to cool to RT. The solvent was evaporated in vacuo, and the crude material was purified by chromatography (0-10% MeOH/DCM). The resulting material was further triturated from MeCN (2.0 mL) to afford the title compound 270 as a pale yellow solid (20 mg, 49%). $R^t$ 1.45 min (Method 2a) m/z 421 $[M+H]^+$ ($ES^+$). $^1H$ NMR (DMSO-$d_6$, 363K): δ, ppm 9.18 (s, 1H), 7.98 (d, J=1.9 Hz, 1H), 7.56 (dd, J=7.4 Hz, 1.6 Hz, 1H), 7.50-7.39 (m, 2H), 7.38 (d, J=1.9 Hz, 1H), 7.32-7.20 (m, 2H), 7.12 (d, J=15.4 Hz, 1H), 5.84 (s, 1H), 4.84 (s, 2H), 4.35 (s, 1H), 3.82-3.74 (m, 1H), 3.60-3.52 (m, 2H), 3.35-3.26 (m, 1H), 3.10 (s, 3H), 2.78-2.69 (m, 1H), 2.28 (s, 3H).

Example 56. Synthesis of 2-hydroxyethan-1-aminium (R,E)-(2-methyl-8-(3-(methyl((3-methylbenzofuran-2-yl)methyl)amino)-3-oxoprop-1-en-1-yl)-4-oxo-1,2,3,4-tetrahydro-5H-pyrido[2,3-b][1,4]diazepin-5-yl)methyl phosphate (Compound 272)

General Synthetic Scheme.

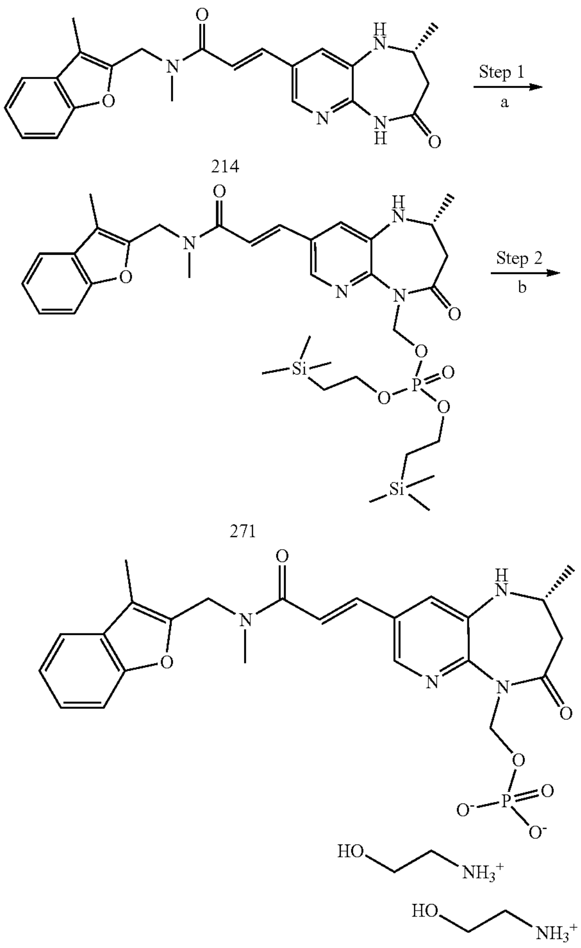

214

271

272

Reaction conditions: a) 1. 18-crown-6, NMP/N-ethylpyrrolidone, RT 2. t-BuOK at -20° C. to -35° C., then chloromethyl bis[2-(trimethylsilyl)ethyl] phosphate 21; b) TFA/DCM, long work-up Step 1. [(2R)-2-Methyl-8-[(E)-3-[methyl-[(3-methylbenzofuran-2-yl)methyl]amino]-3-oxo-prop-1-enyl]-4-oxo-2,3-dihydro-1H-pyrido[2,3-b][1,4]diazepin-5-yl]methyl bis(2-trimethylsilylethyl) phosphate (compound 271). To a 25 mL flask vial under nitrogen, containing (E)-N-methyl-N-[(3-methylbenzofuran-2-yl)methyl]-3-[(2R)-2-methyl-4-oxo-1,2,3,5-tetrahydropyrido[2,3-b][1,4]diazepin-8-yl]prop-2-enamide 214 (1.0 g, 2.47 mmol, 1 eq.) in suspension in anhydrous DMSO (10 mL) at 25° C. was added a solution of potassium 2-methylpropan-2-olate (2.6 mL, 2.6 mmol, 1.05 eq., 1M in THF) over 5 minutes under stirring. Then, the resulting orange solution was stirred at 25° C. for 15 minutes and added dropwise at 25° C. over 30 minutes to a solution of chloromethyl bis(2-(trimethylsilyl)ethyl) phosphate (4.8 mL, 3.46 mmol, 1.4 eq., 30% in hexane) under vigorous stirring. The reaction mixture was then stirred at 25° C. for 10 minutes until nearly completion as indicated by UPLC/MS (method: 3min_acid_standard; 254 nm; $R_t$=1.56 min (starting material; 7%); $R_t$=1.62 min (not determined; 4%); $R_t$=1.79 min (not determined; 4%); $R_t$=2.27 min (other regioisomer; 15%); $R_t$=2.57 min (expected product; 70%). Reaction mixture was washed with n-heptane (2×40 mL) then DMSO phase was quenched with a saturated solution of ammonium acetate (50 mL) and aqueous phase was then extracted with MTBE (4×50 mL). Combined organic phases were then washed with brine (100 mL), dried over $Na_2SO_4$, filtered and concentrated in a vacuum rotary evaporator (bath temperature: 20° C.) to give the crude title compound 271 as a yellow foam (1.686 g, 1.768 mmol, 71.5% yield). UPLC-MS (Method 1c): 3min_acid_standard; 254 nm; 75%.

Step 2. 2-Hydroxyethan-1-aminium (R,E)-(2-methyl-8-(3-(methyl((3-methylbenzofuran-2-yl)methyl)amino)-3-oxoprop-1-en-1-yl)-4-oxo-1,2,3,4-tetrahydro-5H-pyrido[2,3-b][1,4]diazepin-5-yl)methyl phosphate (compound 272). To a 100 mL three-necked flask under nitrogen, containing a solution of [(2R)-2-methyl-8-[(E)-3-[methyl-[(3-methylbenzofuran-2-yl)methyl]amino]-3-oxo-prop-1-enyl]-4-oxo-2,3-dihydro-1H-pyrido[2,3-b][1,4]diazepin-5-yl]methyl bis(2-trimethylsilylethyl) phosphate 271 (1686 mg, 1.77 mmol, 1 eq.) in anhydrous dichloromethane (27.0 mL) at −20° C. under stirring was added dropwise a solution of 2,2,2-trifluoroacetic acid (2.6 mL, 33.6 mmol, 19 eq.) in anhydrous DCM (27 mL) keeping temperature below −15° C. Then, the reaction mixture was stirred at −12° C. over 1 h 30 min until completion as indicated by UPLC/MS (sample was prepared in acetonitrile with one drop of ethanolamine; 3min_acid_standard; 254 nm; $R_t$=1.35 min (expected product; ES−: 513.2; 74%); $R_t$=1.56 min (API; 12%); $R_t$=1.81 min (hemi hydrolyzed phosphate)). Temperature was brought to −20° C. and a solution of ethanolamine (2.7 mL, 44.22 mmol, 25 eq.) in anhydrous DCM (27 mL) was added over 5 minutes. Subsequently, the reaction mixture was stirred at −15° C. for 1 h and was then concentrated (rotavapor) under deep vacuum keeping bath temp at 5° C. Then residue was slurried in 100 mL of cyclopentyl methyl ether and resulting suspension was filtered to give TFA-ethanolamine salt as a yellowish solid. The filtrate was concentrated (rotavapor) under deep vacuum keeping bath temp at 5° C. to give the crude title product as a yellow oil m=3.76 g (UPLC/MS; 3min_acid_standard; 254 nm; purity: 87%). Stored at −20° C. overnight. The product was purified by chromatoflash on Isolera equipment (Biotage). Cartridge: C18 (25 um); 120 g. Injection: crude product (3.76 g) was solubilised in 25 mL of (water 0.2% ethanolamine —$CH_3CN$ 0.2% ethanolamine (95-5)) before injection. Fractions of interest were combined and lyophilised to give the title product 272 as a yellow solid (m=738 mg) which showed an excess of ethanolamine by NMR. Product was slurried in methanol (5 mL), sonicated and suspension was filtered. Resulting pale yellow powder was washed with methanol (2×5 mL) and dried under vacuum to give the title compound 272 as a pale yellow powder (m=300.3 mg; 26.7% yield). UPLC-MS (Method 1c): 3min_acid_standard; 254 nm; purity 100% (AUC), ES−: 513.2. $^1$H NMR (400 MHz, $D_2O$): δ, ppm 8.26 (1H, dd, J=1.8, 15.0 Hz), 7.63 (1H, dd, J=2.0, 16.2 Hz), 7.54-7.32 (3H, m), 7.29-7.16 (2.5H, m), 7.04 (0.5H, d, J=15.6 Hz), 5.48-5.37 (2H, m), 4.81 (0.8H, s), 4.73 (1.2H, s), 3.99 (1H, qd, J=6.1, 18.2 Hz), 3.72 (4H, t, J=5.4 Hz), 3.15 (1.6H, s), 3.04 (4H, t, J=5.0 Hz), 3.00 (1.4H, s), 2.64-2.55 (1H, m), 2.31-2.22 (1H, m), 2.19 (1.6H, s), 2.18 (1.4H, s), 1.20 (3H, dd, J=2.8, 6.1 Hz). TFA-ethanolamine salt content: 0.07% w/w.

Example 57. Synthesis of (E)-N-[(4-amino-3-methyl-benzofuran-2-yl)methyl]-3-[(3S)-3-hydroxy-4-oxo-1,2,3,5-tetrahydropyrido[2,3-b][1,4]diazepin-8-yl]-N-methyl-prop-2-enamide (Compound 274)

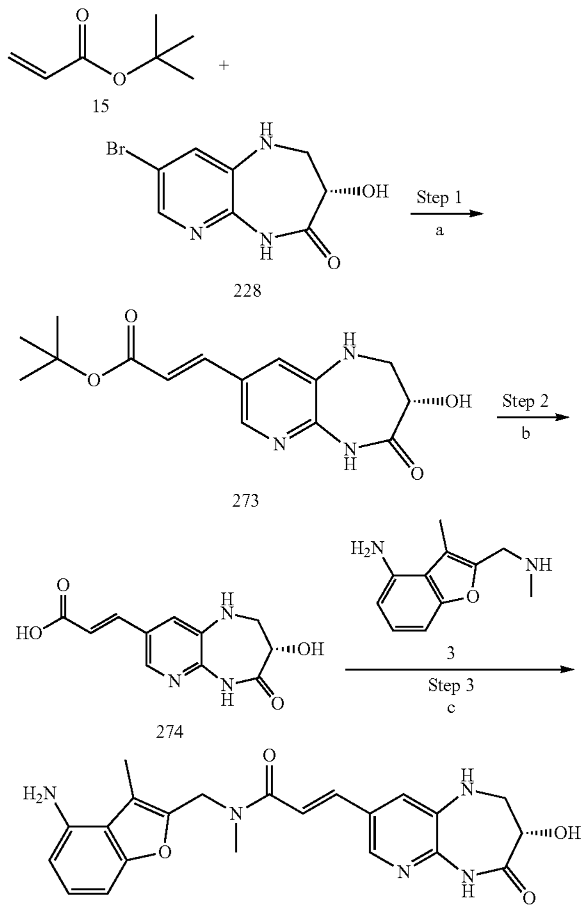

15, 228, 273, 274, 3, 275

Reaction conditions: a) Pd-162, DIPEA, n-$Bu_4NCl$, dioxane-1,4, 90° C., 5 h; TFA/DCM; c) DIPEA, HATU, DMF, rt.

Step 1. tert-Butyl (S,E)-3-(3-hydroxy-4-oxo-2,3,4,5-tetrahydro-1H-pyrido[2,3-b][1,4]diazepin-8-yl)acrylate (compound 273). A mixture of (3S)-8-bromo-3-hydroxy-1,2,3,5-tetrahydropyrido[2,3-b][1,4]diazepin-4-one 228 (182.76 mg, 0.70 mmol, 1 eq.), tetrabutylammonium chloride (23.39 mg, 0.08 mmol, 0.12 eq.), chloro(crotyl)(tri-tert-butylphosphine)palladium(II) (14.72 mg, 0.04 mmol, 0.05 eq.) were added in a flask under nitrogen atmosphere. The flask was purged and backfilled with nitrogen. 1,4-Dioxane (4.95 mL), tert-butyl acrylate 15 (0.24 mL, 1.68 mmol, 2.4 eq.), and DIPEA (0.24 mL, 1.4 mmol, 2.0 eq.) were added and nitrogen bubbled through the mixture for 5 mins. The reaction mixture was heated at 90° C. for 5 h. After cooling, the mixture was filtered using 0.22 uM PTFE filters. Filters were then washed with DCM/MeOH 50/50. The combined filtrate were concentrated under reduced pressure until dryness. ACN was added and the resulting yellow suspension was put in ultrasound bath for a few minutes and then filtered over porosity 3 frit. The resulting yellow solid was washed with a cold ether to afford 273 (110 mg, 0.35 mmol, 51.07% yield) as a yellow solid. UPLC-MS (Method 1c): m/z 306.1 $[M+H]^+$ $(ES^+)$.

Step 2. (S,E)-3-(3-Hydroxy-4-oxo-2,3,4,5-tetrahydro-1H-pyrido[2,3-b][1,4]diazepin-8-yl)acrylic acid (compound 274). tert-Butyl (S,E)-3-(3-hydroxy-4-oxo-2,3,4,5-tetrahydro-1H-pyrido[2,3-b][1,4]diazepin-8-yl)acrylate 273 (110. mg, 0.36 mmol, 1.0 eq.) was diluted with DCM (0.23 mL) and cooled to 0° C. Trifluoroacetic acid (0.23 mL) was added dropwise. The resulting yellow solution was stirred for 3 hours. UPLC analysis showed the complete conversion. Volatiles were removed under reduced pressure and the resulting residue was treated with a cold ether. The resulting suspension was put in ultrasound bath and filtered. The resulting yellow solid was dried overnight under high vacuum to afford the title compound 274 (90 mg, 0.35 mmol, 98.23% yield) as a yellow solid. UPLC-MS (Method 1c): m/z 250.1 $[M+H]^+$ $(ES^+)$.

Step 3. (E)-N-[(4-Amino-3-methyl-benzofuran-2-yl)methyl]-3-[(3S)-3-hydroxy-4-oxo-1,2,3,5-tetrahydropyrido[2,3-b][1,4]diazepin-8-yl]-N-methyl-prop-2-enamide (compound 275). 3-Methyl-2-(methylaminomethyl)benzofuran-4-amine 3 (32.1 mg, 0.169 mmol, 1.2 eq.) and ((S,E)-3-(3-Hydroxy-4-oxo-2,3,4,5-tetrahydro-1H-pyrido[2,3-b][1,4]diazepin-8-yl)acrylic acid 274 (35.1 mg, 0.141 mmol, 1.0 eq.) were dissolved in DMF (0.7 mL). Subsequently, HATU (83.76 mg, 0.21 mmol, 1.5 equiv.) was added in one portion. To this, DIPEA (0.098 mL, 0.564 mmol, 4.0 eq.) was added dropwise at RT and the resulting mixture was stirred at RT for 1 h. The resulting brown reaction mass was concentrated under high vacuum (without work-up), the crude brown material was dissolved in a mixture of $MeCN/H_2O$ (5 mL, 4:1 v/v, 2 injections) and purified by semi-preparative HPLC (98-100-30 min; 90% solvent A, 10% solvent B, 30 min) and lyophilized overnight to afford the title compound 275 as a yellow powder with a purity of 89.19% (49 mg, 82% yield). The solid, thus obtained, was dried and solubilized in DMSO (0.5-1 mL) and added slowly into a water (6 mL). Quickly precipitating product with a purity of 93.14% was recovered by centrifugation and lyophilized overnight. The beige powder was obtained (10.5 mg). UPLC-MS (Method 1c): m/z 422.1 $[M+H]^+$ $(ES^+)$; $t_{ret}$=1.02 min. $^1H$ NMR (400 MHz, DMSO-$d_6$): δ, ppm 10.07 (s, 1H), 7.97-7.94 (m, 1H), 7.37-7.28 (m, 2.4H), 7.06 (d, J=15.4 Hz, 0.6H), 6.84 (t, J=8.0 Hz, 1H), 6.58-6.56 (d, 1H), 6.30 (d, J=7.8 Hz, 1H), 6.02 (br m, 1H), 5.13-5.11 (m, 3H), 4.77, 4.62 (rotamers, 2s, 2H), 4.08-4.06 (m, 1H), 3.41-3.38 (m, 1H), 3.21-3.16 (m, 1H), 3.01, 2.84 (rotomers, 2s, 3H), 2.34 (s, 3H).

Example 58. Synthesis of (S,E)-N-((7-amino-2-methylbenzofuran-3-yl)methyl)-3-(3-hydroxy-4-oxo-2,3,4,5-tetrahydro-1H-pyrido[2,3-b][1,4]diazepin-8-yl)-N-methylacrylamide (Compound 276)

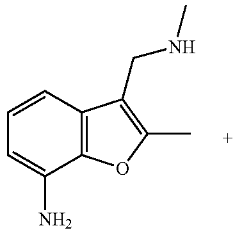

74

-continued

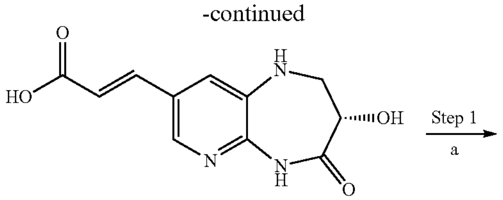

274

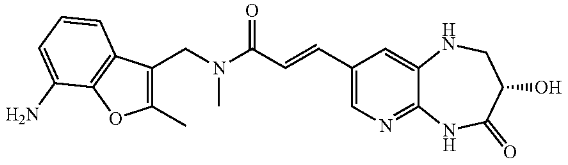

276

Reaction conditions: a) DIPEA, HATU, DMF, rt.

Step 1. (S,E)-N-((7-Amino-2-methylbenzofuran-3-yl)methyl)-3-(3-hydroxy-4-oxo-2,3,4,5-tetrahydro-1H-pyrido[2,3-b][1,4]diazepin-8-yl)-N-methylacrylamide (compound 276). 2-Methyl-3-((methylamino)methyl)benzofuran-7-amine 74 (31 mg, 0.164 mmol, 1.2 eq.) and (S,E)-3-(3-Hydroxy-4-oxo-2,3,4,5-tetrahydro-1H-pyrido[2,3-b][1,4]diazepin-8-yl)acrylic acid 274 (34.14 mg, 0.137 mmol, 1.0 eq.) were dissolved in DMF (0.7 mL). Subsequently, HATU (81.37 mg, 1.5 mmol, 1.5 equiv.) was added in one portion. To this, DIPEA (0.096 mL, 0.54 mmol, 4.0 eq.) was added dropwise at RT and the resulting mixture was stirred at RT for 2 hrs. The resulting brown reaction mass was treated with water (5 mL). Quickly precipitating product was collected by centrifugation. The yellow solid with a purity of 66.53% was isolated (48 mg). The resulting impure material was re-purified by preparative HPLC. The yellow product, was suspended in a mixture of 4 mL of MeOH/DCM (sonication 1-2 min) and transferred into a 4 mL barcoded vial. After solvent evaporation and drying under high vacuum overnight at RT, the yellow solid with a purity of 100% (9.6 mg, 16.6% yield) was obtained. $^1$H NMR (400 MHz, DMSO-$d_6$): δ, ppm 10.14 (s, 1H), 8.05-8.01 (m, 1H), 7.49-7.38 (m, 2.3H), 7.06 (d, J=15.4 Hz, 0.7H), 6.84 (t, J=7.7 Hz, 1H), 6.74, 6.57 (2 d, 1H), 6.48 (d, J=7.5 Hz, 1H), 6.08 (br m, 1H), 5.20 (d, J=4.6 Hz, 2H), 5.16 (s, 1H), 4.82, 4.67 (rotamers, 2s, 2H), 4.15-4-12 (m, 1H), 3.47 (ddd, J=3.3, 6.1 and 12.2 Hz, 1H), 3.28-3.22 (m, 1H), 3.01, 2.82 (rotomers, 2s, 3H), 2.50, 2.45 (rotamers, 2s, 3H). UPLC-MS (Method 1c): m/z 422.1 $[M+H]^+$ $(ES^+)$; $t_{ret}$=1.00 min.

Example 59. Synthesis of (R,E)-(3-hydroxy-3-methyl-8-(3-(methyl((3-methylbenzofuran-2-yl)methyl)amino)-3-oxoprop-1-en-1-yl)-4-oxo-1,2,3,4-tetrahydro-5H-pyrido[2,3-b][1,4]diazepin-5-yl)methyl decanoate (Compound 282)

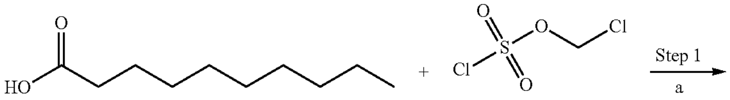

277 278

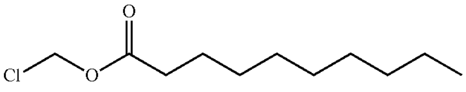

279

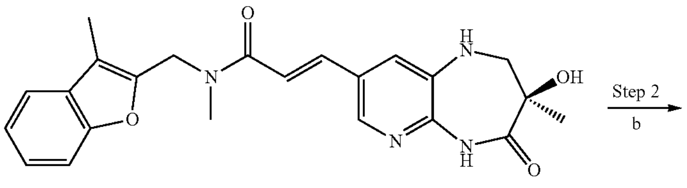

49

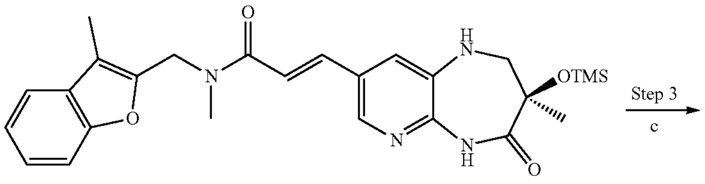

280

-continued

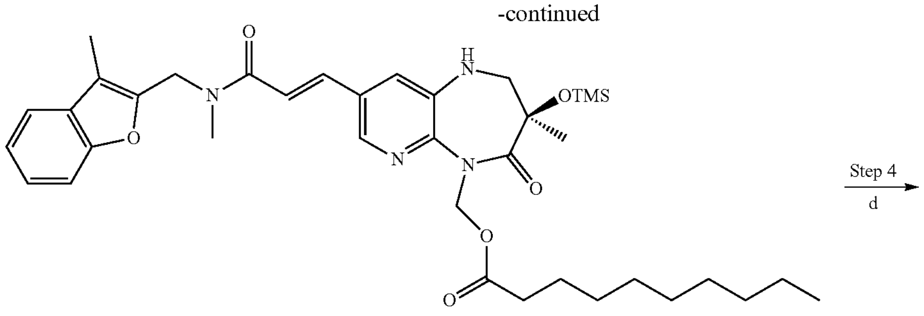

281

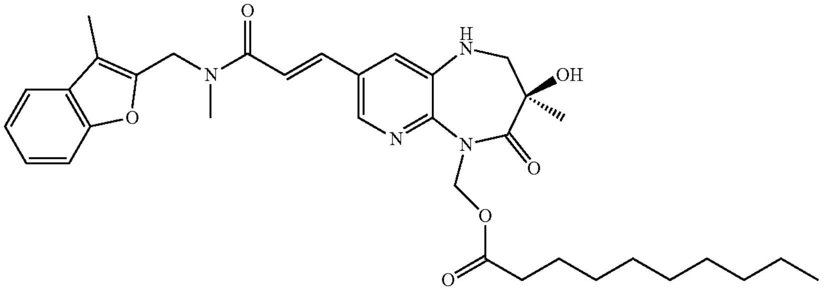

282

Reaction conditions: a) n-$Bu_4$•$HSO_4$, $NaHCO_3$, DCM/$H_2O$ (1:1 V/V), 0° C. to RT, overnight; b) 1-methyl-1H-imidazole, DMSO, RT; c) tBuOK, DMSO, RT, 30 min d) 1M aq. HCl Step 1. Chloromethyl decanoate (compound 279). Decanoic acid 277 (1.0 g, 5.69 mmol, 1.0 eq.), tetrabutylammonium hydrogensulfate (99.57 mg, 0.28 mmol, 0.05 eq.) and sodium bicarbonate (1.92 g, 22.76 mmol, 4.0 eq.) were mixed in the flask. DCM (20 mL) and water (20 mL) were added. The resulting biphasic solution was cooled to 0° C. and then treated with a solution of chloromethyl sulfurochloridate 278 (1.03 g, 6.26 mmol, 1.1 eq.) in DCM (0.5 mL). The mixture was stirred at 0° C. for 40 mins and then at RT overnight. The reaction mixture was diluted with water and was extracted twice with DCM. The combined organic layers were dried over $MgSO_4$ to afford chloromethyl decanoate 279 (0.89 g, 4.06 mmol, 71.35% yield) as a colourless oil.

Step 2. (R,E)-N-Methyl-3-(3-methyl-4-oxo-3-((trimethylsilyl)oxy)-2,3,4,5-tetrahydro-1H-pyrido[2,3-b][1,4]diazepin-8-yl)-N-((3-methylbenzofuran-2-yl)methyl)acrylamide (compound 280). To 1-methyl-1H-imidazole (1.33 mL, 16.65 mmol, 7.0 eq.) in solution in anhydrous DMSO (10 mL) was added (E)-3-[(3R)-3-hydroxy-3-methyl-4-oxo-2,5-dihydro-1H-pyrido[2,3-b][1,4]diazepin-8-yl]-N-methyl-N-[(3-methylbenzofuran-2-yl)methyl]prop-2-enamide 49 (1.0 g, 2.38 mmol, 1.0 eq.) in one portion at RT. The yellow solution was stirred at RT for 5 mins, TMSCl (1.54 mL, 11.89 mmol, 5.0 eq.) was then added in one portion. The reaction mixture was stirred at RT for 1 h, diluted with water and brine (1:1 v/v) and extracted with AcOEt (3×). The combined organic phases were washed with brine, dried over $MgSO_4$, filtered and concentrated to dryness to give the title compound 280 (1.12 g, 2.27 mmol, 95.59% yield) as an yellow solid. UPLC-MS (Method 1c): Rt=2.04 min. ES+=493.3.

Step 3. (R,E)-(3-Methyl-8-(3-(methyl((3-methylbenzofuran-2-yl)methyl)amino)-3-oxoprop-1-en-1-yl)-4-oxo-3-((trimethylsilyl)oxy)-1,2,3,4-tetrahydro-5H-pyrido[2,3-b][1,4]diazepin-5-yl)methyl decanoate (compound 281). (R,E)-N-Methyl-3-(3-methyl-4-oxo-3-((trimethylsilyl)oxy)-2,3,4,5-tetrahydro-1H-pyrido[2,3-b][1,4]diazepin-8-yl)-N-((3-methylbenzofuran-2-yl)methyl)acrylamide 280 (0.569 g, 1.16 mmol, 1.0 eq.) was diluted with DMSO (5 mL). To the resulting yellow solution potassium 2-methylpropan-2-olate (150.07 mg, 1.27 mmol, 1.1 eq.) was added. This reaction mixture was added dropwise over 7 mins to a vial containing chloromethyl decanoate 279 (1.02 g, 4.62 mmol, 4.0 eq). The reaction mass was stirred at RT for 30 mins, diluted with water and extracted twice with EtOAc. The combined organic layers were washed with brine, dried over $MgSO_4$ and was concentrated to dryness. The residue was purified on silicagel using SNAP Ultra column (50 g) and DCM/EtOAc 90/10 to 0/100 as eluent. Good fractions were collected and concentrated to dryness to afford product 281 as a beige foam (67 mg, 24% yield). UPLC-MS (Method 1c): Rt=2.91 min. ES+=677.5.

Step 4. (R,E)-(3-Hydroxy-3-methyl-8-(3-(methyl((3-methylbenzofuran-2-yl)methyl)amino)-3-oxoprop-1-en-1-yl)-4-oxo-1,2,3,4-tetrahydro-5H-pyrido[2,3-b][1,4]diazepin-5-yl)methyl decanoate (compound 282). (R,E)-(3-methyl-8-(3-(methyl((3-methylbenzofuran-2-yl)methyl)amino)-3-oxoprop-1-en-1-yl)-4-oxo-3-((trimethylsilyl)oxy)-1,2,3,4-tetrahydro-5H-pyrido[2,3-b][1,4]diazepin-5-yl)methyl decanoate 281 was dissolved in MeOH (2 mL). 1M HCl in water (0.58 mL, 0.57 mmol, 2.0 eq) was added at RT. After 10 mins of stirring at room temperature, the UPLC analysis showed complete conversion. The reaction mixture was concentrated to dryness to afford an yellow oil which was diluted with EtOAc and washed twice with a sat. aq. solution of $NaHCO_3$. The combined organic layers was dried over $MgSO_4$ and concentrated to dryness. This crude product was purified by flash chromatography using SNAP Ultra column (25 g) and DCM/AcOEt 50/50 to 0/100 as an eluent. Good fractions were collected and concentrated to dryness to afford lipophilic prodrug 282 as a beige solid (103 mg, 0.16 mmol, 56.17% yield). UPLC-MS (Method 1c): Rt=2.46 min ES+=605.4. $^1H$ NMR (400 MHz, DMSO-$d_6$):

δ, ppm 7.88-7.85 (m, 1H), 7.65-7.63 (m, 1H), 7.60 (d, J=15.6 Hz, 1H), 7.50 (d, J=7.3 Hz, 1H), 7.40 (d, J=7.9 Hz, 1H), 7.28-7.20 (m, 2H), 7.20-7.06 (m, 1H), 6.79 (d, J=15.4 Hz, 1H), 5.26-5.17 (m, 2H), 4.86, 4.69 (2s, 2H, rotamers), 4.08 (br s, 1H), 3.72 (d, J=11.9 Hz, 1H), 3.25 (d, J=12.4 Hz, 1H), 3.21, 3.07 (2s, 3H, rotamers), 2.30 (s, 3H), 2.23-2.19 (m, 2H), 1.61 (s, 3H), 1.55-1.51 (m, 2H), 1.15-1.35 (m, 12H), 0.86 (t, J=6.6 Hz, 3H).

Example 60. Synthesis of (R,E)-(3-hydroxy-3-methyl-8-(3-(methyl((3-methylbenzofuran-2-yl)methyl)amino)-3-oxoprop-1-en-1-yl)-4-oxo-1,2,3,4-tetrahydro-5H-pyrido[2,3-b][1,4]diazepin-5-yl)methyl 2-ethylbutanoate (Compound 286)

General Synthetic Scheme.

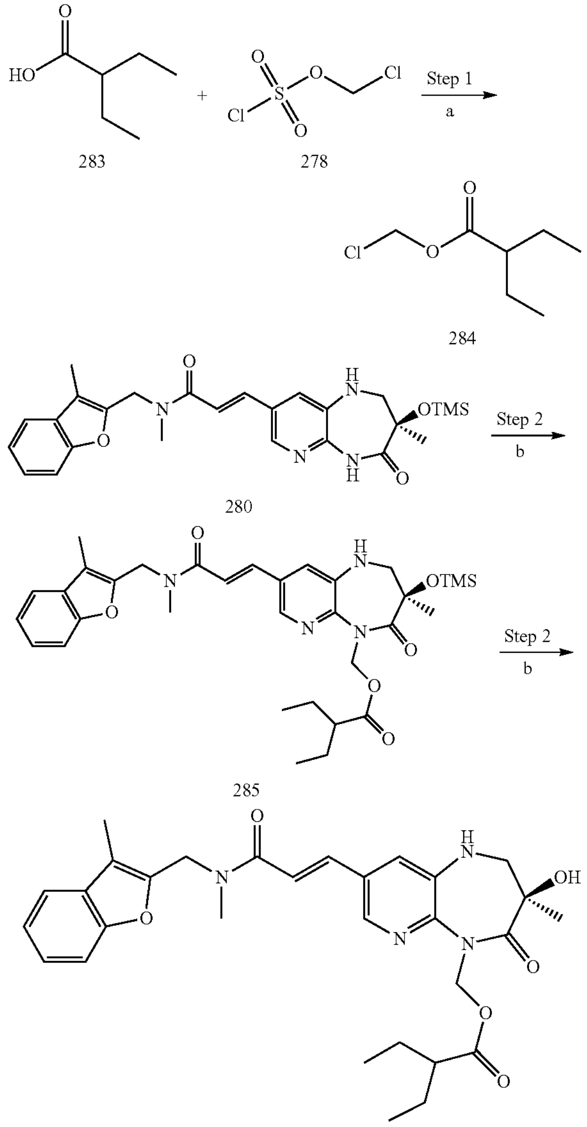

283
278
284
280
285
286

Reaction conditions: a) n-$Bu_4N$•$HSO_4$, $NaHCO_3$, DCM/$H_2O$ (1:1 V/V), 0° C. to RT, overnight; b) tBuOK, DMSO, RT, 30 min; c) 1M aq. HCl Step 1. Chloromethyl 2-ethylbutanoate (compound 284) was synthesized from 2-ethylbutanoic acid (283) and chloromethyl sulfurochloridate 278 as described for compound 279 (77.5% yield).

Step 2. (R,E)-(3-Methyl-8-(3-(methyl((3-methylbenzofuran-2-yl)methyl)amino)-3-oxoprop-1-en-1-yl)-4-oxo-3-((trimethylsilyl)oxy)-1,2,3,4-tetrahydro-5H-pyrido[2,3-b][1,4]diazepin-5-yl)methyl 2-ethylbutanoate (compound 285) was obtained according to the procedure described for compound 281 (49% yield). UPLC-MS (Method 1c): Rt=2.54 min ES+=621.4.

Step 3. (R,E)-(3-Hydroxy-3-methyl-8-(3-(methyl((3-methylbenzofuran-2-yl)methyl)amino)-3-oxoprop-1-en-1-yl)-4-oxo-1,2,3,4-tetrahydro-5H-pyrido[2,3-b][1,4]diazepin-5-yl)methyl 2-ethylbutanoate (compound 286) was obtained as described for compound 282 (79% yield). UPLC-MS (Method 1c): Rt=1.96 min. ES+=549.3. 1H NMR (400 MHz, DMSO-$d_6$): δ, ppm 7.87-7.84 (m, 1H), 7.67 (t, J=6.9 Hz, 1H), 7.59 (d, J=15.4 Hz, 1H), 7.48 (d, J=7.2 Hz, 1H), 7.39 (d, J=7.9 Hz, 1H), 7.28-7.20 (m, 2H), 7.06-7.04 (m, 1.3H), 6.79 (d, J=15.4 Hz, 0.7H), 5.27-5.19 (m, 2H), 4.82, 4.69 (2s, 2H, rotamers), 4.08 (br s, 1H), 3.76 (d, J=11.9 Hz, 1H), 3.21-3.18 (m, 1H), 3.20, 3.08 (2s, 3H, rotamers), 2.30 (s, 3H), 2.15-2.09 (m, 1H), 1.59 (s, 3H), 1.56-1.37 (m, 4H), 0.81-0.72 (m, 6H).

Example 61. Synthesis of (E)-N-((7-amino-2-methylbenzofuran-3-yl)methyl)-3-(2,2-dimethyl-3-oxo-1,2,3,4-tetrahydropyrido[2,3-b]pyrazin-7-yl)-N-methylacrylamide (Compound 287)

General Synthetic Scheme.

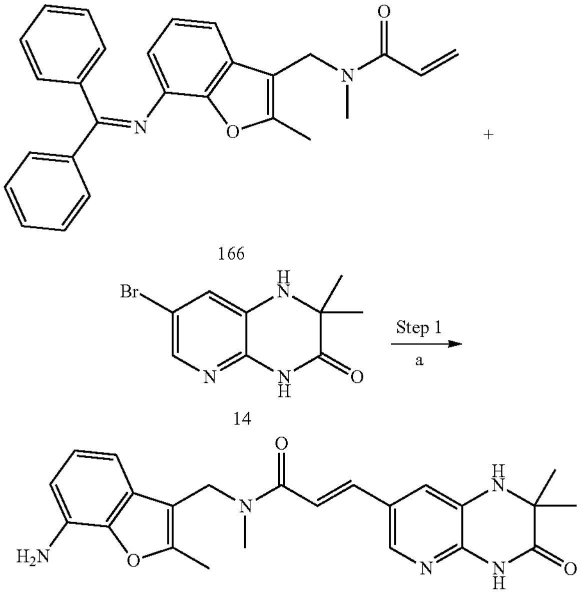

166
14
287

Reaction conditions: a) i) Pd-116, DIPEA, 1,4-dioxane, 80° C.; ii) HCl, MeOH

Step 1. (E)-N-((7-Amino-2-methylbenzofuran-3-yl)methyl)-3-(2,2-dimethyl-3-oxo-1,2,3,4-tetrahydropyrido[2,3-b]pyrazin-7-yl)-N-methylacrylamide (compound 287). To a mixture of N-((7-((diphenylmethylene)amino)-2-methylbenzofuran-3-yl)methyl)-N-methylacrylamide 166 (72 mg, 0.18 mmol), 7-bromo-2,2-dimethyl-1,2-dihydropyrido[2,3-b]pyrazin-3(4H)-one 14 (45 mg, 0.18 mmol) and Pd-116 (9 mg, 0.02 mmol) was added 1,4-dioxane (2 mL) and DIPEA (0.06 mL, 0.35 mmol). The reaction mixture was purged with $N_2$, heated to 80° C. and stirred for 1 h. The reaction mixture was allowed to cool to RT, then was diluted with MeOH (2 mL) and HCl was added (5 mL, 1M Aq). The resulting mixture was stirred for 10 min then was diluted with HCl (5 mL, 1M Aq). The aqueous layer was extracted with DCM (3×10 mL), neutralised with solid $NaHCO_3$ until ~pH 8 and extracted with DCM (3×10 mL). The combined organic layers were washed with brine (20 mL), passed through a phase separator and concentrated in vacuo. The crude product was purified by chromatography (0-10% MeOH/DCM) to afford the title compound 287 as a pale yellow solid (26 mg, 34%). $R^t$ 1.51 min (Method 1a) m/z 420 $(M+H)^+$ $(ES^+)$. $^1H$ NMR (DMSO-$d_6$, 363 K): δ, ppm 10.41 (s, 1H), 7.88 (d, J=1.9 Hz, 1H), 7.46 (d, J=15.4 Hz, 1H), 7.24 (d, J=1.9 Hz, 1H), 7.03 (d, J=15.4 Hz, 1H), 6.88 (t, J=7.7 Hz, 1H), 6.75 (d, J=7.7 Hz, 1H), 6.54 (dd, J=7.8, 1.2 Hz, 1H), 6.04 (s, 1H), 4.88 (s, 2H), 4.72 (s, 2H), 2.98 (s, 3H), 2.47 (s, 3H), 1.30 (s, 6H).

Example 62. Synthesis of (E)-N-((7-amino-2-methylbenzofuran-3-yl)methyl)-3-((2R,3S)-3-hydroxy-2-methyl-4-oxo-2,3,4,5-tetrahydro-1H-pyrido[2,3-b][1,4]diazepin-8-yl)-N-methylacrylamide (Compound 290)

General Synthetic Scheme.

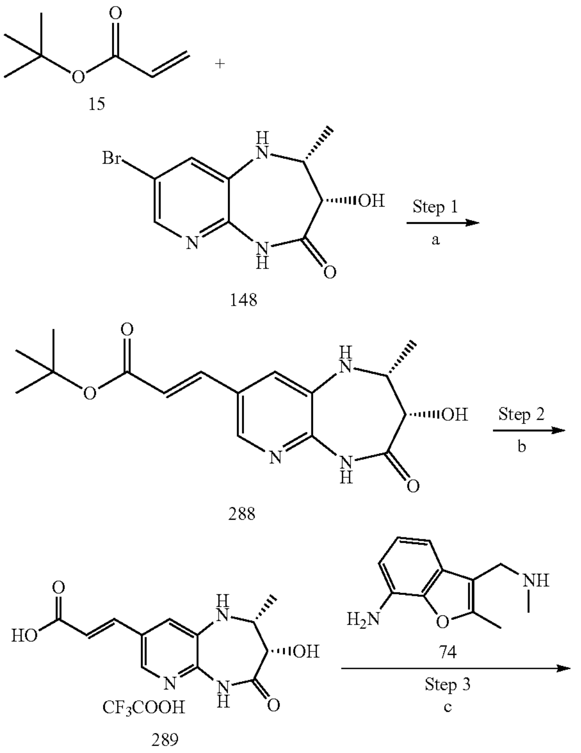

-continued

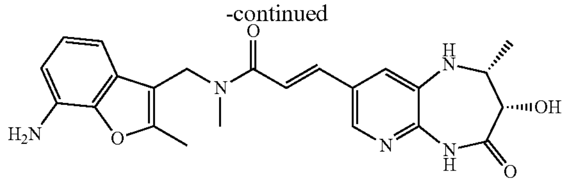

290

Reaction conditions: a) Pd-116, DIPEA, 1,4-dioxane, 90° C.; b) TFA, DCM; c) HATU, DIPEA, DMF Step 1. (E)-tert-Butyl 3-((2R,3S)-3-hydroxy-2-methyl-4-oxo-2,3,4,5-tetrahydro-1H-pyrido[2,3-b][1,4]diazepin-8-yl) acrylate (compound 288). (2R,3S)-8-Bromo-3-hydroxy-2-methyl-2,3-dihydro-1H-pyrido[2,3-b][1,4]diazepin-4(5H)-one 148 (350 mg, 1.29 mmol) and Pd-116 (33 mg, 0.064 mmol) were added to a vial and the vial was evacuated and re-filled with nitrogen (3 times). 1,4-Dioxane (7 mL), DIPEA (0.45 mL, 2.57 mmol), and tert-butyl acrylate 15 (0.37 mL, 2.57 mmol) were added and the reaction was stirred at 90° C. for 1 h. The reaction was allowed to cool to RT and then was concentrated in vacuo. The crude product was purified by chromatography (0-50% EtOAc/isohexane) to give the title compound 288 as a yellow solid (414 mg, 96%). UPLC-MS (Method 1c): $R^t$=1.74 min. m/z 320 $[M+H]^+$ $(ES^+)$. $^1H$ NMR (500 MHz, DMSO-$d_6$): δ, ppm 10.30 (s, 1H), 7.97 (d, J=1.9 Hz, 1H), 7.43 (d, J=16.0 Hz, 1H), 7.36 (d, J=1.9 Hz, 1H), 6.35 (d, J=16.0 Hz, 1H), 6.11 (d, J=5.7 Hz, 1H), 5.15 (d, J=4.8 Hz, 1H), 4.18 (dd, J=4.8, 3.3 Hz, 1H), 3.77-3.69 (m, 1H), 1.48 (s, 9H), 1.08 (d, J=6.5 Hz, 3H).

Step 2. (E)-3-((2R,3S)-3-Hydroxy-2-methyl-4-oxo-2,3,4,5-tetrahydro-1H-pyrido[2,3-b][1,4]diazepin-8-yl)acrylic acid 2,2,2-trifluoroactetate (compound 289). A mixture of (E)-tert-butyl 3-((2R,3S)-3-hydroxy-2-methyl-4-oxo-2,3,4,5-tetrahydro-1H-pyrido[2,3-b][1,4]diazepin-8-yl)acrylate 288 (411 mg, 1.29 mmol) in DCM (5 mL) and TFA (5 mL) was stirred at RT for 1.5 h. The mixture was concentrated under reduced pressure to give a pale orange gum. The gum was triturated with TBME (10 mL) to provide yellow solids which were filtered and washed with further TBME (10 mL) and then MeCN (2×10 mL) to give the title compound 289 as a bright yellow solid (260 mg, 53%). UPLC-MS (Method 1c): $R^t$=0.90 min. m/z 264 $[M+H]^+$ $(ES^+)$. $^1H$ NMR (500 MHz, DMSO-$d_6$): δ, ppm 12.41 (s, 1H), 10.30 (s, 1H), 7.96 (d, J=2.0 Hz, 1H), 7.47 (d, J=16.0 Hz, 1H), 7.36 (d, J=2.0 Hz, 1H), 6.36 (d, J=16.0 Hz, 1H), 6.15 (d, J=5.7 Hz, 1H), 5.15 (br. s, 1H), 4.19 (d, J=3.3 Hz, 1H), 3.78-3.69 (m, 1H), 1.08 (d, J=6.5 Hz, 3H).

Step 3. (E)-N-((7-Amino-2-methylbenzofuran-3-yl)methyl)-3-((2R,3S)-3-hydroxy-2-methyl-4-oxo-2,3,4,5-tetrahydro-1H-pyrido[2,3-b][1,4]diazepin-8-yl)-N-methylacrylamide (compound 290). DIPEA (110 μL, 0.63 mmol) was added to a suspension of (E)-3-((2R,3S)-3-hydroxy-2-methyl-4-oxo-2,3,4,5-tetrahydro-1H-pyrido[2,3-b][1,4]diazepin-8-yl)acrylic acid 2,2,2-trifluoroacetate 289 (60 mg, 0.16 mmol) and HATU (72 mg, 0.19 mmol) in DMF (1 mL) and the mixture was stirred at RT for 2 mins. 2-Methyl-3-((methylamino)methyl)benzofuran-7-amine 74 (30 mg, 0.16 mmol) in DMF (1 mL) was added in a single portion and the reaction mixture was stirred at RT for 1.5 h. $H_2O$ (10 mL) was added and the resultant yellow solids were filtered and washed with $H_2O$ (5 mL). The crude product was purified by chromatography (2.5-5% MeOH/DCM) to afford the title compound 290 as a yellow solid (16 mg, 23%).

$R^t$ 1.36 min (Method 1a) m/z 436 $(M+H)^+$ $(ES^+)$. $^1H$ NMR (500 MHz, DMSO-$d_6$, 363K): δ, ppm 9.80 (s, 1H), 7.97 (d, J=1.9 Hz, 1H), 7.44 (d, J=15.4 Hz, 1H), 7.39 (d, J=1.9 Hz, 1H), 7.15-7.03 (m, 1H), 6.87 (t, J=7.7 Hz, 1H), 6.74 (d, J=7.7 Hz, 1H), 6.53 (d, J=7.7 Hz, 1H), 5.89 (d, J=5.7 Hz, 1H), 4.87 (s, 2H), 4.76 (d, J=4.8 Hz, 1H), 4.71 (s, 2H), 4.21 (t, J=3.9 Hz, 1H), 3.80-3.72 (m, 1H), 2.98 (s, 3H), 2.47 (s, 3H), 1.11 (d, J=6.5 Hz, 3H).

Example 63 Formulation Examples

The compound of the present invention is formulated as a solution at a concentration of 10 mg/ml in a 40% Captisol aqueous vehicle or 30% Kleptose vehicle (30 minutes magnetic stirring at room temperature). This formulation is suitable for IV route.

The compound of the present invention is formulated as a solid dispersion at a drug load of 20% in HPMC AS: The compound and the polymer are solubilized in a mix of methylene chloride: methanol (ratio 3:1 w/w), the polymer concentration being 1.4% w/w in the organic phase (batch scale 85 mg). This solution is then spray dried on a Procept 4M8-Trix spray dryer (process parameters: cyclone S, air speed 0.35 m3/min, inlet temperature 50° C., solution feed rate: 6 g/min, nozzle pressure 10 L/min, air cooling 80 L/min). The recovery is 64%. DSC and XRPD analyses confirm that a solid solution is obtained (amorphous physical form, single Tg at 95° C.). The formulation is then formulated as tablets or granules for the PO route.

The compound of the present invention is formulated (at a concentration of 1 mg/ml to 300 mg/ml) as a nanosuspension or microsuspension in water or oil and stabilized by a polymer such as cellulose, 2-hydroxypropyl ether or Cellulose ethyl ether in a concentration between 0.01 and 10%. Said formulation further comprises a surfactant such as Polyoxyethylene 20 sorbitan monooleate in a concentration of between 0.01 and 10%. This formulation is suitable for administration via the oral route.

The compound of the present invention is formulated (at a concentration of 1 mg/ml to 300 mg/ml) as a nanosuspension or microsuspension in water or oil. The formulation further comprises a polymer such as Polyethylene Glycol 4000 or a-Hydro-o-hydroxypoly(oxy-1,2-ethanediyl) in a concentration of between 0.01 and 10%, and a surfactant such as Polyoxyethylene 20 sorbitan monooleate in a concentration of between 0.01 and 10%. The formulation is a sustained release formulation (sustained release between 12 and 72 h). This formulation is suitable for administration via the intramuscular route.

The compound of the present invention is formulated as a nanosuspension or microsuspension in water at a concentration of 10 mg/ml. The formulation further comprises Polyethylene Glycol 4000 in a concentration of 10%, and Polyoxyethylene 20 sorbitan monooleate in a concentration of 10%. This formulation is suitable for administration via the intramuscular route.

The compound of the present invention is formulated (at a concentration of 1 mg/ml to 300 mg/ml) as a nanosuspension or microsuspension in water in combination with an hydrophilic prodrug of the invention in a ratio (compound: hydrophilic prodrug compound) of from 1:99 to 99:1. The composition further comprises a polymer such as copovidone or acetic acid ethenyl ester polymer with 1-ethenyl-2-pyrrolidinone in a concentration of between 0.01 and 10%, and a surfactant e.g. Polyoxyethylene 20 sorbitan monooleate in a concentration of between 0.01 and 10%. The formulation is a sustained release formulation (sustained release between 12 and 72 h). This formulation is suitable for administration via the intramuscular route.

The compound of the present invention is formulated (at a concentration of 1 mg/ml to 300 mg/ml) as a solid dispersion, made of microgranules, microspheres or of an implant, at a drug load of 10-95% within a PLGA (or other suitable matrix as PLA) in an aqueous or oily media such as sesame oil. The formulation is stabilized by a polymer, such as copovidone or acetic acid ethenyl ester polymer with 1-ethenyl-2-pyrrolidinone, in a concentration of between 0.01 and 10%. Said formulation further comprises a surfactant Polyoxyethylene 20 sorbitan monooleate in a concentration of between 0.01 and 10%. The formulation is a sustained release formulation (sustained release between 12 and 72 h, e.g. 24 and 72 h), this formulation is suitable for administration via the intramuscular route.

The compound of the present invention is formulated (at a concentration of 1 mg/ml to 300 mg/ml) as a hydrogel or an oleogel comprising a polymer such as PEG-PLA Polyethylene glycol-polylactic acid or polysaccharides in a concentration of between 0.01 and 50%. The formulation is a sustained release formulation (sustained release between 12 and 72 h, e.g. 24 and 72 h. This formulation is suitable for administration via the intramuscular route.

The compound of the present invention is formulated as a lipophilic solid or oily prodrug (at a concentration of 1 mg/ml to 300 mg/ml) with oil such as sesame oil and a cosolvent e.g. benzyl alcohol and/or ethanol. The formulation is a sustained release formulation (sustained release between 12 and 72 h). This formulation is suitable for administration via the intramuscular route.

Example 64 Antibacterial Activity

The exemplified compounds were tested for activity, relying on the following test procedures:

*Neisseria gonorrhoeae* FabI Inhibition Assay:

Inhibition of *Neisseria gonorrhoeae* FabI enzyme activity was tested by measuring the rate of NADH consumption (Δabsorbance at 340 nm/min) at 30° C. in 96-well plate format using an automated plate reader in the presence or absence of the test compounds. The assay mixture contained 100 mM Tris-HCl, pH 7.2, 100 mM ammonium acetate, 0.05% pluronic F-68, 25 μM crotonyl ACP, 50 μM NADH, 50 μM recombinant *N. gonorrhoeae* FabI protein, 7.5% DMSO and test compounds at concentrations ranging from 0.17 to 10,000 nM in a final well volume of 100 μl. This dose-response inhibitory assay was performed using an 11-point, serial dilution series for each test compound. $IC_{50}$ values for each test compound were assigned from logistical sigmoid curve-fitting of the inhibition dose response curves.

MIC50: MICs were determined in accordance with the appropriate Clinical and Laboratory Standards Institute (CLSI) methodology by the agar dilution susceptbility testing method in GC agar base. The screening panel of isolates used for evaluation of the activity against diverse *Neisseria gonorrhoeae* strains and to determine MIC50 contained a minimum of 15 clinical isolates of N. gonorrhoea including several strains from the ATCC reference collection and Ciprofloxacine resistant strain. The MIC50 represents the MIC value at which ≥50% of the isolates in a test population are inhibited; it is equivalent to the median MIC value.

Caco-2 assay: Compounds were incubated in a Caco-2 24-transwell system (Solvo Biotechnologies, Hungary) for 120 min, after which samples were taken from the donor and acceptor compartments of the transwell system. The integrity of each cell monolayer was controlled by measuring transepithelial electrical resistance (TEER) before the experiment. *Lucifer* yellow permeability (B to A) was also tested as a control on the same plate (all wells) after the actual experiment. The samples were analyzed using UPLC/MS/MS. The permeation of the compounds was monitored using relative LC/MS/MS peak areas (initial donor solution sample=100%). The data were used to calculate apparent permeability (Papp in cm/s*$10^{-6}$) and recovery during the experiment.

Prediction of hepatic extraction ratio (ER): In vitro metabolic stability was assessed by determining the intrinsic metabolic clearance after incubation of the test compounds with mouse and human liver microsomes. In short, the study compounds were incubated with liver microsomes supplemented with cofactors (1 mM NADPH, 1 mM UDPGA+15 mM alamethicin). At selected time points, the assays were quenched using an equal volume of cold acetonitrile and samples were analyzed by UPLC/HR-MS to monitor disappearance rate of the compounds. Substrate depletion was estimated based on peak areas (0 min=100%), and is used to calculate half-lives and then in vitro clearances (CLint, in µL/min/mg protein). With the use of species-specific physiologically-based scaling factors (PBSF) and the Well-Stirred model of hepatic clearance as modified by Poulin et al, Journal of Pharmaceutical Sciences, vol. 101, no. 2, February 2012 and Poulin et al., Journal of Pharmaceutical Sciences, vol. 101, no. 11, November 2012, the in vitro CLint was further transformed into in vivo CLint and to hepatic extraction ratio (ER) for both mouse and human.

Mouse Cassette PK and oral bioavailability determination: Female BALB/c mice (n=24 per group) received single intravenous (iv, 1 mg/kg) or oral (po, 2 mg/kg) doses of the compounds. Dose volumes were 5 ml/kg and 10 ml/kg for IV and oral administration, respectively. Compounds were co-formulated in a 10% DMSO (v/v) and 40% Captisol (w/v) in saline solution formulation (up to 3 compounds in a cassette). Blood samples (3 mice per time point) were taken at 0.0833, 0.25, 0.5, 1, 2, 4, 6 & 8 hrs after administration and the compound concentrations were measured in plasma using standard HPLC/MS analytical methods. Tmax, Cmax, AUC, clearance, volume of distribution and oral bioavailability were estimated from the plasma concentrations using non-compartmental pharmacokinetic models. In particular, oral bioavailability (F %) was defined as $F=(Dose_{iv}*AUC_{po})/(Dose_{po}*AUC_{iv})*100$ Cytotoxicity HepG2

Day-1: Preparation of Plates C

- Cytotoxicity assays were performed in 96-well microtiter plates (Biofil, TCP 011096), the inner wells (60 inner wells surrounded by sterile water) received 190 µL of culture medium with a predefined number of cells (7,500 viable cells/well). One plate C containing cells was be prepared for 2 compounds (8 concentrations, n=3/concentration). One background plate without cells was prepared for 6 compounds (8 concentrations, n=1/concentration)
- Plates were left on the bench for 30 min to allow homogenous adhesion of cells within wells
- The plates were then Incubated overnight at 37° C. with 5% CO2

Day 0: Preparation of Plate A

- Stock solutions were serially diluted (half-log dilution, 3.16×) in corresponding 100% DMSO in a 96-well PP plate (Greiner Bio-One, 7.651.261): 79 µl of a stock solution at 10,000 µM in 100% DMSO was added in column 3, 54 µl of 100% DMSO was added in columns 4 to 11. 25 µl of compound stock solution was transferred from column 3 to column 4 (pipeted up and down 3×, tips changed after each transfer). This was continued up to column 10. For the positive control Doxorubicin, a stock solution at 11000 M was used as a starting point.

Plate A:

| | | | | | | | | |
|---|---|---|---|---|---|---|---|---|
| Compound 1 10000 uM | 3164.56 | 1001.44 | 316.91 | 100.29 | 31.74 | 10.04 | 3.18 | 100% DMSO |
| Compound 2 10000 uM | 3164.56 | 1001.44 | 316.91 | 100.29 | 31.74 | 10.04 | 3.18 | 100% DMSO |
| Compound 3 10000 uM | 3164.56 | 1001.44 | 316.91 | 100.29 | 31.74 | 10.04 | 3.18 | 100% DMSO |
| Compound 4 10000 uM | 3164.56 | 1001.44 | 316.91 | 100.29 | 31.74 | 10.04 | 3.18 | 100% DMSO |
| Compound 5 10000 uM | 3164.56 | 1001.44 | 316.91 | 100.29 | 31.74 | 10.04 | 3.18 | 100% DMSO |
| Compound 6 10000 uM | 3164.56 | 1001.44 | 316.91 | 100.29 | 31.74 | 10.04 | 3.18 | 100% DMSO |
| Compound 7 10000 uM | 3164.56 | 1001.44 | 316.91 | 100.29 | 31.74 | 10.04 | 3.18 | 100% DMSO |
| Doxorubicin 1000 uM | 316.46 | 100.14 | 31.69 | 10.03 | 3.17 | 1.00 | 0.32 | 100% DMSO |

Preparation of Plate B

- Compounds prepared in Plate A were diluted 5× in 200 µl in complete medium in a 96-well PP plate (Greiner Bio-One, 7.651.261): In column 2, 200 µl of medium containing 16% Tritron X-100 was added. In columns 3 to 11, 160 µl of medium was added. 40 µl of the pre-diluted compounds from plate A were transferred to column 3 to 11 (Pipeted up and down 3×, tips changed after each transfer).

Plate B:

| | | | | | | | | | |
|---|---|---|---|---|---|---|---|---|---|
| 16% Triton X | Compound 1 2000000 nM | 632911.39 | 200288.42 | 63382.41 | 20057.72 | 6347.38 | 2008.66 | 635.65 | 20% DMSO |
| 16% Triton X | Compound 2 2000000 nM | 632911.39 | 200288.42 | 63382.41 | 20057.72 | 6347.38 | 2008.66 | 635.65 | 20% DMSO |
| 16% Triton X | Compound 3 2000000 nM | 632911.39 | 200288.42 | 63382.41 | 20057.72 | 6347.38 | 2008.66 | 635.65 | 20% DMSO |

-continued

| | | | | | | | | | |
|---|---|---|---|---|---|---|---|---|---|
| 16% Triton X | Compound 4 2000000 nM | 632911.39 | 200288.42 | 63382.41 | 20057.72 | 6347.38 | 2008.66 | 635.65 | 20% DMSO |
| 16% Triton X | Compound 5 2000000 nM | 632911.39 | 200288.42 | 63382.41 | 20057.72 | 6347.38 | 2008.66 | 635.65 | 20% DMSO |
| 16% Triton X | Compound 6 2000000 nM | 632911.39 | 200288.42 | 63382.41 | 20057.72 | 6347.38 | 2008.66 | 635.65 | 20% DMSO |
| 16% Triton X | Compound 7 2000000 nM | 632911.39 | 200288.42 | 63382.41 | 20057.72 | 6347.38 | 2008.66 | 635.65 | 20% DMSO |
| 16% Triton X | Doxorubicin 200000 nM | 63291.14 | 20028.84 | 6338.24 | 2005.77 | 634.74 | 200.87 | 63.57 | 20% DMSO |

20× solutions of plate B were diluted in plates C (with and without (background plate) cells): In columns 2 to 11, 10 μl of plate B compound solutions were added(pipet up and down 3×, tips changed after each transfer). 2 compounds were distributed per plate C in triplicates (simplicate for background plate)

Example of Plate C:

| | | | | | | | | | |
|---|---|---|---|---|---|---|---|---|---|
| 0.8% Triton X | Compound 7 100000 nM | 31645.57 | 10014.42 | 3169.12 | 1002.89 | 317.37 | 100.43 | 31.78 | 1% DMSO |
| 0.8% Triton X | Compound 7 100000 nM | 31645.57 | 10014.42 | 3169.12 | 1002.89 | 317.37 | 100.43 | 31.78 | 1% DMSO |
| 0.8% Triton X | Compound 7 100000 nM | 31645.57 | 10014.42 | 3169.12 | 1002.89 | 317.37 | 100.43 | 31.78 | 1% DMSO |
| 0.8% Triton X | Doxorubicin 10000 nM | 3164.56 | 1001.44 | 316.91 | 100.29 | 31.74 | 10.04 | 3.18 | 1% DMSO |
| 0.8% Triton X | Doxorubicin 10000 nM | 3164.56 | 1001.44 | 316.91 | 100.29 | 31.74 | 10.04 | 3.18 | 1% DMSO |
| 0.8% Triton X | Doxorubicin 10000 nM | 3164.56 | 1001.44 | 316.91 | 100.29 | 31.74 | 10.04 | 3.18 | 1% DMSO |

Plates C were incubated for 72 hours at 37° C. with 5% CO2

Day 3:

20 μl of Alamar blue was added and incubated for 6 h at 37° C. with or without C02 fluorescence was read at exc 570 nm and emi 585 nm

Background corrected fluorescence measurements were transformed in % scale by considering vehicle value (1% DMSO) as 100% activity (relative measurements), or they were normalized by considering Triton X-100 values as 0% viability and vehicle values as 100% viability (normalized measurements). Next, relative measurements and absolute measurements were analyzed using GraphPad Prism software to derive relative IC50 and absolute IC50 values respectively The results of these activity tests are summarized in Table 1 below.

TABLE 1

| Compound number (patent example) | ngFabI IC50 (nM) | MIC50 (μg/mL) | Caco-2 Papp A2B (10−6 cm/s) | Predict Human hep ER | Mouse F (%) | Cyto-toxicity % viability at 10 μM |
|---|---|---|---|---|---|---|
| 5 (1) | <10 | <1 | 22.6 | 0.17 | 100 | NA |
| 7 (2) | <10 | <1 | 7.6 | 0.12 | 68 | NA |
| 10 (3) | <10 | <1 | 22.6 | 0.22 | 73 | NA |
| 19 (4) | <10 | <1 | 16 | 0.26 | 62 | 100 |
| 31 (6) | <10 | <1 | 10.9 | 0.18 | NA | NA |
| 32 (6) | <10 | <1 | 10.8 | 0.08 | 42 | NA |
| 33 (6) | <10 | <1 | 11.5 | 0.09 | NA | NA |

TABLE 1-continued

| Compound number (patent example) | ngFabI IC50 (nM) | MIC50 (μg/mL) | Caco-2 Papp A2B (10−6 cm/s) | Predict Human hep ER | Mouse F (%) | Cyto-toxicity % viability at 10 μM |
|---|---|---|---|---|---|---|
| 39 (7) | <10 | <1 | 11.3 | 0.17 | NA | NA |
| 40 (7) | <10 | <1 | 10.3 | 0.21 | 57 | NA |

TABLE 1-continued

| Compound number (patent example) | ngFabI IC50 (nM) | MIC50 (μg/mL) | Caco-2 Papp A2B (10−6 cm/s) | Predict Human hep ER | Mouse F (%) | Cyto-toxicity % viability at 10 μM |
|---|---|---|---|---|---|---|
| 41 (7) | <10 | <1 | 12.2 | 0.09 | NA | NA |
| 49 (8) | <10 | <1 | 26 | 0.13 | 70 | 100 |
| 50 (8) | <10 | <1 | 19.1 | 0.09 | NA | NA |
| 60 (9) | <10 | <1 | 3 | 0.07 | 52 | NA |
| 64 (10) | <10 | <1 | 16.3 | 0.21 | 32 | NA |
| 75 (11) | <10 | <1 | 5.9 | 0.13 | 30 | NA |
| 80 (12) | <10 | <1 | NA | 0.25 | 35 | NA |
| 84 (13) | <10 | <1 | 3.29 | 0.40 | 24 | NA |
| 90 (14) | <10 | <1 | 10.7 | 0.03 | 7 | NA |
| 96 (15) | <10 | <1 | NA | 0.2 | 16 | NA |
| 101 (16) | <10 | <1 | 2.69 | 0.43 | 2 | NA |
| 109 (17) | <10 | <1 | 19.8 | 0.28 | 47 | NA |
| 115 (18) | <10 | <1 | 3.4 | 0.28 | 18 | NA |
| 119 (19) | <10 | <1 | NA | 0.08 | NA | NA |
| 123 (20) | <10 | <1 | 2.5 | 0.13 | 26 | NA |
| 129 (21) | <10 | <1 | NA | 0.02 | 26 | NA |
| 134 (22) | <10 | <1 | NA | 0.43 | 9 | NA |
| 140 (23) | <10 | <1 | NA | 0.13 | 13 | NA |
| 143 (24) | <10 | <1 | 2.3 | 0.06 | 59 | NA |
| 150 (25) | <10 | <1 | 25.1 | 0.08 | 20 | 100 |
| 151 (26) | <10 | <1 | 21.7 | 0.07 | 39 | NA |
| 152 (27) | <10 | <1 | 2.6 | 0.08 | 38 | NA |
| 155 (28) | <10 | <1 | NA | 0.32 | 28 | NA |
| 159 (29) | <10 | <1 | 0.7 | 0.32 | 35 | 100 |
| 164 (30) | <10 | <1 | 0.1 | NA | 10 | NA |
| 167 (31) | <10 | <1 | 5.3 | 0.12 | 35 | 100 |
| 168 (32) | <10 | <1 | 19.6 | 0.15 | 51 | NA |
| 170 (33) | <10 | <1 | 22.9 | 0.15 | 98 | NA |
| 176 (36) | <10 | <1 | 0 | 0.07 | 44 | NA |
| 180 (37) | <10 | <1 | 1.8 | 0.32 | 14 | |

TABLE 1-continued

| Compound number (patent example) | ngFabI IC50 (nM) | MIC50 (μg/mL) | Caco-2 Papp A2B (10−6 cm/s) | Predict Human hep ER | Mouse F (%) | Cyto-toxicity % viability at 10 μM |
|---|---|---|---|---|---|---|
| 182 (38) | <10 | <1 | 0.08 | 0.25 | 12 | NA |
| 183 (39) | <10 | <1 | NA | NA | 16 | NA |
| 186 (40) | <10 | <1 | 0.4 | NA | 23 | NA |
| 194 (41) | <10 | <1 | 0 | NA | 12 | NA |
| 198 (42) | <10 | <1 | 3.2 | 0.18 | 54 | NA |
| 207 (43) | <10 | <1 | NA | NA | NA | NA |
| 208 (44) | <10 | <1 | 0 | 0.21 | NA | NA |
| 209 (44) | <10 | <1 | 3.3 | 0.41 | 25 | NA |
| 214 (45) | <10 | <1 | 17.9 | NA | 88 | NA |
| 229 (46) | <10 | <1 | 20.7 | NA | 76 | NA |
| 230 (46) | <10 | <1 | NA | NA | NA | NA |
| 247 (52) | <10 | <1 | NA | NA | NA | NA |
| 252 (53) | <10 | <1 | NA | NA | NA | NA |
| 260 (54) | <10 | <1 | 35 | 0.03 | 56 | NA |
| 270 (55) | <10 | <1 | 5.5 | 0.05 | NA | NA |
| 275 (57) | <10 | <1 | NA | NA | 51 | NA |
| 276 (58) | <10 | <1 | NA | NA | 43 | NA |
| 287 (61) | <10 | <1 | NA | 0.34 | NA | NA |
| 290 (62) | <10 | <1 | NA | 0.1 | NA | NA |

NA: not available

Example 65 *Chlamydia trachomatis* FabI Inhibition Assay

Inhibition of *Chlamydia trachomatis* FabI enzyme activity was tested by measuring the rate of NADH consumption (Δabsorbance at 340 nm/min) at 30° C. in 96-well plate format using an automated plate reader in the presence or absence of the test compounds. The assay mixture contained 100 mM MES, pH 7.0, 200 mM ammonium acetate, 4.0% glycerol, 0.02% pluronic F-68, 25 μM crotonyl ACP, 50 μM NADH, 0.5 nM recombinant *C. trachomatis* FabI protein, 7.5% DMSO and test compounds at concentrations ranging from 0.17 to 100,000 nM in a final well volume of 100 μl. This dose-response inhibitory assay was performed using an 11-point, serial dilution series for each test compound. $IC_{50}$ values for each test compound were assigned from logistical sigmoid curve-fitting of the inhibition dose response curves. Results are Shown in Table 2.

TABLE 2

| Compound number (PATENT EXAMPLE) | CT FABI $IC_{50}$ (μM) |
|---|---|
| 229 (46) | <1 |
| 49 (8) | <1 |
| 152 (27) | <1 |
| 150 (25) | <1 |
| 32 (6) | <1 |
| 155 (28) | <1 |
| 40 (7) | <5 |
| 151 (26) | <5 |
| 260 (54) | <5 |
| 109 (17) | <5 |
| 214 (45) | <5 |
| 60 (9) | <5 |
| 275 (57) | <5 |

With respect to the designation of the United States of America, the following is stated: "This invention was made with government support under FAIN: IDSEP160030 awarded by HHS/ASPR. The government has certain rights in the invention."

The invention claimed is:

1. A compound, which is selected from the group of compounds represented by general formula I:

I

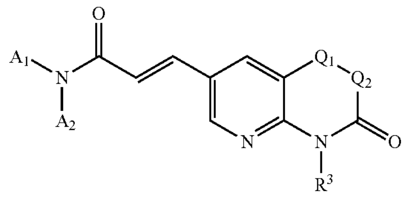

wherein $A_1$ represents a moiety selected from the groups $A_{11}$ and $A_{12}$ having the following structures:

$A_{11}$

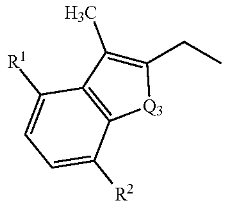

and $A_{12}$

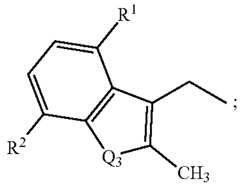

wherein the line connected to the exocyclic methylene group represents a single covalent bond formed with the nitrogen atom of formula I;

$A_2$ represents a methyl group;

or $A_1$ and $A_2$ together with the nitrogen atom to which they are bonded form the following moiety $A_3$:

$A_3$

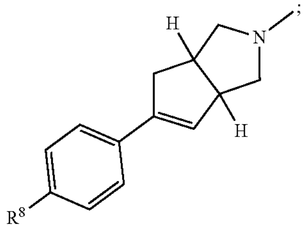

wherein the exocyclic line connected to the nitrogen atom of the bicycle represents the covalent bond between nitrogen and carbonyl group in the left-hand side of formula I;

$Q^1$ represents $CH_2$ or NH;

$Q^2$ represents $CR^4R^5$—$CR^6R^7$, wherein the $CR^4R^5$ group binds to $Q_1$;

$Q^3$ represents O;

$R^1$ represents H;

$R^2$ represents a group selected from H, —O—$Ar^1$, and —$NR^9R^{10}$, wherein $Ar^1$ represents a phenyl group that may optionally be substituted by one or more groups individually selected from —CN and —O—$C_{1-4}$-alkyl;

wherein $R^9$ is selected from H and —$C_{1-4}$-alkyl;

wherein $R^{10}$ is selected from H, —$C_{1-4}$-alkyl and —C(═O)—$CH_3$;

$R^3$ represents H;

each $R^{3a}$ independently represents a hydrogen atom or a cation suitable for forming a pharmaceutically acceptable salt;

$R^4$ represents a group selected from H and $C_{1-4}$-alkyl;

$R^5$ represents a group selected from H, $C_{1-4}$-alkyl, and —OH;

$R^6$ represents a group selected from H, —OH, $C_{1-4}$-alkyl, and —$OPO_3R^{3a}{}_2$;

$R^7$ represents a group selected from H and $C_{1-4}$-alkyl;

with the proviso that at least one of $R^6$ and $R^7$ is not H;

$R^8$ represents —O—$Ar^2$;

wherein $Ar^2$ represents a phenyl group that may optionally be substituted by one or more —O—$C_{1-4}$-alkyl groups;

and pharmaceutically acceptable salts thereof.

2. The compound, or a pharmaceutically acceptable salt thereof, according to claim 1, wherein $R^4$ represents $C_{1-4}$-alkyl.

3. The compound according to claim 1, or a pharmaceutically acceptable salt thereof, selected from the group of compounds represented by general formula II:

II

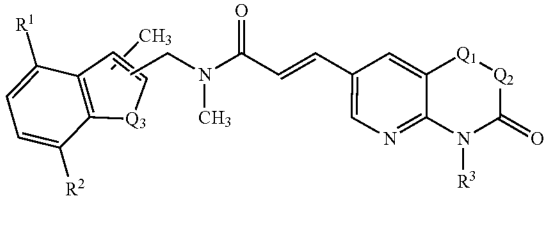

wherein the five-membered heterocycle comprising $Q_3$ is bonded to the methylene-amide moiety at the 2-position and to the methyl group at the 3-position or is bonded to the methylene-amide moiety at the 3-position and to the methyl group at the 2-position.

4. The compound according to claim 3, or a pharmaceutically acceptable salt thereof, selected from the group of compounds represented by general formula III:

III

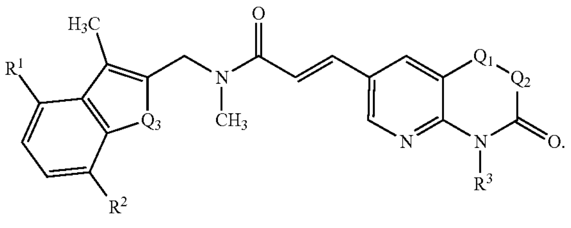

5. The compound according to claim 4, or a pharmaceutically acceptable salt thereof, selected from the group of compounds represented by general formula VI:

VI

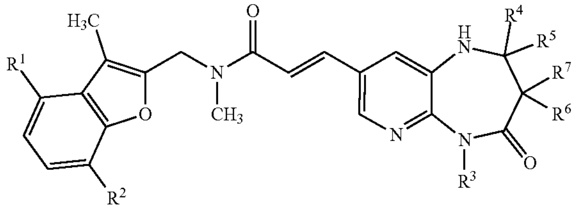

wherein $R^2$ represents H.

6. The compound according to claim 4, or a pharmaceutically acceptable salt thereof, selected from the group of compounds represented by general formula VII:

VII

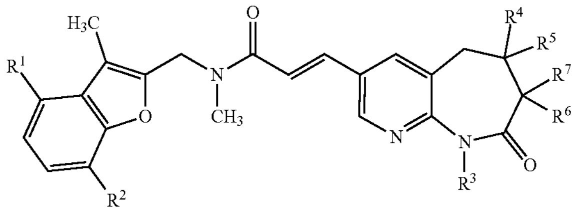

wherein $R^2$ represents H.

7. The compound according to claim 3, or a pharmaceutically acceptable salt thereof, selected from the group of compounds represented by general formula VIII:

VIII

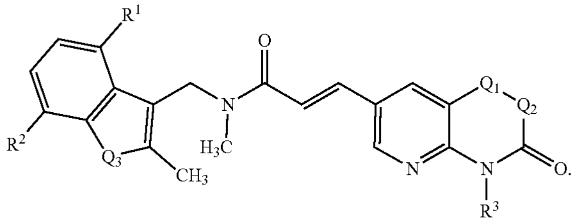

8. The compound according to claim 7, or a pharmaceutically acceptable salt thereof, selected from the group of compounds represented by general formula XI:

XI

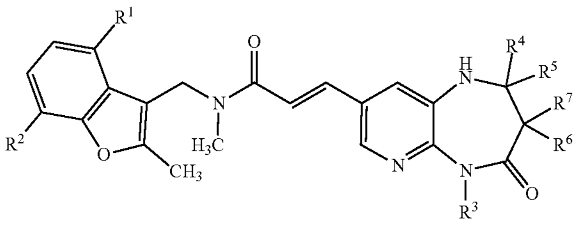

wherein $R^2$ represents a group selected from H, —O—$Ar^1$, and —$NH_2$.

9. The compound according to claim 7, or a pharmaceutically acceptable salt thereof, selected from the group of compounds represented by general formula XII:

XII

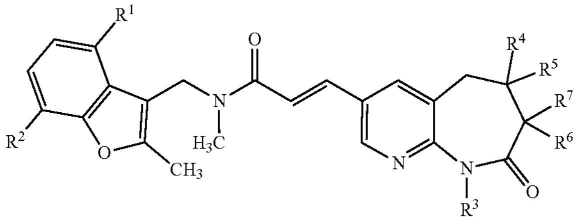

wherein $R^2$ represents a group selected from H, —O—$Ar^1$, —$NH_2$.

10. The compound according to claim 1, or a pharmaceutically acceptable salt thereof, selected from the group of compounds represented by general formula XIII:

XIII

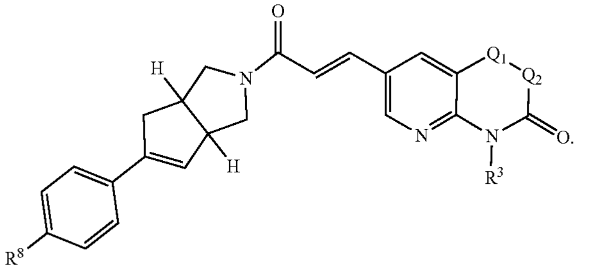

11. The compound according to claim 10, or a pharmaceutically acceptable salt thereof, selected from the group of compounds represented by general formula XV:

XV

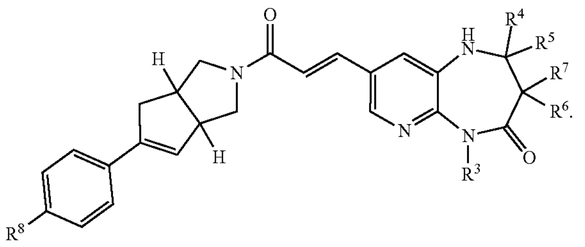

12. The compound according to claim 10, or a pharmaceutically acceptable salt thereof, selected from the group of compounds represented by general formula XVI:

XVI

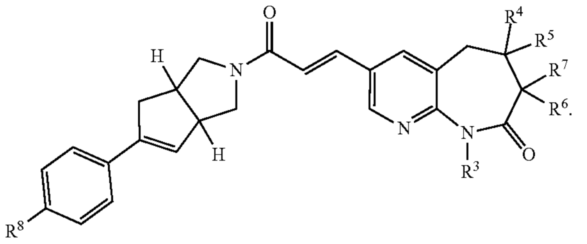

13. A pharmaceutical composition comprising the compound of claim 1, or a pharmaceutically acceptable salt thereof.

14. A method for the treatment of a bacterial infection selected from infections by *N. gonorrhoeae, Bacillus* Spp., *Bartonella* Spp., *Brucella* Spp, *Campylobacter* Spp., *Chlamydia trachomatis, Enterococcus faecalis, Enterococcus faecium, Legionella pneumophila, Listeria* Spp., *Proteus mirabilis, Providencia stuartii, Rickettsia* Spp., *Bordetella pertussis, Bordetella parapertussis, Burkholderia* Spp., *Haemophilus influenza, Kingella kingae, Moraxella catarrhalis, Streptomyces* Spp., *Nocardioides* Spp., *Frankia* Spp. *Propionibacterium acnes, Mycobacterium* Spp., and combinations thereof in a subject comprising administering to the subject a compound, or a pharmaceutically acceptable salt thereof, of claim 1.

15. The compound according to claim 5, wherein $R^5$ is hydrogen.

16. The compound according to claim 5, wherein $R^4$ is methyl.

17. The compound according to claim 5, wherein $R^6$ is OH.

18. The compound according to claim 5, wherein $R^7$ is H.

19. The compound according to claim 1 having the structure:

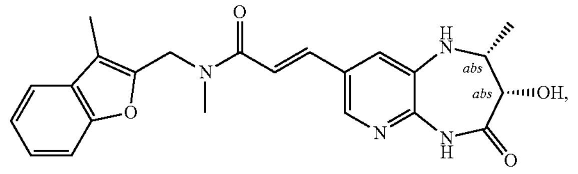 [SMILES: Cc1c(CN(C)C(=O)/C=C/c2cnc3c(c2)N[C@H](C)[C@H](O)C(=O)N3)oc2ccccc12]

or a pharmaceutically acceptable salt thereof.

20. The method of claim 14, wherein the bacterial infection is *N. gonorrhoeae* alone or in combination with *Chlamydia trachomatis.*

* * * * *